US010548963B2

(12) United States Patent
Castado et al.

(10) Patent No.: US 10,548,963 B2
(45) Date of Patent: Feb. 4, 2020

(54) IMMUNOGENIC COMPOSITION FOR USE IN VACCINATION AGAINST STAPHYLOCOCCI

(71) Applicant: GlaxoSmithKline Biologicals S.A., Rixensart (BE)

(72) Inventors: Cindy Castado, Rixensart (BE); Nicolas Pierre Fernand Lecrenier, Rixensart (BE); Cecile Anne Neyt, Rixensart (BE); Jan Poolman, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/046,505

(22) Filed: Jul. 26, 2018

(65) Prior Publication Data

US 2019/0076516 A1 Mar. 14, 2019

Related U.S. Application Data

(63) Continuation of application No. 14/662,003, filed on Mar. 18, 2015, now abandoned, which is a continuation of application No. 11/575,672, filed as application No. PCT/EP2005/010184 on Sep. 20, 2005, now abandoned.

(30) Foreign Application Priority Data

| | | |
|---|---|---|
| Sep. 22, 2004 | (GB) | 0421078.7 |
| Sep. 22, 2004 | (GB) | 0421079.5 |
| Sep. 22, 2004 | (GB) | 0421081.1 |
| Sep. 22, 2004 | (GB) | 0421082.9 |
| Feb. 15, 2005 | (GB) | 0503143.0 |

(51) Int. Cl.

| | |
|---|---|
| ***A61K 39/085*** | (2006.01) |
| ***A61K 39/116*** | (2006.01) |
| ***A61K 39/00*** | (2006.01) |
| ***C07K 16/12*** | (2006.01) |
| ***A61K 47/64*** | (2017.01) |

(52) U.S. Cl.

CPC ........ *A61K 39/085* (2013.01); *C07K 16/1271* (2013.01); *A61K 39/116* (2013.01); *A61K 47/646* (2017.08); *A61K 2039/505* (2013.01)

(58) Field of Classification Search

CPC .... A61K 2039/505; A61K 2039/55505; A61K 2039/6031; A61K 2039/6037; A61K 39/085; A61K 47/6415; A61K 47/646; A61K 2039/55544; A61K 2039/55555; A61K 2039/55572; A61K 2039/55577; A61K 47/643; A61K 2039/522; A61K 2039/55566; A61K 2039/627; A61K 31/70; A61K 39/00; A61K 39/385; A61K 47/48261; A61K 47/48284; A61K 47/4833; A61K 47/61; C07K 16/1271; C07K 2317/21; C07K 2317/73; C07K 14/31; C07K 2316/96; C07K 2317/76; Y10S 530/807; Y10S 424/831; Y02A 50/484

See application file for complete search history.

(56) References Cited

U.S. PATENT DOCUMENTS

| | | | |
|---|---|---|---|
| 3,983,229 | A | 9/1976 | Relyveld |
| 5,801,234 | A | 9/1998 | Hodgson et al. |
| 6,008,341 | A | 12/1999 | Foster et al. |
| 6,627,730 | B1 | 9/2003 | Burnie |
| 6,696,065 | B1 | 2/2004 | Fahim et al. |
| 6,703,025 | B1 | 3/2004 | Patti et al. |
| 2002/0169288 | A1 | 11/2002 | Hook et al. |
| 2003/0087864 | A1 | 5/2003 | Talbot et al. |
| 2003/0113350 | A1 | 6/2003 | Fattom et al. |
| 2004/0072748 | A1 | 4/2004 | Balaban |
| 2005/0118198 | A1 | 6/2005 | Pier et al. |
| 2007/0087014 | A1 | 4/2007 | Pavliak et al. |
| 2008/0085289 | A1 | 4/2008 | Castado et al. |
| 2008/0095777 | A1 | 4/2008 | Castado et al. |
| 2011/0189223 | A1 | 8/2011 | Ballou, Jr. et al. |

FOREIGN PATENT DOCUMENTS

| | | | |
|---|---|---|---|
| EG | NA2007/000295 | | 9/2000 |
| GB | 1100190 | | 1/1968 |
| JP | 2002-523473 | A | 7/2002 |
| WO | 93/09811 | A1 | 5/1993 |
| WO | 99/27109 | A2 | 6/1999 |
| WO | 00/03745 | A2 | 1/2000 |

(Continued)

OTHER PUBLICATIONS

Anderson et al. J. Infect. Dis. 205: 1688-1696, 2012.*

Anderson et al., "Development of a multicomponent *Staphylococcus aureus* vaccine designed to counter multiple bacterial virulence factors," *Human Vaccines & Immunotherapeutics* 8(11):1585-1594, 2012.

Bhakdi et al., "Functionally Inactive *S. aureus* Alpha-Toxin Containing a Single Amino Acid Substitution: Potential Usefulness as a Vaccine," *Behring Inst. Mitt.* 95:80-84, 1994.

Bosseray et al., "Antagonism between two immunogens extracted from *Brucella* (cell wall peptidoglycan and lipopolysaccharide fractions) and inactivity of the brucellin allergen in immunization of the mouse," *Ann Microbiol* (Paris) 131A(2):157-169, 1980. (Abstract Only).

(Continued)

*Primary Examiner* — Sarvamangala Devi

(74) *Attorney, Agent, or Firm* — Seed IP Law Group LLP

(57) ABSTRACT

The present application relates to immunogenic compositions comprising a mixture of staphylococcal antigens which combines antigen having different functions, for instance, combinations including a staphylococcal extracellular component binding protein and a staphylococcal transporter protein or a staphylococcal extracellular component binding protein and a staphylococcal regulator of virulence or toxin or a staphylococcal transporter protein and a staphylococcal regulator of virulence or toxin. Vaccines, methods of treatment, uses of and processes to make a staphylococcal vaccine are also described.

9 Claims, 73 Drawing Sheets

Specification includes a Sequence Listing.

(56) References Cited

FOREIGN PATENT DOCUMENTS

| | | | |
|---|---|---|---|
| WO | 00/12131 | A1 | 3/2000 |
| WO | 02/45742 | A2 | 6/2002 |
| WO | 02/074324 | A1 | 9/2002 |
| WO | 02/094868 | A2 | 11/2002 |
| WO | 02/102829 | A2 | 12/2002 |
| WO | 2004/043405 | A2 | 5/2004 |
| WO | 2004/080490 | A2 | 9/2004 |
| WO | 2006/032472 | A2 | 3/2006 |
| WO | 2006/032475 | A2 | 3/2006 |
| WO | 2006/032500 | A2 | 3/2006 |
| WO | 2010/151544 | A1 | 12/2010 |
| WO | 2012/085872 | A2 | 6/2012 |

OTHER PUBLICATIONS

Brown et al., "Immunization with Components of Two Iron Uptake ABC Transporters Protects Mice against Systemic *Streptococcus pneumoniae* Infection," *Infection and Immunity* 69(11):6702-6706, Nov. 2001.

Burnie et al., "Identification of an Immunodominant ABC Transporter in Methicillin-Resistant *Staphylococcus aureus* Infections," *Infection and Immunity* 68(6):3200-3209, Jun. 2000.

Clarke et al., "IsdA of *Staphylococcus aureus* is a broad spectrum, iron-regulated adhesin," *Molecular Microbiology* 51(5):1509-1519, 2004.

Cockayne et al., "Molecular Cloning of a 32-Kilodalton Lipoprotein Component of a Novel Iron-Regulated *Staphylococcus epidermidis* ABC Transporter," *Infection and Immunity* 66(8): 3767-3774, 1998.

Dagan et al., "Reduced Response to Multiple Vaccines Sharing Common Protein Epitopes That Are Administered Simultaneously to Infants," *Infection and Immunity* 66(5):2093-2098, 1998.

Fattom et al., "A *Staphylococcus aureus* Capsular Polysaccharide (CP) Vaccine and CP-Specific Antibodies Protect Mice against Bacterial Challenge," *Infection and Immunity* 64(5):1659-1665, May 1996.

Fattom et al., "Antigenic Determinants of *Staphylococcus aureus* Type 5 and Type 8 Capsular Polysaccharide Vaccines," *Infection and Immunity* 66(10):4588-4592, Oct. 1998.

Fattom et al., "Synthesis and Immunologic Properties in Mice of Vaccines Composed of *Staphylococcus aureus* Type 5 and Type 8 Capsular Polysaccharides Conjugated to *Pseudomonas aeruginosa* Exotoxin A," *Infection and Immunity* 58(7):2367-2374, Jul. 1990.

Flock, "Extracellular-matrix-binding proteins as targets for the prevention of *Staphylococcus aureus* infections," *Molecular Medicine Today* 5:532-537, Dec. 1999.

Handke et al., "Regulation of *Staphylococcus aureus* MntC Expression and Its Role in Response to Oxidative Stress," *PLOS ONE* 8(10):1-8, 2013.

Harro et al., "The immunogenicity and safety of different formulations of a novel *Staphylococcus aureus* vaccine (V710): Results of two Phase I studies," *Vaccine* 30(9):1729-1736, 2012.

Hawkins et al., "A Recombinant Clumping Factor A—Containing Vaccine Induces Functional Antibodies to *Staphylococcus aureus* That Are Not Observed after Natural Exposure," *Clinical and Vaccine Immunology* 19(10):1641-1650, 2012.

Heilmann et al., "The Multifunctional *Staphylococcus aureus* Autolysin Aaa Mediates Adherence to Immobilized Fibrinogen and Fibronectin," *Infection and Immunity* 73(8):4793-4802, Aug. 2005.

Herbelin et al., "Immune Recruitment and Bactericidal Activity of Neutrophils in Milk of Cows Vaccinated with Staphylococcal α-Toxin," *J Dairy Sci.* 80(9):2025-2034, 1997.

Hume et al., "Immunization with Alpha-Toxin Toxoid Protects the Cornea against Tissue Damage during Experimental *Staphylococcus aureus* Keratitis," *Infection and Immunity* 68(10):6052-6055, 2000.

Hungerer et al., "In vitro and in vivo efficacy of a toxin-neutralizing human staphylococcal immunoglobulin," *Behring Inst. Mitt.*86:170-184, 1990. (Abstract Only) (1 Page).

Japanese Office Action dated Jul. 19, 2013, for corresponding JP Application No. 2007-531712, 9 pages, with English Translation.

Kelly et al., "*Haemophilus influenzae* type b conjugate vaccines," *Immunology* 113(2):163-174, 2004.

Kupferwasser et al., "D-241. Efficacy of a Clumping Factor (ClfA) Based Vaccine in Mitigating Experimental Methicillin-Resistant *Staphylococcus aureus* (MRSA) Endocarditis," in *Abstracts of the 103rd General Meeting of the American Society for Microbiology*, Washington, DC, May 18-22, 2003, pp. 145.

Lee, "Development of Antistaphylococcal Vaccines," *Current Infectious Disease Reports* 3(6):517-524, 2001.

Maione et al., "Identification of a Universal Group B *Streptococcus* Vaccine by Multiple Genome Screen," *Science* 309(5731):148-150, 2005.

Maira-Litran et al., "Biologic properties and vaccine potential of the staphylococcal poly-N-acetyl glucosamine surface polysaccharide," *Vaccine* 22:872-879, 2004.

Mazmanian et al., "An iron-regulated sortase anchors a class of surface protein during *Staphylococcus aureus* pathogenesis," *Proc. Natl. Acad. Sci. USA* 99(4):2293-2298, Feb. 19, 2002.

Menzies et al., "Passive Immunization with Antiserum to a Nontoxic Alpha-Toxin Mutant from *Staphylococcus aureus* Is Protective in a Murine Model," *Infection and Immunity* 64(5):1839-1841, May 1996.

Müller et al., "The *Staphylococcus aureus* Lipoprotein SitC Colocalizes with Toll-Like Receptor 2 (TLR2) in Murine Keratinocytes and Elicits Intracellular TLR2 Accumulation," *Infection and Immunity* 78(10):4243-4250, 2010.

Nordhaug et al., "A Field Trial with an Experimental Vaccine Against *Staphylococcus aureus* Mastitis in Cattle 2. Antibody Response," *J Diary Sci* 77:1276-1284, 1994.

O'Brien et al., "Production of Antibodies to *Staphylococcus aureus* Serotypes 5, 8, and 336 Using Poly($_{DL}$-Lactide-co-Glycolide) Microspheres," *J Diary Sci* 83(8):1758-1766, 2000.

O'Riordan et al., "*Staphylococcus aureus* Capsular Polysaccharides," *Clinical Microbiology Reviews* 17(1):218-234, Jan. 2004.

Oshida et al., "A *Staphylococcus aureus* autolysin that has an N-acetylmuramoyl-L-alanine amidase domain and an endo-β-N-acetylglucosaminidase domain: Cloning , sequence analysis, and characterization," *Proc. Natl. Acad. Sci.* 92:285-289, Jan. 1995.

Park et al., "Immunogenicity of Alpha-Toxin, Capsular Polysaccharide (CPS) and Recombinant Fibronectin-Binding Protein (r-FnBP) of *Staphylococcus aureus* in Rabbit," *Journal of Veterinary Medical Science* 61(9):995-1000, 1999.

Pilpa et al., "Solution Structure of the NEAT (NEAr Transporter) Domain from IsdH/HarA: the Human Hemoglobin Receptor in *Staphylococcus aureus*," *J. Mol. Biol.* 360:435-447, 2006.

Reynaud-Rondier et al., "Conjugation of capsular polysaccharide to α-haemolysin from *Staphylococcus aureus* as a glycoprotein antigen," *FEMS Microbiology Immunity* 76:193-200, 1991.

Robbins et al., "*Staphylococcus aureus* types 5 and 8 capsular polysaccharide-protein conjugate vaccines," *American Heart Journal* 147:593-598, 2004.

Roche et al., "Characterization of novel LPXTG-containing proteins of *Staphylococcus aureus* identified from genome sequences," *Microbiology* 149:643-654, 2003.

Shinefield et al., "Use of a *Staphylococcus aureus* Conjugate Vaccine in Patients Receiving Hemodialysis," *The New England Journal of Medicine* 346(7):491-496, 2002.

Stranger-Jones et al., "Vaccine assembly from surface proteins of *Staphylococcus aureus*," *Proc. Natl. Acad. Sci. USA* 103(45):16942-16947, Nov. 7, 2006.

Tamber et al., "SarZ Promotes the Expression of Virulence Factors and Represses Biofilm Formation by Modulating SarA and agr in *Staphylococcus aureus*," *Infection and Immunity* 77(1):419-428, 2009.

Tollersrud et al., "*Staphylococcus aureus* capsular polysaccharide type 5 conjugate and whole cell vaccines stimulate antibody responses in cattle," *Vaccine* 19:3896-3903, 2001.

U.S. Appl. No. 11/480,517.

U.S. Appl. No. 11/793,938.

U.S. Appl. No. 12/246,333.

(56) References Cited

OTHER PUBLICATIONS

Wann et al., "The Fibronectin-binding MSCRAMM FnbpA of *Staphylococcus aureus* Is a Bifunctional Protein That Also Binds to Fibrinogen," *The Journal of Biological Chemistry* 275(18):13863-13871, 2000.

Wardenburg et al., "Surface Proteins and Exotoxins Are Required for the Pathogenesis of *Staphylococcus aureus* Pneumonia," *Infection and Immunity* 75(2):1040-1044, 2007.

Balaban et al., "Autoinducer of Virulence as a Target for Vaccine and Therapy Against *Staphylococcus aureus," Science* 280:438-440, 1998. (4 Pages).

Frenck Jr. et al., "Safety, tolerability, and immunogenicity of a 4-antigen *Staphylococcus aureus* vaccine (SA4Ag): Results from a first-in-human randomised, placebo-controlled phase 1/2 study," *Vaccine* 35:375-384, 2017.

GenBank, "ABC transporter, substrate-binding protein [*Staphylococcus aureus* subsp. *aureus* COL]," Accession No. AAW37752, Jan. 31, 2014, 2 pages.

GenBank, "S.epidermidis gene encoding ABC transport system," Accession No. X99127, Apr. 18, 2005, 2 pages.

GenBank, "*Staphylococcus aureus* strain 8325-4 manganese-dependent transcriptional repressor (mntR), complete cds; Mn(II) ABC-type uptake transporter operon, complete sequence," Accession No. AF452622, Dec. 27, 2001, 4 pages.

Horsburgh et al., "MntR modulates expression of the PerR regulon and superoxide resistance in *Staphylococcus aureus* through control of manganese uptake," *Molecular Microbiology* 44(5):1269-1286, 2002.

Josefsson et al., "Protection against Experimental *Staphylococcus aureus* Arthritis by Vaccination with Clumping Factor A, a Novel Virulence Determinant," *J. Infect. Dis.* 184(12):1572-1580, 2001.

Lee, "Chapter 18—*Staphylococcus aureus* Vaccine," in Ellis et al. (eds.), *New Bacterial Vaccines*, Eurekah.com and Kluwer Academic / Plenum Publishers, New York, New York, USA, 2003, pp. 283-293.

Lee, "The prospects for developing a vaccine against *Staphylococcus aureus," Trends Microbiol.* 4(4):162-166, 1996.

Li et al., "Complete Genome Sequence of *Staphylococcus aureus* T0131, an ST239-MRSA-SCCmec Type III Clone Isolated in China," *Journal of Bacteriology* 193(13):3411-3412, 2011.

Mazmanian et al., "Passage of Heme-Iron Across the Envelope of *Staphylococcus aureus," Science* 299(5608):906-909, 2003. (5 Pages).

Mei et al., "Identification of *Staphylococcus aureus* virulence genes in a murine model of bacteraemia using signature-tagged mutagenesis," *Molecular Microbiology* 26(2):399-407, 1997.

Rozemeijer et al., "Evaluation of Approaches to Monitor *Staphylococcus aureus* Virulence Factor Expression during Human Disease," *PLoS ONE* 10(2):e0116945, 2015. (14 Pages).

Salazar et al., "*Staphylococcus aureus* Manganese Transport Protein C (MntC) Is an Extracellular Matrix- and Plasminogen-Binding Protein," *PLoS ONE* 9(11):e112730, 2014. (9 Pages).

Timofeyeva et al., "Chapter 4—Immunofluorescence Microscopy for the Detection of Surface Antigens in Methicillin-Resistant *Staphylococcus aureus* (MRSA)," in Ji (ed.), *Methicillin-Resistant Staphylococcus aureus (MRSA) Protocols, 2nd ed.*, Humana Press, New York, New York, USA, 2014, pp. 85-95. (16 Pages).

Van den Berg et al., "Active Immunization with an Octa-Valent *Staphylococcus aureus* Antigen Mixture in Models of *S. aureus* Bacteremia and Skin Infection in Mice," *PLoS ONE* 10(2):e0116847, 2015. (20 Pages).

Vytvytska et al., "Identification of vaccine candidate antigens of *Staphylococcus aureus* by serological proteome analysis," *Proteomics* 2(5):580-590, 2002.

Weichhart et al., "Functional Selection of Vaccine Candidate Peptides from *Staphylococcus aureus* Whole-Genome Expression Libraries In Vitro," *Infection and Immunity* 71(8):4633-4641, 2003.

Wolz et al., "Transcription of Clumping Factor A in Attached and Unattached *Staphylococcus aureus* In Vitro and during Device-Related Infection," *Infection and Immunity* 70(6):2758-2762, 2002.

* cited by examiner

*FIG. 1A*

SEQ ID NO:1 polypeptide sequence
MLQVTDVSLRFGDRKLFEDVNIKFTEGNCYGLIGANGAGKSTFLKILSGELDSQTGHVSLGKNERLAVL
KQDHYAYEDERVLDVVIKGHERLYEVMKEKDEIYMKPDFSDEDGIRAAELEGEFAEMNGWNAEADAANL
LSGLGIDPTLHDKKMAELENNQKIKVLLAQSLFGEPDVLLLDEPTNGLDIPAISWLEDFLINFDNTVIV
VSHDRHFLNNVCTHIADLDFGKIKVYVGNYDFWYQSSQLAQKMAQEQNKKKEEKMKELQDFIARFSANA
SKSKQATSRKKQLEKIELDDIQPSSRRYPFVKFTPEREIGNDLLIVQNLSKTIDGEKVLDNVSFTMNPN
DKAILIGDSEIAKTTLLKILAGEMEPDEGSFKWGVTTSLSYFPKDNSEFFEGVNMNLVDWLRQYAPEDE
QTETFLRGFLGRMLFSGEEVKKKASVLSGGEKVRCMLSKMMLSSANVLLLDEPTNHLDLESITAVNDGL
KSFKGSIIFTSYDFEFINTIANRVIDLNKQGGVSKEIPYEEYLQEIGVLK

SEQ ID NO:2 polypeptide sequence
MLQVTDVSLRFGDRKLFEDVNIKFTEGNCYGLIGANGAGKSTFLKILSGEIDSQTGHVSLGKDERLAVL
KQDHFAYEDERVLDVVIKGHERLYQVMKEKDEIYMKPDFSDEDGIRAAELEGEFAEMNGWNAEADAANL
LSGLGIEPDLHDKNMSELENNQKVKVLLAQSLFGDPDVLLLDEPTNGLDIPAISWLEDFLINFENTVIV
VSHDRHFLNNVCTHIADLDFGKIKLYVGNYDFWYQSSQLAQKMAQEQNKKKEEKMKELQDFIARFSANA
SKSKQATSRKKQLEKIELDDIQPSSRRYPYVKFTPEREIGNDLLTVENLSKTIDGEKVLDNVSFTMNPN
DKAILVGDSEIAKTTLLKILAGEMEPDEGTFKWGVTTSLSYFPKDNSEFFDGVDMNLVEWLRQYAPEDE
QTETFLRGFLGRMLFSGEEVKKKASVLSGGEKVRCMLSKMMLSSANVLLLDEPTNHLDLESITAVNDGL
KSFKGSIIFTSYDFEFINTIANRVIDLNQAGALSKEVPYEEYLQEIGVLQNN

SEQ ID NO:3 polypeptide sequence
MPIITDVYAREVLDSRGNPTVEVEVLTESGAFGRALVPSGASTGEHEAVELRDGDKSRYLGKGVTKAVE
NVNEIIAPEIIEGEFSVLDQVSIDKMMIALDGTPNKGKLGANAILGVSIAVARAAADLLGQPLYKYLGG
FNGKQLPVPMMNIVNGGSHSDAPIAFQEFMILPVGATTFKESLRWGTEIFHNLKSILSKRGLETAVGDE
GGFAPKFEGTEDAVETIIQAIEAAGYKPGEEVFLGFDCASSEFYENGVYDYSKFEGEHGAKRTAAEQVD
YLEQLVDKYPIITIEDGMDENDWDGWKQLTERIGDRVQLVGDDLFVTNTEILAKGIENGIGNSILIKVN
QIGTLTETFDAIEMAQKAGYTAVVSHRSGETEDTTIADIAVATNAGQIKTGSLSRTDRIAKYNQLLRIE
DELFETAKYDGIKSFYNLDK

SEQ ID NO:4 polypeptide sequence
MPIITDVYAREVLDSRGNPTVEVEVLTESGAFGRALVPSGASTGEHEAVELRDGDKSRYLGKGVTKAVE
NVNEMIAPEIVEGEFSVLDQVSIDKMMIQLDGTHNKGKLGANAILGVSIAVARAAADLLGQPLYKYLGG
FNGKQLPVPMMNIVNGGSHSDAPIAFQEFMILPVGAESFKESLRWGAEIFHNLKSILSERGLETAVGDE
GGFAPRFEGTEDAVETIIKAIEKAGYKPGEDVFLGFDCASSEFYENGVYDYTKFEGEHGAKRSAAEQVD
YLEELIGKYPIITIEDGMDENDWEGWKQLTDRIGDKVQLVGDDLFVTNTEILSKGIEQGIGNSILIKVN
QIGTLTETFDAIEMAQKAGYTAVVSHRSGETEDTTIADIAVATNAGQIKTGSLSRTDRIAKYNQLLRIE
DELYETAKFEGIKSFYNLDK

SEQ ID NO:5 polypeptide sequence
MKKIVTATIATAGLATIAFAGHDAQAAEQNNNGYNSNDAQSYSYTYTIDAQGNYHYTWTGNWNPSQLTQ
NNTYYYNNYNTYSYNNASYNNYYNHSYQYNNYTNNSQTATNNYYTGGSGASYSTTSNNVHVTTTAAPSS
NGRSISNGYASGSNLYTSGQCTYYVFDRVGGKIGSTWGNASNWANAAASSGYTVNNTPKVGAIMQTTQG
YYGHVAYVEGVNSNGSVRVSEMNYGHGAGVVTSRTISANQAGSYNFIH

SEQ ID NO:6 polypeptide sequence
MKKIATATIATAGFATIAIASGNQAHASEQDNYGYNPNDPTSYSYTYTIDAQGNYHYTWKGNWHPSQLN
QDNGYYSYYYYNGYNNYNNYNNGYSYNNYSRYNNYSNNNQSYNYNNYNSYNTNSYRTGGLGASYSTSSN
NVQVTTTMAPSSNGRSISSGYTSGRNLYTSGQCTYYVFDRVGGKIGSTWGNASNWANAAARAGYTVNNT
PKAGAIMQTTQGAYGHVAYVESVNSNGSVRVSEMNYGYGPGVVTSRTISASQAAGYNFIH

SEQ ID NO:7 polypeptide sequence
MKKIATATIATAGIATFAFAHHDAQAAEQNNDGYNPNDPYSYSYTYTIDAEGNYHYTWKGNWSPDRVNT
SYNYNNYNNYNYYGYNNYSNYNNYSNYNNYNNYQSNNTQSQRTTQPTGGLGASYSTSSSNVHVTTTSAP
SSNGVSLSNARSASGNLYTSGQCTYYVFDRVGGKIGSTWGNANNWANAAARSGYTVNNSPAKGAILQTS
QGAYGHVAYVEGVNSNGSIRVSEMNYGHGAGVVTSRTISASQAASYNYIH

FIG. 1B

SEQ ID NO:8 polypeptide sequence

MKKLVPLLLALLLLVAACGTGGKQSSDKSNGKLKVVTTNSILYDMAKNVGGDNVDIHSIVPVGQDPHEY
EVKPKDIKKLTDADVILYNGLNLETGNGWFEKALEQAGKSLKDKKVIAVSKDVKPIYLNGEEGNKDKQD
PHAWLSLDNGIKYVKTIQQTFIDNDKKHKADYEKQGNKYIAQLEKLNNDSKDKFNDIPKEQRAMITSEG
AFKYFSKQYGITPGYIWEINTEKQGTPEQMRQAIEFVKKHKLKHLLVETSVDKKAMESLSEETKKDIFG
EVYTDSIGKEGTKGDSYYKMMKSNIETVHGSMK

SEQ ID NO:9 polypeptide sequence

MKKILALAIAFLIILAACGNHSNHEHHSHEGKLKVVTTNSILYDMVKRVGGNKVDVHSIVPVGQDPHEY
EVKPKDIKALTDADVVFYNGLNLETGNGWFEKALDQAGKSTKDKNVIAASNNVKPIYLNGEEGNKNKQD
PHAWLSLENGIKYVKTIQKSLEHHDKKDKSTYEKQGNAYISKLEELNKDSKNKFDDIPKNQRAMMTSEG
AFKYFAQQFDVKPGYIWEINTEKQGTPGQMKQAIKFVKDNHLKHLLVETSVDKKAMQSLSEETKKDIYG
EVFTDSIGKEGTKGDSYYKMMKSNIDTIHGSMK

SEQ ID NO:10 polypeptide sequence

MKKTIMASSLAVALGVTGYAAGTGHQAHAAEVNVDQAHLVDLAHNHQDQLNAAPIKDGAYDIHFVKDGF
QYNFTSNGTTWSWSYEAANGQTAGFSNVAGADYTTSYNQGSDVQSVSYNAQSSNSNVEAVSAPTYHNYS
TSTTSSSVRLSNGNTAGATGSSAAQIMAQRTGVSASTWAAIIARESNGQVNAYNPSGASGLFQTMPGWG
PTNTVDQQINAAVKAYKAQGLGAWGF

SEQ ID NO:11 polypeptide sequence

MKKTVIASTLAVSLGIAGYGLSGHEAHASETTNVDKAHLVDLAQHNPEELNAKPVQAGAYDIHFVDNGY
QYNFTSNGSEWSWSYAVAGSDADYTESSSNQEVSANTQSSNTNVQAVSAPTSSESRSYSTSTTSYSAPS
HNYSSHSSSVRLSNGNTAGSVGSYAAAQMAARTGVSASTWEHIIARESNGQLHARNASGAAGLFQTMPG
WGSTGSVNDQINAAYKAYKAQGLSAWGM

SEQ ID NO:12 polypeptide sequence

MNYRDKIQKFSIRKYTVGTFSTVIATLVFLGFNTSQAHAAETNQPASVVKQKQQSNNEQTENRESQVQN
SQNSQNSQSLSATHENEQPNNSQANLVNQKVAQSSTTNDEQPASQNVNTKKDSATAATTQPDKEESKHK
QNESQSANKNGNDNRAAHVENHEANVVTASDSSDNGNVQHDRNELQAFFDANYHDYRFIDRENADSGTF
NYVKGIFDKINTLLGSNDPINNKDLQLAYKELEQAVALIRTMPQRQQTSRRSNRIQTRSVESRAAEPRS
VSDYQNANSSYYVENANDGSGYPVGTYINASSKGAPYNLPTTPWNTLKASDSKEIALMTAKQTGDGYQW
VIKFNKGHAPHQNMIFWFALPADQVPVGRTDFVTVNSDGTNVQWSHGAGAGANKPLQQMWEYGVNDPDR
SHDFKIRNRSGQVIYSWPTVHVYSLEDLSRASDYFSEAGATPATKAFGRQNFEYINGQKPAESPGVPKV
YTFIGQGDASYTISFKTQGPTVNKLYYAAGGRALEYNQLFMYSQLYVESTQDHQQRLNGLRQVVNRTYR
IGTTKRVEVSQGNVQTKKVLESTNLNIDDFVDDPLSYVKTPSNKVLGFYPTNANTNAFRPGGVQELNEY
QLSQLFTDQKLQEAARTRNPIRLMIGFDYPDGYGNSETLVPVNLTVLPEIQHNIKFFKNDDTQNIAEKP
FSKQAGHPVFYVYAGNQGNASVNLGGSVTSIQPLRINLTSNENFTDKDWQITGIPRTLHIENSTNRTNN
ARERNIELVGNLLPGDYFGTIRFGRKEQLFEIRVKPHTPTITTTAEQLRGTALQKVPVNISGIPLDPSA
LVYLVAPTNQTTNGGSEADQIPSGYTILATGTPDGVHNTITIRPQDYVVFIPPVGKQIRAVVYYNKVVA
SNMSNAVTILPDDIPPTINNPVGINAKYYRGDEVNFTMGVSDRHSGIKNTTITTLPSGWTSNLTKSDNK
NGSLAITGRVSMNQAFNSDITFKVSATDNVNNTTNDSQSKHVSIHVGKISEDAHPIVLGNTEKVVVVNP
TAVSNDEKQSIITAFMNKNQNIRGYLASTDPVTVDNNGNVTLHYRDGSSTTLDATNVMTYEPVVKSEYQ
TANAAKTATVTIAKGQSFNIGDIKQYFTLSNGQAIPNGTFTNITSDRTIPTAQEVSQMNAGTQLYHIVA
SNAYHKDTEDFYISLKIVDVKQPEGDQRVYRTSTYDLTTDEISKVKQAFINANRDVITLAEGDISVTNT
PNGANVSTITVNINKGRLTKSFASNLANMNFLRWVNFPQDYTVTWTNAKIANRPTDGGLSWSDDHKSLI
YRYDATLGTQITTNDILTMLKATTTVPGLRNNITGNEKAQAEAGGRPNYRTTGYSQSNATTDGQRQFTL
NGQVIQILDIINPSNGYGGQPVTNSNTRANHSNSTVVNVNEPAANGAGAFTIDHVVKSNSTHNASDAVY
KAQLYLTPYGPKQYVEHLNQNTGNTTDAINIYFVPSDLVNPTISVGNYTNHQVFSGETFTNTITANDNF
GVQSVTVPNTSQITGTVDNNHQHVSATAPNVTSATSKTINLLATDTSGNTATTSFNVTVKPLRDKYRVG
TSSTAANPVRIANISNNATVSQADQTTIINSLTFTSNAPNRNYATASANEITSKTVSNVSRTGNNANVT
VTVTHQDGTTSTVTVPVKHVIPEIVAHSHYTVQGQDFPAGNGSSAADYFKLSNGSAIPDATITWVSGQA
PNKDNTRIGEDITVTAHILIDGETTPITKTATYKVVRTVPKHVFETARGVLYPGVSDMYDAKQYVKPVN
NSWSTNAQHMNFQFVGTYGPNKDVVGISTRLIRVTYDNRQTEDLTILSKVKPDPPRIDANSVTYKAGLT
NQEIKVNNVLNNSSVKLFKADNTPLNVTNITHGSGFSSVVTVSDALPNGGIKAKSSISMNNVTYTTQDE
HGQVVTVTRNESVDSNDSASVTVTPQLQATTEGAVFIKGGDGFDFGHVERFIQNPPHGATVAWHDSPDT
WKNTVGNTHKTAVVTLPSGQGTRNVEVPVKVYPVANAKAPSRDVKGQNLTHGTNAIDYITFDPNTNTNG

FIG. 1C

SEQ ID NO:12 (continued)

ITAAWANRQQPNNQQAGVQHLNVDVTYPGISAAKRVPVTVNVYQFEFPQTTYTTTVGGTLASGTQASGY
AHMQNASGLPTDGFTYKWNRDTTGTNDANWAAMNKPNTAQVVNAKYDVIYNGHTFATSLPAKFVVKDVQ
PAKPTVTETAAGAITIAPGANQTVNTHAGNVTTYADKLVIKRNGNVVTTFTRRNNTSPWVKEASADNVT
GIVGTNNGITVAAGTFNPADTIQVVATQGSGETISDEQRSDDFTVVAPQPNQATTKIWQNGHIDITPNN
PSGHLINPTQAMDIAYTEKVGNGAEHSKTINVVRGQNNQWTIANKPDYVTLDAQTGKVTFNANTIKPNS
SITITPKAGTGHSVSSNPSTLTAPAAHTVNTTEIVKDYGSNVTAAEINNAVQVANKRTATIKNGTAMPT
NLAGGSTTTIPVTVTYNDGSTEEVQESIFTKADKRELITAKNHLDDPVSTEGKKPGTITQYNNAMHNAQ
QQINTAKTEAQQVINNERATPQQVSDALTKVRAAQTKIDQAKALLQNKEDNSQLVTSKNNLQSSVNQVP
STAGMTQQSIDNYNAKKREAETEITAAQRVIDNGDATAQQISDEKHRVDNALTALNQAKHDLTADTHAL
EQAVQQLNRTGTTTGKKPASITAYNNSIRALQSDLTSAKNSANAIIQKPIRTVQEVQSALTNVNRVNER
LTQAINQLVPLADNSALRTAKTKLDEEINKSVTTDGMTQSSIQAYENAKRAGQTETTNAQNVINNGDAT
DQQIAAEKTKVEEKYNSLKQAIAGLTPDLAPLQTAKTQLQNDIDQPTSTTGMTSASVAAFNDKLSAART
KIQEIDRVLASHPDVATIRQNVTAANAAKTALDQARNGLTVDKAPLENAKNQLQHSIDTQTSTTGMTQD
SINAYNAKLTAARNKVQQINQVLAGSPTVDQINTNTSAANQAKSDLDHARQALTPDKAPLQNAKTQLEQ
SINQPTDTTGMTTASLNAYNQKLQAARQKLTEINQVLNGNPTVQNINDKVAEANQAKDQLNTARQGLTL
DRQPALTTLHGASNLNQAQQNNFTQQINAAQNHAALETIKSNITALNTAMTKLKDSVADNNTIKSGQNY
TDATPANKQAYDNAVNAAKGVIGETTNPTMDVNTVNQKAASVKSTKDALDGQQNLQRAKTEATNAITHA
SDLNQAQKNALTQQVNSAQNVQAVNDIKQTTQSLNTAMTGLKRGVANHNQVVQSDNYVNADTNKKNDYN
NAYNHANDIINGNAQHPVITPSDVNNALSNVTSKEHALNGEAKLNAAKQEANTALGHLNNLNNVQRQNL
QSQINGAHQIDAVNTIKQNATNLNSAMGNLRQAVADKDQVKRTEDYADADTAKQNAYNSAVSSAETIIN
QTANPTMSVDDVNRATSAVTTNKNALNGDEKLVQSKTDAARAIDALPHLNNAQKADVKSKINAASNIAG
VNTVKQQGTDLNTAMGNLQGAINDEQTTLNSQNYQDATPSKKTAYTNAVQAAKDILNKSNGQNKTKDQV
TEAMNQVNSAKNNLDGTRLLDQAKQTAKQQLNNMTHLTTAQKTNLTNQINSGTTVAGVHTVQSNANTLD
QAMNTLRQSIANNDATKASEDYVDANNDKQTAYNNAVAAAETIINANSNPEMNPSTITQKAEQVNSSKT
ALNGDENLATAKQNAKTYLNTLTSITDAQKNNLISQISSATRVSGVDTVKQNAQHLDQAMANLQNGINN
ESQVKSSEKYRDADTNKQQEYDNAITAAKAILNKSTGPNTAQNAVEAALQRVNTAKDALNGDAKLIAAQ
NAAKQHLGTLTHITTAQRNDLTNQIS

SEQ ID NO:13 polypeptide sequence

MGNLQTAINDKSGTLASQNFLDADEQKRNAYNQAISAAETILNKQTGPNTAKTAVEQALNNVNSAKHAL
NGTQNLNNAKQAAITAINGASDLNQKQKDALKAQANGAQRVSNANDVQRNATELNTAMGQLQHAIADKT
NTLASSKYVNADSTKQNAYTTKVTNAEHIISGTPTVVTTPSEVTAAANQVNSAKQELNGDERLRVAKQN
ANTAIDALTQLNTPQKAKLKEQVGQANRLEDVQSVQTNGQSLNNAMKGLRDSIANETTVKASQNYTDAS
PNNQSTYNSAVSNAKGIINQTNNPTMDTSAITQATTQVNNAKNGLNGAENLRNAQNTAKQNLNTLSHLT
NNQKSAISSQIDRAGHVSEVTAAKNAATELNAQMGNLEQAIHDQNTVKQGVNFTDADKAKRDAYTNAVS
RAETILNKTQGANTSKQDVEAAIQNVTSAKNALNGDQNVTNAKNAAKNALNNLTSINNAQKRDLTTKID
QATTVAGVEAVSNTGTQLNTAMANLQNGINDKANTLASENYHDADSDKKTAYTQAVTNAENILNKNSGS
NLDKAAVENALSQVTNAKGALNGNHNLEQAKSNANTTINGLQHLTTAQKDKLKQQVQQAQNVAGVDTVK
SSANTLNGAMGTLRNSIQDNTATKNGQNYLDATERNKTNYNNAVDSANGVINATSNPNMDANAINQIAT
QVTSTKNALDGTHNLTQAKQTATNAIDGATNLNKAQKDALKAQVTSAQRVANVTSIQQTANELNTAMGQ
LQHGIDDENATKQTQKYRDAEQSKKTAYDQAVAAAKAILNKQTGSNSDKAAVDRALQQVTSTKDALNGD
AKLAEAKAAARQNLGTLNHITNAQRTALEGQINQATTVDGVNTVKTNANTLDGAMNSLQGAINDKDATL
RNQNYLDADESKRNAYTQAVTAAEGILNKQTGGNTSKADVDNALNAVTRAKAALNGAENLRNAKTSATN
TINGLPNLTQLQKDNLKHQVEQAQNVVGVNGVKDKGNTLNTAMGALRTSIQNDNTTKTSQNYLDASDSN
KNNYNTAVNNANGVINATNNPNMDANAINDMANQVNTTKAALNGAQNLAQAKTNATNTINNAQDLNQKQ
KDALKTQVNNAQRVSDANNVQHTATELNGAMTALKAAIADKERTKASGNYVNADQEKRQAYDSKVTNAE
NIINGTPNATLTVNDVNSAASQVNAAKTALNGDNNLRVAKEHANNTIDGLAQLNNVQKAKLKEQVQSAT
TLDGVQTVKNSSQTLNTAMKGLRDSIANEATIKAGQNYTDASPNNRNEYDSAVTAAKAIINQTSNPTME
PNTITQATSQVTTKEHALNGAQNLAQAKTTAKNNLNNLTSINNAQKDALTRNIDGATTVAGVNQETAKA
TELNNAMHSLQNGINDETQTKQTQKYLDAEPSKKSAYDQAVNAAKAILTKASGQNVDKAAVEQALQNVN
STKTALNGDAKLNEAKAAAKQTLGTLTHINNAQRNALDNEITQATNVEGVNTVKAKAQQLDGAMGQLET
SIRDKDTTLQSQNYQDADDAKRTAYSQAVNAAATILNKTAGGNTPKADVERAMQAVTQANTALNGIQNL
ERAKQAANTAITNASDLNTKQKEALKAQVTSAGRVSAANGVEHTATELNTAMTALKRAIADKADTKASG
NYVNADANKRQAYDEKVTAAEHIVSGTPTPTLTPSDVTNAATQVTNAKTQLNGNHNLEVAKQNANTAID
GLTSLNGPQKAKLKEQVGQATTLPNVQTVRDNAQTLNTAMKGLRDSIANEATIKAGQNYTDASQNKQND
YNNAVTAAKAIIGQTTSPSMIAQEINQAKDQVTAKQQALNGQENLRTAQTNAKQHLNGLSDLTNAQKDA
AKRQIEGATHVNEVTQAQNNADALNTAMTNLKNGIQDQNTIKQGVNFTDADEAKRNAYTNAVTQAEQIL
NKAQGPNTAKDGVETALQNVQRAKNELNGNQNVANAKTTAKNALNNLTSINNAQKAALKSQIEGATTVA

FIG. 1D

SEQ ID NO:13 (continued)

GVNQVSTMASELNTAMSNLQRGINDEAATKAAQKYTEADRDKQTAYNDAVTAAKTLLDKTAGSNDNKVA
VEQALQRVNTAKTALNGDARLNEAKNTAKQQLATMSHLTNAQKANLTEQIERGTTVAGVQGIQANAGTL
NQAMNQLRQSIASKDATKSSEDYQDANADLQNAYNDAVTNAEGIISATNNPEMNPDTINQKASQVNSAK
SALNGDEKLAAVKQTAKSDIGRLTDLNNAQRTAANAEVDQAPNLAAVTAAKNKATSLNTAMGNLKHALA
EKDNTKRSVNYTDADQPKQQAYDTAVTQAEAITNANGSNANETQVQAALNQLNQAKNDLNGDNKVAQAK
ETAKRALASYSNLNNAQSTAATSQIDNATTVADVTAAQNTANELNTAMGQLQNGINDQNTVKQQVNFTD
ADQGKKDAYTNAVTNAQGILDKANGQNMTKAQVEAALNQVTTAKNALNGDANVRQAKSDAKANLGTLTH
LNNAQKQDLTSQIEGATTVNGVNSVKTKAQDLDGAMQRLESAIANKDQTKASENYIDADPTKKTAFDNA
ITQAESYLNKDHGTNKDKQAVEQAIQSVTSTENALNGDANLQCAKTEATQAIDNLTQLNTPQKTALKQQ
VNAAQRVSGVTDLKNSATSLNNAMDQLKQAIGDHDTIVAGGNYTNASPDKQGAYTDAYNAAKNIVNGSP
NVITNAADVTAATQRVNNAETSLNGDTNLATAKQQAKDALRQMTHLSDAQKQSITGQIDSATQVTGVQS
VKDNATNLDNAMNQLRNSIANKDEVKASQPYVDADTDKQNAYNTAVTSAENIINATSQPTLDPSAVTQA
ANQVNTNKTALNGAQNLANKKQETTANINRLSHLNNAQKQDLNTQVTNAPNISTVNQVKTKAEQLDQAM
ERLINGIQDKDQVKQSVNFTDADPEKQTAYNNAVTAAENIINQANGTNANQSQVEAALSTVTTTKQALN
GDRKVTDAKNNANQTLSTLDNLNNAQKGAVTGNINQAHTVAEVTQAIQTAQELNTAMGNLKNSLNDKDT
TLGSQNFADADPEKKNAYNEAVRNAENILNKSTGTNVPKDQVEAAMNQVNTTKAALNGTQNLEKAKQHA
NTAIDGLSHLTNAQKEALKQLVQQSTTVAEAQGNEQKANNVDAAMDKLRQSIADNATTKQNQNYTDASP
NKKDAYNNAVTTAQGIIDQTTNPSLDPTVINQAAGQVSTSKNALNGNENLEAAKQQATQSLGSLDNLNN
AQKQAVTNQINGAHTVDEANQIKQNAQNLNTAMGNLKQAIADKDATKATVNFTDADQAKQQAYNTAVTN
AENIISKANGGNATQTEVEQAIQQVNAAKQALNGNANVQHAKDEATALINNSNDLNQAQKDALKQQVQN
ATTVAGVNNVKQTAQELNNAMTQLKQGIADKEQTKADGNFVNADSDKQNAYNQAVAKAEALISGTPDVV
VTPSEITAALNKVTQAKNDLNGNTNLATAKQNVQHAIDQLPNLNQAQRDEYSKQITQATLVPNVNAIQQ
AATTLNDAMTQLKQGIANKAQIKGSENYHDADTDKQTAYDNAVTKAEELLKQTTNPTMDPNTIQQALTK
VNDTNQALNGNQKLADAKQDAKTTLGTLDHLNDAQKQALTTQVEQAPDIATVNNVKQNAQNLNNAMTNL
NNALQDKTETLNSINFTDADQAKKDDYTNAVSHAEGILSKANGSNASQTEVEQAMQRVNEAKQALNGND
NVQRAKDAAKQVITNANDLNQAQKDALKQQVDAAQTVANVNTIKQTAQDLNQAMTQLKQGIADKDQTKA
NGNFVNADTDKQNAYNNAVAHAEQIISGTPNANVDPQQVAQALQQVNQAKGDLNGNHNLQVAKDNANTA
IDQLPNLNQPQKTALKDQVSHAELVTGVNAIKQNADALNNAMGTLKQQIQANSQVPQSVDFTQADQDKQ
QAYNNAANQAQQIANGTPTPVLAPDTVTKAVTTMNQAKDALNGDEKLAQAKQDALANLDTLRDLNQPQR
DALRNQINQAQALATVEQTKQNAQNVNTAMGNLKQGIANKDTVKASENYHDADVDKQTAYTNAVSQAEG
IINQTTNPTLNPDDITRALTQVTDAKNSLNGEAKLATEKQNAKDAVSGMTHLNDAQKQALKGQIDQSPE
IATVNQVKQTATSLDQAMDQLSQAINDKDQILADGNYLNADPDKQNAYKQAVAKAEALLNKQSGTNEVQ
AQVESITNEVNAAKQALNGNDNLANAKQQAKQQLANLTHLNDAQKQSFESQITQAPLVTDVTTINQKAQ
TLDHAMELLRNSVADNQTTLASEDYHDATAQRQNDYNKAVTAANNIINQTTSPTMNPDDVNGATTQVNN
TKVALDGDENLAAAKQQANNRLDQLDHLNNAQKQQLQSQITQSSDIAAVNGHKQTAESLNTAMGNLINA
IADHQAVEQRGNFINADTDKQTAYNTAVNEAAAMINKQTGQNANQTEVEQAITKVQTTLQALNGDHNLQ
VAKTNATQAIDVLTSLNDPQKTALKDQVTAATLVTAVHQIEQNANTLNQAMHGLRQSIQDNAATKANSK
YINEDQPEQQNYDQAVQAANNIINEQTATLDNNAINQVAATVNTTKAALHGDVKLQNDKDHAKQTVSQL
AHLNNAQKHMEDTLIDSETTRTAVKQDLTEVQALDQLMDALQQSIADKDATRASSAYVNAEPNKKQAYD
EAVQNAESIIAGLNNPTINKGNVSSATQAVISSKNALDGVERLAQDKQTAGNSLNHLDQLTPAQQQALE
NQINNATTCDKVAEIIAQAQALNEAMKALKESIKDQPQTEASSKFINEDQAQKDAYTQAVQHAKDLINK
TTDPTLAKSIIDQATQAVTDAKNNLHGDQKLAQDKQRATETLNNLSNLNTPQRQALENQINNAATRGEV
AQKLTEAQALNQAMEALRNSIQDQQQTESGSKFINEDKPQKDAYQAAVQNAKDLINQTGNPTLDKAQVE
QLTHAFKQAKDNLHGDQKLADDKQHAVTDLNQLNGLNNPQRQALESQINNAATRGEVAQKLAEAKALDQ
AMQALRNSIQDQQQTEAGSKFINEDKPQKDAYQAAVQNAKDLINQTGNPTLDKSQVEQLTQAVTTAKDN
LHGDQKLARDQQQAVTTVNALPNLNHAQQQTLTDAINAAPTRTEVAQHVQTATELDHAMETLKNKVDQV
NTDKAQPNYTEASTDKKEAVDQALQAAQSITDPTNGSNANKDAVEQALTKLQEKVNELNGNERVAEAKT
QAKQTIDQLTHLNADQIATAKQNIDQATKLQPIAELVDQATQLNQSMDQLQQAVNEHANVEQTIDYTQA
DSDKQKAYKQAIADAENVLKQNANKQQVDQALQNILNAKQALNGDERVALAKTNGKHDIDQLNALNNAQ
QDGFKGRIDQSNDLNQIQQIVDEAKALNRAMDQLSQEITGNEGRTKGSTNYVNADTQVKQVYDEAVDKA
KQALDKSSGQNLTAEQVIKLNDAVTAAKKALNGEERLNNRKAEALQRLDQLTHLNNAQRQLAIQQINNA
ETLNKASRAINRATKLDNAMGAVQQYIDEQHLGVISSTNYINADDNLKANYDNAIANAAHELDKVQGNA
IAKAEAEQLKQNIIDAQNALNGDQNLANAKDKANAFVNSLNGLNQQQQDLAHKAINNADTVSDVTDIVN
NQIDLNDAMETLKHLVDNEIPNAEQTVNYQNADDNAKTNFDDAKRLANTLLNSDNTNVNDINGAIQAVN
DAIHNLNGDQRLQDAKDKAIQSINQALANKLKEIEASNATDQDKLIAKNKAEELANSIINNINKATSNQ
AVSQVQTAGNHAIEQVHANEIPKAKIDANKDVDKQVQALIDEIDRNPNLTDKEKQALKDRINQILQQGH
NDINNALTKEEIEQAKAQLAQALQDIKDLVKAKEDAKQDVDKQVQALIDEIDQNPNLTDKEKQALKDRI
NQILQQGHNGINNAMTKEEIEQAKAQLAQALKEIKDLVKAKENAKQDVDKQVQALIDEIDQNPNLTDKE

FIG. 1E

SEQ ID NO:13 (continued)

KQALKDRINQILQQGHNDINNAMTKEEIEQAKAQLAQALQDIKDLVKAKEDAKNAIKALANAKRDQINS
NPDLTPEQKAKALKEIDEAEKRALQNVENAQTIDQLNRGLNLGLDDIRNTHVWEVDEQPAVNEIFEATP
EQILVNGELIVHRDDIITEQDILAHINLIDQLSAEVIDTPSTATISDSLTAKVEVTLLDGSKVIVNVPV
KVVEKELSVVKQQAIESIENAAQQKIDEINNSVTLTLEQKEAAIAEVNKLKQQAIDHVNNAPDVHSVEE
IQQQEQAYIEQFNPEQFTIEQAKSNAIKSIEDAIQHMIDEIKARTDLTDKEKQEAIAKLNQLKEQAIQA
IQRAQSISEITEQLEQFKAQMKAANPTAKELAKRKQEAISRIKDFSNEKINSIRNSEIGTADEKQAAMN
QINEIVLETIRDINNAHTLQQVEAALNNGIARISAVQIVISDRAKQSSSTGNESNSHLTIGYGTANHPF
NSSTIGHKKKLDEDDDIDPLHMRHFSNNFGNVIKNAIGVVGISGLLASFWFFIAKRRRKEDEEEELEIR
DNNKDSIKETLDDTKHLPLLFAKRRRKEDEEDVTVEEKDSLNNGESLDKVKHTPFFLPKRRRKEDEEDV
EVTNENTDEKVLKDNEHSPLLFAKRRKDKEEDVETTTSIESKDEDVPLLLAKKKNQKDNQSKDKKSASK
NTSKKVAAKKKKKKSKKNKK

SEQ ID NO:14 polypeptide sequence

MNNRDKLQKFSIRKYAIGTFSTVIATLVFMGINTNHASADELNQNQKLIKQLNQTDDDDSNTHSQEIEN
NKQNSSGQTESLRSSTSQNQANARLSDQFKDTNETSQQLPTNVSDDSINQSHSEANMNNEPLKVDNSTM
QAHSKIVSDSDGNASENKHHKLTENVLAESRASKNDKEKENLQEKDKSQQVHPPLDKNALQAFFDASYH
NYRMIDRDRADATEYQKVKSTFDYVNDLLGNNQNIPSEQLVSAYQQLEKALELARTLPQQSTTEKRGRR
STRSVVENRSSRSDYLDARTEYYVSKDDDDSGFPPGTFFHASNRRWPYNLPRSRNILRASDVQGNAYIT
TKRLKDGYQWDILFNSNHKGHEYMYYWFGLPSDQTPTGPVTFTIINRDGSSTSTGGVGFGSGAPLPQFW
RSAGAINSSVANDFKHGSATNYAFYDGVNNFSDFARGGELYFDREGATQTNKYYGDENFALLNSEKPDQ
IRGLDTIYSFKGSGDVSYRISFKTQGAPTARLYYAAGARSGEYKQATNYNQLYVEPYKNYRNRVQSNVQ
VKNRTLHLKRTIRQFDPTLQRTTDVPILDSDGSGSIDSVYDPLSYVKNVTGTVLGIYPSYLPYNQERWQ
GANAMNAYQIEELFSQENLQNAARSGRPIQFLVGFDVEDSHHNPETLLPVNLYVKPELKHTIELYHDNE
KQDRKEFSVSK

SEQ ID NO:15 polypeptide sequence

MSGTLHNTVGSGILPYQQEIRIKLTSNEPIKDSEWSITGYPNTLTLQNAVGRTNNATEKNLALVGHIDP
GNYFITVKFGDKVEQFEIRSKPTPPRIITTANELRGNPNHKPEIRVTDIPNDTTAKIKLVMGGTDGDHD
PEINPYTVPENYTVVAEAYHDNDPSKNGVLTFRSSDYLKDLPLSGELKAIVYYNQYVQSNFSKSVPFSS
DTTPPTINEPAGLVHKYYRGDHVEITLPVTDNTGGSGLRDVNVNLPQGWTKTFTINPNNNTEGTLKLIG
NIPSNEAYNTTYHFNITATDNSGNTTNPAKTFILNVGKLADDLNPVGLSRDQLQLVTDPSSLSNSEREE
VKRKISEANANIRSYLLQNNPILAGVNGDVTFYYRDGSVDVIDAENVITYEPERKSIFSENGNTNKKEA
VITIARGQNYTIGPNLRKYFSLSNGSDLPNRDFTSISAIGSLPSSSEISRLNVGNYNYRVNAKNAYHKT
QQELNLKLKIVEVNAPTGNNRVYRVSTYNLTNDEINKIKQAFKAANSGLNLNDNDITVSNNFDHRNVSS
VTVTIRKGDLIKEFSSNLNNMNFLRWVNIRDDYTISWTSSKIQGRNTDGGLEWSPDHKSLIYKYDATLG
RQINTNDVLTLLQATAKNSNLRSNINSNEKQLAERGSNGYSKSIIRDDGEKSYLLNSNPIQVLDLVEPD
NGYGGRQVSHSNVIYNEKNSSIVNGQVPEANGASAFNIDKVVKANAANNGIMGVIYKAQLYLAPYSPKG
YIEKLGQNLSNTNNVINVYFVPSDKVNPSITVGNYDHHTVYSGETFKNTINVNDNYGLNTVASTSDSAI
TMTRNNNELVGQAPNVTNSINKIVKVKATDKSGNESIVSFTVNIKPLNEKYRITTSSSNQTPVRISNIQ
NNANLSIEDQNRVKSSLSMTKILGTRNYVNESNNDVRSQVVSKVNRSGNNATVNVTTTFSDGTTNTITV
PVKHVLLEVVPTTRTTVRGQQFPTGKGTSPNDFFSLRTGGPVDARIVWVNNQGPDINSNQIGRDLTLHA
EIFFDGETTPIRKDTTYKLSQSIPKQIYETTINGRFNSSGDAYPGNFVQAVNQYWPEHMDFRWAQGSGT
PSSRNAGSFTKTVTVVYQNGQTENVNVLFKVKPNKPVIDSNSVISKGQLNGQQILVRNVPQNAQVTLYQ
SNGTVIPNTNTTIDSNGIATVTIQGTLPTGNITAKTSMTNNVTYTKQNSSGIASNTTEDISVFSENSDQ
VNVTAGMQAKNDGIKIIKGTNYNFNDFNSFISNIPAHSTLTWNEEPNSWKNNIGTTTKTVTVTLPNHQG
TRTVDIPITIYPTVTAKNPVRDQKGRNLTNGTDVYNYIIFENNNRLGGTASWKDNRQPDKNIAGVQNLI
ALVNYPGISTPLEVPVKVWVYNFDFTQPIYKIQVGDTFPKGTWAGYYKHLENGEGLPIDGWKFYWNQQS
TGTTSDQWQSLAYTRTPFVKTGTYDVVNPSNWGVWQTSQSAKFIVTNAKPNQPTITQSKTGDVTVTPGA
VRNILISGTNDYIQASADKIVINKNGNKLTTFVKNNDGRWTVETGSPDINGIGPTNNGTAISLSRLAVR
PGDSIEAIATEGSGETISTSATSEIYIVKAPQPEQVATHTYDNGTFDILPDNSRNSLNPTERVEINYTE
KLNGNETQKSFTITKNNNGKWTINNKPNYVEFNQDNGKVVFSANTIKPNSQITITPKAGQGNTENTNPT
VIQAPAQHTLTINEIVKEQGQNVTNDDINNAVQVPNKNRVAIKQGNALPTNLAGGSTSHIPVVIYYSDG
SSEEATETVRTKVNKTELINARRRLDEEISKENKTPSSIRNFDQAMNRAQSQINTAKSDADQVIGTEFA
TPQQVNSALSKVQAAQNKINEAKALLQNKADNSQLVRAKEQLQQSIQPAASTDGMTQDSTRNYNNKRQA
AEQAIQHANSVINNGDATSQQINDAKNTVEQAQRDYVEAKSNLRADKSQLQSAYDTLNRDVLTNDKKPA
SVRRYNEAISNIRKELDTAKADASSTLRNTNPSVEQVRDALNKINTVQPKVNQAIALLQPKENNSELVQ
AKKRLQDAVNDIPQTQGMTQQTINNYNDKQREAERALTSAQRVIDNGDATTQEITSEKSKVEQAMQALT
NAKSNLRADKNELQTAYNKLIENVSTNGKKPASIRQYETAKARIQNQINDAKNEAERILGNDNPQVSQV

FIG. 1F

SEQ ID NO:15 (continued)

TQALNKIKAIQPKLTEAINMLQNKENNTELVNAKNRLENAVNDTDPTHGMTQETINNYNAKKREAQNEI
QKANMIINNGDATAQDISSEKSKVEQVLQALQNAKNDLRADKRELQTAYNKLIQNVNTNGKKPSSIQNY
KSARRNIENQYNTAKNEAHNVLENTNPTVNAVEDALRKINAIQPEVTKAINILQDKEDNSELVRAKEKL
DQAINSQPSLNGMTQESINNYTTKRREAQNIASSADTIINNGDASIEQITENKIRVEEATNALNEAKQH
LTADTTSLKTEVRKLSRRGDTNNKKPSSVSAYNNTIHSLQSEITQTENRANTIINKPIRSVEEVNNALH
EVNQLNQRLTDTINLLQPLANKESLKEARNRLESKINETVQTDGMTQQSVENYKQAKIKAQNESSIAQT
LINNGDASDQEVSTEIEKLNQKLSELTNSINHLTVNKEPLETAKNQLQANIDQKPSTDGMTQQSVQSYE
RKLQEAKDKINSINNVLANNPDVNAIRTNKVETEQINNELTQAKQGLTVDKQPLINAKTALQQSLDNQP
STTGMTEATIQNYNAKRQKAEQVIQNANKIIENAQPSVQQVSDEKSKVEQALSELNNAKSALRADKQEL
QQAYNQLIQPTDLNNKKPASITAYNQRYQQFSNELNSTKTNTDRILKEQNPSVADVNNALNKVREVQQK
LNEARALLQNKEDNSALVRAKEQLQQAVDQVPSTEGMTQQTKDDYNSKQQAAQQEISKAQQVIDNGDAT
TQQISNAKTNVERALEALNNAKTGLRADKEELQNAYNQLTQNIDTSGKTPASIRKYNEAKSRIQTQIDS
AKNEANSILTNDNPQVSQVTAALNKIKAVQPELDKAIAMLKNKENNNALVQAKQQLQQIVNEVDPTQGM
TTDTANNYKSKKREAEDEIQKAQQIINNGDATEQQITNETNRVNQAINAINKAKNDLRADKSQLENAYN
QLIQNVDTNGKKPASIQQYQAARQAIETQYNNAKSEAHQILENSNPSVNEVAQALQKVEAVQLKVNDAI
HILQNKENNSALVTAKNQLQQSVNDQPLTTGMTQDSINNYEAKRNEAQSAIRNAEAVINNGDATAKQIS
DEKSKVEQALAHLNDAKQQLTADTTELQTAVQQLNRRGDTNNKKPRSINAYNKAIQSLETQITSAKDNA
NAVIQKPIRTVQEVNNALQQVNQLNQQLTEAINQLQPLSNNDALKAARLNLENKINQTVQTDGMTQQSI
EAYQNAKRVAQNESNTALALINNGDADEQQITTETDRVNQQTTNLTQAINGLTVNKEPLETAKTALQNN
IDQVPSTDGMTQQSVANYNQKLQIAKNEINTINNVLANNPDVNAIKTNKAEAERISNDLTQAKNNLQVD
TQPLEKIKRQLQDEIDQGTNTDGMTQDSVDNYNDSLSAAIIEKGKVNKLLKRNPTVEQVKESVANAQQV
IQDLQNARTSLVPDKTQLQEAKNRLENSINQQTDTDGMTQDSLNNYNDKLAKARQNLEKISKVLGGQPT
VAEIRQNTDEANAHKQALDTARSQLTLNREPYINHINNESHLNNAQKDNFKAQVNSAPNHNTLETIKNK
ADTLNQSMTALSESIADYENQKQQENYLDASNNKRQDYDNAVNAAKGILNQTQSPTMSADVIDQKAEDV
KRTKTALDGNQRLEVAKQQALNHLNTLNDLNDAQRQTLTDTINHSPNINSVNQAKEKANTVNTAMTQLK
QTIANYDDELHDGNYINADKDKKDAYNNAVNNAKQLINQSDANQAQLDPAEINKVTQRVNTTKNDLNGN
DKLAEAKRDANTTIDGLTYLNEAQRNKAKENVGKASTKTNITSQLQDYNQLNIAMQALRNSVNDVNNVK
ANSNYINEDNGPKEAYNQAVTHAQTLINAQSNPEMSRDVVNQKTQAVNTAHQNLHGQQKLEQAQSSANT
EIGNLPNLTNTQKAKEKELVNSKQTRTEVQEQLNQAKSLDSSMGTLKSLVAKQPTVQKTSVYINEDQPE
QSAYNDSITMGQTIINKTADPVLDKTLVDNAISNISTKENALHGEQKLTTAKTEAINALNTLADLNTPQ
KEAIKTAINTAHTRTDVTAEQSKANQINSAMHTLRQNISDNESVTNESNYINAEPEKQHAFTEALNNAK
EIVNEQQATLDANSINQKAQAILTTKNALDGEEQLRRAKENADQEINTLNQLTDAQRNSEKGLVNSSQT
RTEVASQLAKAKELNKVMEQLNHLINGKNQMINSSKFINEDANQQQAYSNAIASAEALKNKSQNPELDK
VTIEQAINNINSAINNLNGEAKLTKAKEDAVASINNLSGLTNEQKTKENQAVNGAQTRDQVANKLRDAE
ALDQSMQTLRDLVNNQNAIHSTSNYFNEDSTQKNTYDNAIDNGSTYITGQHNPELNKSTIDQTISRINT
AKNDLHGVEKLQRDKGTANQEIGQLGYLNDPQKSGEESLVNGSNTRSEVEEHLNEAKSLNNAMKQLRDK
VAEKTNVKQSSDYINDSTEHQRGYDQALQEAENIINEIGNPTLNKSEIEQKLQQLTDAQNALQGSHLLE
EAKNNAITGINKLTALNDAQRQKAIENVQAQQTIPAVNQQLTLDREINTAMQALRDKVGQQNNVHQQSN
YFNEDEQPKHNYDNSVQAGQTIIDKLQDPIMNKNEIEQAINQINTTQTALSGENKLHTDQESTNRQIEG
LSSLNTAQINAEKDLVNQAKTRTDVAQKLAAAKEINSAMSNLRDGIQNKEDIKRSSAYINADPTKVTAY
DQALQNAENIINATPNVELNKATIEQALSRVQQAQQDLDGVQQLANAKQQATQTVNGLNSLNDGQKREL
NLLINSANTRTKVQEELNKATELNHAMEALRNSVQNVDQVKQSSNYVNEDQPEQHNYDNAVNEAQATIN
NNAQPVLDKLAIERLTQTVNTTKDALHGAQKLTQDQQAAETGIRGLTSLNEPQKNAEVAKVTAATTRDE
VRNIRQEATTLDTAMLGLRKSIKDKNDTKNSSKYINEDHDQQQAYDNAVNNAQQVIDETQATLSSDTIN
QLANAVTQAKSNLHGDTKLQHDKDSAKQTIAQLQNLNSAQKHMEDSLIDNESTRTQVQHDLTEAQALDG
LMGALKESIKDYTNIVSNGNYINAEPSKKQAYDAAVQNAQNIINGTNQPTINKGNVTTATQTVKNTKDA
LDGDHRLEEAKNNANQTIRNLSNLNNAQKDAEKNLVNSASTLEQVQQNLQTAQQLDNAMGELRQSIAKK
DQVKADSKYLNEDPQIKQNYDDAVQRVETIINETQNPELLKANIDQATQSVQNAEQALHGAEKLNQDKQ
TSSTELDGLTDLTDAQREKLREQINTSNSRDDIKQKIEQAKALNDAMKKLKEQVAQKDGVHANSDYTNE
DSAQKDAYNNALKQAEDIINNSSNPNLNAQDITNALNNIKQAQDNLHGAQKLQQDKNTTNQAIGNLNHL
NQPQKDALIQAINGATSRDQVAEKLKEAEALDEAMKQLEDQVNQDDQISNSSPFINEDSDKQKTYNDKI
QAAKEIINQTSNPTLDKQKIADTLQNIKDAVNNLHGDQKLAQSKQDANNQLNHLDDLTEEQKNHFKPLI
NNADTRDEVNKQLEIAKQLNGDMSTLHKVINDKDQIQHLSNYINADNDKKQNYDNAIKEAEDLIHNHPD
TLDHKALQDLLNKIDQAHNELNGESRFKQALDNALNDIDSLNSLNVPQRQTVKDNINHVTTLESLAQEL
QKAKELNDAMKAMRDSIMNQEQIRKNSNYTNEDLAQQNAYNHAVDKINNIIGEDNATMDPQIIKQATQD
INTAINGLNGDQKLQDAKTDAKQQITNFTGLTEPQKQALENIINQQTSRANVAKQLSHAKFLNGKMEEL
KVAVAKASLVRQNSNYINEDVSEKEAYEQAIAKGQEIINSENNPTISSTDINRTIQEINDAEQNLHGDN
KLRQAQEIAKNEIQNLDGLNSAQITKLIQDIGRTTTKPAVTQKLEEAKAINQAMQQLKQSIADKDATLN

FIG. 1G

SEQ ID NO:15 (continued)

SSNYLNEDSEKKLAYDNAVSQAEQLINQLNDPTMDISNIQAITQKVIQAKDSLHGANKLAQNQADSNLI
INQSTNLNDKQKQALNDLINHAQTKQQVAEIIAQANKLNNEMGTLKTLVEEQSNVHQQSKYINEDPQVQ
NIYNDSIQKGREILNGTTDDVLNNNKIADAIQNIHLTKNDLHGDQKLQKAQQDATNELNYLTNLNNSQR
QSEHDEINSAPSRTEVSNDLNHAKALNEAMRQLENEVALENSVKKLSDFINEDEAAQNEYSNALQKAKD
IINGVPSSTLDKATIEDALLELQNARESLHGEQKLQEAKNQAVAEIDNLQALNPGQVLAEKTLVNQAST
KPEVQEALQKAKELNEAMKALKTEINKKEQIKADSRYVNADSGLQANYNSALNYGSQIIATTQPPELNK
DVINRATQTIKTAENNLNGQSKLAEAKSDGNQSIEHLQGLTQSQKDKQHDLINQAQTKQQVDDIVNNSK
QLDNSMNQLQQIVNNDNTVKQNSDFINEDSSQQDAYNHAIQAAKDLITAHPTIMDKNQIDQAIENIKQA
LNDLHGSNKLSEDKKEASEQLQNLNSLTNGQKDTILNHIFSAPTRSQVGEKIASAKQLNNTMKALRDSI
ADNNEILQSSKYFNEDSEQQNAYNQAVNKAKNIINDQPTPVMANDEIQSVLNEVKQTKDNLHGDQKLAN
DKTDAQATLNALNYLNQAQRGNLETKVQNSNSRPEVQKVVQLANQLNDAMKKLDDALTGNDAIKQTSNY
INEDTSQQVNFDEYTDRGKNIVAEQTNPNMSPTNINTIADKITEAKNDLHGVQKLKQAQQQSINTINQM
TGLNQAQKEQLNQEIQQTQTRSEVHQVINKAQALNDSMNTLRQSITDEHEVKQTSNYINETVGNQTAYN
NAVDRVKQIINQTSNPTMNPLEVERATSNVKISKDALHGERELNDNKNSKTFAVNHLDNLNQAQKEALT
HEIEQATIVSQVNNIYNKAKALNNDMKKLKDIVAQQDNVRQSNNYINEDSTPQNMYNDTINHAQSIIDQ
VANPTMSHDEIENAINNIKHAINALDGEHKLQQAKENANLLINSLNDLNAPQRDAINRLVNEAQTREKV
AEQLQSAQALNDAMKHLRNSIQNQSSVRQESKYINASDAKKEQYNHAVREVENIINEQHPTLDKEIIKQ
LTDGVNQANNDLNGVELLDADKQNAHQSIPTLMHLNQAQQNALNEKINNAVTRTEVAAIIGQAKLLDHA
MENLEESIKDKEQVKQSSNYINEDSDVQETYDNAVDHVTEILNQTVNPTLSIEDIEHAINEVNQAKKQL
RGKQKLYQTIDLADKELSKLDDLTSQQSSSISNQIYTAKTRTEVAQAIEKAKSLNHAMKALNKVYKNAD
KVLDSSRFINEDQPEKKAYQQAINHVDSIIHRQTNPEMDPTVINSITHELETAQNNLHGDQKLAHAQQD
AANVINGLIHLNVAQREVMINTNTNATTREKVAKNLDNAQALDKAMETLQQVVAHKNNILNDSKYLNED
SKYQQQYDRVIADAEQLLNQTTNPTLEPYKVDIVKDNVLANEKILFGAEKLSYDKSNANDEIKHMNYLN
NAQKQSIKDMISHAALRTEVKQLLQQAKILDEAMKSLEDKTQVVITDTTLPNYTEASEDKKEKVDQTVS
HAQAIIDKINGSNVSLDQVRQALEQLTQASENLDGDQRVEEAKVHANQTIDQLTHLNSLQQQTAKESVK
NATKLEEIATVSNNAQALNKVMGKLEQFINHADSVENSDNYRQADDDKIIAYDEALEHGQDIQKTNATQ
NETKQALQQLIYAETSLNGFERLNHARPRALEYIKSLEKINNAQKSALEDKVTQSHDLLELEHIVNEGT
NLNDIMGELANAIVNNYAPTKASINYINADNLRKDNFTQAINNARDALNKTQGQNLDFNAIDTFKDDIF
KTKDALNGIERLTAAKSKAEKLIDSLKFINKAQFTHANDEIMNTNSIAQLSRIVNQAFDLNDAMKSLRD
ELNNQAFPVQASSNYINSDEDLKQQFDHALSNARKVLAKENGKNLDEKQIQGLKQVIEDTKDALNGIQR
LSKAKAKAIQYVQSLSYINDAQRHIAENNIHNSDDLSSLANTLSKASDLDNAMKDLRDTIESNSTSVPN
SVNYINADKNLQIEFDEALQQASATSSKTSENPATIEEVLGLSQAIYDTKNALNGEQRLATEKSKDLKL
IKGLKDLNKAQLEDVTNKVNSANTLTELSQLTQSTLELNDKMKLLRDKLKTLVNPVKASLNYRNADYNL
KRQFNKALKEAKGVLNKNSGTNVNINDIQHLLTQIDNAKDQLNGERRLKEHQQKSEVFIIKELDILNNA
QKAAIINQIRASKDIKIINQIVDNAIELNDAMQGLKEHVAQLTATTKDNIEYLNADEDHKLQYDYAINL
ANNVLDKENGTNKDANIIIGMIQNMDDARALLNGIERLKDAQTKAHNDIKDTLKRQLDEIEHANATSNS
KAQAKQMVNEEARKALSNINDATSNDLVNQAKDEGQSAIEHIHADELPKAKLDANQMIDQKVEDINHLI
SQNPNLSNEEKNKLISQINKLVNGIKNEIQQAINKQQIENATTKLDEVIETTKKLIIAKAEAKQMIKEL
SQKKRDAINNNTDLTPSQKAHALADIDKTEKDALQHIENSNSIDDINNNKEHAFNTLAHIIIWDTDQQP
LVFELPELSLQNALVTSEVVVHRDETISLESIIGAMTLTDELKVNIVSLPNTDKVADHLTAKVKVILAD
GSYVTVNVPVKVVEKELQIAKKDAIKTIDVLVKQKIKDIDSNNELTSTQREDAKAEIERLKKQAIDKVN
HSKSIKDIETVKRTDFEEIDQFDPKRFTLNKAKKDIITDVNTQIQNGFKEIETIKGLTSNEKTQFDKQL
TALQKEFLEKVEHAHNLVELNQLQQEFNNRYKHILNQAHLLGEKHIAEHKLGYVVVNKTQQILNNQSAS
YFIKQWALDRIKQIQLETMNSIRGAHTVQDVHKALLQGIEQILKVNVSIINQSFNDSLHNFNYLHSKFD
ARLREKDVANHIVQTETFKEVLKGTGVEPGKINKETQQPKLHKNDNDSLFKHLVDNFGKTVGVITLTGL
LSSFWLVLAKRRKKEEEEKQSIKNHHKDIRLSDTDKIDPIVITKRKIDKEEQIQNDDKHSIPVAKHKKS
KEKQLSEEDIHSIPVVKRKQNSDNKDTKQKKVTSKKKKTPQSTKKVVKTKKRSKK

FIG. 1H

SEQ ID NO:16 polypeptide sequence

MRDKKGPVNKRVDFLSNKLNKYSIRKFTVGTASILIGSLMYLGTQQEAEAAENNIENPTTLKDNVQSKE
VKIEEVTNKDTAPQGVEAKSEVTSNKDTIEHEASVKAEDISKKEDTPKEVANVAEVQPKSSVTHNAEAP
KVRKARSVDEGSFDITRDSKNVVESTPITIQGKEHFEGYGSVDIQKNPTDLGVSEVTRFNVGNESNGLI
GALQLKNKIDFSKDFNFKVRVANNHQSNTTGADGWGFLFSKGNAEEYLTNGGILGDKGLVNSGGFKIDT
GYIYTSSMDKTEKQAGQGYRGYGAFVKNDSSGNSQMVGENIDKSKTNFLNYADNSTNTSDGKFHGQRLN
DVILTYVASTGKMRAEYAGKTWETSITDLGLSKNQAYNFLITSSQRWGLNQGINANGWMRTDLKGSEFT
FTPEAPKTITELEKKVEEIPFKKERKFNPDLAPGTEKVTREGQKGEKTITTPTLKNPLTGEIISKGESK
EEITKDPINELTEYGPETIAPGHRDEFDPKLPTGEKEEVPGKPGIKNPETGDVVRPPVDSVTKYGPVKG
DSIVEKEEIPFEKERKFNPDLAPGTEKVTREGQKGEKTITTPTLKNPLTGEIISKGESKEEITKDPINE
LTEYGPETIAPGHRDEFDPKLPTGEKEEVPGKPGIKNPETGDVVRPPVDSVTKYGPVKGDSIVEKEEIP
FKKERKFNPDLAPGTEKVTREGQKGEKTITTPTLKNPLTGEIISKGESKEEITKDPINELTEYGPETIT
PGHRDEFDPKLPTGEKEEVPGKPGIKNPETGDVVRPPVDSVTKYGPVKGDSIVEKEEIPFEKERKFNPD
LAPGTEKVTREGQKGEKTITTPTLKNPLTGEIISKGESKEEITKDPVNELTEFGGEKIPQGHKDIFDPN
LPTDQTEKVPGKPGIKNPDTGKVIEEPVDDVIKHGPKTGTPETKTVEIPFETKREFNPKLQPGEERVKQ
EGQPGSKTITTPITVNPLTGEKVGEGQPTEEITKQPVDKIVEFGGEKPKDPKGPENPEKPSRPTHPSGP
VNPNNPGLSKDRAKPNGPVHSMDKNDKVKKSKIAKESVANQEKKRAELPKTGLESTQKGLIFSSIIGIA
GLMLLARRRKN

SEQ ID NO:17 polypeptide sequence

MGKRRQGPINKKVDFLPNKLNKYSIRKFTVGTASILLGSTLIFGSSSHEAKAAEEKQVDPITQANQNDS
SERSLENTNQPTVNNEAPQMSSTLQAEEGSNAEAPNVPTIKANSDNDTQTQFSEAPTRNDLARKEDIPA
VSKNEELQSSQPNTDSKIEPTTSEPVNLNYSSPFMSLLSMPADSSSNNTKNTIDIPPTTVKGRDNYDFY
GRVDIQSNPTDLNATNLTRYNYGQPPGTTTAGAVQFKNQVSFDKDFDFNIRVANNRQSNTTGADGWGFM
FSKKDGDDFLKNGGILREKGTPSAAGFRIDTGYYNNDPLDKIQKQAGQGYRGYGTFVKNDSQGNTSKVG
SGTPSTDFLNYADNTTNDLDGKFHGQKLNNVNLKYNASNQTFTATYAGKTWTATLSELGLSPTDSYNFL
VTSSQYGNGNSGTYADGVMRADLDGATLTYTPKAVDGDPITSTKEIPFNKKREFDPNLAPGTEKVVQKG
EPGIETTTTPTYVNPNTGEKVGEGTPTTKITKQPVDEIVHYGGEEIKPGHKDEFDPNAPKGSQTTQPGK
PGVKNPDTGEVVTPPVDDVTKYGPVDGDPITSTEEIPFDKKREFNPDLKPGEERVKQKGEPGTKTITTP
TTKNPLTGEKVGEGEPTEKITKQPVDEITEYGGEEIKPGHKDEFDPNAPKGSQEDVPGKPGVKNPDTGE
VVTPPVDDVTKYGPVDGDPITSTEEIPFDKKREFDPNLAPGTEKVVQKGEPGTKTITTPTTKNPLTGEK
VGEGEPTEKITKQPVDEIVHYGGEEIKPGHKDEFDPNAPKGSQEDVPGKPGVKNPDTGEVVTPPVDDVT
KYGPVDGDPITSTEEIPFDKKREFNPDLKPGEERVKQKGEPGTKTITTPTTKNPLTGEKVGEGEPTEKV
TKQPVDEIVHYGGEEIKPGHKDEFDPNAPKGSQEDVPGKPGVKNPDTGEVVTPPVDDVTKYGPVDGDPI
TSTEEIPFDKKREFDPNLAPGTEKVVQKGEPGTKTITTPTTKNPLTGEKVGEGEPTEKITKQPVDEIVH
YGGEEIKPGHKDEFDPNAPKGSQTTQPGKPGVKNPDTGEVVTPPVDDVTKYGPVDGDPITSTEEIPFDK
KREFDPNLAPGTEKVVQKGEPGTKTITTPTTKNPLTGEKVGEGEPTEKITKQPVDEIVHYGGEQIPQGH
KDEFDPNAPVDSKTEVPGKPGVKNPDTGEVVTPPVDDVTKYGPKVGNPITSTEEIPFDKKRVFNPDLKP
GEERVKQKGEPGTKTITTPILVNPITGEKVGEGKSTEKVTKQPVDEIVEYGPTKAEPGKPAEPGKPAEP
GKPAEPGKPAEPGTPAEPGKPAEPGKPAEPGKPAEPGKPAEPGKPAEPGTPAEPGKPAEPGKPAEPGKP
AEPGTPAEPGKPAEPGTPAEPGKPAEPGTPTQSGAPEQPNRSMHSTDNKNQLPDTGENRQANEGTLVGS
LLAIVGSLFIFGRRKKGNEK

SEQ ID NO:18 polypeptide sequence

MKKLYTSYGTYGFLHQIKINNPTHQLFQFSASDTSVIFEETDGETVLKSPSIYEVIKEIGEFSEHHFYC
AIFIPSTEDHAYQLEKKLISVDDNFRNFGGFKSYRLLRPAKGTTYKIYFGFADRHAYEDFKQSDAFNDH
FSKDALSHYFGSSGQHSSYFERYLYPIKE

SEQ ID NO:19 polypeptide sequence

MYLYTSYGTYQFLNQIKLNHQERSLFQFSTNDSSIILEESEGKSILKHPSAYQVIDSTGEFNEHHFYSA
IFVPTSEDHRQQLEKKLLLVDVPLRNFGGFKSYRLLKPTEGSTYKIYFGFANRTAYEDFKASDIFNENF
SKDALSQYFGASGQHSSYFERYLYPIEDH

FIG. 1I

SEQ ID NO:20 polypeptide sequence

MINRDNKKAITKKGMISNRLNKFSIRKYTVGTASILVGTTLIFGLGNQEAKAAENTSTENAKQDDATTS
DNKEVVSETENNSTTENDSTNPIKKETNTDSQPEAKEESTTSSTQQQNNVTATTETKPQNIEKENVKP
STDKTATEDTSVILEEKKAPNYTNNDVTTKPSTSEIQTKPTTPQESTNIENSQPQPTPSKVDNQVTDAT
NPKEPVNVSKEELKNNPEKLKELVRNDNNTDRSTKPVATAPTSVAPKRLNAKMRFAVAQPAAVASNNVN
DLITVTKQTIKVGDGKDNVAAAHDGKDIEYDTEFTIDNKVKKGDTMTINYDKNVIPSDLTDKNDPIDIT
DPSGEVIAKGTFDKATKQITYTFTDYVDKYEDIKARLTLYSYIDKQAVPNETSLNLTFATAGKETSQNV
SVDYQDPMVHGDSNIQSIFTKLDENKQTIEQQIYVNPLKKTATNTKVDIAGSQVDDYGNIKLGNGSTII
DQNTEIKVYKVNPNQQLPQSNRIYDFSQYEDVTSQFDNKKSFSNNVATLDFGDINSAYIIKVVSKYTPT
SDGELDIAQGTSMRTTDKYGYYNYAGYSNFIVTSNDTGGGDGTVKPEEKLYKIGDYVWEDVDKDGVQGT
DSKEKPMANVLVTLTYPDGTTKSVRTDANGHYEFGGLKDGETYTVKFETPAGYLPTKVNGTTDGEKDSN
GSSITVKINGKDDMSLDTGFYKEPKYNLGDYVWEDTNKDGIQDANEPGIKDVKVTLKDSTGKVIGTTTT
DASGKYKFTDLDNGNYTVEFETPAGYTPTVKNTTAEDKDSNGLTTTGVIKDADNMTLDSGFYKTPKYSL
GDYVWYDSNKDGKQDSTEKGIKDVKVTLLNEKGEVIGTTKTDENGKYRFDNLDSGKYKVIFEKPAGLTQ
TVTNTTEDDKDADGGEVDVTITDHDDFILDNGYFEEDTSDSDSDSDSDSDSDSDSDSDSDSDSDSDSDS
DSDSDSDSDSDSDSDSDSDSDSDSDSDSDSDSDSDSDSDSDSDSDSDSDSDSDSDSDSDSDSDSDSDSD
SDSDSDSDSDSDSDSDSDSDSDSDSDSDSDSDSDSDSDSDSDSDSDSDAGKHTPVKPMSTTKDHHNKAKAL
PETGSENNGSNNATLFGGLFAALGSLLLFGRRKKQNK

SEQ ID NO:21 polypeptide sequence

MINKKNNLLTKKKPIANKSNKYAIRKFTVGTASIVIGATLLFGLGHNEAKAEENSVQDVKDSNTDDELS
DSNDQSSDEEKNDVINNNQSINTDDNNQIIKKEETNNYDGIEKRSEDRTESTTNVDENEATFLQKTPQD
NTHLTEEEVKESSSVESSNSSIDTAQQPSHTTINREESVQTSDNVEDSHVSDFANSKIKESNTESGKEE
NTIEQPNKVKEDSTTSQPSGYTNIDEKISNQDELLNLPINEYENKARPLSTTSAQPSIKRVTVNQLAAE
QGSNVNHLIKVTDQSITEGYDDSEGVIKAHDAENLIYDVTFEVDDKVKSGDTMTVDIDKNTVPSDLTDS
FTIPKIKDNSGEIIATGTYDNKNKQITYTFTDYVDKYENIKAHLKLTSYIDKSKVPNNNTKLDVEYKTA
LSSVNKTITVEYQRPNENRTANLQSMFTNIDTKNHTVEQTIYINPLRYSAKETNVNISGNGDEGSTIID
DSTIIKVYKVGDNQNLPDSNRIYDYSEYEDVTNDDYAQLGNNNDVNINFGNIDSPYIIKVISKYDPNKD
DYTTIQQTVTMQTTINEYTGEFRTASYDNTIAFSTSSGQGQGDLPPEKTYKIGDYVWEDVDKDGIQNTN
DNEKPLSNVLVTLTYPDGTSKSVRTDEDGKYQFDGLKNGLTYKITFETPEGYTPTLKHSGTNPALDSEG
NSVWVTINGQDDMTIDSGFYQTPKYSLGNYVWYDTNKDGIQGDDEKGISGVKVTLKDENGNIISTTTTD
ENGKYQFDNLNSGNYIVHFDKPSGMTQTTTDSGDDDEQDADGEEVHVTITDHDDFSIDNGYYDDESDSD
SDSDSDSDSDSDSDSDSDSDSDSDSDSDSDSDSDSDSDSDSDSDSDSDSDSDSDSDSDSDSDSDSDSDS
DSDSDSDSDSDSDSDSDSDSDSDSDSDSDSDSDSDSDSDSDSDSDSDSDSDSDSDSDSDSDSDSDSDSD
SDSDSDSDSDSDSDSDSDSDSDSDSDSDSDSDSDSDSDNDSDLGNSSDKSTKDKLPDTGANEDYGSKGTLLGT
LFAGLGALLLGKRRKNRKNKN

SEQ ID NO:22 polypeptide sequence

MSNNFKDDFEKNRQSIDTNSHQDHTEDVEKDQSELEHQDTIENTEQQFPPRNAQRRKRRRDLATNHNKQ
VHNESQTSEDNVQNEAGTIDDRQVESSHSTESQEPSHQDSTPQHEEEYYNKNAFAMDKSHPEPIEDNDK
HETIKDAENNTEHSTVSDKSIAEQSQQPKPYFATGANQANTSKDKHDDVTVKQDKDESKDHHSGKKGAA
IGAGTAGVAGAAGAMGVSKAKKHSNDAQNKSNSDKSNNSTEDKASQDKSKDHHNGKKGAAIGAGTAGLA
GGAASKSASAASKPHASNNASQNHDEHDNHDRDKERKKGGMAKVLLPLIAAVLIIGALAIFGGMALNNH
NNGTKENKIANTNKNNADESKDKDTSKDASKDKSKSTDSDKSKEDQDKATKDESDNDQNNANQANNQAQ
NNQNQQQANQNQQQQQQRQGGGQRHTVNGQENLYRIAIQYYGSGSPENVEKIRRANGLSGNNIRNG
QQIVIP

SEQ ID NO:23 polypeptide sequence

MIELIKMEGMIVVSNNNFKDDFEKNRQSINPDEQQTELKEDDKTNENKKEADSQNSLSNNSNQQFPPRN
AQRRKRRRETATNQSKQQDDKHQKNSDAKTTEGSLDDRYDEAQLQQQHDKSQQQNKTEKQSQDNRMKDG
KDAAIVNGTSESPEHKSKSTQNRPGPKAQQQKRKSESTQSKPSTNKDKKAATGAGIAGAAGVAGAAETS
KRHHNKKDKQDSKHSNHENDEKSVKNDDQKQSKKGKKAAVGAGAAAGVGAAGVAHHNNQNKHHNEEKNS
NQNNQYNDQSEGKKKGGFMKILLPLIAAILILGAIAIFGGMALNNHNDSKSDDQKIANQSKKDSDKKDG
AQSEDNKDKKSDSNKDKKSDSDKNADDDSDNSSSNPNATSTNNNDNVANNNSNYTNQNQQDNANQNSNN
QQATQGQQSHTVYGQENLYRIAIQYYGEGTQANVDKIKRANGLSSNNIHNGQTLVIPQ

FIG. 1J

SEQ ID NO:24 polypeptide sequence

MKNKLIAKSLLTIAAIGITTTTIASTADASEGYGPREKKPVSINHNIVEYNDGTFKYQSRPKFNSTPKY
IKFKHDYNILEFNDGTFEYGARPQFNKPAAKTDATIKKEQKLIQAQNLVREFEKTHTVSAHRKAQKAVN
LVSFEYKVKKMVLQERIDNVLKQGLVR

SEQ ID NO:25 polypeptide sequence

MKTRIVSSVTTTLLLGSILMNPVANAADSDINIKTGTTDIGSNTTVKTGDLVTYDKENGMHKKVFYSFI
DDKNHNKKLLVIRTKGTIAGQYRVYSEEGANKSGLAWPSAFKVQLQLPDNEVAQISDYYPRNSIDTKEY
MSTLTYGFNGNVTGDDTGKIGGLIGANVSIGHTLKYVQPDFKTILESPTDKKVGWKVIFNNMVNQNWGP
YDRDSWNPVYGNQLFMKTRNGSMKAAENFLDPNKASSLLSSGFSPDFATVITMDRKASKQQTNIDVIYE
RVRDDYQLHWTSTNWKGTNTKDKWTDRSSERYKIDWEKEEMTN

SEQ ID NO:26 polypeptide sequence

MHMKNKYISKLLVGAATITLATMISNGEAKASENTQQTSTKHQTTQNNYVTDQQKAFYQVLHLKGITEE
QRNQYIKTLREHPERAQEVFSESLKDSKNPDRRVAQQNAFYNVLKNDNLTEQEKNNYIAQIKENPDRSQ
QVWVESVQSSKAKERQNIENADKAIKDFQDNKAPHDKSAAYEANSKLPKDLRDKNNRFVEKVSIEKAIV
RHDERVKSANDAISKLNEKDSIENRRLAQREVNKAPMDVKEHLQKQLDALVAQKDAEKKVAPKVEAPQI
QSPQIEKPKAESPKVEVPQSKLLGYYQSLKDSFNYGYKYLTDTYKSYKEKYDTAKYYYNTYYKYKGAID
QTVLTVLGSGSKSYIQPLKVDDKNGYLAKSYAQVRNYVTESINTGKVLYTFYQNPTLVKTAIKAQETAS
SIKNTLSNLLSFWK

SEQ ID NO:27 polypeptide sequence

MTKHYLNSKYQSEQRSSAMKKITMGTASIILGSLVYIGADSQQVNAATEATNATNNQSTQVSQATSQPI
NFQVQKDGSSEKSHMDDYMQHPGKVIKQNNKYYFQTVLNNASFWKEYKFYNANNQELATTVVNDNKKAD
TRTINVAVEPGYKSLTTKVHIVVPQINYNHRYTTHLEFEKAIPTLADAAKPNNVKPVQPKPAQPKTPTE
QTKPVQPKVEKVKPTVTTTSKVEDNHSTKVVSTDTTKDQTKTQTAHTVKTAQTAQEQNKVQTPVKDVAT
AKSESNNQAVSDNKSQQTNKVTKHNETPKQASKAKELPKTGLTSVDNFISTVAFATLALLGSLSLLLFK
RKESK

SEQ ID NO:28 polypeptide sequence

MNKQQKEFKSFYSIRKSSLGVASVAISTLLLLMSNGEAQAAAEETGGTNTEAQPKTEAVASPTTTSEKA
PETKPVANAVSVSNKEVEAPTSETKEAKEVKEVKAPKETKAVKPAAKATNNTYPILNQELREAIKNPAI
KDKDHSAPNSRPIDFEMKKENGEQQFYHYASSVKPARVIFTDSKPEIELGLQSGQFWRKFEVYEGDKKL
PIKLVSYDTVKDYAYIRFSVSNGTKAVKIVSSTHFNNKEEKYDYTLMEFAQPIYNSADKFKTEEDYKAE
KLLAPYKKAKTLERQVYELNKIQDKLPEKLKAEYKKKLEDTKKALDEQVKSAITEFQNVQPTNEKMTDL
QDTKYVVYESVENNESMMDTFVKHPIKTGMLNGKKYMVMETTNDDYWKDFMVEGQRVRTISKDAKNNTR
TIIFPYVEGKTLYDAIVKVHVKTIDYDGQYHVRIVDKEAFTKANTDKSNKKEQQDNSAKKEATPATPSK
PTPSPVEKESQKQDSQKDDNKQLPSVEKENDASSESGKDKTPATKPTKGEVESSSTTPTKVVSTTQNVA
KPTTASSKTTKDVVQTSAGSSEAKDSAPLQKANIKNTNDGHTQSQNNKNTQENKAKSLPQTGEESNKDM
TLPLMALLALSSIVAFVLPRKRKN

SEQ ID NO:29 polypeptide sequence

MNNKKTATNRKGMIPNRLNKFSIRKYSVGTASILVGTTLIFGLSGHEAKAAEHTNGELNQSKNETTAPS
ENKTTEKVDSRQLKDNTQTATADQPKVTMSDSATVKETSSNMQSPQNATASQSTTQTSNVTTNDKSSTT
YSNETDKSNLTQAKNVSTTPKTTTIKQRALNRMAVNTVAAPQQGTNVNDKVHFTNIDIAIDKGHVNKTT
GNTEFWATSSDVLKLKANYTIDDSVKEGDTFTFKYGQYFRPGSVRLPSQTQNLYNAQGNIIAKGIYDSK
TNTTTYTFTNYVDQYTNVSGSFEQVAFAKRENATTDKTAYKMEVTLGNDTYSKDVIVDYGNQKGQQLIS
STNYINNEDLSRNMTVYVNQPKKTYTKETFVTNLTGYKFNPDAKNFKIYEVTDQNQFVDSFTPDTSKLK
DVTGQFDVIYSNDNKTATVDLLNGQSSSDKQYIIQQVAYPDNSSTDNGKIDYTLETQNGKSSWSNSYSN
VNGSSTANGDQKKYNLGDYVWEDTNKDGKQDANEKGIKGVYVILKDSNGKELDRTTTDENGKYQFTGLS
NGTYSVEFSTPAGYTPTTANAGTDDAVDSDGLTTTGVIKDADNMTLDSGFYKTPKYSLGDYVWYDSNKD
GKQDSTEKGIKGVKVTLQNEKGEVIGTTETDENGKYRFDNLDSGKYKVIFEKPAGLTQTGTNTTEDDKD
ADGGEVDVTITDHDDFTLDNGYYEEETSDSDSDSDSDSDSDSDSDSDSDSDSDSDSDSDSDSDSDSDSD
SDSDSDSDSDSDSESDSDSDSDSDSDSDSDSDSDSDSDSDSDSDSDSDSDSDSDSDSDSDSDSDNDSDS
DSDSDSDSDSDSDSDSDSDSDSDSDSDSDSDSDSDSDSDSDSDSDSDSDSDSDSDSDSDSDSDSDAGKH
TPTKPMSTVKDQHKTAKALPETGSENNNSNNGTLFGGLFAALGSLLLFGRRKKQNK

FIG. 1K

SEQ ID NO:30 polypeptide sequence

MNMKKKEKHAIRKKSIGVASVLVGTLIGFGLLSSKEADASENSVTQSDSASNESKSNDSSSVSAAPKTD
DTNVSDTKTSSNTNNGETSVAQNPAQQETTQSSSTNATTEETPVTGEATTTTTNQANTPATTQSSNTNA
EELVNQTSNETTSNDTNTVSSVNSPQNSTNAENVSTTQDTSTEATPSNNESAPQNTDASNKDVVSQAVN
PSTPRMRAFSLAAVAADAPAAGTDITNQLTDVKVTIDSGTTVYPHQAGYVKLNYGFSVPNSAVKGDTFK
ITVPKELNLNGVTSTAKVPPIMAGDQVLANGVIDSDGNVIYTFTDYVDNKENVTANITMPAYIDPENVT
KTGNVTLTTGIGTNTASKTVLIDYEKYGQFHNLSIKGTIDQIDKTNNTYRQTIYVNPSGDNVVLPALTG
NLIPNTKSNALIDAKNTDIKVYRVDNANDLSESYYVNPSDFEDVTNQVRISFPNANQYKVEFPTDDDQI
TTPYIVVVNGHIDPASTGDLALRSTFYGYDSNFIWRSMSWDNEVAFNNGSGSGDGIDKPVVPEQPDEPG
EIEPIPEDSDSDPGSDSGSDSNSDSGSDSGSDSTSDSGSDSASDSDSASDSDSASDSDSASDSDSASDS
DSASDSDSASDSDSASDSDSASDSDSASDSDSASDSDSASDSDSASDSDSDSDSDSDSDSDSDSDSDSD
SDSDSDSDSDSDSDSDSDSDSDSDSDSDSDSDSDSDSDSDSDSDSDSDSDSDSDSDSDSDSDSDSDSDS
DSDSDSDSASDSDSDSDSESDSDSDSDSDSDSDSDSDSDSDSDSESDSDSDSDSESDSDSDSDSDSDSA
SDSDSGSDSDSSSDSDSDSTSDTGSDNDSDSDSNSDSESGSNNNVVPPNSPKNGTNASNKNEAKDSKEP
LPDTGSEDEANTSLIWGLLASLGSLLLFRRKKENKDKK

SEQ ID NO:31 polypeptide sequence

MKNNLRYGIRKHKLGAASVFLGTMIVVGMGQDKEAAASEQKTTTVEENGNSATDNKTSETQTTATNVNH
IEETQSYNATVTEQPSNATQVTTEEAPKAVQAPQTAQPANVETVKEEEKPQVKETTQPQDNSGNQRQVD
LTPKKVTQNQGTETQVEVAQPRTASESKPRVTRSADVAEAKEASDVSEVKGTDVTSKVTVESGSIEAPQ
GNKVEPHAGQRVVLKYKLKFADGLKRGDYFDFTLSNNVNTYGVSTARKVPEIKNGSVVMATGEILGNGN
IRYTFTNEIEHKVEVTANLEINLFIDPKTVQSNGEQKITSKLNGEETEKTIPVVYNPGVSNSYTNVNGS
IETFNKESNKFTHIAYIKPMNGNQSNTVSVTGTLTEGSNLAGGQPTVKVYEYLGKKDELPQSVYANTSD
TNKFKDVTKEMNGKLSVQDNGSYSLNLDKLDKTYVIHYTGEYLQGSDQVNFRTELYGYPERAYKSYYVY
GGYRLTWDNGLVLYSNKADGNGKNGQIIQDNDFEYKEDTAKGTMSGQYDAKQIIETEENQDNTPLDIDY
HTAIDGEGGYVDGYIETIEETDSSAIDIDYHTAVDSEVGHVGGYTESSEESNPIDFEESTHENSKHHAD
VVEYEEDTNPGGGQVTTESNLVEFDEESTKGIVTGAVSDHTTIEDTKEYTTESNLIELVDELPEEHGQA
QGPIEEITENNHHISHSGLGTENGHGNYGVIEEIEENSHVDIKSELGYEGGQNSGNQSFEEDTEEDKPK
YEQGGNIVDIDFDSVPQIHGQNKGDQSFEEDTEKDKPKYEHGGNIIDIDFDSVPQIHGFNKHNEIIEED
TNKDKPNYQFGGHNSVDFEEDTLPKVSGQNEGQQTIEEDTTPPTPPTPEVPSEPETPMPPTPEVPSEPE
TPTPPTPEVPSEPETPTPPTPEVPSEPETPTPPTPEVPSEPETPTPPTPEVPAEPGKPVPPAKEEPKKP
SKPVEQGKVVTPVIEINEKVKAVAPTKKAQSKKSELPETGGEESTNKGMLFGGLFSILGLALLRRNKKN
NKA

SEQ ID NO:32 polypeptide sequence

MKKRIDYLSNKQNKYSIRRFTVGTTSVIVGATILFGIGNHQAQASEQSNDTTQSSKNNASADSEKNNMI
ETPQLNTTANDTSDISANTNSANVDSTTKPMSTQTSNTTTTEPASTNETPQPTAIKNQATAAKMQDQTV
PQEANSQVDNKTTNDANSIATNSELKNSQTLDLPQSSPQTISNAQGTSKPSVRTRAVRSLAVAEPVVNA
ADAKGTNVNDKVTASNFKLEKTTFDPNQSGNTFMAANFTVTDKVKSGDYFTAKLPDSLTGNGDVDYSNS
NNTMPIADIKSTNGDVVAKATYDILTKTYTFVFTDYVNNKENINGQFSLPLFTDRAKAPKSGTYDANIN
IADEMFNNKITYNYSSPIAGIDKPNGANISSQIIGVDTASGQNTYKQTVFVNPKQRVLGNTWVYIKGYQ
DKIEESSGKVSATDTKLRIFEVNDTSKLSDSYYADPNDSNLKEVTDQFKNRIYYEHPNVASIKFGDITK
TYVVLVEGHYDNTGKNLKTQVIQENVDPVTNRDYSIFGWNNENVVRYGGGSADGDSAVNPKDPTPGPPV
DPEPSPDPEPEPTPDPEPSPDPEPEPSPDPDPDSDSDSDSGSDSDSGSDSDSESDSDSDSDSDSDSDSD
SESDSDSESDSDSDSDSDSDSDSDSESDSDSDSDSDSDSDSDSESDSDSESDSESDSDSDSDSDSDSDS
DSDSDSDSDSDSDSDSDSDSDSESDSDSDSDSDSDSDSDSDSDSDSDSDSDSDSDSDSDSDSDSDSDSD
SDSDSDSDSDSDSDSDSDSDSDSDSDSDSDSDSDSDSDSDSDSDSRVTPPNNEQKAPSNPKGEVNHSNK
VSKQHKTDALPETGDKSENTNATLFGAMMALLGSLLLFRKRKQDHKEKA

FIG. 1L

SEQ ID NO:33 polypeptide sequence

MKKQIISLGALAVASSLFTWDNKADAIVTKDYSKESRVNEKSKKGATVSDYYYWKIIDSLEAQFTGAID
LLEDYKYGDPIYKEAKDRLMTRVLGEDQYLLKKKIDEYELYKKWYKSSNKNTNMLTFHKYNLYNLTMNE
YNDIFNSLKDAVYQFNKEVKEIEHKNVDLKQFDKDGEDKATKEVYDLVSEIDTLVVTYYADKDYGEHAK
ELRAKLDLILGDTDNPHKITNERIKKEMIDDLNSIIDDFFMETKQNRPNSITKYDPTKHNFKEKSENKP
NFDKLVEETKKAVKEADESWKNKTVKKYEETVTKSPVVKEEKKVEEPQLPKVGNQQEVKTTAGKAEETT
QPVAQPLVKIPQETIYGETVKGPEYPTMENKTLQGEIVQGPDFLTMEQNRPSLSDNYTQPTTTPNPILEG
LEGSSSKLEIKPQGTESTLKGIQGESSDIEVKPQATETTEASQYGPRPQFNKTPKYVKYRDAGTGIREY
NDGTFGYEARPRFNKPSETNAYNVTTNQDGTVSYGARPTQNKPSETNAYNVTTHANGQVSYGARPTQKK
PSKTNAYNVTTHANGQVSYGARPTQKKPSKTNAYNVTTHANGQVSYGARPTYKKPSETNAYNVTTHANG
QVSYGARPTQKKPSETNAYNVTTHADGTATYGPRVTK

SEQ ID NO:67 polypeptide sequence

MKSNLRYGIRKHKLGAASVFLGTMIVVGMGQEKEAAASEQNNTTVEESGSSATESKASETQTTTNNVNT
IDETQSYSATSTEQPSKSTQVTTEEAPTTVQAPKVETEMKSQEDLPSEKVADKETTGTQVDIAQPSNVS
EIKPRMKRSADVTAVSEKEVAEEAKATGTDVTNKVEVTESSLEGHNKDSNIVNPHNAQRVTLKYKWKFG
EGIKAGDYFDFTLSDNVETHGISTLRKVPEIKSSTEDKVMANGQVINERTIRYTFTDYINNKKDLTAEL
NLNLFIDPTTVTKQGSQKVEVTLGQNKVSKEFDIKYLDGVKDRMGVTVNGRIDTLNKEEGKFSHFAYVK
PNNQSLTSVTVTGQVTSGYKQSANNPTVKVYKHIGSDELAESVYAKLDDTSKFEDVTEKVNLSYTSNGG
YTLNLGDLDNSKDYVIKYEGEYDQNAKDLNFRTHLSGYHKYYPYYPYYPYYPVQLTWNNGVAFYSNNAK
GDGKDKPNDPIIEKSEPIDLDIKSEPPVEKHELTGTIEESNDSKPIDFEYHTAVEGAEGHAEGIIETEE
DSIHVDFEESTHENSKHHADVVEYEEDTNPGGGQVTTESNLVEFDEESTKGIVTGAVSDHTTVEDTKEY
TTESNLIELVDELPEEHGQAQGPIEEITENNHHISHSGLGTENGHGNYGVIDEIEENSHVDIKSELGYE
GGQNSGNQSFEEDTEEDKPKYEQGGNIVDIDFDSVPQIHGQNNGNQSFEEDTEEDKPKYEQGGNIIDID
FDSVPQIHGFNKHNEIIEEDTNKDKPNYQFGGHNSVDFEEDTLPKVSGQNEGQQTIEEDTTPPTPPTPE
VPSEPETPTPPTPEVPSEPGEPTPPKPEVPSEPETPVPPTPEVPSEPGKPVPPAKEEPKKPSKPVEQGK
VVTPVIEINEKVKAVAPTKQKQSKKSELPETGGEESTNKGMLFGGLFSILGLVLLRRNKKNNKA

SEQ ID NO:68 polypeptide sequence

MKFKSLITTTLALGVIASTGANFNTNEASAAAKPLDKSSSTLHHGHSNIQIPYTITVNGTSQNILSSLT
FNKNQNISYKDIENKVKSVLYFNRGISDIDLRLSKQAEYTVHFKNGTKRVIDLKSGIYTADLINTSDIK
AISVNVDTKKQPKDKAKANVQVPYTITVNGTSQNILSNLTFNKNQNISYKDLEGKVKSVLESNRGITDV
DLRLSKQAKYTVNFKNGTKKVIDLKSGIYTANLINSSDIKSININVDTKKHIENKAKRNYQVPYSINLN
GTSTNILSNLSFSNKPWTNYKNLTSQIKSVLKHDRGISEQDLKYAKKAYYTVYFKNGGKRILQLNSKNY
TANLVHAKDVKRIEITVKTGTKAKADRYVPYTIAVNGTSTPILSKLKISNKQLISYKYLNDKVKSVLKS
ERGISDLDLKFAKQAKYTVYFKNGKKQVVNLKSDIFTPNLFSAKDIKKIDIDVKQYTKSKKKINKSNNV
KFPVTINKFENIVSNEFVFYNASKITINDLSIKLKSAMANDQGITKHDIGLAERAVYKVYFKNGSSKYV
DLKTEYKDERVFKATDIKKVDIELKF

SEQ ID NO: 69 polypeptide sequence

MNNKKTATNRKGMIPNRLNKFSIRKYSVGTASILVGTTLIFGLSGHEAKAAEHTNGELNQ
SKNETTAPSENKTTKKVDSRQLKDNTQTATADQPKVTMSDSATVKETSSNMQSPQNATAN
QSTTKTSNVTTNDKSSTTYSNETDKSNLTQAKDVSTTPKTTTIKPRTLNRMAVNTVAAPQ
QGTNVNDKVHFSNIDIAIDKGHVNQTTGKTEFWATSSDVLKLKANYTIDDSVKEGDTFTF
KYGQYFRPGSVRLPSQTQNLYNAQGNIIAKGIYDSTTNTTTYTFTNYVDQYTNVRGSFEQ
VAFAKRKNATTDKTAYKMEVTLGNDTYSEEIIVDYGNKKAQPLISSTNYINNEDLSRNMT
AYVNQPKNTYTKQTFVTNLTGYKFNPNAKNFKIYEVTDQNQFVDSFTPDTSKLKDVTDQF
DVIYSNDNKTATVDLMKGQTSSNKQYIIQQVAYPDNSSTDNGKIDYTLDTDKTKYSWSNS
YSNVNGSSTANGDQKKYNLGDYVWEDTNKDGKQDANEKGIKGVYVILKDSNGKELDRTTT
DENGKYQFTGLSNGTYSVEFSTPAGYTPTTANVGTDDAVDSDGLTTTGVIKDADNMTLDS
GFYKTPKYSLGDYVWYDSNKDGKQDSTEKGIKGVKVTLQNEKGEVIGTTETDENGKYRFD
NLDSGKYKVIFEKPAGLTQTGTNTTEDDKDADGGEVDVTITDHDDFTLDNGYYEEETSDS
DSDSDSDSDSDSDSDSDSDSDSDSDSDSDSDSDSDSDSDSDSDSDSDSDSDSDSDSDSDS
DSDSDSDSDSDSDSDSDSDSDSDSDSDSDSDSDSDSDSDSDSDSDSDSDSDSDSDSDSDS
DSDSDSDSDSDSDSDSDNDSDSDSDSDSDSDSDSDSDSDSDSDSDSDSDSDSDSDSDSDS
DSDSDSDSDSDSDSDSDSDSDSDNDSDSDSDSDSDAGKHTPAKPMSTVKDQHKTAKALPE
TGSENNNSNNGTLFGGLFAALGSLLLFGRRKKQNK

FIG. 1M

SEQ ID NO: 70 polypeptide sequence

EENSVQDVKDSNTDDELSDSNDQSSDEEKNDVINNNQSINTDDNNQIIKKEETNNYDGIE
KRSEDRTESTTNVDENEATFLQKTPQDNTHLTEEEVKESSSVESSNSSIDTAQQPSHTTI
NREESVQTSDNVEDSHVSDFANSKIKESNTESGKEENTIEQPNKVKEDSTTSQPSGYTNI
DEKISNQDELLNLPINEYENKARPLSTTSAQPSIKRVTVNQLAAEQGSNVNHLIKVTDQS
ITEGYDDSEGVIKAHDAENLIYDVTFEVDDKVKSGDTMTVDIDKNTVPSDLTDSFTIPKI
KDNSGEIIATGTYDNKNKQITYTFTDYVDKYENIKAHLKLTSYIDKSKVPNNNTKLDVEY
KTALSSVNKTITVEYQRPNENRTANLQSMFTNIDTKNHTVEQTIYINPLRYSAKETNVNI
SGNGDEGSTIIDDSTIIKVYKVGDNQNLPDSNRIYDYSEYEDVTNDDYAQLGNNNDVNIN
FGNIDSPYIIKVISKYDPNKDDYTTIQQTVTMQTTINEYTGEFRTASYDNTIAFSTSSGQ
GQGDLPPEKTYKIGDYVWEDVDKDGIQNTNDNEKPLSNVLVTLTYPDGTSKSVRTDEDGK
YQFDGLKNGLTYKITFETPEGYTPTLKHSGTNPALDSEGNSVWVTINGQDDMTIDSGFYQ
TPKYSLGNYVWYDTNKDGIQGDDEKGISGVKVTLKDENGNIISTTTTDENGKYQFDNLNS
GNYIVHFDKPSGMTQTTTDSGDDDEQDADGEEVHVTITDHDDFSIDNGYYDDE

FIG. 2A

SEQ ID NO:34 polynucleotide sequence

ATGTTACAAGTAACTGATGTGAGTTTACGTTTTGGAGATCGTAAACTATTTGAAGATGTAAATATTAAA
TTTACAGAAGGTAATTGTTATGGATTAATTGGTGCGAATGGTGCAGGTAAATCAACATTCTTAAAAATA
TTATCTGGTGAATTAGATTCTCAAACAGGACATGTTTCATTAGGTAAAAATGAACGTCTAGCTGTTTTA
AAACAGGACCACTATGCTTATGAAGATGAACGCGTGCTTGATGTTGTAATTAAAGGTCACGAACGTCTT
TATGAGGTTATGAAAGAAAAAGATGAAATCTATATGAAGCCAGATTTCAGTGATGAAGATGGTATCCGT
GCTGCTGAACTTGAAGGTGAATTTGCAGAAATGAATGGTTGGAATGCTGAAGCTGATGCTGCTAACCTT
TTATCTGGTTTAGGTATCGATCCAACTTTACACGATAAAAAAATGGCTGAATTAGAAAACAACCAAAAA
ATTAAAGTATTATTAGCGCAAAGTTTATTCGGTGAACCAGACGTACTATTACTGGATGAGCCTACTAAC
GGTCTCGATATTCCAGCAATCAGTTGGTTAGAAGATTTCTTAATTAACTTTGATAATACTGTTATCGTA
GTATCGCATGACCGTCATTTCTTAAATAATGTATGTACTCATATCGCTGATTTAGACTTCGGTAAAATT
AAAGTTTATGTTGGTAACTATGATTTTTGGTATCAATCTAGTCAGTTAGCTCAAAAGATGGCTCAAGAA
CAAAACAAGAAAAAAGAAGAAAAAATGAAAGAGTTACAGGACTTTATTGCACGTTTCTCAGCTAACGCT
TCTAAATCTAAACAAGCAACAAGTCGTAAAAAACAACTTGAGAAAATTGAATTAGATGATATTCAACCA
TCATCAAGAAGATATCCTTTCGTTAAATTCACGCCTGAGCGTGAGATTGGTAACGACTTATTAATCGTT
CAAAATCTTTCTAAAACAATTGACGGCGAAAAAGTATTAGATAATGTATCATTCACAATGAATCCAAAT
GATAAAGCGATTTTAATTGGAGATAGTGAAATTGCAAAAACAACATTACTTAAAATATTAGCTGGCGAA
ATGGAACCAGACGAAGGTTCATTTAAATGGGGTGTTACTACATCATTAAGTTACTTCCCTAAAGATAAC
TCAGAGTTCTTTGAGGGTGTAAATATGAATCTCGTTGATTGGTTAAGACAATATGCTCCTGAAGATGAA
CAAACAGAAACATTTTTACGTGGTTTCTTAGGTCGTATGTTATTTAGTGGTGAAGAAGTTAAGAAAAAA
GCTAGTGTGCTTTCAGGTGGAGAAAAAGTACGTTGTATGCTAAGTAAAATGATGTTATCAAGTGCGAAT
GTACTTTTACTTGACGAACCTACTAACCACTTAGACTTAGAAAGTATTACTGCTGTCAATGATGGTCTT
AAATCATTTAAAGGTTCTATCATCTTTACTTCTTATGACTTCGAATTTATCAACACGATTGCAAACCGT
GTTATCGATTTAAATAAACAAGGCGGCGTTTCAAAAGAAATTCCATATGAAGAATACTTGCAAGAAATC
GGCGTTTTAAAATAA

SEQ ID NO:35 polynucleotide sequence

ATGTTACAAGTAACTGATGTAAGTTTACGTTTTGGTGATCGTAAACTATTTGAAGATGTAAATATAAAA
TTTACAGAGGGTAATTGTTATGGATTAATTGGTGCAAATGGTGCTGGGAAATCTACATTCTTGAAGATT
TTATCAGGCGAAATTGATTCACAGACTGGTCATGTATCTCTAGGTAAAGATGAGCGTTTGGCTGTGTTA
AAACAAGATCATTTTGCTTATGAAGATGAACGTGTTTTAGATGTTGTGATTAAAGGACATGAACGTTTG
TATCAAGTGATGAAAGAGAAAGATGAAATTTATATGAAACCTGATTTCAGCGATGAGGACGGTATTCGC
GCTGCAGAACTTGAAGGAGAATTTGCAGAAATGAACGGTTGGAATGCTGAAGCTGATGCTGCTAACTTA
TTATCAGGATTAGGCATAGAACCTGACTTACATGATAAAAATATGTCTGAACTTGAAAATAATCAAAAA
GTTAAGGTATTGTTAGCTCAAAGTTTATTTGGTGATCCTGACGTTCTTTTACTAGATGAGCCTACCAAT
GGTTTAGATATACCAGCAATAAGTTGGTTAGAAGACTTTTTAATTAATTTTGAAAATACTGTCATTGTC
GTTTCGCATGACCGTCACTTCTTAAATAATGTTTGTACTCATATTGCTGATTTAGACTTTGGCAAAATT
AAACTTTATGTTGGTAACTATGATTTTTGGTATCAATCAAGTCAATTAGCACAAAAAATGGCACAAGAA
CAAAATAAGAAAAAAGAAGAAAAAATGAAAGAGTTACAGGATTTCATCGCACGCTTCTCAGCAAATGCT
TCTAAATCTAAACAGGCAACAAGTCGTAAGAAACAATTAGAAAAAATTGAATTAGATGATATCCAGCCA
TCATCTCGTAGATACCCTTACGTGAAATTTACTCCTGAACGTGAAATTGGAAATGATTTACTTACAGTA
GAAAATCTTTCTAAAACAATTGACGGCGAAAAAGTACTAGACAATGTTTCATTCACTATGAATCCTAAT
GATAAAGCTATTTTAGTTGGTGATAGCGAAATTGCTAAAACAACATTGTTAAAAATTTTAGCTGGAGAA
ATGGAACCAGATGAAGGTACATTTAAATGGGGTGTAACGACATCTTTAAGTTACTTCCCTAAAGATAAC
TCTGAGTTCTTTGATGGTGTCGATATGAATTTAGTTGAATGGTTACGTCAATACGCTCCAGAAGATGAA
CAAACTGAAACATTTTTACGTGGTTTCTTAGGTCGCATGTTATTTAGTGGTGAGGAAGTTAAGAAAAAA
GCAAGCGTGCTTTCAGGTGGAGAAAAAGTACGTTGCATGTTAAGTAAAATGATGTTATCAAGTGCTAAC
GTACTTTTACTTGATGAGCCAACAAACCATTTAGATTTGGAAAGTATCACTGCTGTAAATGACGGATTA
AAATCATTTAAAGGTTCTATCATCTTCACTTCTTATGATTTTGAATTTATTAATACAATCGCAAATCGA
GTGATTGACTTGAATCAAGCTGGTGCCCTTTCTAAAGAAGTACCTTATGAGGAATACTTACAAGAAATT
GGTGTATTACAAAATAATTAA

FIG. 2B

SEQ ID NO:36 polynucleotide sequence

ATGCCAATTATTACAGATGTTTACGCTCGCGAAGTCTTAGACTCTCGTGGTAACCCAACTGTTGAAGTA
GAAGTATTAACTGAAAGTGGCGCATTTGGTCGTGCATTAGTACCATCAGGTGCTTCAACTGGTGAACAC
GAAGCTGTTGAATTACGTGATGGAGACAAATCACGTTATTTAGGTAAAGGTGTTACTAAAGCAGTTGAA
AACGTTAATGAAATCATCGCACCAGAAATTATTGAAGGTGAATTTTCAGTATTAGATCAAGTATCTATT
GATAAAATGATGATCGCATTAGACGGTACTCCAAACAAAGGTAAATTAGGTGCAAATGCTATTTTAGGT
GTATCTATCGCAGTAGCACGTGCAGCAGCTGACTTATTAGGTCAACCACTTTACAAATATTTAGGTGGA
TTTAATGGTAAGCAGTTACCAGTACCAATGATGAACATCGTTAATGGTGGTTCTCACTCAGATGCTCCA
ATTGCATTCCAAGAATTCATGATTTTACCTGTAGGTGCTACAACGTTCAAAGAATCATTACGTTGGGGT
ACTGAAATTTTCCACAACTTAAAATCAATTTTAAGCAAACGTGGTTTAGAAACTGCAGTAGGTGACGAA
GGTGGTTTCGCTCCTAAATTTGAAGGTACTGAAGATGCTGTTGAAACAATTATCCAAGCAATCGAAGCA
GCTGGTTACAAACCAGGTGAAGAAGTATTCTTAGGATTTGACTGTGCATCATCAGAATTCTATGAAAAT
GGTGTATATGACTACAGTAAGTTCGAAGGCGAACACGGTGCAAAACGTACAGCTGCAGAACAAGTTGAC
TACTTAGAACAATTAGTAGACAAATATCCTATCATTACAATTGAAGACGGTATGGACGAAAACGACTGG
GATGGTTGGAAACAACTTACAGAACGTATCGGTGACCGTGTACAATTAGTAGGTGACGATTTATTCGTA
ACAAACACTGAAATTTTAGCAAAAGGTATTGAAAACGGAATTGGTAACTCAATCTTAATTAAAGTTAAC
CAAATCGGTACATTAACTGAAACATTTGATGCAATCGAAATGGCTCAAAAAGCTGGTTACACAGCAGTA
GTTTCTCACCGTTCAGGTGAAACAGAAGATACAACAATTGCTGATATTGCTGTTGCTACAAACGCTGGT
CAAATTAAAACTGGTTCATTATCACGTACTGACCGTATTGCTAAATACAATCAATTATTACGTATCGAA
GATGAATTATTTGAAACTGCTAAATATGACGGTATCAAATCATTCTATAACTTAGATAAATAA

SEQ ID NO:37 polynucleotide sequence

ATGCCAATTATTACAGATGTTTACGCTCGCGAAGTCTTAGACTCACGTGGTAACCCAACAGTTGAAGTT
GAAGTATTAACTGAAAGCGGTGCTTTCGGACGTGCATTAGTACCTTCTGGTGCTTCTACTGGTGAACAT
GAAGCAGTTGAATTACGTGATGGAGATAAATCACGTTATTTAGGTAAAGGTGTGACTAAAGCGGTAGAA
AATGTTAACGAAATGATCGCACCAGAAATCGTTGAAGGTGAATTTTCAGTTTTAGATCAAGTATCTATT
GATAAAATGATGATTCAATTAGACGGTACACACAACAAAGGTAAATTAGGTGCAAATGCCATTTTAGGT
GTTTCTATTGCCGTAGCTCGTGCAGCTGCTGACTTATTAGGTCAACCATTATATAAATATTTAGGTGGA
TTTAATGGTAAACAATTGCCAGTACCTATGATGAATATTGTTAATGGTGGTTCTCACTCAGATGCACCA
ATTGCTTTCCAAGAGTTCATGATTTTACCTGTAGGTGCTGAGTCATTCAAAGAATCATTACGTTGGGGT
GCAGAAATCTTCCATAACCTTAAATCAATCTTAAGTGAACGTGGTTTAGAAACTGCAGTAGGTGATGAA
GGTGGTTTCGCTCCTAGATTTGAAGGCACTGAAGACGCTGTAGAAACTATTATTAAAGCTATCGAAAAA
GCAGGATACAAACCAGGTGAAGATGTATTCTTAGGATTTGACTGTGCTTCTTCTGAATTCTATGAAAAT
GGTGTTTATGATTACACTAAATTCGAAGGTGAACACGGTGCTAAACGTAGTGCAGCAGAGCAAGTTGAC
TACTTAGAAGAATTAATTGGTAAATATCCAATCATCACTATTGAAGATGGTATGGATGAAAACGATTGG
GAAGGTTGGAAACAATTAACTGATCGTATCGGTGATAAAGTTCAATTAGTTGGTGATGATTTATTCGTA
ACTAACACTGAAATTTTATCTAAAGGTATCGAACAAGGTATTGGTAACTCAATCTTAATCAAAGTAAAC
CAAATCGGTACATTAACTGAAACATTCGATGCTATTGAAATGGCTCAAAAAGCTGGATATACTGCGGTT
GTATCTCACCGTTCTGGTGAAACTGAAGATACTACAATTGCTGATATCGCAGTTGCTACAAATGCAGGC
CAAATTAAAACAGGTTCATTATCTAGAACTGACCGTATTGCTAAATACAATCAATTATTACGTATTGAA
GATGAATTATACGAAACAGCTAAATTTGAAGGAATTAAATCTTTCTACAATTTAGATAAATAA

SEQ ID NO:38 polynucleotide sequence

ATGAAAAAAATCGTTACAGCTACAATCGCTACAGCAGGACTTGCCACTATCGCATTTGCAGGACATGAT
GCACAAGCCGCAGAACAAAATAACAATGGATATAATTCTAATGACGCTCAATCATACAGCTATACGTAT
ACAATTGATGCACAAGGTAATTATCATTACACTTGGACAGGAAATTGGAATCCAAGTCAATTAACGCAA
AACAACACATACTACTACAACAACTACAATACTTATAGTTATAACAATGCATCTTACAATAACTACTAT
AATCATTCATATCAATACAATAACTATACAAACAATAGCCAAACAGCAACAAATAACTATTATACTGGT
GGTTCAGGTGCAAGTTATAGCACAACAAGTAATAATGTTCATGTGACTACAACTGCAGCGCCATCTTCA
AATGGTCGTTCAATTTCTAATGGTTATGCATCAGGAAGTAACTTATATACTTCAGGACAATGTACTTAT
TATGTATTTGATCGTGTTGGTGGGAAAATTGGTTCAACATGGGGTAACGCAAGTAATTGGGCTAACGCA
GCTGCATCATCTGGCTATACAGTGAACAATACACCAAAAGTTGGTGCTATCATGCAAACAACACAAGGC
TATTACGGTCATGTTGCTTACGTTGAAGGCGTTAACAGCAACGGTTCTGTTCGTGTTTCAGAAATGAAC
TATGGACATGGTGCTGGTGTGGTTACGTCTCGTACAATTTCAGCAAACCAAGCAGGTTCATATAATTTC
ATTCATTAA

FIG. 2C

SEQ ID NO:39 polynucleotide sequence

ATGAAGAAAATCGCTACAGCTACTATCGCAACTGCAGGATTCGCTACAATCGCAATTGCATCAGGAAAT
CAAGCTCATGCTTCTGAGCAAGATAACTACGGTTATAATCCAAACGACCCAACATCATATAGCTATACT
TACACTATTGATGCACAAGGTAACTACCATTACACATGGAAAGGTAACTGGCATCCAAGTCAATTAAAC
CAAGATAATGGCTACTACAGCTATTACTACTACAATGGCTACAATAACTACAACAATTACAACAATGGT
TATAGCTACAATAATTACAGCCGTTACAACAACTACTCAAATAATAATCAATCATATAACTACAATAAC
TATAATAGTTACAACACAAACAGCTACCGTACTGGTGGTTTAGGTGCAAGCTACAGCACTTCAAGCAAC
AATGTTCAAGTAACTACAACTATGGCTCCATCATCAAATGGCCGTTCAATCTCAAGTGGTTATACTTCA
GGACGTAACTTATACACTTCTGGTCAATGTACATACTACGTATTTGATCGTGTAGGTGGTAAAATCGGT
TCAACTTGGGGCAATGCAAGTAACTGGGCTAACGCAGCTGCAAGAGCTGGTTACACAGTGAACAATACA
CCAAAAGCTGGTGCAATTATGCAAACAACTCAAGGTGCATACGGTCACGTTGCATACGTTGAAAGTGTT
AACAGCAATGGTTCAGTAAGAGTTTCAGAAATGAACTATGGTTATGGCCCAGGTGTTGTAACTTCACGT
ACAATCTCAGCTAGCCAAGCTGCTGGTTATAACTTCATTCACTAA

SEQ ID NO:40 polynucleotide sequence

ATGAAAAAAATCGCTACAGCTACAATTGCAACTGCAGGAATCGCTACTTTCGCATTTGCACACCATGAC
GCACAAGCAGCAGAACAAAATAATGATGGGTACAATCCAAACGACCCTTATTCATATAGCTACACTTAC
ACAATCGATGCTGAAGGTAACTACCACTACACTTGGAAAGGTAACTGGAGTCCAGATCGTGTAAATACT
TCATATAACTATAATAATTATAATAACTACAACTACTATGGTTACAATAACTATAGCAACTACAATAAC
TACAGTAATTACAACAATTACAACAACTATCAATCAAACAACACGCAATCACAAAGAACAACTCAACCG
ACTGGTGGTTTAGGCGCAAGCTATTCAACATCAAGTAGTAATGTTCACGTTACAACAACTTCTGCGCCA
TCATCAAACGGTGTATCTTTATCAAACGCTCGCTCAGCATCTGGTAACTTATACACTTCAGGTCAATGT
ACATATTATGTATTTGACAGAGTAGGTGGCAAAATCGGTTCAACGTGGGGTAACGCAAACAACTGGGCA
AACGCTGCAGCACGTTCTGGTTACACAGTAAACAATTCGCCTGCTAAAGGTGCAATCTTACAAACGTCA
CAAGGTGCATACGGACACGTAGCATACGTTGAAGGTGTAAACAGCAATGGTTCAATCAGAGTTTCAGAA
ATGAACTACGGTCACGGTGCAGGTGTTGTCACTTCACGTACAATCTCTGCGAGCCAAGCTGCTTCATAT
AACTATATTCACTAA

SEQ ID NO:41 polynucleotide sequence

ATGAAAAAATTAGTACCTTTATTATTAGCCTTATTACTTCTAGTTGCTGCATGTGGTACTGGTGGTAAA
CAAAGCAGTGATAAGTCAAATGGCAAATTAAAAGTAGTAACGACGAATTCAATTTTATATGATATGGCT
AAAAATGTTGGTGGAGACAACGTCGATATTCATAGTATTGTACCTGTTGGTCAAGATCCTCATGAATAT
GAAGTTAAACCTAAAGATATTAAAAAGTTAACTGACGCTGACGTTATTTTATACAACGGATTAAATTTA
GAGACTGGTAACGGTTGGTTTGAAAAAGCCTTAGAACAGGCTGGTAAATCATTAAAAGATAAAAAAGTT
ATCGCAGTATCAAAAGATGTTAAACCTATCTATTTAAACGGTGAAGAAGGCAACAAAGATAAACAAGAT
CCACACGCATGGTTAAGTTTAGATAATGGTATTAAATACGTAAAAACAATTCAACAAACATTTATCGAT
AACGACAAAAAACATAAAGCAGATTATGAAAAGCAAGGTAACAAATACATTGCTCAATTGGAAAAATTA
AATAATGACAGTAAAGACAAATTTAATGACATTCCAAAAGAACAACGTGCCATGATTACAAGTGAAGGT
GCCTTCAAGTACTTCTCAAAACAATACGGTATTACACCAGGTTATATTTGGGAAATTAACACTGAAAAA
CAAGGTACACCTGAACAAATGAGACAAGCTATTGAGTTTGTTAAAAAGCACAAATTAAAACACTTATTA
GTAGAAACAAGTGTTGATAAGAAAGCAATGGAAAGTTTATCTGAAGAAACGAAGAAAGATATCTTTGGT
GAAGTGTACACAGATTCAATCGGTAAAGAAGGCACTAAAGGTGACTCTTACTACAAAATGATGAAATCA
AATATTGAAACTGTACACGGAAGCATGAAATAA

FIG. 2D

SEQ ID NO:42 polynucleotide sequence
GTGAAAAAAATTCTCGCTTTAGCAATAGCATTTTTAATTATCCTTGCCGCATGTGGGAATCACAGTAAC
CATGAACATCACTCACATGAAGGAAAATTAAAAGTTGTAACTACAAACTCTATTCTCTATGACATGGTT
AAACGTGTCGGTGGAAATAAGGTCGATGTTCATAGCATCGTTCCAGTAGGACAAGACCCACATGAATAT
GAGGTTAAACCTAAAGATATTAAAGCATTAACAGATGCTGACGTTGTATTTTATAACGGTTTAAACCTA
GAAACTGGAAATGGTTGGTTTGAAAAAGCACTTGACCAAGCAGGAAAATCAACAAAAGATAAAAATGTG
ATAGCAGCATCAAATAATGTTAAACCAATATACTTAAATGGTGAGGAAGGTAACAAAAACAAACAAGAT
CCACATGCATGGTTAAGTTTAGAGAATGGAATTAAATACGTAAAAACAATACAAAAATCACTAGAACAT
CATGATAAAAAAGATAAGTCTACATATGAAAAACAAGGGAATGCATATATATCAAAATTAGAAGAACTT
AATAAAGATAGTAAAAATAAATTTGATGACATACCCAAAAATCAACGTGCCATGATGACAAGTGAAGGT
GCATTTAAATATTTTGCTCAACAATTCGATGTTAAACCAGGTTATATTTGGGAGATAAACACAGAAAAA
CAAGGTACACCTGGTCAAATGAAACAAGCCATTAAATTTGTTAAAGATAATCATTTAAAACATTTATTA
GTCGAAACAAGCGTAGATAAAAAAGCTATGCAAAGTTTATCAGAAGAAACTAAGAAAGATATTTATGGT
GAAGTATTTACCGACTCTATAGGTAAGGAAGGTACTAAAGGTGACTCATACTATAAAATGATGAAATCT
AATATTGATACAATACATGGTAGTATGAAATAA

SEQ ID NO:43 polynucleotide sequence
ATGAAAAAGACAATTATGGCATCATCATTAGCAGTGGCATTAGGTGTAACAGGTTACGCAGCAGGTACA
GGACATCAAGCACACGCTGCTGAAGTAAACGTTGATCAAGCACACTTAGTTGACTTAGCGCATAATCAC
CAAGATCAATTAAATGCAGCTCCAATCAAAGATGGTGCATATGACATCCACTTTGTAAAAGATGGTTTC
CAATATAACTTTACTTCAAATGGTACTACATGGTCATGGAGCTATGAAGCAGCTAATGGTCAAACTGCT
GGTTTCTCAAACGTTGCAGGTGCAGACTACACTACTTCATACAACCAAGGTTCAGATGTACAATCAGTA
AGCTACAATGCACAATCAAGTAACTCAAACGTTGAAGCTGTTTCAGCTCCAACTTACCATAACTACAGC
ACTTCAACTACTTCAAGTTCAGTGAGATTAAGCAATGGTAATACTGCAGGTGCTACTGGTTCATCAGCA
GCTCAAATCATGGCTCAACGTACTGGTGTTTCAGCTTCTACATGGGCTGCAATCATCGCTCGTGAATCA
AATGGTCAAGTAAATGCTTACAACCCATCAGGTGCTTCAGGTTTATTCCAAACTATGCCAGGTTGGGGT
CCGACAAACACTGTTGACCAACAAATCAACGCAGCTGTTAAAGCATACAAAGCACAAGGTTTAGGTGCT
TGGGGATTCTAA

SEQ ID NO:44 polynucleotide sequence
ATGAAAAAAACAGTTATCGCTTCTACATTAGCAGTATCTTTAGGAATTGCAGGTTACGGTTTATCAGGA
CATGAAGCACACGCTTCAGAAACTACAAACGTTGATAAAGCACACTTAGTAGATTTAGCACAACATAAT
CCTGAAGAATTAAATGCTAAACCAGTTCAAGCTGGTGCTTACGATATTCATTTCGTAGACAATGGATAC
CAATACAACTTCACTTCAAATGGTTCTGAATGGTCATGGAGCTACGCTGTAGCTGGTTCAGATGCTGAT
TACACAGAATCATCATCAAACCAAGAAGTAAGTGCAAATACACAATCTAGTAACACAAATGTACAAGCT
GTTTCAGCTCCAACTTCTTCAGAAAGTCGTAGCTACAGCACATCAACTACTTCATACTCAGCACCAAGC
CATAACTACAGCTCTCACAGTAGTTCAGTAAGATTATCAAATGGTAATACTGCTGGTTCTGTAGGTTCA
TATGCTGCTGCTCAAATGGCTGCACGTACTGGTGTATCTGCTTCAACATGGGAACACATCATTGCTAGA
GAATCAAATGGTCAATTACATGCACGTAATGCTTCAGGTGCTGCTGGATTATTCCAAACTATGCCAGGT
TGGGGTTCAACTGGTTCAGTAAATGATCAAATCAATGCCGCTTATAAAGCATATAAAGCACAAGGTTTA
TCTGCTTGGGGTATGTAA

SEQ ID NO:45 polynucleotide sequence
GTGAATTATCGTGATAAAATTCAAAAGTTTAGTATTCGTAAATATACAGTTGGTACATTTTCAACTGTC
ATTGCGACATTGGTATTTTTAGGATTCAATACATCACAAGCACATGCTGCTGAAACAAATCAACCAGCA
AGCGTGGTTAAACAGAAACAACAAAGTAATAATGAACAGACTGAGAATCGAGAATCTCAAGTACAAAAT
TCTCAAAATTCACAAAATAGTCAATCATTATCCGCTACTCATGAAAATGAGCAACCAAATAATAGTCAA
GCTAATTTAGTAAATCAAAAAGTAGCGCAATCATCTACTACTAATGATGAACAACCAGCATCTCAAAAT
GTAAATACAAAGAAAGATTCGGCAACGGCTGCGACAACACAACCAGATAAAGAAGAAAGTAAGCATAAA
CAAAACGAAAGTCAATCTGCTAATAAAAATGGAAACGACAATAGAGCGGCTCATGTAGAAAATCATGAA
GCAAATGTAGTAACAGCTTCAGATTCATCTGATAATGGTAACGTACAACATGACCGAAATGAATTACAA
GCATTTTTTGATGCAAATTATCATGATTATCGCTTTATTGACCGTGAAAATGCAGATTCTGGCACATTT
AACTATGTAAAAGGCATTTTTGACAAGATTAATACTTTATTAGGCAGTAATGATCCAATTAACAATAAA
GACTTGCAACTTGCATACAAAGAATTGGAACAAGCTGTTGCTTTAATTCGTACAATGCCTCAACGTCAA
CAAACTAGCCGTCGATCAAACAGAATTCAAACGCGTTCTGTTGAGTCTAGAGCTGCAGAGCCTAGATCA
GTATCAGACTATCAAAATGCAAATTCATCATATTATGTTGAAAATGCTAATGATGGTTCAGGATATCCT
GTAGGTACATATATCAATGCTTCTAGTAAAGGGGCGCCATATAATTTACCAACTACACCATGGAATACA

FIG. 2E

SEQ ID NO:45 (continued)

TTGAAGGCCTCTGACTCAAAGGAAATTGCTCTTATGACAGCGAAACAAACTGGAGATGGCTACCAATGG
GTTATTAAGTTTAATAAAGGACATGCTCCACATCAAAATATGATTTTCTGGTTTGCATTACCAGCAGAC
CAAGTGCCAGTAGGAAGAACTGACTTTGTAACAGTTAATTCAGATGGAACAAATGTACAATGGAGTCAT
GGAGCAGGAGCAGGTGCAAATAAACCACTTCAACAAATGTGGGAATATGGAGTAAATGATCCTGATCGT
TCACATGACTTTAAAATAAGAAATAGAAGTGGCCAAGTAATATATAGCTGGCCAACTGTCCATGTTTAT
TCTTTAGAAGATTTATCTAGAGCGAGTGATTATTTTAGTGAAGCTGGAGCGACACCTGCTACTAAAGCA
TTTGGTAGACAAAATTTTGAATATATTAATGGTCAAAAACCTGCTGAATCACCGGGTGTTCCTAAAGTT
TATACTTTCATCGGTCAAGGTGATGCAAGTTATACAATTTCATTTAAAACACAAGGTCCAACTGTTAAT
AAATTGTATTATGCAGCAGGTGGGCGTGCTTTAGAGTACAATCAATTATTTATGTACAGTCAACTATAC
GTCGAATCAACGCAAGACCATCAACAACGTCTTAATGGTTTAAGACAAGTGGTTAATCGTACATATCGC
ATAGGTACAACTAAACGTGTAGAAGTGAGTCAAGGAAATGTACAAACGAAAAAGGTATTAGAAAGTACA
AACCTAAATATAGATGATTTTGTTGATGATCCTTTAAGTTATGTTAAGACGCCGAGTAATAAAGTGTTA
GGTTTTTACCCAACTAATGCAAATACTAACGCTTTTAGACCGGGGGGCGTTCAAGAATTAAATGAATAT
CAATTAAGTCAATTATTTACTGATCAAAAATTACAAGAAGCAGCAAGAACTAGAAACCCAATAAGATTA
ATGATTGGTTTCGACTATCCTGATGGTTATGGTAATAGTGAAACTTTAGTTCCTGTTAACTTAACGGTA
TTACCTGAAATCCAACATAATATTAAATTCTTTAAAAATGACGATACTCAAAATATTGCTGAAAAACCA
TTTTCAAAACAAGCTGGGCATCCAGTTTTCTATGTATATGCAGGTAACCAAGGGAATGCTTCCGTGAAT
TTAGGTGGTAGCGTAACATCTATTCAACCATTACGTATTAATTTAACAAGTAATGAGAATTTTACAGAT
AAAGATTGGCAAATTACAGGTATTCCGCGTACATTACACATTGAAAACTCGACAAATAGAACTAATAAT
GCTAGAGAACGTAACATTGAACTTGTTGGTAATTTATTACCAGGGGATTACTTTGGTACGATACGTTTT
GGACGTAAAGAACAATTATTTGAAATTCGTGTTAAACCACATACACCAACAATTACAACGACAGCTGAG
CAATTAAGAGGTACAGCATTACAAAAAGTGCCTGTTAATATTTCGGGAATACCGTTGGATCCATCGGCA
TTGGTTTATTTAGTTGCACCAACAAATCAAACTACGAATGGTGGTAGTGAGGCAGATCAAATACCATCT
GGTTATACGATACTTGCGACTGGTACACCTGATGGGGTGCATAATACAATTACTATACGACCGCAAGAT
TATGTTGTATTCATACCACCTGTAGGTAAACAAATTAGAGCAGTAGTTTATTATAATAAAGTAGTTGCA
TCTAATATGAGTAATGCTGTTACTATTTTGCCAGATGACATTCCACCAACAATCAATAATCCTGTTGGA
ATAAATGCCAAATACTATCGAGGCGACGAAGTCAACTTTACAATGGGAGTCTCTGATAGACATTCTGGT
ATAAAAAATACAACTATTACTACTTTGCCAAGTGGTTGGACATCAAATTTAACTAAATCCGACAACAAA
AACGGCTCATTAGCTATTACAGGTAGAGTCTCTATGAATCAGGCATTTAACAGTGATATTACATTTAAA
GTATCAGCGACAGACAATGTCAATAATACGACAAATGATAGTCAATCTAAACATGTGTCAATTCATGTA
GGTAAAATTAGTGAAGATGCTCATCCGATTGTATTAGGAAATACTGAGAAAGTTGTAGTAGTCAATCCG
ACTGCTGTATCTAATGATGAAAAGCAAAGCATAATTACTGCCTTTATGAATAAAAACCAAAATATAAGA
GGATATTTAGCATCAACTGATCCAGTAACTGTCGATAATAATGGTAACGTCACATTACATTACCGTGAT
GGCTCATCAACAACGCTTGATGCTACAAATGTGATGACATACGAACCAGTTGTGAAATCTGAATATCAA
ACTGCCAATGCTGCTAAAACAGCAACGGTAACGATTGCTAAAGGACAATCATTTAATATTGGTGATATT
AAACAATATTTTACTTTAAGTAATGGACAAGCTATTCCAAATGGCACATTTACAAATATTACATCTGAT
AGAACTATTCCAACTGCACAAGAAGTTAGTCAAATGAATGCAGGTACGCAGTTATATCATATAGTTGCT
TCAAATGCATATCATAAAGACACTGAAGATTTCTATATTAGTTTAAAAATCGTTGATGTGAAACAACCT
GAAGGCGATCAACGTGTCTATCGTACGTCAACATATGATTTAACCACTGATGAAATCTCAAAAGTAAAA
CAAGCTTTTATTAATGCAAATAGAGATGTAATTACGCTTGCCGAAGGTGATATTTCAGTTACAAATACA
CCTAATGGTGCTAATGTAAGTACTATTACAGTAAATATTAATAAAGGTCGATTAACGAAATCATTCGCG
TCTAACCTAGCTAATATGAATTTCTTGCGTTGGGTTAATTTCCCACAAGATTATACAGTGACATGGACG
AATGCAAAAATTGCAAACAGACCAACAGATGGTGGTTTATCATGGTCCGATGACCATAAATCTTTAATT
TATCGTTATGATGCTACATTAGGCACACAAATTACAACTAATGATATTTTAACGATGCTAAAAGCGACT
ACTACAGTGCCTGGATTGCGTAATAATATTACTGGTAATGAAAAAGCACAAGCAGAAGCAGGTGGAAGA
CCAAACTATAGAACAACTGGTTATTCACAATCAAATGCGACAACTGATGGTCAACGTCAATTTACGTTG
AATGGTCAAGTGATTCAAATATTAGACATCATCAACCCTTCAAACGGTTATGGTGGCAACCTGTTACA
AATTCAAATACTCGTGCAAACCATAGTAACTCAACTGTTGTTAACGTAAACGAACCGGCAGCTAATGGT
GCTGGCGCATTTACAATTGACCACGTTGTAAAAAGTAATTCTACACATAATGCAAGTGATGCAGTTTAT
AAAGCGCAGTTATACTTAACGCCATATGGTCCAAAACAATATGTTGAACATTTAAATCAAAATACAGGA
AATACTACTGACGCTATTAACATTTATTTTGTACCAAGTGACTTAGTGAATCCAACAATTTCAGTAGGT
AATTACACTAATCATCAAGTGTTCTCAGGTGAAACATTTACAAATACGATTACAGCGAATGATAACTTT
GGTGTGCAATCGGTAACTGTACCAAATACATCACAAATTACAGGTACTGTTGATAATAACCATCAACAT
GTTTCTGCAACGGCACCAAATGTGACATCAGCAACTAGTAAGACAATCAATTTATTAGCAACTGATACA
AGTGGTAATACAGCTACAACTTCATTCAATGTAACAGTGAAACCTTTGCGTGATAAATATCGAGTTGGT
ACTTCATCAACGGCTGCTAATCCTGTTAGAATTGCCAATATTTCGAATAATGCGACAGTATCACAAGCT
GATCAAACGACAATTATTAATTCGTTAACGTTTACAAGTAATGCACCAAATAGAAACTATGCAACAGCA
AGCGCAAATGAAATCACTAGTAAAACAGTTAGTAATGTCAGTCGTACTGGAAATAATGCCAATGTCACA

FIG. 2F

SEQ ID NO:45 (continued)

GTAACTGTTACTCATCAAGATGGAACAACATCAACAGTGACTGTACCTGTAAAGCATGTCATTCCAGAA
ATCGTTGCACATTCGCATTACACTGTACAAGGCCAAGACTTCCCAGCAGGTAATGGTTCTAGTGCAGCA
GATTACTTTAAGTTATCTAATGGTAGTGCCATTCCAGATGCAACGATTACATGGGTAAGTGGACAAGCG
CCAAATAAAGATAATACACGTATTGGTGAAGATATAACAGTAACTGCACATATCTTAATTGATGGCGAA
ACAACGCCGATTACGAAAACAGCAACATATAAAGTAGTAAGAACTGTACCGAAACATGTCTTTGAAACA
GCCAGAGGTGTTTTATACCCAGGTGTTTCAGATATGTATGATGCGAAACAATATGTTAAGCCAGTAAAT
AATTCTTGGTCGACAAATGCGCAACATATGAATTTTCAATTTGTTGGAACATATGGTCCTAACAAAGAT
GTTGTAGGTATATCAACGCGTCTTATTAGAGTGACTTATGATAATAGACAAACTGAAGATTTAACTATT
TTATCTAAAGTTAAACCTGACCCACCAAGAATTGACGCAAACTCTGTGACATATAAAGCAGGTCTTACA
AACCAAGAAATTAAAGTTAATAACGTATTAAATAACTCGTCAGTAAAATTATTTAAAGCAGATAATACA
CCATTAAATGTCACAAATATTACTCATGGTAGTGGTTTTAGTTCGGTTGTGACAGTAAGTGACGCGTTA
CCAAATGGCGGAATTAAAGCAAAATCTTCAATTTCAATGAACAATGTGACGTATACGACGCAAGACGAA
CATGGTCAAGTTGTTACAGTAACAAGAAATGAATCTGTTGATTCAAATGATAGTGCTTCTGTTACAGTA
ACACCACAATTACAAGCAACTACTGAAGGCGCTGTATTTATTAAAGGTGGCGACGGTTTTGATTTCGGT
CATGTAGAACGATTTATTCAAAATCCGCCACATGGGGCAACGGTCGCATGGCATGATAGTCCAGATACA
TGGAAGAATACAGTCGGCAACACACATAAAACTGCGGTTGTAACATTACCTAGTGGTCAAGGTACGCGT
AATGTTGAAGTTCCAGTCAAAGTTTATCCAGTTGCTAATGCTAAGGCGCCATCACGTGATGTGAAAGGT
CAAAATTTGACACATGGTACAAACGCTATTGATTACATTACATTTGATCCAAATACTAATACGAATGGT
ATTACAGCAGCATGGGCAAATAGACAACAACCAAATAACCAGCAAGCAGGCGTTCAACATTTAAATGTC
GATGTCACATATCCAGGTATTTCAGCTGCTAAACGAGTTCCTGTAACTGTGAACGTATATCAATTTGAA
TTCCCTCAAACTACTTATACAACAACAGTTGGTGGCACTTTAGCAAGTGGTACGCAAGCATCAGGATAT
GCACATATGCAAAACGCTTCAGGTTTACCAACAGATGGATTTACGTATAAATGGAATCGTGATACTACG
GGTACAAACGATGCAAACTGGGCAGCAATGAATAAACCAAATACTGCACAAGTCGTTAATGCAAAATAT
GATGTCATCTATAATGGACATACATTTGCAACATCTTTACCAGCGAAATTTGTAGTAAAAGATGTTCAA
CCAGCGAAACCAACTGTCACTGAAACAGCGGCAGGAGCGATTACAATTGCACCTGGTGCGAACCAAACA
GTCAATACTCATGCTGGTAATGTTACGACATATGCTGACAAATTAGTTATTAAACGTAATGGAAATGTT
GTAACGACATTTACACGTCGTAATAATACGAGCCCATGGGTGAAAGAAGCATCAGCAGATAATGTAACA
GGTATTGTTGGAACTAATAATGGTATTACTGTGGCAGCAGGTACTTTCAATCCTGCTGATACAATTCAA
GTTGTTGCAACACAAGGTAGTGGCGAAACAATCAGTGACGAGCAACGTAGTGATGATTTCACAGTTGTC
GCACCACAACCGAACCAAGCGACTACGAAAATTTGGCAAAATGGTCATATTGATATCACGCCTAATAAT
CCATCAGGACATTTAATTAATCCAACACAAGCAATGGATATTGCTTACACTGAAAAAGTGGGTAATGGT
GCAGAACATAGTAAGACAATTAATGTTGTTCGTGGTCAAAATAATCAATGGACAATTGCGAATAAGCCT
GACTATGTAACGTTAGATGCACAAACTGGTAAAGTGACGTTCAATGCCAATACTATAAAACCAAATTCA
TCAATCACAATTACTCCGAAAGCAGGTACAGGTCACTCAGTAAGTAGTAATCCAAGTACATTAACTGCA
CCGGCAGCTCATACTGTCAACACAACTGAAATTGTGAAAGATTATGGTTCAAATGTAACAGCAGCTGAA
ATTAACAATGCAGTTCAAGTTGCTAATAAACGTACTGCAACGATTAAAAATGGCACAGCAATGCCTACT
AATTTAGCTGGTGGTAGCACAACGACGATTCCTGTGACAGTAACTTACAATGATGGTAGTACTGAAGAA
GTACAAGAGTCCATTTTCACAAAAGCGGATAAACGTGAGTTAATCACAGCTAAAAATCATTTAGATGAT
CCAGTAAGCACTGAAGGTAAAAAGCCAGGTACAATTACGCAGTACAATAATGCAATGCATAATGCGCAA
CAACAAATCAATACCGCGAAAACAGAAGCACAACAAGTGATTAATAATGAGCGTGCAACACCACAACAA
GTTTCTGACGCACTAACTAAAGTTCGTGCAGCACAAACTAAGATTGATCAAGCTAAAGCATTACTTCAA
AATAAAGAAGATAATAGCCAATTAGTAACGTCTAAAAATAACTTACAAAGTTCTGTGAACCAAGTACCA
TCAACTGCTGGTATGACGCAACAAAGTATTGATAACTATAATGCGAAGAAGCGTGAAGCAGAAACTGAA
ATAACTGCAGCTCAACGTGTTATTGACAATGGCGATGCAACTGCACAACAAATTTCAGATGAAAAACAT
CGTGTCGATAACGCATTAACAGCATTAAACCAAGCGAAACATGATTTAACTGCAGATACACATGCCTTA
GAGCAAGCAGTGCAACAATTGAATCGCACAGGTACAACGACTGGTAAGAAGCCGGCAAGTATTACTGCT
TACAATAATTCGATTCGTGCACTTCAAAGTGACTTAACAAGTGCTAAAAATAGCGCTAATGCTATCATT
CAGAAGCCAATAAGAACAGTGCAAGAGGTACAATCTGCGTTAACAAATGTAAATCGTGTCAATGAGCGA
TTAACGCAAGCAATTAATCAATTAGTACCTTTAGCTGATAATAGTGCTTTAAGAACTGCTAAGACGAAA
CTTGATGAAGAAATCAATAAATCAGTAACTACTGATGGTATGACACAATCATCAATCCAAGCATATGAA
AATGCTAAACGTGCAGGTCAAACAGAAACAACAAATGCACAAAATGTTATTAACAATGGTGACGCGACA
GACCAACAAATTGCCGCAGAAAAAACAAAAGTAGAAGAAAAATATAATAGCTTAAAACAAGCAATTGCT
GGATTAACACCAGACTTGGCACCATTACAAACTGCAAAAACTCAGTTGCAAAATGATATTGATCAGCCA
ACGAGTACGACTGGTATGACAAGCGCATCTGTTGCTGCATTTAATGACAAACTTTCAGCAGCTAGAACT
AAAATTCAAGAAATTGATCGCGTACTAGCATCTCATCCAGATGTAGCAACGATTCGTCAAAACGTGACA
GCAGCGAATGCTGCTAAAACAGCACTTGATCAAGCGCGCAATGGCTTAACAGTCGATAAAGCACCTTTA
GAAAATGCGAAAAATCAACTACAACATAGTATTGATACGCAAACAAGTACAACTGGTATGACACAAGAC
TCTATAAATGCATACAATGCGAAGTTAACAGCTGCACGTAATAAGGTTCAACAAATCAATCAAGTATTA

FIG. 2G

SEQ ID NO:45 (continued)

GCAGGTTCACCTACTGTAGATCAAATTAATACAAATACGTCTGCAGCAAATCAAGCGAAATCTGATTTA
GATCATGCACGTCAAGCGTTAACACCAGATAAAGCGCCGCTTCAAAATGCGAAAACGCAATTAGAACAA
AGCATTAATCAACCAACAGATACAACAGGTATGACAACCGCTTCGTTAAATGCATACAACCAAAAATTA
CAAGCAGCACGTCAAAAGTTAACTGAAATTAATCAAGTGTTGAATGGCAACCCAACTGTCCAAAATATC
AATGATAAAGTGGCAGAGGCAAACCAAGCTAAGGATCAATTAAATACAGCACGTCAAGGTTTAACATTA
GATAGACAGCCAGCGTTAACAACATTACATGGTGCATCTAACTTAAACCAAGCACAACAAAATAATTTC
ACGCAACAAATTAATGCTGCTCAAAATCATGCTGCGCTTGAAACAATTAAGTCTAACATTACGGCTTTA
AATACTGCGATGACGAAATTAAAAGACAGTGTTGCGGATAATAATACAATTAAATCAGGTCAAAATTAC
ACTGACGCAACACCAGCTAATAAACAAGCCTATGATAATGCAGTTAATGCGGCTAAAGGTGTCATTGGA
GAAACGACTAATCCAACGATGGATGTTAACACAGTGAACCAAAAAGCAGCATCTGTTAAATCGACGAAA
GATGCTTTAGATGGTCAACAAAACTTACAACGTGCGAAAACAGAAGCAACAAATGCGATTACGCATGCA
AGTGATTTAAACCAAGCACAAAAGAATGCATTAACACAACAAGTGAATAGTGCACAAAACGTGCAAGCA
GTAAATGATATTAAACAAACGACTCAAAGCTTAAATACTGCTATGACAGGTTTAAAACGTGGCGTTGCT
AATCATAACCAAGTCGTACAAAGTGATAATTATGTCAACGCAGATACTAATAAGAAAAATGATTACAAC
AATGCATACAACCATGCGAATGACATTATTAATGGTAATGCACAACATCCAGTTATAACACCAAGTGAT
GTTAACAATGCTTTATCAAATGTCACAAGTAAAGAACATGCATTGAATGGTGAAGCTAAGTTAAATGCT
GCGAAACAAGAAGCGAATACTGCATTAGGTCATTTAAACAATTTAAATAATGTACAACGTCAAAACTTA
CAATCGCAAATTAATGGTGCGCATCAAATTGATGCAGTTAATACAATTAAGCAAAATGCAACAAACTTG
AATAGTGCAATGGGTAACTTAAGACAAGCTGTTGCAGATAAAGATCAAGTGAAACGTACAGAAGATTAT
GCGGATGCAGATACAGCTAAACAAAATGCATATAACAGTGCAGTTTCAAGTGCTGAAACAATTATTAAT
CAAACAGCTAATCCGACAATGTCTGTTGATGATGTTAATCGTGCAACTTCAGCTGTTACTACTAATAAA
AATGCATTAAATGGTGATGAAAAATTAGTACAATCTAAAACAGATGCTGCAAGAGCAATTGATGCATTA
CCACATTTAAATAATGCACAAAAAGCAGATGTTAAATCTAAAATTAATGCTGCATCAAATATTGCTGGT
GTAAATACCGTTAAACAACAAGGTACAGATTTAAATACAGCGATGGGTAACTTGCAGGGTGCAATCAAT
GATGAACAAACGACGCTTAATAGTCAAAATTATCAAGATGCGACACCTAGTAAGAAAACAGCATACACA
AATGCGGTGCAAGCTGCGAAAGATATTTTAAATAAATCAAATGGTCAAAATAAAACGAAAGATCAAGTT
ACTGAAGCGATGAATCAAGTGAATTCGGCTAAAAATAACTTAGATGGTACGCGTTTATTAGATCAAGCG
AAGCAAACAGCGAAACAGCAGTTAAATAATATGACGCATTTAACAACTGCACAAAAAACGAATTTAACA
AATCAAATTAATAGTGGTACTACTGTTGCTGGTGTTCATACGGTTCAATCAAATGCCAACACATTAGAT
CAAGCGATGAATACGTTAAGACAAAGTATTGCTAACAATGATGCGACTAAAGCAAGTGAAGATTACGTA
GATGCTAATAATGATAAGCAAACAGCATATAACAACGCGGTAGCTGCTGCTGAAACGATTATTAATGCG
AATAGTAATCCAGAAATGAATCCAAGTACGATTACACAAAAAGCAGAGCAAGTGAATAGTTCTAAAACG
GCACTTAACGGTGATGAAAACTTAGCTACGGCAAAACAAAATGCGAAAACGTACTTAAACACATTAACG
AGTATTACAGATGCTCAAAAGAACAATTTGATTAGTCAAATTAGTAGTGCGACAAGAGTGAGTGGTGTT
GATACTGTAAAACAAAATGCACAACATTTAGATCAAGCTATGGCTAACTTACAAAATGGTATTAACAAC
GAATCTCAAGTGAAATCATCTGAGAAATATCGTGATGCTGATACAAATAAACAACAAGAGTATGATAAT
GCTATTACTGCAGCGAAAGCGATTTTAAATAAATCGACAGGTCCAAACACTGCGCAAAATGCAGTTGAA
GCAGCATTGCAACGTGTTAATACTGCGAAAGATGCATTGAATGGTGATGCAAAATTAATTGCAGCTCAA
AACGCAGCGAAACAACATTTAGGTACTTTAACGCATATCACTACAGCACAACGCAATGATTTAACAAAT
CAAATTTCA

SEQ ID NO:46 polynucleotide sequence

ATGGGTAACTTACAAACGGCTATCAACGATAAGTCAGGAACATTAGCGAGCCAAAACTTCTTGGATGCT
GATGAGCAAAAACGTAATGCTTACAATCAAGCTATATCAGCTGCCGAAACCATTTTAAATAAACAAACT
GGACCGAATACAGCGAAAACAGCGGTTGAACAAGCACTTAATAATGTTAATAGTGCGAAACATGCATTA
AATGGTACGCAAAACTTAAATAATGCGAAACAAGCAGCGATTACAGCAATTAATGGCGCATCTGATTTA
AATCAAAAACAAAAAGATGCATTAAAAGCACAAGCTAATGGTGCTCAACGCGTATCTAATGCAAATGAT
GTACAACGTAATGCGACTGAACTGAACACGGCAATGGGTCAATTACAACATGCCATCGCAGATAAGACG
AATACGTTAGCAAGCAGTAAATATGTCAACGCCGATAGCACTAAACAAAATGCTTACACAACTAAAGTT
ACCAATGCTGAACATATTATTAGCGGTACGCCAACGGTTGTTACAACACCTTCAGAAGTAACAGCTGCA
GCTAATCAAGTAAACAGCGCGAAACAAGAATTAAATGGTGACGAAAGATTACGTGTTGCAAAACAAAAC
GCCAATACTGCTATTGATGCATTAACGCAATTAAATACTCCTCAAAAAGCTAAATTAAAAGAACAAGTG
GGACAAGCCAATAGATTAGAAGACGTACAATCTGTTCAAACAAATGGACAATCATTGAACAATGCAATG
AAAGGCTTAAGAGATAGTATTGCTAACGAAACAACAGTCAAAGCAAGTCAAAACTATACAGACGCAAGT
CCGAATAACCAATCAACATATAATAGCGCTGTGTCAAATGCGAAAGGTATCATTAATCAAACTAACAAT
CCAACTATGGATACTAGTGCGATTACCCAAGCTACAACACAAGTGAATAATGCTAAAAATGGTTTAAAC
GGTGCTGAAAACTTAAGAAATGCACAAAACACTGCTAAGCAAAACTTAAATACGTTATCACACTTAACA
AATAACCAAAAAATCTGCAATCTCATCACAAATTGATCGTGCAGGTCATGTGAGTGAGGTAACAGCTGCT

FIG. 2H

SEQ ID NO:46 (continued)

AAAAATGCAGCAACTGAGTTAAACGCGCAAATGGGCAACTTGGAACAAGCTATCCATGATCAAAACACA
GTTAAACAAGGTGTTAACTTCACTGATGCAGATAAAGCTAAACGTGATGCTTATACAAATGCGGTAAGC
AGAGCAGAAACAATTCTGAATAAAACGCAAGGTGCAAATACGTCTAAACAAGATGTTGAAGCGGCTATT
CAAAATGTTACAAGTGCTAAAAATGCATTGAATGGTGATCAAAACGTTACAAATGCGAAGAATGCAGCT
AAAAATGCATTAAATAACTTAACGTCAATTAATAATGCACAAAAACGTGACTTAACAACTAAAATTGAT
CAAGCAACAACAGTAGCTGGTGTTGAAGCGGTATCTAATACAGGTACACAATTGAATACAGCGATGGCT
AACTTGCAAAATGGTATTAATGATAAAGCGAATACTTTAGCGAGCGAAAACTATCATGATGCTGATTCA
GATAAGAAAACTGCTTATACTCAAGCCGTTACGAACGCAGAAAATATTTTAAATAAAAATAGTGGATCA
AATTTAGATAAAGCTGCCGTTGAAAACGCGTTGTCACAAGTGACAAATGCGAAAGGTGCCCTAAATGGT
AACCATAATTTAGAGCAAGCTAAATCAAATGCAAACACTACTATAAACGGCCTTCAACATTTAACAACA
GCACAAAAAGATAAATTGAAACAACAAGTGCAACAAGCACAAAATGTTGCAGGTGTAGATACTGTTAAA
TCAAGTGCCAACACATTAAATGGTGCTATGGGTACGTTAAGAAATAGCATACAAGATAACACAGCTACG
AAAAATGGCCAAAACTATCTTGATGCTACAGAACGTAACAAAACAAACTATAACAATGCTGTTGATAGT
GCTAATGGTGTCATTAATGCAACAAGCAATCCAAATATGGATGCTAATGCAATTAACCAAATCGCTACA
CAAGTGACATCAACGAAAAATGCATTAGATGGTACACATAATTTAACGCAAGCGAAACAAACAGCAACA
AATGCCATCGATGGTGCTACTAACTTAAATAAAGCGCAAAAAGATGCGTTAAAAGCACAAGTTACAAGT
GCGCAACGTGTTGCAAATGTAACAAGTATCCAACAAACTGCAAATGAACTTAATACAGCTATGGGTCAA
TTACAACATGGTATTGATGATGAAAATGCAACAAAACAAACTCAAAAATATCGTGACGCTGAACAAAGT
AAGAAAACTGCTTATGATCAAGCTGTAGCTGCTGCGAAAGCAATTTTAAATAAACAAACAGGTTCCAAT
TCAGATAAAGCAGCAGTTGACCGTGCATTACAACAAGTAACAAGTACGAAAGATGCATTGAATGGGGAT
GCTAAACTGGCAGAAGCGAAAGCGGCAGCTAGACAAAACTTAGGTACTTTAAACCATATTACGAATGCA
CAACGTACTGCGTTAGAAGGTCAAATCAATCAAGCGACGACTGTTGATGGCGTTAATACTGTAAAAACA
AATGCCAATACATTAGACGGCGCTATGAATAGCTTACAAGGTGCAATCAATGATAAAGATGCGACATTA
AGAAATCAAAATTATCTTGATGCAGATGAATCAAAACGAAATGCATATACGCAAGCTGTCACAGCGGCT
GAAGGCATTTTAAATAAACAAACAGGTGGTAACACATCTAAAGCAGACGTTGATAATGCATTAAATGCA
GTTACAAGAGCGAAAGCGGCTTTAAATGGTGCTGAAAACTTAAGAAATGCGAAAACTTCAGCAACAAAT
ACGATTAATGGTTTACCTAACTTAACACAATTACAAAAAGACAACTTGAAGCATCAAGTTGAACAAGCG
CAAAATGTAGTTGGTGTAAATGGTGTTAAAGATAAAGGTAATACATTAAATACTGCCATGGGTGCATTA
CGTACAAGTATCCAAAATGATAATACGACGAAAACAAGTCAAAATTATCTTGATGCATCTGATAGCAAC
AAAAATAATTACAATACTGCTGTAAATAATGCAAATGGTGTTATTAATGCAACGAACAATCCAAATATG
GATGCTAATGCGATTAATGACATGGCAAATCAAGTCAATACAACAAAAGCAGCGTTAAATGGTGCACAA
AACTTAGCTCAAGCTAAAACAAATGCGACGAACACAATTAACAACGCGCAAGACTTAAACCAAAAACAA
AAAGATGCATTAAAAACACAAGTTAACAATGCACAACGTGTATCTGATGCAAATAACGTTCAACATACA
GCTACTGAATTGAACGGTGCGATGACAGCACTTAAAGCAGCTATTGCGGATAAAGAAAGAACAAAAGCA
AGCGGTAATTATGTCAATGCTGATCAAGAAAAACGTCAAGCGTATGATTCAAAAGTGACTAACGCTGAA
AATATCATTAATGGTACACCAAATGCGACATTAACAGTCAATGACGTAAATAGTGCGGCATCACAAGTC
AATGCGGCTAAAACAGCATTAAATGGTGATAACAACTTACGTGTAGCGAAAGAGCATGCTAACAATACA
ATTGACGGCTTAGCACAATTGAATAATGTACAAAAAGCAAAATTAAAAGAACAAGTTCAAAGTGCAACT
ACATTAGATGGTGTTCAAACTGTTAAAAATAGTTCTCAAACGTTGAATACAGCGATGAAAGGCTTAAGA
GATAGTATTGCGAATGAAGCAACGATTAAAGCAGGTCAAAACTACACTGACGCAAGTCCAAATAATCGT
AACGAGTACGACAGCGCAGTTACTGCAGCAAAAGCAATCATTAATCAAACATCGAACCCAACGATGGAA
CCAAATACTATTACGCAAGCAACATCACAAGTGACAACTAAAGAACATGCATTAAATGGTGCGCAAAAC
TTAGCTCAAGCTAAGACAACAGCGAAAAACAACTTGAATAACTTAACATCAATTAACAATGCACAAAAA
GATGCGTTAACGCGTAACATTGATGGTGCAACTACAGTAGCTGGTGTAAATCAAGAAACTGCAAAAGCA
ACAGAATTAAATAACGCAATGCACAGTTTACAAAATGGTATCAATGATGAGACACAAACAAAACAAACT
CAGAAATACCTAGATGCTGAGCCAAGTAAGAAATCAGCTTATGATCAAGCAGTAAATGCAGCAAAAGCA
ATTTTAACAAAAGCTAGTGGTCAAAATGTAGACAAAGCAGCAGTTGAACAAGCATTACAAAATGTGAAC
AGTACGAAGACGGCGTTGAACGGTGATGCGAAATTAAATGAAGCTAAAGCTGCTGCGAAACAAACGTTA
GGTACATTAACACACATTAATAATGCACAACGTAATGCGTTAGATAATGAAATTACACAAGCAACAAAT
GTTGAAGGTGTTAATACAGTTAAAGCCAAAGCGCAACAATTAGATGGTGCTATGGGTCAATTAGAAACA
TCAATTCGTGATAAAGACACGACGTTACAAAGTCAAAATTATCAAGATGCTGATGATGCTAAACGAACG
GCTTATTCTCAAGCAGTAAATGCAGCAGCAACTATTTTAAATAAAACAGCTGGAGGAAATACACCTAAA
GCAGATGTCGAAAGAGCAATGCAAGCTGTTACACAAGCCAATACTGCATTAAACGGTATTCAAAACTTA
GAACGTGCGAAACAGGCTGCGAACACAGCGATTACAAATGCTTCGGACTTAAATACAAAACAAAAAGAA
GCATTGAAAGCACAAGTAACAAGTGCAGGACGCGTATCTGCAGCAAATGGTGTTGAACATACTGCGACT
GAATTAAATACTGCGATGACAGCTTTAAAACGTGCCATTGCTGATAAAGCTGACACAAAAGCTAGTGGT
AATTATGTCAATGCTGATGCGAATAAACGCCAAGCATATGATGAAAAAGTGACAGCTGCAGAACATATC
GTTAGTGGTACACCAACACCAACGTTAACACCATCAGATGTTACAAATGCAGCAACGCAAGTAACGAAT

FIG. 2I

SEQ ID NO:46 (continued)

GCGAAGACGCAGTTAAACGGTAATCATAATTTAGAAGTAGCGAAACAAAATGCTAACACAGCAATTGAT
GGTTTAACTTCTTTAAATGGTCCGCAAAAAGCAAAACTTAAAGAACAAGTGGGTCAAGCGACGACGTTG
CCAAATGTTCAAACTGTTCGTGATAATGCACAAACATTAAACACTGCAATGAAAGGTCTACGAGATAGC
ATTGCGAATGAAGCAACGATTAAAGCAGGTCAAAACTACACAGATGCAAGTCAAAACAAACAAAATGAC
TACAACAATGCAGTCACTGCAGCAAAAGCAATCATTGGTCAAACAACTAGTCCATCAATGATTGCGCAA
GAAATTAATCAAGCGAAAGACCAAGTGACAGCTAAACAACAAGCGTTAAACGGTCAAGAAAACTTAAGA
ACTGCGCAAACAAATGCGAAGCAACATTTGAATGGCTTAAGTGACTTAACTAATGCACAAAAAGATGCA
GCGAAACGCCAAATCGAAGGTGCAACGCATGTTAATGAAGTAACACAAGCGCAAAATAATGCGGACGCA
TTAAATACAGCTATGACGAACTTGAAAAATGGTATTCAAGATCAAAATACGATTAAGCAAGGTGTTAAC
TTCACTGATGCAGATGAAGCGAAACGTAATGCATATACAAATGCAGTGACGCAAGCTGAACAAATTTTA
AATAAAGCACAAGGTCCAAATACTGCAAAAGACGGTGTCGAAACTGCGTTACAAAATGTACAACGTGCT
AAAAACGAATTGAACGGTAATCAAAATGTTGCGAACGCTAAGACAACTGCGAAAAATGCATTGAATAAC
CTTACATCAATTAATAATGCACAAAAAGCAGCATTGAAATCACAAATTGAAGGTGCGACAACAGTTGCA
GGTGTAAATCAAGTGTCTACAATGGCATCTGAATTAAATACTGCAATGAGCAACTTACAACGTGGTATT
AATGACGAAGCAGCTACAAAAGCAGCTCAGAAATATACTGAAGCAGATAGAGATAAACAAACTGCATAC
AATGATGCTGTAACAGCAGCTAAAACGTTATTAGATAAAACAGCTGGTTCAAATGACAATAAAGTAGCC
GTTGAACAAGCATTACAACGTGTGAATACTGCTAAAACAGCATTAAATGGTGACGCGCGATTAAATGAA
GCGAAGAACACAGCTAAACAACAATTAGCGACAATGTCACATTTAACTAATGCTCAAAAAGCAAACTTA
ACAGAACAAATTGAACGTGGTACAACTGTTGCTGGTGTTCAAGGCATCCAAGCAAATGCTGGTACTTTA
AATCAAGCAATGAATCAATTAAGACAAAGTATTGCTTCTAAAGATGCGACTAAATCAAGCGAAGATTAT
CAAGACGCGAATGCAGATTTACAAAATGCATACAATGATGCGGTAACTAATGCTGAAGGTATTATTAGT
GCAACGAATAACCCTGAAATGAATCCTGATACAATTAACCAAAAAGCGAGCCAAGTGAACAGTGCGAAG
TCTGCATTGAACGGTGATGAAAAATTAGCAGCAGTAAAACAAACTGCGAAATCAGATATCGGTCGTTTG
ACAGACTTGAACAATGCACAACGAACTGCGGCAAATGCTGAAGTGGATCAAGCACCAAATCTTGCAGCT
GTCACAGCGGCTAAAAATAAAGCAACATCGTTAAACACAGCGATGGGTAATTTGAAACATGCACTTGCT
GAAAAGGATAATACGAAACGTAGTGTCAATTACACAGATGCGGATCAACCAAAACAACAAGCGTATGAT
ACTGCAGTTACACAAGCAGAAGCAATTACTAATGCAAATGGCAGTAACGCGAATGAAACACAAGTTCAA
GCAGCGCTTAACCAATTGAATCAAGCTAAAAACGACTTGAATGGTGATAATAAAGTTGCTCAAGCGAAA
GAAACAGCAAAACGTGCATTAGCTTCATATAGTAACTTGAATAACGCGCAATCAACTGCAGCAACTAGT
CAAATTGACAATGCAACGACAGTAGCAGACGTAACTGCTGCACAAAATACTGCTAATGAATTAAATACA
GCAATGGGTCAACTTCAAAATGGTATTAATGACCAAAACACTGTTAAACAACAAGTGAACTTTACAGAT
GCTGACCAAGGTAAGAAAGATGCTTACACAAATGCTGTTACGAATGCTCAAGGTATTTTAGATAAAGCA
AACGGTCAAAATATGACAAAAGCACAAGTTGAAGCTGCATTAAATCAAGTAACGACTGCTAAGAATGCT
TTAAACGGTGATGCAAATGTAAGACAAGCAAAATCAGATGCGAAAGCAAACTTAGGTACATTAACACAC
TTAAATAATGCACAAAAACAAGATTTAACATCACAAATCGAAGGTGCAACAACAGTCAACGGTGTAAAT
AGTGTTAAAACGAAAGCACAAGACTTAGATGGTGCAATGCAACGATTAGAGTCAGCAATCGCAAATAAA
GATCAAACTAAAGCGAGCGAAAACTACATTGACGCAGATCCAACTAAGAAAACAGCATTTGATAATGCC
ATCACACAAGCTGAATCTTACTTAAATAAAGATCATGGTACGAATAAAGATAAGCAAGCTGTTGAACAA
GCAATTCAAAGTGTAACGTCTACTGAAAATGCTTTGAACGGTGACGCGAACTTACAATGCGCTAAAACT
GAAGCTACACAAGCTATCGATAACTTGACACAATTGAATACACCGCAAAAAACAGCATTGAAACAACAA
GTGAATGCTGCACAACGCGTATCAGGTGTAACTGATCTGAAAAATAGTGCTACATCACTTAATAATGCG
ATGGATCAATTAAAACAAGCAATTGGTGATCATGACACAATTGTAGCTGGTGGTAATTACACTAACGCA
AGTCCTGATAAACAAGGTGCTTACACTGATGCATATAATGCTGCGAAGAATATCGTAAATGGTTCACCT
AATGTGATTACAAATGCAGCAGATGTTACTGCGGCAACACAACGTGTCAATAATGCTGAAACAAGTTTA
AATGGTGATACAAACTTAGCAACTGCGAAGCAACAAGCTAAAGATGCATTACGTCAAATGACACATTTA
TCTGATGCACAAAAACAAAGTATTACTGGTCAAATTGATAGCGCGACACAAGTAACTGGTGTACAAAGT
GTGAAAGACAATGCAACAAATCTTGACAATGCAATGAATCAACTTCGAAATAGTATTGCGAATAAAGAT
GAAGTAAAAGCGAGTCAACCATATGTTGATGCAGATACAGATAAACAAAATGCATACAATACAGCAGTT
ACAAGTGCTGAAAATATCATTAATGCAACGAGTCAGCCAACACTTGATCCATCTGCAGTAACACAAGCA
GCTAATCAAGTGAACACTAACAAAACTGCGCTTAATGGTGCGCAAAACTTAGCAAATAAAAAGCAAGAA
ACAACTGCTAACATCAACCGATTAAGTCATTTAAACAATGCTCAAAAGCAAGATTTAAATACACAAGTG
ACAAATGCACCAAATATTAGCACAGTAAATCAAGTGAAAACTAAAGCTGAACAATTAGATCAAGCAATG
GAACGTTTAATCAACGGAATCCAAGACAAAGATCAAGTGAAACAAAGTGTTAACTTTACAGATGCAGAT
CCAGAAAAACAAACAGCATACAACAATGCGGTAACTGCTGCTGAAAATATTATTAATCAAGCAAATGGT
ACAAATGCGAACCAATCACAAGTTGAAGCAGCACTTTCAACTGTAACAACTACTAAACAAGCGTTGAAT
GGTGATAGAAAAGTAACAGATGCTAAAAACAATGCAAACCAAACATTATCTACGTTAGATAACTTAAAC
AATGCACAAAAAGGTGCTGTTACTGGAAACATCAATCAAGCGCACACTGTAGCTGAAGTAACGCAAGCC
ATTCAAACCGCTCAGGAACTGAATACAGCGATGGGTAACTTGAAAAATAGCTTGAATGATAAAGACACT

*FIG. 2J*

SEQ ID NO:46 (continued)

ACACTTGGCAGTCAAAACTTTGCAGATGCAGATCCAGAGAAGAAAAATGCATACAATGAAGCGGTTCGT
AATGCTGAAAATATTTTAAATAAATCTACAGGTACGAACGTGCCTAAAGATCAAGTTGAAGCAGCTATG
AATCAAGTGAATACTACAAAAGCAGCGCTTAATGGTACTCAAAACCTTGAAAAAGCGAAACAACACGCA
AATACAGCAATTGACGGTTTAAGCCATTTAACAAATGCACAAAAAGAGGCATTAAAACAATTGGTACAA
CAATCGACTACTGTTGCAGAAGCACAAGGTAATGAACAAAAAGCAAACAATGTTGATGCAGCAATGGAC
AAATTACGTCAAAGTATTGCAGATAATGCGACAACAAAACAAAACCAAAATTATACTGATGCAAGTCCG
AATAAAAAGGATGCGTACAATAATGCTGTCACAACTGCACAAGGTATTATTGATCAAACTACAAACCCT
TCATTAGATCCGACTGTTATCAATCAAGCTGCTGGACAAGTAAGCACGTCTAAAAATGCTTTAAATGGT
AATGAAAACTTAGAGGCAGCGAAGCAACAAGCAACGCAATCTTTAGGTTCATTAGACAACTTAAATAAT
GCGCAAAAACAAGCTGTTACTAATCAAATTAATGGCGCGCATACTGTTGATGAAGCAAATCAAATTAAG
CAAAATGCGCAAAACTTAAATACTGCGATGGGTAACTTGAAACAAGCGATAGCTGATAAAGATGCTACG
AAAGCAACAGTTAACTTCACTGATGCAGATCAAGCAAAACAACAAGCATATAACACTGCAGTTACAAAT
GCTGAAAATATCATTTCAAAAGCTAATGGTGGTAATGCAACACAAACTGAAGTTGAACAAGCAATCCAA
CAAGTAAATGCAGCAAAACAAGCATTAAATGGTAATGCCAACGTTCAACATGCAAAAGACGAAGCAACA
GCATTAATTAATAACTCTAATGATCTTAACCAAGCACAGAAAGATGCATTAAAACAACAAGTACAAAAT
GCAACTACTGTAGCTGGTGTAAACAATGTTAAACAAACGGCGCAAGAGTTAAACAATGCGATGACACAA
TTAAAACAAGGCATTGCAGATAAAGAACAAACAAAAGCTGATGGTAACTTTGTCAATGCAGATTCTGAC
AAGCAAAATGCATATAATCAAGCAGTAGCGAAAGCTGAAGCATTAATTAGTGGTACGCCTGATGTTGTC
GTTACACCTAGCGAAATTACTGCAGCGTTAAATAAAGTTACGCAAGCTAAAAATGATTTAAATGGTAAT
ACAAACTTAGCAACGGCGAAACAAAATGTTCAACATGCTATTGATCAATTGCCAAACTTAAACCAAGCG
CAACGTGATGAATACAGCAAACAAATCACGCAAGCAACACTTGTACCAAACGTCAATGCTATTCAACAA
GCGGCAACAACGCTTAATGACGCGATGACACAATTGAAACAAGGTATTGCGAATAAAGCACAAATTAAA
GGTAGCGAGAACTATCACGATGCTGATACTGACAAGCAAACAGCATATGATAATGCAGTAACAAAAGCA
GAAGAATTGTTAAAACAAACAACAAATCCAACAATGGATCCAAATACAATTCAACAAGCATTAACTAAA
GTGAATGACACAAATCAAGCACTTAACGGTAATCAAAAATTAGCTGATGCCAAACAAGATGCTAAGACA
ACACTTGGTACACTAGATCATTTAAATGATGCTCAAAAACAAGCGCTAACAACTCAAGTTGAACAAGCA
CCAGATATTGCAACAGTTAATAATGTTAAGCAAAATGCTCAAAATCTGAATAATGCTATGACTAACTTA
AACAATGCATTACAAGATAAAACTGAGACATTAAATAGCATTAACTTTACTGATGCAGATCAAGCTAAG
AAAGATGATTATACTAATGCGGTTTCACATGCAGAAGGTATTTTATCTAAAGCAAATGGCAGCAATGCA
AGTCAAACTGAAGTGGAACAAGCGATGCAACGTGTGAACGAAGCGAAACAAGCATTGAATGGTAATGAC
AATGTACAACGTGCAAAAGATGCAGCGAAACAAGTAATTACAAATGCAAATGATTTAAATCAAGCGCAA
AAAGATGCATTAAAACAACAAGTCGATGCTGCGCAAACTGTTGCAAATGTAAACACGATTAAGCAAACA
GCACAAGATTTAAATCAAGCAATGACACAATTGAAACAAGGTATTGCAGATAAAGACCAAACTAAAGCA
AATGGTAACTTTGTCAATGCTGATACTGATAAGCAAAATGCATATAACAATGCGGTAGCGCATGCTGAA
CAAATCATTAGTGGTACACCAAATGCAAACGTGGATCCACAACAAGTGGCTCAAGCGTTACAACAAGTG
AATCAAGCTAAGGGTGATTTAAACGGTAACCACAACTTACAAGTTGCTAAAGACAATGCAAATACAGCC
ATTGATCAGTTACCAAACTTAAATCAACCACAAAAAACAGCATTAAAAGACCAAGTGTCGCATGCAGAA
CTTGTTACAGGTGTTAATGCTATTAAGCAAAATGCTGATGCGTTAAATAATGCAATGGGTACGTTGAAA
CAACAAATTCAAGCGAATAGTCAAGTACCACAATCAGTTGACTTTACACAAGCGGATCAAGACAAACAA
CAAGCTTATAACAATGCAGCTAACCAAGCGCAACAAATCGCAAATGGCACACCAACACCTGTATTGGCG
CCTGATACAGTAACAAAAGCAGTTACAACTATGAATCAAGCGAAAGATGCATTAAACGGTGATGAAAAA
TTAGCGCAAGCGAAACAAGATGCTTTAGCAAATCTTGATACGTTACGTGACTTAAATCAACCACAACGT
GATGCATTACGAAACCAAATCAATCAAGCACAAGCTTTAGCTACAGTTGAACAAACTAAACAAAATGCA
CAAAATGTGAATACAGCAATGGGTAACTTGAAACAAGGTATTGCAAATAAAGATACTGTGAAAGCAAGT
GAGAACTACCACGATGCTGATGTCGATAAGCAAACAGCATATACAAATGCAGTGTCTCAAGCGGAAGGT
ATTATCAATCAAACGACAAATCCAACGCTTAACCCAGATGACATTACTCGTGCATTAACTCAAGTGACT
GATGCTAAAAATAGCTTAAACGGTGAAGCTAAATTAGCCACTGAAAAGCAAAATGCTAAAGATGCCGTA
AGTGGAATGACGCATTTAAACGATGCTCAAAAACAAGCATTAAAAGGTCAAATCGATCAATCGCCTGAA
ATTGCTACAGTGAACCAAGTTAAACAAACAGCAACGAGCCTAGATCAAGCAATGGATCAATTATCACAA
GCTATTAATGATAAAGATCAAATATTAGCGGACGGTAATTACTTAAATGCAGATCCTGACAAACAAAAT
GCGTATAAACAGGCAGTAGCAAAAGCTGAAGCATTATTGAATAAACAAAGTGGTACTAATGAAGTACAA
GCACAAGTTGAAAGCATCACTAATGAAGTGAACGCAGCGAAACAAGCATTAAATGGTAATGACAATTTG
GCAAATGCAAAACAACAAGCAAAACAACAATTGGCGAACTTAACACACTTAAATGATGCACAAAAACAA
TCATTTGAAAGTCAAATTACACAAGCGCCACTTGTTACAGATGTCACTACGATTAATCAAAAAGCACAA
ACGTTAGATCATGCGATGGAATTATTAAGAAATAGTGTTGCGGATAATCAAACGACATTAGCGTCTGAA
GATTATCATGATGCAACTGCGCAAAGACAAAATGACTATAACAAAGCTGTAACAGCTGCTAATAATATC
ATTAATCAAACTACATCGCCTACGATGAATCCAGATGATGTTAATGGTGCAACGACACAAGTGAATAAT
ACGAAAGTTGCATTAGATGGTGATGAAAACCTTGCAGCAGCTAAACAACAAGCAAACAACAGACTTGAT

FIG. 2K

SEQ ID NO:46 (continued)

CAATTAGATCATTTGAATAATGCGCAAAAGCAACAGTTACAATCACAAATTACGCAATCATCTGATATT
GCTGCAGTTAATGGTCACAAACAAACAGCAGAATCTTTAAATACTGCGATGGGTAACTTAATTAATGCG
ATTGCAGATCATCAAGCCGTTGAACAACGTGGTAACTTCATCAATGCTGATACTGATAAACAAACTGCT
TATAATACAGCGGTAAATGAAGCAGCAGCAATGATTAACAAACAAACTGGTCAAAATGCGAACCAAACA
GAAGTAGAACAAGCTATTACTAAAGTTCAAACAACACTTCAAGCGTTAAATGGAGATCATAATTTACAA
GTTGCTAAAACAAATGCGACGCAAGCAATTGATGTTTTAACAAGCTTAAATGATCCTCAAAAAACAGCA
TTAAAAGACCAAGTTACAGCTGCAACTTTAGTAACTGCAGTTCATCAAATTGAACAAAATGCGAATACG
CTTAACCAAGCAATGCATGGTTTAAGACAGAGCATTCAAGATAACGCAGCAACTAAAGCAAATAGCAAA
TATATCAACGAAGATCAACCAGAGCAACAAAACTATGATCAAGCTGTTCAAGCCGCAAATAATATTATC
AATGAACAAACTGCAACATTAGATAATAATGCGATTAATCAAGTAGCGGCAACTGTGAATACAACGAAA
GCAGCATTACATGGTGATGTGAAATTACAAAATGATAAAGATCATGCTAAACAAACGGTTAGCCAATTA
GCACATCTAAACAATGCACAAAAACATATGGAAGATACGTTAATTGATAGTGAAACAACTAGAACAGCA
GTTAAGCAAGATTTGACTGAAGTACAAGCATTAGATCAACTTATGGATGCATTACAACAAAGTATTGCT
GACAAAGATGCAACACGTGCGAGCAGTGCATATGTCAATGCAGAACCGAATAAAAAACAAGCCTATGAT
GAAGCAGTTCAAAATGCTGAGTCTATCATTGCAGGATTAAATAATCCAACTATCAATAAAGGTAATGTA
TCAAGTGCGACTCAAGCAGTAATATCATCTAAAAATGCATTAGATGGTGTTGAACGATTAGCTCAAGAT
AAGCAAACTGCTGGAAATTCTCTAAATCATTTAGATCAATTAACACCAGCTCAACAACAAGCGCTAGAA
AATCAAATTAATAATGCAACAACTTGTGATAAAGTGGCTGAAATCATTGCACAAGCGCAAGCATTAAAT
GAAGCGATGAAAGCATTAAAAGAAAGTATTAAGGATCAACCACAAACTGAAGCAAGTAGTAAATTTATT
AACGAGGATCAAGCGCAAAAAGATGCATATACGCAAGCAGTACAACACGCGAAAGATTTGATTAACAAA
ACAACTGATCCTACATTAGCTAAATCAATCATTGATCAAGCGACACAGGCAGTGACTGATGCTAAAAAC
AATTTACATGGTGATCAAAAACTAGCTCAAGATAAGCAACGTGCAACAGAAACGTTAAATAACTTGTCT
AACTTGAATACACCACAACGTCAAGCACTTGAAAATCAAATCAATAATGCAGCAACTCGTGGTGAAGTA
GCACAAAAATTAACTGAAGCACAAGCACTTAACCAAGCAATGGAAGCTTTACGTAATAGCATTCAAGAT
CAACAACAAACAGAATCTGGTAGCAAGTTTATTAATGAAGATAAACCGCAAAAAGATGCTTACCAAGCA
GCAGTTCAAAATGCAAAAGATTTAATTAACCAAACAGGTAATCCAACGCTTGATAAAGCACAAGTTGAA
CAATTGACACATGCTTTTAAACAAGCTAAAGATAACCTACACGGTGATCAAAAACTTGCAGACGATAAA
CAACATGCGGTTACTGATTTAAATCAATTAAATGGTTTGAATAATCCGCAACGTCAAGCACTTGAAA
GCCAAATAAACAACGCAGCAACTCGTGGCGAAGTAGCGCAAAAATTAGCTGAAGCAAAAGCGCTTGATC
AAGCAATGCAAGCATTACGAAATAGTATTCAAGATCAACAACAAACGGAAGCGGGTAGCAAGTTTATCA
ATGAAGATAAACCGCAAAAAGATGCTTACCAAGCAGCAGTTCAAAATGCAAAAGATTTAATTAACCAAA
CAGGTAATCCAACACTCGACAAATCACAAGTAGAACAATTAACACAAGCAGTAACAACTGCAAAAGATA
ATCTACATGGTGATCAAAAACTTGCTCGTGATCAACAACAAGCAGTAACAACTGTAAATGCATTGCCAA
ACTTAAATCATGCACAACAACAAACATTAACTGATGCTATAAATGCAGCGCCTACAAGAACAGAGGTTG
CACAACATGTTCAAACTGCTACTGAACTTGATCACGCGATGGAAACATTGAAAAATAAAGTTGATCAAG
TGAATACAGATAAGGCTCAACCAAATTACACTGAAGCGTCAACTGATAAAAAAGAAGCAGTAGATCAAG
CGTTACAAGCTGCACAAAGCATTACAGATCCAACTAATGGTTCAAATGCGAATAAAGACGCTGTAGAAC
AAGCATTAACTAAGCTTCAAGAAAAAGTGAATGAGTTAAATGGTAATGAGAGAGTCGCTGAAGCTAAAA
CACAAGCGAAACAAACTATTGACCAATTAACACATTTAAATGCTGATCAAATTGCAACTGCTAAACAAA
ATATTGATCAAGCGACGAAACTTCAACCAATCGCTGAATTAGTAGATCAAGCAACGCAATTGAACCAAT
CAATGGATCAATTACAACAAGCAGTTAATGAACATGCTAACGTTGAGCAAACTATAGATTACACACAAG
CAGATTCAGATAAGCAAAAGGCTTATAAACAAGCGATTGCTGATGCTGAAAATGTATTGAAACAAAATG
CGAATAAGCAACAAGTGGATCAAGCACTTCAAAATATTTTAAATGCAAAACAAGCATTAAATGGTGATG
AACGTGTAGCACTTGCTAAAACAAATGGTAAACATGACATCGACCAATTGAATGCATTAAACAATGCTC
AACAAGATGGATTTAAAGGTCGCATCGATCAATCAAACGATTTAAATCAAATCCAACAAATTGTAGATG
AGGCTAAGGCACTTAATCGTGCAATGGATCAATTGTCACAAGAAATCACTGGCAATGAAGGACGCACGA
AAGGTAGCACGAACTATGTCAATGCAGATACACAAGTCAAACAAGTATATGATGAAGCGGTTGATAAAG
CGAAACAAGCACTTGATAAATCGTCTGGGCAAAACTTAACTGCAGAACAAGTTATCAAATTAAATGATG
CAGTCACTGCAGCTAAGAAAGCATTAAATGGTGAAGAAAGACTTAATAATCGTAAAGCTGAAGCATTAC
AAAGATTGGATCAATTAACACATCTAAACAATGCTCAAAGACAATTAGCAATCCAACAAATTAATAATG
CTGAAACGCTAAATAAAGCATCTCGAGCAATTAATAGAGCAACTAAATTAGATAATGCAATGGGTGCAG
TACAACAATATATTGACGAACAGCACCTTGGTGTTATCAGCAGCACAAATTACATCAATGCAGATGACA
ATTTGAAAGCAAATTATGATAATGCAATTGCGAATGCAGCACATGAGTTAGATAAAGTGCAAGGTAATG
CAATTGCAAAAGCTGAAGCAGAGCAATTGAAACAAAATATTATCGATGCTCAAAATGCATTAAATGGAG
ACCAAAACCTTGCAAATGCCAAAGATAAAGCAAATGCGTTTGTTAATTCGTTAAATGGATTAAATCAAC
AGCAACAAGATCTTGCACATAAAGCAATTAACAATGCCGATACTGTATCAGATGTAACAGATATTGTTA
ATAATCAAATTGACTTAAATGATGCAATGGAAACATTGAAACATTTAGTTGACAATGAAATTCCAAATG
CAGAGCAAACTGTCAATTACCAAAACGCTGACGATAATGCTAAAACAAACTTCGATGATGCCAAACGTC

FIG. 2L

SEQ ID NO:46 (continued)

TAGCAAATACATTGCTAAATAGTGATAACACAAATGTGAATGATATCAATGGCGCAATCCAAGCAGTCA
ATGATGCAATCCATAATCTTAATGGTGATCAACGACTACAAGATGCTAAAGACAAGGCAATTCAATCAA
TTAATCAAGCTTTAGCTAATAAGCTAAAAGAAATCGAAGCTTCAAATGCGACGGATCAAGACAAGCTTA
TTGCGAAAAATAAAGCAGAAGAATTGGCAAACAGCATCATCAACAACATTAATAAAGCAACAAGTAATC
AGGCTGTATCTCAAGTTCAAACAGCAGGCAACCACGCGATTGAACAAGTGCATGCTAATGAAATACCAA
AAGCAAAAATTGATGCCAATAAAGACGTTGATAAGCAAGTTCAAGCATTAATTGACGAAATTGATCGAA
ATCCAAATCTAACAGATAAGGAAAAACAAGCACTTAAAGATCGTATTAATCAAATACTTCAACAAGGTC
ATAACGACATTAACAATGCGCTGACTAAAGAAGAAATTGAACAAGCTAAAGCACAACTTGCGCAAGCAT
TACAAGACATCAAAGATTTAGTGAAAGCTAAAGAAGATGCGAAACAAGATGTTGATAAACAAGTTCAAG
CATTAATTGACGAAATCGATCAAAATCCAAATCTAACAGATAAGGAAAAACAAGCACTTAAAGATCGTA
TTAATCAAATACTTCAACAAGGTCATAACGGCATTAACAATGCGATGACTAAAGAAGAAATTGAACAAG
CCAAAGCACAACTTGCACAAGCATTAAAAGAAATTAAAGATTTAGTGAAAGCTAAAGAAAATGCGAAAC
AAGATGTTGATAAACAAGTTCAAGCATTAATTGACGAAATCGATCAAAATCCAAATCTAACAGATAAGG
AAAAACAAGCGCTTAAAGATCGAATCAATCAAATACTGCAACAAGGTCATAACGACATTAACAATGCGA
TGACTAAAGAAGAAATTGAACAAGCCAAAGCACAACTTGCACAAGCATTACAAGACATCAAAGATTTAG
TGAAAGCTAAAGAAGATGCGAAAAATGCAATAAAAGCCTTAGCTAATGCGAAGCGTGATCAAATCAATT
CAAATCCAGATTTAACACCTGAGCAAAAAGCAAAAGCGCTCAAAGAAATTGACGAAGCTGAAAAAACGAG
CACTACAAAACGTTGAGAATGCTCAAACTATAGATCAATTAAATCGAGGATTAAACTTAGGTTTAGATG
ACATTAGAAATACACATGTATGGGAGGTTGATGAACAACCTGCTGTAAATGAAATTTTTGAAGCAACAC
CTGAGCAAATCCTAGTTAATGGTGAACTCATTGTACATCGTGATGACATCATTACAGAACAAGATATTC
TTGCACACATAAACTTAATTGATCAGCTTTCAGCAGAAGTTATTGATACACCATCAACTGCAACGATTT
CTGATAGCTTAACAGCAAAAGTTGAAGTTACATTGCTTGATGGATCAAAAGTGATTGTTAATGTTCCTG
TAAAAGTTGTAGAAAAAGAATTGTCAGTAGTCAAACAACAGGCAATTGAATCAATCGAAAATGCGGCAC
AACAAAAGATTGATGAAATCAATAATAGTGTGACATTAACACTGGAACAAAAAGAAGCTGCAATTGCAG
AAGTTAATAAGCTTAAACAACAAGCAATTGATCATGTTAACAATGCACCTGATGTTCATTCAGTTGAAG
AAATTCAACAACAAGAACAAGCGTATATTGAACAATTTAATCCAGAACAATTTACGATTGAACAAGCAA
AATCAAATGCAATTAAATCGATTGAAGATGCAATTCAACATATGATTGATGAAATCAAAGCTCGTACTG
ATCTAACAGATAAAGAGAAGCAAGAAGCTATTGCTAAGTTAAATCAATTAAAAGAACAAGCAATTCAAG
CGATTCAACGTGCGCAAAGCATCAGTGAAATAACTGAGCAATTGGAACAATTTAAAGCTCAAATGAAAG
CAGCTAATCCAACAGCAAAAGAACTAGCTAAACGCAAGCAAGAAGCTATTAGTAGAATTAAAGACTTTT
CAAATGAAAAAATAAATAGTATTCGAAATAGTGAAATTGGCACAGCTGATGAAAAACAAGCAGCAATGA
ATCAAATTAACGAAATTGTGCTTGAAACAATTAGAGATATTAATAATGCGCATACATTACAGCAAGTTG
AGGCTGCATTGAACAATGGTATTGCTCGAATTTCAGCAGTACAAATTGTAATATCTGATCGTGCTAAAC
AATCGTCAAGTACTGGAAATGAATCTAATAGCCATTTAACAATTGGTTATGGAACTGCAAATCATCCAT
TTAACAGTTCGACTATTGGACATAAAAAGAAACTTGATGAAGATGATGACATTGATCCACTTCATATGC
GTCACTTTAGTAATAATTTCGGTAATGTTATTAAAAACGCTATTGGTGTGGTGGGTATCTCTGGCTTAC
TAGCTAGTTTCTGGTTCTTCATTGCCAAACGTCGTCGTAAAGAAGATGAAGAGGAAGAATTAGAAATAA
GAGATAATAATAAAGATTCAATAAAAGAGACTTTAGACGATACAAAACATTTACCACTTTTATTTGCGA
AACGTCGCAGAAAAGAAGATGAAGAAGATGTTACTGTTGAAGAAAAAGATTCGCTAAATAATGGCGAGT
CACTCGATAAAGTTAAACATACGCCGTTCTTCTTACCAAAACGTCGTCGTAAAGAAGATGAAGAAGATG
TGGAAGTTACAAATGAAAACACAGATGAAAAAGTGTTGAAAGATAACGAACATTCACCACTCTTATTCG
CAAAACGACGCAAAGATAAAGAGGAAGATGTTGAAACAACAACTAGTATTGAATCTAAAGATGAGGACG
TTCCTTTATTATTGGCTAAAAAGAAAAATCAAAAAGATAACCAATCCAAAGACAAAAAGTCAGCATCAA
AAAATACTTCTAAAAAGGTAGCAGCTAAAAAGAAGAAAAAGAAATCTAAGAAAAATAAAAAA

FIG. 2M

SEQ ID NO:47 polynucleotide sequence

TTGAATAATCGTGATAAATTACAAAAATTTAGTATTCGAAAATACGCAATTGGAACATTTTCTACTGTG
ATTGCAACACTTGTGTTCATGGGTATCAATACAAACCATGCAAGTGCCGACGAGTTGAATCAAAATCAA
AAGTTAATTAAACAATTAAATCAAACAGATGATGATGATTCGAATACGCATAGTCAAGAAATCGAAAAT
AACAAACAAAATTCTAGTGGGCAGACTGAATCATTACGTTCATCAACTAGTCAAAATCAAGCAAATGCA
CGACTGTCGGATCAATTCAAAGACACTAATGAAACATCGCAACAATTACCTACAAATGTTTCGGATGAT
AGTATCAATCAATCGCATAGTGAAGCAAATATGAATAACGAACCATTGAAAGTTGATAATAGTACTATG
CAAGCACATAGTAAAATAGTAAGCGATAGCGATGGGAATGCTTCTGAAAATAAACATCATAAACTAACA
GAAAATGTACTTGCAGAAAGCCGAGCAAGTAAAAATGACAAAGAGAAAGAGAATCTACAAGAGAAAGAT
AAATCGCAGCAAGTACATCCACCATTAGATAAAAATGCATTACAAGCTTTTTTTGACGCATCATATCAC
AATTACAGAATGATTGATAGAGATCGTGCGGATGCAACAGAATATCAAAAAGTCAAATCTACTTTTGAC
TACGTCAATGACTTACTAGGTAATAATCAAAATATTCCTTCAGAACAGCTTGTTTCGGCATATCAACAA
TTAGAGAAAGCATTAGAACTTGCACGTACGTTACCACAACAATCTACTACAGAAAAACGTGGTAGAAGA
AGTACGAGAAGTGTTGTTGAGAATCGTTCATCAAGAAGCGATTACTTAGATGCTAGAACTGAATATTAT
GTTTCAAAAGACGATGATGATTCTGGTTTCCCTCCTGGTACTTTCTTCCATGCTTCAAATAGAAGATGG
CCTTATAATTTACCAAGATCTAGGAACATCTTACGTGCTTCTGATGTACAAGGTAATGCTTATATCACT
ACAAAACGACTTAAAGATGGATATCAATGGGATATTTTATTTAATAGTAATCATAAAGGGCATGAATAT
ATGTACTATTGGTTTGGACTTCCAAGTGATCAAACACCAACTGGTCCAGTAACTTTCACTATTATCAAC
CGTGATGGTTCAAGTACATCTACTGGTGGCGTTGGATTTGGATCAGGTGCACCACTACCTCAATTTTGG
AGATCAGCAGGTGCTATTAATTCTAGCGTAGCGAATGATTTTAAACATGGCTCCGCTACAAATTATGCA
TTTTATGATGGTGTTAATAATTTTTCTGACTTTGCTAGAGGGGGAGAATTATACTTCGACAGAGAAGGC
GCTACACAAACTAATAAATATTATGGCGATGAAAACTTCGCATTGCTAAATAGTGAGAAACCAGATCAA
ATAAGAGGATTAGATACAATATATAGTTTTAAAGGTAGTGGTGATGTAAGTTATCGTATTTCATTTAAA
ACTCAAGGAGCTCCAACTGCAAGATTGTATTATGCTGCTGGCGCGCGTTCTGGTGAATATAAACAAGCA
ACGAACTATAACCAACTCTATGTCGAACCTTATAAGAATTATCGAAATCGAGTACAGTCAAATGTCCAA
GTTAAAAATCGTACACTTCATTTAAAAAGAACAATCAGACAATTCGATCCTACATTACAGAGAACTACT
GATGTTCCTATTTTGGATAGTGACGGTTCCGGAAGTATTGATTCGGTATACGACCCATTAAGTTATGTA
AAGAATGTGACTGGTACAGTCCTAGGTATTTATCCATCTTATCTTCCTTATAATCAGGAAAGATGGCAG
GGAGCTAATGCAATGAATGCCTATCAAATTGAAGAACTTTTTTCACAAGAAAATCTTCAAAATGCAGCA
CGTTCAGGCCGTCCAATTCAATTTCTTGTAGGTTTTGATGTTGAAGATAGCCATCATAACCCTGAAACT
CTTTTACCAGTAAATTTATATGTAAAACCTGAGTTAAAACATACAATTGAGTTATATCACGATAATGAA
AAACAAGATAGAAAGGAATTTTCAGTATCGAAA

SEQ ID NO:48 polynucleotide sequence

ATGAGTGGAACGCTTCATAACACTGTAGGATCAGGAATATTACCTTATCAACAAGAGATACGTATCAAA
CTTACTAGTAATGAACCAATTAAAGATAGTGAATGGTCTATTACAGGATATCCTAACACGCTTACATTA
CAAAACGCTGTGGGTAGAACAAATAATGCTACTGAAAAAAACTTAGCTCTTGTTGGTCATATTGATCCA
GGAAATTATTTCATCACTGTTAAGTTTGGTGATAAAGTAGAACAATTTGAAATTAGATCAAAACCAACT
CCACCAAGAATCATTACAACTGCTAATGAATTACGTGGAAATCCTAACCATAAGCCTGAAATAAGAGTA
ACAGATATACCAAATGATACTACTGCTAAAATCAAACTTGTGATGGGCGGAACCGATGGCGATCATGAT
CCAGAAATAAATCCATATACTGTCCCTGAAAACTACACAGTAGTTGCAGAAGCATACCATGATAATGAT
CCAAGTAAAAATGGGGTCTTAACATTCCGTTCATCAGACTACCTTAAAGATCTACCATTAAGCGGTGAA
TTAAAGGCAATTGTTTATTACAATCAATATGTACAATCAAACTTTAGTAAAAGCGTTCCGTTTAGTAGC
GATACAACACCACCTACAATTAATGAACCGGCAGGACTAGTTCATAAGTATTACAGGGGAGATCATGTA
GAAATTACTCTTCCAGTCACTGATAATACTGGCGGTTCAGGTTTAAGAGATGTAAACGTCAATTTACCT
CAAGGTTGGACAAAAACCTTTACAATCAATCCTAATAATAATACTGAGGGTACGCTTAAGTTAATTGGT
AATATACCTAGTAATGAAGCATATAATACGACATATCATTTCAATATTACTGCAACCGATAATTCTGGA
AATACAACAAATCCAGCTAAAACCTTTATTTAAATGTTGGTAAGTTGGCTGATGATTTAAATCCAGTC
GGATTATCTAGAGATCAACTACAATTAGTGACAGACCCTTCTTCATTATCTAATTCCGAACGAGAAGAG
GTAAAAAGAAAAATAAGTGAAGCAAATGCTAATATAAGATCATATTTATTACAAAATAACCCAATACTC
GCTGGAGTAAACGGCGATGTTACATTTTATTATAGAGATGGTTCTGTAGATGTTATTGATGCTGAAAAT
GTAATCACATATGAGCCCGAAAGAAAATCCATTTTCAGTGAAAATGGTAATACAAATAAAAAAGAAGCA
GTAATCACTATTGCTAGAGGACAAAACTATACCATTGGTCCAAACTTAAGAAAATATTTCTCATTAAGT
AATGGTTCGGATTTACCTAATAGAGATTTCACCTCTATATCAGCTATTGGATCTTTACCTTCATCGAGT
GAAATTAGTCGACTCAATGTTGGAAATTATAACTATAGAGTTAATGCTAAAAATGCTTATCATAAGACT
CAACAAGAACTTAATTTAAAACTTAAAATAGTAGAGGTTAATGCACCTACTGGTAATAATCGTGTATAT
AGAGTTAGTACTTATAATTTAACTAATGATGAAATCAATAAAATCAAACAAGCATTTAAAGCAGCTAAT
TCTGGACTTAATTTAAACGATAACGATATCACTGTTTCGAATAACTTTGACCATAGAAATGTTAGTAGT
GTGACAGTAACTATACGTAAGGGCGATTTGATAAAAGAGTTTTCATCAAATCTCAATAATATGAATTTC

FIG. 2N

SEQ ID NO:48 (continued)

TTACGTTGGGTTAATATAAGGGATGATTATACCATTTCGTGGACTTCTAGTAAGATTCAAGGTAGAAAT
ACAGATGGTGGATTAGAATGGTCACCAGATCATAAATCACTTATTTATAAATATGATGCAACATTAGGT
AGACAAATAAATACTAATGACGTGTTAACTTTACTTCAAGCAACAGCTAAAAACTCAAATTTACGTTCA
AATATCAATAGTAATGAAAAACAGTTAGCAGAACGAGGGTCTAATGGGTATTCTAAATCTATAATTAGA
GATGATGGCGAGAAATCTTATTTACTTAACTCAAATCCTATTCAAGTATTAGACTTAGTAGAACCAGAT
AATGGTTACGGTGGACGTCAAGTCAGTCATTCTAACGTTATATATAATGAAAAAAATTCTTCTATCGTA
AATGGTCAAGTTCCAGAAGCTAATGGGGCATCCGCTTTTAATATTGATAAAGTTGTTAAAGCTAATGCG
GCAAATAATGGTATTATGGGTGTTATCTATAAGGCACAATTATACTTAGCACCATACAGTCCAAAAGGT
TACATTGAAAAATTAGGCCAAAATTTAAGCAATACCAATAACGTGATTAATGTTTATTTTGTGCCTTCT
GATAAAGTAAATCCTAGTATAACTGTAGGTAATTACGACCATCATACGGTATATTCTGGTGAAACATTT
AAAAATACTATCAATGTAAATGATAATTATGGATTAAATACAGTAGCTTCTACAAGTGATAGTGCAATT
ACTATGACCAGAAACAACAACGAGTTAGTAGGTCAGGCTCCTAATGTTACTAATAGCATAAATAAAATT
GTAAAAGTTAAAGCCACAGATAAAAGTGGAAATGAAAGTATTGTTTCTTTCACAGTAAATATAAAACCA
TTAAACGAGAAATATAGAATAACAACTTCATCAAGTAATCAAACACCAGTGAGAATTAGTAATATTCAA
AACAATGCTAACCTTTCAATTGAAGATCAAAATAGAGTAAAATCTTCACTCAGCATGACTAAAATTTTA
GGTACAAGAAATTATGTCAATGAGTCAAATAATGACGTTCGTAGTCAAGTTGTAAGTAAAGTAAATAGA
AGTGGGAACAATGCTACAGTTAATGTTACAACTACATTTTCTGATGGTACAACTAATACAATAACCGTT
CCAGTTAAACATGTGTTATTAGAAGTTGTACCTACTACTAGAACAACAGTAAGAGGACAACAATTTCCA
ACCGGCAAAGGAACTTCCCCAAATGATTTCTTTAGTTTAAGAACGGGAGGTCCAGTTGATGCGAGAATA
GTTTGGGTTAATAATCAGGGACCCGATATAAATAGTAATCAAATTGGTAGAGATTTAACATTACACGCT
GAAATATTCTTTGATGGTGAAACAACACCAATTAGAAAAGATACTACTTACAAACTTAGTCAATCTATT
CCAAAGCAAATATATGAAACAACTATCAATGGTCGATTTAATTCATCAGGTGATGCATATCCAGGAAAT
TTTGTTCAAGCAGTAAATCAATATTGGCCAGAACATATGGACTTCAGATGGGCCCAAGGATCAGGCACA
CCAAGTTCTCGTAATGCAGGTTCATTTACTAAAACAGTTACGGTAGTTTATCAAAACGGCCAAACTGAA
AACGTTAATGTACTATTCAAAGTCAAACCAAATAAACCTGTTATTGATAGTAATAGTGTGATTTCAAAA
GGACAATTAAATGGTCAACAAATTTTAGTTCGAAATGTTCCACAAAATGCACAAGTCACTCTATATCAA
TCAAATGGAACTGTTATTCCTAATACAAATACAACTATAGATTCTAATGGTATAGCTACTGTAACAATT
CAAGGCACTCTACCAACCGGAAATATTACTGCTAAAACCTCAATGACAAATAATGTAACGTACACTAAA
CAAAATAGTAGTGGAATTGCTTCAAATACAACTGAAGATATAAGTGTTTTTTCAGAAAACAGTGATCAA
GTAAATGTTACCGCTGGCATGCAAGCTAAAAATGATGGTATTAAAATAATTAAAGGTACAAACTATAAT
TTTAATGACTTCAATAGTTTCATAAGTAATATACCAGCCCATTCTACTCTTACATGGAACGAGGAGCCT
AATAGTTGGAAAAACAACATCGGTACTACAACAAAAACTGTTACAGTTACTCTACCTAATCATCAAGGT
ACGAGAACTGTAGATATTCCAATAACAATCTATCCAACAGTTACAGCTAAGAATCCAGTAAGAGATCAA
AAAGGACGAAACTTAACCAATGGTACTGACGTTTATAATTATATTATTTTTGAAAATAATAACCGTCTT
GGAGGAACAGCTTCTTGGAAAGACAATCGTCAACCTGATAAAAACATAGCCGGTGTACAAAATTTAATT
GCACTTGTTAATTATCCTGGCATATCTACACCATTAGAAGTTCCTGTTAAAGTGTGGGTATATAATTTT
GATTTCACTCAACCTATCTACAAAATTCAAGTAGGAGATACATTCCCTAAAGGAACATGGGCAGGCTAT
TACAAACATCTTGAAAATGGAGAGGGATTACCAATAGATGGTTGGAAATTTTATTGGAACCAGCAAAGT
ACAGGAACTACTAGTGATCAATGGCAATCATTAGCATATACTAGAACTCCTTTTGTTAAAACTGGTACT
TATGATGTCGTTAATCCTAGCAACTGGGGTGTTTGGCAAACATCACAATCAGCTAAATTTATAGTTACA
AATGCTAAACCTAATCAACCAACCATAACTCAGTCTAAAACTGGTGATGTAACAGTAACACCTGGTGCT
GTGCGTAATATACTAATAAGTGGGACAAATGATTATATCCAAGCATCTGCAGATAAGATTGTTATTAAT
AAAAATGGAAATAAATTAACTACATTTGTTAAAAATAATGATGGTCGTTGGACTGTTGAAACTGGGTCA
CCTGACATAAATGGTATCGGACCAACAAATAACGGAACTGCTATATCTTTAAGTCGATTAGCAGTTAGA
CCTGGGGATTCAATAGAAGCAATAGCGACTGAAGGTTCCGGAGAAACTATAAGTACTTCAGCAACTAGT
GAAATTTATATTGTCAAAGCTCCACAACCTGAACAAGTAGCAACTCATACTTATGATAATGGAACATTC
GATATATTACCTGACAATTCACGTAATTCTTTAAATCCAACTGAACGTGTCGAAATTAATTACACTGAA
AAATTAAATGGCAATGAAACACAAAAATCATTCACTATTACTAAAAATAACAACGGCAAATGGACGATA
AATAATAAACCAAATTATGTCGAGTTCAATCAGGATAATGGTAAAGTTGTATTTTCGGCCAATACAATT
AAACCTAATTCTCAAATTACAATAACTCCTAAAGCAGGTCAGGGTAACACTGAAAACACAAATCCTACT
GTAATTCAAGCACCTGCGCAACATACTTTAACAATCAATGAAATTGTTAAAGAACAGGGTCAAAATGTG
ACTAATGATGATATTAATAATGCGGTTCAAGTGCCAAATAAAAATAGAGTTGCGATTAAACAAGGAAAC
GCTCTTCCAACAAATTTAGCTGGTGGTAGTACATCACATATTCCAGTAGTTATTTATTACAGTGATGGA
AGTTCTGAAGAAGCTACTGAGACTGTTAGAACTAAAGTTAATAAAACCGAATTAATCAATGCTCGTCGT
CGACTAGATGAAGAAATTAGTAAAGAGAACAAAACACCATCAAGTATCAGAAACTTTGATCAAGCTATG
AATCGTGCTCAATCACAAATTAATACAGCTAAAAGTGATGCTGACCAAGTTATAGGCACAGAATTTGCA
ACACCTCAACAAGTAAATTCAGCTTTATCTAAAGTTCAAGCGGCACAAAATAAAATAAATGAAGCTAAA
GCATTATTACAAAACAAGGCTGATAATAGTCAACTTGTGAGAGCAAAAGAACAATTACAACAATCGATT

FIG. 2O

SEQ ID NO:48 (continued)

CAACCAGCCGCTTCAACTGATGGTATGACTCAAGATAGCACAAGGAACTACAACAATAAACGCCAAGCA
GCTGAACAAGCAATACAACATGCAAATAGCGTTATAAATAATGGAGATGCAACATCCCAACAAATTAAT
GATGCTAAAAACACAGTTGAACAGGCACAGAGAGATTATGTTGAAGCTAAAAGCAACTTACGTGCTGAT
AAGTCACAGTTACAAAGCGCTTATGATACGTTAAATAGAGATGTTTTAACAAATGATAAAAAGCCAGCA
TCTGTAAGACGCTATAATGAAGCCATTTCAAATATTAGAAAAGAATTAGATACAGCTAAAGCGGATGCA
AGTAGTACTTTGCGAAACACCAATCCTTCCGTTGAACAAGTTAGAGACGCTTTAAATAAAATAAATACT
GTTCAACCTAAAGTGAATCAAGCAATTGCTTTACTTCAACCAAAAGAAAATAATTCAGAACTTGTACAA
GCTAAAAAACGTTTACAAGACGCTGTAAATGACATACCTCAAACACAAGGTATGACACAACAAACAATT
AATAATTATAATGACAAACAACGTGAAGCTGAAAGAGCACTTACATCTGCACAAAGAGTGATTGATAAT
GGGGATGCTACAACTCAAGAAATTACTTCTGAAAAATCTAAAGTAGAGCAAGCAATGCAAGCTTTAACT
AATGCTAAAAGTAATCTGAGAGCTGATAAGAATGAGTTACAGACTGCATATAACAAATTAATTGAGAAC
GTATCTACCAATGGTAAAAAACCGGCGAGTATACGTCAATACGAAACAGCCAAAGCCAGAATACAAAAT
CAAATTAATGATGCTAAAAATGAAGCGGAGCGAATTTTAGGTAATGATAATCCACAAGTATCACAAGTA
ACTCAAGCATTGAACAAAATCAAAGCTATTCAACCAAAATTAACAGAAGCTATCAACATGCTTCAAAAC
AAAGAAAATAATACAGAATTAGTCAATGCTAAAAACAGACTTGAAAATGCAGTAAATGATACAGATCCA
ACACACGGTATGACTCAAGAAACAATTAATAATTACAACGCTAAAAAGCGAGAAGCTCAAAATGAAATA
CAAAAAGCGAACATGATTATTAATAATGGAGATGCTACTGCTCAAGATATTTCTTCTGAAAAATCTAAA
GTAGAGCAAGTATTACAAGCATTACAAAATGCTAAGAATGACTTAAGAGCTGATAAAAGAGAATTACAG
ACTGCATACAATAAACTTATACAAAATGTTAATACCAATGGTAAAAAACCATCTAGTATTCAAAACTAT
AAGTCTGCAAGACGAAATATCGAAAACCAATATAATACCGCTAAAAATGAAGCACATAATGTTCTTGAA
AATACAAACCCTACTGTAAATGCAGTAGAAGATGCTTTACGTAAGATAAATGCAATTCAACCAGAGGTT
ACAAAAGCTATTAATATACTTCAAGATAAAGAAGATAATAGCGAACTTGTTAGAGCAAAAGAAAAATTA
GATCAAGCGATTAATAGTCAACCATCACTAAATGGTATGACTCAAGAATCTATTAATAATTACACAACA
AAACGTAGAGAAGCACAAAATATAGCAAGTTCTGCTGACACTATTATTAATAATGGGGATGCATCTATT
GAACAAATAACAGAAAATAAAATTCGAGTTGAAGAGGCAACTAATGCACTTAACGAAGCAAAACAACAT
TTAACGGCAGATACAACTTCTTTAAAAACTGAAGTACGGAAATTAAGTAGGAGAGGCGACACAAACAAC
AAAAAGCCTAGCAGTGTTAGTGCTTATAACAATACTATTCATTCGCTACAATCTGAAATTACACAGACT
GAAAATAGAGCAAATACTATCATCAATAAGCCTATTCGTTCTGTTGAAGAAGTAAATAATGCATTGCAT
GAAGTAAACCAATTGAACCAACGCTTAACAGATACAATTAACTTATTACAACCTTTAGCGAATAAAGAA
AGCTTAAAAGAAGCTCGTAATCGACTTGAAAGTAAAATTAATGAAACCGTTCAAACAGACGGTATGACT
CAACAATCTGTTGAGAATTATAAGCAAGCTAAAATAAAAGCTCAAAATGAATCTAGTATTGCACAAACT
CTTATTAATAATGGTGATGCATCTGATCAAGAAGTTTCTACAGAAATAGAAAAATTAAATCAAAAGCTG
TCTGAATTAACAAATTCAATCAATCACTTAACAGTTAATAAAGAACCTTTAGAAACTGCCAAAAATCAG
TTACAAGCAAATATTGACCAAAAACCTAGCACTGATGGTATGACGCAACAATCTGTACAAAGCTATGAA
CGTAAACTACAAGAAGCCAAAGATAAAATAAACTCAATTAATAATGTCTTAGCTAACAATCCAGATGTT
AATGCTATCAGAACAAACAAAGTTGAGACGGAACAAATCAATAATGAATTAACACAGGCGAAACAAGGT
CTTACTGTTGATAAACAACCATTGATTAATGCAAAAACTGCTTTGCAACAAAGTCTAGATAATCAACCA
AGTACTACTGGTATGACTGAAGCAACAATTCAAAATTATAACGCTAAACGTCAAAAAGCAGAGCAAGTT
ATACAAAATGCAAATAAAATTATTGAAAACGCTCAACCTAGTGTACAACAAGTGTCTGATGAGAAATCT
AAGGTAGAGCAAGCACTCAGTGAATTGAACAACGCCAAATCAGCGCTTAGAGCTGATAAACAAGAATTA
CAGCAAGCATATAATCAGTTGATTCAACCAACGGATTTAAATAATAAGAAACCAGCTTCTATCACTGCG
TACAATCAAAGATATCAACAATTTAGTAACGAATTGAACAGCACTAAAACAAATACAGATCGCATTTTA
AAAGAGCAAAATCCAAGTGTAGCTGATGTCAACAATGCACTAAATAAAGTAAGAGAAGTACAACAAAAA
TTAAACGAAGCCAGAGCACTTTTACAAAATAAAGAAGATAATAGTGCACTAGTTCGAGCCAAAGAACAA
CTTCAACAGGCAGTTGACCAAGTCCCTTCAACAGAAGGTATGACGCAACAAACTAAAGATGATTACAAT
TCAAAACAACAAGCTGCTCAACAAGAAATATCAAAAGCACAACAAGTTATCGATAATGGCGATGCGACT
ACACAACAAATTTCTAACGCCAAAACAAATGTTGAACGCGCTTTAGAAGCATTAAATAATGCAAAAACT
GGTTTAAGAGCAGATAAAGAGGAACTTCAAAATGCATATAATCAATTAACTCAAAATATTGATACGAGC
GGTAAAACGCCTGCAAGTATCAGGAAATACAATGAAGCTAAGTCACGTATTCAAACTCAAATTGATTCA
GCTAAAAATGAAGCAAACAGTATTTTAACAAATGACAATCCTCAAGTATCACAAGTGACTGCTGCGTTA
AACAAAATAAAAGCTGTTCAACCTGAATTAGATAAAGCGATAGCAATGCTTAAAAATAAAGAGAATAAT
AATGCATTGGTTCAAGCGAAACAACAACTTCAACAAATTGTTAATGAAGTAGATCCAACACAAGGCATG
ACAACAGATACTGCTAATAACTATAAATCAAAAAAACGTGAAGCTGAAGATGAAATACAAAAAGCTCAA
CAAATCATTAACAATGGCGATGCCACTGAGCAACAAATTACTAACGAAACAAATAGAGTAAATCAAGCG
ATTAATGCAATAAACAAAGCCAAAAACGATTTACGTGCTGATAAGTCTCAATTGGAAAATGCTTATAAC
CAATTAATACAAAATGTTGATACAAATGGTAAAAAACCTGCTAGTATTCAACAATACCAAGCTGCTCGA
CAAGCTATTGAGACGCAATACAATAACGCTAAATCAGAAGCACATCAAATTCTTGAAAATAGTAACCCT
TCAGTTAATGAAGTAGCACAAGCATTACAAAAAGTTGAAGCTGTACAACTTAAAGTTAATGACGCGATT

FIG. 2P

SEQ ID NO:48 (continued)

CATATACTTCAAAATAAAGAGAATAATAGTGCACTTGTCACAGCTAAAAATCAACTTCAGCAATCAGTT
AATGATCAACCATTAACAACAGGTATGACTCAAGATTCTATTAATAACTATGAAGCTAAGAGAAATGAG
GCTCAAAGTGCTATCAGAAATGCAGAAGCTGTCATCAACAATGGCGATGCAACTGCAAAACAAATTTCA
GACGAGAAATCTAAAGTTGAACAAGCACTAGCACATTTGAATGATGCTAAACAGCAATTAACTGCAGAT
ACTACTGAATTACAAACAGCAGTTCAACAATTAAACAGAAGAGGCGATACAAATAATAAAAAGCCAAGA
AGTATCAATGCATATAATAAAGCAATTCAATCATTAGAAACACAAATTACTTCTGCTAAAGATAATGCC
AACGCTGTGATACAAAAACCTATACGTACTGTTCAAGAGGTAAATAATGCATTACAACAAGTAAATCAG
TTGAATCAACAATTAACTGAAGCAATTAATCAACTTCAACCGCTATCAAATAATGATGCATTAAAAGCT
GCAAGATTAAATTTAGAAAATAAAATTAATCAAACTGTACAAACTGATGGTATGACACAACAATCTATA
GAGGCTTATCAAAACGCTAAACGCGTAGCCCAAAATGAATCTAACACTGCTTTAGCATTAATTAATAAC
GGCGATGCCGATGAACAACAAATTACAACTGAAACAGACCGAGTCAATCAGCAAACTACAAACTTAACT
CAAGCAATTAACGGGTTAACAGTTAATAAAGAACCATTAGAAACCGCTAAAACAGCGTTACAAAATAAC
ATCGACCAGGTACCTAGTACAGATGGTATGACTCAGCAATCTGTTGCAAATTATAATCAAAAACTACAA
ATAGCTAAAAACGAAATTAACACAATTAATAACGTTTTAGCGAACAATCCAGATGTTAATGCAATCAAA
ACGAATAAAGCAGAAGCGGAACGAATCAGTAACGATTTAACACAAGCTAAGAATAACTTACAAGTTGAT
ACTCAACCTTTAGAAAAAATAAAAAGACAACTTCAAGATGAAATTGATCAAGGTACTAACACAGATGGA
ATGACTCAAGATTCAGTGGATAATTACAATGATAGCTTAAGTGCAGCAATTATAGAAAAAGGCAAAGTA
AATAAATTACTTAAACGTAATCCGACAGTAGAACAAGTTAAAGAGAGCGTTGCTAATGCACAACAAGTC
ATACAAGATTTACAAAATGCTCGAACTTCACTTGTTCCAGACAAAACTCAACTTCAAGAAGCTAAAAAT
AGATTAGAAAACAGTATTAACCAACAAACAGATACTGACGGCATGACTCAAGATTCGCTTAACAATTAT
AATGATAAATTAGCAAAAGCTAGACAAAACCTTGAAAAAATATCTAAAGTTTTAGGTGGTCAACCTACT
GTAGCTGAAATTAGACAAAATACAGATGAAGCAAATGCACATAAACAAGCATTAGACACTGCACGTTCT
CAACTTACATTAAATAGAGAGCCATATATCAATCATATTAATAATGAAAGTCATTTAAATAACGCGCAA
AAAGATAATTTTAAAGCTCAAGTTAACTCAGCACCTAATCATAATACTTTAGAAACGATTAAAAATAAG
GCTGATACTTTAAATCAATCTATGACAGCATTAAGTGAAAGTATTGCAGATTACGAAAATCAAAAACAA
CAAGAAAATTATTTAGATGCATCTAACAATAAACGTCAAGACTATGACAATGCAGTCAATGCGGCTAAA
GGTATTTTAAACCAAACTCAAAGTCCGACAATGAGTGCTGATGTGATTGATCAAAAAGCTGAAGATGTT
AAACGTACGAAAACTGCGTTAGATGGAAATCAAAGATTAGAAGTTGCTAAACAACAAGCACTTAATCAT
TTAAATACCTTAAATGATTTAAACGATGCTCAGCGACAAACTTTAACTGATACTATAAATCACTCTCCA
AACATCAATTCAGTGAATCAAGCTAAAGAAAAAGCTAATACTGTTAACACAGCAATGACTCAACTGAAA
CAAACTATTGCTAACTATGACGATGAATTGCATGACGGCAATTACATTAATGCAGATAAAGACAAAAAA
GATGCTTATAATAACGCTGTTAACAATGCTAAACAACTGATTAATCAATCTGATGCTAATCAAGCACAA
CTTGATCCAGCTGAAATTAATAAAGTTACACAAAGAGTCAATACGACTAAAAATGATCTAAATGGTAAT
GACAAATTGGCTGAAGCTAAAAGAGATGCTAATACAACCATTGATGGTTTAACTTATCTAAATGAAGCT
CAACGTAACAAAGCTAAAGAAAATGTAGGCAAAGCTTCTACAAAAACAAATATTACGAGTCAGTTACAA
GATTACAATCAATTGAATATTGCTATGCAAGCATTACGTAACAGTGTGAACGACGTTAACAATGTTAAA
GCAAATAGCAATTATATAAATGAAGATAATGGTCCAAAAGAAGCTTACAATCAAGCCGTTACTCATGCT
CAAACATTGATAAATGCACAATCTAACCCTGAAATGAGCCGTGACGTAGTAAATCAAAAAACACAAGCA
GTAAATACTGCCCATCAGAATTTACATGGACAACAAAAGTTAGAACAAGCACAAAGTAGTGCTAATACA
GAAATCGGTAACTTACCAAACTTAACTAATACTCAAAAAGCTAAAGAAAAGGAACTGGTAAATAGTAAA
CAAACTCGTACGGAAGTACAAGAACAACTTAACCAAGCTAAGTCACTAGATAGTTCTATGGGCACGTTA
AAATCATTAGTTGCTAAACAACCTACAGTACAAAAAACAAGTGTTTATATTAACGAAGATCAACCTGAG
CAATCTGCCTACAATGATTCCATTACAATGGGACAAACTATAATTAATAAAACAGCTGATCCAGTACTT
GATAAAACTTTAGTTGATAACGCAATCAGTAACATTTCAACTAAAGAGAATGCACTGCATGGTGAACAA
AAATTAACAACTGCTAAAACGGAAGCAATTAATGCACTTAATACATTAGCTGATTTAAACACACCTCAG
AAAGAGGCTATTAAAACAGCTATTAACACTGCTCATACAAGAACTGATGTAACTGCAGAGCAAAGTAAG
GCTAATCAAATAAATAGTGCAATGCACACGTTGAGACAAAACATTTCTGACAACGAATCAGTAACAAAC
GAAAGTAATTATATTAACGCTGAACCCGAAAAACAACATGCCTTTACTGAGGCTCTAAATAATGCTAAA
GAAATAGTTAATGAACAACAAGCCACTCTTGATGCCAATTCAATTAACCAAAAAGCACAAGCGATTCTT
ACTACTAAAAATGCTTTAGATGGTGAAGAACAATTACGTCGTGCTAAAGAAAATGCCGATCAAGAAATC
AATACGTTAAATCAATTGACTGATGCGCAAAGAAATAGTGAAAAAGGTTTAGTCAACAGTTCTCAAACT
AGAACAGAAGTTGCTTCTCAATTAGCAAAAGCTAAAGAACTAAATAAGGTGATGGAACAACTGAATCAC
CTTATCAATGGTAAAAACCAAATGATAAATAGCAGTAAATTTATCAATGAAGATGCGAACCAACAACAA
GCATATTCAAATGCGATTGCAAGTGCAGAAGCGCTTAAAAACAAATCACAAAACCCTGAATTAGATAAA
GTAACAATTGAACAAGCAATTAATAATATTAATTCTGCAATTAACAATCTAAACGGTGAAGCTAAACTG
ACTAAAGCTAAAGAAGATGCTGTTGCTTCAATAAACAACCTAAGCGGATTAACAAACGAGCAAAAAACA
AAAGAAAATCAAGCCGTTAATGGCGCTCAAACTAGAGACCAAGTTGCTAATAAATTACGTGATGCTGAA

FIG. 2Q

SEQ ID NO:48 (continued)

GCATTAGATCAATCAATGCAAACATTACGTGACTTAGTTAACAATCAAAATGCAATACATTCAACAAGT
AATTATTTTAACGAGGATTCAACTCAAAAGAATACTTATGATAATGCAATTGATAATGGCTCGACATAT
ATAACTGGTCAACACAATCCAGAATTAAATAAATCTACTATTGATCAAACGATTAGCCGAATTAACACA
GCTAAAAATGATTTACATGGTGTAGAAAAGTTACAAAGAGATAAGGGAACTGCTAATCAAGAAATTGGA
CAATTAGGTTATTTAAATGACCCTCAAAAATCTGGTGAGGAATCCTTAGTCAACGGTTCAAATACACGT
TCTGAAGTAGAAGAGCATCTTAATGAAGCTAAATCATTAAATAATGCAATGAAACAATTAAGAGATAAA
GTAGCTGAAAAGACTAATGTCAAACAAAGTAGCGATTACATTAATGATTCAACTGAACATCAACGTGGG
TATGATCAAGCACTTCAAGAAGCAGAAAATATTATTAATGAAATCGGTAATCCAACATTAAATAAATCG
GAAATTGAACAAAAGTTACAACAATTGACTGACGCTCAAAATGCGTTACAAGGTTCACATCTATTAGAA
GAAGCTAAAAATAATGCGATTACTGGAATCAATAAACTTACAGCATTAAATGATGCACAACGTCAAAAA
GCAATTGAAAATGTTCAAGCACAGCAGACAATCCCAGCAGTTAATCAACAATTAACTTTGGATAGAGAA
ATAAATACTGCAATGCAAGCTTTACGAGATAAAGTAGGCCAACAAAATAACGTTCACCAACAAAGTAAT
TATTTCAATGAAGATGAACAACCAAAACATAACTATGATAATTCTGTACAAGCCGGTCAAACTATTATT
GATAAACTTCAAGATCCAATCATGAACAAAAATGAAATTGAGCAGGCTATTAATCAAATCAATACGACT
CAAACAGCGTTAAGTGGAGAAAATAAATTACACACTGACCAAGAAAGCACAAATAGACAAATAGAAGGT
TTATCTAGTTTGAACACAGCTCAAATCAACGCCGAAAAAGATTTAGTCAATCAAGCTAAAACAAGAACA
GATGTTGCTCAAAAGTTAGCTGCAGCTAAAGAAATAAATTCTGCTATGAGTAATTTAAGAGATGGCATT
CAAAATAAAGAGGACATCAAACGTAGCAGTGCATATATCAACGCAGATCCGACTAAAGTTACAGCTTAC
GATCAAGCACTACAGAACGCAGAAAATATCATCAATGCCACACCAAACGTAGAGCTTAATAAAGCTACA
ATTGAACAAGCGCTATCACGCGTTCAACAAGCACAACAAGATCTTGATGGTGTTCAACAATTAGCTAAT
GCTAAACAACAAGCTACACAAACTGTCAATGGGTTAAATAGCTTAAATGACGGTCAAAAGCGTGAATTA
AATCTATTAATTAATTCAGCTAATACCCGTACAAAAGTACAAGAAGAATTAAACAAAGCAACTGAATTG
AACCATGCGATGGAAGCTTTAAGAAACAGTGTTCAAAACGTTGATCAAGTAAAACAAAGTAGCAATTAT
GTCAATGAAGATCAACCTGAACAGCACAATTATGATAATGCTGTCAATGAAGCTCAAGCTACAATCAAC
AACAATGCTCAACCTGTTCTAGACAAATTAGCTATAGAACGTTTAACTCAAACTGTTAACACTACAAAA
GATGCATTACATGGTGCTCAAAAACTGACACAAGACCAACAAGCTGCTGAAACTGGAATACGTGGTTTA
ACGAGTCTCAATGAACCTCAGAAAAATGCTGAAGTAGCTAAAGTAACTGCAGCAACAACACGTGATGAA
GTGAGAAATATTCGTCAAGAAGCAACAACATTAGATACTGCAATGCTTGGTTTACGTAAAAGCATTAAA
GATAAAAACGATACTAAAAATAGTAGTAAATATATTAATGAGGATCATGACCAACAACAAGCTTATGAC
AATGCTGTAAATAATGCTCAACAAGTTATCGATGAAACTCAAGCAACGTTAAGCTCAGATACAATCAAT
CAATTGGCAAATGCCGTAACTCAAGCTAAATCTAATCTTCATGGAGATACTAAACTACAACACGATAAA
GATAGTGCTAAACAAACGATTGCTCAATTACAGAATTTGAATTCAGCTCAAAAACATATGGAAGATTCT
TTAATTGATAATGAATCTACACGTACGCAAGTCCAACACGATTTAACAGAAGCTCAAGCTTTAGATGGT
TTAATGGGTGCCTTAAAAGAAAGTATTAAAGATTATACTAATATTGTTTCAAACGGTAATTACATCAAT
GCGGAACCATCTAAGAAACAAGCATATGATGCAGCTGTACAAAATGCTCAAAATATAATAAATGGAACG
AATCAACCAACAATTAATAAAGGTAATGTCACTACAGCAACACAAACCGTGAAAAATACTAAAGATGCC
TTAGACGGTGATCATAGATTAGAGGAAGCTAAAAATAATGCCAATCAAACAATCAGAAATCTATCTAAT
TTGAACAATGCCCAAAAAGATGCAGAGAAAAATCTAGTTAATAGCGCATCAACATTAGAACAAGTTCAA
CAAAACTTACAAACCGCTCAACAATTAGATAATGCTATGGGTGAGTTACGACAAAGTATTGCTAAAAAA
GATCAAGTGAAAGCAGATAGTAAATATCTAAATGAAGATCCTCAAATTAAGCAAAACTATGATGATGCA
GTTCAACGTGTTGAAACTATTATTAACGAAACTCAAAACCCTGAATTACTTAAAGCAAACATTGACCAA
GCAACTCAATCCGTTCAAAATGCAGAACAAGCTTTACATGGTGCTGAAAAATTAAATCAAGACAAACAA
ACGTCTTCGACAGAACTAGATGGATTAACAGATTTAACAGATGCACAACGTGAAAAACTCAGAGAACAA
ATTAACACTTCTAATAGTAGAGATGATATTAAGCAAAAAATTGAGCAAGCAAAAGCACTAAATGACGCA
ATGAAAAAACTTAAAGAACAAGTTGCGCAAAAAGATGGTGTTCATGCTAACAGTGATTATACAAATGAA
GATTCTGCACAAAAAGATGCGTATAATAATGCACTTAAACAAGCGGAAGACATTATTAATAACAGCTCA
AATCCTAACTTAAATGCACAAGACATTACTAATGCTTTAAATAATATTAAACAAGCACAAGATAACCTT
CATGGAGCTCAAAAATTACAGCAAGACAAAAATACAACTAATCAAGCCATTGGTAACTTAAATCATCTT
AATCAACCTCAAAAAGATGCGCTTATACAAGCTATTAATGGAGCTACATCTAGGGACCAAGTTGCAGAA
AAACTTAAAGAGGCCGAAGCGCTTGATGAAGCTATGAAACAACTTGAAGATCAAGTGAATCAAGATGAT
CAAATTTCAAATAGCAGCCCATTCATAAATGAAGACTCAGACAAACAAAAAACTTATAATGATAAAATC
CAAGCTGCAAAAGAAATAATTAATCAAACATCTAATCCAACCTTAGATAAACAAAAAATTGCTGATACA
CTTCAAAATATTAAAGATGCAGTGAATAATTTACATGGTGATCAAAAATTAGCTCAATCTAAACAAGAT
GCTAATAATCAATTAAATCATTTAGATGACTTAACCGAAGAACAAAAAAACCATTTTAAACCGTTAATT
AATAATGCTGATACTCGAGATGAGGTAAATAAACAACTAGAGATTGCTAAACAATTAAATGGTGATATG
AGTACACTTCATAAAGTCATAAATGATAAAGATCAAATTCAACATTTAAGCAATTACATTAATGCTGAT
AATGATAAAAAACAAAATTATGATAATGCTATTAAAGAAGCTGAGGATTTAATTCATAATCATCCAGAT

FIG. 2R

SEQ ID NO:48 (continued)

ACATTAGATCATAAAGCATTACAAGATTTATTAAACAAGATAGACCAAGCGCATAACGAATTAAATGGA
GAATCCAGATTTAAACAGGCTTTAGACAATGCTTTAAACGACATAGATAGCTTAAACAGTCTCAATGTT
CCACAACGCCAAACTGTTAAGGATAACATCAACCATGTGACAACTCTAGAAAGTTTAGCTCAAGAATTG
CAGAAAGCAAAAGAGCTTAATGATGCTATGAAAGCAATGAGAGATAGCATTATGAATCAAGAGCAAATT
CGTAAAAATAGCAATTATACTAATGAAGACTTAGCTCAACAAAATGCCTATAATCATGCAGTAGATAAA
ATAAATAACATTATTGGTGAAGACAATGCGACGATGGATCCTCAAATAATCAAACAAGCAACTCAAGAT
ATAAATACAGCTATAAATGGATTAAATGGAGATCAAAAACTTCAAGATGCAAAGACAGATGCTAAACAA
CAAATTACTAACTTTACTGGTTTAACTGAACCACAAAAACAAGCATTGGAAAACATCATTAACCAACAA
ACAAGCAGAGCAAATGTTGCTAAACAGTTAAGTCATGCTAAATTCTTAAATGGAAAAATGGAAGAATTA
AAAGTTGCAGTAGCCAAAGCGTCATTAGTAAGACAAAATAGTAACTATATTAATGAAGATGTCTCTGAA
AAAGAAGCATATGAACAAGCTATCGCAAAAGGTCAGGAAATAATTAATTCAGAAAATAATCCAACAATA
AGTAGTACTGATATCAATCGTACCATTCAAGAAATTAATGATGCTGAACAAAATCTTCATGGTGATAAT
AAATTAAGACAAGCACAGGAAATTGCAAAGAATGAAATACAAAATCTAGACGGATTAAATTCAGCTCAA
ATAACAAAATTAATCCAAGATATAGGCAGAACAACAACTAAACCTGCAGTAACTCAGAAACTAGAAGAA
GCAAAAGCAATAAACCAAGCTATGCAACAACTTAAACAAAGTATAGCCGATAAGGATGCTACTCTAAAT
TCTAGTAACTATCTCAATGAAGATTCTGAGAAAAAGTTAGCGTACGATAATGCTGTAAGCCAAGCTGAA
CAACTCATAAATCAACTTAACGACCCAACTATGGATATAAGTAATATTCAAGCTATTACTCAAAAGGTC
ATTCAAGCAAAAGATTCATTGCACGGTGCGAATAAACTTGCACAAAATCAAGCAGATTCAAATTTAATA
ATAAATCAATCAACAAATTTAAATGATAAACAAAAGCAAGCATTAAATGACTTAATTAATCATGCTCAA
ACTAAACAGCAAGTGGCAGAAATAATTGCACAAGCTAATAAGTTAAATAACGAAATGGGCACACTAAAA
ACACTCGTAGAAGAACAGTCAAACGTTCATCAACAAAGTAAATATATTAATGAAGATCCGCAAGTTCAA
AATATTTATAATGACTCCATTCAAAAAGGTCGAGAAATATTAAACGGCACTACAGATGATGTTTTAAAC
AACAATAAAATAGCAGATGCCATTCAAAACATTCATTTAACTAAAAACGATTTACATGGTGATCAAAAA
TTACAAAAAGCACAACAAGATGCAACCAATGAATTAAACTATTTAACAAATCTAAACAATTCTCAAAGA
CAAAGCGAGCATGATGAGATTAACTCTGCTCCTTCAAGAACTGAAGTTTCTAATGATTTAAATCATGCT
AAAGCACTTAATGAAGCTATGCGTCAACTTGAGAATGAAGTTGCTCTTGAAAACAGTGTTAAAAAATTA
AGCGACTTTATCAATGAAGATGAAGCGGCACAAAATGAATATAGTAATGCACTTCAAAAAGCTAAAGAC
ATTATCAACGGCGTTCCAAGTAGCACTTTAGATAAAGCTACAATTGAAGATGCTTTATTAGAATTGCAA
AATGCTAGAGAAAGTTTACATGGTGAGCAAAAACTTCAAGAGGCTAAAAATCAAGCTGTTGCTGAAATT
GATAATTTACAAGCATTAAATCCTGGACAGGTTCTTGCTGAAAAAACATTAGTTAACCAAGCATCAACC
AAACCAGAAGTTCAAGAAGCCTTACAAAAAGCAAAAGAACTTAATGAAGCTATGAAAGCACTGAAAACT
GAAATAAATAAAAAAGAACAAATCAAGGCTGATAGTAGATATGTAAATGCTGACAGTGGTCTTCAAGCA
AATTACAATTCTGCGTTAAATTATGGTTCTCAAATTATTGCAACTACCCAACCACCAGAGCTTAATAAA
GATGTAATAAATAGAGCAACTCAAACGATTAAAACTGCTGAAAATAATTTAAATGGGCAATCTAAATTA
GCAGAGGCTAAGTCAGACGGAAATCAAAGCATCGAACATTTGCAAGGATTAACACAATCACAAAAAGAT
AAACAACATGATTTAATTAATCAAGCTCAAACTAAACAACAGGTAGATGATATCGTAAATAACTCTAAA
CAATTAGATAACTCTATGAATCAACTACAACAAATTGTTAACAATGACAATACAGTAAAACAAAATAGT
GATTTCATTAATGAAGATTCCAGCCAACAGGATGCTTATAATCATGCAATTCAAGCAGCAAAAGATTTG
ATAACTGCTCATCCAACTATCATGGATAAAAATCAAATAGATCAAGCTATTGAAAATATCAAACAAGCA
CTTAATGATTTACACGGTAGTAATAAACTATCAGAAGATAAAAAAGAAGCTTCAGAACAACTACAAAAC
CTTAATAGCTTGACGAACGGGCAAAAAGATACGATTTTAAATCATATTTTCAGTGCACCAACAAGAAGC
CAAGTAGGAGAAAAAATTGCAAGTGCTAAACAATTAAATAATACAATGAAAGCACTTAGAGATTCTATT
GCTGATAATAATGAAATTTTACAAAGTAGTAAGTACTTCAATGAAGATTCTGAACAACAAAATGCTTAT
AATCAAGCCGTAAATAAAGCTAAAAATATAATTAATGATCAACCAACACCAGTAATGGCAAATGATGAG
ATTCAAAGTGTCCTAAATGAAGTTAAACAAACTAAAGATAATTTACATGGTGATCAAAAACTTGCTAAC
GACAAGACAGATGCTCAAGCAACATTAAATGCGTTAAATTACTTAAATCAAGCGCAAAGAGGTAATCTT
GAAACTAAAGTTCAAAACTCTAATTCTAGACCAGAAGTACAAAAAGTAGTTCAATTAGCAAATCAACTT
AATGATGCGATGAAAAAATTAGATGATGCTTTAACTGGTAATGACGCAATAAAACAAACGAGTAATTAT
ATTAATGAAGATACTTCTCAACAAGTTAACTTTGATGAGTATACAGATAGAGGTAAAAACATAGTTGCT
GAACAAACAAATCCAAATATGTCTCCAACTAATATTAACACTATTGCTGATAAAATTACTGAAGCTAAA
AACGATTTACATGGCGTACAAAAACTAAAACAAGCTCAACAACAGTCCATCAATACTATTAATCAAATG
ACTGGTCTAAACCAAGCTCAAAAAGAACAATTAAATCAAGAAATTCAACAAACTCAAACCCGTTCTGAA
GTACATCAAGTAATTAATAAAGCACAAGCTTTAAATGATTCAATGAATACTTTACGTCAAAGTATTACT
GATGAACATGAAGTTAAACAAACAAGTAACTACATCAATGAAACTGTTGGTAATCAAACTGCATATAAC
AATGCCGTTGATCGTGTAAAACAAATAATCAATCAAACATCTAATCCAACTATGAATCCTTTAGAGGTG
GAACGTGCAACATCAAATGTAAAAAATTTCTAAAGATGCACTTCATGGTGAACGTGAATTGAATGACAAT
AAAAATTCAAAAACTTTTGCAGTCAATCACTTAGATAACCTCAATCAAGCTCAAAAAGAAGCATTAACT
CATGAAATTGAACAAGCAACTATAGTTTCACAAGTAAATAATATCTATAACAAAGCGAAAGCTTTAAAT

FIG. 2S

SEQ ID NO:48 (continued)

AATGATATGAAAAAACTTAAAGATATCGTTGCTCAACAAGATAATGTGAGACAATCAAACAATTATATA
AACGAGGATAGTACACCTCAAAATATGTACAACGATACAATTAATCATGCACAATCAATCATTGATCAA
GTAGCAAACCCTACGATGTCTCATGACGAAATAGAGAATGCAATCAATAACATAAAGCATGCCATCAAT
GCACTCGATGGAGAACATAAATTACAACAAGCAAAAGAAAATGCAAACTTATTGATTAATAGTTTAAAC
GATTTAAATGCACCACAAAGAGATGCCATAAATAGATTGGTTAATGAAGCTCAAACAAGAGAAAAAGTA
GCTGAACAACTTCAAAGTGCTCAAGCTTTAAATGACGCTATGAAGCATTTAAGAAACAGCATTCAAAAT
CAATCATCCGTAAGACAAGAGAGCAAATATATTAATGCAAGTGATGCTAAAAAAGAGCAATATAATCAC
GCAGTTAGAGAAGTCGAAAATATTATCAATGAACAACATCCAACATTGGATAAAGAAATAATTAAGCAA
CTAACGGATGGTGTAAATCAAGCGAATAATGACTTAAATGGCGTTGAATTATTAGATGCTGATAAGCAA
AACGCACATCAATCGATACCTACATTGATGCACTTAAATCAAGCACAACAAAACGCATTAAATGAAAAA
ATTAATAACGCAGTTACCAGAACTGAAGTTGCGGCTATTATTGGCCAAGCAAAACTACTCGATCATGCT
ATGGAGAATTTAGAAGAAAGTATCAAAGATAAAGAGCAAGTCAAACAGTCAAGTAACTATATTAATGAA
GATTCTGATGTTCAAGAAACATACGATAACGCCGTTGATCATGTGACAGAAATACTTAATCAAACAGTA
AATCCAACTTTATCTATTGAAGATATAGAGCATGCTATCAACGAAGTTAATCAAGCGAAAAAACAACTC
AGAGGTAAACAAAAACTTTATCAAACTATCGATTTAGCTGATAAAGAATTAAGTAAATTGGATGATTTA
ACATCACAACAAAGCAGTTCAATATCTAATCAAATATATACTGCTAAAACGAGAACAGAAGTTGCCCAA
GCAATTGAAAAAGCAAAATCATTAAATCATGCAATGAAAGCACTTAACAAAGTATATAAAAATGCAGAT
AAAGTGTTAGATAGTAGTCGATTCATTAACGAAGATCAACCTGAAAAAAAGGCGTATCAACAAGCTATA
AATCATGTTGATTCAATCATTCATAGACAAACAAATCCTGAAATGGATCCAACAGTAATCAATAGCATA
ACTCATGAACTCGAAACAGCTCAAAATAACTTACATGGTGATCAGAAACTTGCTCATGCACAACAAGAT
GCCGCTAATGTAATTAATGGTCTAATTCATCTTAATGTTGCTCAACGTGAGGTAATGATAAATACGAAT
ACAAATGCTACAACACGCGAAAAAGTTGCAAAGAACTTAGATAATGCTCAAGCTCTTGATAAAGCTATG
GAAACACTACAACAAGTAGTTGCTCATAAAAATAATATATTGAACGATAGTAAATATTTAAATGAAGAT
TCAAAATATCAACAACAATACGATCGAGTTATTGCTGATGCCGAACAACTACTTAATCAGACAACAAAT
CCAACATTAGAACCTTATAAAGTCGATATTGTTAAGGATAATGTCCTAGCTAACGAAAAAATACTATTT
GGCGCAGAAAAACTATCATATGACAAATCAAATGCAAATGATGAAATTAAACATATGAATTATCTTAAT
AATGCACAAAAGCAATCTATAAAAGATATGATTTCTCACGCAGCATTAAGAACTGAAGTTAAACAACTT
CTGCAACAAGCTAAAATCCTTGATGAAGCCATGAAATCACTTGAAGATAAAACTCAAGTAGTGATTACA
GATACTACTTTGCCTAATTACACTGAAGCTTCAGAGGATAAAAAGGAAAAAGTAGACCAAACTGTATCA
CATGCTCAAGCGATTATTGATAAAATAAATGGCTCAAATGTAAGTTTAGATCAAGTACGACAAGCACTA
GAACAATTAACTCAAGCATCAGAAAACCTCGATGGTGATCAGCGAGTTGAAGAAGCTAAAGTTCATGCT
AATCAAACAATTGATCAATTAACACATCTTAATTCATTACAACAACAAACTGCGAAAGAAAGTGTTAAA
AACGCAACAAAACTAGAAGAAATCGCTACTGTTAGTAACAATGCTCAGGCATTAAACAAAGTAATGGGT
AAATTAGAACAATTCATTAATCATGCTGATTCTGTTGAAAATAGTGATAATTATAGACAAGCCGACGAC
GACAAAATCATCGCTTATGATGAAGCACTTGAACATGGACAAGATATACAAAAAACTAACGCAACCCAA
AATGAAACAAAACAAGCGTTACAACAATTAATATATGCAGAAACATCGTTAAATGGTTTCGAAAGATTA
AATCATGCTAGACCACGAGCTTTAGAATATATCAAATCACTAGAAAAAATAAACAATGCTCAAAAGTCT
GCTTTAGAGGATAAAGTAACGCAATCGCATGATTTATTAGAATTAGAACATATTGTCAACGAGGGCACA
AACCTCAATGACATTATGGGTGAATTAGCTAACGCAATCGTTAATAACTATGCTCCAACCAAAGCAAGT
ATAAATTATATTAACGCCGATAACCTACGCAAAGATAACTTTACTCAAGCTATCAACAATGCACGTGAT
GCACTCAACAAAACTCAAGGTCAGAACTTAGATTTCAATGCAATTGATACATTTAAAGATGATATATTC
AAAACTAAAGATGCACTTAACGGTATTGAACGTTTAACAGCTGCAAAATCAAAAGCAGAAAAACTAATT
GATAGTTTAAAATTTATTAATAAAGCTCAATTCACACATGCAAATGATGAAATTATGAATACTAATTCT
ATTGCACAATTGTCTAGAATCGTGAATCAAGCATTTGATTTAAATGATGCAATGAAATCTTTAAGAGAT
GAACTTAATAATCAAGCTTTTCCTGTCCAAGCAAGCTCAAATTATATAAATTCAGATGAAGATTTAAAA
CAACAATTTGACCATGCTTTAAGTAATGCTCGAAAAGTTCTTGCAAAAGAAAATGGTAAAAATTTAGAT
GAAAAACAAATTCAGGGACTCAAACAAGTGATTGAGGATACTAAAGATGCTTTAAATGGTATCCAACGT
TTATCAAAAGCTAAAGCTAAAGCAATTCAATACGTACAATCTTTATCTTATATCAATGATGCACAGCGT
CATATTGCTGAAAATAATATTCACAACTCTGATGATTTATCATCTTTAGCAAATACATTATCTAAAGCT
AGTGATTTAGATAATGCAATGAAAGACTTACGAGATACTATAGAAAGTAATTCAACTTCTGTTCCAAAT
AGTGTGAATTATATTAATGCTGATAAGAATTTACAAATTGAATTTGATGAGGCGCTACAACAAGCAAGT
GCAACAAGTTCTAAAACTTCAGAAAATCCAGCAACGATTGAAGAAGTATTAGGTCTTAGTCAAGCCATT
TACGATACAAAAAATGCATTAAATGGTGAACAACGACTTGCAACTGAGAAGAGCAAAGATCTAAAATTA
ATAAAAGGATTAAAAGATTTAAATAAAGCACAACTTGAAGATGTCACAAACAAGGTAAATTCAGCAAAT
ACTTTAACAGAGTTATCTCAGCTCACTCAATCAACGTTAGAATTAAACGATAAAATGAAATTATTGAGA
GATAAGCTTAAAACTTTAGTAAATCCTGTTAAAGCAAGTTTAAATTATAGAAACGCTGATTATAATTTA
AAACGTCAATTTAACAAAGCTTTAAAAGAAGCTAAAGGCGTATTAAATAAAAATAGCGGTACAAATGTC
AATATCAATGACATTCAACATCTTTTAACACAAATAGATAATGCTAAAGACCAATTAAATGGTGAACGA

*FIG. 2T*

SEQ ID NO:48 (continued)

CGTCTAAAAGAACATCAACAAAAATCTGAAGTATTTATTATTAAAGAATTAGATATACTTAATAATGCT
CAAAAAGCTGCAATAATTAATCAGATTAGAGCGTCTAAAGACATTAAAATAATTAATCAAATCGTTGAT
AATGCAATAGAATTAAATGATGCTATGCAAGGTTTAAAAGAACATGTAGCTCAATTAACAGCAACTACA
AAAGACAACATTGAATATTTAAATGCTGATGAAGACCATAAATTACAATATGATTACGCTATCAACTTA
GCGAATAATGTTCTTGACAAAGAAAACGGTACAAATAAAGACGCTAATATCATAATTGGAATGATTCAA
AACATGGATGATGCTAGAGCACTTCTAAATGGAATTGAAAGACTTAAAGATGCTCAAACAAAAGCACAT
AATGACATTAAAGATACGCTCAAACGTCAACTTGATGAAATTGAACACGCTAATGCAACATCAAATTCT
AAAGCTCAAGCTAAACAAATGGTAAATGAGGAAGCTAGAAAAGCGCTTTCTAATATTAATGACGCAACA
TCAAATGATTTAGTTAATCAAGCAAAAGATGAAGGGCAATCTGCAATTGAACACATACATGCAGATGAA
TTACCTAAAGCAAAACTAGATGCTAATCAAATGATTGACCAAAAAGTTGAAGATATAAATCACTTAATT
AGTCAAAATCCAAACTTATCAAATGAAGAAAAAAATAAACTAATATCTCAAATTAATAAGTTAGTAAAT
GGAATTAAGAATGAAATTCAACAAGCTATAAACAAACAACAAATAGAAAATGCTACAACAAAACTAGAT
GAAGTCATTGAAACTACTAAAAAATTAATTATCGCCAAAGCAGAAGCTAAACAAATGATAAAAGAGTTA
TCACAAAAGAAACGAGATGCAATAAATAACAACACTGATTTAACACCTTCTCAAAAGGCACATGCTTTA
GCAGATATTGATAAAACAGAAAAAGATGCACTTCAACATATCGAAAATTCTAATTCAATTGATGATATC
AATAACAATAAAGAGCATGCATTTAATACTTTAGCTCATATCATTATTTGGGATACTGATCAGCAACCA
TTAGTTTTTGAACTACCTGAATTGAGCCTTCAAAATGCTCTAGTAACAAGTGAGGTGGTTGTTCACAGA
GATGAAACTATTTCATTAGAATCTATAATTGGAGCTATGACTTTAACTGATGAACTTAAAGTCAATATT
GTTTCATTACCGAACACTGATAAAGTAGCTGATCACCTAACCGCTAAAGTTAAGGTTATTTTAGCTGAT
GGCTCATATGTCACTGTAAATGTTCCAGTCAAAGTTGTAGAAAAAGAATTACAAATAGCTAAAAAGGAT
GCTATAAAAACAATTGATGTTCTGGTAAAACAAAAAATCAAAGATATAGATTCTAATAACGAATTAACG
TCTACTCAACGTGAAGATGCAAAAGCTGAAATTGAAAGATTGAAAAAGCAAGCCATCGATAAAGTGAAT
CATTCAAAATCGATTAAAGATATTGAAACAGTAAAACGAACTGATTTTGAAGAAATAGATCAGTTTGAT
CCTAAACGCTTTACGCTAAATAAAGCTAAAAAGGATATCATTACTGATGTTAATACTCAAATCCAAAAT
GGTTTCAAAGAAATTGAAACAATAAAAGGTTTAACTTCTAATGAAAAAACTCAGTTTGATAAACAATTA
ACTGCACTACAAAAAGAATTTTTAGAAAAAGTCGAGCATGCTCATAATTTAGTAGAATTAAATCAATTA
CAACAAGAGTTTAATAATAGATATAAACATATTTTAAACCAAGCACATTTACTAGGTGAAAAACATATA
GCAGAACATAAATTAGGATATGTTGTAGTAAACAAAACTCAGCAAATACTAAATAATCAATCTGCTTCT
TACTTTATAAAACAATGGGCACTTGATAGAATTAAACAAATTCAACTAGAAACGATGAATTCAATTCGT
GGTGCGCATACCGTACAAGATGTACACAAAGCATTATTACAAGGTATAGAGCAAATCTTGAAAGTAAAT
GTAAGTATTATAAATCAATCTTTCAACGATTCCTTGCATAACTTTAATTATCTTCATTCAAAATTTGAT
GCTAGATTAAGAGAAAAGGATGTTGCAAACCATATCGTACAAACTGAAACATTCAAAGAAGTTCTAAAA
GGAACGGGTGTTGAACCAGGTAAAATCAACAAAGAAACACAGCAACCAAAACTTCATAAGAATGATAAT
GATAGCCTATTCAAACATTTAGTTGATAATTTCGGCAAAACTGTAGGTGTTATTACATTAACTGGTTTA
CTTTCTAGTTTCTGGTTAGTTTTGGCTAAAAGACGTAAAAAAGAAGAAGAAAAACAATCGATAAAA
AATCATCACAAAGATATTCGTCTTTCAGATACTGATAAAATAGATCCAATTGTAATAACTAAGCGTAAA
ATAGATAAAGAAGAACAAATTCAAAACGATGACAAACATTCAATTCCAGTTGCTAAACATAAGAAATCT
AAAGAAAAGCAATTGAGTGAAGAGGATATTCATTCAATCCCCGTCGTTAAGCGTAAACAAAACAGTGAT
AACAAAGATACAAAACAGAAGAAAGTTACTTCTAAAAAGAAGAAAACGCCTCAGTCAACTAAAAAAGTT
GTAAAAACCAAAAAGCGTTCTAAAAAG

FIG. 2U

SEQ ID NO:49 polynucleotide sequence

ATGAGAGATAAGAAAGGACCGGTAAATAAAAGAGTAGATTTTCTATCAAATAAATTGAATAAATATTCA
ATAAGAAAATTTACAGTTGGAACAGCATCTATTTTAATTGGCTCACTAATGTATTTGGGAACTCAACAA
GAAGCAGAAGCAGCTGAAAACAATATTGAGAATCCAACTACATTAAAAGATAATGTCCAATCAAAAGAA
GTGAAGATTGAAGAAGTAACAAACAAAGACACTGCACCACAAGGTGTAGAAGCTAAATCTGAAGTAACT
TCAAACAAAGACACAATCGAACATGAAGCATCAGTAAAAGCTGAAGATATATCAAAAAAGGAGGATACA
CCAAAAGAAGTAGCTAATGTTGCTGAAGTTCAGCCGAAATCGTCAGTCACTCATAACGCAGAGGCACCT
AAGGTTAGAAAAGCTCGTTCTGTTGATGAAGGCTCTTTTGATATTACAAGAGATTCTAAAAATGTAGTT
GAATCTACCCCAATTACAATTCAAGGTAAAGAACATTTTGAAGGTTACGGAAGTGTTGATATACAAAAA
AACCCAACAGATTTAGGGGTATCAGAGGTAACCAGGTTTAATGTTGGTAATGAAAGTAATGGTTTGATA
GGAGCTTTACAATTAAAAAATAAAATAGATTTTAGTAAGGATTTCAATTTTAAAGTTAGAGTGGCAAAT
AACCATCAATCAAATACCACAGGTGCTGATGGTTGGGGGTTCTTATTTAGTAAAGGAAATGCAGAAGAA
TATTTAACTAATGGTGGAATCCTTGGGGATAAAGGTCTGGTAAATTCAGGCGGATTTAAAATTGATACT
GGATACATTTATACAAGTTCCATGGACAAAACTGAAAAGCAAGCTGGACAAGGTTATAGAGGATACGGA
GCTTTTGTGAAAAATGACAGTTCTGGTAATTCACAAATGGTTGGAGAAAATATTGATAAATCAAAAACT
AATTTTTTAAACTATGCGGACAATTCAACTAATACATCAGATGGAAAGTTTCATGGGCAACGTTTAAAT
GATGTCATCTTAACTTATGTTGCTTCAACTGGTAAAATGAGAGCAGAATATGCTGGTAAAACTTGGGAG
ACTTCAATAACAGATTTAGGTTTATCTAAAAATCAGGCATATAATTTCTTAATTACATCTAGTCAAAGA
TGGGGCCTTAATCAAGGGATAAATGCAAATGGCTGGATGAGAACTGACTTGAAAGGTTCAGAGTTTACT
TTTACACCAGAAGCGCCAAAAACAATAACAGAATTAGAAAAAAAAGTTGAAGAGATTCCATTCAAGAAA
GAACGTAAATTTAATCCGGATTTAGCACCAGGGACAGAAAAAGTAACAAGAGAAGGACAAAAAGGTGAG
AAGACAATAACAACACCAACACTAAAAAATCCATTAACTGGAGAAATTATTAGTAAAGGTGAATCGAAA
GAAGAGATCACAAAAGATCCGATTAATGAATTAACAGAATACGGACCAGAAACGATAGCACCAGGTCAT
CGAGACGAATTTGATCCGAAGTTACCAACAGGAGAGAAAGAAGAAGTTCCAGGTAAACCAGGAATTAAG
AATCCAGAAACAGGAGACGTAGTTAGACCACCGGTCGATAGTGTAACAAAATATGGACCTGTAAAAGGA
GACTCGATTGTAGAAAAAGAAGAAATTCCATTCGAGAAAGAACGTAAATTTAATCCTGATTTAGCACCA
GGAACAGAAAAAGTAACAAGAGAAGGACAAAAAGGTGAGAAGACAATAACGACACCAACACTAAAAAAT
CCATTAACTGGAGAAATTATTAGTAAAGGTGAATCGAAAGAAGAGATCACAAAAGATCCGATTAATGAA
TTAACAGAATACGGACCTGAAACAATAGCGCCAGGTCATCGAGACGAATTTGATCCGAAGTTACCAACA
GGAGAGAAAGAAGAAGTTCCAGGTAAACCAGGAATTAAGAATCCAGAAACAGGAGACGTAGTTAGACCG
CCGGTCGATAGCGTAACAAAATATGGACCTGTAAAAGGAGACTCGATTGTAGAAAAAGAAGAAATTCCA
TTCAAGAAAGAACGTAAATTTAATCCTGATTTAGCACCAGGGACAGAAAAAGTAACAAGAGAAGGACAA
AAAGGTGAGAAGACAATAACGACGCCAACACTAAAAAATCCATTAACTGGAGAAATTATTAGTAAAGGT
GAATCGAAAGAAGAAATCACAAAAGATCCGATTAATGAATTAACAGAATACGGACCAGAAACGATAACA
CCAGGTCATCGAGACGAATTTGATCCGAAGTTACCAACAGGAGAGAAAGAGGAAGTTCCAGGTAAACCA
GGAATTAAGAATCCAGAAACAGGAGATGTAGTTAGACCACCGGTCGATAGCGTAACAAAATATGGACCT
GTAAAAGGAGACTCGATTGTAGAAAAAGAAGAAATTCCATTCGAGAAAGAACGTAAATTTAATCCTGAT
TTAGCACCAGGGACAGAAAAAGTAACAAGAGAAGGACAAAAAGGTGAGAAGACAATAACGACGCCAACA
CTAAAAAATCCATTAACTGGAGAAATTATTAGTAAAGGTGAATCGAAAGAAGAAATCACAAAAGATCCA
GTTAATGAATTAACAGAATTCGGTGGCGAGAAAATACCGCAAGGTCATAAAGATATCTTTGATCCAAAC
TTACCAACAGATCAAACGGAAAAAGTACCAGGTAAACCAGGAATCAAGAATCCAGACACAGGAAAAGTG
ATCGAAGAGCCAGTGGATGATGTGATTAAACACGGACCAAAAACGGGTACACCAGAAACAAAAACAGTA
GAGATACCGTTTGAAACAAAACGTGAGTTTAATCCAAAATTACAACCTGGTGAAGAGCGAGTGAAACAA
GAAGGACAACCAGGAAGTAAGACAATCACAACACCAATCACAGTGAACCCATTAACAGGTGAAAAAGTT
GGCGAGGGTCAACCAACAGAAGAGATCACAAAACAACCAGTAGATAAGATTGTAGAGTTCGGTGGAGAG
AAACCAAAAGATCCAAAAGGACCTGAAAACCCAGAGAAGCCGAGCAGACCAACTCATCCAAGTGGCCCA
GTAAATCCTAACAATCCAGGATTATCGAAAGACAGAGCAAAACCAAATGGCCCAGTTCATTCAATGGAT
AAAAATGATAAAGTTAAAAAATCTAAAATTGCTAAAGAATCAGTAGCTAATCAAGAGAAAAAACGAGCA
GAATTACCAAAAACAGGTTTAGAAAGCACGCAAAAAGGTTTGATCTTTAGTAGTATAATTGGAATTGCT
GGATTAATGTTATTGGCTCGTAGAAGAAAGAATTAA

SEQ ID NO:50 polynucleotide sequence

ATGGGCAAACGTAGACAAGGTCCTATTAATAAAAAAGTGGATTTTTTACCTAACAAATTAAACAAGTAT
TCTATAAGAAAATTCACTGTTGGTACGGCCTCAATATTACTTGGTTCGACACTTATTTTTGGAAGTAGT
AGCCATGAAGCGAAAGCTGCAGAAGAAAAACAAGTTGATCCAATTACACAAGCTAATCAAAATGATAGT
AGTGAAAGATCACTTGAAAACACAAATCAACCTACTGTAAACAATGAAGCACCACAGATGTCTTCTACA
TTGCAAGCAGAAGAAGGAAGCAATGCAGAAGCACCGAATGTTCCAACTATCAAAGCTAATTCAGATAAT
GATACACAAACACAATTTTCAGAAGCCCCTACAAGAAATGACCTAGCTAGAAAAGAAGATATCCCTGCT
GTTTCTAAAAACGAGGAATTACAATCATCACAACCAAACACTGACAGTAAAATAGAACCTACAACTTCA

FIG. 2V

SEQ ID NO:50 (continued)

GAACCTGTGAATTTAAATTATAGTTCTCCGTTTATGTCCTTATTAAGCATGCCTGCTGATAGTTCATCC
AATAACACTAAAAATACAATAGATATACCGCCAACTACGGTTAAAGGTAGAGATAATTACGATTTTTAC
GGTAGAGTAGATATCCAAAGTAATCCTACAGATTTAAATGCGACAAATTTAACGAGATATAATTATGGA
CAGCCACCTGGTACAACAACAGCTGGTGCAGTTCAATTTAAAAATCAAGTTAGTTTTGATAAAGATTTC
GACTTTAACATTAGAGTAGCAAACAATCGTCAAAGTAATACAACTGGTGCAGATGGTTGGGGCTTTATG
TTCAGCAAGAAAGATGGGGATGATTTCCTAAAAAACGGTGGTATCTTACGTGAAAAAGGTACACCTAGT
GCAGCTGGTTTCAGAATTGATACAGGATATTATAATAACGATCCATTAGATAAAATACAGAAACAAGCT
GGTCAAGGCTATAGAGGGTATGGGACATTTGTTAAAAATGACTCCCAAGGTAATACTTCTAAAGTAGGA
TCAGGTACTCCATCAACAGATTTTCTTAACTACGCAGATAATACTACTAATGATTTAGATGGTAAATTC
CATGGTCAAAAATTAAATAATGTTAATTTGAAATATAATGCTTCAAATCAAACTTTTACAGCTACTTAT
GCTGGTAAAACTTGGACGGCTACGTTATCTGAATTAGGATTGAGTCCAACTGATAGTTACAATTTTTA
GTTACATCAAGTCAATATGGAAATGGTAATAGTGGTACATACGCAGATGGCGTTATGAGAGCTGATTTA
GATGGTGCAACATTGACATATACTCCTAAAGCAGTCGATGGAGACCCAATTACATCAACTAAGGAAATA
CCATTTAATAAAAAACGCGAATTTGATCCAAACTTAGCGCCAGGTACAGAAAAAGTCGTTCAAAAAGGT
GAACCAGGAATTGAAACAACAACAACACCAACTTATGTCAATCCTAATACTGGAGAAAAAGTAGGTGAA
GGCACACCTACAACAAAGATCACTAAACAACCAGTGGATGAAATCGTTCATTATGGTGGCGAAGAAATC
AAGCCAGGACATAAAGATGAATTTGATCCAAATGCACCGAAAGGTAGTCAAACAACGCAACCAGGTAAG
CCAGGAGTTAAAAATCCTGATACAGGCGAAGTAGTCACACCACCAGTGGATGATGTGACAAAATATGGT
CCAGTTGATGGAGATCCGATTACGTCAACGGAAGAAATTCCATTCGACAAGAAACGTGAATTCAATCCT
GATTTAAAACCAGGTGAAGAGCGTGTTAAACAAAAAGGTGAACCAGGAACAAAAACAATTACAACACCA
ACAACTAAGAACCCATTAACAGGGGAAAAAGTTGGCGAAGGTGAACCAACAGAAAAAATAACAAAACAA
CCAGTAGATGAAATCACAGAATATGGTGGCGAAGAAATCAAGCCAGGCCATAAGGATGAATTTGATCCG
AACGCACCGAAAGGTAGCCAAGAGGACGTTCCAGGTAAACCAGGAGTTAAAAATCCTGATACAGGCGAA
GTAGTCACACCACCAGTGGATGATGTGACAAAATATGGTCCAGTTGATGGAGATCCGATTACGTCAACG
GAAGAAATTCCGTTTGATAAAAAACGCGAATTTGATCCAAACTTAGCGCCAGGTACAGAGAAAGTCGTT
CAAAAAGGTGAACCAGGAACAAAAACAATTACAACACCAACAACTAAGAACCCATTAACAGGAGAAAAA
GTTGGCGAAGGTGAACCAACAGAAAAAATAACAAAACAACCAGTGGATGAAATCGTTCATTATGGTGGC
GAAGAAATCAAGCCAGGCCATAAGGATGAATTTGATCCGAACGCACCGAAAGGTAGCCAAGAGGACGTT
CCAGGTAAGCCAGGAGTTAAAAATCCTGATACAGGCGAAGTAGTCACACCACCAGTGGATGATGTGACA
AAATATGGTCCAGTTGATGGAGATCCGATTACGTCAACGGAAGAAATTCCATTCGACAAGAAACGTGAA
TTCAATCCTGATTTAAAACCAGGTGAAGAGCGTGTTAAACAAAAAGGTGAACCAGGAACAAAAACAATT
ACAACACCAACAACTAAGAACCCATTAACAGGGGAAAAAGTTGGCGAAGGTGAACCAACAGAAAAAGTA
ACAAAACAACCAGTGGATGAAATCGTTCATTATGGTGGCGAAGAAATCAAGCCAGGCCATAAGGATGAA
TTTGATCCAAATGCACCGAAAGGTAGCCAAGAAGACGTTCCAGGTAAACCAGGAGTTAAAAACCCTGAT
ACAGGCGAAGTAGTTACTCCACCAGTGGATGATGTGACAAAATATGGTCCAGTTGATGGAGATCCGATT
ACGTCAACGGAAGAAATTCCGTTTGATAAAAAACGCGAATTTGATCCAAACTTAGCGCCAGGTACAGAG
AAAGTCGTTCAAAAAGGTGAACCAGGAACAAAAACAATTACAACACCAACAACTAAGAACCCATTAACA
GGAGAAAAAGTTGGCGAAGGTGAACCAACAGAAAAAATAACAAAACAACCAGTGGATGAGATCGTTCAT
TATGGTGGCGAAGAAATCAAGCCAGGCCATAAGGATGAATTTGATCCGAACGCACCGAAAGGTAGTCAA
ACAACGCAACCAGGTAAGCCAGGAGTTAAAAATCCTGATACAGGCGAAGTAGTCACACCACCAGTGGAT
GATGTGACAAAATATGGTCCAGTTGATGGAGATCCGATTACGTCAACGGAAGAAATTCCGTTTGATAAA
AAACGCGAATTTGATCCAAACTTAGCGCCAGGTACAGAGAAAGTCGTTCAAAAAGGTGAACCAGGAACA
AAAACAATTACAACGCCAACAACTAAGAACCCATTAACAGGAGAAAAAGTTGGCGAAGGTGAACCAACA
GAAAAAATAACAAAACAACCAGTGGATGAGATTGTTCATTATGGTGGTGAACAAATACCACAAGGTCAT
AAAGATGAATTTGATCCAAATGCACCTGTAGATAGTAAAACTGAAGTTCCAGGTAAACCAGGAGTTAAA
AATCCTGATACAGGTGAAGTTGTTACCCCACCAGTGGATGATGTGACAAAATATGGTCCGAAAGTTGGT
AATCCAATCACATCAACGGAAGAGATTCCATTTGATAAGAAACGTGTATTTAATCCTGATTTAAAACCA
GGTGAAGAGCGCGTTAAACAAAAAGGTGAACCAGGAACAAAAACAATTACAACACCAATATTAGTTAAT
CCTATTACAGGAGAAAAAGTTGGCGAAGGTAAATCAACAGAAAAAGTCACTAAACAACCTGTTGACGAA
ATTGTTGAGTATGGTCCAACAAAAGCAGAACCAGGTAAACCAGCGGAACCAGGTAAACCAGCGGAACCA
GGTAAACCAGCGGAACCAGGTAAACCAGCGGAACCAGGTACGCCAGCAGAACCAGGTAAACCAGCGGAA
CCAGGTAAACCAGCGGAACCAGGTAAACCAGCGGAACCAGGTAAACCAGCGGAACCAGGTAAACCAGCG
GAACCAGGTACGCCAGCAGAACCAGGTAAACCAGCGGAACCAGGTAAACCAGCGGAACCAGGTAAACCA
GCGGAACCAGGTACGCCAGCAGAACCAGGTAAACCAGCGGAACCAGGTACGCCAGCAGAACCAGGTAAA
CCAGCGGAACCAGGTACGCCAACACAATCAGGTGCACCAGAACAACCAAATAGATCAATGCATTCAACA
GATAATAAAAATCAATTACCTGATACAGGTGAAAATCGTCAAGCTAATGAGGGAACTTTAGTCGGATCT
CTATTAGCAATTGTCGGATCATTGTTCATATTTGGTCGTCGTAAAAAAGGTAATGAAAAATAA

*FIG. 2W*

SEQ ID NO:51 polynucleotide sequence

ATGAAGAAACTATATACATCTTATGGCACTTATGGATTTTTACATCAAATAAAAATCAATAACCCGACC
CATCAACTATTCCAATTTTCAGCATCAGATACTTCAGTTATTTTTGAAGAAACTGATGGTGAGACTGTT
TTAAAATCACCTTCAATATATGAAGTTATTAAAGAAATTGGTGAATTCAGTGAACATCATTTCTATTGT
GCAATCTTCATTCCTTCAACAGAAGATCATGCATATCAACTTGAAAAGAAACTGATTAGTGTAGACGAT
AATTTCAGAAACTTTGGTGGCTTTAAAAGCTATCGTTTGTTAAGACCTGCTAAAGGTACAACATATAAA
ATTTATTTCGGATTTGCTGATCGACATGCATACGAAGACTTTAAGCAATCTGATGCCTTTAATGACCAT
TTTTCAAAAGACGCATTAAGTCATTACTTTGGTTCAAGCGGACAACATTCAAGTTATTTTGAAAGATAT
CTATACCCAATAAAAGAATAG

SEQ ID NO:52 polynucleotide sequence

ATGTATTTATATACATCTTATGGGACTTACCAATTTTTAAATCAAATTAAACTTAATCATCAAGAACGT
AGTTTATTTCAATTTTCCACTAATGATTCCTCAATAATCTTAGAAGAGTCTGAGGGAAAATCAATCTTA
AAACATCCTAGTGCATATCAAGTGATTGATAGCACAGGTGAATTTAACGAACATCATTTTTATAGTGCT
ATTTTTGTCCCTACATCTGAAGATCATCGTCAACAGCTAGAGAAAAAATTATTACTCGTAGACGTACCT
TTAAGAAATTTTGGTGGTTTTAAAAGCTATCGTTTATTAAAACCCACTGAGGGGTCTACCTACAAAATT
TACTTTGGTTTTGCAAATCGAACAGCATATGAAGATTTCAAAGCTTCTGATATATTTAATGAAAACTTT
TCAAAAGATGCATTGAGCCAATACTTTGGTGCTAGTGGTCAACATTCTAGCTACTTTGAAAGATATTTA
TATCCAATAGAAGATCATTAA

*FIG. 2X*

SEQ ID NO:53 polynucleotide sequence

ATGATTAACAGGGATAATAAAAAGGCAATAACAAAAAAGGGTATGATTTCAAATCGCTTAAACAAATTT
TCGATTAGAAAGTATACTGTAGGAACTGCATCGATTTTAGTAGGTACGACATTGATTTTTGGTCTAGGG
AACCAAGAAGCTAAAGCTGCTGAAAACACTAGTACAGAAAATGCGAAACAAGATGATGCAACGACTAGT
GATAATAAAGAAGTAGTGTCGGAAACTGAAAATAATTCGACAACAGAAAATGATTCAACAAATCCAATT
AAGAAAGAAACAAATACTGATTCACAACCAGAAGCTAAAGAAGAATCAACTACATCAAGTACTCAACAA
CAGCAAAATAACGTTACAGCTACAACTGAAACTAAGCCTCAAAACATTGAAAAAGAAAATGTTAAACCT
TCAACTGATAAAACTGCGACAGAAGATACATCTGTTATTTTAGAAGAGAAGAAAGCACCAAATTATACA
AATAACGATGTAACTACAAAACCATCTACAAGTGAAATTCAAACAAAACCAACTACACCTCAAGAATCT
ACAAATATTGAAAATTCACAACCGCAACCAACGCCTTCAAAAGTAGACAATCAAGTTACAGATGCAACT
AATCCAAAAGAACCAGTAAATGTGTCAAAAGAAGAACTTAAAAATAATCCTGAGAAATTAAAAGAATTA
GTTAGAAATGATAACAATACAGATCGTTCAACTAAACCAGTTGCTACAGCTCCAACAAGTGTTGCACCA
AAACGATTAAATGCGAAAATGCGTTTTGCAGTTGCACAACCAGCAGCAGTTGCTTCAAATAATGTAAAT
GACTTAATTACAGTTACGAAACAGACGATCAAAGTTGGCGATGGTAAAGATAATGTGGCAGCAGCGCAT
GACGGTAAAGATATTGAATATGATACAGAGTTTACAATTGACAATAAAGTCAAAAAAGGCGATACAATG
ACGATTAATTATGATAAGAATGTAATTCCTTCGGATTTAACAGATAAAAATGATCCTATCGATATTACT
GATCCATCAGGAGAGGTCATTGCCAAAGGAACATTTGATAAAGCGACTAAGCAAATCACATATACATTT
ACAGATTATGTAGATAAATATGAAGATATAAAAGCACGTTTAACTTTATACTCATATATTGATAAGCAA
GCAGTACCTAATGAAACTAGTTTGAATTTAACGTTTGCAACAGCAGGTAAAGAAACTAGCCAAAACGTT
TCTGTTGATTATCAAGACCCAATGGTTCATGGTGATTCAAACATTCAATCTATCTTTACAAAGTTAGAT
GAAAACAAACAAACTATTGAACAACAAATTTATGTTAATCCTTTGAAAAAAACAGCAACTAACACTAAA
GTTGATATAGCTGGTAGTCAAGTAGATGATTATGGAAATATTAAACTAGGAAATGGTAGTACCATTATT
GACCAAAATACAGAAATAAAAGTTTATAAAGTTAACCCTAATCAACAATTGCCTCAAAGTAATAGAATC
TATGATTTTAGTCAATACGAAGATGTAACAAGTCAATTTGATAATAAAAAATCATTTAGTAATAATGTA
GCAACATTGGATTTTGGTGATATTAATTCAGCCTATATTATCAAAGTTGTTAGTAAATATACACCTACA
TCAGATGGCGAACTAGATATTGCTCAAGGTACTAGTATGAGAACAACTGATAAATATGGTTATTATAAT
TATGCAGGATATTCAAACTTCATCGTAACTTCTAATGACACTGGCGGTGGCGACGGTACTGTTAAACCT
GAAGAAAAGTTATACAAAATTGGTGACTATGTATGGGAAGACGTTGATAAAGACGGTGTCCAAGGTACA
GATTCGAAAGAAAAGCCAATGGCAAACGTTTTAGTTACATTAACTTACCCGGACGGTACTACAAAATCA
GTAAGAACAGATGCTAACGGTCATTATGAATTCGGTGGTTTGAAAGACGGAGAAACTTATACAGTTAAA
TTCGAAACGCCAGCTGGATATCTTCCAACAAAAGTAAATGGAACAACTGATGGTGAAAAAGACTCAAAT
GGTAGTTCTATAACTGTTAAAATTAATGGTAAAGATGATATGTCTTTAGACACTGGTTTTTATAAAGAA
CCTAAATATAATCTTGGTGACTATGTATGGGAAGATACAAATAAAGATGGTATCCAAGATGCTAATGAA
CCTGGTATCAAAGATGTTAAGGTTACATTAAAAGATAGTACTGGAAAAGTTATTGGTACAACTACTACT
GATGCCTCGGGTAAATATAAATTTACAGATTTAGATAATGGTAACTATACAGTAGAATTTGAAACACCA
GCAGGTTACACGCCAACGGTTAAAAATACTACAGCTGAAGATAAAGATTCTAATGGTTTAACAACAACA
GGTGTCATTAAAGATGCAGATAATATGACATTAGACAGTGGTTTCTATAAAACACCAAAATACAGTTTA
GGTGATTATGTTTGGTACGACAGTAATAAAGACGGTAAACAAGATTCAACTGAAAAAGGTATCAAAGAT
GTTAAAGTTACTTTATTAAATGAAAAAGGCGAAGTAATTGGAACAACTAAAACAGATGAAAATGGTAAA
TATCGTTTCGATAATTTAGATAGCGGTAAATACAAAGTTATTTTTGAAAAGCCTGCTGGCTTAACACAA
ACAGTTACAAATACAACTGAAGATGATAAAGATGCCGATGGTGGCGAAGTTGACGTAACAATTACGGAT
CATGATGATTTCATACTTGATAACGGATACTTCGAAGAAGATACATCAGACAGTGATTCAGACTCAGAC
AGTGATTCAGACTCAGACAGCGACTCAGATTCAGACAGTGATTCAGACTCAGATAGCGATTCAGATTCA
GACAGCGACTCAGACTCAGATAGCGACTCAGACTCAGACAGCGACTCAGACTCAGATAGCGACTCAGAT
TCGGACAGCGATTCAGACTCAGATAGCGACTCAGATTCAGACAGCGATTCAGACTCAGATAGCGACTCA
GATTCAGACAGTGACTCAGACTCAGATAGCGACTCAGACTCAGACAGTGACTCAGACTCAGACAGCGAT
TCAGATTCAGATAGCGACTCAGATTCGGACAGTGATTCAGACTCAGATAGCGACTCAGATTCAGACAGC
GACTCAGACTCAGATAGCGACTCAGACTCAGACAGTGATTCAGACTCAGATAGCGATTCGGACTCGGAT
GCAGGAAAACATACACCTGTTAAACCAATGAGTACTACTAAAGACCATCACAATAAAGCAAAAGCATTA
CCAGAAACAGGTAGTGAAAATAACGGCTCAAATAACGCAACGTTATTTGGTGGATTATTTGCAGCATTA
GGTTCATTATTGTTATTCGGTCGTCGCAAAAAACAAAACAAATAA

FIG. 2Y

SEQ ID NO:54 polynucleotide sequence

ATGATTAATAAAAAAAATAATTTACTAACTAAAAAGAAACCTATAGCAAATAAATCCAATAAATATGCA
ATTAGAAAATTCACAGTAGGTACAGCGTCTATTGTAATAGGTGCAACATTATTGTTTGGTTTAGGTCAT
AATGAGGCCAAAGCCGAGGAGAATTCAGTACAAGACGTTAAAGATTCGAATACGGATGATGAATTATCA
GACAGCAATGATCAGTCTAGTGATGAAGAAAAGAATGATGTGATCAATAATAATCAGTCAATAAACACC
GACGATAATAACCAAATAATTAAAAAAGAAGAAACGAATAACTACGATGGCATAGAAAAACGCTCAGAA
GATAGAACAGAGTCAACAACAAATGTAGATGAAAACGAAGCAACATTTTTACAAAAGACCCCTCAAGAT
AATACTCATCTTACAGAAGAAGAGGTAAAAGAATCCTCATCAGTCGAATCCTCAAATTCATCAATTGAT
ACTGCCCAACAACCATCTCACACAACAATAAATAGAGAAGAATCTGTTCAAACAAGTGATAATGTAGAA
GATTCACACGTATCAGATTTTGCTAACTCTAAAATAAAAGAGAGTAACACTGAATCTGGTAAAGAAGAG
AATACTATAGAGCAACCTAATAAAGTAAAAGAAGATTCAACAACAAGTCAGCCGTCTGGCTATACAAAT
ATAGATGAAAAAATTTCAAATCAAGATGAGTTATTAAATTTACCAATAAATGAATATGAAAATAAGGCT
AGACCATTATCTACAACATCTGCCCAACCATCGATTAAACGTGTAACCGTAAATCAATTAGCGGCGGAA
CAAGGTTCGAATGTTAATCATTTAATTAAAGTTACTGATCAAAGTATTACTGAAGGATATGATGATAGT
GAAGGTGTTATTAAAGCACATGATGCTGAAAACTTAATCTATGATGTAACTTTTGAAGTAGATGATAAG
GTGAAATCTGGTGATACGATGACAGTGGATATAGATAAGAATACAGTTCCATCAGATTTAACCGATAGC
TTTACAATACCAAAAATAAAAGATAATTCTGGAGAAATCATCGCTACAGGTACTTATGATAACAAAAAT
AAACAAATCACCTATACTTTTACAGATTATGTAGATAAGTATGAAAATATTAAAGCACACCTTAAATTA
ACGTCATACATTGATAAATCAAAGGTTCCAAATAATAATACCAAGTTAGATGTAGAATATAAAACGGCC
CTTTCATCAGTAAATAAAACAATTACGGTTGAATATCAAAGACCTAACGAAAATCGGACTGCTAACCTT
CAAAGTATGTTTACAAACATAGATACGAAAAATCATACAGTTGAGCAAACGATTTATATTAACCCTCTT
CGTTATTCAGCCAAGGAAACAAATGTAAATATTTCAGGGAATGGTGATGAAGGTTCAACAATTATAGAC
GATAGCACAATAATTAAAGTTTATAAGGTTGGAGATAATCAAAATTTACCAGATAGTAACAGAATTTAT
GATTACAGTGAATATGAAGATGTCACAAATGATGATTATGCCCAATTAGGAAATAATAATGATGTGAAT
ATTAATTTTGGTAATATAGATTCACCATATATTATTAAAGTTATTAGTAAATATGACCCTAATAAGGAT
GATTACACGACTATACAGCAAACTGTGACAATGCAGACGACTATAAATGAGTATACTGGTGAGTTTAGA
ACAGCATCCTATGATAATACAATTGCTTTCTCTACAAGTTCAGGTCAAGGACAAGGTGACTTGCCTCCT
GAAAAAACTTATAAAATCGGAGATTACGTATGGGAAGATGTAGATAAAGATGGTATTCAAAATACAAAT
GATAATGAAAAACCGCTTAGTAATGTATTGGTAACTTTGACGTATCCTGATGGAACTTCAAAATCAGTC
AGAACAGATGAAGATGGGAAATATCAATTTGATGGATTGAAAAACGGATTGACTTATAAAATTACATTC
GAAACACCTGAAGGATATACGCCGACGCTTAAACATTCAGGAACAAATCCTGCACTAGACTCAGAAGGT
AATTCTGTATGGGTAACTATTAATGGACAAGACGATATGACGATTGATAGTGGATTTTATCAAACACCT
AAATACAGCTTAGGGAACTATGTATGGTATGACACTAATAAAGATGGTATTCAAGGTGATGATGAAAAA
GGAATCTCTGGAGTTAAAGTGACGTTAAAAGATGAAAACGGAAATATCATTAGTACAACTACAACCGAT
GAAAATGGAAAGTATCAATTTGATAATTTAAATAGTGGTAATTATATTGTTCATTTTGATAAACCTTCA
GGTATGACTCAAACAACAACAGATTCTGGTGATGATGACGAACAGGATGCTGATGGGGAAGAAGTTCAT
GTAACAATTACTGATCATGATGACTTTAGTATAGATAACGGATACTATGATGACGAATCGGATTCCGAT
AGTGACTCAGACAGCGACTCAGATTCCGATAGTGATTCAGACTCCGATAGCGACTCGGATTCAGACAGC
GACTCAGATTCAGACAGCGACTCGGATTCTGATAGCGACTCGGATTCAGACAGCGACTCAGACTCAGAC
AGTGATTCAGATTCAGACAGCGACTCAGATTCCGATAGTGATTCAGACTCAGACAGCGACTCAGATTCT
GATAGTGATTCAGACTCAGACAGTGATTCAGATTCAGACAGCGACTCAGATTCCGATAGTGATTCAGAC
TCAGACAGCGACTCAGATTCCGATAGTGATTCAGACTCAGACAGCGACTCAGATTCTGATAGTGATTCA
GACTCAGACAGTGATTCAGATTCCGATAGTGATTCAGACTCCGATAGCGACTCAGACTCGGATAGTGAC
TCAGATTCTGATAGTGATTCAGACTCAGACAGTGATTCGGATTCCGATAGTGATTCAGACTCAGACAGC
GACTCAGATTCTGATAGTGATTCAGACTCAGACAACGACTCAGATTTAGGCAATAGCTCAGATAAGAGT
ACAAAAGATAAATTACCTGATACAGGAGCTAATGAAGATTATGGCTCTAAAGGCACGTTACTTGGAACT
CTGTTTGCAGGTTTAGGAGCGTTATTATTAGGGAAACGTCGCAAAAAATAGAAAAAATAAAAATTAA

FIG. 2Z

SEQ ID NO:55 polynucleotide sequence

ATGTCTAATAATTTTAAAGATGACTTTGAAAAAAATCGTCAATCGATAGACACAAATTCACATCAAGAC
CATACGGAAGATGTTGAAAAAGACCAATCAGAATTAGAACATCAGGATACAATAGAGAATACGGAGCAA
CAGTTTCCGCCAAGAAATGCCCAAAGAAGAAAAAGACGCCGTGATTTAGCAACGAATCATAATAAACAA
GTTCACAATGAATCACAAACATCTGAAGACAATGTTCAAAATGAGGCTGGCACAATAGATGATCGTCAA
GTCGAATCATCACACAGTACTGAAAGTCAAGAACCTAGCCATCAAGACAGTACACCTCAACATGAAGAG
GAATATTATAATAAGAATGCTTTTGCAATGGATAAATCACATCCAGAACCAATCGAAGACAATGATAAA
CACGAGACTATTAAAGATGCAGAAAATAACACTGAGCATTCAACAGTTTCTGATAAGAGTATAGCTGAA
CAATCTCAGCAACCTAAACCATATTTTGCAACAGGTGCTAACCAAGCAAATACATCAAAAGATAAACAT
GATGATGTAACTGTTAAGCAAGACAAAGATGAATCTAAAGATCATCATAGTGGTAAAAAAGGCGCAGCA
ATTGGTGCTGGAACAGCGGGTGTTGCAGGTGCAGCTGGTGCAATGGGTGTTTCTAAAGCTAAGAAACAT
TCAAATGACGCTCAAAACAAAAGTAATTCTGACAAGTCGAATAACTCGACTGAGGATAAAGCGTCTCAA
GATAAGTCTAAAGATCATCATAATGGCAAAAAAGGTGCAGCGATCGGTGCTGGAACAGCAGGTTTGGCT
GGAGGCGCAGCAAGTAAAAGTGCTTCTGCCGCTTCAAAACCACATGCCTCTAATAATGCAAGCCAAAAC
CATGATGAACATGACAATCATGACAGAGATAAAGAACGTAAAAAAGGTGGCATGGCCAAAGTATTGTTA
CCATTAATTGCAGCTGTACTAATTATCGGTGCATTAGCGATATTTGGAGGCATGGCATTAAACAATCAT
AATAATGGTACAAAAGAAAATAAAATCGCGAATACAAATAAAAATAATGCTGATGAAAGTAAAGACAAA
GACACATCTAAAGACGCTTCTAAAGATAAATCAAAATCTACAGACAGTGATAAATCAAAAGAGGATCAA
GACAAAGCGACTAAAGATGAATCTGATAATGATCAAAACAACGCTAATCAAGCGAACAATCAAGCACAA
AATAATCAAAATCAACAACAAGCTAATCAAAATCAACAACAGCAACAACAACGTCAAGGTGGTGGCCAA
AGACATACAGTGAATGGTCAAGAAAACTTATACCGTATCGCAATTCAATACTACGGTTCAGGTTCACCG
GAAAATGTTGAAAAAATTAGACGTGCCAATGGTTTAAGTGGTAACAATATTAGAAACGGTCAACAAATC
GTTATTCCATAA

SEQ ID NO:56 polynucleotide sequence

GTGATTGAATTAATTAAAATGGAAGGGATGATAGTTGTGTCTAATAATAATTTTAAAGATGATTTCGAA
AAGAATCGTCAATCTATTAATCCAGACGAACAGCAAACAGAATTAAAAGAAGATGATAAAACAAATGAA
AATAAAAAAGAAGCTGACTCTCAAAACAGTTTATCTAATAACTCAAATCAACAATTTCCTCCGAGAAAT
GCCCAACGACGAAAAAGACGTAGAGAGACAGCAACTAATCAAAGCAAACAACAAGACGACAAACATCAA
AAAAATAGTGACGCTAAAACTACAGAAGGTTCATTAGATGACCGTTATGACGAAGCACAGTTACAGCAA
CAACATGATAAATCGCAACAACAAAATAAAACTGAAAAACAATCACAAGATAATAGAATGAAAGATGGA
AAAGATGCAGCTATTGTAAATGGAACATCTGAGTCACCAGAACATAAATCAAAATCAACACAAAATAGA
CCCGGCCCTAAAGCTCAACAACAAAAGCGTAAATCAGAAAGTACGCAATCAAAACCGTCAACAAACAAA
GATAAAAAAGCAGCTACAGGTGCTGGAATAGCTGGTGCAGCTGGTGTTGCTGGTGCAGCAGAAACATCC
AAACGTCATCATAATAAAAAAGATAAACAAGATTCTAAACACTCAAACCATGAGAATGACGAAAAATCT
GTTAAAAATGATGACCAAAAGCAATCTAAAAAAGGCAAAAAAGCAGCAGTCGGTGCTGGCGCAGCTGCA
GGAGTTGGTGCGGCTGGTGTTGCGCATCATAATAATCAAAATAAACATCATAATGAGGAAAAAAATTCT
AATCAAAACAATCAGTACAATGACCAATCAGAAGGTAAGAAAAAAAGGTGGTTTCATGAAAATCTTGTTA
CCACTTATAGCAGCCATTCTTATTCTAGGTGCAATAGCAATATTCGGTGGTATGGCTCTAAATAATCAC
AACGATAGTAAAAGTGATGACCAAAAAATAGCGAATCAAAGTAAGAAAGACTCAGATAAAAAAGATGGT
GCGCAATCCGAAGATAACAAAGACAAAAAATCTGATAGTAACAAAGACAAAAAATCTGATTCTGATAAG
AACGCAGATGATGACTCTGATAATAGTTCCTCAAATCCTAACGCTACTTCAACTAATAATAACGATAAT
GTAGCCAATAATAACTCAAATTATACAAACCAAAATCAACAAGATAATGCAAACCAAAATAGCAATAAT
CAACAGGCAACTCAAGGTCAACAATCACATACAGTATACGGTCAAGAAAACTTATATCGTATCGCCATA
CAATATTATGGAGAAGGAACTCAAGCTAACGTAGATAAAATTAAACGTGCGAATGGATTAAGCAGTAAT
AATATTCATAATGGTCAAACATTAGTTATTCCTCAATAA

SEQ ID NO:57 polynucleotide sequence

ATGAAAAATAAATTGATAGCAAAATCTTTATTAACAATAGCGGCAATTGGTATTACTACAACTACAATT
GCGTCAACAGCAGATGCGAGCGAAGGATACGGTCCAAGAGAAAAGAAACCAGTGAGTATTAATCACAAT
ATCGTAGAGTACAATGATGGTACTTTTAAATATCAATCTAGACCAAAATTTAACTCAACACCTAAATAT
ATTAAATTCAAACATGACTATAATATTTTAGAATTTAACGATGGTACATTCGAATATGGTGCACGTCCA
CAATTTAATAAACCAGCAGCGAAAACTGATGCAACTATTAAAAAAGAACAAAAATTGATTCAAGCTCAA
AATCTTGTGAGAGAATTTGAAAAAACACATACTGTCAGTGCACACAGAAAAGCACAAAAGGCAGTCAAC
TTAGTTTCGTTTGAATACAAAGTGAAGAAAATGGTCTTACAAGAGCGAATTGATAATGTATTAAAACAA
GGATTAGTGAGATAA

*FIG. 2AA*

SEQ ID NO:58 polynucleotide sequence

ATGAAAACACGTATAGTCAGCTCAGTAACAACAACACTATTGCTAGGTTCCATATTAATGAATCCTGTC
GCTAATGCCGCAGATTCTGATATTAATATTAAAACCGGTACTACAGATATTGGAAGCAATACTACAGTA
AAAACAGGTGATTTAGTCACTTATGATAAAGAAAATGGCATGCACAAAAAAGTATTTTATAGTTTTATC
GATGATAAAAATCACAATAAAAAACTGCTAGTTATTAGAACGAAAGGTACCATTGCTGGTCAATATAGA
GTTTATAGCGAAGAAGGTGCTAACAAAAGTGGTTTAGCCTGGCCTTCAGCCTTTAAGGTACAGTTGCAA
CTACCTGATAATGAAGTAGCTCAAATATCTGATTACTATCCAAGAAATTCGATTGATACAAAAGAGTAT
ATGAGTACTTTAACTTATGGATTCAACGGTAATGTTACTGGTGATGATACAGGAAAAATTGGCGGCCTT
ATTGGTGCAAATGTTTCGATTGGTCATACACTGAAATATGTTCAACCTGATTTCAAAACAATTTTAGAG
AGCCCAACTGATAAAAAAGTAGGCTGGAAAGTGATATTTAACAATATGGTGAATCAAAATTGGGGACCA
TATGATAGAGATTCTTGGAACCCGGTATATGGCAATCAACTTTTCATGAAAACTAGAAATGGTTCTATG
AAAGCAGCAGAGAACTTCCTTGATCCTAACAAAGCAAGTTCTCTATTATCTTCAGGGTTTTCACCAGAC
TTCGCTACAGTTATTACTATGGATAGAAAAGCATCCAAACAACAAACAAATATAGATGTAATATACGAA
CGAGTTCGTGATGACTACCAATTGCATTGGACTTCAACAAATTGGAAAGGTACCAATACTAAAGATAAA
TGGACAGATCGTTCTTCAGAAAGATATAAAATCGATTGGGAAAAAGAAGAAATGACAAATTAA

SEQ ID NO:59 polynucleotide sequence

ATACACATGAAAAATAAATATATCTCGAAGTTGCTAGTTGGGGCAGCAACAATTACTTTAGCTACAATG
ATTTCAAATGGGGAAGCAAAAGCGAGTGAAAACACGCAACAAACTTCAACTAAGCACCAAACAACTCAA
AACAACTACGTAACAGATCAACAAAAAGCTTTTTATCAAGTATTACATCTAAAAGGTATCACAGAAGAA
CAACGTAACCAATACATCAAAACATTACGCGAACACCCAGAACGTGCACAAGAAGTATTCTCTGAATCA
CTTAAAGACAGCAAGAACCCAGACCGACGTGTTGCACAACAAAACGCTTTTTACAATGTTCTTAAAAAT
GATAACTTAACTGAACAAGAAAAAAATAATTACATTGCACAAATTAAAGAAAACCCTGATAGAAGCCAA
CAAGTTTGGGTAGAATCAGTACAATCTTCTAAAGCTAAAGAACGTCAAAATATTGAAAATGCGGATAAA
GCAATTAAAGATTTCCAAGATAACAAAGCACCACACGATAAATCAGCAGCATATGAAGCTAACTCAAAA
TTACCTAAAGATTTACGCGATAAAAATAACCGCTTTGTAGAAAAAGTTTCAATTGAAAAAGCAATCGTT
CGTCATGATGAGCGTGTGAAATCAGCAAATGATGCAATCTCAAAATTAAATGAAAAAGATTCAATTGAA
AACAGACGTTTAGCACAACGTGAAGTTAACAAAGCACCTATGGATGTAAAAGAGCATTTACAGAAACAA
TTAGACGCATTAGTAGCTCAAAAAGATGCTGAAAAGAAAGTGGCGCCAAAAGTTGAGGCTCCTCAAATT
CAATCACCACAAATTGAAAAACCTAAAGCAGAATCACCAAAAGTTGAAGTCCCTCAATCTAAATTATTA
GGTTACTACCAATCATTAAAAGATTCATTTAACTATGGTTACAAGTATTTAACAGATACTTATAAAAGC
TATAAAGAAAAATATGATACAGCAAAGTACTACTATAATACGTACTATAAATACAAAGGTGCGATTGAT
CAAACAGTATTAACAGTACTAGGTAGTGGTTCTAAATCTTACATCCAACCATTGAAAGTTGATGATAAA
AACGGCTACTTAGCTAAATCATATGCACAAGTAAGAAACTATGTAACTGAGTCAATCAATACTGGTAAA
GTATTATATACTTTCTACCAAAACCCAACATTAGTAAAAACAGCTATTAAAGCTCAAGAAACTGCATCA
TCAATCAAAAATACATTAAGTAATTTATTATCATTCTGGAAATAA

SEQ ID NO:60 polynucleotide sequence

ATGACAAAACATTATTTAAACAGTAAGTATCAATCAGAACAACGTTCATCAGCTATGAAAAAGATTACA
ATGGGTACAGCATCTATCATTTTAGGTTCCCTTGTATACATAGGCGCAGACAGCCAACAAGTCAATGCG
GCAACAGAAGCTACGAACGCAACTAATAATCAAAGCACACAAGTTTCTCAAGCAACATCACAACCAATT
AATTTCCAAGTGCAAAAAGATGGCTCTTCAGAGAAGTCACACATGGATGACTATATGCAACACCCTGGT
AAAGTAATTAAACAAAATAATAAATATTATTTCCAAACCGTGTTAAACAATGCATCATTCTGGAAAGAA
TACAAATTTTACAATGCAAACAATCAAGAATTAGCAACAACTGTTGTTAACGATAATAAAAAAGCGGAT
ACTAGAACAATCAATGTTGCAGTTGAACCTGGATATAAGAGCTTAACTACTAAAGTACATATTGTCGTG
CCACAAATTAATTACAATCATAGATATACTACGCATTTGGAATTTGAAAAAGCAATTCCTACATTAGCT
GACGCAGCAAAACCAAACAATGTTAAACCGGTTCAACCAAAACCAGCTCAACCTAAAACACCTACTGAG
CAAACTAAACCAGTTCAACCTAAAGTTGAAAAAGTTAAACCTACTGTAACTACAACAAGCAAAGTTGAA
GACAATCACTCTACTAAAGTTGTAAGTACTGACACAACAAAAGATCAAACTAAAACACAAACTGCTCAT
ACAGTTAAAACAGCACAAACTGCTCAAGAACAAAATAAAGTTCAAACACCTGTTAAAGATGTTGCAACA
GCGAAATCTGAAAGCAACAATCAAGCTGTAAGTGATAATAAATCACAACAAACTAACAAAGTTACAAAA
CATAACGAAACGCCTAAACAAGCATCTAAAGCTAAAGAATTACCAAAAACTGGTTTAACTTCAGTTGAT
AACTTTATTAGCACAGTTGCCTTCGCAACACTTGCCCTTTTAGGTTCATTATCTTTATTACTTTTCAAA
AGAAAAGAATCTAAATAA

*FIG. 2BB*

SEQ ID NO:61 polynucleotide sequence

ATGAACAAACAGCAAAAAGAATTTAAATCATTTTATTCAATTAGAAAGTCATCACTAGGCGTTGCATCT
GTAGCGATTAGTACACTTTTATTATTAATGTCAAATGGCGAAGCACAAGCAGCAGCTGAAGAAACAGGT
GGTACAAATACAGAAGCACAACCAAAAACTGAAGCAGTTGCAAGTCCAACAACAACATCTGAAAAAGCT
CCAGAAACTAAACCAGTAGCTAATGCTGTCTCAGTATCTAATAAAGAAGTTGAGGCCCCTACTTCTGAA
ACAAAAGAAGCTAAAGAAGTTAAAGAAGTTAAAGCCCCTAAGGAAACAAAAGCAGTTAAACCAGCAGCA
AAAGCCACTAACAATACATATCCTATTTTGAATCAGGAACTTAGAGAAGCGATTAAAAACCCTGCAATA
AAAGATAAAGATCATAGCGCACCAAACTCTCGTCCAATTGATTTTGAAATGAAAAAGAAAATGGTGAG
CAACAATTTTATCATTATGCCAGCTCTGTTAAACCTGCTAGAGTTATTTTCACTGATTCAAAACCAGAA
ATTGAATTAGGATTACAATCAGGTCAATTTTGGAGAAAATTTGAAGTTTATGAAGGTGACAAAAAGTTG
CCAATTAAATTAGTATCATACGATACTGTTAAAGATTACGCTTACATTCGCTTCTCTGTTTCAAATGGA
ACAAAAGCCGTTAAAATTGTAAGTTCAACTCACTTCAATAACAAAGAAGAAAAATACGATTACACATTA
ATGGAATTCGCACAACCAATTTATAACAGTGCAGATAAATTCAAAACTGAAGAAGATTATAAAGCTGAA
AAATTATTAGCGCCATATAAAAAAGCGAAAACACTAGAAAGACAAGTTTATGAATTAAATAAAATTCAA
GATAAACTTCCTGAAAAATTAAAGGCTGAGTACAAGAAGAAATTAGAGGATACAAAGAAAGCTTTAGAT
GAGCAAGTGAAATCAGCTATTACTGAATTCCAAAATGTACAACCAACAAATGAAAAAATGACTGATTTA
CAAGATACAAAATATGTTGTTTATGAAAGTGTTGAGAATAACGAATCTATGATGGATACTTTTGTTAAA
CACCCTATTAAAACAGGTATGCTTAACGGCAAAAAATATATGGTCATGGAAACTACTAATGACGATTAC
TGGAAAGATTTCATGGTTGAAGGTCAACGTGTTAGAACTATAAGCAAAGATGCTAAAAATAATACTAGA
ACAATTATTTTCCCATATGTTGAAGGTAAAACTCTATATGATGCTATCGTTAAAGTTCACGTAAAAACG
ATTGATTATGATGGACAATACCATGTCAGAATCGTTGATAAAGAAGCATTTACAAAAGCCAATACCGAT
AAATCTAACAAAAAAGAACAACAAGATAACTCAGCTAAGAAGGAAGCTACTCCAGCTACGCCTAGCAAA
CCAACACCATCACCTGTTGAAAAAGAATCACAAAAACAAGACAGCCAAAAAGATGACAATAAACAATTA
CCAAGTGTTGAAAAAGAAAATGACGCATCTAGTGAGTCAGGTAAAGACAAAACGCCTGCTACAAAACCA
ACTAAAGGTGAAGTAGAATCAAGTAGTACAACTCCAACTAAGGTAGTATCTACGACTCAAAATGTTGCA
AAACCAACAACTGCTTCATCAAAAACAACAAAAGATGTTGTTCAAACTTCAGCAGGTTCTAGCGAAGCA
AAAGATAGTGCTCCATTACAAAAAGCAAACATTAAAAACACAAATGATGGACACACTCAAAGCCAAAAC
AATAAAAATACACAAGAAAATAAAGCAAAATCATTACCACAAACTGGTGAAGAATCAAATAAAGATATG
ACATTACCATTAATGGCATTACTAGCTTTAAGTAGCATCGTTGCATTCGTATTACCTAGAAAACGTAAA
AACTAA

*FIG. 2CC*

SEQ ID NO:62 polynucleotide sequence

ATGAATAATAAAAAGACAGCAACAAATAGAAAAGGCATGATACCAAATCGATTAAACAAATTTTCGATA
AGAAAGTATTCTGTAGGTACTGCTTCAATTTTAGTAGGGACAACATTGATTTTTGGGTTAAGTGGTCAT
GAAGCTAAAGCGGCAGAACATACGAATGGAGAATTAAATCAATCAAAAAATGAAACGACAGCCCCAAGT
GAGAATAAAACAACTGAAAAAGTTGATAGTCGTCAACTAAAAGACAATACGCAAACTGCAACTGCAGAT
CAGCCTAAAGTGACAATGAGTGATAGTGCAACAGTTAAAGAAACTAGTAGTAACATGCAATCACCACAA
AACGCTACAGCTAGTCAATCTACTACACAAACTAGCAATGTAACAACAAATGATAAATCATCAACTACA
TATAGTAATGAAACTGATAAAAGTAATTTAACACAAGCAAAAAACGTTTCAACTACACCTAAAACAACG
ACTATTAAACAAAGAGCTTTAAATCGCATGGCAGTGAATACTGTTGCAGCTCCACAACAAGGAACAAAT
GTTAATGATAAAGTACATTTTACGAACATTGATATTGCGATTGATAAAGGACATGTTAATAAAACAACA
GGAAATACTGAATTTTGGGCAACTTCAAGTGATGTTTTAAAATTAAAAGCGAATTACACAATCGATGAT
TCTGTTAAAGAGGGCGATACATTTACTTTTAAATATGGTCAATATTTCCGTCCAGGTTCTGTAAGATTA
CCTTCACAAACTCAAAATTTATATAATGCCCAAGGTAATATTATTGCAAAAGGTATTTACGATAGTAAA
ACAAATACAACAACGTATACTTTTACGAATTATGTAGATCAATACACAAATGTTAGCGGTAGCTTTGAA
CAAGTCGCATTTGCGAAACGTGAAAATGCAACAACTGATAAAACTGCTTATAAAATGGAAGTAACTTTA
GGTAATGATACATATAGTAAAGATGTCATTGTCGATTATGGTAATCAAAAAGGTCAACAACTTATTTCG
AGTACAAATTATATTAATAATGAAGATTTGTCACGTAATATGACTGTTTATGTAAATCAACCTAAAAAG
ACCTATACAAAAGAAACATTTGTAACAAATTTAACTGGTTATAAATTTAATCCAGATGCTAAAAACTTC
AAAATTTACGAAGTGACAGATCAAAATCAATTTGTGGATAGTTTCACCCCAGATACTTCAAAACTTAAA
GATGTTACTGGTCAATTCGATGTTATTTATAGTAATGATAATAAGACGGCGACAGTAGATTTATTGAAT
GGTCAATCTAGTAGTGATAAACAGTACATCATTCAACAAGTTGCTTATCCAGATAATAGTTCAACAGAT
AATGGGAAAATTGATTATACTTTAGAAACACAAAATGGAAAAAGTAGTTGGTCAAACAGTTATTCAAAT
GTGAATGGCTCATCAACTGCAAATGGCGACCAAAAGAAATATAATCTAGGTGACTATGTATGGGAAGAT
ACAAATAAAGATGGTAAACAAGATGCCAATGAAAAAGGGATTAAAGGTGTTTATGTCATTCTTAAAGAT
AGTAACGGTAAAGAATTAGATCGTACGACAACAGATGAAAATGGTAAATATCAGTTCACTGGTTTAAGC
AATGGAACTTATAGTGTAGAGTTTTCAACACCAGCCGGTTATACACCGACAACTGCAAATGCAGGTACA
GATGATGCTGTAGATTCTGATGGACTAACTACAACAGGTGTCATTAAAGACGCTGACAACATGACATTA
GATAGTGGATTCTACAAAACACCAAAATATAGTTTAGGTGATTATGTTTGGTACGACAGTAATAAAGAT
GGTAAACAAGATTCGACTGAAAAAGGAATTAAAGGTGTTAAAGTTACTTTGCAAAACGAAAAAGGCGAA
GTAATTGGTACAACTGAAACAGATGAAAATGGTAAATACCGCTTTGATAATTTAGATAGTGGTAAATAC
AAAGTTATCTTTGAAAAGCCTGCTGGTTTAACTCAAACAGGTACAAATACAACTGAAGATGATAAAGAT
GCCGATGGTGGCGAAGTTGATGTAACAATTACGGATCATGATGATTTCACACTTGATAATGGCTACTAC
GAAGAAGAAACATCAGATAGTGACTCAGATTCGGACAGCGATTCAGACTCAGATAGCGACTCAGATTCA
GATAGTGACTCAGACTCAGATAGCGACTCAGACTCAGATAGCGACTCAGACAGCGACTCAGACTCAGAT
AGTGATTCAGATTCGGACAGCGACTCAGATTCAGACAGCGAATCAGATTCGGATAGCGACTCAGACTCA
GATAGCGACTCAGACAGCGACTCAGATTCAGACAGTGACTCAGACTCAGACAGCGACTCAGATTCAGAC
AGCGATTCAGATTCGGATAGCGACTCAGATTCAGATAGCGATTCGGACTCAGACAACGACTCAGATTCT
GACAGCGATTCAGACTCAGATAGCGACTCAGATTCAGACAGCGACTCAGATTCAGACAGCGATTCAGAT
TCAGATAGCGATTCAGATTCAGACAGCGACTCAGATTCAGATAGCGACTCAGACTCAGACAGCGATTCA
GACTCAGATAGCGACTCAGACAGCGATTCAGATTCGGATAGCGATTCAGATTCAGATGCAGGTAAACAT
ACTCCGACTAAACCAATGAGTACGGTTAAAGATCAGCATAAAACAGCTAAAGCATTACCAGAAACAGGT
AGTGAAAATAATAATTCAAATAATGGCACATTATTCGGTGGATTATTCGCGGCATTAGGATCATTATTG
TTATTCGGTCGTCGTAAAAAACAAAATAAATAA

FIG. 2DD

SEQ ID NO:63 polynucleotide sequence

ATGAATATGAAGAAAAAAGAAAAACACGCAATTCGGAAAAAATCGATTGGCGTGGCTTCAGTGCTTGTA
GGTACGTTAATCGGTTTTGGACTACTCAGCAGTAAAGAAGCAGATGCAAGTGAAAATAGTGTTACGCAA
TCTGATAGCGCAAGTAACGAAAGCAAAAGTAATGATTCAAGTAGCGTTAGTGCTGCACCTAAAACAGAC
GACACAAACGTGAGTGATACTAAAACATCGTCAAACACTAATAATGGCGAAACGAGTGTGGCGCAAAAT
CCAGCACAACAGGAAACGACACAATCATCATCAACAAATGCAACTACGGAAGAAACGCCGGTAACTGGT
GAAGCTACTACTACGACAACGAATCAAGCTAATACACCGGCAACAACTCAATCAAGCAATACAAATGCG
GAGGAATTAGTGAATCAAACAAGTAATGAAACGACTTCTAATGATACTAATACAGTATCATCTGTAAAT
TCACCTCAAAATTCTACAAATGCGGAAAATGTTTCAACAACGCAAGATACTTCAACTGAAGCAACACCT
TCAAACAATGAATCAGCTCCACAGAATACAGATGCAAGTAATAAAGATGTAGTTAGTCAAGCGGTTAAT
CCAAGTACGCCTAGAATGAGAGCATTTAGTTTAGCGGCAGTAGCTGCAGATGCACCGGCAGCTGGCACA
GATATTACGAATCAGTTGACAGATGTGAAAGTTACTATTGACTCTGGTACGACTGTGTATCCGCACCAA
GCAGGTTATGTCAAACTGAATTATGGTTTTTCAGTGCCTAATTCTGCTGTTAAAGGTGACACATTCAAA
ATAACTGTACCTAAAGAATTAAACTTAAATGGTGTAACTTCAACTGCTAAAGTGCCACCAATTATGGCT
GGAGATCAAGTATTGGCAAATGGTGTAATCGATAGTGATGGTAATGTTATTTATACATTTACAGACTAT
GTTGATAATAAAGAAAATGTAACAGCTAATATTACTATGCCAGCTTATATTGACCCTGAAAATGTTACA
AAGACAGGTAATGTGACATTGACAACTGGCATAGGAACCAATACTGCTAGTAAGACAGTATTAATCGAC
TATGAGAAATATGGACAATTCCATAATTTATCAATTAAAGGTACGATTGATCAAATCGATAAAACAAAT
AATACGTATCGCCAAACAATTTATGTCAATCCAAGCGGAGATAACGTTGTGTTACCTGCCTTAACAGGT
AATTTAATTCCTAATACAAAGAGTAATGCGTTAATAGATGCAAAAAACACTGATATTAAAGTTTATAGA
GTCGATAATGCTAATGATTTATCTGAAAGTTATTATGTGAATCCTAGCGATTTTGAAGATGTAACTAAT
CAAGTTAGAATTTCATTTCCAAATGCTAATCAATACAAAGTAGAATTTCCTACGGACGATGACCAAATT
ACAACACCGTATATTGTAGTTGTTAATGGCCATATTGATCCTGCTAGTACAGGTGATTTAGCACTACGT
TCGACATTTTATGGTTATGATTCTAATTTTATATGGAGATCTATGTCATGGGACAACGAAGTAGCATTT
AATAACGGATCAGGTTCTGGTGACGGTATCGATAAACCAGTTGTTCCTGAACAACCTGATGAGCCTGGT
GAAATTGAACCAATTCCAGAGGATTCAGATTCTGACCCAGGTTCAGATTCTGGCAGCGATTCTAATTCA
GATAGCGGTTCAGATTCTGGCAGTGATTCTACATCAGATAGTGGTTCAGATTCAGCGAGTGATTCAGAT
TCAGCAAGTGATTCAGACTCAGCGAGTGATTCAGATTCAGCAAGTGATTCAGATTCAGCAAGTGATTCA
GATTCAGCAAGTGATTCAGACTCAGCAAGTGATTCAGATTCAGCAAGTGATTCAGATTCAGCAAGCGAT
TCAGATTCAGCGAGCGATTCAGATTCAGCGAGCGATTCAGATTCAGCGAGTGATTCCGACTCAGCGAGC
GATTCAGACTCAGATAGTGACTCAGATTCCGATAGCGATTCCGACTCAGATAGCGACTCAGATTCAGAC
AGCGATTCTGACTCAGACAGCGATTCTGACTCAGACAGTGACTCAGATTCCGATAGCGATTCTGACTCA
GACAGTGACTCAGATTCCGATAGCGATTCAGATTCAGACAGTGATTCAGACTCAGATAGCGATTCAGAT
TCCGACAGTGACTCAGACTCAGACAGCGATTCAGATTCCGATAGCGATTCAGATTCCGACAGTGACTCA
GATTCCGATAGTGACTCGGATTCAGCGAGTGATTCAGATTCAGATAGCGATTCAGAATCAGATAGTGAC
TCAGACTCAGACAGTGATTCAGATTCAGATAGTGACTCAGACTCAGACAGCGATTCAGAATCAGATAGT
GACTCCGATTCAGACAGCGATTCAGAATCAGATAGTGACTCCGATTCAGATAGCGATTCGGATTCAGCG
AGTGATTCAGACTCAGGTAGTGACTCCGATTCATCAAGTGATTCAGATTCCGATTCAACGAGTGACACA
GGATCAGACAACGACTCAGACAGTGATTCAAATAGCGATTCCGAGTCAGGTTCTAACAATAATGTAGTT
CCGCCTAATTCACCTAAAAATGGTACTAATGCTTCTAATAAAAATGAGGCTAAAGATAGTAAAGAACCA
TTACCAGATACAGGTTCTGAAGATGAAGCGAATACGTCACTAATTTGGGGATTATTAGCATCATTAGGT
TCATTACTACTTTTCAGAAGAAAAAAAGAAAATAAAGATAAGAAATAA

FIG. 2EE

SEQ ID NO:64 polynucleotide sequence

GTGAAAAACAATCTTAGGTACGGCATTAGAAAACATAAATTGGGAGCAGCATCAGTATTCTTAGGAACA
ATGATCGTTGTTGGGATGGGACAAGATAAAGAAGCTGCAGCATCAGAACAAAAGACAACTACAGTAGAA
GAAAATGGGAATTCAGCTACTGATAATAAAACAAGTGAAACACAAACAACTGCTACTAACGTTAATCAT
ATAGAAGAAACTCAATCATATAACGCAACAGTAACAGAACAACCGTCAAACGCAACACAAGTAACAACT
GAAGAAGCACCAAAAGCAGTACAAGCACCACAAACTGCACAACCAGCAAATGTAGAAACAGTTAAAGAA
GAAGAGAAACCTCAAGTTAAGGAAACGACACAACCTCAAGACAATAGCGGAAATCAAAGACAAGTAGAT
TTAACACCTAAAAAGGTTACACAAAATCAAGGGACAGAAACACAAGTTGAAGTGGCACAGCCAAGAACG
GCATCAGAAAGTAAGCCACGTGTGACAAGATCAGCAGATGTAGCGGAAGCTAAGGAAGCTAGTGACGTT
TCAGAAGTTAAAGGCACAGATGTTACAAGTAAAGTTACAGTAGAAAGTGGTTCTATTGAGGCACCTCAA
GGAAATAAAGTAGAGCCACATGCTGGTCAACGTGTCGTATTGAAATACAAATTGAAATTCGCAGATGGA
TTAAAAAGAGGAGATTATTTTGATTTTACATTATCAAATAATGTAAATACTTATGGGGTTTCAACAGCT
AGAAAGGTACCAGAGATTAAAAATGGCTCAGTTGTAATGGCTACAGGTGAGATCTTAGGGAATGGTAAC
ATAAGATATACATTTACTAACGAAATTGAACACAAGGTAGAGGTAACAGCTAATTTAGAAATCAACTTA
TTTATTGACCCTAAAACTGTACAAAGCAATGGAGAACAAAAGATTACTTCTAAATTAAATGGTGAAGAA
ACAGAAAAAAACAATACCAGTTGTTTATAATCCAGGTGTTAGCAATAGTTATACAAATGTAAATGGATCA
ATTGAAACATTTAATAAAGAATCTAATAAATTTACACATATAGCTTATATTAAGCCAATGAATGGAAAC
CAGTCAAACACTGTATCAGTAACAGGGACGTTGACTGAAGGTAGTAATTTAGCTGGTGGACAACCTACT
GTTAAAGTATATGAATATCTAGGGAAAAAAGATGAATTGCCACAAAGTGTTTATGCAAATACATCAGAT
ACTAACAAATTCAAAGATGTAACAAAGGAAATGAATGGAAAATTGAGTGTGCAAGACAATGGTAGTTAC
TCATTGAATTTAGATAAGTTGGATAAAACGTATGTCATTCATTATACAGGTGAATATTTGCAAGGGTCA
GATCAGGTTAATTTTAGAACTGAATTATATGGGTATCCAGAACGAGCATATAAATCTTACTATGTTTAT
GGGGGATATCGTTTAACTTGGGATAATGGTTTAGTTTTATATAGCAATAAAGCTGACGGCAATGGTAAA
AATGGACAAATTATTCAAGATAATGATTTTGAATATAAAGAAGATACTGCAAAAGGAACTATGAGCGGG
CAGTACGATGCCAAGCAAATTATTGAAACAGAAGAAAATCAAGACAATACACCGCTTGACATTGATTAC
CACACAGCTATAGATGGTGAGGGTGGTTATGTTGATGGGTATATTGAAACAATAGAAGAAACGGATTCA
TCAGCTATTGATATCGATTACCATACTGCTGTGGATAGTGAAGTGGGTCACGTTGGAGGATACACTGAG
TCCTCTGAGGAATCAAATCCAATTGACTTTGAAGAATCGACACATGAAAATTCAAAACATCACGCTGAT
GTTGTTGAATATGAAGAGGATACAAATCCAGGTGGTGGCCAAGTAACAACTGAGTCTAACTTAGTTGAA
TTTGACGAAGAGTCTACAAAAGGTATTGTAACTGGCGCAGTGAGCGACCATACAACAATTGAAGATACG
AAAGAATATACGACTGAAAGTAATCTGATTGAACTAGTAGATGAACTACCTGAAGAACATGGTCAAGCA
CAAGGACCAATCGAGGAAATTACTGAAAACAATCATCATATTTCTCATTCTGGTTTAGGAACTGAAAAT
GGTCACGGTAATTATGGCGTGATTGAAGAAATCGAAGAAAATAGCCACGTTGATATTAAGAGTGAATTA
GGTTACGAAGGTGGCCAAAATAGCGGTAACCAGTCATTCGAGGAAGACACAGAAGAAGACAAACCTAAA
TATGAACAAGGTGGCAATATCGTAGATATCGATTTCGACAGTGTACCTCAAATTCATGGTCAAAATAAA
GGTGACCAGTCATTCGAAGAAGATACAGAGAAAGACAAGCCTAAATATGAACATGGCGGTAATATCATT
GATATCGACTTCGACAGTGTGCCACAAATTCATGGATTCAATAAGCATAATGAAATTATTGAAGAAGAT
ACAAACAAAGATAAACCTAATTATCAATTCGGTGGACACAATAGTGTTGACTTTGAAGAAGATACACTT
CCAAAAGTAAGCGGCCAAAATGAAGGTCAACAAACGATTGAAGAAGATACAACGCCGCCAACGCCACCG
ACACCAGAAGTACCGAGTGAGCCGGAAACACCAATGCCACCGACACCAGAAGTACCGAGTGAGCCGGAA
ACACCAACGCCACCAACACCAGAGGTACCAAGTGAGCCGGAAACACCAACACCACCGACTCCGGAAGTA
CCAAGTGAGCCGGAAACACCAACACCACCGACACCAGAAGTGCCGAGTGAGCCAGAAACACCAACACCG
CCAACACCAGAGGTACCAGCTGAACCTGGTAAACCAGTACCACCCGCAAAAGAAGAACCTAAAAAGCCT
TCTAAACCAGTGGAACAAGGTAAAGTAGTAACACCTGTTATTGAAATCAATGAAAAGGTTAAAGCAGTG
GCACCAACTAAAAAAGCACAATCTAAGAAATCTGAACTACCTGAAACAGGTGGAGAAGAATCAACAAAC
AAAGGTATGTTGTTCGGCGGATTATTCAGCATTCTAGGTTTAGCATTATTACGCAGAAATAAAAAGAAT
AACAAAGCATAA

*FIG. 2FF*

SEQ ID NO:65 polynucleotide sequence

TTGAAAAAAAGAATTGATTATTTGTCGAATAAGCAGAATAAGTATTCGATTAGACGTTTTACAGTAGGT
ACCACATCAGTAATAGTAGGGGCAACTATACTATTTGGGATAGGCAATCATCAAGCACAAGCTTCAGAA
CAATCGAACGATACAACGCAATCTTCGAAAAATAATGCAAGTGCAGATTCCGAAAAAAACAATATGATA
GAAACACCTCAATTAAATACAACGGCTAATGATACATCTGATATTAGTGCAAACACAAACAGTGCGAAT
GTAGATAGCACAACAAAACCAATGTCTACACAAACGAGCAATACCACTACAACAGAGCCAGCTTCAACA
AATGAAACACCTCAACCGACGGCAATTAAAAATCAAGCAACTGCTGCAAAAATGCAAGATCAAACTGTT
CCTCAAGAAGCAAATTCTCAAGTAGATAATAAAACAACGAATGATGCTAATAGCATAGCAACAAACAGT
GAGCTTAAAAATTCTCAAACATTAGATTTACCACAATCATCACCACAAACGATTTCCAATGCGCAAGGA
ACTAGTAAACCAAGTGTTAGAACGAGAGCTGTACGTAGTTTAGCTGTTGCTGAACCGGTAGTAAATGCT
GCTGATGCTAAAGGTACAAATGTAAATGATAAAGTTACGGCAAGTAATTTCAAGTTAGAAAAGACTACA
TTTGACCCTAATCAAAGTGGTAACACATTTATGGCGGCAAATTTTACAGTGACAGATAAAGTGAAATCA
GGGGATTATTTTACAGCGAAGTTACCAGATAGTTTAACTGGTAATGGAGACGTGGATTATTCTAATTCA
AATAATACGATGCCAATTGCAGACATTAAAAGTACGAATGGCGATGTTGTAGCTAAAGCAACATATGAT
ATCTTGACTAAGACGTATACATTTGTCTTTACAGATTATGTAAATAATAAAGAAAATATTAACGGACAA
TTTTCATTACCTTTATTTACAGACCGAGCAAAGGCACCTAAATCAGGAACATATGATGCGAATATTAAT
ATTGCGGATGAAATGTTTAATAATAAAATTACTTATAACTATAGTTCGCCAATTGCAGGAATTGATAAA
CCAAATGGCGCGAACATTTCTTCTCAAATTATTGGTGTAGATACAGCTTCAGGTCAAAACACATACAAG
CAAACAGTATTTGTTAACCCTAAGCAACGAGTTTTAGGTAATACGTGGGTGTATATTAAAGGCTACCAA
GATAAAATCGAAGAAAGTAGCGGTAAAGTAAGTGCTACAGATACAAAACTGAGAATTTTTGAAGTGAAT
GATACATCTAAATTATCAGATAGCTACTATGCAGATCCAAATGACTCTAACCTTAAAGAAGTAACAGAC
CAATTTAAAAATAGAATCTATTATGAGCATCCAAATGTAGCTAGTATTAAATTTGGTGATATTACTAAA
ACATATGTAGTATTAGTAGAAGGGCATTACGACAATACAGGTAAGAACTTAAAAACTCAGGTTATTCAA
GAAAATGTTGATCCTGTAACAAATAGAGACTACAGTATTTTCGGTTGGAATAATGAGAATGTTGTACGT
TATGGTGGTGGAAGTGCTGATGGTGATTCAGCAGTAAATCCGAAAGACCCAACTCCAGGGCCGCCGGTT
GACCCAGAACCAAGTCCAGACCCAGAACCAGAACCAACGCCAGATCCAGAACCAAGTCCAGACCCAGAA
CCGGAACCAAGCCCAGACCCGGATCCGGATTCGGATTCAGACAGTGACTCAGGCTCAGACAGCGACTCA
GGTTCAGATAGCGACTCAGAATCAGATAGCGATTCGGATTCAGACAGTGATTCAGATTCAGACAGCGAC
TCAGAATCAGATAGCGATTCAGAATCAGATAGCGACTCAGATTCAGATAGCGATTCAGATTCAGATAGC
GATTCAGAATCAGATAGCGATTCGGATTCAGACAGTGATTCAGATTCAGACAGCGACTCAGAATCAGAT
AGCGACTCAGAATCAGATAGTGAGTCAGATTCAGACAGTGACTCGGACTCAGACAGTGATTCAGACTCA
GATAGCGATTCAGACTCAGATAGCGATTCAGACTCAGACAGCGATTCAGATTCAGACAGCGACTCAGAA
TCAGACAGCGACTCAGACTCAGATAGCGACTCAGACTCAGACAGCGACTCAGATTCAGATAGCGATTCA
GACTCAGACAGCGACTCAGACTCAGACAGCGACTCAGACTCAGATAGCGATTCAGACTCAGACAGCGAC
TCAGATTCAGATAGCGATTCGGACTCAGACAGCGATTCAGATTCAGACAGCGACTCAGACTCGGATAGC
GATTCAGATTCAGACAGCGACTCAGACTCGGATAGCGACTCGGATTCAGATAGTGACTCCGATTCAAGA
GTTACACCACCAAATAATGAACAGAAAGCACCATCAAATCCTAAAGGTGAAGTAAACCATTCTAATAAG
GTATCAAAACAACACAAAACTGATGCTTTACCAGAAACAGGAGATAAGAGCGAAAACACAAATGCAACT
TTATTTGGTGCAATGATGGCATTATTAGGATCATTACTATTGTTTAGAAAACGCAAGCAAGATCATAAA
GAAAAAGCGTAA

FIG. 2GG

SEQ ID NO:66 polynucleotide sequence

ATGAAAAAGCAAATAATTTCGCTAGGCGCATTAGCAGTTGCATCTAGCTTATTTACATGGGATAACAAA
GCAGATGCGATAGTAACAAAGGATTATAGTAAAGAATCAAGAGTGAATGAGAAAAGTAAAAAGGGAGCT
ACTGTTTCAGATTATTACTATTGGAAAATAATTGATAGTTTAGAGGCACAATTTACTGGAGCAATAGAC
TTATTGGAAGATTATAAATATGGAGATCCTATCTATAAAGAAGCGAAAGATAGATTGATGACAAGAGTA
TTAGGAGAAGACCAGTATTTATTAAAGAAAAAGATTGATGAATATGAGCTTTATAAAAAGTGGTATAAA
AGTTCAAATAAGAACACTAATATGCTTACTTTCCATAAATATAATCTTTACAATTTAACAATGAATGAA
TATAACGATATTTTTAACTCTTTGAAAGATGCAGTTTATCAATTTAATAAAGAAGTTAAAGAAATAGAG
CATAAAAATGTTGACTTGAAGCAGTTTGATAAAGATGGAGAAGACAAGGCAACTAAAGAAGTTTATGAC
CTTGTTTCTGAAATTGATACATTAGTTGTAACTTATTATGCTGATAAGGATTATGGGGAGCATGCGAAA
GAGTTACGAGCAAAACTGGACTTAATCCTTGGAGATACAGACAATCCACATAAAATTACAAATGAGCGT
ATAAAAAAAGAAATGATCGATGACTTAAATTCAATTATAGATGATTTCTTTATGGAGACTAAACAAAAT
AGACCGAATTCTATAACAAAATATGATCCAACAAAACACAATTTTAAAGAGAAGAGTGAAAATAAACCT
AATTTTGATAAATTAGTTGAAGAAACAAAAAAAGCAGTTAAAGAAGCAGACGAATCTTGGAAAAATAAA
ACTGTCAAAAAATACGAGGAAACTGTAACAAAATCTCCTGTTGTAAAAGAAGAGAAGAAAGTTGAAGAA
CCTCAATTACCTAAAGTTGGAAACCAGCAAGAGGTTAAAACTACGGCTGGTAAAGCTGAAGAAACAACA
CAACCAGTGGCACAGCCATTAGTAAAAATTCCACAAGAAACAATCTATGGTGAAACTGTAAAAGGTCCA
GAATATCCAACGATGGAAAATAAAACGTTACAAGGTGAAATCGTTCAAGGTCCCGATTTTCTAACAATG
GAACAAAACAGACCATCTTTAAGCGATAATTATACTCAACCGACGACACCGAACCCTATTTTAGAAGGT
CTTGAAGGTAGCTCATCTAAACTTGAAATAAAACCACAAGGTACTGAATCAACGTTGAAAGGTATTCAA
GGAGAATCAAGTGATATTGAAGTTAAACCTCAAGCAACTGAAACAACAGAAGCTTCTCAATATGGTCCG
AGACCGCAATTTAACAAAACACCTAAGTATGTGAAATATAGAGATGCTGGTACAGGTATCCGTGAATAC
AACGATGGAACATTTGGATATGAAGCGAGACCAAGATTCAACAAGCCAAGTGAAACAAATGCATACAAC
GTAACGACAAATCAAGATGGCACAGTATCATACGGAGCTCGCCCAACACAAAACAAGCCAAGTGAAACA
AACGCATATAACGTAACAACACATGCAAATGGTCAAGTATCATACGGTGCTCGCCCAACACAAAAAAAG
CCAAGCAAAACAAATGCATACAACGTAACAACACATGCAAATGGTCAAGTATCATATGGCGCTCGCCCG
ACACAAAAAAAGCCAAGCAAAACAAATGCATATAACGTAACAACACATGCAAATGGTCAAGTATCATAC
GGAGCTCGCCCGACATACAAGAAGCCAAGCGAAACAAATGCATACAACGTAACAACACATGCAAATGGT
CAAGTATCATATGGCGCTCGCCCGACACAAAAAAAGCCAAGCGAAACAAACGCATATAACGTAACAACA
CATGCAGATGGTACTGCGACATATGGGCCTAGAGTAACAAAATAA

FIG. 2HH

SEQ ID NO:71 polynucleotide sequence

GTGAAAAGCAATCTTAGATACGGCATAAGAAAACACAAATTGGGAGCGGCCTCAGTATTCTTAGGAACA
ATGATCGTTGTTGGAATGGGACAAGAAAAAGAAGCTGCAGCATCGGAACAAAACAATACTACAGTAGAG
GAAAGTGGGAGTTCAGCTACTGAAAGTAAAGCAAGCGAAACACAAACAACTACAAATAACGTTAATACA
ATAGATGAAACACAATCATACAGCGCGACATCAACTGAGCAACCATCAAAATCAACTCAAGTAACAACA
GAAGAAGCACCAACAACTGTGCAAGCACCAAAAGTAGAAACCGAAATGAAATCACAAGAAGATTTACCA
TCAGAAAAAGTTGCTGATAAGGAAACTACAGGAACTCAAGTTGACATAGCTCAACCAAGTAACGTCTCA
GAAATTAAACCAAGAATGAAAAGATCAGCTGACGTTACAGCAGTTTCAGAGAAAGAAGTAGCGGAAGAA
GCTAAAGCGACAGGTACAGATGTAACAAATAAAGTGGAAGTTACTGAAAGCTCTTTAGAAGGACATAAT
AAAGATTCGAATATTGTTAATCCGCATAATGCTCAAAGAGTAACTTTAAAATACAAATGGAAATTTGGA
GAAGGAATTAAGGCAGGAGATTATTTTGATTTCACATTAAGTGATAATGTTGAAACACATGGTATATCA
ACACTGCGTAAAGTTCCGGAGATAAAAAGTTCAACAGAAGATAAAGTTATGGCAAATGGTCAAGTTATA
AATGAACGTACAATTCGCTATACATTTACTGATTATATAAATAACAAAAAAGATTTAACTGCTGAATTA
AACTTAAACCTATTCATTGACCCAACAACAGTGACAAAGCAAGGGAGTCAAAAAGTTGAAGTAACACTA
GGTCAAAATAAAGTCTCAAAAGAATTTGATATCAAATATTTAGACGGCGTTAAAGATAGAATGGGTGTT
ACTGTTAATGGTCGTATTGATACTTTGAATAAAGAAGAGGGTAAATTTAGCCATTTTGCATATGTGAAG
CCTAACAACCAGTCGTTAACTTCTGTCACAGTAACTGGTCAAGTAACATCTGGATATAAACAAAGTGCT
AATAATCCAACAGTCAAAGTATATAAACACATTGGTTCAGATGAATTAGCTGAAAGTGTTTATGCAAAG
CTTGATGATACCAGTAAATTTGAAGATGTGACTGAAAAAGTAAATCTATCTTACACAAGTAATGGTGGG
TACACATTGAACCTTGGCGATTTAGATAATTCGAAAGACTATGTAATTAAATATGAAGGTGAATATGAT
CAAAATGCTAAGGATCTAAATTTCCGAACACATCTTTCAGGATATCATAAATACTACCCATACTATCCT
TATTACCCGTATTATCCAGTTCAATTAACTTGGAACAACGGTGTTGCATTTTACTCTAATAATGCTAAA
GGCGATGGTAAAGATAAACCAAATGATCCTATCATTGAGAAGAGTGAACCAATTGATTTAGACATTAAA
TCAGAGCCACCAGTGGAGAAGCATGAATTGACTGGTACAATCGAAGAAAGTAACGATTCTAAGCCAATT
GATTTTGAATATCATACAGCTGTTGAAGGTGCAGAAGGTCATGCAGAAGGTATTATTGAAACTGAAGAA
GATTCTATTCATGTGGATTTTGAAGAATCTACACATGAAAATTCAAAACATCACGCTGATGTTGTTGAA
TATGAAGAGGATACAAACCCAGGTGGTGGCCAAGTAACAACTGAGTCTAACTTAGTTGAATTTGACGAA
GAGTCTACAAAAGGTATTGTAACTGGCGCAGTGAGCGACCATACAACAGTTGAAGATACGAAAGAATAT
ACAACTGAAAGTAATCTGATTGAATTAGTGGATGAATTACCTGAAGAACATGGTCAAGCACAAGGGCCA
ATCGAGGAAATTACTGAAAACAATCATCATATTTCTCATTCTGGTTTAGGAACTGAAAATGGTCACGGT
AATTATGGCGTGATTGATGAAATCGAAGAAAATAGCCACGTTGATATTAAGAGTGAATTAGGTTATGAA
GGTGGCCAAAATAGCGGTAATCAGTCATTCGAGGAAGACACAGAAGAAGATAAACCTAAATATGAACAA
GGTGGTAATATCGTAGATATCGATTTCGACAGTGTACCTCAAATTCATGGTCAAAATAATGGTAACCAG
TCATTCGAGGAAGACACAGAAGAAGACAAGCCTAAGTATGAACAAGGTGGTAACATCATTGATATCGAC
TTCGACAGTGTGCCACAAATTCATGGATTCAATAAGCATAATGAAATTATTGAAGAAGATACAAACAAA
GATAAACCTAATTATCAATTTGGTGGACACAACAGTGTTGATTTTGAAGAAGATACACTTCCAAAAGTA
AGTGGTCAAAATGAAGGTCAACAAACGATTGAAGAAGATACAACGCCGCCAACACCGCCAACACCAGAG
GTACCAAGTGAGCCGGAAACACCAACACCACCAACACCAGAAGTACCGAGTGAGCCAGGCGAACCAACG
CCACCAAAACCGGAAGTACCAAGTGAGCCGGAAACACCAGTACCACCAACACCAGAGGTACCATCTGAA
CCTGGTAAACCAGTACCACCTGCTAAAGAAGAACCTAAAAAACCTTCTAAACCAGTGGAACAAGGTAAG
GTAGTAACACCTGTTATTGAAATCAATGAAAAGGTTAAAGCAGTGGCACCAACTAAACAAAAACAATCT
AAGAAATCTGAACTACCTGAAACAGGTGGAGAAGAATCAACAAACAAAGGTATGTTGTTCGGCGGATTA
TTCAGCATTCTAGGTTTAGTATTATTACGCAGAAATAAAAAGAATAACAAAGCATAA

FIG. 2II

SEQ ID NO:72 polynucleotide sequence

ATGAAATTTAAGTCATTGATTACAACAACATTAGCATTAGGCGTTATAGCATCAACAGGAGCAAACTTT
AATACTAACGAAGCATCTGCCGCAGCTAAGCCATTAGATAAATCATCAAGTACATTACACCATGGACAT
TCTAACATCCAGATTCCATATACAATTACTGTGAACGGTACAAGCCAAAACATTTTATCAAGCTTAACA
TTTAATAAGAATCAAAATATTAGTTATAAAGATATAGAGAATAAAGTTAAATCAGTTTTATACTTTAAT
AGAGGTATTAGTGATATCGATTTAAGACTTTCAAAGCAAGCGGAATATACGGTTCATTTTAAAAATGGA
ACAAAAAGAGTTATCGATTTGAAATCAGGTATCTACACAGCTGACTTAATCAATACAAGTGACATTAAA
GCTATCAGTGTTAACGTAGATACTAAAAAGCAACCTAAAGATAAAGCTAAAGCAAATGTTCAAGTGCCA
TATACAATCACAGTGAACGGCACAAGCCAAAACATTTTATCAAACCTAACATTTAATAAAAATCAAAAT
ATTAGTTACAAAGATTTAGAGGGTAAAGTTAAATCAGTTTTAGAATCAAATAGAGGTATTACTGATGTT
GATTTAAGACTTTCGAAGCAAGCGAAATATACAGTTAATTTTAAAAATGGAACGAAGAAAGTTATCGAT
TTGAAATCAGGTATTTACACAGCGAATTTAATCAATTCAAGTGATATTAAAAGTATCAATATTAACGTA
GATACAAAAAAACATATCGAAAATAAAGCTAAAAGAAACTATCAAGTTCCATATTCAATTAATCTAAAT
GGTACATCTACAAACATTTTATCGAATCTTTCATTTTCAAATAAACCTTGGACAAATTACAAAAATTTA
ACTAGTCAAATAAAATCAGTACTGAAGCATGATAGAGGTATTAGTGAACAAGATTTAAAATATGCTAAG
AAAGCTTATTATACTGTTTATTTTAAAAATGGTGGTAAAAGAATCTTACAGTTAAATTCAAAAAATTAC
ACAGCAAACTTAGTTCATGCGAAAGATGTTAAGAGAATTGAAATTACTGTTAAAACAGGAACTAAAGCG
AAAGCAGACAGATATGTACCATACACAATTGCAGTAAATGGCACATCAACACCAATTTTATCAAAACTA
AAAATTTCGAATAAACAATTAATTAGTTACAAATATTTAAACGACAAAGTGAAATCTGTATTAAAAAGT
GAAAGAGGTATCAGTGATCTTGACTTAAAATTTGCGAAACAAGCAAAATATACAGTATATTTCAAAAAT
GGAAAGAAACAAGTAGTGAATTTAAAATCAGACATCTTTACACCTAATTTATTTAGTGCCAAAGATATT
AAAAAGATTGATATTGATGTAAAACAATACACTAAATCAAAAAAAAAAATAAATAAATCTAATAATGTG
AAATTCCCAGTAACAATAAATAAATTTGAAAACATAGTTTCAAATGAATTTGTGTTCTATAATGCAAGC
AAAATTACAATTAATGATTTAAGTATAAAACTTAAATCAGCAATGGCAAATGATCAAGGGATAACTAAA
CATGACATAGGACTTGCTGAACGCGCAGTGTATAAAGTGTATTTTAAAAATGGTTCGTCAAAATATGTA
GACTTAAAAACTGAGTATAAAGATGAAAGAGTATTTAAAGCAACTGACATTAAAAAGGTAGATATTGAA
CTTAAATTCTAA

FIG. 2JJ

SEQ ID NO:73 polynucleotide sequence

ATGAATAATAAAAAGACAGCAACAAATAGAAAAGGCATGATACCAAATCGATTAAACAAA
TTTTCGATAAGAAAGTATTCTGTAGGTACTGCTTCAATTTTAGTAGGGACAACATTGATT
TTTGGGTTAAGTGGTCATGAAGCTAAAGCGGCAGAACATACGAATGGAGAATTAAATCAA
TCAAAAAATGAAACGACAGCCCCAAGTGAGAATAAAACAACTAAAAAAGTTGATAGTCGT
CAACTAAAAGACAATACGCAAACTGCAACTGCAGATCAGCCTAAAGTGACAATGAGTGAT
AGTGCAACAGTTAAAGAAACTAGTAGTAACATGCAATCACCACAAAACGCTACAGCTAAT
CAATCTACTACAAAAACTAGCAATGTAACAACAAATGATAAATCATCAACTACATATAGT
AATGAAACTGATAAAAGTAATTTAACACAAGCAAAAGATGTTTCAACTACACCTAAAACA
ACGACTATTAAACCAAGAACTTTAAATCGCATGGCAGTGAATACTGTTGCAGCTCCACAA
CAAGGAACAAATGTTAATGATAAAGTACATTTTTCAAATATTGACATTGCGATTGATAAA
GGACATGTTAATCAGACTACTGGTAAAACTGAATTTTGGGCAACTTCAAGTGATGTTTTA
AAATTAAAAGCAAATTACACAATCGATGATTCTGTTAAAGAGGGCGATACATTTACTTTT
AAATATGGTCAATATTTCCGTCCAGGATCAGTAAGATTACCTTCACAAACTCAAAATTTA
TATAATGCCCAAGGTAATATTATTGCAAAAGGTATTTATGATAGTACAACAAACACAACA
ACATATACTTTTACGAACTATGTAGATCAATATACAAATGTTAGAGGTAGCTTTGAACAA
GTTGCATTTGCGAAACGTAAAAATGCAACAACTGATAAAACAGCTTATAAAATGGAAGTA
ACTTTAGGTAATGATACATATAGCGAAGAAATCATTGTCGATTATGGTAATAAAAAAGCA
CAACCGCTTATTTCAAGTACAAACTATATTAACAATGAAGATTTATCGCGTAATATGACT
GCATATGTAAATCAACCTAAAAATACATATACTAAACAAACGTTTGTTACTAATTTAACT
GGATATAAATTTAATCCAAATGCAAAAAACTTCAAAATTTACGAAGTGACAGATCAAAAT
CAATTTGTGGATAGTTTCACCCCTGATACTTCAAAACTTAAAGATGTTACTGATCAATTC
GATGTTATTTATAGTAATGATAATAAAACAGCTACAGTCGATTTAATGAAAGGCCAAACA
AGCAGCAATAAACAATACATCATTCAACAAGTTGCTTATCCAGATAATAGTTCAACAGAT
AATGGAAAAATTGATTATACTTTAGACACTGACAAAACTAAATATAGTTGGTCAAATAGT
TATTCAAATGTGAATGGCTCATCAACTGCTAATGGCGACCAAAAGAAATATAATCTAGGT
GACTATGTATGGGAAGATACAAATAAAGATGGTAAACAAGATGCCAATGAAAAAGGGATT
AAAGGTGTTTATGTCATTCTTAAAGATAGTAACGGTAAAGAATTAGATCGTACGACAACA
GATGAAAATGGTAAATATCAGTTCACTGGTTTAAGCAATGGAACTTATAGTGTAGAGTTT
TCAACACCAGCCGGTTATACACCGACAACTGCAAATGTAGGTACAGATGATGCTGTAGAT
TCTGATGGACTAACTACAACAGGTGTCATTAAAGACGCTGACAACATGACATTAGATAGT
GGATTCTACAAAACACCAAAATATAGTTTAGGTGATTATGTTTGGTACGACAGTAATAAA
GATGGTAAACAAGATTCGACTGAAAAAGGAATTAAAGGTGTTAAAGTTACTTTGCAAAAC
GAAAAAGGCGAAGTAATTGGTACAACTGAAACAGATGAAAATGGTAAATACCGCTTTGAT
AATTTAGATAGTGGTAAATACAAAGTTATCTTTGAAAAACCTGCTGGCTTAACTCAAACA
GGTACAAATACAACTGAAGATGATAAAGATGCCGATGGTGGCGAAGTTGATGTAACAATT
ACGGATCATGATGATTTCACACTTGATAATGGCTACTACGAAGAAGAAACATCAGATAGC
GACTCAGATTCTGACAGCGATTCAGACTCAGATAGCGACTCAGATTCAGATAGCGACTCA
GATTCAGACAGCGATTCAGACAGCGACTCAGACTCAGATAGCGATTCAGATTCAGACAGC
GACTCAGACTCAGACAGCGATTCAGACTCGGATAGCGACTCAGACTCAGATAGCGACTCA
GATTCGGATAGCGACTCAGACTCAGATAGCGATTCAGATTCAGATAGCGATTCGGACTCA
GACAGTGATTCAGATTCAGACTCAGATAGCGACTCAGATTCTGACAGCGATTCAGACTCA
GACAGCGACTCAGACTCAGACAGTGATTCAGATTCAGACAGCGACTCAGATTCAGATAGC
GACTCAGACTCAGATAGCGACTCAGATTCAGATAGCGATTCGGACTCAGACAACGACTCA
GATTCAGATAGCGATTCAGATTCAGATAGCGACTCAGATTCGGACAGCGATTCAGACTCA
GATAGCGATTCAGACTCAGACAGCGATTCAGATTCAGATAGCGACTCAGACTCAGATAGC
GACTCAGACTCGGATAGCGATTCAGATTCAGACAGCGACTCAGATTCAGATAGCGATTCG
GACTCAGACAACGACTCAGATTCAGATAGCGATTCAGATTCAGATGCAGGTAAACATACT
CCGGCTAAACCAATGAGTACGGTTAAAGATCAGCATAAAACAGCTAAAGCATTACCAGAA
ACAGGTAGTGAAAATAATAATTCAAATAATGGCACATTATTCGGTGGATTATTCGCGGCA
TTAGGATCATTATTGTTATTCGGTCGTCGTAAAAAACAAAATAAATAA

FIG. 2KK

SEQ ID NO: 74 polynucleotide sequence

GAGGAGAATTCAGTACAAGACGTTAAAGATTCGAATACGGATGATGAATTATCAGACAGC
AATGATCAGTCTAGTGATGAAGAAAAGAATGATGTGATCAATAATAATCAGTCAATAAAC
ACCGACGATAATAACCAAATAATTAAAAAAGAAGAAACGAATAACTACGATGGCATAGAA
AAACGCTCAGAAGATAGAACAGAGTCAACAACAAATGTAGATGAAAACGAAGCAACATTT
TTACAAAAGACCCCTCAAGATAATACTCATCTTACAGAAGAAGAGGTAAAAGAATCCTCA
TCAGTCGAATCCTCAAATTCATCAATTGATACTGCCCAACAACCATCTCACACAACAATA
AATAGAGAAGAATCTGTTCAAACAAGTGATAATGTAGAAGATTCACACGTATCAGATTTT
GCTAACTCTAAAATAAAAGAGAGTAACACTGAATCTGGTAAAGAAGAGAATACTATAGAG
CAACCTAATAAAGTAAAAGAAGATTCAACAACAAGTCAGCCGTCTGGCTATACAAATATA
GATGAAAAAATTTCAAATCAAGATGAGTTATTAAATTTACCAATAAATGAATATGAAAAT
AAGGCTAGACCATTATCTACAACATCTGCCCAACCATCGATTAAACGTGTAACCGTAAAT
CAATTAGCGGCGGAACAAGGTTCGAATGTTAATCATTTAATTAAAGTTACTGATCAAAGT
ATTACTGAAGGATATGATGATAGTGAAGGTGTTATTAAAGCACATGATGCTGAAAACTTA
ATCTATGATGTAACTTTTGAAGTAGATGATAAGGTGAAATCTGGTGATACGATGACAGTG
GATATAGATAAGAATACAGTTCCATCAGATTTAACCGATAGCTTTACAATACCAAAAATA
AAAGATAATTCTGGAGAAATCATCGCTACAGGTACTTATGATAACAAAAATAAACAAATC
ACCTATACTTTTACAGATTATGTAGATAAGTATGAAAATATTAAAGCACACCTTAAATTA
ACGTCATACATTGATAAATCAAAGGTTCCAAATAATAATACCAAGTTAGATGTAGAATAT
AAAACGGCCCTTTCATCAGTAAATAAAACAATTACGGTTGAATATCAAAGACCTAACGAA
AATCGGACTGCTAACCTTCAAAGTATGTTTACAAACATAGATACGAAAAATCATACAGTT
GAGCAAACGATTTATATTAACCCTCTTCGTTATTCAGCCAAGGAAACAAATGTAAATATT
TCAGGGAATGGTGATGAAGGTTCAACAATTATAGACGATAGCACAATAATTAAAGTTTAT
AAGGTTGGAGATAATCAAAATTTACCAGATAGTAACAGAATTTATGATTACAGTGAATAT
GAAGATGTCACAAATGATGATTATGCCCAATTAGGAAATAATAATGATGTGAATATTAAT
TTTGGTAATATAGATTCACCATATATTATTAAAGTTATTAGTAAATATGACCCTAATAAG
GATGATTACACGACTATACAGCAAACTGTGACAATGCAGACGACTATAAATGAGTATACT
GGTGAGTTTAGAACAGCATCCTATGATAATACAATTGCTTTCTCTACAAGTTCAGGTCAA
GGACAAGGTGACTTGCCTCCTGAAAAAACTTATAAAATCGGAGATTACGTATGGGAAGAT
GTAGATAAAGATGGTATTCAAAATACAAATGATAATGAAAAACCGCTTAGTAATGTATTG
GTAACTTTGACGTATCCTGATGGAACTTCAAAATCAGTCAGAACAGATGAAGATGGGAAA
TATCAATTTGATGGATTGAAAAACGGATTGACTTATAAAATTACATTCGAAACACCTGAA
GGATATACGCCGACGCTTAAACATTCAGGAACAAATCCTGCACTAGACTCAGAAGGTAAT
TCTGTATGGGTAACTATTAATGGACAAGACGATATGACGATTGATAGTGGATTTTATCAA
ACACCTAAATACAGCTTAGGGAACTATGTATGGTATGACACTAATAAAGATGGTATTCAA
GGTGATGATGAAAAAGGAATCTCTGGAGTTAAAGTGACGTTAAAAGATGAAAACGGAAAT
ATCATTAGTACAACTACAACCGATGAAAATGGAAAGTATCAATTTGATAATTTAAATAGT
GGTAATTATATTGTTCATTTTGATAAACCTTCAGGTATGACTCAAACAACAACAGATTCT
GGTGATGATGACGAACAGGATGCTGATGGGGAAGAAGTTCATGTAACAATTACTGATCAT
GATGACTTTAGTATAGATAACGGATACTATGATGACGAA

*FIG. 3*
Purification of alpha toxin
A
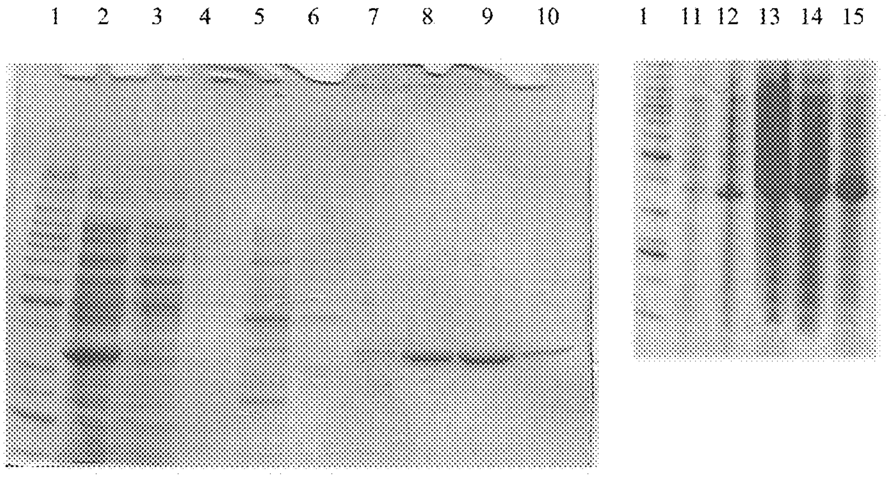
B
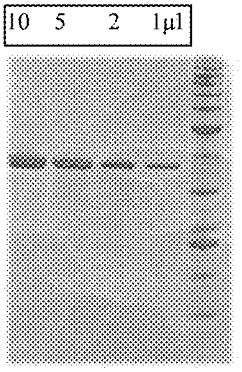

Purification of SdrC

FIG. 6A
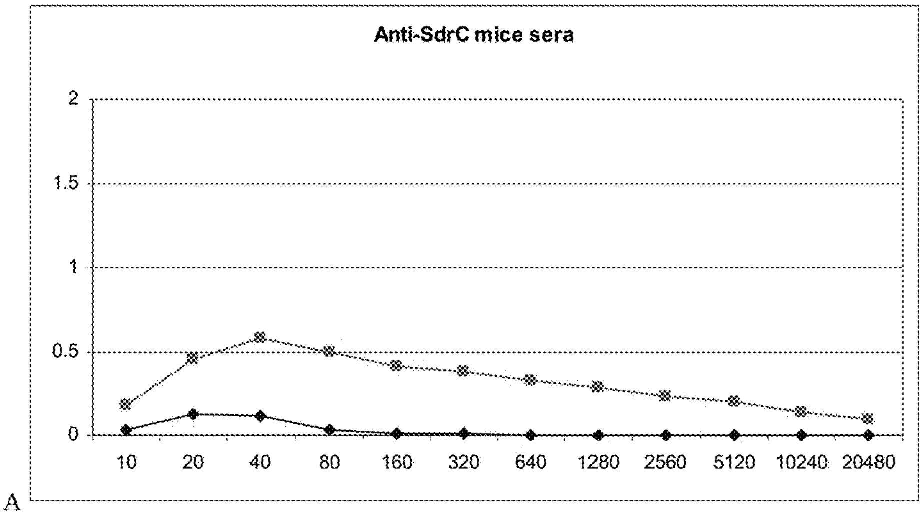
A
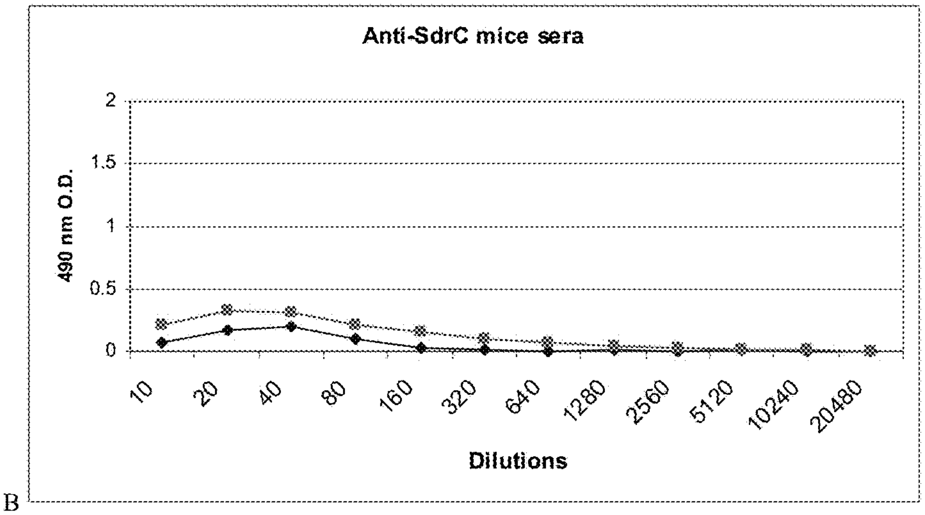
B
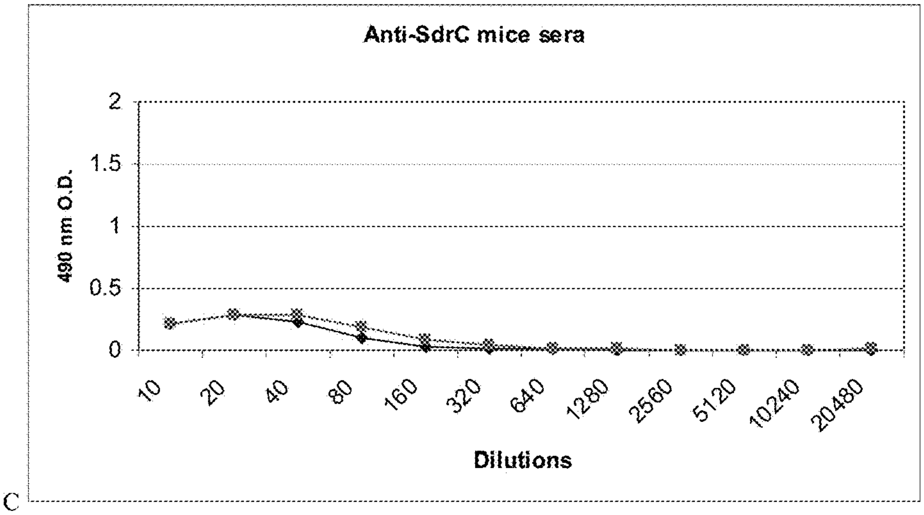
C

*FIG. 6C*
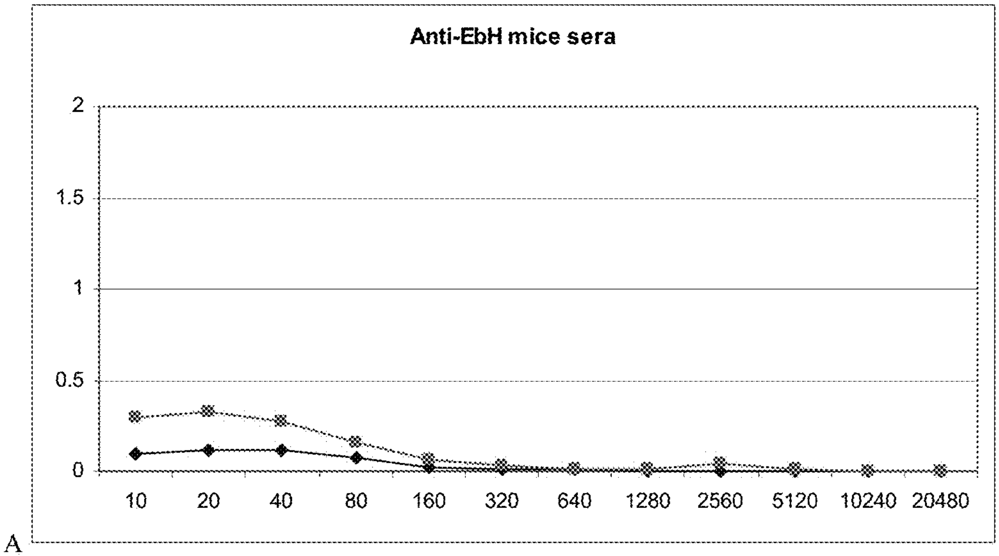
A
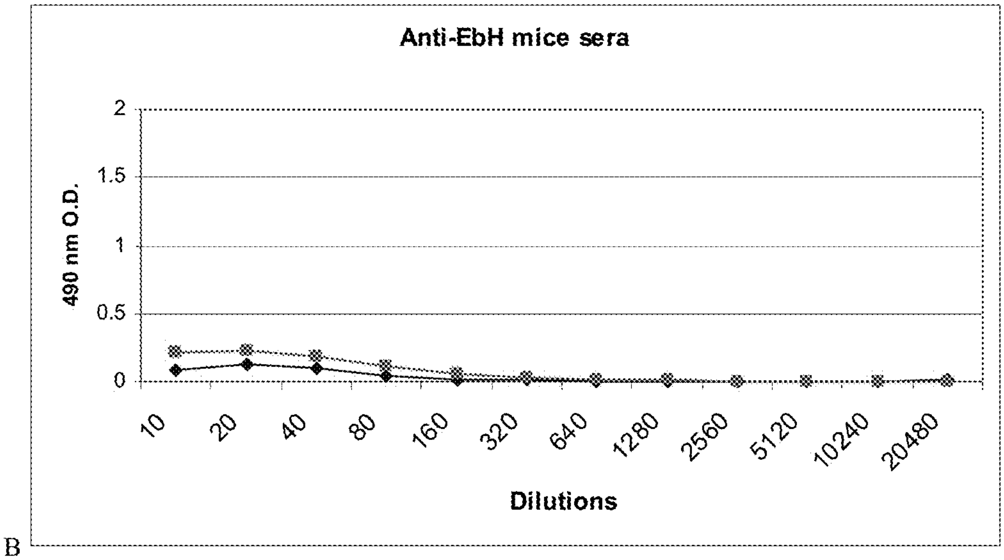
B
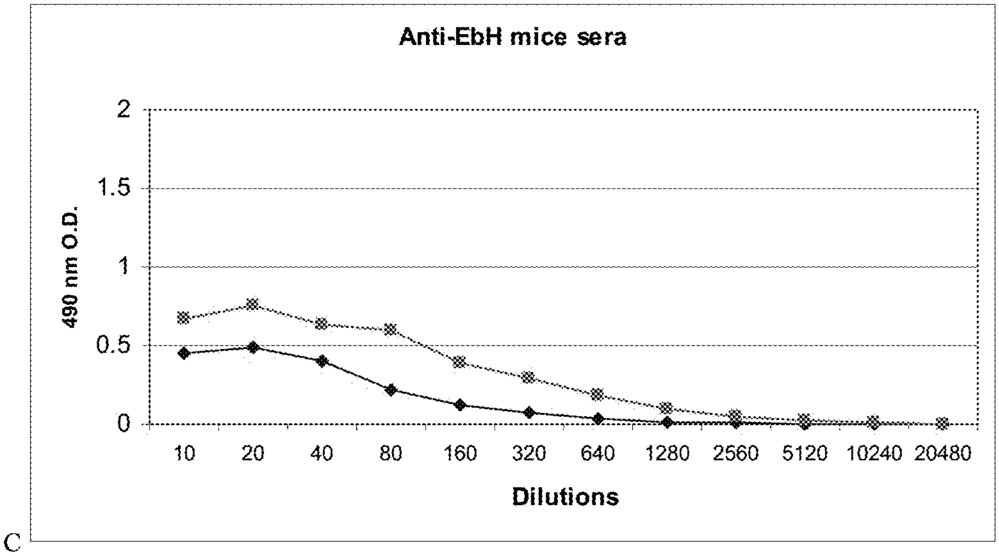
C

A

B

C

FIG. 7A
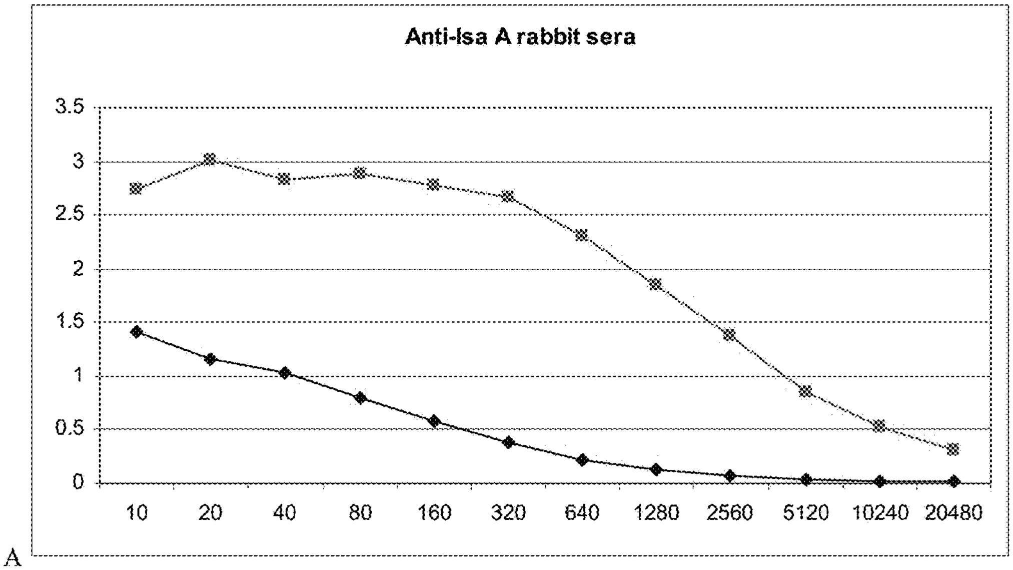
A
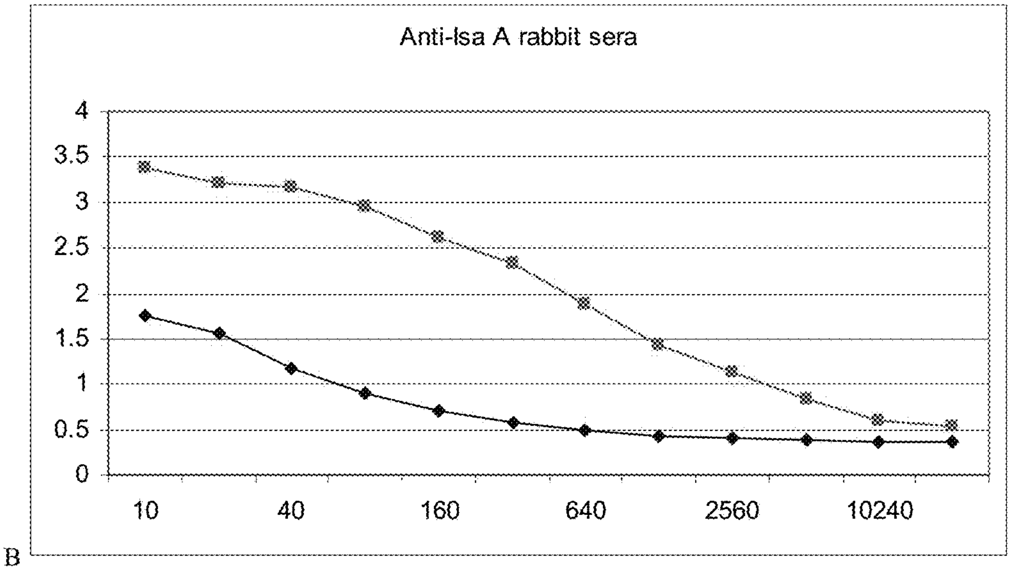
B
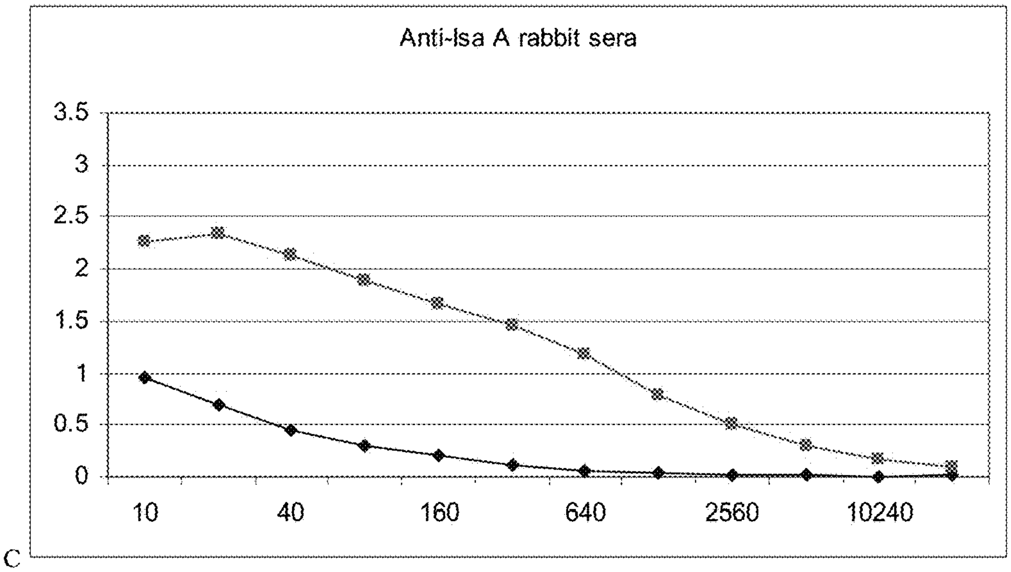
C

FIG. 7B
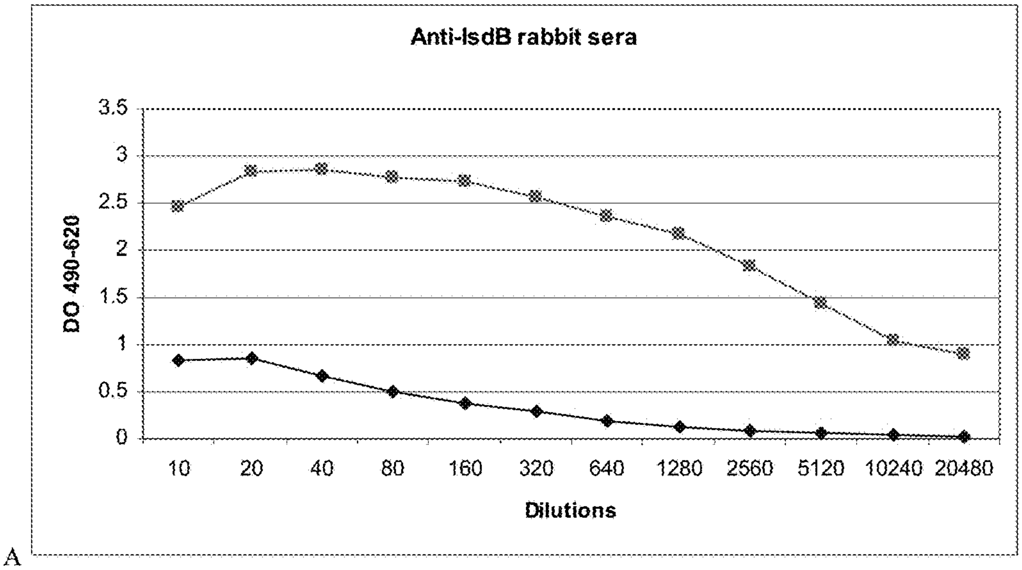
A
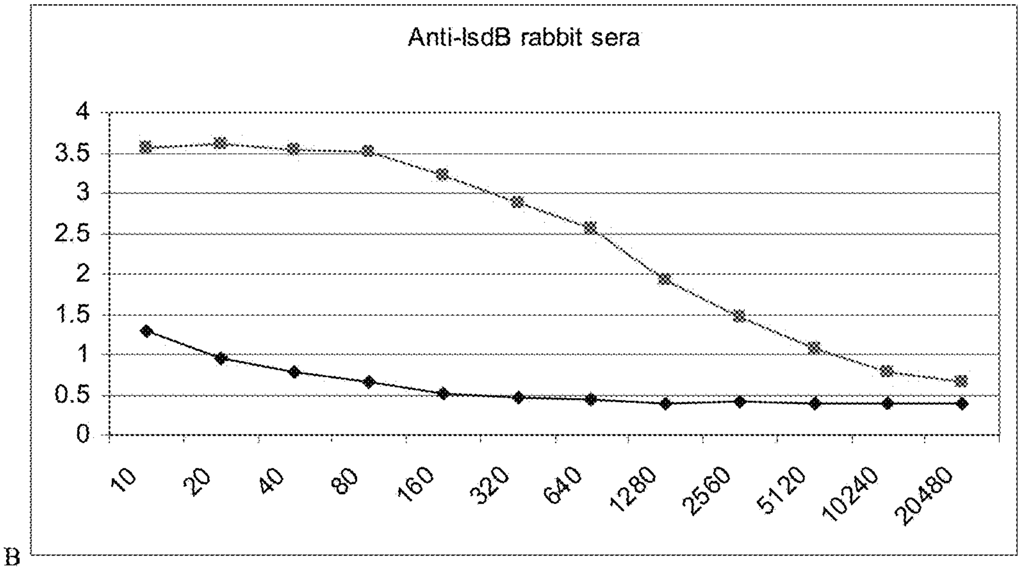
B
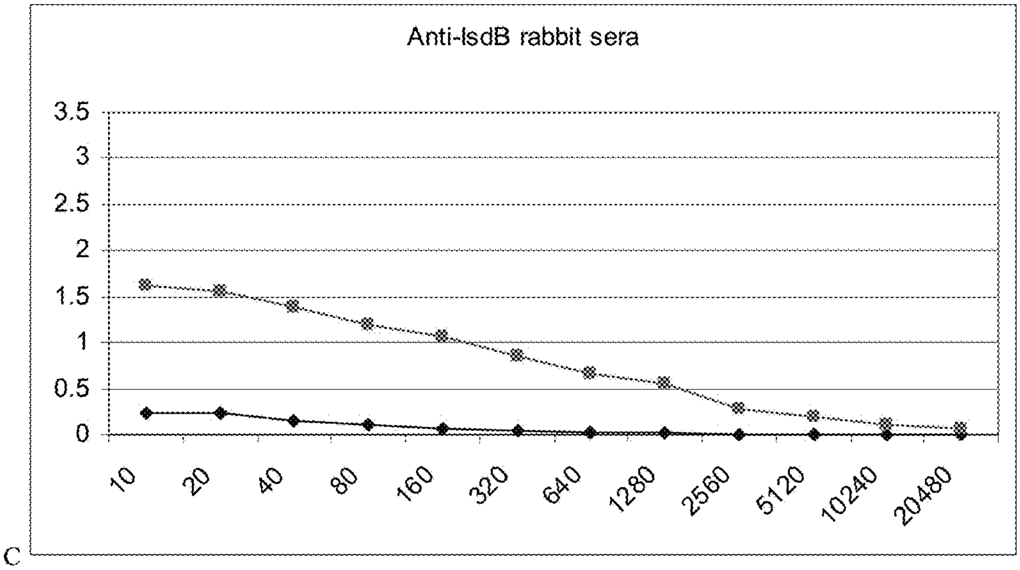
C

FIG. 7C
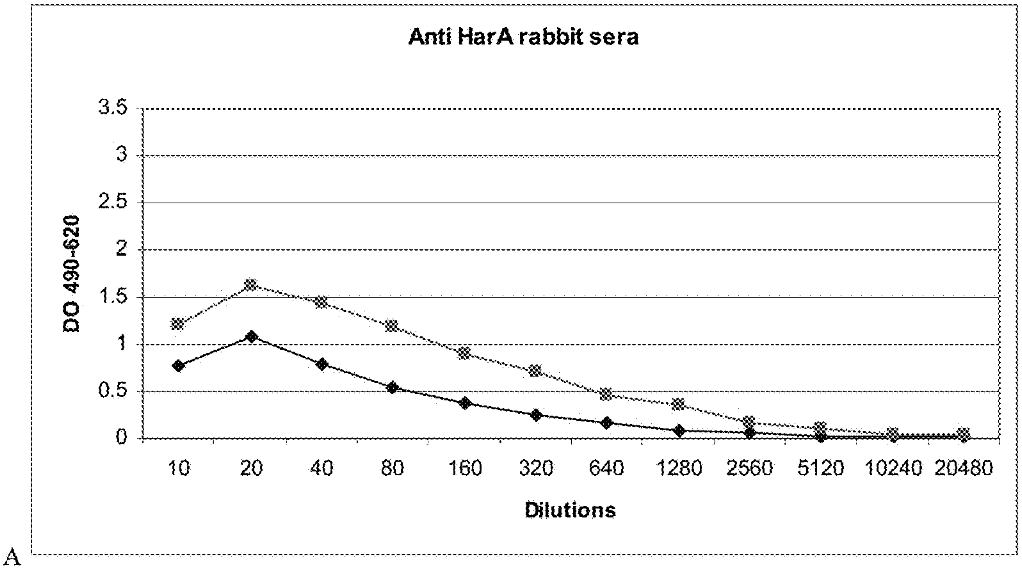
A
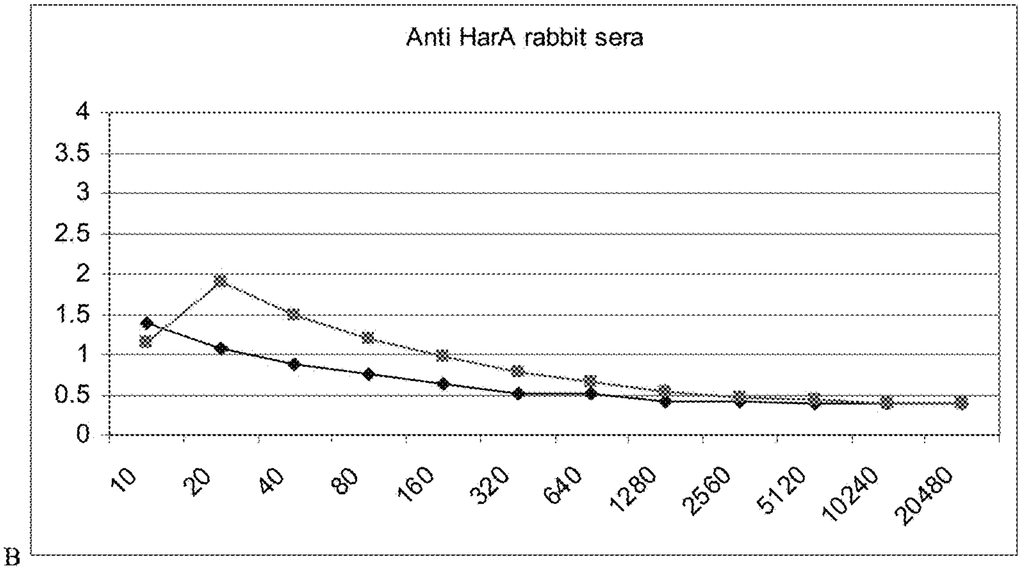
B
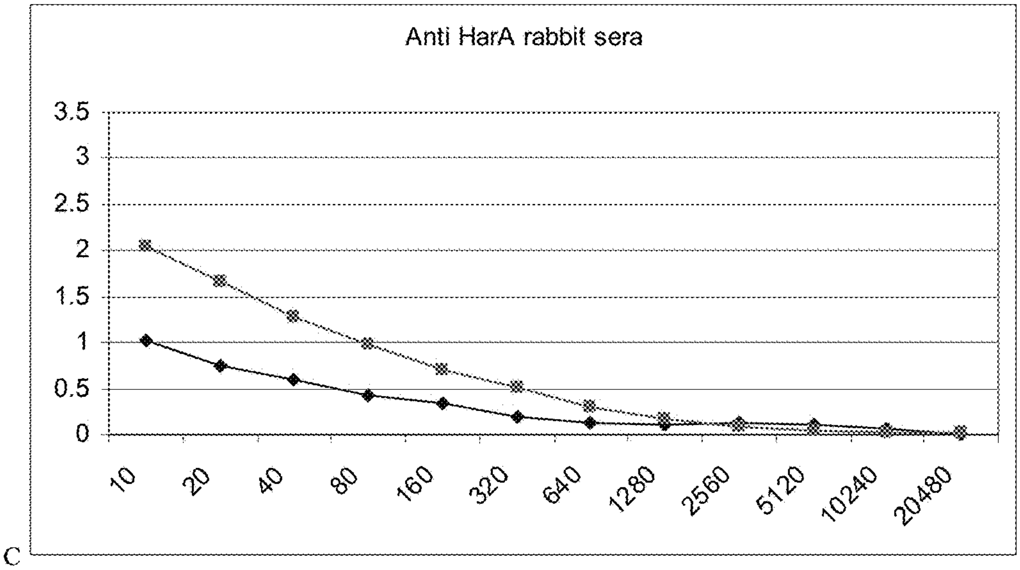
C

*FIG. 7E*
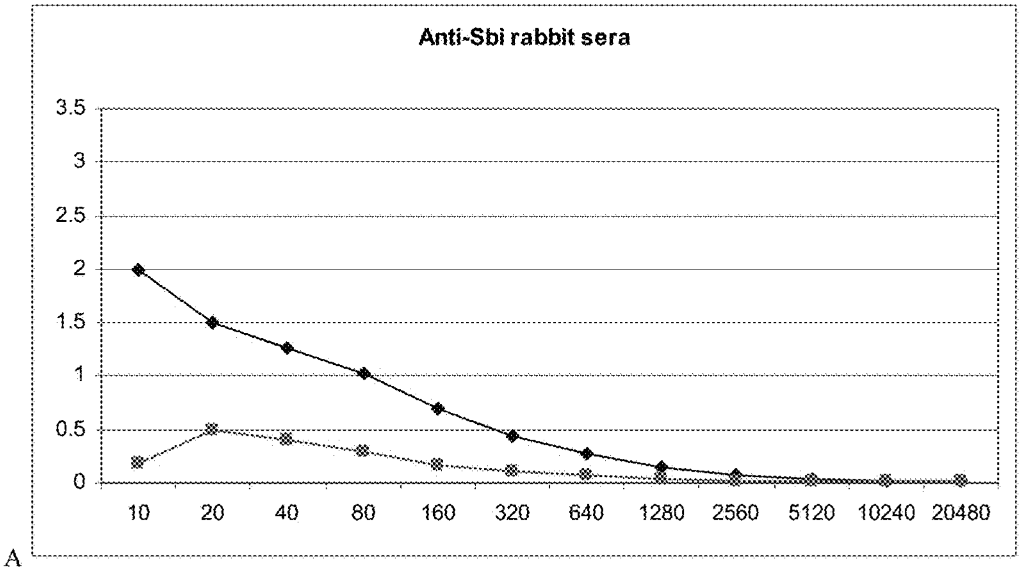
A
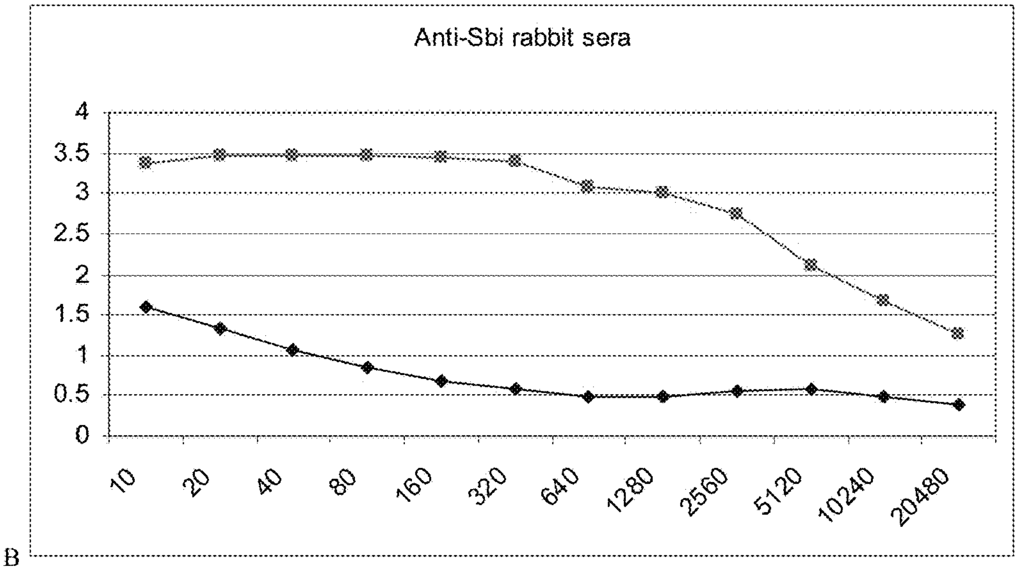
B
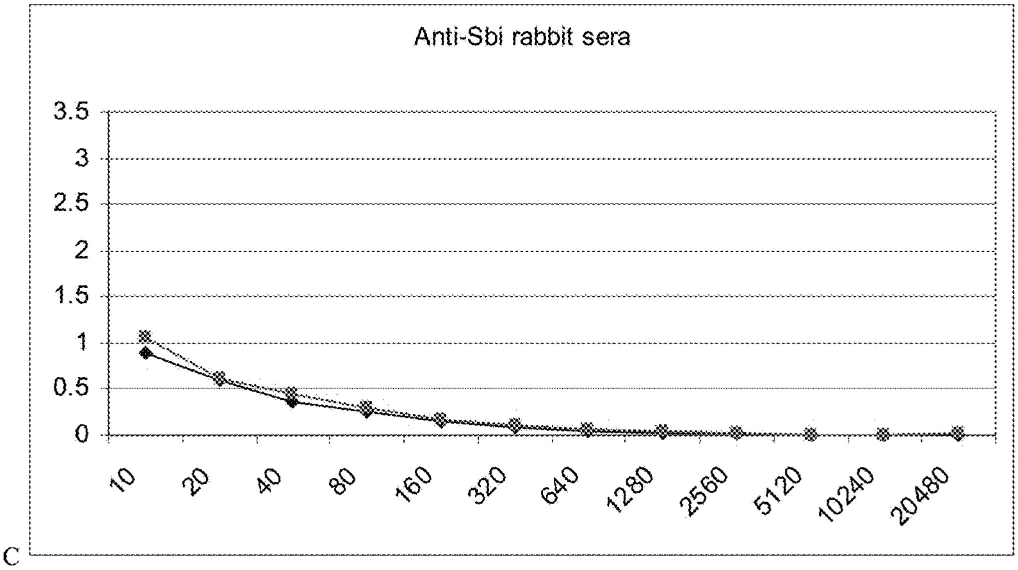
C

FIG. 7H
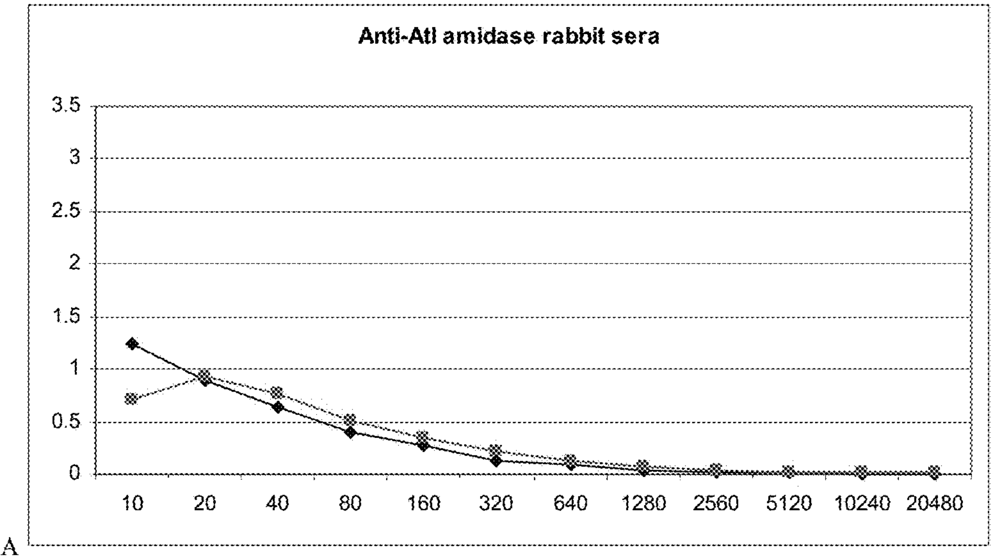
A
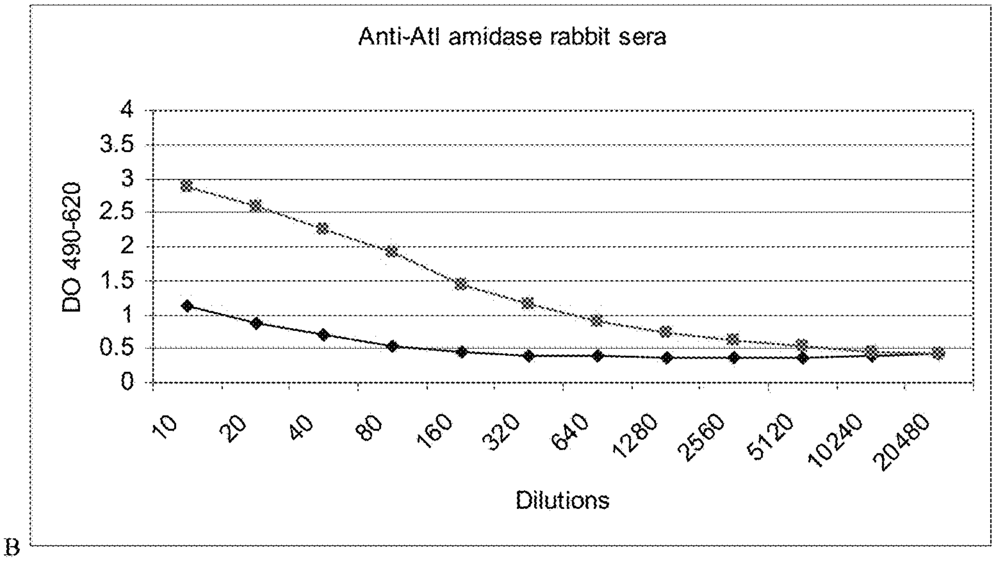
B
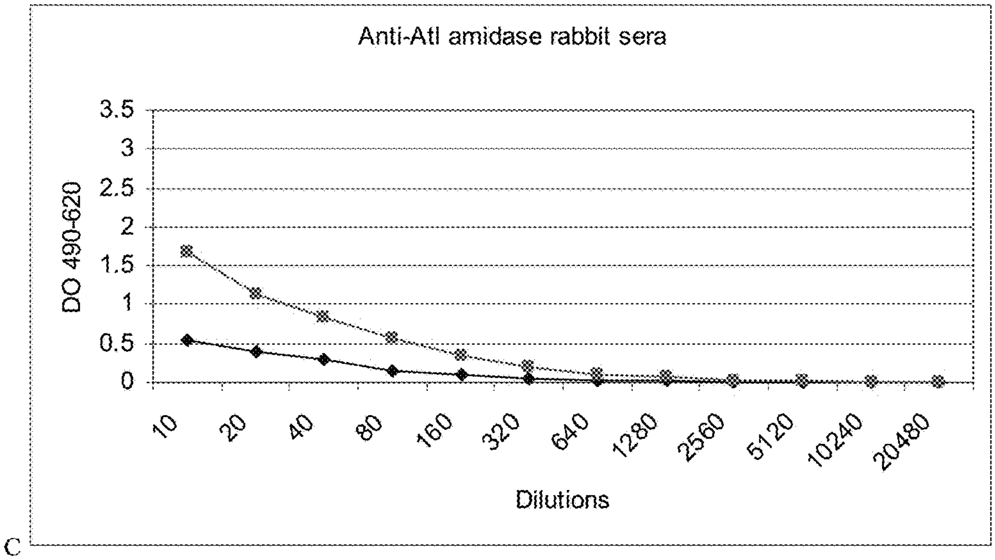
C

SEQUENCE LISTING

```
<160> NUMBER OF SEQ ID NOS: 154

<210> SEQ ID NO 1
<211> LENGTH: 533
<212> TYPE: PRT
<213> ORGANISM: Staphylococcus sp.

<400> SEQUENCE: 1

Met Leu Gln Val Thr Asp Val Ser Leu Arg Phe Gly Asp Arg Lys Leu
1               5                   10                  15

Phe Glu Asp Val Asn Ile Lys Phe Thr Glu Gly Asn Cys Tyr Gly Leu
            20                  25                  30

Ile Gly Ala Asn Gly Ala Gly Lys Ser Thr Phe Leu Lys Ile Leu Ser
        35                  40                  45

Gly Glu Leu Asp Ser Gln Thr Gly His Val Ser Leu Gly Lys Asn Glu
    50                  55                  60

Arg Leu Ala Val Leu Lys Gln Asp His Tyr Ala Tyr Glu Asp Glu Arg
65                  70                  75                  80

Val Leu Asp Val Val Ile Lys Gly His Glu Arg Leu Tyr Glu Val Met
                85                  90                  95

Lys Glu Lys Asp Glu Ile Tyr Met Lys Pro Asp Phe Ser Asp Glu Asp
            100                 105                 110

Gly Ile Arg Ala Ala Glu Leu Glu Gly Glu Phe Ala Glu Met Asn Gly
        115                 120                 125

Trp Asn Ala Glu Ala Asp Ala Ala Asn Leu Leu Ser Gly Leu Gly Ile
    130                 135                 140

Asp Pro Thr Leu His Asp Lys Lys Met Ala Glu Leu Glu Asn Asn Gln
145                 150                 155                 160

Lys Ile Lys Val Leu Leu Ala Gln Ser Leu Phe Gly Glu Pro Asp Val
```

-continued

```
                165                 170                 175

Leu Leu Leu Asp Glu Pro Thr Asn Gly Leu Asp Ile Pro Ala Ile Ser
            180                 185                 190

Trp Leu Glu Asp Phe Leu Ile Asn Phe Asp Asn Thr Val Ile Val Val
        195                 200                 205

Ser His Asp Arg His Phe Leu Asn Asn Val Cys Thr His Ile Ala Asp
    210                 215                 220

Leu Asp Phe Gly Lys Ile Lys Val Tyr Val Gly Asn Tyr Asp Phe Trp
225                 230                 235                 240

Tyr Gln Ser Ser Gln Leu Ala Gln Lys Met Ala Gln Glu Gln Asn Lys
                245                 250                 255

Lys Lys Glu Glu Lys Met Lys Glu Leu Gln Asp Phe Ile Ala Arg Phe
            260                 265                 270

Ser Ala Asn Ala Ser Lys Ser Lys Gln Ala Thr Ser Arg Lys Lys Gln
        275                 280                 285

Leu Glu Lys Ile Glu Leu Asp Asp Ile Gln Pro Ser Ser Arg Arg Tyr
    290                 295                 300

Pro Phe Val Lys Phe Thr Pro Glu Arg Glu Ile Gly Asn Asp Leu Leu
305                 310                 315                 320

Ile Val Gln Asn Leu Ser Lys Thr Ile Asp Gly Glu Lys Val Leu Asp
                325                 330                 335

Asn Val Ser Phe Thr Met Asn Pro Asn Asp Lys Ala Ile Leu Ile Gly
            340                 345                 350

Asp Ser Glu Ile Ala Lys Thr Thr Leu Leu Lys Ile Leu Ala Gly Glu
        355                 360                 365

Met Glu Pro Asp Glu Gly Ser Phe Lys Trp Gly Val Thr Thr Ser Leu
    370                 375                 380

Ser Tyr Phe Pro Lys Asp Asn Ser Glu Phe Phe Glu Gly Val Asn Met
385                 390                 395                 400

Asn Leu Val Asp Trp Leu Arg Gln Tyr Ala Pro Glu Asp Glu Gln Thr
                405                 410                 415

Glu Thr Phe Leu Arg Gly Phe Leu Gly Arg Met Leu Phe Ser Gly Glu
            420                 425                 430

Glu Val Lys Lys Lys Ala Ser Val Leu Ser Gly Gly Glu Lys Val Arg
        435                 440                 445

Cys Met Leu Ser Lys Met Met Leu Ser Ser Ala Asn Val Leu Leu Leu
    450                 455                 460

Asp Glu Pro Thr Asn His Leu Asp Leu Glu Ser Ile Thr Ala Val Asn
465                 470                 475                 480

Asp Gly Leu Lys Ser Phe Lys Gly Ser Ile Ile Phe Thr Ser Tyr Asp
                485                 490                 495

Phe Glu Phe Ile Asn Thr Ile Ala Asn Arg Val Ile Asp Leu Asn Lys
            500                 505                 510

Gln Gly Gly Val Ser Lys Glu Ile Pro Tyr Glu Glu Tyr Leu Gln Glu
        515                 520                 525

Ile Gly Val Leu Lys
    530
```

<210> SEQ ID NO 2
<211> LENGTH: 535
<212> TYPE: PRT
<213> ORGANISM: Staphylococcus sp.

<400> SEQUENCE: 2

-continued

```
Met Leu Gln Val Thr Asp Val Ser Leu Arg Phe Gly Asp Arg Lys Leu
1               5                   10                  15

Phe Glu Asp Val Asn Ile Lys Phe Thr Glu Gly Asn Cys Tyr Gly Leu
            20                  25                  30

Ile Gly Ala Asn Gly Ala Gly Lys Ser Thr Phe Leu Lys Ile Leu Ser
        35                  40                  45

Gly Glu Ile Asp Ser Gln Thr Gly His Val Ser Leu Gly Lys Asp Glu
    50                  55                  60

Arg Leu Ala Val Leu Lys Gln Asp His Phe Ala Tyr Glu Asp Glu Arg
65                  70                  75                  80

Val Leu Asp Val Val Ile Lys Gly His Glu Arg Leu Tyr Gln Val Met
                85                  90                  95

Lys Glu Lys Asp Glu Ile Tyr Met Lys Pro Asp Phe Ser Asp Glu Asp
            100                 105                 110

Gly Ile Arg Ala Ala Glu Leu Glu Gly Glu Phe Ala Glu Met Asn Gly
        115                 120                 125

Trp Asn Ala Glu Ala Asp Ala Ala Asn Leu Leu Ser Gly Leu Gly Ile
    130                 135                 140

Glu Pro Asp Leu His Asp Lys Asn Met Ser Glu Leu Glu Asn Asn Gln
145                 150                 155                 160

Lys Val Lys Val Leu Leu Ala Gln Ser Leu Phe Gly Asp Pro Asp Val
                165                 170                 175

Leu Leu Leu Asp Glu Pro Thr Asn Gly Leu Asp Ile Pro Ala Ile Ser
            180                 185                 190

Trp Leu Glu Asp Phe Leu Ile Asn Phe Glu Asn Thr Val Ile Val Val
        195                 200                 205

Ser His Asp Arg His Phe Leu Asn Asn Val Cys Thr His Ile Ala Asp
    210                 215                 220

Leu Asp Phe Gly Lys Ile Lys Leu Tyr Val Gly Asn Tyr Asp Phe Trp
225                 230                 235                 240

Tyr Gln Ser Ser Gln Leu Ala Gln Lys Met Ala Gln Glu Gln Asn Lys
                245                 250                 255

Lys Lys Glu Glu Lys Met Lys Glu Leu Gln Asp Phe Ile Ala Arg Phe
            260                 265                 270

Ser Ala Asn Ala Ser Lys Ser Lys Gln Ala Thr Ser Arg Lys Lys Gln
        275                 280                 285

Leu Glu Lys Ile Glu Leu Asp Asp Ile Gln Pro Ser Ser Arg Arg Tyr
    290                 295                 300

Pro Tyr Val Lys Phe Thr Pro Glu Arg Glu Ile Gly Asn Asp Leu Leu
305                 310                 315                 320

Thr Val Glu Asn Leu Ser Lys Thr Ile Asp Gly Glu Lys Val Leu Asp
                325                 330                 335

Asn Val Ser Phe Thr Met Asn Pro Asn Asp Lys Ala Ile Leu Val Gly
            340                 345                 350

Asp Ser Glu Ile Ala Lys Thr Thr Leu Leu Lys Ile Leu Ala Gly Glu
        355                 360                 365

Met Glu Pro Asp Glu Gly Thr Phe Lys Trp Gly Val Thr Thr Ser Leu
    370                 375                 380

Ser Tyr Phe Pro Lys Asp Asn Ser Glu Phe Phe Asp Gly Val Asp Met
385                 390                 395                 400

Asn Leu Val Glu Trp Leu Arg Gln Tyr Ala Pro Glu Asp Glu Gln Thr
                405                 410                 415

Glu Thr Phe Leu Arg Gly Phe Leu Gly Arg Met Leu Phe Ser Gly Glu
```

```
            420                 425                 430

Glu Val Lys Lys Lys Ala Ser Val Leu Ser Gly Gly Glu Lys Val Arg
        435                 440                 445

Cys Met Leu Ser Lys Met Met Leu Ser Ser Ala Asn Val Leu Leu Leu
    450                 455                 460

Asp Glu Pro Thr Asn His Leu Asp Leu Glu Ser Ile Thr Ala Val Asn
465                 470                 475                 480

Asp Gly Leu Lys Ser Phe Lys Gly Ser Ile Ile Phe Thr Ser Tyr Asp
                485                 490                 495

Phe Glu Phe Ile Asn Thr Ile Ala Asn Arg Val Ile Asp Leu Asn Gln
            500                 505                 510

Ala Gly Ala Leu Ser Lys Glu Val Pro Tyr Glu Glu Tyr Leu Gln Glu
        515                 520                 525

Ile Gly Val Leu Gln Asn Asn
    530                 535


<210> SEQ ID NO 3
<211> LENGTH: 434
<212> TYPE: PRT
<213> ORGANISM: Staphylococcus sp.

<400> SEQUENCE: 3

Met Pro Ile Ile Thr Asp Val Tyr Ala Arg Glu Val Leu Asp Ser Arg
1               5                   10                  15

Gly Asn Pro Thr Val Glu Val Glu Val Leu Thr Glu Ser Gly Ala Phe
            20                  25                  30

Gly Arg Ala Leu Val Pro Ser Gly Ala Ser Thr Gly Glu His Glu Ala
        35                  40                  45

Val Glu Leu Arg Asp Gly Asp Lys Ser Arg Tyr Leu Gly Lys Gly Val
    50                  55                  60

Thr Lys Ala Val Glu Asn Val Asn Glu Ile Ile Ala Pro Glu Ile Ile
65                  70                  75                  80

Glu Gly Glu Phe Ser Val Leu Asp Gln Val Ser Ile Asp Lys Met Met
                85                  90                  95

Ile Ala Leu Asp Gly Thr Pro Asn Lys Gly Lys Leu Gly Ala Asn Ala
            100                 105                 110

Ile Leu Gly Val Ser Ile Ala Val Ala Arg Ala Ala Ala Asp Leu Leu
        115                 120                 125

Gly Gln Pro Leu Tyr Lys Tyr Leu Gly Gly Phe Asn Gly Lys Gln Leu
    130                 135                 140

Pro Val Pro Met Met Asn Ile Val Asn Gly Gly Ser His Ser Asp Ala
145                 150                 155                 160

Pro Ile Ala Phe Gln Glu Phe Met Ile Leu Pro Val Gly Ala Thr Thr
                165                 170                 175

Phe Lys Glu Ser Leu Arg Trp Gly Thr Glu Ile Phe His Asn Leu Lys
            180                 185                 190

Ser Ile Leu Ser Lys Arg Gly Leu Glu Thr Ala Val Gly Asp Glu Gly
        195                 200                 205

Gly Phe Ala Pro Lys Phe Glu Gly Thr Glu Asp Ala Val Glu Thr Ile
    210                 215                 220

Ile Gln Ala Ile Glu Ala Ala Gly Tyr Lys Pro Gly Glu Glu Val Phe
225                 230                 235                 240

Leu Gly Phe Asp Cys Ala Ser Ser Glu Phe Tyr Glu Asn Gly Val Tyr
                245                 250                 255
```

```
Asp Tyr Ser Lys Phe Glu Gly Glu His Gly Ala Lys Arg Thr Ala Ala
            260                 265                 270

Glu Gln Val Asp Tyr Leu Glu Gln Leu Val Asp Lys Tyr Pro Ile Ile
        275                 280                 285

Thr Ile Glu Asp Gly Met Asp Glu Asn Asp Trp Asp Gly Trp Lys Gln
    290                 295                 300

Leu Thr Glu Arg Ile Gly Asp Arg Val Gln Leu Val Gly Asp Asp Leu
305                 310                 315                 320

Phe Val Thr Asn Thr Glu Ile Leu Ala Lys Gly Ile Glu Asn Gly Ile
                325                 330                 335

Gly Asn Ser Ile Leu Ile Lys Val Asn Gln Ile Gly Thr Leu Thr Glu
            340                 345                 350

Thr Phe Asp Ala Ile Glu Met Ala Gln Lys Ala Gly Tyr Thr Ala Val
        355                 360                 365

Val Ser His Arg Ser Gly Glu Thr Glu Asp Thr Thr Ile Ala Asp Ile
    370                 375                 380

Ala Val Ala Thr Asn Ala Gly Gln Ile Lys Thr Gly Ser Leu Ser Arg
385                 390                 395                 400

Thr Asp Arg Ile Ala Lys Tyr Asn Gln Leu Leu Arg Ile Glu Asp Glu
                405                 410                 415

Leu Phe Glu Thr Ala Lys Tyr Asp Gly Ile Lys Ser Phe Tyr Asn Leu
            420                 425                 430

Asp Lys


<210> SEQ ID NO 4
<211> LENGTH: 434
<212> TYPE: PRT
<213> ORGANISM: Staphylococcus sp.

<400> SEQUENCE: 4

Met Pro Ile Ile Thr Asp Val Tyr Ala Arg Glu Val Leu Asp Ser Arg
1               5                   10                  15

Gly Asn Pro Thr Val Glu Val Glu Val Leu Thr Glu Ser Gly Ala Phe
            20                  25                  30

Gly Arg Ala Leu Val Pro Ser Gly Ala Ser Thr Gly Glu His Glu Ala
        35                  40                  45

Val Glu Leu Arg Asp Gly Asp Lys Ser Arg Tyr Leu Gly Lys Gly Val
    50                  55                  60

Thr Lys Ala Val Glu Asn Val Asn Glu Met Ile Ala Pro Glu Ile Val
65                  70                  75                  80

Glu Gly Glu Phe Ser Val Leu Asp Gln Val Ser Ile Asp Lys Met Met
                85                  90                  95

Ile Gln Leu Asp Gly Thr His Asn Lys Gly Lys Leu Gly Ala Asn Ala
            100                 105                 110

Ile Leu Gly Val Ser Ile Ala Val Ala Arg Ala Ala Ala Asp Leu Leu
        115                 120                 125

Gly Gln Pro Leu Tyr Lys Tyr Leu Gly Gly Phe Asn Gly Lys Gln Leu
    130                 135                 140

Pro Val Pro Met Met Asn Ile Val Asn Gly Gly Ser His Ser Asp Ala
145                 150                 155                 160

Pro Ile Ala Phe Gln Glu Phe Met Ile Leu Pro Val Gly Ala Glu Ser
                165                 170                 175

Phe Lys Glu Ser Leu Arg Trp Gly Ala Glu Ile Phe His Asn Leu Lys
            180                 185                 190
```

```
Ser Ile Leu Ser Glu Arg Gly Leu Glu Thr Ala Val Gly Asp Glu Gly
        195                 200                 205

Gly Phe Ala Pro Arg Phe Glu Gly Thr Glu Asp Ala Val Glu Thr Ile
    210                 215                 220

Ile Lys Ala Ile Glu Lys Ala Gly Tyr Lys Pro Gly Glu Asp Val Phe
225                 230                 235                 240

Leu Gly Phe Asp Cys Ala Ser Ser Glu Phe Tyr Glu Asn Gly Val Tyr
                245                 250                 255

Asp Tyr Thr Lys Phe Glu Gly Glu His Gly Ala Lys Arg Ser Ala Ala
            260                 265                 270

Glu Gln Val Asp Tyr Leu Glu Glu Leu Ile Gly Lys Tyr Pro Ile Ile
        275                 280                 285

Thr Ile Glu Asp Gly Met Asp Glu Asn Asp Trp Glu Gly Trp Lys Gln
    290                 295                 300

Leu Thr Asp Arg Ile Gly Asp Lys Val Gln Leu Val Gly Asp Asp Leu
305                 310                 315                 320

Phe Val Thr Asn Thr Glu Ile Leu Ser Lys Gly Ile Glu Gln Gly Ile
                325                 330                 335

Gly Asn Ser Ile Leu Ile Lys Val Asn Gln Ile Gly Thr Leu Thr Glu
            340                 345                 350

Thr Phe Asp Ala Ile Glu Met Ala Gln Lys Ala Gly Tyr Thr Ala Val
        355                 360                 365

Val Ser His Arg Ser Gly Glu Thr Glu Asp Thr Thr Ile Ala Asp Ile
    370                 375                 380

Ala Val Ala Thr Asn Ala Gly Gln Ile Lys Thr Gly Ser Leu Ser Arg
385                 390                 395                 400

Thr Asp Arg Ile Ala Lys Tyr Asn Gln Leu Leu Arg Ile Glu Asp Glu
                405                 410                 415

Leu Tyr Glu Thr Ala Lys Phe Glu Gly Ile Lys Ser Phe Tyr Asn Leu
            420                 425                 430

Asp Lys


<210> SEQ ID NO 5
<211> LENGTH: 255
<212> TYPE: PRT
<213> ORGANISM: Staphylococcus sp.

<400> SEQUENCE: 5

Met Lys Lys Ile Val Thr Ala Thr Ile Ala Thr Ala Gly Leu Ala Thr
1               5                   10                  15

Ile Ala Phe Ala Gly His Asp Ala Gln Ala Ala Glu Gln Asn Asn Asn
            20                  25                  30

Gly Tyr Asn Ser Asn Asp Ala Gln Ser Tyr Ser Tyr Thr Tyr Thr Ile
        35                  40                  45

Asp Ala Gln Gly Asn Tyr His Tyr Thr Trp Thr Gly Asn Trp Asn Pro
    50                  55                  60

Ser Gln Leu Thr Gln Asn Asn Thr Tyr Tyr Tyr Asn Asn Tyr Asn Thr
65                  70                  75                  80

Tyr Ser Tyr Asn Asn Ala Ser Tyr Asn Asn Tyr Tyr Asn His Ser Tyr
                85                  90                  95

Gln Tyr Asn Asn Tyr Thr Asn Asn Ser Gln Thr Ala Thr Asn Asn Tyr
            100                 105                 110

Tyr Thr Gly Gly Ser Gly Ala Ser Tyr Ser Thr Thr Ser Asn Asn Val
        115                 120                 125
```

```
His Val Thr Thr Thr Ala Ala Pro Ser Ser Asn Gly Arg Ser Ile Ser
    130                 135                 140

Asn Gly Tyr Ala Ser Gly Ser Asn Leu Tyr Thr Ser Gly Gln Cys Thr
145                 150                 155                 160

Tyr Tyr Val Phe Asp Arg Val Gly Gly Lys Ile Gly Ser Thr Trp Gly
                165                 170                 175

Asn Ala Ser Asn Trp Ala Asn Ala Ala Ala Ser Ser Gly Tyr Thr Val
            180                 185                 190

Asn Asn Thr Pro Lys Val Gly Ala Ile Met Gln Thr Thr Gln Gly Tyr
        195                 200                 205

Tyr Gly His Val Ala Tyr Val Glu Gly Val Asn Ser Asn Gly Ser Val
    210                 215                 220

Arg Val Ser Glu Met Asn Tyr Gly His Gly Ala Gly Val Val Thr Ser
225                 230                 235                 240

Arg Thr Ile Ser Ala Asn Gln Ala Gly Ser Tyr Asn Phe Ile His
                245                 250                 255


<210> SEQ ID NO 6
<211> LENGTH: 267
<212> TYPE: PRT
<213> ORGANISM: Staphylococcus sp.

<400> SEQUENCE: 6

Met Lys Lys Ile Ala Thr Ala Thr Ile Ala Thr Ala Gly Phe Ala Thr
1               5                   10                  15

Ile Ala Ile Ala Ser Gly Asn Gln Ala His Ala Ser Glu Gln Asp Asn
            20                  25                  30

Tyr Gly Tyr Asn Pro Asn Asp Pro Thr Ser Tyr Ser Tyr Thr Tyr Thr
        35                  40                  45

Ile Asp Ala Gln Gly Asn Tyr His Tyr Thr Trp Lys Gly Asn Trp His
    50                  55                  60

Pro Ser Gln Leu Asn Gln Asp Asn Gly Tyr Tyr Ser Tyr Tyr Tyr Tyr
65                  70                  75                  80

Asn Gly Tyr Asn Asn Tyr Asn Asn Tyr Asn Asn Gly Tyr Ser Tyr Asn
                85                  90                  95

Asn Tyr Ser Arg Tyr Asn Asn Tyr Ser Asn Asn Asn Gln Ser Tyr Asn
            100                 105                 110

Tyr Asn Asn Tyr Asn Ser Tyr Asn Thr Asn Ser Tyr Arg Thr Gly Gly
        115                 120                 125

Leu Gly Ala Ser Tyr Ser Thr Ser Ser Asn Asn Val Gln Val Thr Thr
    130                 135                 140

Thr Met Ala Pro Ser Ser Asn Gly Arg Ser Ile Ser Ser Gly Tyr Thr
145                 150                 155                 160

Ser Gly Arg Asn Leu Tyr Thr Ser Gly Gln Cys Thr Tyr Tyr Val Phe
                165                 170                 175

Asp Arg Val Gly Gly Lys Ile Gly Ser Thr Trp Gly Asn Ala Ser Asn
            180                 185                 190

Trp Ala Asn Ala Ala Ala Arg Ala Gly Tyr Thr Val Asn Asn Thr Pro
        195                 200                 205

Lys Ala Gly Ala Ile Met Gln Thr Thr Gln Gly Ala Tyr Gly His Val
    210                 215                 220

Ala Tyr Val Glu Ser Val Asn Ser Asn Gly Ser Val Arg Val Ser Glu
225                 230                 235                 240

Met Asn Tyr Gly Tyr Gly Pro Gly Val Val Thr Ser Arg Thr Ile Ser
                245                 250                 255
```

```
Ala Ser Gln Ala Ala Gly Tyr Asn Phe Ile His
            260                 265


<210> SEQ ID NO 7
<211> LENGTH: 257
<212> TYPE: PRT
<213> ORGANISM: Staphylococcus sp.

<400> SEQUENCE: 7

Met Lys Lys Ile Ala Thr Ala Thr Ile Ala Thr Ala Gly Ile Ala Thr
1               5                   10                  15

Phe Ala Phe Ala His His Asp Ala Gln Ala Ala Glu Gln Asn Asn Asp
            20                  25                  30

Gly Tyr Asn Pro Asn Asp Pro Tyr Ser Tyr Ser Tyr Thr Tyr Thr Ile
        35                  40                  45

Asp Ala Glu Gly Asn Tyr His Tyr Thr Trp Lys Gly Asn Trp Ser Pro
    50                  55                  60

Asp Arg Val Asn Thr Ser Tyr Asn Tyr Asn Asn Tyr Asn Asn Tyr Asn
65                  70                  75                  80

Tyr Tyr Gly Tyr Asn Asn Tyr Ser Asn Tyr Asn Asn Tyr Ser Asn Tyr
                85                  90                  95

Asn Asn Tyr Asn Asn Tyr Gln Ser Asn Asn Thr Gln Ser Gln Arg Thr
            100                 105                 110

Thr Gln Pro Thr Gly Gly Leu Gly Ala Ser Tyr Ser Thr Ser Ser Ser
        115                 120                 125

Asn Val His Val Thr Thr Thr Ser Ala Pro Ser Ser Asn Gly Val Ser
    130                 135                 140

Leu Ser Asn Ala Arg Ser Ala Ser Gly Asn Leu Tyr Thr Ser Gly Gln
145                 150                 155                 160

Cys Thr Tyr Tyr Val Phe Asp Arg Val Gly Gly Lys Ile Gly Ser Thr
                165                 170                 175

Trp Gly Asn Ala Asn Asn Trp Ala Asn Ala Ala Ala Arg Ser Gly Tyr
            180                 185                 190

Thr Val Asn Asn Ser Pro Ala Lys Gly Ala Ile Leu Gln Thr Ser Gln
        195                 200                 205

Gly Ala Tyr Gly His Val Ala Tyr Val Glu Gly Val Asn Ser Asn Gly
    210                 215                 220

Ser Ile Arg Val Ser Glu Met Asn Tyr Gly His Gly Ala Gly Val Val
225                 230                 235                 240

Thr Ser Arg Thr Ile Ser Ala Ser Gln Ala Ala Ser Tyr Asn Tyr Ile
                245                 250                 255

His


<210> SEQ ID NO 8
<211> LENGTH: 309
<212> TYPE: PRT
<213> ORGANISM: Staphylococcus sp.

<400> SEQUENCE: 8

Met Lys Lys Leu Val Pro Leu Leu Leu Ala Leu Leu Leu Leu Val Ala
1               5                   10                  15

Ala Cys Gly Thr Gly Gly Lys Gln Ser Ser Asp Lys Ser Asn Gly Lys
            20                  25                  30

Leu Lys Val Val Thr Thr Asn Ser Ile Leu Tyr Asp Met Ala Lys Asn
        35                  40                  45
```

-continued

```
Val Gly Gly Asp Asn Val Asp Ile His Ser Ile Val Pro Val Gly Gln
    50                  55                  60

Asp Pro His Glu Tyr Glu Val Lys Pro Lys Asp Ile Lys Lys Leu Thr
65                  70                  75                  80

Asp Ala Asp Val Ile Leu Tyr Asn Gly Leu Asn Leu Glu Thr Gly Asn
                85                  90                  95

Gly Trp Phe Glu Lys Ala Leu Glu Gln Ala Gly Lys Ser Leu Lys Asp
            100                 105                 110

Lys Lys Val Ile Ala Val Ser Lys Asp Val Lys Pro Ile Tyr Leu Asn
        115                 120                 125

Gly Glu Glu Gly Asn Lys Asp Lys Gln Asp Pro His Ala Trp Leu Ser
    130                 135                 140

Leu Asp Asn Gly Ile Lys Tyr Val Lys Thr Ile Gln Gln Thr Phe Ile
145                 150                 155                 160

Asp Asn Asp Lys Lys His Lys Ala Asp Tyr Glu Lys Gln Gly Asn Lys
                165                 170                 175

Tyr Ile Ala Gln Leu Glu Lys Leu Asn Asn Asp Ser Lys Asp Lys Phe
            180                 185                 190

Asn Asp Ile Pro Lys Glu Gln Arg Ala Met Ile Thr Ser Glu Gly Ala
        195                 200                 205

Phe Lys Tyr Phe Ser Lys Gln Tyr Gly Ile Thr Pro Gly Tyr Ile Trp
    210                 215                 220

Glu Ile Asn Thr Glu Lys Gln Gly Thr Pro Glu Gln Met Arg Gln Ala
225                 230                 235                 240

Ile Glu Phe Val Lys Lys His Lys Leu Lys His Leu Leu Val Glu Thr
                245                 250                 255

Ser Val Asp Lys Lys Ala Met Glu Ser Leu Ser Glu Glu Thr Lys Lys
            260                 265                 270

Asp Ile Phe Gly Glu Val Tyr Thr Asp Ser Ile Gly Lys Glu Gly Thr
        275                 280                 285

Lys Gly Asp Ser Tyr Tyr Lys Met Met Lys Ser Asn Ile Glu Thr Val
    290                 295                 300

His Gly Ser Met Lys
305
```

<210> SEQ ID NO 9
<211> LENGTH: 309
<212> TYPE: PRT
<213> ORGANISM: Staphylococcus sp.

<400> SEQUENCE: 9

```
Met Lys Lys Ile Leu Ala Leu Ala Ile Ala Phe Leu Ile Ile Leu Ala
1               5                   10                  15

Ala Cys Gly Asn His Ser Asn His Glu His His Ser His Glu Gly Lys
            20                  25                  30

Leu Lys Val Val Thr Thr Asn Ser Ile Leu Tyr Asp Met Val Lys Arg
        35                  40                  45

Val Gly Gly Asn Lys Val Asp Val His Ser Ile Val Pro Val Gly Gln
    50                  55                  60

Asp Pro His Glu Tyr Glu Val Lys Pro Lys Asp Ile Lys Ala Leu Thr
65                  70                  75                  80

Asp Ala Asp Val Val Phe Tyr Asn Gly Leu Asn Leu Glu Thr Gly Asn
                85                  90                  95

Gly Trp Phe Glu Lys Ala Leu Asp Gln Ala Gly Lys Ser Thr Lys Asp
            100                 105                 110
```

```
Lys Asn Val Ile Ala Ala Ser Asn Asn Val Lys Pro Ile Tyr Leu Asn
        115                 120                 125

Gly Glu Glu Gly Asn Lys Asn Lys Gln Asp Pro His Ala Trp Leu Ser
    130                 135                 140

Leu Glu Asn Gly Ile Lys Tyr Val Lys Thr Ile Gln Lys Ser Leu Glu
145                 150                 155                 160

His His Asp Lys Lys Asp Lys Ser Thr Tyr Glu Lys Gln Gly Asn Ala
                165                 170                 175

Tyr Ile Ser Lys Leu Glu Glu Leu Asn Lys Asp Ser Lys Asn Lys Phe
            180                 185                 190

Asp Asp Ile Pro Lys Asn Gln Arg Ala Met Met Thr Ser Glu Gly Ala
        195                 200                 205

Phe Lys Tyr Phe Ala Gln Gln Phe Asp Val Lys Pro Gly Tyr Ile Trp
    210                 215                 220

Glu Ile Asn Thr Glu Lys Gln Gly Thr Pro Gly Gln Met Lys Gln Ala
225                 230                 235                 240

Ile Lys Phe Val Lys Asp Asn His Leu Lys His Leu Leu Val Glu Thr
                245                 250                 255

Ser Val Asp Lys Lys Ala Met Gln Ser Leu Ser Glu Glu Thr Lys Lys
            260                 265                 270

Asp Ile Tyr Gly Glu Val Phe Thr Asp Ser Ile Gly Lys Glu Gly Thr
        275                 280                 285

Lys Gly Asp Ser Tyr Tyr Lys Met Met Lys Ser Asn Ile Asp Thr Ile
    290                 295                 300

His Gly Ser Met Lys
305
```

<210> SEQ ID NO 10
<211> LENGTH: 233
<212> TYPE: PRT
<213> ORGANISM: Staphylococcus sp.

<400> SEQUENCE: 10

```
Met Lys Lys Thr Ile Met Ala Ser Ser Leu Ala Val Ala Leu Gly Val
1               5                   10                  15

Thr Gly Tyr Ala Ala Gly Thr Gly His Gln Ala His Ala Ala Glu Val
            20                  25                  30

Asn Val Asp Gln Ala His Leu Val Asp Leu Ala His Asn His Gln Asp
        35                  40                  45

Gln Leu Asn Ala Ala Pro Ile Lys Asp Gly Ala Tyr Asp Ile His Phe
    50                  55                  60

Val Lys Asp Gly Phe Gln Tyr Asn Phe Thr Ser Asn Gly Thr Thr Trp
65                  70                  75                  80

Ser Trp Ser Tyr Glu Ala Ala Asn Gly Gln Thr Ala Gly Phe Ser Asn
                85                  90                  95

Val Ala Gly Ala Asp Tyr Thr Thr Ser Tyr Asn Gln Gly Ser Asp Val
            100                 105                 110

Gln Ser Val Ser Tyr Asn Ala Gln Ser Ser Asn Ser Asn Val Glu Ala
        115                 120                 125

Val Ser Ala Pro Thr Tyr His Asn Tyr Ser Thr Ser Thr Thr Ser Ser
    130                 135                 140

Ser Val Arg Leu Ser Asn Gly Asn Thr Ala Gly Ala Thr Gly Ser Ser
145                 150                 155                 160

Ala Ala Gln Ile Met Ala Gln Arg Thr Gly Val Ser Ala Ser Thr Trp
```

```
                165                 170                 175

Ala Ala Ile Ile Ala Arg Glu Ser Asn Gly Gln Val Asn Ala Tyr Asn
            180                 185                 190

Pro Ser Gly Ala Ser Gly Leu Phe Gln Thr Met Pro Gly Trp Gly Pro
        195                 200                 205

Thr Asn Thr Val Asp Gln Gln Ile Asn Ala Ala Val Lys Ala Tyr Lys
    210                 215                 220

Ala Gln Gly Leu Gly Ala Trp Gly Phe
225                 230


<210> SEQ ID NO 11
<211> LENGTH: 235
<212> TYPE: PRT
<213> ORGANISM: Staphylococcus sp.

<400> SEQUENCE: 11

Met Lys Lys Thr Val Ile Ala Ser Thr Leu Ala Val Ser Leu Gly Ile
1               5                   10                  15

Ala Gly Tyr Gly Leu Ser Gly His Glu Ala His Ala Ser Glu Thr Thr
            20                  25                  30

Asn Val Asp Lys Ala His Leu Val Asp Leu Ala Gln His Asn Pro Glu
        35                  40                  45

Glu Leu Asn Ala Lys Pro Val Gln Ala Gly Ala Tyr Asp Ile His Phe
    50                  55                  60

Val Asp Asn Gly Tyr Gln Tyr Asn Phe Thr Ser Asn Gly Ser Glu Trp
65                  70                  75                  80

Ser Trp Ser Tyr Ala Val Ala Gly Ser Asp Ala Asp Tyr Thr Glu Ser
                85                  90                  95

Ser Ser Asn Gln Glu Val Ser Ala Asn Thr Gln Ser Ser Asn Thr Asn
            100                 105                 110

Val Gln Ala Val Ser Ala Pro Thr Ser Ser Glu Ser Arg Ser Tyr Ser
        115                 120                 125

Thr Ser Thr Thr Ser Tyr Ser Ala Pro Ser His Asn Tyr Ser Ser His
    130                 135                 140

Ser Ser Ser Val Arg Leu Ser Asn Gly Asn Thr Ala Gly Ser Val Gly
145                 150                 155                 160

Ser Tyr Ala Ala Ala Gln Met Ala Ala Arg Thr Gly Val Ser Ala Ser
                165                 170                 175

Thr Trp Glu His Ile Ile Ala Arg Glu Ser Asn Gly Gln Leu His Ala
            180                 185                 190

Arg Asn Ala Ser Gly Ala Ala Gly Leu Phe Gln Thr Met Pro Gly Trp
        195                 200                 205

Gly Ser Thr Gly Ser Val Asn Asp Gln Ile Asn Ala Ala Tyr Lys Ala
    210                 215                 220

Tyr Lys Ala Gln Gly Leu Ser Ala Trp Gly Met
225                 230                 235


<210> SEQ ID NO 12
<211> LENGTH: 3890
<212> TYPE: PRT
<213> ORGANISM: Staphylococcus sp.

<400> SEQUENCE: 12

Met Asn Tyr Arg Asp Lys Ile Gln Lys Phe Ser Ile Arg Lys Tyr Thr
1               5                   10                  15

Val Gly Thr Phe Ser Thr Val Ile Ala Thr Leu Val Phe Leu Gly Phe
```

-continued

```
            20                  25                  30

Asn Thr Ser Gln Ala His Ala Ala Glu Thr Asn Gln Pro Ala Ser Val
        35                  40                  45

Val Lys Gln Lys Gln Gln Ser Asn Asn Glu Gln Thr Glu Asn Arg Glu
    50                  55                  60

Ser Gln Val Gln Asn Ser Gln Asn Ser Gln Asn Ser Gln Ser Leu Ser
65                  70                  75                  80

Ala Thr His Glu Asn Glu Gln Pro Asn Asn Ser Gln Ala Asn Leu Val
                85                  90                  95

Asn Gln Lys Val Ala Gln Ser Ser Thr Thr Asn Asp Glu Gln Pro Ala
            100                 105                 110

Ser Gln Asn Val Asn Thr Lys Lys Asp Ser Ala Thr Ala Ala Thr Thr
        115                 120                 125

Gln Pro Asp Lys Glu Glu Ser Lys His Lys Gln Asn Glu Ser Gln Ser
    130                 135                 140

Ala Asn Lys Asn Gly Asn Asp Asn Arg Ala Ala His Val Glu Asn His
145                 150                 155                 160

Glu Ala Asn Val Val Thr Ala Ser Asp Ser Ser Asp Asn Gly Asn Val
                165                 170                 175

Gln His Asp Arg Asn Glu Leu Gln Ala Phe Phe Asp Ala Asn Tyr His
            180                 185                 190

Asp Tyr Arg Phe Ile Asp Arg Glu Asn Ala Asp Ser Gly Thr Phe Asn
        195                 200                 205

Tyr Val Lys Gly Ile Phe Asp Lys Ile Asn Thr Leu Leu Gly Ser Asn
    210                 215                 220

Asp Pro Ile Asn Asn Lys Asp Leu Gln Leu Ala Tyr Lys Glu Leu Glu
225                 230                 235                 240

Gln Ala Val Ala Leu Ile Arg Thr Met Pro Gln Arg Gln Gln Thr Ser
                245                 250                 255

Arg Arg Ser Asn Arg Ile Gln Thr Arg Ser Val Glu Ser Arg Ala Ala
            260                 265                 270

Glu Pro Arg Ser Val Ser Asp Tyr Gln Asn Ala Asn Ser Ser Tyr Tyr
        275                 280                 285

Val Glu Asn Ala Asn Asp Gly Ser Gly Tyr Pro Val Gly Thr Tyr Ile
    290                 295                 300

Asn Ala Ser Ser Lys Gly Ala Pro Tyr Asn Leu Pro Thr Thr Pro Trp
305                 310                 315                 320

Asn Thr Leu Lys Ala Ser Asp Ser Lys Glu Ile Ala Leu Met Thr Ala
                325                 330                 335

Lys Gln Thr Gly Asp Gly Tyr Gln Trp Val Ile Lys Phe Asn Lys Gly
            340                 345                 350

His Ala Pro His Gln Asn Met Ile Phe Trp Phe Ala Leu Pro Ala Asp
        355                 360                 365

Gln Val Pro Val Gly Arg Thr Asp Phe Val Thr Val Asn Ser Asp Gly
    370                 375                 380

Thr Asn Val Gln Trp Ser His Gly Ala Gly Ala Gly Ala Asn Lys Pro
385                 390                 395                 400

Leu Gln Gln Met Trp Glu Tyr Gly Val Asn Asp Pro Asp Arg Ser His
                405                 410                 415

Asp Phe Lys Ile Arg Asn Arg Ser Gly Gln Val Ile Tyr Ser Trp Pro
            420                 425                 430

Thr Val His Val Tyr Ser Leu Glu Asp Leu Ser Arg Ala Ser Asp Tyr
        435                 440                 445
```

-continued

```
Phe Ser Glu Ala Gly Ala Thr Pro Ala Thr Lys Ala Phe Gly Arg Gln
    450                 455                 460

Asn Phe Glu Tyr Ile Asn Gly Gln Lys Pro Ala Glu Ser Pro Gly Val
465                 470                 475                 480

Pro Lys Val Tyr Thr Phe Ile Gly Gln Gly Asp Ala Ser Tyr Thr Ile
                485                 490                 495

Ser Phe Lys Thr Gln Gly Pro Thr Val Asn Lys Leu Tyr Tyr Ala Ala
            500                 505                 510

Gly Gly Arg Ala Leu Glu Tyr Asn Gln Leu Phe Met Tyr Ser Gln Leu
        515                 520                 525

Tyr Val Glu Ser Thr Gln Asp His Gln Gln Arg Leu Asn Gly Leu Arg
    530                 535                 540

Gln Val Val Asn Arg Thr Tyr Arg Ile Gly Thr Thr Lys Arg Val Glu
545                 550                 555                 560

Val Ser Gln Gly Asn Val Gln Thr Lys Lys Val Leu Glu Ser Thr Asn
                565                 570                 575

Leu Asn Ile Asp Asp Phe Val Asp Asp Pro Leu Ser Tyr Val Lys Thr
            580                 585                 590

Pro Ser Asn Lys Val Leu Gly Phe Tyr Pro Thr Asn Ala Asn Thr Asn
        595                 600                 605

Ala Phe Arg Pro Gly Gly Val Gln Glu Leu Asn Glu Tyr Gln Leu Ser
    610                 615                 620

Gln Leu Phe Thr Asp Gln Lys Leu Gln Glu Ala Ala Arg Thr Arg Asn
625                 630                 635                 640

Pro Ile Arg Leu Met Ile Gly Phe Asp Tyr Pro Asp Gly Tyr Gly Asn
                645                 650                 655

Ser Glu Thr Leu Val Pro Val Asn Leu Thr Val Leu Pro Glu Ile Gln
            660                 665                 670

His Asn Ile Lys Phe Phe Lys Asn Asp Asp Thr Gln Asn Ile Ala Glu
        675                 680                 685

Lys Pro Phe Ser Lys Gln Ala Gly His Pro Val Phe Tyr Val Tyr Ala
    690                 695                 700

Gly Asn Gln Gly Asn Ala Ser Val Asn Leu Gly Gly Ser Val Thr Ser
705                 710                 715                 720

Ile Gln Pro Leu Arg Ile Asn Leu Thr Ser Asn Glu Asn Phe Thr Asp
                725                 730                 735

Lys Asp Trp Gln Ile Thr Gly Ile Pro Arg Thr Leu His Ile Glu Asn
            740                 745                 750

Ser Thr Asn Arg Thr Asn Asn Ala Arg Glu Arg Asn Ile Glu Leu Val
        755                 760                 765

Gly Asn Leu Leu Pro Gly Asp Tyr Phe Gly Thr Ile Arg Phe Gly Arg
    770                 775                 780

Lys Glu Gln Leu Phe Glu Ile Arg Val Lys Pro His Thr Pro Thr Ile
785                 790                 795                 800

Thr Thr Thr Ala Glu Gln Leu Arg Gly Thr Ala Leu Gln Lys Val Pro
                805                 810                 815

Val Asn Ile Ser Gly Ile Pro Leu Asp Pro Ser Ala Leu Val Tyr Leu
            820                 825                 830

Val Ala Pro Thr Asn Gln Thr Thr Asn Gly Gly Ser Glu Ala Asp Gln
        835                 840                 845

Ile Pro Ser Gly Tyr Thr Ile Leu Ala Thr Gly Thr Pro Asp Gly Val
    850                 855                 860
```

-continued

```
His Asn Thr Ile Thr Ile Arg Pro Gln Asp Tyr Val Val Phe Ile Pro
865                 870                 875                 880

Pro Val Gly Lys Gln Ile Arg Ala Val Val Tyr Tyr Asn Lys Val Val
                885                 890                 895

Ala Ser Asn Met Ser Asn Ala Val Thr Ile Leu Pro Asp Asp Ile Pro
            900                 905                 910

Pro Thr Ile Asn Asn Pro Val Gly Ile Asn Ala Lys Tyr Tyr Arg Gly
        915                 920                 925

Asp Glu Val Asn Phe Thr Met Gly Val Ser Asp Arg His Ser Gly Ile
    930                 935                 940

Lys Asn Thr Thr Ile Thr Thr Leu Pro Ser Gly Trp Thr Ser Asn Leu
945                 950                 955                 960

Thr Lys Ser Asp Asn Lys Asn Gly Ser Leu Ala Ile Thr Gly Arg Val
                965                 970                 975

Ser Met Asn Gln Ala Phe Asn Ser Asp Ile Thr Phe Lys Val Ser Ala
            980                 985                 990

Thr Asp Asn Val Asn Asn Thr Thr Asn Asp Ser Gln Ser Lys His Val
        995                 1000                1005

Ser Ile His Val Gly Lys Ile Ser Glu Asp Ala His Pro Ile Val Leu
    1010                1015                1020

Gly Asn Thr Glu Lys Val Val Val Val Asn Pro Thr Ala Val Ser Asn
1025                1030                1035                1040

Asp Glu Lys Gln Ser Ile Ile Thr Ala Phe Met Asn Lys Asn Gln Asn
                1045                1050                1055

Ile Arg Gly Tyr Leu Ala Ser Thr Asp Pro Val Thr Val Asp Asn Asn
            1060                1065                1070

Gly Asn Val Thr Leu His Tyr Arg Asp Gly Ser Ser Thr Thr Leu Asp
        1075                1080                1085

Ala Thr Asn Val Met Thr Tyr Glu Pro Val Val Lys Ser Glu Tyr Gln
    1090                1095                1100

Thr Ala Asn Ala Ala Lys Thr Ala Thr Val Thr Ile Ala Lys Gly Gln
1105                1110                1115                1120

Ser Phe Asn Ile Gly Asp Ile Lys Gln Tyr Phe Thr Leu Ser Asn Gly
                1125                1130                1135

Gln Ala Ile Pro Asn Gly Thr Phe Thr Asn Ile Thr Ser Asp Arg Thr
            1140                1145                1150

Ile Pro Thr Ala Gln Glu Val Ser Gln Met Asn Ala Gly Thr Gln Leu
        1155                1160                1165

Tyr His Ile Val Ala Ser Asn Ala Tyr His Lys Asp Thr Glu Asp Phe
    1170                1175                1180

Tyr Ile Ser Leu Lys Ile Val Asp Val Lys Gln Pro Glu Gly Asp Gln
1185                1190                1195                1200

Arg Val Tyr Arg Thr Ser Thr Tyr Asp Leu Thr Thr Asp Glu Ile Ser
                1205                1210                1215

Lys Val Lys Gln Ala Phe Ile Asn Ala Asn Arg Asp Val Ile Thr Leu
            1220                1225                1230

Ala Glu Gly Asp Ile Ser Val Thr Asn Thr Pro Asn Gly Ala Asn Val
        1235                1240                1245

Ser Thr Ile Thr Val Asn Ile Asn Lys Gly Arg Leu Thr Lys Ser Phe
    1250                1255                1260

Ala Ser Asn Leu Ala Asn Met Asn Phe Leu Arg Trp Val Asn Phe Pro
1265                1270                1275                1280

Gln Asp Tyr Thr Val Thr Trp Thr Asn Ala Lys Ile Ala Asn Arg Pro
```

-continued

```
                1285                1290                1295

Thr Asp Gly Gly Leu Ser Trp Ser Asp Asp His Lys Ser Leu Ile Tyr
            1300                1305                1310

Arg Tyr Asp Ala Thr Leu Gly Thr Gln Ile Thr Thr Asn Asp Ile Leu
        1315                1320                1325

Thr Met Leu Lys Ala Thr Thr Thr Val Pro Gly Leu Arg Asn Asn Ile
    1330                1335                1340

Thr Gly Asn Glu Lys Ala Gln Ala Glu Ala Gly Gly Arg Pro Asn Tyr
1345                1350                1355                1360

Arg Thr Thr Gly Tyr Ser Gln Ser Asn Ala Thr Thr Asp Gly Gln Arg
                1365                1370                1375

Gln Phe Thr Leu Asn Gly Gln Val Ile Gln Ile Leu Asp Ile Ile Asn
            1380                1385                1390

Pro Ser Asn Gly Tyr Gly Gly Gln Pro Val Thr Asn Ser Asn Thr Arg
        1395                1400                1405

Ala Asn His Ser Asn Ser Thr Val Val Asn Val Asn Glu Pro Ala Ala
    1410                1415                1420

Asn Gly Ala Gly Ala Phe Thr Ile Asp His Val Val Lys Ser Asn Ser
1425                1430                1435                1440

Thr His Asn Ala Ser Asp Ala Val Tyr Lys Ala Gln Leu Tyr Leu Thr
                1445                1450                1455

Pro Tyr Gly Pro Lys Gln Tyr Val Glu His Leu Asn Gln Asn Thr Gly
            1460                1465                1470

Asn Thr Thr Asp Ala Ile Asn Ile Tyr Phe Val Pro Ser Asp Leu Val
        1475                1480                1485

Asn Pro Thr Ile Ser Val Gly Asn Tyr Thr Asn His Gln Val Phe Ser
    1490                1495                1500

Gly Glu Thr Phe Thr Asn Thr Ile Thr Ala Asn Asp Asn Phe Gly Val
1505                1510                1515                1520

Gln Ser Val Thr Val Pro Asn Thr Ser Gln Ile Thr Gly Thr Val Asp
                1525                1530                1535

Asn Asn His Gln His Val Ser Ala Thr Ala Pro Asn Val Thr Ser Ala
            1540                1545                1550

Thr Ser Lys Thr Ile Asn Leu Leu Ala Thr Asp Thr Ser Gly Asn Thr
        1555                1560                1565

Ala Thr Thr Ser Phe Asn Val Thr Val Lys Pro Leu Arg Asp Lys Tyr
    1570                1575                1580

Arg Val Gly Thr Ser Ser Thr Ala Ala Asn Pro Val Arg Ile Ala Asn
1585                1590                1595                1600

Ile Ser Asn Asn Ala Thr Val Ser Gln Ala Asp Gln Thr Thr Ile Ile
                1605                1610                1615

Asn Ser Leu Thr Phe Thr Ser Asn Ala Pro Asn Arg Asn Tyr Ala Thr
            1620                1625                1630

Ala Ser Ala Asn Glu Ile Thr Ser Lys Thr Val Ser Asn Val Ser Arg
        1635                1640                1645

Thr Gly Asn Asn Ala Asn Val Thr Val Thr Val Thr His Gln Asp Gly
    1650                1655                1660

Thr Thr Ser Thr Val Thr Val Pro Val Lys His Val Ile Pro Glu Ile
1665                1670                1675                1680

Val Ala His Ser His Tyr Thr Val Gln Gly Gln Asp Phe Pro Ala Gly
                1685                1690                1695

Asn Gly Ser Ser Ala Ala Asp Tyr Phe Lys Leu Ser Asn Gly Ser Ala
            1700                1705                1710
```

-continued

```
Ile Pro Asp Ala Thr Ile Thr Trp Val Ser Gly Gln Ala Pro Asn Lys
        1715                1720                1725

Asp Asn Thr Arg Ile Gly Glu Asp Ile Thr Val Thr Ala His Ile Leu
    1730                1735                1740

Ile Asp Gly Glu Thr Thr Pro Ile Thr Lys Thr Ala Thr Tyr Lys Val
1745                1750                1755                1760

Val Arg Thr Val Pro Lys His Val Phe Glu Thr Ala Arg Gly Val Leu
                1765                1770                1775

Tyr Pro Gly Val Ser Asp Met Tyr Asp Ala Lys Gln Tyr Val Lys Pro
            1780                1785                1790

Val Asn Asn Ser Trp Ser Thr Asn Ala Gln His Met Asn Phe Gln Phe
        1795                1800                1805

Val Gly Thr Tyr Gly Pro Asn Lys Asp Val Val Gly Ile Ser Thr Arg
    1810                1815                1820

Leu Ile Arg Val Thr Tyr Asp Asn Arg Gln Thr Glu Asp Leu Thr Ile
1825                1830                1835                1840

Leu Ser Lys Val Lys Pro Asp Pro Pro Arg Ile Asp Ala Asn Ser Val
                1845                1850                1855

Thr Tyr Lys Ala Gly Leu Thr Asn Gln Glu Ile Lys Val Asn Asn Val
            1860                1865                1870

Leu Asn Asn Ser Ser Val Lys Leu Phe Lys Ala Asp Asn Thr Pro Leu
        1875                1880                1885

Asn Val Thr Asn Ile Thr His Gly Ser Gly Phe Ser Ser Val Val Thr
    1890                1895                1900

Val Ser Asp Ala Leu Pro Asn Gly Gly Ile Lys Ala Lys Ser Ser Ile
1905                1910                1915                1920

Ser Met Asn Asn Val Thr Tyr Thr Thr Gln Asp Glu His Gly Gln Val
                1925                1930                1935

Val Thr Val Thr Arg Asn Glu Ser Val Asp Ser Asn Asp Ser Ala Ser
            1940                1945                1950

Val Thr Val Thr Pro Gln Leu Gln Ala Thr Thr Glu Gly Ala Val Phe
        1955                1960                1965

Ile Lys Gly Gly Asp Gly Phe Asp Phe Gly His Val Glu Arg Phe Ile
    1970                1975                1980

Gln Asn Pro Pro His Gly Ala Thr Val Ala Trp His Asp Ser Pro Asp
1985                1990                1995                2000

Thr Trp Lys Asn Thr Val Gly Asn Thr His Lys Thr Ala Val Val Thr
                2005                2010                2015

Leu Pro Ser Gly Gln Gly Thr Arg Asn Val Glu Val Pro Val Lys Val
            2020                2025                2030

Tyr Pro Val Ala Asn Ala Lys Ala Pro Ser Arg Asp Val Lys Gly Gln
        2035                2040                2045

Asn Leu Thr His Gly Thr Asn Ala Ile Asp Tyr Ile Thr Phe Asp Pro
    2050                2055                2060

Asn Thr Asn Thr Asn Gly Ile Thr Ala Ala Trp Ala Asn Arg Gln Gln
2065                2070                2075                2080

Pro Asn Asn Gln Gln Ala Gly Val Gln His Leu Asn Val Asp Val Thr
                2085                2090                2095

Tyr Pro Gly Ile Ser Ala Ala Lys Arg Val Pro Val Thr Val Asn Val
            2100                2105                2110

Tyr Gln Phe Glu Phe Pro Gln Thr Thr Tyr Thr Thr Thr Val Gly Gly
        2115                2120                2125
```

```
Thr Leu Ala Ser Gly Thr Gln Ala Ser Gly Tyr Ala His Met Gln Asn
    2130                2135                2140

Ala Ser Gly Leu Pro Thr Asp Gly Phe Thr Tyr Lys Trp Asn Arg Asp
2145                2150                2155                2160

Thr Thr Gly Thr Asn Asp Ala Asn Trp Ala Ala Met Asn Lys Pro Asn
                2165                2170                2175

Thr Ala Gln Val Val Asn Ala Lys Tyr Asp Val Ile Tyr Asn Gly His
            2180                2185                2190

Thr Phe Ala Thr Ser Leu Pro Ala Lys Phe Val Val Lys Asp Val Gln
        2195                2200                2205

Pro Ala Lys Pro Thr Val Thr Glu Thr Ala Ala Gly Ala Ile Thr Ile
    2210                2215                2220

Ala Pro Gly Ala Asn Gln Thr Val Asn Thr His Ala Gly Asn Val Thr
2225                2230                2235                2240

Thr Tyr Ala Asp Lys Leu Val Ile Lys Arg Asn Gly Asn Val Val Thr
                2245                2250                2255

Thr Phe Thr Arg Arg Asn Asn Thr Ser Pro Trp Val Lys Glu Ala Ser
            2260                2265                2270

Ala Asp Asn Val Thr Gly Ile Val Gly Thr Asn Asn Gly Ile Thr Val
        2275                2280                2285

Ala Ala Gly Thr Phe Asn Pro Ala Asp Thr Ile Gln Val Val Ala Thr
    2290                2295                2300

Gln Gly Ser Gly Glu Thr Ile Ser Asp Glu Gln Arg Ser Asp Asp Phe
2305                2310                2315                2320

Thr Val Val Ala Pro Gln Pro Asn Gln Ala Thr Thr Lys Ile Trp Gln
                2325                2330                2335

Asn Gly His Ile Asp Ile Thr Pro Asn Asn Pro Ser Gly His Leu Ile
            2340                2345                2350

Asn Pro Thr Gln Ala Met Asp Ile Ala Tyr Thr Glu Lys Val Gly Asn
        2355                2360                2365

Gly Ala Glu His Ser Lys Thr Ile Asn Val Val Arg Gly Gln Asn Asn
    2370                2375                2380

Gln Trp Thr Ile Ala Asn Lys Pro Asp Tyr Val Thr Leu Asp Ala Gln
2385                2390                2395                2400

Thr Gly Lys Val Thr Phe Asn Ala Asn Thr Ile Lys Pro Asn Ser Ser
                2405                2410                2415

Ile Thr Ile Thr Pro Lys Ala Gly Thr Gly His Ser Val Ser Ser Asn
            2420                2425                2430

Pro Ser Thr Leu Thr Ala Pro Ala Ala His Thr Val Asn Thr Thr Glu
        2435                2440                2445

Ile Val Lys Asp Tyr Gly Ser Asn Val Thr Ala Ala Glu Ile Asn Asn
    2450                2455                2460

Ala Val Gln Val Ala Asn Lys Arg Thr Ala Thr Ile Lys Asn Gly Thr
2465                2470                2475                2480

Ala Met Pro Thr Asn Leu Ala Gly Gly Ser Thr Thr Thr Ile Pro Val
                2485                2490                2495

Thr Val Thr Tyr Asn Asp Gly Ser Thr Glu Glu Val Gln Glu Ser Ile
            2500                2505                2510

Phe Thr Lys Ala Asp Lys Arg Glu Leu Ile Thr Ala Lys Asn His Leu
        2515                2520                2525

Asp Asp Pro Val Ser Thr Glu Gly Lys Lys Pro Gly Thr Ile Thr Gln
    2530                2535                2540

Tyr Asn Asn Ala Met His Asn Ala Gln Gln Gln Ile Asn Thr Ala Lys
```

```
2545                2550                2555                2560

Thr Glu Ala Gln Gln Val Ile Asn Asn Glu Arg Ala Thr Pro Gln Gln
                2565                2570                2575

Val Ser Asp Ala Leu Thr Lys Val Arg Ala Ala Gln Thr Lys Ile Asp
            2580                2585                2590

Gln Ala Lys Ala Leu Leu Gln Asn Lys Glu Asp Asn Ser Gln Leu Val
        2595                2600                2605

Thr Ser Lys Asn Asn Leu Gln Ser Ser Val Asn Gln Val Pro Ser Thr
    2610                2615                2620

Ala Gly Met Thr Gln Gln Ser Ile Asp Asn Tyr Asn Ala Lys Lys Arg
2625                2630                2635                2640

Glu Ala Glu Thr Glu Ile Thr Ala Ala Gln Arg Val Ile Asp Asn Gly
                2645                2650                2655

Asp Ala Thr Ala Gln Gln Ile Ser Asp Glu Lys His Arg Val Asp Asn
            2660                2665                2670

Ala Leu Thr Ala Leu Asn Gln Ala Lys His Asp Leu Thr Ala Asp Thr
        2675                2680                2685

His Ala Leu Glu Gln Ala Val Gln Gln Leu Asn Arg Thr Gly Thr Thr
    2690                2695                2700

Thr Gly Lys Lys Pro Ala Ser Ile Thr Ala Tyr Asn Asn Ser Ile Arg
2705                2710                2715                2720

Ala Leu Gln Ser Asp Leu Thr Ser Ala Lys Asn Ser Ala Asn Ala Ile
                2725                2730                2735

Ile Gln Lys Pro Ile Arg Thr Val Gln Glu Val Gln Ser Ala Leu Thr
            2740                2745                2750

Asn Val Asn Arg Val Asn Glu Arg Leu Thr Gln Ala Ile Asn Gln Leu
        2755                2760                2765

Val Pro Leu Ala Asp Asn Ser Ala Leu Arg Thr Ala Lys Thr Lys Leu
    2770                2775                2780

Asp Glu Glu Ile Asn Lys Ser Val Thr Thr Asp Gly Met Thr Gln Ser
2785                2790                2795                2800

Ser Ile Gln Ala Tyr Glu Asn Ala Lys Arg Ala Gly Gln Thr Glu Thr
                2805                2810                2815

Thr Asn Ala Gln Asn Val Ile Asn Asn Gly Asp Ala Thr Asp Gln Gln
            2820                2825                2830

Ile Ala Ala Glu Lys Thr Lys Val Glu Glu Lys Tyr Asn Ser Leu Lys
        2835                2840                2845

Gln Ala Ile Ala Gly Leu Thr Pro Asp Leu Ala Pro Leu Gln Thr Ala
    2850                2855                2860

Lys Thr Gln Leu Gln Asn Asp Ile Asp Gln Pro Thr Ser Thr Thr Gly
2865                2870                2875                2880

Met Thr Ser Ala Ser Val Ala Ala Phe Asn Asp Lys Leu Ser Ala Ala
                2885                2890                2895

Arg Thr Lys Ile Gln Glu Ile Asp Arg Val Leu Ala Ser His Pro Asp
            2900                2905                2910

Val Ala Thr Ile Arg Gln Asn Val Thr Ala Ala Asn Ala Ala Lys Thr
        2915                2920                2925

Ala Leu Asp Gln Ala Arg Asn Gly Leu Thr Val Asp Lys Ala Pro Leu
    2930                2935                2940

Glu Asn Ala Lys Asn Gln Leu Gln His Ser Ile Asp Thr Gln Thr Ser
2945                2950                2955                2960

Thr Thr Gly Met Thr Gln Asp Ser Ile Asn Ala Tyr Asn Ala Lys Leu
                2965                2970                2975
```

```
Thr Ala Ala Arg Asn Lys Val Gln Gln Ile Asn Gln Val Leu Ala Gly
            2980                2985                2990

Ser Pro Thr Val Asp Gln Ile Asn Thr Asn Thr Ser Ala Ala Asn Gln
        2995                3000                3005

Ala Lys Ser Asp Leu Asp His Ala Arg Gln Ala Leu Thr Pro Asp Lys
    3010                3015                3020

Ala Pro Leu Gln Asn Ala Lys Thr Gln Leu Glu Gln Ser Ile Asn Gln
3025                3030                3035                3040

Pro Thr Asp Thr Thr Gly Met Thr Thr Ala Ser Leu Asn Ala Tyr Asn
                3045                3050                3055

Gln Lys Leu Gln Ala Ala Arg Gln Lys Leu Thr Glu Ile Asn Gln Val
            3060                3065                3070

Leu Asn Gly Asn Pro Thr Val Gln Asn Ile Asn Asp Lys Val Ala Glu
        3075                3080                3085

Ala Asn Gln Ala Lys Asp Gln Leu Asn Thr Ala Arg Gln Gly Leu Thr
    3090                3095                3100

Leu Asp Arg Gln Pro Ala Leu Thr Thr Leu His Gly Ala Ser Asn Leu
3105                3110                3115                3120

Asn Gln Ala Gln Gln Asn Asn Phe Thr Gln Gln Ile Asn Ala Ala Gln
                3125                3130                3135

Asn His Ala Ala Leu Glu Thr Ile Lys Ser Asn Ile Thr Ala Leu Asn
            3140                3145                3150

Thr Ala Met Thr Lys Leu Lys Asp Ser Val Ala Asp Asn Asn Thr Ile
        3155                3160                3165

Lys Ser Gly Gln Asn Tyr Thr Asp Ala Thr Pro Ala Asn Lys Gln Ala
    3170                3175                3180

Tyr Asp Asn Ala Val Asn Ala Ala Lys Gly Val Ile Gly Glu Thr Thr
3185                3190                3195                3200

Asn Pro Thr Met Asp Val Asn Thr Val Asn Gln Lys Ala Ala Ser Val
                3205                3210                3215

Lys Ser Thr Lys Asp Ala Leu Asp Gly Gln Gln Asn Leu Gln Arg Ala
            3220                3225                3230

Lys Thr Glu Ala Thr Asn Ala Ile Thr His Ala Ser Asp Leu Asn Gln
        3235                3240                3245

Ala Gln Lys Asn Ala Leu Thr Gln Gln Val Asn Ser Ala Gln Asn Val
    3250                3255                3260

Gln Ala Val Asn Asp Ile Lys Gln Thr Thr Gln Ser Leu Asn Thr Ala
3265                3270                3275                3280

Met Thr Gly Leu Lys Arg Gly Val Ala Asn His Asn Gln Val Val Gln
                3285                3290                3295

Ser Asp Asn Tyr Val Asn Ala Asp Thr Asn Lys Lys Asn Asp Tyr Asn
            3300                3305                3310

Asn Ala Tyr Asn His Ala Asn Asp Ile Ile Asn Gly Asn Ala Gln His
        3315                3320                3325

Pro Val Ile Thr Pro Ser Asp Val Asn Asn Ala Leu Ser Asn Val Thr
    3330                3335                3340

Ser Lys Glu His Ala Leu Asn Gly Glu Ala Lys Leu Asn Ala Ala Lys
3345                3350                3355                3360

Gln Glu Ala Asn Thr Ala Leu Gly His Leu Asn Asn Leu Asn Asn Val
                3365                3370                3375

Gln Arg Gln Asn Leu Gln Ser Gln Ile Asn Gly Ala His Gln Ile Asp
            3380                3385                3390
```

-continued

```
Ala Val Asn Thr Ile Lys Gln Asn Ala Thr Asn Leu Asn Ser Ala Met
        3395                3400                3405

Gly Asn Leu Arg Gln Ala Val Ala Asp Lys Asp Gln Val Lys Arg Thr
    3410                3415                3420

Glu Asp Tyr Ala Asp Ala Asp Thr Ala Lys Gln Asn Ala Tyr Asn Ser
3425                3430                3435                3440

Ala Val Ser Ser Ala Glu Thr Ile Ile Asn Gln Thr Ala Asn Pro Thr
                3445                3450                3455

Met Ser Val Asp Asp Val Asn Arg Ala Thr Ser Ala Val Thr Thr Asn
            3460                3465                3470

Lys Asn Ala Leu Asn Gly Asp Glu Lys Leu Val Gln Ser Lys Thr Asp
        3475                3480                3485

Ala Ala Arg Ala Ile Asp Ala Leu Pro His Leu Asn Asn Ala Gln Lys
    3490                3495                3500

Ala Asp Val Lys Ser Lys Ile Asn Ala Ala Ser Asn Ile Ala Gly Val
3505                3510                3515                3520

Asn Thr Val Lys Gln Gln Gly Thr Asp Leu Asn Thr Ala Met Gly Asn
                3525                3530                3535

Leu Gln Gly Ala Ile Asn Asp Glu Gln Thr Thr Leu Asn Ser Gln Asn
            3540                3545                3550

Tyr Gln Asp Ala Thr Pro Ser Lys Lys Thr Ala Tyr Thr Asn Ala Val
        3555                3560                3565

Gln Ala Ala Lys Asp Ile Leu Asn Lys Ser Asn Gly Gln Asn Lys Thr
    3570                3575                3580

Lys Asp Gln Val Thr Glu Ala Met Asn Gln Val Asn Ser Ala Lys Asn
3585                3590                3595                3600

Asn Leu Asp Gly Thr Arg Leu Leu Asp Gln Ala Lys Gln Thr Ala Lys
                3605                3610                3615

Gln Gln Leu Asn Asn Met Thr His Leu Thr Thr Ala Gln Lys Thr Asn
            3620                3625                3630

Leu Thr Asn Gln Ile Asn Ser Gly Thr Thr Val Ala Gly Val His Thr
        3635                3640                3645

Val Gln Ser Asn Ala Asn Thr Leu Asp Gln Ala Met Asn Thr Leu Arg
    3650                3655                3660

Gln Ser Ile Ala Asn Asn Asp Ala Thr Lys Ala Ser Glu Asp Tyr Val
3665                3670                3675                3680

Asp Ala Asn Asn Asp Lys Gln Thr Ala Tyr Asn Asn Ala Val Ala Ala
                3685                3690                3695

Ala Glu Thr Ile Ile Asn Ala Asn Ser Asn Pro Glu Met Asn Pro Ser
            3700                3705                3710

Thr Ile Thr Gln Lys Ala Glu Gln Val Asn Ser Ser Lys Thr Ala Leu
        3715                3720                3725

Asn Gly Asp Glu Asn Leu Ala Thr Ala Lys Gln Asn Ala Lys Thr Tyr
    3730                3735                3740

Leu Asn Thr Leu Thr Ser Ile Thr Asp Ala Gln Lys Asn Asn Leu Ile
3745                3750                3755                3760

Ser Gln Ile Ser Ser Ala Thr Arg Val Ser Gly Val Asp Thr Val Lys
                3765                3770                3775

Gln Asn Ala Gln His Leu Asp Gln Ala Met Ala Asn Leu Gln Asn Gly
            3780                3785                3790

Ile Asn Asn Glu Ser Gln Val Lys Ser Ser Glu Lys Tyr Arg Asp Ala
        3795                3800                3805

Asp Thr Asn Lys Gln Gln Glu Tyr Asp Asn Ala Ile Thr Ala Ala Lys
```

-continued

```
    3810                3815                3820

Ala Ile Leu Asn Lys Ser Thr Gly Pro Asn Thr Ala Gln Asn Ala Val
3825                3830                3835                3840

Glu Ala Ala Leu Gln Arg Val Asn Thr Ala Lys Asp Ala Leu Asn Gly
                3845                3850                3855

Asp Ala Lys Leu Ile Ala Ala Gln Asn Ala Ala Lys Gln His Leu Gly
            3860                3865                3870

Thr Leu Thr His Ile Thr Thr Ala Gln Arg Asn Asp Leu Thr Asn Gln
        3875                3880                3885

Ile Ser
    3890


<210> SEQ ID NO 13
<211> LENGTH: 6713
<212> TYPE: PRT
<213> ORGANISM: Staphylococcus sp.

<400> SEQUENCE: 13

Met Gly Asn Leu Gln Thr Ala Ile Asn Asp Lys Ser Gly Thr Leu Ala
1               5                   10                  15

Ser Gln Asn Phe Leu Asp Ala Asp Glu Gln Lys Arg Asn Ala Tyr Asn
            20                  25                  30

Gln Ala Ile Ser Ala Ala Glu Thr Ile Leu Asn Lys Gln Thr Gly Pro
        35                  40                  45

Asn Thr Ala Lys Thr Ala Val Glu Gln Ala Leu Asn Asn Val Asn Ser
    50                  55                  60

Ala Lys His Ala Leu Asn Gly Thr Gln Asn Leu Asn Asn Ala Lys Gln
65                  70                  75                  80

Ala Ala Ile Thr Ala Ile Asn Gly Ala Ser Asp Leu Asn Gln Lys Gln
                85                  90                  95

Lys Asp Ala Leu Lys Ala Gln Ala Asn Gly Ala Gln Arg Val Ser Asn
            100                 105                 110

Ala Asn Asp Val Gln Arg Asn Ala Thr Glu Leu Asn Thr Ala Met Gly
        115                 120                 125

Gln Leu Gln His Ala Ile Ala Asp Lys Thr Asn Thr Leu Ala Ser Ser
    130                 135                 140

Lys Tyr Val Asn Ala Asp Ser Thr Lys Gln Asn Ala Tyr Thr Thr Lys
145                 150                 155                 160

Val Thr Asn Ala Glu His Ile Ile Ser Gly Thr Pro Thr Val Val Thr
                165                 170                 175

Thr Pro Ser Glu Val Thr Ala Ala Ala Asn Gln Val Asn Ser Ala Lys
            180                 185                 190

Gln Glu Leu Asn Gly Asp Glu Arg Leu Arg Val Ala Lys Gln Asn Ala
        195                 200                 205

Asn Thr Ala Ile Asp Ala Leu Thr Gln Leu Asn Thr Pro Gln Lys Ala
    210                 215                 220

Lys Leu Lys Glu Gln Val Gly Gln Ala Asn Arg Leu Glu Asp Val Gln
225                 230                 235                 240

Ser Val Gln Thr Asn Gly Gln Ser Leu Asn Asn Ala Met Lys Gly Leu
                245                 250                 255

Arg Asp Ser Ile Ala Asn Glu Thr Thr Val Lys Ala Ser Gln Asn Tyr
            260                 265                 270

Thr Asp Ala Ser Pro Asn Asn Gln Ser Thr Tyr Asn Ser Ala Val Ser
        275                 280                 285
```

-continued

```
Asn Ala Lys Gly Ile Ile Asn Gln Thr Asn Asn Pro Thr Met Asp Thr
    290                 295                 300

Ser Ala Ile Thr Gln Ala Thr Thr Gln Val Asn Asn Ala Lys Asn Gly
305                 310                 315                 320

Leu Asn Gly Ala Glu Asn Leu Arg Asn Ala Gln Asn Thr Ala Lys Gln
                325                 330                 335

Asn Leu Asn Thr Leu Ser His Leu Thr Asn Asn Gln Lys Ser Ala Ile
            340                 345                 350

Ser Ser Gln Ile Asp Arg Ala Gly His Val Ser Glu Val Thr Ala Ala
        355                 360                 365

Lys Asn Ala Ala Thr Glu Leu Asn Ala Gln Met Gly Asn Leu Glu Gln
    370                 375                 380

Ala Ile His Asp Gln Asn Thr Val Lys Gln Gly Val Asn Phe Thr Asp
385                 390                 395                 400

Ala Asp Lys Ala Lys Arg Asp Ala Tyr Thr Asn Ala Val Ser Arg Ala
                405                 410                 415

Glu Thr Ile Leu Asn Lys Thr Gln Gly Ala Asn Thr Ser Lys Gln Asp
            420                 425                 430

Val Glu Ala Ala Ile Gln Asn Val Thr Ser Ala Lys Asn Ala Leu Asn
        435                 440                 445

Gly Asp Gln Asn Val Thr Asn Ala Lys Asn Ala Ala Lys Asn Ala Leu
    450                 455                 460

Asn Asn Leu Thr Ser Ile Asn Asn Ala Gln Lys Arg Asp Leu Thr Thr
465                 470                 475                 480

Lys Ile Asp Gln Ala Thr Thr Val Ala Gly Val Glu Ala Val Ser Asn
                485                 490                 495

Thr Gly Thr Gln Leu Asn Thr Ala Met Ala Asn Leu Gln Asn Gly Ile
            500                 505                 510

Asn Asp Lys Ala Asn Thr Leu Ala Ser Glu Asn Tyr His Asp Ala Asp
        515                 520                 525

Ser Asp Lys Lys Thr Ala Tyr Thr Gln Ala Val Thr Asn Ala Glu Asn
    530                 535                 540

Ile Leu Asn Lys Asn Ser Gly Ser Asn Leu Asp Lys Ala Ala Val Glu
545                 550                 555                 560

Asn Ala Leu Ser Gln Val Thr Asn Ala Lys Gly Ala Leu Asn Gly Asn
                565                 570                 575

His Asn Leu Glu Gln Ala Lys Ser Asn Ala Asn Thr Thr Ile Asn Gly
            580                 585                 590

Leu Gln His Leu Thr Thr Ala Gln Lys Asp Lys Leu Lys Gln Gln Val
        595                 600                 605

Gln Gln Ala Gln Asn Val Ala Gly Val Asp Thr Val Lys Ser Ser Ala
    610                 615                 620

Asn Thr Leu Asn Gly Ala Met Gly Thr Leu Arg Asn Ser Ile Gln Asp
625                 630                 635                 640

Asn Thr Ala Thr Lys Asn Gly Gln Asn Tyr Leu Asp Ala Thr Glu Arg
                645                 650                 655

Asn Lys Thr Asn Tyr Asn Asn Ala Val Asp Ser Ala Asn Gly Val Ile
            660                 665                 670

Asn Ala Thr Ser Asn Pro Asn Met Asp Ala Asn Ala Ile Asn Gln Ile
        675                 680                 685

Ala Thr Gln Val Thr Ser Thr Lys Asn Ala Leu Asp Gly Thr His Asn
    690                 695                 700

Leu Thr Gln Ala Lys Gln Thr Ala Thr Asn Ala Ile Asp Gly Ala Thr
```

-continued

```
705                 710                 715                 720

Asn Leu Asn Lys Ala Gln Lys Asp Ala Leu Lys Ala Gln Val Thr Ser
                725                 730                 735

Ala Gln Arg Val Ala Asn Val Thr Ser Ile Gln Gln Thr Ala Asn Glu
            740                 745                 750

Leu Asn Thr Ala Met Gly Gln Leu Gln His Gly Ile Asp Asp Glu Asn
        755                 760                 765

Ala Thr Lys Gln Thr Gln Lys Tyr Arg Asp Ala Glu Gln Ser Lys Lys
    770                 775                 780

Thr Ala Tyr Asp Gln Ala Val Ala Ala Ala Lys Ala Ile Leu Asn Lys
785                 790                 795                 800

Gln Thr Gly Ser Asn Ser Asp Lys Ala Ala Val Asp Arg Ala Leu Gln
                805                 810                 815

Gln Val Thr Ser Thr Lys Asp Ala Leu Asn Gly Asp Ala Lys Leu Ala
            820                 825                 830

Glu Ala Lys Ala Ala Ala Arg Gln Asn Leu Gly Thr Leu Asn His Ile
        835                 840                 845

Thr Asn Ala Gln Arg Thr Ala Leu Glu Gly Gln Ile Asn Gln Ala Thr
    850                 855                 860

Thr Val Asp Gly Val Asn Thr Val Lys Thr Asn Ala Asn Thr Leu Asp
865                 870                 875                 880

Gly Ala Met Asn Ser Leu Gln Gly Ala Ile Asn Asp Lys Asp Ala Thr
                885                 890                 895

Leu Arg Asn Gln Asn Tyr Leu Asp Ala Asp Glu Ser Lys Arg Asn Ala
            900                 905                 910

Tyr Thr Gln Ala Val Thr Ala Ala Glu Gly Ile Leu Asn Lys Gln Thr
        915                 920                 925

Gly Gly Asn Thr Ser Lys Ala Asp Val Asp Asn Ala Leu Asn Ala Val
    930                 935                 940

Thr Arg Ala Lys Ala Ala Leu Asn Gly Ala Glu Asn Leu Arg Asn Ala
945                 950                 955                 960

Lys Thr Ser Ala Thr Asn Thr Ile Asn Gly Leu Pro Asn Leu Thr Gln
                965                 970                 975

Leu Gln Lys Asp Asn Leu Lys His Gln Val Glu Gln Ala Gln Asn Val
            980                 985                 990

Val Gly Val Asn Gly Val Lys Asp Lys Gly Asn Thr Leu Asn Thr Ala
        995                 1000                1005

Met Gly Ala Leu Arg Thr Ser Ile Gln Asn Asp Asn Thr Thr Lys Thr
    1010                1015                1020

Ser Gln Asn Tyr Leu Asp Ala Ser Asp Ser Asn Lys Asn Asn Tyr Asn
1025                1030                1035                1040

Thr Ala Val Asn Asn Ala Asn Gly Val Ile Asn Ala Thr Asn Asn Pro
                1045                1050                1055

Asn Met Asp Ala Asn Ala Ile Asn Asp Met Ala Asn Gln Val Asn Thr
            1060                1065                1070

Thr Lys Ala Ala Leu Asn Gly Ala Gln Asn Leu Ala Gln Ala Lys Thr
        1075                1080                1085

Asn Ala Thr Asn Thr Ile Asn Asn Ala Gln Asp Leu Asn Gln Lys Gln
    1090                1095                1100

Lys Asp Ala Leu Lys Thr Gln Val Asn Asn Ala Gln Arg Val Ser Asp
1105                1110                1115                1120

Ala Asn Asn Val Gln His Thr Ala Thr Glu Leu Asn Gly Ala Met Thr
                1125                1130                1135
```

-continued

```
Ala Leu Lys Ala Ala Ile Ala Asp Lys Glu Arg Thr Lys Ala Ser Gly
            1140                1145                1150

Asn Tyr Val Asn Ala Asp Gln Glu Lys Arg Gln Ala Tyr Asp Ser Lys
        1155                1160                1165

Val Thr Asn Ala Glu Asn Ile Ile Asn Gly Thr Pro Asn Ala Thr Leu
    1170                1175                1180

Thr Val Asn Asp Val Asn Ser Ala Ala Ser Gln Val Asn Ala Ala Lys
1185                1190                1195                1200

Thr Ala Leu Asn Gly Asp Asn Asn Leu Arg Val Ala Lys Glu His Ala
                1205                1210                1215

Asn Asn Thr Ile Asp Gly Leu Ala Gln Leu Asn Asn Val Gln Lys Ala
            1220                1225                1230

Lys Leu Lys Glu Gln Val Gln Ser Ala Thr Thr Leu Asp Gly Val Gln
        1235                1240                1245

Thr Val Lys Asn Ser Ser Gln Thr Leu Asn Thr Ala Met Lys Gly Leu
    1250                1255                1260

Arg Asp Ser Ile Ala Asn Glu Ala Thr Ile Lys Ala Gly Gln Asn Tyr
1265                1270                1275                1280

Thr Asp Ala Ser Pro Asn Asn Arg Asn Glu Tyr Asp Ser Ala Val Thr
                1285                1290                1295

Ala Ala Lys Ala Ile Ile Asn Gln Thr Ser Asn Pro Thr Met Glu Pro
            1300                1305                1310

Asn Thr Ile Thr Gln Ala Thr Ser Gln Val Thr Thr Lys Glu His Ala
        1315                1320                1325

Leu Asn Gly Ala Gln Asn Leu Ala Gln Ala Lys Thr Thr Ala Lys Asn
    1330                1335                1340

Asn Leu Asn Asn Leu Thr Ser Ile Asn Asn Ala Gln Lys Asp Ala Leu
1345                1350                1355                1360

Thr Arg Asn Ile Asp Gly Ala Thr Thr Val Ala Gly Val Asn Gln Glu
                1365                1370                1375

Thr Ala Lys Ala Thr Glu Leu Asn Asn Ala Met His Ser Leu Gln Asn
            1380                1385                1390

Gly Ile Asn Asp Glu Thr Gln Thr Lys Gln Thr Gln Lys Tyr Leu Asp
        1395                1400                1405

Ala Glu Pro Ser Lys Lys Ser Ala Tyr Asp Gln Ala Val Asn Ala Ala
    1410                1415                1420

Lys Ala Ile Leu Thr Lys Ala Ser Gly Gln Asn Val Asp Lys Ala Ala
1425                1430                1435                1440

Val Glu Gln Ala Leu Gln Asn Val Asn Ser Thr Lys Thr Ala Leu Asn
                1445                1450                1455

Gly Asp Ala Lys Leu Asn Glu Ala Lys Ala Ala Ala Lys Gln Thr Leu
            1460                1465                1470

Gly Thr Leu Thr His Ile Asn Asn Ala Gln Arg Asn Ala Leu Asp Asn
        1475                1480                1485

Glu Ile Thr Gln Ala Thr Asn Val Glu Gly Val Asn Thr Val Lys Ala
    1490                1495                1500

Lys Ala Gln Gln Leu Asp Gly Ala Met Gly Gln Leu Glu Thr Ser Ile
1505                1510                1515                1520

Arg Asp Lys Asp Thr Thr Leu Gln Ser Gln Asn Tyr Gln Asp Ala Asp
                1525                1530                1535

Asp Ala Lys Arg Thr Ala Tyr Ser Gln Ala Val Asn Ala Ala Ala Thr
            1540                1545                1550
```

-continued

```
Ile Leu Asn Lys Thr Ala Gly Gly Asn Thr Pro Lys Ala Asp Val Glu
        1555                1560                1565

Arg Ala Met Gln Ala Val Thr Gln Ala Asn Thr Ala Leu Asn Gly Ile
    1570                1575                1580

Gln Asn Leu Glu Arg Ala Lys Gln Ala Ala Asn Thr Ala Ile Thr Asn
1585                1590                1595                1600

Ala Ser Asp Leu Asn Thr Lys Gln Lys Glu Ala Leu Lys Ala Gln Val
                1605                1610                1615

Thr Ser Ala Gly Arg Val Ser Ala Ala Asn Gly Val Glu His Thr Ala
            1620                1625                1630

Thr Glu Leu Asn Thr Ala Met Thr Ala Leu Lys Arg Ala Ile Ala Asp
        1635                1640                1645

Lys Ala Asp Thr Lys Ala Ser Gly Asn Tyr Val Asn Ala Asp Ala Asn
    1650                1655                1660

Lys Arg Gln Ala Tyr Asp Glu Lys Val Thr Ala Ala Glu His Ile Val
1665                1670                1675                1680

Ser Gly Thr Pro Thr Pro Thr Leu Thr Pro Ser Asp Val Thr Asn Ala
                1685                1690                1695

Ala Thr Gln Val Thr Asn Ala Lys Thr Gln Leu Asn Gly Asn His Asn
            1700                1705                1710

Leu Glu Val Ala Lys Gln Asn Ala Asn Thr Ala Ile Asp Gly Leu Thr
        1715                1720                1725

Ser Leu Asn Gly Pro Gln Lys Ala Lys Leu Lys Glu Gln Val Gly Gln
    1730                1735                1740

Ala Thr Thr Leu Pro Asn Val Gln Thr Val Arg Asp Asn Ala Gln Thr
1745                1750                1755                1760

Leu Asn Thr Ala Met Lys Gly Leu Arg Asp Ser Ile Ala Asn Glu Ala
                1765                1770                1775

Thr Ile Lys Ala Gly Gln Asn Tyr Thr Asp Ala Ser Gln Asn Lys Gln
            1780                1785                1790

Asn Asp Tyr Asn Asn Ala Val Thr Ala Ala Lys Ala Ile Ile Gly Gln
        1795                1800                1805

Thr Thr Ser Pro Ser Met Ile Ala Gln Glu Ile Asn Gln Ala Lys Asp
    1810                1815                1820

Gln Val Thr Ala Lys Gln Gln Ala Leu Asn Gly Gln Glu Asn Leu Arg
1825                1830                1835                1840

Thr Ala Gln Thr Asn Ala Lys Gln His Leu Asn Gly Leu Ser Asp Leu
                1845                1850                1855

Thr Asn Ala Gln Lys Asp Ala Ala Lys Arg Gln Ile Glu Gly Ala Thr
            1860                1865                1870

His Val Asn Glu Val Thr Gln Ala Gln Asn Asn Ala Asp Ala Leu Asn
        1875                1880                1885

Thr Ala Met Thr Asn Leu Lys Asn Gly Ile Gln Asp Gln Asn Thr Ile
    1890                1895                1900

Lys Gln Gly Val Asn Phe Thr Asp Ala Asp Glu Ala Lys Arg Asn Ala
1905                1910                1915                1920

Tyr Thr Asn Ala Val Thr Gln Ala Glu Gln Ile Leu Asn Lys Ala Gln
                1925                1930                1935

Gly Pro Asn Thr Ala Lys Asp Gly Val Glu Thr Ala Leu Gln Asn Val
            1940                1945                1950

Gln Arg Ala Lys Asn Glu Leu Asn Gly Asn Gln Asn Val Ala Asn Ala
        1955                1960                1965

Lys Thr Thr Ala Lys Asn Ala Leu Asn Asn Leu Thr Ser Ile Asn Asn
```

-continued

```
    1970                1975                1980

Ala Gln Lys Ala Ala Leu Lys Ser Gln Ile Glu Gly Ala Thr Thr Val
1985                1990                1995                2000

Ala Gly Val Asn Gln Val Ser Thr Met Ala Ser Glu Leu Asn Thr Ala
                2005                2010                2015

Met Ser Asn Leu Gln Arg Gly Ile Asn Asp Glu Ala Ala Thr Lys Ala
            2020                2025                2030

Ala Gln Lys Tyr Thr Glu Ala Asp Arg Asp Lys Gln Thr Ala Tyr Asn
        2035                2040                2045

Asp Ala Val Thr Ala Ala Lys Thr Leu Leu Asp Lys Thr Ala Gly Ser
    2050                2055                2060

Asn Asp Asn Lys Val Ala Val Glu Gln Ala Leu Gln Arg Val Asn Thr
2065                2070                2075                2080

Ala Lys Thr Ala Leu Asn Gly Asp Ala Arg Leu Asn Glu Ala Lys Asn
                2085                2090                2095

Thr Ala Lys Gln Gln Leu Ala Thr Met Ser His Leu Thr Asn Ala Gln
            2100                2105                2110

Lys Ala Asn Leu Thr Glu Gln Ile Glu Arg Gly Thr Thr Val Ala Gly
        2115                2120                2125

Val Gln Gly Ile Gln Ala Asn Ala Gly Thr Leu Asn Gln Ala Met Asn
    2130                2135                2140

Gln Leu Arg Gln Ser Ile Ala Ser Lys Asp Ala Thr Lys Ser Ser Glu
2145                2150                2155                2160

Asp Tyr Gln Asp Ala Asn Ala Asp Leu Gln Asn Ala Tyr Asn Asp Ala
                2165                2170                2175

Val Thr Asn Ala Glu Gly Ile Ile Ser Ala Thr Asn Asn Pro Glu Met
            2180                2185                2190

Asn Pro Asp Thr Ile Asn Gln Lys Ala Ser Gln Val Asn Ser Ala Lys
        2195                2200                2205

Ser Ala Leu Asn Gly Asp Glu Lys Leu Ala Ala Val Lys Gln Thr Ala
    2210                2215                2220

Lys Ser Asp Ile Gly Arg Leu Thr Asp Leu Asn Asn Ala Gln Arg Thr
2225                2230                2235                2240

Ala Ala Asn Ala Glu Val Asp Gln Ala Pro Asn Leu Ala Ala Val Thr
                2245                2250                2255

Ala Ala Lys Asn Lys Ala Thr Ser Leu Asn Thr Ala Met Gly Asn Leu
            2260                2265                2270

Lys His Ala Leu Ala Glu Lys Asp Asn Thr Lys Arg Ser Val Asn Tyr
        2275                2280                2285

Thr Asp Ala Asp Gln Pro Lys Gln Gln Ala Tyr Asp Thr Ala Val Thr
    2290                2295                2300

Gln Ala Glu Ala Ile Thr Asn Ala Asn Gly Ser Asn Ala Asn Glu Thr
2305                2310                2315                2320

Gln Val Gln Ala Ala Leu Asn Gln Leu Asn Gln Ala Lys Asn Asp Leu
                2325                2330                2335

Asn Gly Asp Asn Lys Val Ala Gln Ala Lys Glu Thr Ala Lys Arg Ala
            2340                2345                2350

Leu Ala Ser Tyr Ser Asn Leu Asn Asn Ala Gln Ser Thr Ala Ala Thr
        2355                2360                2365

Ser Gln Ile Asp Asn Ala Thr Thr Val Ala Asp Val Thr Ala Ala Gln
    2370                2375                2380

Asn Thr Ala Asn Glu Leu Asn Thr Ala Met Gly Gln Leu Gln Asn Gly
2385                2390                2395                2400
```

-continued

```
Ile Asn Asp Gln Asn Thr Val Lys Gln Gln Val Asn Phe Thr Asp Ala
                2405                2410                2415

Asp Gln Gly Lys Lys Asp Ala Tyr Thr Asn Ala Val Thr Asn Ala Gln
            2420                2425                2430

Gly Ile Leu Asp Lys Ala Asn Gly Gln Asn Met Thr Lys Ala Gln Val
        2435                2440                2445

Glu Ala Ala Leu Asn Gln Val Thr Thr Ala Lys Asn Ala Leu Asn Gly
    2450                2455                2460

Asp Ala Asn Val Arg Gln Ala Lys Ser Asp Ala Lys Ala Asn Leu Gly
2465                2470                2475                2480

Thr Leu Thr His Leu Asn Asn Ala Gln Lys Gln Asp Leu Thr Ser Gln
                2485                2490                2495

Ile Glu Gly Ala Thr Thr Val Asn Gly Val Asn Ser Val Lys Thr Lys
            2500                2505                2510

Ala Gln Asp Leu Asp Gly Ala Met Gln Arg Leu Glu Ser Ala Ile Ala
        2515                2520                2525

Asn Lys Asp Gln Thr Lys Ala Ser Glu Asn Tyr Ile Asp Ala Asp Pro
    2530                2535                2540

Thr Lys Lys Thr Ala Phe Asp Asn Ala Ile Thr Gln Ala Glu Ser Tyr
2545                2550                2555                2560

Leu Asn Lys Asp His Gly Thr Asn Lys Asp Lys Gln Ala Val Glu Gln
                2565                2570                2575

Ala Ile Gln Ser Val Thr Ser Thr Glu Asn Ala Leu Asn Gly Asp Ala
            2580                2585                2590

Asn Leu Gln Cys Ala Lys Thr Glu Ala Thr Gln Ala Ile Asp Asn Leu
        2595                2600                2605

Thr Gln Leu Asn Thr Pro Gln Lys Thr Ala Leu Lys Gln Gln Val Asn
    2610                2615                2620

Ala Ala Gln Arg Val Ser Gly Val Thr Asp Leu Lys Asn Ser Ala Thr
2625                2630                2635                2640

Ser Leu Asn Asn Ala Met Asp Gln Leu Lys Gln Ala Ile Gly Asp His
                2645                2650                2655

Asp Thr Ile Val Ala Gly Gly Asn Tyr Thr Asn Ala Ser Pro Asp Lys
            2660                2665                2670

Gln Gly Ala Tyr Thr Asp Ala Tyr Asn Ala Ala Lys Asn Ile Val Asn
        2675                2680                2685

Gly Ser Pro Asn Val Ile Thr Asn Ala Ala Asp Val Thr Ala Ala Thr
    2690                2695                2700

Gln Arg Val Asn Asn Ala Glu Thr Ser Leu Asn Gly Asp Thr Asn Leu
2705                2710                2715                2720

Ala Thr Ala Lys Gln Gln Ala Lys Asp Ala Leu Arg Gln Met Thr His
                2725                2730                2735

Leu Ser Asp Ala Gln Lys Gln Ser Ile Thr Gly Gln Ile Asp Ser Ala
            2740                2745                2750

Thr Gln Val Thr Gly Val Gln Ser Val Lys Asp Asn Ala Thr Asn Leu
        2755                2760                2765

Asp Asn Ala Met Asn Gln Leu Arg Asn Ser Ile Ala Asn Lys Asp Glu
    2770                2775                2780

Val Lys Ala Ser Gln Pro Tyr Val Asp Ala Asp Thr Asp Lys Gln Asn
2785                2790                2795                2800

Ala Tyr Asn Thr Ala Val Thr Ser Ala Glu Asn Ile Ile Asn Ala Thr
                2805                2810                2815
```

-continued

```
Ser Gln Pro Thr Leu Asp Pro Ser Ala Val Thr Gln Ala Ala Asn Gln
            2820                2825                2830

Val Asn Thr Asn Lys Thr Ala Leu Asn Gly Ala Gln Asn Leu Ala Asn
        2835                2840                2845

Lys Lys Gln Glu Thr Thr Ala Asn Ile Asn Arg Leu Ser His Leu Asn
    2850                2855                2860

Asn Ala Gln Lys Gln Asp Leu Asn Thr Gln Val Thr Asn Ala Pro Asn
2865                2870                2875                2880

Ile Ser Thr Val Asn Gln Val Lys Thr Lys Ala Glu Gln Leu Asp Gln
                2885                2890                2895

Ala Met Glu Arg Leu Ile Asn Gly Ile Gln Asp Lys Asp Gln Val Lys
            2900                2905                2910

Gln Ser Val Asn Phe Thr Asp Ala Asp Pro Glu Lys Gln Thr Ala Tyr
        2915                2920                2925

Asn Asn Ala Val Thr Ala Ala Glu Asn Ile Ile Asn Gln Ala Asn Gly
    2930                2935                2940

Thr Asn Ala Asn Gln Ser Gln Val Glu Ala Ala Leu Ser Thr Val Thr
2945                2950                2955                2960

Thr Thr Lys Gln Ala Leu Asn Gly Asp Arg Lys Val Thr Asp Ala Lys
                2965                2970                2975

Asn Asn Ala Asn Gln Thr Leu Ser Thr Leu Asp Asn Leu Asn Asn Ala
            2980                2985                2990

Gln Lys Gly Ala Val Thr Gly Asn Ile Asn Gln Ala His Thr Val Ala
        2995                3000                3005

Glu Val Thr Gln Ala Ile Gln Thr Ala Gln Glu Leu Asn Thr Ala Met
    3010                3015                3020

Gly Asn Leu Lys Asn Ser Leu Asn Asp Lys Asp Thr Thr Leu Gly Ser
3025                3030                3035                3040

Gln Asn Phe Ala Asp Ala Asp Pro Glu Lys Lys Asn Ala Tyr Asn Glu
                3045                3050                3055

Ala Val Arg Asn Ala Glu Asn Ile Leu Asn Lys Ser Thr Gly Thr Asn
            3060                3065                3070

Val Pro Lys Asp Gln Val Glu Ala Ala Met Asn Gln Val Asn Thr Thr
        3075                3080                3085

Lys Ala Ala Leu Asn Gly Thr Gln Asn Leu Glu Lys Ala Lys Gln His
    3090                3095                3100

Ala Asn Thr Ala Ile Asp Gly Leu Ser His Leu Thr Asn Ala Gln Lys
3105                3110                3115                3120

Glu Ala Leu Lys Gln Leu Val Gln Gln Ser Thr Thr Val Ala Glu Ala
                3125                3130                3135

Gln Gly Asn Glu Gln Lys Ala Asn Asn Val Asp Ala Ala Met Asp Lys
            3140                3145                3150

Leu Arg Gln Ser Ile Ala Asp Asn Ala Thr Thr Lys Gln Asn Gln Asn
        3155                3160                3165

Tyr Thr Asp Ala Ser Pro Asn Lys Lys Asp Ala Tyr Asn Asn Ala Val
    3170                3175                3180

Thr Thr Ala Gln Gly Ile Ile Asp Gln Thr Thr Asn Pro Ser Leu Asp
3185                3190                3195                3200

Pro Thr Val Ile Asn Gln Ala Ala Gly Gln Val Ser Thr Ser Lys Asn
                3205                3210                3215

Ala Leu Asn Gly Asn Glu Asn Leu Glu Ala Ala Lys Gln Gln Ala Thr
            3220                3225                3230

Gln Ser Leu Gly Ser Leu Asp Asn Leu Asn Asn Ala Gln Lys Gln Ala
```

-continued

```
        3235                3240                3245

Val Thr Asn Gln Ile Asn Gly Ala His Thr Val Asp Glu Ala Asn Gln
    3250                3255                3260

Ile Lys Gln Asn Ala Gln Asn Leu Asn Thr Ala Met Gly Asn Leu Lys
3265                3270                3275                3280

Gln Ala Ile Ala Asp Lys Asp Ala Thr Lys Ala Thr Val Asn Phe Thr
                3285                3290                3295

Asp Ala Asp Gln Ala Lys Gln Gln Ala Tyr Asn Thr Ala Val Thr Asn
            3300                3305                3310

Ala Glu Asn Ile Ile Ser Lys Ala Asn Gly Gly Asn Ala Thr Gln Thr
        3315                3320                3325

Glu Val Glu Gln Ala Ile Gln Gln Val Asn Ala Ala Lys Gln Ala Leu
    3330                3335                3340

Asn Gly Asn Ala Asn Val Gln His Ala Lys Asp Glu Ala Thr Ala Leu
3345                3350                3355                3360

Ile Asn Asn Ser Asn Asp Leu Asn Gln Ala Gln Lys Asp Ala Leu Lys
                3365                3370                3375

Gln Gln Val Gln Asn Ala Thr Thr Val Ala Gly Val Asn Asn Val Lys
            3380                3385                3390

Gln Thr Ala Gln Glu Leu Asn Asn Ala Met Thr Gln Leu Lys Gln Gly
        3395                3400                3405

Ile Ala Asp Lys Glu Gln Thr Lys Ala Asp Gly Asn Phe Val Asn Ala
    3410                3415                3420

Asp Ser Asp Lys Gln Asn Ala Tyr Asn Gln Ala Val Ala Lys Ala Glu
3425                3430                3435                3440

Ala Leu Ile Ser Gly Thr Pro Asp Val Val Val Thr Pro Ser Glu Ile
                3445                3450                3455

Thr Ala Ala Leu Asn Lys Val Thr Gln Ala Lys Asn Asp Leu Asn Gly
            3460                3465                3470

Asn Thr Asn Leu Ala Thr Ala Lys Gln Asn Val Gln His Ala Ile Asp
        3475                3480                3485

Gln Leu Pro Asn Leu Asn Gln Ala Gln Arg Asp Glu Tyr Ser Lys Gln
    3490                3495                3500

Ile Thr Gln Ala Thr Leu Val Pro Asn Val Asn Ala Ile Gln Gln Ala
3505                3510                3515                3520

Ala Thr Thr Leu Asn Asp Ala Met Thr Gln Leu Lys Gln Gly Ile Ala
                3525                3530                3535

Asn Lys Ala Gln Ile Lys Gly Ser Glu Asn Tyr His Asp Ala Asp Thr
            3540                3545                3550

Asp Lys Gln Thr Ala Tyr Asp Asn Ala Val Thr Lys Ala Glu Glu Leu
        3555                3560                3565

Leu Lys Gln Thr Thr Asn Pro Thr Met Asp Pro Asn Thr Ile Gln Gln
    3570                3575                3580

Ala Leu Thr Lys Val Asn Asp Thr Asn Gln Ala Leu Asn Gly Asn Gln
3585                3590                3595                3600

Lys Leu Ala Asp Ala Lys Gln Asp Ala Lys Thr Thr Leu Gly Thr Leu
                3605                3610                3615

Asp His Leu Asn Asp Ala Gln Lys Gln Ala Leu Thr Thr Gln Val Glu
            3620                3625                3630

Gln Ala Pro Asp Ile Ala Thr Val Asn Asn Val Lys Gln Asn Ala Gln
        3635                3640                3645

Asn Leu Asn Asn Ala Met Thr Asn Leu Asn Asn Ala Leu Gln Asp Lys
    3650                3655                3660
```

Thr Glu Thr Leu Asn Ser Ile Asn Phe Thr Asp Ala Asp Gln Ala Lys
3665 3670 3675 3680

Lys Asp Asp Tyr Thr Asn Ala Val Ser His Ala Glu Gly Ile Leu Ser
3685 3690 3695

Lys Ala Asn Gly Ser Asn Ala Ser Gln Thr Glu Val Glu Gln Ala Met
3700 3705 3710

Gln Arg Val Asn Glu Ala Lys Gln Ala Leu Asn Gly Asn Asp Asn Val
3715 3720 3725

Gln Arg Ala Lys Asp Ala Ala Lys Gln Val Ile Thr Asn Ala Asn Asp
3730 3735 3740

Leu Asn Gln Ala Gln Lys Asp Ala Leu Lys Gln Gln Val Asp Ala Ala
3745 3750 3755 3760

Gln Thr Val Ala Asn Val Asn Thr Ile Lys Gln Thr Ala Gln Asp Leu
3765 3770 3775

Asn Gln Ala Met Thr Gln Leu Lys Gln Gly Ile Ala Asp Lys Asp Gln
3780 3785 3790

Thr Lys Ala Asn Gly Asn Phe Val Asn Ala Asp Thr Asp Lys Gln Asn
3795 3800 3805

Ala Tyr Asn Asn Ala Val Ala His Ala Glu Gln Ile Ile Ser Gly Thr
3810 3815 3820

Pro Asn Ala Asn Val Asp Pro Gln Gln Val Ala Gln Ala Leu Gln Gln
3825 3830 3835 3840

Val Asn Gln Ala Lys Gly Asp Leu Asn Gly Asn His Asn Leu Gln Val
3845 3850 3855

Ala Lys Asp Asn Ala Asn Thr Ala Ile Asp Gln Leu Pro Asn Leu Asn
3860 3865 3870

Gln Pro Gln Lys Thr Ala Leu Lys Asp Gln Val Ser His Ala Glu Leu
3875 3880 3885

Val Thr Gly Val Asn Ala Ile Lys Gln Asn Ala Asp Ala Leu Asn Asn
3890 3895 3900

Ala Met Gly Thr Leu Lys Gln Gln Ile Gln Ala Asn Ser Gln Val Pro
3905 3910 3915 3920

Gln Ser Val Asp Phe Thr Gln Ala Asp Gln Asp Lys Gln Gln Ala Tyr
3925 3930 3935

Asn Asn Ala Ala Asn Gln Ala Gln Gln Ile Ala Asn Gly Thr Pro Thr
3940 3945 3950

Pro Val Leu Ala Pro Asp Thr Val Thr Lys Ala Val Thr Thr Met Asn
3955 3960 3965

Gln Ala Lys Asp Ala Leu Asn Gly Asp Glu Lys Leu Ala Gln Ala Lys
3970 3975 3980

Gln Asp Ala Leu Ala Asn Leu Asp Thr Leu Arg Asp Leu Asn Gln Pro
3985 3990 3995 4000

Gln Arg Asp Ala Leu Arg Asn Gln Ile Asn Gln Ala Gln Ala Leu Ala
4005 4010 4015

Thr Val Glu Gln Thr Lys Gln Asn Ala Gln Asn Val Asn Thr Ala Met
4020 4025 4030

Gly Asn Leu Lys Gln Gly Ile Ala Asn Lys Asp Thr Val Lys Ala Ser
4035 4040 4045

Glu Asn Tyr His Asp Ala Asp Val Asp Lys Gln Thr Ala Tyr Thr Asn
4050 4055 4060

Ala Val Ser Gln Ala Glu Gly Ile Ile Asn Gln Thr Thr Asn Pro Thr
4065 4070 4075 4080

-continued

```
Leu Asn Pro Asp Asp Ile Thr Arg Ala Leu Thr Gln Val Thr Asp Ala
                4085                4090                4095

Lys Asn Ser Leu Asn Gly Glu Ala Lys Leu Ala Thr Glu Lys Gln Asn
            4100                4105                4110

Ala Lys Asp Ala Val Ser Gly Met Thr His Leu Asn Asp Ala Gln Lys
        4115                4120                4125

Gln Ala Leu Lys Gly Gln Ile Asp Gln Ser Pro Glu Ile Ala Thr Val
    4130                4135                4140

Asn Gln Val Lys Gln Thr Ala Thr Ser Leu Asp Gln Ala Met Asp Gln
4145                4150                4155                4160

Leu Ser Gln Ala Ile Asn Asp Lys Asp Gln Ile Leu Ala Asp Gly Asn
                4165                4170                4175

Tyr Leu Asn Ala Asp Pro Asp Lys Gln Asn Ala Tyr Lys Gln Ala Val
            4180                4185                4190

Ala Lys Ala Glu Ala Leu Leu Asn Lys Gln Ser Gly Thr Asn Glu Val
        4195                4200                4205

Gln Ala Gln Val Glu Ser Ile Thr Asn Glu Val Asn Ala Ala Lys Gln
    4210                4215                4220

Ala Leu Asn Gly Asn Asp Asn Leu Ala Asn Ala Lys Gln Gln Ala Lys
4225                4230                4235                4240

Gln Gln Leu Ala Asn Leu Thr His Leu Asn Asp Ala Gln Lys Gln Ser
                4245                4250                4255

Phe Glu Ser Gln Ile Thr Gln Ala Pro Leu Val Thr Asp Val Thr Thr
            4260                4265                4270

Ile Asn Gln Lys Ala Gln Thr Leu Asp His Ala Met Glu Leu Leu Arg
        4275                4280                4285

Asn Ser Val Ala Asp Asn Gln Thr Thr Leu Ala Ser Glu Asp Tyr His
    4290                4295                4300

Asp Ala Thr Ala Gln Arg Gln Asn Asp Tyr Asn Lys Ala Val Thr Ala
4305                4310                4315                4320

Ala Asn Asn Ile Ile Asn Gln Thr Thr Ser Pro Thr Met Asn Pro Asp
                4325                4330                4335

Asp Val Asn Gly Ala Thr Thr Gln Val Asn Asn Thr Lys Val Ala Leu
            4340                4345                4350

Asp Gly Asp Glu Asn Leu Ala Ala Ala Lys Gln Gln Ala Asn Asn Arg
        4355                4360                4365

Leu Asp Gln Leu Asp His Leu Asn Asn Ala Gln Lys Gln Gln Leu Gln
    4370                4375                4380

Ser Gln Ile Thr Gln Ser Ser Asp Ile Ala Ala Val Asn Gly His Lys
4385                4390                4395                4400

Gln Thr Ala Glu Ser Leu Asn Thr Ala Met Gly Asn Leu Ile Asn Ala
                4405                4410                4415

Ile Ala Asp His Gln Ala Val Glu Gln Arg Gly Asn Phe Ile Asn Ala
            4420                4425                4430

Asp Thr Asp Lys Gln Thr Ala Tyr Asn Thr Ala Val Asn Glu Ala Ala
        4435                4440                4445

Ala Met Ile Asn Lys Gln Thr Gly Gln Asn Ala Asn Gln Thr Glu Val
    4450                4455                4460

Glu Gln Ala Ile Thr Lys Val Gln Thr Thr Leu Gln Ala Leu Asn Gly
4465                4470                4475                4480

Asp His Asn Leu Gln Val Ala Lys Thr Asn Ala Thr Gln Ala Ile Asp
                4485                4490                4495

Val Leu Thr Ser Leu Asn Asp Pro Gln Lys Thr Ala Leu Lys Asp Gln
```

```
            4500                4505                4510

Val Thr Ala Ala Thr Leu Val Thr Ala Val His Gln Ile Glu Gln Asn
        4515                4520                4525

Ala Asn Thr Leu Asn Gln Ala Met His Gly Leu Arg Gln Ser Ile Gln
    4530                4535                4540

Asp Asn Ala Ala Thr Lys Ala Asn Ser Lys Tyr Ile Asn Glu Asp Gln
4545                4550                4555                4560

Pro Glu Gln Gln Asn Tyr Asp Gln Ala Val Gln Ala Ala Asn Asn Ile
                4565                4570                4575

Ile Asn Glu Gln Thr Ala Thr Leu Asp Asn Asn Ala Ile Asn Gln Val
            4580                4585                4590

Ala Ala Thr Val Asn Thr Thr Lys Ala Ala Leu His Gly Asp Val Lys
        4595                4600                4605

Leu Gln Asn Asp Lys Asp His Ala Lys Gln Thr Val Ser Gln Leu Ala
    4610                4615                4620

His Leu Asn Asn Ala Gln Lys His Met Glu Asp Thr Leu Ile Asp Ser
4625                4630                4635                4640

Glu Thr Thr Arg Thr Ala Val Lys Gln Asp Leu Thr Glu Val Gln Ala
                4645                4650                4655

Leu Asp Gln Leu Met Asp Ala Leu Gln Gln Ser Ile Ala Asp Lys Asp
            4660                4665                4670

Ala Thr Arg Ala Ser Ser Ala Tyr Val Asn Ala Glu Pro Asn Lys Lys
        4675                4680                4685

Gln Ala Tyr Asp Glu Ala Val Gln Asn Ala Glu Ser Ile Ile Ala Gly
    4690                4695                4700

Leu Asn Asn Pro Thr Ile Asn Lys Gly Asn Val Ser Ser Ala Thr Gln
4705                4710                4715                4720

Ala Val Ile Ser Ser Lys Asn Ala Leu Asp Gly Val Glu Arg Leu Ala
                4725                4730                4735

Gln Asp Lys Gln Thr Ala Gly Asn Ser Leu Asn His Leu Asp Gln Leu
            4740                4745                4750

Thr Pro Ala Gln Gln Gln Ala Leu Glu Asn Gln Ile Asn Asn Ala Thr
        4755                4760                4765

Thr Cys Asp Lys Val Ala Glu Ile Ile Ala Gln Ala Gln Ala Leu Asn
    4770                4775                4780

Glu Ala Met Lys Ala Leu Lys Glu Ser Ile Lys Asp Gln Pro Gln Thr
4785                4790                4795                4800

Glu Ala Ser Ser Lys Phe Ile Asn Glu Asp Gln Ala Gln Lys Asp Ala
                4805                4810                4815

Tyr Thr Gln Ala Val Gln His Ala Lys Asp Leu Ile Asn Lys Thr Thr
            4820                4825                4830

Asp Pro Thr Leu Ala Lys Ser Ile Ile Asp Gln Ala Thr Gln Ala Val
        4835                4840                4845

Thr Asp Ala Lys Asn Asn Leu His Gly Asp Gln Lys Leu Ala Gln Asp
    4850                4855                4860

Lys Gln Arg Ala Thr Glu Thr Leu Asn Asn Leu Ser Asn Leu Asn Thr
4865                4870                4875                4880

Pro Gln Arg Gln Ala Leu Glu Asn Gln Ile Asn Asn Ala Ala Thr Arg
                4885                4890                4895

Gly Glu Val Ala Gln Lys Leu Thr Glu Ala Gln Ala Leu Asn Gln Ala
            4900                4905                4910

Met Glu Ala Leu Arg Asn Ser Ile Gln Asp Gln Gln Gln Thr Glu Ser
        4915                4920                4925
```

-continued

```
Gly Ser Lys Phe Ile Asn Glu Asp Lys Pro Gln Lys Asp Ala Tyr Gln
    4930                4935                4940

Ala Ala Val Gln Asn Ala Lys Asp Leu Ile Asn Gln Thr Gly Asn Pro
4945                4950                4955                4960

Thr Leu Asp Lys Ala Gln Val Glu Gln Leu Thr His Ala Phe Lys Gln
                4965                4970                4975

Ala Lys Asp Asn Leu His Gly Asp Gln Lys Leu Ala Asp Asp Lys Gln
            4980                4985                4990

His Ala Val Thr Asp Leu Asn Gln Leu Asn Gly Leu Asn Asn Pro Gln
        4995                5000                5005

Arg Gln Ala Leu Glu Ser Gln Ile Asn Asn Ala Ala Thr Arg Gly Glu
    5010                5015                5020

Val Ala Gln Lys Leu Ala Glu Ala Lys Ala Leu Asp Gln Ala Met Gln
5025                5030                5035                5040

Ala Leu Arg Asn Ser Ile Gln Asp Gln Gln Gln Thr Glu Ala Gly Ser
                5045                5050                5055

Lys Phe Ile Asn Glu Asp Lys Pro Gln Lys Asp Ala Tyr Gln Ala Ala
            5060                5065                5070

Val Gln Asn Ala Lys Asp Leu Ile Asn Gln Thr Gly Asn Pro Thr Leu
        5075                5080                5085

Asp Lys Ser Gln Val Glu Gln Leu Thr Gln Ala Val Thr Thr Ala Lys
    5090                5095                5100

Asp Asn Leu His Gly Asp Gln Lys Leu Ala Arg Asp Gln Gln Gln Ala
5105                5110                5115                5120

Val Thr Thr Val Asn Ala Leu Pro Asn Leu Asn His Ala Gln Gln Gln
                5125                5130                5135

Thr Leu Thr Asp Ala Ile Asn Ala Ala Pro Thr Arg Thr Glu Val Ala
            5140                5145                5150

Gln His Val Gln Thr Ala Thr Glu Leu Asp His Ala Met Glu Thr Leu
        5155                5160                5165

Lys Asn Lys Val Asp Gln Val Asn Thr Asp Lys Ala Gln Pro Asn Tyr
    5170                5175                5180

Thr Glu Ala Ser Thr Asp Lys Lys Glu Ala Val Asp Gln Ala Leu Gln
5185                5190                5195                5200

Ala Ala Gln Ser Ile Thr Asp Pro Thr Asn Gly Ser Asn Ala Asn Lys
                5205                5210                5215

Asp Ala Val Glu Gln Ala Leu Thr Lys Leu Gln Glu Lys Val Asn Glu
            5220                5225                5230

Leu Asn Gly Asn Glu Arg Val Ala Glu Ala Lys Thr Gln Ala Lys Gln
        5235                5240                5245

Thr Ile Asp Gln Leu Thr His Leu Asn Ala Asp Gln Ile Ala Thr Ala
    5250                5255                5260

Lys Gln Asn Ile Asp Gln Ala Thr Lys Leu Gln Pro Ile Ala Glu Leu
5265                5270                5275                5280

Val Asp Gln Ala Thr Gln Leu Asn Gln Ser Met Asp Gln Leu Gln Gln
                5285                5290                5295

Ala Val Asn Glu His Ala Asn Val Glu Gln Thr Ile Asp Tyr Thr Gln
            5300                5305                5310

Ala Asp Ser Asp Lys Gln Lys Ala Tyr Lys Gln Ala Ile Ala Asp Ala
        5315                5320                5325

Glu Asn Val Leu Lys Gln Asn Ala Asn Lys Gln Gln Val Asp Gln Ala
    5330                5335                5340
```

-continued

```
Leu Gln Asn Ile Leu Asn Ala Lys Gln Ala Leu Asn Gly Asp Glu Arg
5345                5350                5355                5360

Val Ala Leu Ala Lys Thr Asn Gly Lys His Asp Ile Asp Gln Leu Asn
                5365                5370                5375

Ala Leu Asn Asn Ala Gln Gln Asp Gly Phe Lys Gly Arg Ile Asp Gln
            5380                5385                5390

Ser Asn Asp Leu Asn Gln Ile Gln Gln Ile Val Asp Glu Ala Lys Ala
        5395                5400                5405

Leu Asn Arg Ala Met Asp Gln Leu Ser Gln Glu Ile Thr Gly Asn Glu
    5410                5415                5420

Gly Arg Thr Lys Gly Ser Thr Asn Tyr Val Asn Ala Asp Thr Gln Val
5425                5430                5435                5440

Lys Gln Val Tyr Asp Glu Ala Val Asp Lys Ala Lys Gln Ala Leu Asp
                5445                5450                5455

Lys Ser Ser Gly Gln Asn Leu Thr Ala Glu Gln Val Ile Lys Leu Asn
            5460                5465                5470

Asp Ala Val Thr Ala Ala Lys Lys Ala Leu Asn Gly Glu Glu Arg Leu
        5475                5480                5485

Asn Asn Arg Lys Ala Glu Ala Leu Gln Arg Leu Asp Gln Leu Thr His
    5490                5495                5500

Leu Asn Asn Ala Gln Arg Gln Leu Ala Ile Gln Gln Ile Asn Asn Ala
5505                5510                5515                5520

Glu Thr Leu Asn Lys Ala Ser Arg Ala Ile Asn Arg Ala Thr Lys Leu
                5525                5530                5535

Asp Asn Ala Met Gly Ala Val Gln Gln Tyr Ile Asp Glu Gln His Leu
            5540                5545                5550

Gly Val Ile Ser Ser Thr Asn Tyr Ile Asn Ala Asp Asp Asn Leu Lys
        5555                5560                5565

Ala Asn Tyr Asp Asn Ala Ile Ala Asn Ala Ala His Glu Leu Asp Lys
    5570                5575                5580

Val Gln Gly Asn Ala Ile Ala Lys Ala Glu Ala Glu Gln Leu Lys Gln
5585                5590                5595                5600

Asn Ile Ile Asp Ala Gln Asn Ala Leu Asn Gly Asp Gln Asn Leu Ala
                5605                5610                5615

Asn Ala Lys Asp Lys Ala Asn Ala Phe Val Asn Ser Leu Asn Gly Leu
            5620                5625                5630

Asn Gln Gln Gln Gln Asp Leu Ala His Lys Ala Ile Asn Asn Ala Asp
        5635                5640                5645

Thr Val Ser Asp Val Thr Asp Ile Val Asn Asn Gln Ile Asp Leu Asn
    5650                5655                5660

Asp Ala Met Glu Thr Leu Lys His Leu Val Asp Asn Glu Ile Pro Asn
5665                5670                5675                5680

Ala Glu Gln Thr Val Asn Tyr Gln Asn Ala Asp Asp Asn Ala Lys Thr
                5685                5690                5695

Asn Phe Asp Asp Ala Lys Arg Leu Ala Asn Thr Leu Leu Asn Ser Asp
            5700                5705                5710

Asn Thr Asn Val Asn Asp Ile Asn Gly Ala Ile Gln Ala Val Asn Asp
        5715                5720                5725

Ala Ile His Asn Leu Asn Gly Asp Gln Arg Leu Gln Asp Ala Lys Asp
    5730                5735                5740

Lys Ala Ile Gln Ser Ile Asn Gln Ala Leu Ala Asn Lys Leu Lys Glu
5745                5750                5755                5760

Ile Glu Ala Ser Asn Ala Thr Asp Gln Asp Lys Leu Ile Ala Lys Asn
```

```
                5765                5770                5775

Lys Ala Glu Glu Leu Ala Asn Ser Ile Ile Asn Asn Ile Asn Lys Ala
            5780                5785                5790

Thr Ser Asn Gln Ala Val Ser Gln Val Gln Thr Ala Gly Asn His Ala
        5795                5800                5805

Ile Glu Gln Val His Ala Asn Glu Ile Pro Lys Ala Lys Ile Asp Ala
    5810                5815                5820

Asn Lys Asp Val Asp Lys Gln Val Gln Ala Leu Ile Asp Glu Ile Asp
5825                5830                5835                5840

Arg Asn Pro Asn Leu Thr Asp Lys Glu Lys Gln Ala Leu Lys Asp Arg
                5845                5850                5855

Ile Asn Gln Ile Leu Gln Gln Gly His Asn Asp Ile Asn Asn Ala Leu
            5860                5865                5870

Thr Lys Glu Glu Ile Glu Gln Ala Lys Ala Gln Leu Ala Gln Ala Leu
        5875                5880                5885

Gln Asp Ile Lys Asp Leu Val Lys Ala Lys Glu Asp Ala Lys Gln Asp
    5890                5895                5900

Val Asp Lys Gln Val Gln Ala Leu Ile Asp Glu Ile Asp Gln Asn Pro
5905                5910                5915                5920

Asn Leu Thr Asp Lys Glu Lys Gln Ala Leu Lys Asp Arg Ile Asn Gln
                5925                5930                5935

Ile Leu Gln Gln Gly His Asn Gly Ile Asn Asn Ala Met Thr Lys Glu
            5940                5945                5950

Glu Ile Glu Gln Ala Lys Ala Gln Leu Ala Gln Ala Leu Lys Glu Ile
        5955                5960                5965

Lys Asp Leu Val Lys Ala Lys Glu Asn Ala Lys Gln Asp Val Asp Lys
    5970                5975                5980

Gln Val Gln Ala Leu Ile Asp Glu Ile Asp Gln Asn Pro Asn Leu Thr
5985                5990                5995                6000

Asp Lys Glu Lys Gln Ala Leu Lys Asp Arg Ile Asn Gln Ile Leu Gln
                6005                6010                6015

Gln Gly His Asn Asp Ile Asn Asn Ala Met Thr Lys Glu Glu Ile Glu
            6020                6025                6030

Gln Ala Lys Ala Gln Leu Ala Gln Ala Leu Gln Asp Ile Lys Asp Leu
        6035                6040                6045

Val Lys Ala Lys Glu Asp Ala Lys Asn Ala Ile Lys Ala Leu Ala Asn
    6050                6055                6060

Ala Lys Arg Asp Gln Ile Asn Ser Asn Pro Asp Leu Thr Pro Glu Gln
6065                6070                6075                6080

Lys Ala Lys Ala Leu Lys Glu Ile Asp Glu Ala Glu Lys Arg Ala Leu
                6085                6090                6095

Gln Asn Val Glu Asn Ala Gln Thr Ile Asp Gln Leu Asn Arg Gly Leu
            6100                6105                6110

Asn Leu Gly Leu Asp Asp Ile Arg Asn Thr His Val Trp Glu Val Asp
        6115                6120                6125

Glu Gln Pro Ala Val Asn Glu Ile Phe Glu Ala Thr Pro Glu Gln Ile
    6130                6135                6140

Leu Val Asn Gly Glu Leu Ile Val His Arg Asp Asp Ile Ile Thr Glu
6145                6150                6155                6160

Gln Asp Ile Leu Ala His Ile Asn Leu Ile Asp Gln Leu Ser Ala Glu
                6165                6170                6175

Val Ile Asp Thr Pro Ser Thr Ala Thr Ile Ser Asp Ser Leu Thr Ala
            6180                6185                6190
```

```
Lys Val Glu Val Thr Leu Leu Asp Gly Ser Lys Val Ile Val Asn Val
        6195                6200                6205

Pro Val Lys Val Val Glu Lys Glu Leu Ser Val Val Lys Gln Gln Ala
    6210                6215                6220

Ile Glu Ser Ile Glu Asn Ala Ala Gln Gln Lys Ile Asp Glu Ile Asn
6225                6230                6235                6240

Asn Ser Val Thr Leu Thr Leu Glu Gln Lys Glu Ala Ala Ile Ala Glu
                6245                6250                6255

Val Asn Lys Leu Lys Gln Gln Ala Ile Asp His Val Asn Asn Ala Pro
            6260                6265                6270

Asp Val His Ser Val Glu Glu Ile Gln Gln Gln Glu Gln Ala Tyr Ile
        6275                6280                6285

Glu Gln Phe Asn Pro Glu Gln Phe Thr Ile Glu Gln Ala Lys Ser Asn
    6290                6295                6300

Ala Ile Lys Ser Ile Glu Asp Ala Ile Gln His Met Ile Asp Glu Ile
6305                6310                6315                6320

Lys Ala Arg Thr Asp Leu Thr Asp Lys Glu Lys Gln Glu Ala Ile Ala
                6325                6330                6335

Lys Leu Asn Gln Leu Lys Glu Gln Ala Ile Gln Ala Ile Gln Arg Ala
            6340                6345                6350

Gln Ser Ile Ser Glu Ile Thr Glu Gln Leu Glu Gln Phe Lys Ala Gln
        6355                6360                6365

Met Lys Ala Ala Asn Pro Thr Ala Lys Glu Leu Ala Lys Arg Lys Gln
    6370                6375                6380

Glu Ala Ile Ser Arg Ile Lys Asp Phe Ser Asn Glu Lys Ile Asn Ser
6385                6390                6395                6400

Ile Arg Asn Ser Glu Ile Gly Thr Ala Asp Glu Lys Gln Ala Ala Met
                6405                6410                6415

Asn Gln Ile Asn Glu Ile Val Leu Glu Thr Ile Arg Asp Ile Asn Asn
            6420                6425                6430

Ala His Thr Leu Gln Gln Val Glu Ala Ala Leu Asn Asn Gly Ile Ala
        6435                6440                6445

Arg Ile Ser Ala Val Gln Ile Val Ile Ser Asp Arg Ala Lys Gln Ser
    6450                6455                6460

Ser Ser Thr Gly Asn Glu Ser Asn Ser His Leu Thr Ile Gly Tyr Gly
6465                6470                6475                6480

Thr Ala Asn His Pro Phe Asn Ser Ser Thr Ile Gly His Lys Lys Lys
                6485                6490                6495

Leu Asp Glu Asp Asp Asp Ile Asp Pro Leu His Met Arg His Phe Ser
            6500                6505                6510

Asn Asn Phe Gly Asn Val Ile Lys Asn Ala Ile Gly Val Val Gly Ile
        6515                6520                6525

Ser Gly Leu Leu Ala Ser Phe Trp Phe Phe Ile Ala Lys Arg Arg Arg
    6530                6535                6540

Lys Glu Asp Glu Glu Glu Glu Leu Glu Ile Arg Asp Asn Asn Lys Asp
6545                6550                6555                6560

Ser Ile Lys Glu Thr Leu Asp Asp Thr Lys His Leu Pro Leu Leu Phe
                6565                6570                6575

Ala Lys Arg Arg Arg Lys Glu Asp Glu Glu Asp Val Thr Val Glu Glu
            6580                6585                6590

Lys Asp Ser Leu Asn Asn Gly Glu Ser Leu Asp Lys Val Lys His Thr
        6595                6600                6605
```

```
Pro Phe Phe Leu Pro Lys Arg Arg Arg Lys Glu Asp Glu Glu Asp Val
    6610                6615                6620

Glu Val Thr Asn Glu Asn Thr Asp Glu Lys Val Leu Lys Asp Asn Glu
6625                6630                6635                6640

His Ser Pro Leu Leu Phe Ala Lys Arg Arg Lys Asp Lys Glu Glu Asp
                6645                6650                6655

Val Glu Thr Thr Thr Ser Ile Glu Ser Lys Asp Glu Asp Val Pro Leu
            6660                6665                6670

Leu Leu Ala Lys Lys Lys Asn Gln Lys Asp Asn Gln Ser Lys Asp Lys
        6675                6680                6685

Lys Ser Ala Ser Lys Asn Thr Ser Lys Lys Val Ala Ala Lys Lys Lys
    6690                6695                6700

Lys Lys Lys Ser Lys Lys Asn Lys Lys
6705                6710


<210> SEQ ID NO 14
<211> LENGTH: 701
<212> TYPE: PRT
<213> ORGANISM: Staphylococcus sp.

<400> SEQUENCE: 14

Met Asn Asn Arg Asp Lys Leu Gln Lys Phe Ser Ile Arg Lys Tyr Ala
1               5                   10                  15

Ile Gly Thr Phe Ser Thr Val Ile Ala Thr Leu Val Phe Met Gly Ile
            20                  25                  30

Asn Thr Asn His Ala Ser Ala Asp Glu Leu Asn Gln Asn Gln Lys Leu
        35                  40                  45

Ile Lys Gln Leu Asn Gln Thr Asp Asp Asp Asp Ser Asn Thr His Ser
    50                  55                  60

Gln Glu Ile Glu Asn Asn Lys Gln Asn Ser Ser Gly Gln Thr Glu Ser
65                  70                  75                  80

Leu Arg Ser Ser Thr Ser Gln Asn Gln Ala Asn Ala Arg Leu Ser Asp
                85                  90                  95

Gln Phe Lys Asp Thr Asn Glu Thr Ser Gln Gln Leu Pro Thr Asn Val
            100                 105                 110

Ser Asp Asp Ser Ile Asn Gln Ser His Ser Glu Ala Asn Met Asn Asn
        115                 120                 125

Glu Pro Leu Lys Val Asp Asn Ser Thr Met Gln Ala His Ser Lys Ile
    130                 135                 140

Val Ser Asp Ser Asp Gly Asn Ala Ser Glu Asn Lys His His Lys Leu
145                 150                 155                 160

Thr Glu Asn Val Leu Ala Glu Ser Arg Ala Ser Lys Asn Asp Lys Glu
                165                 170                 175

Lys Glu Asn Leu Gln Glu Lys Asp Lys Ser Gln Gln Val His Pro Pro
            180                 185                 190

Leu Asp Lys Asn Ala Leu Gln Ala Phe Phe Asp Ala Ser Tyr His Asn
        195                 200                 205

Tyr Arg Met Ile Asp Arg Asp Arg Ala Asp Ala Thr Glu Tyr Gln Lys
    210                 215                 220

Val Lys Ser Thr Phe Asp Tyr Val Asn Asp Leu Leu Gly Asn Asn Gln
225                 230                 235                 240

Asn Ile Pro Ser Glu Gln Leu Val Ser Ala Tyr Gln Gln Leu Glu Lys
                245                 250                 255

Ala Leu Glu Leu Ala Arg Thr Leu Pro Gln Gln Ser Thr Thr Glu Lys
            260                 265                 270
```

-continued

```
Arg Gly Arg Arg Ser Thr Arg Ser Val Val Glu Asn Arg Ser Ser Arg
        275                 280                 285

Ser Asp Tyr Leu Asp Ala Arg Thr Glu Tyr Tyr Val Ser Lys Asp Asp
    290                 295                 300

Asp Asp Ser Gly Phe Pro Pro Gly Thr Phe Phe His Ala Ser Asn Arg
305                 310                 315                 320

Arg Trp Pro Tyr Asn Leu Pro Arg Ser Arg Asn Ile Leu Arg Ala Ser
                325                 330                 335

Asp Val Gln Gly Asn Ala Tyr Ile Thr Thr Lys Arg Leu Lys Asp Gly
            340                 345                 350

Tyr Gln Trp Asp Ile Leu Phe Asn Ser Asn His Lys Gly His Glu Tyr
        355                 360                 365

Met Tyr Tyr Trp Phe Gly Leu Pro Ser Asp Gln Thr Pro Thr Gly Pro
    370                 375                 380

Val Thr Phe Thr Ile Ile Asn Arg Asp Gly Ser Ser Thr Ser Thr Gly
385                 390                 395                 400

Gly Val Gly Phe Gly Ser Gly Ala Pro Leu Pro Gln Phe Trp Arg Ser
                405                 410                 415

Ala Gly Ala Ile Asn Ser Ser Val Ala Asn Asp Phe Lys His Gly Ser
            420                 425                 430

Ala Thr Asn Tyr Ala Phe Tyr Asp Gly Val Asn Asn Phe Ser Asp Phe
        435                 440                 445

Ala Arg Gly Gly Glu Leu Tyr Phe Asp Arg Glu Gly Ala Thr Gln Thr
    450                 455                 460

Asn Lys Tyr Tyr Gly Asp Glu Asn Phe Ala Leu Leu Asn Ser Glu Lys
465                 470                 475                 480

Pro Asp Gln Ile Arg Gly Leu Asp Thr Ile Tyr Ser Phe Lys Gly Ser
                485                 490                 495

Gly Asp Val Ser Tyr Arg Ile Ser Phe Lys Thr Gln Gly Ala Pro Thr
            500                 505                 510

Ala Arg Leu Tyr Tyr Ala Ala Gly Ala Arg Ser Gly Glu Tyr Lys Gln
        515                 520                 525

Ala Thr Asn Tyr Asn Gln Leu Tyr Val Glu Pro Tyr Lys Asn Tyr Arg
    530                 535                 540

Asn Arg Val Gln Ser Asn Val Gln Val Lys Asn Arg Thr Leu His Leu
545                 550                 555                 560

Lys Arg Thr Ile Arg Gln Phe Asp Pro Thr Leu Gln Arg Thr Thr Asp
                565                 570                 575

Val Pro Ile Leu Asp Ser Asp Gly Ser Gly Ser Ile Asp Ser Val Tyr
            580                 585                 590

Asp Pro Leu Ser Tyr Val Lys Asn Val Thr Gly Thr Val Leu Gly Ile
        595                 600                 605

Tyr Pro Ser Tyr Leu Pro Tyr Asn Gln Glu Arg Trp Gln Gly Ala Asn
    610                 615                 620

Ala Met Asn Ala Tyr Gln Ile Glu Glu Leu Phe Ser Gln Glu Asn Leu
625                 630                 635                 640

Gln Asn Ala Ala Arg Ser Gly Arg Pro Ile Gln Phe Leu Val Gly Phe
                645                 650                 655

Asp Val Glu Asp Ser His His Asn Pro Glu Thr Leu Leu Pro Val Asn
            660                 665                 670

Leu Tyr Val Lys Pro Glu Leu Lys His Thr Ile Glu Leu Tyr His Asp
        675                 680                 685
```

```
Asn Glu Lys Gln Asp Arg Lys Glu Phe Ser Val Ser Lys
    690                 695                 700
```

<210> SEQ ID NO 15
<211> LENGTH: 9439
<212> TYPE: PRT
<213> ORGANISM: Staphylococcus sp.

<400> SEQUENCE: 15

```
Met Ser Gly Thr Leu His Asn Thr Val Gly Ser Gly Ile Leu Pro Tyr
1               5                   10                  15

Gln Gln Glu Ile Arg Ile Lys Leu Thr Ser Asn Glu Pro Ile Lys Asp
            20                  25                  30

Ser Glu Trp Ser Ile Thr Gly Tyr Pro Asn Thr Leu Thr Leu Gln Asn
        35                  40                  45

Ala Val Gly Arg Thr Asn Asn Ala Thr Glu Lys Asn Leu Ala Leu Val
    50                  55                  60

Gly His Ile Asp Pro Gly Asn Tyr Phe Ile Thr Val Lys Phe Gly Asp
65                  70                  75                  80

Lys Val Glu Gln Phe Glu Ile Arg Ser Lys Pro Thr Pro Pro Arg Ile
                85                  90                  95

Ile Thr Thr Ala Asn Glu Leu Arg Gly Asn Pro Asn His Lys Pro Glu
            100                 105                 110

Ile Arg Val Thr Asp Ile Pro Asn Asp Thr Thr Ala Lys Ile Lys Leu
        115                 120                 125

Val Met Gly Gly Thr Asp Gly Asp His Asp Pro Glu Ile Asn Pro Tyr
    130                 135                 140

Thr Val Pro Glu Asn Tyr Thr Val Val Ala Glu Ala Tyr His Asp Asn
145                 150                 155                 160

Asp Pro Ser Lys Asn Gly Val Leu Thr Phe Arg Ser Ser Asp Tyr Leu
                165                 170                 175

Lys Asp Leu Pro Leu Ser Gly Glu Leu Lys Ala Ile Val Tyr Tyr Asn
            180                 185                 190

Gln Tyr Val Gln Ser Asn Phe Ser Lys Ser Val Pro Phe Ser Ser Asp
        195                 200                 205

Thr Thr Pro Pro Thr Ile Asn Glu Pro Ala Gly Leu Val His Lys Tyr
    210                 215                 220

Tyr Arg Gly Asp His Val Glu Ile Thr Leu Pro Val Thr Asp Asn Thr
225                 230                 235                 240

Gly Gly Ser Gly Leu Arg Asp Val Asn Val Asn Leu Pro Gln Gly Trp
                245                 250                 255

Thr Lys Thr Phe Thr Ile Asn Pro Asn Asn Asn Thr Glu Gly Thr Leu
            260                 265                 270

Lys Leu Ile Gly Asn Ile Pro Ser Asn Glu Ala Tyr Asn Thr Thr Tyr
        275                 280                 285

His Phe Asn Ile Thr Ala Thr Asp Asn Ser Gly Asn Thr Thr Asn Pro
    290                 295                 300

Ala Lys Thr Phe Ile Leu Asn Val Gly Lys Leu Ala Asp Asp Leu Asn
305                 310                 315                 320

Pro Val Gly Leu Ser Arg Asp Gln Leu Gln Leu Val Thr Asp Pro Ser
                325                 330                 335

Ser Leu Ser Asn Ser Glu Arg Glu Glu Val Lys Arg Lys Ile Ser Glu
            340                 345                 350

Ala Asn Ala Asn Ile Arg Ser Tyr Leu Leu Gln Asn Asn Pro Ile Leu
        355                 360                 365
```

-continued

```
Ala Gly Val Asn Gly Asp Val Thr Phe Tyr Tyr Arg Asp Gly Ser Val
    370                 375                 380

Asp Val Ile Asp Ala Glu Asn Val Ile Thr Tyr Glu Pro Glu Arg Lys
385                 390                 395                 400

Ser Ile Phe Ser Glu Asn Gly Asn Thr Asn Lys Lys Glu Ala Val Ile
                405                 410                 415

Thr Ile Ala Arg Gly Gln Asn Tyr Thr Ile Gly Pro Asn Leu Arg Lys
            420                 425                 430

Tyr Phe Ser Leu Ser Asn Gly Ser Asp Leu Pro Asn Arg Asp Phe Thr
        435                 440                 445

Ser Ile Ser Ala Ile Gly Ser Leu Pro Ser Ser Ser Glu Ile Ser Arg
    450                 455                 460

Leu Asn Val Gly Asn Tyr Asn Tyr Arg Val Asn Ala Lys Asn Ala Tyr
465                 470                 475                 480

His Lys Thr Gln Gln Glu Leu Asn Leu Lys Leu Lys Ile Val Glu Val
                485                 490                 495

Asn Ala Pro Thr Gly Asn Asn Arg Val Tyr Arg Val Ser Thr Tyr Asn
            500                 505                 510

Leu Thr Asn Asp Glu Ile Asn Lys Ile Lys Gln Ala Phe Lys Ala Ala
        515                 520                 525

Asn Ser Gly Leu Asn Leu Asn Asp Asn Asp Ile Thr Val Ser Asn Asn
    530                 535                 540

Phe Asp His Arg Asn Val Ser Ser Val Thr Val Thr Ile Arg Lys Gly
545                 550                 555                 560

Asp Leu Ile Lys Glu Phe Ser Ser Asn Leu Asn Asn Met Asn Phe Leu
                565                 570                 575

Arg Trp Val Asn Ile Arg Asp Asp Tyr Thr Ile Ser Trp Thr Ser Ser
            580                 585                 590

Lys Ile Gln Gly Arg Asn Thr Asp Gly Gly Leu Glu Trp Ser Pro Asp
        595                 600                 605

His Lys Ser Leu Ile Tyr Lys Tyr Asp Ala Thr Leu Gly Arg Gln Ile
    610                 615                 620

Asn Thr Asn Asp Val Leu Thr Leu Leu Gln Ala Thr Ala Lys Asn Ser
625                 630                 635                 640

Asn Leu Arg Ser Asn Ile Asn Ser Asn Glu Lys Gln Leu Ala Glu Arg
                645                 650                 655

Gly Ser Asn Gly Tyr Ser Lys Ser Ile Ile Arg Asp Asp Gly Glu Lys
            660                 665                 670

Ser Tyr Leu Leu Asn Ser Asn Pro Ile Gln Val Leu Asp Leu Val Glu
        675                 680                 685

Pro Asp Asn Gly Tyr Gly Gly Arg Gln Val Ser His Ser Asn Val Ile
    690                 695                 700

Tyr Asn Glu Lys Asn Ser Ser Ile Val Asn Gly Gln Val Pro Glu Ala
705                 710                 715                 720

Asn Gly Ala Ser Ala Phe Asn Ile Asp Lys Val Val Lys Ala Asn Ala
                725                 730                 735

Ala Asn Asn Gly Ile Met Gly Val Ile Tyr Lys Ala Gln Leu Tyr Leu
            740                 745                 750

Ala Pro Tyr Ser Pro Lys Gly Tyr Ile Glu Lys Leu Gly Gln Asn Leu
        755                 760                 765

Ser Asn Thr Asn Asn Val Ile Asn Val Tyr Phe Val Pro Ser Asp Lys
    770                 775                 780
```

-continued

```
Val Asn Pro Ser Ile Thr Val Gly Asn Tyr Asp His His Thr Val Tyr
785                 790                 795                 800

Ser Gly Glu Thr Phe Lys Asn Thr Ile Asn Val Asn Asp Asn Tyr Gly
                805                 810                 815

Leu Asn Thr Val Ala Ser Thr Ser Asp Ser Ala Ile Thr Met Thr Arg
            820                 825                 830

Asn Asn Asn Glu Leu Val Gly Gln Ala Pro Asn Val Thr Asn Ser Ile
        835                 840                 845

Asn Lys Ile Val Lys Val Lys Ala Thr Asp Lys Ser Gly Asn Glu Ser
    850                 855                 860

Ile Val Ser Phe Thr Val Asn Ile Lys Pro Leu Asn Glu Lys Tyr Arg
865                 870                 875                 880

Ile Thr Thr Ser Ser Ser Asn Gln Thr Pro Val Arg Ile Ser Asn Ile
                885                 890                 895

Gln Asn Asn Ala Asn Leu Ser Ile Glu Asp Gln Asn Arg Val Lys Ser
            900                 905                 910

Ser Leu Ser Met Thr Lys Ile Leu Gly Thr Arg Asn Tyr Val Asn Glu
        915                 920                 925

Ser Asn Asn Asp Val Arg Ser Gln Val Val Ser Lys Val Asn Arg Ser
    930                 935                 940

Gly Asn Asn Ala Thr Val Asn Val Thr Thr Thr Phe Ser Asp Gly Thr
945                 950                 955                 960

Thr Asn Thr Ile Thr Val Pro Val Lys His Val Leu Leu Glu Val Val
                965                 970                 975

Pro Thr Thr Arg Thr Thr Val Arg Gly Gln Gln Phe Pro Thr Gly Lys
            980                 985                 990

Gly Thr Ser Pro Asn Asp Phe Phe Ser Leu Arg Thr Gly Gly Pro Val
        995                 1000                1005

Asp Ala Arg Ile Val Trp Val Asn Asn Gln Gly Pro Asp Ile Asn Ser
    1010                1015                1020

Asn Gln Ile Gly Arg Asp Leu Thr Leu His Ala Glu Ile Phe Phe Asp
1025                1030                1035                1040

Gly Glu Thr Thr Pro Ile Arg Lys Asp Thr Thr Tyr Lys Leu Ser Gln
                1045                1050                1055

Ser Ile Pro Lys Gln Ile Tyr Glu Thr Thr Ile Asn Gly Arg Phe Asn
            1060                1065                1070

Ser Ser Gly Asp Ala Tyr Pro Gly Asn Phe Val Gln Ala Val Asn Gln
        1075                1080                1085

Tyr Trp Pro Glu His Met Asp Phe Arg Trp Ala Gln Gly Ser Gly Thr
    1090                1095                1100

Pro Ser Ser Arg Asn Ala Gly Ser Phe Thr Lys Thr Val Thr Val Val
1105                1110                1115                1120

Tyr Gln Asn Gly Gln Thr Glu Asn Val Asn Val Leu Phe Lys Val Lys
                1125                1130                1135

Pro Asn Lys Pro Val Ile Asp Ser Asn Ser Val Ile Ser Lys Gly Gln
            1140                1145                1150

Leu Asn Gly Gln Gln Ile Leu Val Arg Asn Val Pro Gln Asn Ala Gln
        1155                1160                1165

Val Thr Leu Tyr Gln Ser Asn Gly Thr Val Ile Pro Asn Thr Asn Thr
    1170                1175                1180

Thr Ile Asp Ser Asn Gly Ile Ala Thr Val Thr Ile Gln Gly Thr Leu
1185                1190                1195                1200

Pro Thr Gly Asn Ile Thr Ala Lys Thr Ser Met Thr Asn Asn Val Thr
```

-continued

```
                1205                1210                1215

Tyr Thr Lys Gln Asn Ser Ser Gly Ile Ala Ser Asn Thr Thr Glu Asp
            1220                1225                1230

Ile Ser Val Phe Ser Glu Asn Ser Asp Gln Val Asn Val Thr Ala Gly
        1235                1240                1245

Met Gln Ala Lys Asn Asp Gly Ile Lys Ile Ile Lys Gly Thr Asn Tyr
    1250                1255                1260

Asn Phe Asn Asp Phe Asn Ser Phe Ile Ser Asn Ile Pro Ala His Ser
1265                1270                1275                1280

Thr Leu Thr Trp Asn Glu Glu Pro Asn Ser Trp Lys Asn Asn Ile Gly
                1285                1290                1295

Thr Thr Thr Lys Thr Val Thr Val Thr Leu Pro Asn His Gln Gly Thr
            1300                1305                1310

Arg Thr Val Asp Ile Pro Ile Thr Ile Tyr Pro Thr Val Thr Ala Lys
        1315                1320                1325

Asn Pro Val Arg Asp Gln Lys Gly Arg Asn Leu Thr Asn Gly Thr Asp
    1330                1335                1340

Val Tyr Asn Tyr Ile Ile Phe Glu Asn Asn Asn Arg Leu Gly Gly Thr
1345                1350                1355                1360

Ala Ser Trp Lys Asp Asn Arg Gln Pro Asp Lys Asn Ile Ala Gly Val
                1365                1370                1375

Gln Asn Leu Ile Ala Leu Val Asn Tyr Pro Gly Ile Ser Thr Pro Leu
            1380                1385                1390

Glu Val Pro Val Lys Val Trp Val Tyr Asn Phe Asp Phe Thr Gln Pro
        1395                1400                1405

Ile Tyr Lys Ile Gln Val Gly Asp Thr Phe Pro Lys Gly Thr Trp Ala
    1410                1415                1420

Gly Tyr Tyr Lys His Leu Glu Asn Gly Glu Gly Leu Pro Ile Asp Gly
1425                1430                1435                1440

Trp Lys Phe Tyr Trp Asn Gln Gln Ser Thr Gly Thr Thr Ser Asp Gln
                1445                1450                1455

Trp Gln Ser Leu Ala Tyr Thr Arg Thr Pro Phe Val Lys Thr Gly Thr
            1460                1465                1470

Tyr Asp Val Val Asn Pro Ser Asn Trp Gly Val Trp Gln Thr Ser Gln
        1475                1480                1485

Ser Ala Lys Phe Ile Val Thr Asn Ala Lys Pro Asn Gln Pro Thr Ile
    1490                1495                1500

Thr Gln Ser Lys Thr Gly Asp Val Thr Val Thr Pro Gly Ala Val Arg
1505                1510                1515                1520

Asn Ile Leu Ile Ser Gly Thr Asn Asp Tyr Ile Gln Ala Ser Ala Asp
                1525                1530                1535

Lys Ile Val Ile Asn Lys Asn Gly Asn Lys Leu Thr Thr Phe Val Lys
            1540                1545                1550

Asn Asn Asp Gly Arg Trp Thr Val Glu Thr Gly Ser Pro Asp Ile Asn
        1555                1560                1565

Gly Ile Gly Pro Thr Asn Asn Gly Thr Ala Ile Ser Leu Ser Arg Leu
    1570                1575                1580

Ala Val Arg Pro Gly Asp Ser Ile Glu Ala Ile Ala Thr Glu Gly Ser
1585                1590                1595                1600

Gly Glu Thr Ile Ser Thr Ser Ala Thr Ser Glu Ile Tyr Ile Val Lys
                1605                1610                1615

Ala Pro Gln Pro Glu Gln Val Ala Thr His Thr Tyr Asp Asn Gly Thr
            1620                1625                1630
```

-continued

```
Phe Asp Ile Leu Pro Asp Asn Ser Arg Asn Ser Leu Asn Pro Thr Glu
        1635                1640                1645

Arg Val Glu Ile Asn Tyr Thr Glu Lys Leu Asn Gly Asn Glu Thr Gln
    1650                1655                1660

Lys Ser Phe Thr Ile Thr Lys Asn Asn Asn Gly Lys Trp Thr Ile Asn
1665                1670                1675                1680

Asn Lys Pro Asn Tyr Val Glu Phe Asn Gln Asp Asn Gly Lys Val Val
                1685                1690                1695

Phe Ser Ala Asn Thr Ile Lys Pro Asn Ser Gln Ile Thr Ile Thr Pro
            1700                1705                1710

Lys Ala Gly Gln Gly Asn Thr Glu Asn Thr Asn Pro Thr Val Ile Gln
        1715                1720                1725

Ala Pro Ala Gln His Thr Leu Thr Ile Asn Glu Ile Val Lys Glu Gln
    1730                1735                1740

Gly Gln Asn Val Thr Asn Asp Asp Ile Asn Asn Ala Val Gln Val Pro
1745                1750                1755                1760

Asn Lys Asn Arg Val Ala Ile Lys Gln Gly Asn Ala Leu Pro Thr Asn
                1765                1770                1775

Leu Ala Gly Gly Ser Thr Ser His Ile Pro Val Val Ile Tyr Tyr Ser
            1780                1785                1790

Asp Gly Ser Ser Glu Glu Ala Thr Glu Thr Val Arg Thr Lys Val Asn
        1795                1800                1805

Lys Thr Glu Leu Ile Asn Ala Arg Arg Arg Leu Asp Glu Glu Ile Ser
    1810                1815                1820

Lys Glu Asn Lys Thr Pro Ser Ser Ile Arg Asn Phe Asp Gln Ala Met
1825                1830                1835                1840

Asn Arg Ala Gln Ser Gln Ile Asn Thr Ala Lys Ser Asp Ala Asp Gln
                1845                1850                1855

Val Ile Gly Thr Glu Phe Ala Thr Pro Gln Gln Val Asn Ser Ala Leu
            1860                1865                1870

Ser Lys Val Gln Ala Ala Gln Asn Lys Ile Asn Glu Ala Lys Ala Leu
        1875                1880                1885

Leu Gln Asn Lys Ala Asp Asn Ser Gln Leu Val Arg Ala Lys Glu Gln
    1890                1895                1900

Leu Gln Gln Ser Ile Gln Pro Ala Ala Ser Thr Asp Gly Met Thr Gln
1905                1910                1915                1920

Asp Ser Thr Arg Asn Tyr Asn Asn Lys Arg Gln Ala Ala Glu Gln Ala
                1925                1930                1935

Ile Gln His Ala Asn Ser Val Ile Asn Asn Gly Asp Ala Thr Ser Gln
            1940                1945                1950

Gln Ile Asn Asp Ala Lys Asn Thr Val Glu Gln Ala Gln Arg Asp Tyr
        1955                1960                1965

Val Glu Ala Lys Ser Asn Leu Arg Ala Asp Lys Ser Gln Leu Gln Ser
    1970                1975                1980

Ala Tyr Asp Thr Leu Asn Arg Asp Val Leu Thr Asn Asp Lys Lys Pro
1985                1990                1995                2000

Ala Ser Val Arg Arg Tyr Asn Glu Ala Ile Ser Asn Ile Arg Lys Glu
                2005                2010                2015

Leu Asp Thr Ala Lys Ala Asp Ala Ser Ser Thr Leu Arg Asn Thr Asn
            2020                2025                2030

Pro Ser Val Glu Gln Val Arg Asp Ala Leu Asn Lys Ile Asn Thr Val
        2035                2040                2045
```

-continued

Gln Pro Lys Val Asn Gln Ala Ile Ala Leu Leu Gln Pro Lys Glu Asn
    2050                2055                2060

Asn Ser Glu Leu Val Gln Ala Lys Lys Arg Leu Gln Asp Ala Val Asn
2065                2070                2075                2080

Asp Ile Pro Gln Thr Gln Gly Met Thr Gln Gln Thr Ile Asn Asn Tyr
                2085                2090                2095

Asn Asp Lys Gln Arg Glu Ala Glu Arg Ala Leu Thr Ser Ala Gln Arg
            2100                2105                2110

Val Ile Asp Asn Gly Asp Ala Thr Thr Gln Glu Ile Thr Ser Glu Lys
        2115                2120                2125

Ser Lys Val Glu Gln Ala Met Gln Ala Leu Thr Asn Ala Lys Ser Asn
    2130                2135                2140

Leu Arg Ala Asp Lys Asn Glu Leu Gln Thr Ala Tyr Asn Lys Leu Ile
2145                2150                2155                2160

Glu Asn Val Ser Thr Asn Gly Lys Lys Pro Ala Ser Ile Arg Gln Tyr
                2165                2170                2175

Glu Thr Ala Lys Ala Arg Ile Gln Asn Gln Ile Asn Asp Ala Lys Asn
            2180                2185                2190

Glu Ala Glu Arg Ile Leu Gly Asn Asp Asn Pro Gln Val Ser Gln Val
        2195                2200                2205

Thr Gln Ala Leu Asn Lys Ile Lys Ala Ile Gln Pro Lys Leu Thr Glu
    2210                2215                2220

Ala Ile Asn Met Leu Gln Asn Lys Glu Asn Asn Thr Glu Leu Val Asn
2225                2230                2235                2240

Ala Lys Asn Arg Leu Glu Asn Ala Val Asn Asp Thr Asp Pro Thr His
                2245                2250                2255

Gly Met Thr Gln Glu Thr Ile Asn Asn Tyr Asn Ala Lys Lys Arg Glu
            2260                2265                2270

Ala Gln Asn Glu Ile Gln Lys Ala Asn Met Ile Ile Asn Asn Gly Asp
        2275                2280                2285

Ala Thr Ala Gln Asp Ile Ser Ser Glu Lys Ser Lys Val Glu Gln Val
    2290                2295                2300

Leu Gln Ala Leu Gln Asn Ala Lys Asn Asp Leu Arg Ala Asp Lys Arg
2305                2310                2315                2320

Glu Leu Gln Thr Ala Tyr Asn Lys Leu Ile Gln Asn Val Asn Thr Asn
                2325                2330                2335

Gly Lys Lys Pro Ser Ser Ile Gln Asn Tyr Lys Ser Ala Arg Arg Asn
            2340                2345                2350

Ile Glu Asn Gln Tyr Asn Thr Ala Lys Asn Glu Ala His Asn Val Leu
        2355                2360                2365

Glu Asn Thr Asn Pro Thr Val Asn Ala Val Glu Asp Ala Leu Arg Lys
    2370                2375                2380

Ile Asn Ala Ile Gln Pro Glu Val Thr Lys Ala Ile Asn Ile Leu Gln
2385                2390                2395                2400

Asp Lys Glu Asp Asn Ser Glu Leu Val Arg Ala Lys Glu Lys Leu Asp
                2405                2410                2415

Gln Ala Ile Asn Ser Gln Pro Ser Leu Asn Gly Met Thr Gln Glu Ser
            2420                2425                2430

Ile Asn Asn Tyr Thr Thr Lys Arg Arg Glu Ala Gln Asn Ile Ala Ser
        2435                2440                2445

Ser Ala Asp Thr Ile Ile Asn Asn Gly Asp Ala Ser Ile Glu Gln Ile
    2450                2455                2460

Thr Glu Asn Lys Ile Arg Val Glu Glu Ala Thr Asn Ala Leu Asn Glu

```
2465                2470                2475                2480

Ala Lys Gln His Leu Thr Ala Asp Thr Thr Ser Leu Lys Thr Glu Val
                2485                2490                2495

Arg Lys Leu Ser Arg Arg Gly Asp Thr Asn Asn Lys Lys Pro Ser Ser
            2500                2505                2510

Val Ser Ala Tyr Asn Asn Thr Ile His Ser Leu Gln Ser Glu Ile Thr
        2515                2520                2525

Gln Thr Glu Asn Arg Ala Asn Thr Ile Ile Asn Lys Pro Ile Arg Ser
    2530                2535                2540

Val Glu Glu Val Asn Asn Ala Leu His Glu Val Asn Gln Leu Asn Gln
2545                2550                2555                2560

Arg Leu Thr Asp Thr Ile Asn Leu Leu Gln Pro Leu Ala Asn Lys Glu
                2565                2570                2575

Ser Leu Lys Glu Ala Arg Asn Arg Leu Glu Ser Lys Ile Asn Glu Thr
            2580                2585                2590

Val Gln Thr Asp Gly Met Thr Gln Gln Ser Val Glu Asn Tyr Lys Gln
        2595                2600                2605

Ala Lys Ile Lys Ala Gln Asn Glu Ser Ser Ile Ala Gln Thr Leu Ile
    2610                2615                2620

Asn Asn Gly Asp Ala Ser Asp Gln Glu Val Ser Thr Glu Ile Glu Lys
2625                2630                2635                2640

Leu Asn Gln Lys Leu Ser Glu Leu Thr Asn Ser Ile Asn His Leu Thr
                2645                2650                2655

Val Asn Lys Glu Pro Leu Glu Thr Ala Lys Asn Gln Leu Gln Ala Asn
            2660                2665                2670

Ile Asp Gln Lys Pro Ser Thr Asp Gly Met Thr Gln Gln Ser Val Gln
        2675                2680                2685

Ser Tyr Glu Arg Lys Leu Gln Glu Ala Lys Asp Lys Ile Asn Ser Ile
    2690                2695                2700

Asn Asn Val Leu Ala Asn Asn Pro Asp Val Asn Ala Ile Arg Thr Asn
2705                2710                2715                2720

Lys Val Glu Thr Glu Gln Ile Asn Asn Glu Leu Thr Gln Ala Lys Gln
                2725                2730                2735

Gly Leu Thr Val Asp Lys Gln Pro Leu Ile Asn Ala Lys Thr Ala Leu
            2740                2745                2750

Gln Gln Ser Leu Asp Asn Gln Pro Ser Thr Thr Gly Met Thr Glu Ala
        2755                2760                2765

Thr Ile Gln Asn Tyr Asn Ala Lys Arg Gln Lys Ala Glu Gln Val Ile
    2770                2775                2780

Gln Asn Ala Asn Lys Ile Ile Glu Asn Ala Gln Pro Ser Val Gln Gln
2785                2790                2795                2800

Val Ser Asp Glu Lys Ser Lys Val Glu Gln Ala Leu Ser Glu Leu Asn
                2805                2810                2815

Asn Ala Lys Ser Ala Leu Arg Ala Asp Lys Gln Glu Leu Gln Gln Ala
            2820                2825                2830

Tyr Asn Gln Leu Ile Gln Pro Thr Asp Leu Asn Asn Lys Lys Pro Ala
        2835                2840                2845

Ser Ile Thr Ala Tyr Asn Gln Arg Tyr Gln Gln Phe Ser Asn Glu Leu
    2850                2855                2860

Asn Ser Thr Lys Thr Asn Thr Asp Arg Ile Leu Lys Glu Gln Asn Pro
2865                2870                2875                2880

Ser Val Ala Asp Val Asn Asn Ala Leu Asn Lys Val Arg Glu Val Gln
                2885                2890                2895
```

```
Gln Lys Leu Asn Glu Ala Arg Ala Leu Leu Gln Asn Lys Glu Asp Asn
            2900                2905                2910

Ser Ala Leu Val Arg Ala Lys Glu Gln Leu Gln Gln Ala Val Asp Gln
        2915                2920                2925

Val Pro Ser Thr Glu Gly Met Thr Gln Gln Thr Lys Asp Asp Tyr Asn
    2930                2935                2940

Ser Lys Gln Gln Ala Ala Gln Gln Glu Ile Ser Lys Ala Gln Gln Val
2945                2950                2955                2960

Ile Asp Asn Gly Asp Ala Thr Thr Gln Gln Ile Ser Asn Ala Lys Thr
                2965                2970                2975

Asn Val Glu Arg Ala Leu Glu Ala Leu Asn Asn Ala Lys Thr Gly Leu
            2980                2985                2990

Arg Ala Asp Lys Glu Glu Leu Gln Asn Ala Tyr Asn Gln Leu Thr Gln
        2995                3000                3005

Asn Ile Asp Thr Ser Gly Lys Thr Pro Ala Ser Ile Arg Lys Tyr Asn
    3010                3015                3020

Glu Ala Lys Ser Arg Ile Gln Thr Gln Ile Asp Ser Ala Lys Asn Glu
3025                3030                3035                3040

Ala Asn Ser Ile Leu Thr Asn Asp Asn Pro Gln Val Ser Gln Val Thr
                3045                3050                3055

Ala Ala Leu Asn Lys Ile Lys Ala Val Gln Pro Glu Leu Asp Lys Ala
            3060                3065                3070

Ile Ala Met Leu Lys Asn Lys Glu Asn Asn Asn Ala Leu Val Gln Ala
        3075                3080                3085

Lys Gln Gln Leu Gln Gln Ile Val Asn Glu Val Asp Pro Thr Gln Gly
    3090                3095                3100

Met Thr Thr Asp Thr Ala Asn Asn Tyr Lys Ser Lys Lys Arg Glu Ala
3105                3110                3115                3120

Glu Asp Glu Ile Gln Lys Ala Gln Gln Ile Ile Asn Asn Gly Asp Ala
                3125                3130                3135

Thr Glu Gln Gln Ile Thr Asn Glu Thr Asn Arg Val Asn Gln Ala Ile
            3140                3145                3150

Asn Ala Ile Asn Lys Ala Lys Asn Asp Leu Arg Ala Asp Lys Ser Gln
        3155                3160                3165

Leu Glu Asn Ala Tyr Asn Gln Leu Ile Gln Asn Val Asp Thr Asn Gly
    3170                3175                3180

Lys Lys Pro Ala Ser Ile Gln Gln Tyr Gln Ala Ala Arg Gln Ala Ile
3185                3190                3195                3200

Glu Thr Gln Tyr Asn Asn Ala Lys Ser Glu Ala His Gln Ile Leu Glu
                3205                3210                3215

Asn Ser Asn Pro Ser Val Asn Glu Val Ala Gln Ala Leu Gln Lys Val
            3220                3225                3230

Glu Ala Val Gln Leu Lys Val Asn Asp Ala Ile His Ile Leu Gln Asn
        3235                3240                3245

Lys Glu Asn Asn Ser Ala Leu Val Thr Ala Lys Asn Gln Leu Gln Gln
    3250                3255                3260

Ser Val Asn Asp Gln Pro Leu Thr Thr Gly Met Thr Gln Asp Ser Ile
3265                3270                3275                3280

Asn Asn Tyr Glu Ala Lys Arg Asn Glu Ala Gln Ser Ala Ile Arg Asn
                3285                3290                3295

Ala Glu Ala Val Ile Asn Asn Gly Asp Ala Thr Ala Lys Gln Ile Ser
            3300                3305                3310
```

-continued

```
Asp Glu Lys Ser Lys Val Glu Gln Ala Leu Ala His Leu Asn Asp Ala
        3315                3320                3325

Lys Gln Gln Leu Thr Ala Asp Thr Thr Glu Leu Gln Thr Ala Val Gln
    3330                3335                3340

Gln Leu Asn Arg Arg Gly Asp Thr Asn Asn Lys Lys Pro Arg Ser Ile
3345                3350                3355                3360

Asn Ala Tyr Asn Lys Ala Ile Gln Ser Leu Glu Thr Gln Ile Thr Ser
                3365                3370                3375

Ala Lys Asp Asn Ala Asn Ala Val Ile Gln Lys Pro Ile Arg Thr Val
            3380                3385                3390

Gln Glu Val Asn Asn Ala Leu Gln Gln Val Asn Gln Leu Asn Gln Gln
        3395                3400                3405

Leu Thr Glu Ala Ile Asn Gln Leu Gln Pro Leu Ser Asn Asn Asp Ala
    3410                3415                3420

Leu Lys Ala Ala Arg Leu Asn Leu Glu Asn Lys Ile Asn Gln Thr Val
3425                3430                3435                3440

Gln Thr Asp Gly Met Thr Gln Gln Ser Ile Glu Ala Tyr Gln Asn Ala
                3445                3450                3455

Lys Arg Val Ala Gln Asn Glu Ser Asn Thr Ala Leu Ala Leu Ile Asn
            3460                3465                3470

Asn Gly Asp Ala Asp Glu Gln Gln Ile Thr Thr Glu Thr Asp Arg Val
        3475                3480                3485

Asn Gln Gln Thr Thr Asn Leu Thr Gln Ala Ile Asn Gly Leu Thr Val
    3490                3495                3500

Asn Lys Glu Pro Leu Glu Thr Ala Lys Thr Ala Leu Gln Asn Asn Ile
3505                3510                3515                3520

Asp Gln Val Pro Ser Thr Asp Gly Met Thr Gln Gln Ser Val Ala Asn
                3525                3530                3535

Tyr Asn Gln Lys Leu Gln Ile Ala Lys Asn Glu Ile Asn Thr Ile Asn
            3540                3545                3550

Asn Val Leu Ala Asn Asn Pro Asp Val Asn Ala Ile Lys Thr Asn Lys
        3555                3560                3565

Ala Glu Ala Glu Arg Ile Ser Asn Asp Leu Thr Gln Ala Lys Asn Asn
    3570                3575                3580

Leu Gln Val Asp Thr Gln Pro Leu Glu Lys Ile Lys Arg Gln Leu Gln
3585                3590                3595                3600

Asp Glu Ile Asp Gln Gly Thr Asn Thr Asp Gly Met Thr Gln Asp Ser
                3605                3610                3615

Val Asp Asn Tyr Asn Asp Ser Leu Ser Ala Ala Ile Ile Glu Lys Gly
            3620                3625                3630

Lys Val Asn Lys Leu Leu Lys Arg Asn Pro Thr Val Glu Gln Val Lys
        3635                3640                3645

Glu Ser Val Ala Asn Ala Gln Gln Val Ile Gln Asp Leu Gln Asn Ala
    3650                3655                3660

Arg Thr Ser Leu Val Pro Asp Lys Thr Gln Leu Gln Glu Ala Lys Asn
3665                3670                3675                3680

Arg Leu Glu Asn Ser Ile Asn Gln Gln Thr Asp Thr Asp Gly Met Thr
                3685                3690                3695

Gln Asp Ser Leu Asn Asn Tyr Asn Asp Lys Leu Ala Lys Ala Arg Gln
            3700                3705                3710

Asn Leu Glu Lys Ile Ser Lys Val Leu Gly Gly Gln Pro Thr Val Ala
        3715                3720                3725

Glu Ile Arg Gln Asn Thr Asp Glu Ala Asn Ala His Lys Gln Ala Leu
```

3730 3735 3740

Asp Thr Ala Arg Ser Gln Leu Thr Leu Asn Arg Glu Pro Tyr Ile Asn
3745 3750 3755 3760

His Ile Asn Asn Glu Ser His Leu Asn Asn Ala Gln Lys Asp Asn Phe
3765 3770 3775

Lys Ala Gln Val Asn Ser Ala Pro Asn His Asn Thr Leu Glu Thr Ile
3780 3785 3790

Lys Asn Lys Ala Asp Thr Leu Asn Gln Ser Met Thr Ala Leu Ser Glu
3795 3800 3805

Ser Ile Ala Asp Tyr Glu Asn Gln Lys Gln Gln Glu Asn Tyr Leu Asp
3810 3815 3820

Ala Ser Asn Asn Lys Arg Gln Asp Tyr Asp Asn Ala Val Asn Ala Ala
3825 3830 3835 3840

Lys Gly Ile Leu Asn Gln Thr Gln Ser Pro Thr Met Ser Ala Asp Val
3845 3850 3855

Ile Asp Gln Lys Ala Glu Asp Val Lys Arg Thr Lys Thr Ala Leu Asp
3860 3865 3870

Gly Asn Gln Arg Leu Glu Val Ala Lys Gln Gln Ala Leu Asn His Leu
3875 3880 3885

Asn Thr Leu Asn Asp Leu Asn Asp Ala Gln Arg Gln Thr Leu Thr Asp
3890 3895 3900

Thr Ile Asn His Ser Pro Asn Ile Asn Ser Val Asn Gln Ala Lys Glu
3905 3910 3915 3920

Lys Ala Asn Thr Val Asn Thr Ala Met Thr Gln Leu Lys Gln Thr Ile
3925 3930 3935

Ala Asn Tyr Asp Asp Glu Leu His Asp Gly Asn Tyr Ile Asn Ala Asp
3940 3945 3950

Lys Asp Lys Lys Asp Ala Tyr Asn Asn Ala Val Asn Asn Ala Lys Gln
3955 3960 3965

Leu Ile Asn Gln Ser Asp Ala Asn Gln Ala Gln Leu Asp Pro Ala Glu
3970 3975 3980

Ile Asn Lys Val Thr Gln Arg Val Asn Thr Thr Lys Asn Asp Leu Asn
3985 3990 3995 4000

Gly Asn Asp Lys Leu Ala Glu Ala Lys Arg Asp Ala Asn Thr Thr Ile
4005 4010 4015

Asp Gly Leu Thr Tyr Leu Asn Glu Ala Gln Arg Asn Lys Ala Lys Glu
4020 4025 4030

Asn Val Gly Lys Ala Ser Thr Lys Thr Asn Ile Thr Ser Gln Leu Gln
4035 4040 4045

Asp Tyr Asn Gln Leu Asn Ile Ala Met Gln Ala Leu Arg Asn Ser Val
4050 4055 4060

Asn Asp Val Asn Asn Val Lys Ala Asn Ser Asn Tyr Ile Asn Glu Asp
4065 4070 4075 4080

Asn Gly Pro Lys Glu Ala Tyr Asn Gln Ala Val Thr His Ala Gln Thr
4085 4090 4095

Leu Ile Asn Ala Gln Ser Asn Pro Glu Met Ser Arg Asp Val Val Asn
4100 4105 4110

Gln Lys Thr Gln Ala Val Asn Thr Ala His Gln Asn Leu His Gly Gln
4115 4120 4125

Gln Lys Leu Glu Gln Ala Gln Ser Ser Ala Asn Thr Glu Ile Gly Asn
4130 4135 4140

Leu Pro Asn Leu Thr Asn Thr Gln Lys Ala Lys Glu Lys Glu Leu Val
4145 4150 4155 4160

```
Asn Ser Lys Gln Thr Arg Thr Glu Val Gln Glu Gln Leu Asn Gln Ala
                4165                4170                4175

Lys Ser Leu Asp Ser Ser Met Gly Thr Leu Lys Ser Leu Val Ala Lys
            4180                4185                4190

Gln Pro Thr Val Gln Lys Thr Ser Val Tyr Ile Asn Glu Asp Gln Pro
        4195                4200                4205

Glu Gln Ser Ala Tyr Asn Asp Ser Ile Thr Met Gly Gln Thr Ile Ile
    4210                4215                4220

Asn Lys Thr Ala Asp Pro Val Leu Asp Lys Thr Leu Val Asp Asn Ala
4225                4230                4235                4240

Ile Ser Asn Ile Ser Thr Lys Glu Asn Ala Leu His Gly Glu Gln Lys
                4245                4250                4255

Leu Thr Thr Ala Lys Thr Glu Ala Ile Asn Ala Leu Asn Thr Leu Ala
            4260                4265                4270

Asp Leu Asn Thr Pro Gln Lys Glu Ala Ile Lys Thr Ala Ile Asn Thr
        4275                4280                4285

Ala His Thr Arg Thr Asp Val Thr Ala Glu Gln Ser Lys Ala Asn Gln
    4290                4295                4300

Ile Asn Ser Ala Met His Thr Leu Arg Gln Asn Ile Ser Asp Asn Glu
4305                4310                4315                4320

Ser Val Thr Asn Glu Ser Asn Tyr Ile Asn Ala Glu Pro Glu Lys Gln
                4325                4330                4335

His Ala Phe Thr Glu Ala Leu Asn Asn Ala Lys Glu Ile Val Asn Glu
            4340                4345                4350

Gln Gln Ala Thr Leu Asp Ala Asn Ser Ile Asn Gln Lys Ala Gln Ala
        4355                4360                4365

Ile Leu Thr Thr Lys Asn Ala Leu Asp Gly Glu Glu Gln Leu Arg Arg
    4370                4375                4380

Ala Lys Glu Asn Ala Asp Gln Glu Ile Asn Thr Leu Asn Gln Leu Thr
4385                4390                4395                4400

Asp Ala Gln Arg Asn Ser Glu Lys Gly Leu Val Asn Ser Ser Gln Thr
                4405                4410                4415

Arg Thr Glu Val Ala Ser Gln Leu Ala Lys Ala Lys Glu Leu Asn Lys
            4420                4425                4430

Val Met Glu Gln Leu Asn His Leu Ile Asn Gly Lys Asn Gln Met Ile
        4435                4440                4445

Asn Ser Ser Lys Phe Ile Asn Glu Asp Ala Asn Gln Gln Gln Ala Tyr
    4450                4455                4460

Ser Asn Ala Ile Ala Ser Ala Glu Ala Leu Lys Asn Lys Ser Gln Asn
4465                4470                4475                4480

Pro Glu Leu Asp Lys Val Thr Ile Glu Gln Ala Ile Asn Asn Ile Asn
                4485                4490                4495

Ser Ala Ile Asn Asn Leu Asn Gly Glu Ala Lys Leu Thr Lys Ala Lys
            4500                4505                4510

Glu Asp Ala Val Ala Ser Ile Asn Asn Leu Ser Gly Leu Thr Asn Glu
        4515                4520                4525

Gln Lys Thr Lys Glu Asn Gln Ala Val Asn Gly Ala Gln Thr Arg Asp
    4530                4535                4540

Gln Val Ala Asn Lys Leu Arg Asp Ala Glu Ala Leu Asp Gln Ser Met
4545                4550                4555                4560

Gln Thr Leu Arg Asp Leu Val Asn Asn Gln Asn Ala Ile His Ser Thr
                4565                4570                4575
```

```
Ser Asn Tyr Phe Asn Glu Asp Ser Thr Gln Lys Asn Thr Tyr Asp Asn
            4580                4585                4590

Ala Ile Asp Asn Gly Ser Thr Tyr Ile Thr Gly Gln His Asn Pro Glu
        4595                4600                4605

Leu Asn Lys Ser Thr Ile Asp Gln Thr Ile Ser Arg Ile Asn Thr Ala
    4610                4615                4620

Lys Asn Asp Leu His Gly Val Glu Lys Leu Gln Arg Asp Lys Gly Thr
4625                4630                4635                4640

Ala Asn Gln Glu Ile Gly Gln Leu Gly Tyr Leu Asn Asp Pro Gln Lys
                4645                4650                4655

Ser Gly Glu Glu Ser Leu Val Asn Gly Ser Asn Thr Arg Ser Glu Val
            4660                4665                4670

Glu Glu His Leu Asn Glu Ala Lys Ser Leu Asn Asn Ala Met Lys Gln
        4675                4680                4685

Leu Arg Asp Lys Val Ala Glu Lys Thr Asn Val Lys Gln Ser Ser Asp
    4690                4695                4700

Tyr Ile Asn Asp Ser Thr Glu His Gln Arg Gly Tyr Asp Gln Ala Leu
4705                4710                4715                4720

Gln Glu Ala Glu Asn Ile Ile Asn Glu Ile Gly Asn Pro Thr Leu Asn
                4725                4730                4735

Lys Ser Glu Ile Glu Gln Lys Leu Gln Gln Leu Thr Asp Ala Gln Asn
            4740                4745                4750

Ala Leu Gln Gly Ser His Leu Leu Glu Glu Ala Lys Asn Asn Ala Ile
        4755                4760                4765

Thr Gly Ile Asn Lys Leu Thr Ala Leu Asn Asp Ala Gln Arg Gln Lys
    4770                4775                4780

Ala Ile Glu Asn Val Gln Ala Gln Gln Thr Ile Pro Ala Val Asn Gln
4785                4790                4795                4800

Gln Leu Thr Leu Asp Arg Glu Ile Asn Thr Ala Met Gln Ala Leu Arg
                4805                4810                4815

Asp Lys Val Gly Gln Gln Asn Asn Val His Gln Gln Ser Asn Tyr Phe
            4820                4825                4830

Asn Glu Asp Glu Gln Pro Lys His Asn Tyr Asp Asn Ser Val Gln Ala
        4835                4840                4845

Gly Gln Thr Ile Ile Asp Lys Leu Gln Asp Pro Ile Met Asn Lys Asn
    4850                4855                4860

Glu Ile Glu Gln Ala Ile Asn Gln Ile Asn Thr Thr Gln Thr Ala Leu
4865                4870                4875                4880

Ser Gly Glu Asn Lys Leu His Thr Asp Gln Glu Ser Thr Asn Arg Gln
                4885                4890                4895

Ile Glu Gly Leu Ser Ser Leu Asn Thr Ala Gln Ile Asn Ala Glu Lys
            4900                4905                4910

Asp Leu Val Asn Gln Ala Lys Thr Arg Thr Asp Val Ala Gln Lys Leu
        4915                4920                4925

Ala Ala Ala Lys Glu Ile Asn Ser Ala Met Ser Asn Leu Arg Asp Gly
    4930                4935                4940

Ile Gln Asn Lys Glu Asp Ile Lys Arg Ser Ser Ala Tyr Ile Asn Ala
4945                4950                4955                4960

Asp Pro Thr Lys Val Thr Ala Tyr Asp Gln Ala Leu Gln Asn Ala Glu
                4965                4970                4975

Asn Ile Ile Asn Ala Thr Pro Asn Val Glu Leu Asn Lys Ala Thr Ile
            4980                4985                4990

Glu Gln Ala Leu Ser Arg Val Gln Gln Ala Gln Gln Asp Leu Asp Gly
```

-continued

```
        4995                5000                5005

Val Gln Gln Leu Ala Asn Ala Lys Gln Gln Ala Thr Gln Thr Val Asn
    5010                5015                5020

Gly Leu Asn Ser Leu Asn Asp Gly Gln Lys Arg Glu Leu Asn Leu Leu
5025                5030                5035                5040

Ile Asn Ser Ala Asn Thr Arg Thr Lys Val Gln Glu Glu Leu Asn Lys
                5045                5050                5055

Ala Thr Glu Leu Asn His Ala Met Glu Ala Leu Arg Asn Ser Val Gln
            5060                5065                5070

Asn Val Asp Gln Val Lys Gln Ser Ser Asn Tyr Val Asn Glu Asp Gln
        5075                5080                5085

Pro Glu Gln His Asn Tyr Asp Asn Ala Val Asn Glu Ala Gln Ala Thr
    5090                5095                5100

Ile Asn Asn Asn Ala Gln Pro Val Leu Asp Lys Leu Ala Ile Glu Arg
5105                5110                5115                5120

Leu Thr Gln Thr Val Asn Thr Thr Lys Asp Ala Leu His Gly Ala Gln
                5125                5130                5135

Lys Leu Thr Gln Asp Gln Gln Ala Ala Glu Thr Gly Ile Arg Gly Leu
            5140                5145                5150

Thr Ser Leu Asn Glu Pro Gln Lys Asn Ala Glu Val Ala Lys Val Thr
        5155                5160                5165

Ala Ala Thr Thr Arg Asp Glu Val Arg Asn Ile Arg Gln Glu Ala Thr
    5170                5175                5180

Thr Leu Asp Thr Ala Met Leu Gly Leu Arg Lys Ser Ile Lys Asp Lys
5185                5190                5195                5200

Asn Asp Thr Lys Asn Ser Ser Lys Tyr Ile Asn Glu Asp His Asp Gln
                5205                5210                5215

Gln Gln Ala Tyr Asp Asn Ala Val Asn Asn Ala Gln Gln Val Ile Asp
            5220                5225                5230

Glu Thr Gln Ala Thr Leu Ser Ser Asp Thr Ile Asn Gln Leu Ala Asn
        5235                5240                5245

Ala Val Thr Gln Ala Lys Ser Asn Leu His Gly Asp Thr Lys Leu Gln
    5250                5255                5260

His Asp Lys Asp Ser Ala Lys Gln Thr Ile Ala Gln Leu Gln Asn Leu
5265                5270                5275                5280

Asn Ser Ala Gln Lys His Met Glu Asp Ser Leu Ile Asp Asn Glu Ser
                5285                5290                5295

Thr Arg Thr Gln Val Gln His Asp Leu Thr Glu Ala Gln Ala Leu Asp
            5300                5305                5310

Gly Leu Met Gly Ala Leu Lys Glu Ser Ile Lys Asp Tyr Thr Asn Ile
        5315                5320                5325

Val Ser Asn Gly Asn Tyr Ile Asn Ala Glu Pro Ser Lys Lys Gln Ala
    5330                5335                5340

Tyr Asp Ala Ala Val Gln Asn Ala Gln Asn Ile Ile Asn Gly Thr Asn
5345                5350                5355                5360

Gln Pro Thr Ile Asn Lys Gly Asn Val Thr Thr Ala Thr Gln Thr Val
                5365                5370                5375

Lys Asn Thr Lys Asp Ala Leu Asp Gly Asp His Arg Leu Glu Glu Ala
            5380                5385                5390

Lys Asn Asn Ala Asn Gln Thr Ile Arg Asn Leu Ser Asn Leu Asn Asn
        5395                5400                5405

Ala Gln Lys Asp Ala Glu Lys Asn Leu Val Asn Ser Ala Ser Thr Leu
    5410                5415                5420
```

```
Glu Gln Val Gln Gln Asn Leu Gln Thr Ala Gln Gln Leu Asp Asn Ala
5425                5430                5435                5440

Met Gly Glu Leu Arg Gln Ser Ile Ala Lys Lys Asp Gln Val Lys Ala
                5445                5450                5455

Asp Ser Lys Tyr Leu Asn Glu Asp Pro Gln Ile Lys Gln Asn Tyr Asp
            5460                5465                5470

Asp Ala Val Gln Arg Val Glu Thr Ile Ile Asn Glu Thr Gln Asn Pro
        5475                5480                5485

Glu Leu Leu Lys Ala Asn Ile Asp Gln Ala Thr Gln Ser Val Gln Asn
    5490                5495                5500

Ala Glu Gln Ala Leu His Gly Ala Glu Lys Leu Asn Gln Asp Lys Gln
5505                5510                5515                5520

Thr Ser Ser Thr Glu Leu Asp Gly Leu Thr Asp Leu Thr Asp Ala Gln
                5525                5530                5535

Arg Glu Lys Leu Arg Glu Gln Ile Asn Thr Ser Asn Ser Arg Asp Asp
            5540                5545                5550

Ile Lys Gln Lys Ile Glu Gln Ala Lys Ala Leu Asn Asp Ala Met Lys
        5555                5560                5565

Lys Leu Lys Glu Gln Val Ala Gln Lys Asp Gly Val His Ala Asn Ser
    5570                5575                5580

Asp Tyr Thr Asn Glu Asp Ser Ala Gln Lys Asp Ala Tyr Asn Asn Ala
5585                5590                5595                5600

Leu Lys Gln Ala Glu Asp Ile Ile Asn Asn Ser Ser Asn Pro Asn Leu
                5605                5610                5615

Asn Ala Gln Asp Ile Thr Asn Ala Leu Asn Asn Ile Lys Gln Ala Gln
            5620                5625                5630

Asp Asn Leu His Gly Ala Gln Lys Leu Gln Gln Asp Lys Asn Thr Thr
        5635                5640                5645

Asn Gln Ala Ile Gly Asn Leu Asn His Leu Asn Gln Pro Gln Lys Asp
    5650                5655                5660

Ala Leu Ile Gln Ala Ile Asn Gly Ala Thr Ser Arg Asp Gln Val Ala
5665                5670                5675                5680

Glu Lys Leu Lys Glu Ala Glu Ala Leu Asp Glu Ala Met Lys Gln Leu
                5685                5690                5695

Glu Asp Gln Val Asn Gln Asp Asp Gln Ile Ser Asn Ser Ser Pro Phe
            5700                5705                5710

Ile Asn Glu Asp Ser Asp Lys Gln Lys Thr Tyr Asn Asp Lys Ile Gln
        5715                5720                5725

Ala Ala Lys Glu Ile Ile Asn Gln Thr Ser Asn Pro Thr Leu Asp Lys
    5730                5735                5740

Gln Lys Ile Ala Asp Thr Leu Gln Asn Ile Lys Asp Ala Val Asn Asn
5745                5750                5755                5760

Leu His Gly Asp Gln Lys Leu Ala Gln Ser Lys Gln Asp Ala Asn Asn
                5765                5770                5775

Gln Leu Asn His Leu Asp Asp Leu Thr Glu Glu Gln Lys Asn His Phe
            5780                5785                5790

Lys Pro Leu Ile Asn Asn Ala Asp Thr Arg Asp Glu Val Asn Lys Gln
        5795                5800                5805

Leu Glu Ile Ala Lys Gln Leu Asn Gly Asp Met Ser Thr Leu His Lys
    5810                5815                5820

Val Ile Asn Asp Lys Asp Gln Ile Gln His Leu Ser Asn Tyr Ile Asn
5825                5830                5835                5840
```

-continued

```
Ala Asp Asn Asp Lys Lys Gln Asn Tyr Asp Asn Ala Ile Lys Glu Ala
                5845                5850                5855

Glu Asp Leu Ile His Asn His Pro Asp Thr Leu Asp His Lys Ala Leu
            5860                5865                5870

Gln Asp Leu Leu Asn Lys Ile Asp Gln Ala His Asn Glu Leu Asn Gly
        5875                5880                5885

Glu Ser Arg Phe Lys Gln Ala Leu Asp Asn Ala Leu Asn Asp Ile Asp
    5890                5895                5900

Ser Leu Asn Ser Leu Asn Val Pro Gln Arg Gln Thr Val Lys Asp Asn
5905                5910                5915                5920

Ile Asn His Val Thr Thr Leu Glu Ser Leu Ala Gln Glu Leu Gln Lys
                5925                5930                5935

Ala Lys Glu Leu Asn Asp Ala Met Lys Ala Met Arg Asp Ser Ile Met
            5940                5945                5950

Asn Gln Glu Gln Ile Arg Lys Asn Ser Asn Tyr Thr Asn Glu Asp Leu
        5955                5960                5965

Ala Gln Gln Asn Ala Tyr Asn His Ala Val Asp Lys Ile Asn Asn Ile
    5970                5975                5980

Ile Gly Glu Asp Asn Ala Thr Met Asp Pro Gln Ile Ile Lys Gln Ala
5985                5990                5995                6000

Thr Gln Asp Ile Asn Thr Ala Ile Asn Gly Leu Asn Gly Asp Gln Lys
                6005                6010                6015

Leu Gln Asp Ala Lys Thr Asp Ala Lys Gln Gln Ile Thr Asn Phe Thr
            6020                6025                6030

Gly Leu Thr Glu Pro Gln Lys Gln Ala Leu Glu Asn Ile Ile Asn Gln
        6035                6040                6045

Gln Thr Ser Arg Ala Asn Val Ala Lys Gln Leu Ser His Ala Lys Phe
    6050                6055                6060

Leu Asn Gly Lys Met Glu Glu Leu Lys Val Ala Val Ala Lys Ala Ser
6065                6070                6075                6080

Leu Val Arg Gln Asn Ser Asn Tyr Ile Asn Glu Asp Val Ser Glu Lys
                6085                6090                6095

Glu Ala Tyr Glu Gln Ala Ile Ala Lys Gly Gln Glu Ile Ile Asn Ser
            6100                6105                6110

Glu Asn Asn Pro Thr Ile Ser Ser Thr Asp Ile Asn Arg Thr Ile Gln
        6115                6120                6125

Glu Ile Asn Asp Ala Glu Gln Asn Leu His Gly Asp Asn Lys Leu Arg
    6130                6135                6140

Gln Ala Gln Glu Ile Ala Lys Asn Glu Ile Gln Asn Leu Asp Gly Leu
6145                6150                6155                6160

Asn Ser Ala Gln Ile Thr Lys Leu Ile Gln Asp Ile Gly Arg Thr Thr
                6165                6170                6175

Thr Lys Pro Ala Val Thr Gln Lys Leu Glu Glu Ala Lys Ala Ile Asn
            6180                6185                6190

Gln Ala Met Gln Gln Leu Lys Gln Ser Ile Ala Asp Lys Asp Ala Thr
        6195                6200                6205

Leu Asn Ser Ser Asn Tyr Leu Asn Glu Asp Ser Glu Lys Lys Leu Ala
    6210                6215                6220

Tyr Asp Asn Ala Val Ser Gln Ala Glu Gln Leu Ile Asn Gln Leu Asn
6225                6230                6235                6240

Asp Pro Thr Met Asp Ile Ser Asn Ile Gln Ala Ile Thr Gln Lys Val
                6245                6250                6255

Ile Gln Ala Lys Asp Ser Leu His Gly Ala Asn Lys Leu Ala Gln Asn
```

6260 6265 6270

Gln Ala Asp Ser Asn Leu Ile Ile Asn Gln Ser Thr Asn Leu Asn Asp
6275 6280 6285

Lys Gln Lys Gln Ala Leu Asn Asp Leu Ile Asn His Ala Gln Thr Lys
6290 6295 6300

Gln Gln Val Ala Glu Ile Ile Ala Gln Ala Asn Lys Leu Asn Asn Glu
6305 6310 6315 6320

Met Gly Thr Leu Lys Thr Leu Val Glu Glu Gln Ser Asn Val His Gln
6325 6330 6335

Gln Ser Lys Tyr Ile Asn Glu Asp Pro Gln Val Gln Asn Ile Tyr Asn
6340 6345 6350

Asp Ser Ile Gln Lys Gly Arg Glu Ile Leu Asn Gly Thr Thr Asp Asp
6355 6360 6365

Val Leu Asn Asn Asn Lys Ile Ala Asp Ala Ile Gln Asn Ile His Leu
6370 6375 6380

Thr Lys Asn Asp Leu His Gly Asp Gln Lys Leu Gln Lys Ala Gln Gln
6385 6390 6395 6400

Asp Ala Thr Asn Glu Leu Asn Tyr Leu Thr Asn Leu Asn Asn Ser Gln
6405 6410 6415

Arg Gln Ser Glu His Asp Glu Ile Asn Ser Ala Pro Ser Arg Thr Glu
6420 6425 6430

Val Ser Asn Asp Leu Asn His Ala Lys Ala Leu Asn Glu Ala Met Arg
6435 6440 6445

Gln Leu Glu Asn Glu Val Ala Leu Glu Asn Ser Val Lys Lys Leu Ser
6450 6455 6460

Asp Phe Ile Asn Glu Asp Glu Ala Ala Gln Asn Glu Tyr Ser Asn Ala
6465 6470 6475 6480

Leu Gln Lys Ala Lys Asp Ile Ile Asn Gly Val Pro Ser Ser Thr Leu
6485 6490 6495

Asp Lys Ala Thr Ile Glu Asp Ala Leu Leu Glu Leu Gln Asn Ala Arg
6500 6505 6510

Glu Ser Leu His Gly Glu Gln Lys Leu Gln Glu Ala Lys Asn Gln Ala
6515 6520 6525

Val Ala Glu Ile Asp Asn Leu Gln Ala Leu Asn Pro Gly Gln Val Leu
6530 6535 6540

Ala Glu Lys Thr Leu Val Asn Gln Ala Ser Thr Lys Pro Glu Val Gln
6545 6550 6555 6560

Glu Ala Leu Gln Lys Ala Lys Glu Leu Asn Glu Ala Met Lys Ala Leu
6565 6570 6575

Lys Thr Glu Ile Asn Lys Lys Glu Gln Ile Lys Ala Asp Ser Arg Tyr
6580 6585 6590

Val Asn Ala Asp Ser Gly Leu Gln Ala Asn Tyr Asn Ser Ala Leu Asn
6595 6600 6605

Tyr Gly Ser Gln Ile Ile Ala Thr Thr Gln Pro Pro Glu Leu Asn Lys
6610 6615 6620

Asp Val Ile Asn Arg Ala Thr Gln Thr Ile Lys Thr Ala Glu Asn Asn
6625 6630 6635 6640

Leu Asn Gly Gln Ser Lys Leu Ala Glu Ala Lys Ser Asp Gly Asn Gln
6645 6650 6655

Ser Ile Glu His Leu Gln Gly Leu Thr Gln Ser Gln Lys Asp Lys Gln
6660 6665 6670

His Asp Leu Ile Asn Gln Ala Gln Thr Lys Gln Gln Val Asp Asp Ile
6675 6680 6685

-continued

```
Val Asn Asn Ser Lys Gln Leu Asp Asn Ser Met Asn Gln Leu Gln Gln
    6690                6695                6700

Ile Val Asn Asn Asp Asn Thr Val Lys Gln Asn Ser Asp Phe Ile Asn
6705                6710                6715                6720

Glu Asp Ser Ser Gln Gln Asp Ala Tyr Asn His Ala Ile Gln Ala Ala
                6725                6730                6735

Lys Asp Leu Ile Thr Ala His Pro Thr Ile Met Asp Lys Asn Gln Ile
            6740                6745                6750

Asp Gln Ala Ile Glu Asn Ile Lys Gln Ala Leu Asn Asp Leu His Gly
        6755                6760                6765

Ser Asn Lys Leu Ser Glu Asp Lys Lys Glu Ala Ser Glu Gln Leu Gln
    6770                6775                6780

Asn Leu Asn Ser Leu Thr Asn Gly Gln Lys Asp Thr Ile Leu Asn His
6785                6790                6795                6800

Ile Phe Ser Ala Pro Thr Arg Ser Gln Val Gly Glu Lys Ile Ala Ser
                6805                6810                6815

Ala Lys Gln Leu Asn Asn Thr Met Lys Ala Leu Arg Asp Ser Ile Ala
            6820                6825                6830

Asp Asn Asn Glu Ile Leu Gln Ser Ser Lys Tyr Phe Asn Glu Asp Ser
        6835                6840                6845

Glu Gln Gln Asn Ala Tyr Asn Gln Ala Val Asn Lys Ala Lys Asn Ile
    6850                6855                6860

Ile Asn Asp Gln Pro Thr Pro Val Met Ala Asn Asp Glu Ile Gln Ser
6865                6870                6875                6880

Val Leu Asn Glu Val Lys Gln Thr Lys Asp Asn Leu His Gly Asp Gln
                6885                6890                6895

Lys Leu Ala Asn Asp Lys Thr Asp Ala Gln Ala Thr Leu Asn Ala Leu
            6900                6905                6910

Asn Tyr Leu Asn Gln Ala Gln Arg Gly Asn Leu Glu Thr Lys Val Gln
        6915                6920                6925

Asn Ser Asn Ser Arg Pro Glu Val Gln Lys Val Val Gln Leu Ala Asn
    6930                6935                6940

Gln Leu Asn Asp Ala Met Lys Lys Leu Asp Asp Ala Leu Thr Gly Asn
6945                6950                6955                6960

Asp Ala Ile Lys Gln Thr Ser Asn Tyr Ile Asn Glu Asp Thr Ser Gln
                6965                6970                6975

Gln Val Asn Phe Asp Glu Tyr Thr Asp Arg Gly Lys Asn Ile Val Ala
            6980                6985                6990

Glu Gln Thr Asn Pro Asn Met Ser Pro Thr Asn Ile Asn Thr Ile Ala
        6995                7000                7005

Asp Lys Ile Thr Glu Ala Lys Asn Asp Leu His Gly Val Gln Lys Leu
    7010                7015                7020

Lys Gln Ala Gln Gln Gln Ser Ile Asn Thr Ile Asn Gln Met Thr Gly
7025                7030                7035                7040

Leu Asn Gln Ala Gln Lys Glu Gln Leu Asn Gln Glu Ile Gln Gln Thr
                7045                7050                7055

Gln Thr Arg Ser Glu Val His Gln Val Ile Asn Lys Ala Gln Ala Leu
            7060                7065                7070

Asn Asp Ser Met Asn Thr Leu Arg Gln Ser Ile Thr Asp Glu His Glu
        7075                7080                7085

Val Lys Gln Thr Ser Asn Tyr Ile Asn Glu Thr Val Gly Asn Gln Thr
    7090                7095                7100
```

-continued

```
Ala Tyr Asn Asn Ala Val Asp Arg Val Lys Gln Ile Ile Asn Gln Thr
7105                7110                7115                7120

Ser Asn Pro Thr Met Asn Pro Leu Glu Val Glu Arg Ala Thr Ser Asn
                7125                7130                7135

Val Lys Ile Ser Lys Asp Ala Leu His Gly Glu Arg Glu Leu Asn Asp
            7140                7145                7150

Asn Lys Asn Ser Lys Thr Phe Ala Val Asn His Leu Asp Asn Leu Asn
        7155                7160                7165

Gln Ala Gln Lys Glu Ala Leu Thr His Glu Ile Glu Gln Ala Thr Ile
    7170                7175                7180

Val Ser Gln Val Asn Asn Ile Tyr Asn Lys Ala Lys Ala Leu Asn Asn
7185                7190                7195                7200

Asp Met Lys Lys Leu Lys Asp Ile Val Ala Gln Gln Asp Asn Val Arg
                7205                7210                7215

Gln Ser Asn Asn Tyr Ile Asn Glu Asp Ser Thr Pro Gln Asn Met Tyr
            7220                7225                7230

Asn Asp Thr Ile Asn His Ala Gln Ser Ile Ile Asp Gln Val Ala Asn
        7235                7240                7245

Pro Thr Met Ser His Asp Glu Ile Glu Asn Ala Ile Asn Asn Ile Lys
    7250                7255                7260

His Ala Ile Asn Ala Leu Asp Gly Glu His Lys Leu Gln Gln Ala Lys
7265                7270                7275                7280

Glu Asn Ala Asn Leu Leu Ile Asn Ser Leu Asn Asp Leu Asn Ala Pro
                7285                7290                7295

Gln Arg Asp Ala Ile Asn Arg Leu Val Asn Glu Ala Gln Thr Arg Glu
            7300                7305                7310

Lys Val Ala Glu Gln Leu Gln Ser Ala Gln Ala Leu Asn Asp Ala Met
        7315                7320                7325

Lys His Leu Arg Asn Ser Ile Gln Asn Gln Ser Ser Val Arg Gln Glu
    7330                7335                7340

Ser Lys Tyr Ile Asn Ala Ser Asp Ala Lys Lys Glu Gln Tyr Asn His
7345                7350                7355                7360

Ala Val Arg Glu Val Glu Asn Ile Ile Asn Glu Gln His Pro Thr Leu
                7365                7370                7375

Asp Lys Glu Ile Ile Lys Gln Leu Thr Asp Gly Val Asn Gln Ala Asn
            7380                7385                7390

Asn Asp Leu Asn Gly Val Glu Leu Leu Asp Ala Asp Lys Gln Asn Ala
        7395                7400                7405

His Gln Ser Ile Pro Thr Leu Met His Leu Asn Gln Ala Gln Gln Asn
    7410                7415                7420

Ala Leu Asn Glu Lys Ile Asn Asn Ala Val Thr Arg Thr Glu Val Ala
7425                7430                7435                7440

Ala Ile Ile Gly Gln Ala Lys Leu Leu Asp His Ala Met Glu Asn Leu
                7445                7450                7455

Glu Glu Ser Ile Lys Asp Lys Glu Gln Val Lys Gln Ser Ser Asn Tyr
            7460                7465                7470

Ile Asn Glu Asp Ser Asp Val Gln Glu Thr Tyr Asp Asn Ala Val Asp
        7475                7480                7485

His Val Thr Glu Ile Leu Asn Gln Thr Val Asn Pro Thr Leu Ser Ile
    7490                7495                7500

Glu Asp Ile Glu His Ala Ile Asn Glu Val Asn Gln Ala Lys Lys Gln
7505                7510                7515                7520

Leu Arg Gly Lys Gln Lys Leu Tyr Gln Thr Ile Asp Leu Ala Asp Lys
```

-continued

```
                7525                7530                7535

Glu Leu Ser Lys Leu Asp Asp Leu Thr Ser Gln Gln Ser Ser Ile
            7540                7545                7550

Ser Asn Gln Ile Tyr Thr Ala Lys Thr Arg Thr Glu Val Ala Gln Ala
        7555                7560                7565

Ile Glu Lys Ala Lys Ser Leu Asn His Ala Met Lys Ala Leu Asn Lys
    7570                7575                7580

Val Tyr Lys Asn Ala Asp Lys Val Leu Asp Ser Ser Arg Phe Ile Asn
7585                7590                7595                7600

Glu Asp Gln Pro Glu Lys Lys Ala Tyr Gln Gln Ala Ile Asn His Val
                7605                7610                7615

Asp Ser Ile Ile His Arg Gln Thr Asn Pro Glu Met Asp Pro Thr Val
            7620                7625                7630

Ile Asn Ser Ile Thr His Glu Leu Glu Thr Ala Gln Asn Asn Leu His
        7635                7640                7645

Gly Asp Gln Lys Leu Ala His Ala Gln Gln Asp Ala Ala Asn Val Ile
    7650                7655                7660

Asn Gly Leu Ile His Leu Asn Val Ala Gln Arg Glu Val Met Ile Asn
7665                7670                7675                7680

Thr Asn Thr Asn Ala Thr Thr Arg Glu Lys Val Ala Lys Asn Leu Asp
                7685                7690                7695

Asn Ala Gln Ala Leu Asp Lys Ala Met Glu Thr Leu Gln Gln Val Val
            7700                7705                7710

Ala His Lys Asn Asn Ile Leu Asn Asp Ser Lys Tyr Leu Asn Glu Asp
        7715                7720                7725

Ser Lys Tyr Gln Gln Gln Tyr Asp Arg Val Ile Ala Asp Ala Glu Gln
    7730                7735                7740

Leu Leu Asn Gln Thr Thr Asn Pro Thr Leu Glu Pro Tyr Lys Val Asp
7745                7750                7755                7760

Ile Val Lys Asp Asn Val Leu Ala Asn Glu Lys Ile Leu Phe Gly Ala
                7765                7770                7775

Glu Lys Leu Ser Tyr Asp Lys Ser Asn Ala Asn Asp Glu Ile Lys His
            7780                7785                7790

Met Asn Tyr Leu Asn Asn Ala Gln Lys Gln Ser Ile Lys Asp Met Ile
        7795                7800                7805

Ser His Ala Ala Leu Arg Thr Glu Val Lys Gln Leu Leu Gln Gln Ala
    7810                7815                7820

Lys Ile Leu Asp Glu Ala Met Lys Ser Leu Glu Asp Lys Thr Gln Val
7825                7830                7835                7840

Val Ile Thr Asp Thr Thr Leu Pro Asn Tyr Thr Glu Ala Ser Glu Asp
                7845                7850                7855

Lys Lys Glu Lys Val Asp Gln Thr Val Ser His Ala Gln Ala Ile Ile
            7860                7865                7870

Asp Lys Ile Asn Gly Ser Asn Val Ser Leu Asp Gln Val Arg Gln Ala
        7875                7880                7885

Leu Glu Gln Leu Thr Gln Ala Ser Glu Asn Leu Asp Gly Asp Gln Arg
    7890                7895                7900

Val Glu Glu Ala Lys Val His Ala Asn Gln Thr Ile Asp Gln Leu Thr
7905                7910                7915                7920

His Leu Asn Ser Leu Gln Gln Gln Thr Ala Lys Glu Ser Val Lys Asn
                7925                7930                7935

Ala Thr Lys Leu Glu Glu Ile Ala Thr Val Ser Asn Asn Ala Gln Ala
            7940                7945                7950
```

```
Leu Asn Lys Val Met Gly Lys Leu Glu Gln Phe Ile Asn His Ala Asp
        7955                7960                7965

Ser Val Glu Asn Ser Asp Asn Tyr Arg Gln Ala Asp Asp Asp Lys Ile
    7970                7975                7980

Ile Ala Tyr Asp Glu Ala Leu Glu His Gly Gln Asp Ile Gln Lys Thr
7985                7990                7995                8000

Asn Ala Thr Gln Asn Glu Thr Lys Gln Ala Leu Gln Gln Leu Ile Tyr
                8005                8010                8015

Ala Glu Thr Ser Leu Asn Gly Phe Glu Arg Leu Asn His Ala Arg Pro
            8020                8025                8030

Arg Ala Leu Glu Tyr Ile Lys Ser Leu Glu Lys Ile Asn Asn Ala Gln
        8035                8040                8045

Lys Ser Ala Leu Glu Asp Lys Val Thr Gln Ser His Asp Leu Leu Glu
    8050                8055                8060

Leu Glu His Ile Val Asn Glu Gly Thr Asn Leu Asn Asp Ile Met Gly
8065                8070                8075                8080

Glu Leu Ala Asn Ala Ile Val Asn Asn Tyr Ala Pro Thr Lys Ala Ser
                8085                8090                8095

Ile Asn Tyr Ile Asn Ala Asp Asn Leu Arg Lys Asp Asn Phe Thr Gln
            8100                8105                8110

Ala Ile Asn Asn Ala Arg Asp Ala Leu Asn Lys Thr Gln Gly Gln Asn
        8115                8120                8125

Leu Asp Phe Asn Ala Ile Asp Thr Phe Lys Asp Asp Ile Phe Lys Thr
    8130                8135                8140

Lys Asp Ala Leu Asn Gly Ile Glu Arg Leu Thr Ala Ala Lys Ser Lys
8145                8150                8155                8160

Ala Glu Lys Leu Ile Asp Ser Leu Lys Phe Ile Asn Lys Ala Gln Phe
                8165                8170                8175

Thr His Ala Asn Asp Glu Ile Met Asn Thr Asn Ser Ile Ala Gln Leu
            8180                8185                8190

Ser Arg Ile Val Asn Gln Ala Phe Asp Leu Asn Asp Ala Met Lys Ser
        8195                8200                8205

Leu Arg Asp Glu Leu Asn Asn Gln Ala Phe Pro Val Gln Ala Ser Ser
    8210                8215                8220

Asn Tyr Ile Asn Ser Asp Glu Asp Leu Lys Gln Gln Phe Asp His Ala
8225                8230                8235                8240

Leu Ser Asn Ala Arg Lys Val Leu Ala Lys Glu Asn Gly Lys Asn Leu
                8245                8250                8255

Asp Glu Lys Gln Ile Gln Gly Leu Lys Gln Val Ile Glu Asp Thr Lys
            8260                8265                8270

Asp Ala Leu Asn Gly Ile Gln Arg Leu Ser Lys Ala Lys Ala Lys Ala
        8275                8280                8285

Ile Gln Tyr Val Gln Ser Leu Ser Tyr Ile Asn Asp Ala Gln Arg His
    8290                8295                8300

Ile Ala Glu Asn Asn Ile His Asn Ser Asp Asp Leu Ser Ser Leu Ala
8305                8310                8315                8320

Asn Thr Leu Ser Lys Ala Ser Asp Leu Asp Asn Ala Met Lys Asp Leu
                8325                8330                8335

Arg Asp Thr Ile Glu Ser Asn Ser Thr Ser Val Pro Asn Ser Val Asn
            8340                8345                8350

Tyr Ile Asn Ala Asp Lys Asn Leu Gln Ile Glu Phe Asp Glu Ala Leu
        8355                8360                8365
```

Gln Gln Ala Ser Ala Thr Ser Ser Lys Thr Ser Glu Asn Pro Ala Thr
8370 8375 8380

Ile Glu Glu Val Leu Gly Leu Ser Gln Ala Ile Tyr Asp Thr Lys Asn
8385 8390 8395 8400

Ala Leu Asn Gly Glu Gln Arg Leu Ala Thr Glu Lys Ser Lys Asp Leu
8405 8410 8415

Lys Leu Ile Lys Gly Leu Lys Asp Leu Asn Lys Ala Gln Leu Glu Asp
8420 8425 8430

Val Thr Asn Lys Val Asn Ser Ala Asn Thr Leu Thr Glu Leu Ser Gln
8435 8440 8445

Leu Thr Gln Ser Thr Leu Glu Leu Asn Asp Lys Met Lys Leu Leu Arg
8450 8455 8460

Asp Lys Leu Lys Thr Leu Val Asn Pro Val Lys Ala Ser Leu Asn Tyr
8465 8470 8475 8480

Arg Asn Ala Asp Tyr Asn Leu Lys Arg Gln Phe Asn Lys Ala Leu Lys
8485 8490 8495

Glu Ala Lys Gly Val Leu Asn Lys Asn Ser Gly Thr Asn Val Asn Ile
8500 8505 8510

Asn Asp Ile Gln His Leu Leu Thr Gln Ile Asp Asn Ala Lys Asp Gln
8515 8520 8525

Leu Asn Gly Glu Arg Arg Leu Lys Glu His Gln Gln Lys Ser Glu Val
8530 8535 8540

Phe Ile Ile Lys Glu Leu Asp Ile Leu Asn Asn Ala Gln Lys Ala Ala
8545 8550 8555 8560

Ile Ile Asn Gln Ile Arg Ala Ser Lys Asp Ile Lys Ile Ile Asn Gln
8565 8570 8575

Ile Val Asp Asn Ala Ile Glu Leu Asn Asp Ala Met Gln Gly Leu Lys
8580 8585 8590

Glu His Val Ala Gln Leu Thr Ala Thr Thr Lys Asp Asn Ile Glu Tyr
8595 8600 8605

Leu Asn Ala Asp Glu Asp His Lys Leu Gln Tyr Asp Tyr Ala Ile Asn
8610 8615 8620

Leu Ala Asn Asn Val Leu Asp Lys Glu Asn Gly Thr Asn Lys Asp Ala
8625 8630 8635 8640

Asn Ile Ile Ile Gly Met Ile Gln Asn Met Asp Asp Ala Arg Ala Leu
8645 8650 8655

Leu Asn Gly Ile Glu Arg Leu Lys Asp Ala Gln Thr Lys Ala His Asn
8660 8665 8670

Asp Ile Lys Asp Thr Leu Lys Arg Gln Leu Asp Glu Ile Glu His Ala
8675 8680 8685

Asn Ala Thr Ser Asn Ser Lys Ala Gln Ala Lys Gln Met Val Asn Glu
8690 8695 8700

Glu Ala Arg Lys Ala Leu Ser Asn Ile Asn Asp Ala Thr Ser Asn Asp
8705 8710 8715 8720

Leu Val Asn Gln Ala Lys Asp Glu Gly Gln Ser Ala Ile Glu His Ile
8725 8730 8735

His Ala Asp Glu Leu Pro Lys Ala Lys Leu Asp Ala Asn Gln Met Ile
8740 8745 8750

Asp Gln Lys Val Glu Asp Ile Asn His Leu Ile Ser Gln Asn Pro Asn
8755 8760 8765

Leu Ser Asn Glu Glu Lys Asn Lys Leu Ile Ser Gln Ile Asn Lys Leu
8770 8775 8780

Val Asn Gly Ile Lys Asn Glu Ile Gln Gln Ala Ile Asn Lys Gln Gln

-continued

```
8785                8790                8795                8800

Ile Glu Asn Ala Thr Thr Lys Leu Asp Glu Val Ile Glu Thr Thr Lys
                8805                8810                8815

Lys Leu Ile Ile Ala Lys Ala Glu Ala Lys Gln Met Ile Lys Glu Leu
            8820                8825                8830

Ser Gln Lys Lys Arg Asp Ala Ile Asn Asn Asn Thr Asp Leu Thr Pro
        8835                8840                8845

Ser Gln Lys Ala His Ala Leu Ala Asp Ile Asp Lys Thr Glu Lys Asp
    8850                8855                8860

Ala Leu Gln His Ile Glu Asn Ser Asn Ser Ile Asp Asp Ile Asn Asn
8865                8870                8875                8880

Asn Lys Glu His Ala Phe Asn Thr Leu Ala His Ile Ile Ile Trp Asp
                8885                8890                8895

Thr Asp Gln Gln Pro Leu Val Phe Glu Leu Pro Glu Leu Ser Leu Gln
            8900                8905                8910

Asn Ala Leu Val Thr Ser Glu Val Val Val His Arg Asp Glu Thr Ile
        8915                8920                8925

Ser Leu Glu Ser Ile Ile Gly Ala Met Thr Leu Thr Asp Glu Leu Lys
    8930                8935                8940

Val Asn Ile Val Ser Leu Pro Asn Thr Asp Lys Val Ala Asp His Leu
8945                8950                8955                8960

Thr Ala Lys Val Lys Val Ile Leu Ala Asp Gly Ser Tyr Val Thr Val
                8965                8970                8975

Asn Val Pro Val Lys Val Val Glu Lys Glu Leu Gln Ile Ala Lys Lys
            8980                8985                8990

Asp Ala Ile Lys Thr Ile Asp Val Leu Val Lys Gln Lys Ile Lys Asp
        8995                9000                9005

Ile Asp Ser Asn Asn Glu Leu Thr Ser Thr Gln Arg Glu Asp Ala Lys
    9010                9015                9020

Ala Glu Ile Glu Arg Leu Lys Lys Gln Ala Ile Asp Lys Val Asn His
9025                9030                9035                9040

Ser Lys Ser Ile Lys Asp Ile Glu Thr Val Lys Arg Thr Asp Phe Glu
                9045                9050                9055

Glu Ile Asp Gln Phe Asp Pro Lys Arg Phe Thr Leu Asn Lys Ala Lys
            9060                9065                9070

Lys Asp Ile Ile Thr Asp Val Asn Thr Gln Ile Gln Asn Gly Phe Lys
        9075                9080                9085

Glu Ile Glu Thr Ile Lys Gly Leu Thr Ser Asn Glu Lys Thr Gln Phe
    9090                9095                9100

Asp Lys Gln Leu Thr Ala Leu Gln Lys Glu Phe Leu Glu Lys Val Glu
9105                9110                9115                9120

His Ala His Asn Leu Val Glu Leu Asn Gln Leu Gln Gln Glu Phe Asn
                9125                9130                9135

Asn Arg Tyr Lys His Ile Leu Asn Gln Ala His Leu Leu Gly Glu Lys
            9140                9145                9150

His Ile Ala Glu His Lys Leu Gly Tyr Val Val Val Asn Lys Thr Gln
        9155                9160                9165

Gln Ile Leu Asn Asn Gln Ser Ala Ser Tyr Phe Ile Lys Gln Trp Ala
    9170                9175                9180

Leu Asp Arg Ile Lys Gln Ile Gln Leu Glu Thr Met Asn Ser Ile Arg
9185                9190                9195                9200

Gly Ala His Thr Val Gln Asp Val His Lys Ala Leu Leu Gln Gly Ile
                9205                9210                9215
```

Glu Gln Ile Leu Lys Val Asn Val Ser Ile Ile Asn Gln Ser Phe Asn
9220 9225 9230

Asp Ser Leu His Asn Phe Asn Tyr Leu His Ser Lys Phe Asp Ala Arg
9235 9240 9245

Leu Arg Glu Lys Asp Val Ala Asn His Ile Val Gln Thr Glu Thr Phe
9250 9255 9260

Lys Glu Val Leu Lys Gly Thr Gly Val Glu Pro Gly Lys Ile Asn Lys
9265 9270 9275 9280

Glu Thr Gln Gln Pro Lys Leu His Lys Asn Asp Asn Asp Ser Leu Phe
9285 9290 9295

Lys His Leu Val Asp Asn Phe Gly Lys Thr Val Gly Val Ile Thr Leu
9300 9305 9310

Thr Gly Leu Leu Ser Ser Phe Trp Leu Val Leu Ala Lys Arg Arg Lys
9315 9320 9325

Lys Glu Glu Glu Glu Lys Gln Ser Ile Lys Asn His His Lys Asp Ile
9330 9335 9340

Arg Leu Ser Asp Thr Asp Lys Ile Asp Pro Ile Val Ile Thr Lys Arg
9345 9350 9355 9360

Lys Ile Asp Lys Glu Glu Gln Ile Gln Asn Asp Asp Lys His Ser Ile
9365 9370 9375

Pro Val Ala Lys His Lys Lys Ser Lys Glu Lys Gln Leu Ser Glu Glu
9380 9385 9390

Asp Ile His Ser Ile Pro Val Val Lys Arg Lys Gln Asn Ser Asp Asn
9395 9400 9405

Lys Asp Thr Lys Gln Lys Lys Val Thr Ser Lys Lys Lys Lys Thr Pro
9410 9415 9420

Gln Ser Thr Lys Lys Val Val Lys Thr Lys Lys Arg Ser Lys Lys
9425 9430 9435

<210> SEQ ID NO 16
<211> LENGTH: 1115
<212> TYPE: PRT
<213> ORGANISM: Staphylococcus sp.

<400> SEQUENCE: 16

Met Arg Asp Lys Lys Gly Pro Val Asn Lys Arg Val Asp Phe Leu Ser
1 5 10 15

Asn Lys Leu Asn Lys Tyr Ser Ile Arg Lys Phe Thr Val Gly Thr Ala
20 25 30

Ser Ile Leu Ile Gly Ser Leu Met Tyr Leu Gly Thr Gln Gln Glu Ala
35 40 45

Glu Ala Ala Glu Asn Asn Ile Glu Asn Pro Thr Thr Leu Lys Asp Asn
50 55 60

Val Gln Ser Lys Glu Val Lys Ile Glu Glu Val Thr Asn Lys Asp Thr
65 70 75 80

Ala Pro Gln Gly Val Glu Ala Lys Ser Glu Val Thr Ser Asn Lys Asp
85 90 95

Thr Ile Glu His Glu Ala Ser Val Lys Ala Glu Asp Ile Ser Lys Lys
100 105 110

Glu Asp Thr Pro Lys Glu Val Ala Asn Val Ala Glu Val Gln Pro Lys
115 120 125

Ser Ser Val Thr His Asn Ala Glu Ala Pro Lys Val Arg Lys Ala Arg
130 135 140

Ser Val Asp Glu Gly Ser Phe Asp Ile Thr Arg Asp Ser Lys Asn Val

-continued

```
145                 150                 155                 160

Val Glu Ser Thr Pro Ile Thr Ile Gln Gly Lys Glu His Phe Glu Gly
                165                 170                 175

Tyr Gly Ser Val Asp Ile Gln Lys Asn Pro Thr Asp Leu Gly Val Ser
            180                 185                 190

Glu Val Thr Arg Phe Asn Val Gly Asn Glu Ser Asn Gly Leu Ile Gly
        195                 200                 205

Ala Leu Gln Leu Lys Asn Lys Ile Asp Phe Ser Lys Asp Phe Asn Phe
    210                 215                 220

Lys Val Arg Val Ala Asn Asn His Gln Ser Asn Thr Thr Gly Ala Asp
225                 230                 235                 240

Gly Trp Gly Phe Leu Phe Ser Lys Gly Asn Ala Glu Glu Tyr Leu Thr
                245                 250                 255

Asn Gly Gly Ile Leu Gly Asp Lys Gly Leu Val Asn Ser Gly Gly Phe
            260                 265                 270

Lys Ile Asp Thr Gly Tyr Ile Tyr Thr Ser Ser Met Asp Lys Thr Glu
        275                 280                 285

Lys Gln Ala Gly Gln Gly Tyr Arg Gly Tyr Gly Ala Phe Val Lys Asn
    290                 295                 300

Asp Ser Ser Gly Asn Ser Gln Met Val Gly Glu Asn Ile Asp Lys Ser
305                 310                 315                 320

Lys Thr Asn Phe Leu Asn Tyr Ala Asp Asn Ser Thr Asn Thr Ser Asp
                325                 330                 335

Gly Lys Phe His Gly Gln Arg Leu Asn Asp Val Ile Leu Thr Tyr Val
            340                 345                 350

Ala Ser Thr Gly Lys Met Arg Ala Glu Tyr Ala Gly Lys Thr Trp Glu
        355                 360                 365

Thr Ser Ile Thr Asp Leu Gly Leu Ser Lys Asn Gln Ala Tyr Asn Phe
    370                 375                 380

Leu Ile Thr Ser Ser Gln Arg Trp Gly Leu Asn Gln Gly Ile Asn Ala
385                 390                 395                 400

Asn Gly Trp Met Arg Thr Asp Leu Lys Gly Ser Glu Phe Thr Phe Thr
                405                 410                 415

Pro Glu Ala Pro Lys Thr Ile Thr Glu Leu Glu Lys Lys Val Glu Glu
            420                 425                 430

Ile Pro Phe Lys Lys Glu Arg Lys Phe Asn Pro Asp Leu Ala Pro Gly
        435                 440                 445

Thr Glu Lys Val Thr Arg Glu Gly Gln Lys Gly Glu Lys Thr Ile Thr
    450                 455                 460

Thr Pro Thr Leu Lys Asn Pro Leu Thr Gly Glu Ile Ile Ser Lys Gly
465                 470                 475                 480

Glu Ser Lys Glu Glu Ile Thr Lys Asp Pro Ile Asn Glu Leu Thr Glu
                485                 490                 495

Tyr Gly Pro Glu Thr Ile Ala Pro Gly His Arg Asp Glu Phe Asp Pro
            500                 505                 510

Lys Leu Pro Thr Gly Glu Lys Glu Glu Val Pro Gly Lys Pro Gly Ile
        515                 520                 525

Lys Asn Pro Glu Thr Gly Asp Val Val Arg Pro Pro Val Asp Ser Val
    530                 535                 540

Thr Lys Tyr Gly Pro Val Lys Gly Asp Ser Ile Val Glu Lys Glu Glu
545                 550                 555                 560

Ile Pro Phe Glu Lys Glu Arg Lys Phe Asn Pro Asp Leu Ala Pro Gly
                565                 570                 575
```

Thr Glu Lys Val Thr Arg Glu Gly Gln Lys Gly Glu Lys Thr Ile Thr
580 585 590

Thr Pro Thr Leu Lys Asn Pro Leu Thr Gly Glu Ile Ile Ser Lys Gly
595 600 605

Glu Ser Lys Glu Glu Ile Thr Lys Asp Pro Ile Asn Glu Leu Thr Glu
610 615 620

Tyr Gly Pro Glu Thr Ile Ala Pro Gly His Arg Asp Glu Phe Asp Pro
625 630 635 640

Lys Leu Pro Thr Gly Glu Lys Glu Glu Val Pro Gly Lys Pro Gly Ile
645 650 655

Lys Asn Pro Glu Thr Gly Asp Val Val Arg Pro Pro Val Asp Ser Val
660 665 670

Thr Lys Tyr Gly Pro Val Lys Gly Asp Ser Ile Val Glu Lys Glu Glu
675 680 685

Ile Pro Phe Lys Lys Glu Arg Lys Phe Asn Pro Asp Leu Ala Pro Gly
690 695 700

Thr Glu Lys Val Thr Arg Glu Gly Gln Lys Gly Glu Lys Thr Ile Thr
705 710 715 720

Thr Pro Thr Leu Lys Asn Pro Leu Thr Gly Glu Ile Ile Ser Lys Gly
725 730 735

Glu Ser Lys Glu Glu Ile Thr Lys Asp Pro Ile Asn Glu Leu Thr Glu
740 745 750

Tyr Gly Pro Glu Thr Ile Thr Pro Gly His Arg Asp Glu Phe Asp Pro
755 760 765

Lys Leu Pro Thr Gly Glu Lys Glu Glu Val Pro Gly Lys Pro Gly Ile
770 775 780

Lys Asn Pro Glu Thr Gly Asp Val Val Arg Pro Pro Val Asp Ser Val
785 790 795 800

Thr Lys Tyr Gly Pro Val Lys Gly Asp Ser Ile Val Glu Lys Glu Glu
805 810 815

Ile Pro Phe Glu Lys Glu Arg Lys Phe Asn Pro Asp Leu Ala Pro Gly
820 825 830

Thr Glu Lys Val Thr Arg Glu Gly Gln Lys Gly Glu Lys Thr Ile Thr
835 840 845

Thr Pro Thr Leu Lys Asn Pro Leu Thr Gly Glu Ile Ile Ser Lys Gly
850 855 860

Glu Ser Lys Glu Glu Ile Thr Lys Asp Pro Val Asn Glu Leu Thr Glu
865 870 875 880

Phe Gly Gly Glu Lys Ile Pro Gln Gly His Lys Asp Ile Phe Asp Pro
885 890 895

Asn Leu Pro Thr Asp Gln Thr Glu Lys Val Pro Gly Lys Pro Gly Ile
900 905 910

Lys Asn Pro Asp Thr Gly Lys Val Ile Glu Glu Pro Val Asp Asp Val
915 920 925

Ile Lys His Gly Pro Lys Thr Gly Thr Pro Glu Thr Lys Thr Val Glu
930 935 940

Ile Pro Phe Glu Thr Lys Arg Glu Phe Asn Pro Lys Leu Gln Pro Gly
945 950 955 960

Glu Glu Arg Val Lys Gln Glu Gly Gln Pro Gly Ser Lys Thr Ile Thr
965 970 975

Thr Pro Ile Thr Val Asn Pro Leu Thr Gly Glu Lys Val Gly Glu Gly
980 985 990

-continued

Gln Pro Thr Glu Glu Ile Thr Lys Gln Pro Val Asp Lys Ile Val Glu
995 1000 1005

Phe Gly Gly Glu Lys Pro Lys Asp Pro Lys Gly Pro Glu Asn Pro Glu
1010 1015 1020

Lys Pro Ser Arg Pro Thr His Pro Ser Gly Pro Val Asn Pro Asn Asn
1025 1030 1035 1040

Pro Gly Leu Ser Lys Asp Arg Ala Lys Pro Asn Gly Pro Val His Ser
1045 1050 1055

Met Asp Lys Asn Asp Lys Val Lys Lys Ser Lys Ile Ala Lys Glu Ser
1060 1065 1070

Val Ala Asn Gln Glu Lys Lys Arg Ala Glu Leu Pro Lys Thr Gly Leu
1075 1080 1085

Glu Ser Thr Gln Lys Gly Leu Ile Phe Ser Ser Ile Ile Gly Ile Ala
1090 1095 1100

Gly Leu Met Leu Leu Ala Arg Arg Arg Lys Asn
1105 1110 1115

<210> SEQ ID NO 17
<211> LENGTH: 1469
<212> TYPE: PRT
<213> ORGANISM: Staphylococcus sp.

<400> SEQUENCE: 17

Met Gly Lys Arg Arg Gln Gly Pro Ile Asn Lys Lys Val Asp Phe Leu
1 5 10 15

Pro Asn Lys Leu Asn Lys Tyr Ser Ile Arg Lys Phe Thr Val Gly Thr
20 25 30

Ala Ser Ile Leu Leu Gly Ser Thr Leu Ile Phe Gly Ser Ser Ser His
35 40 45

Glu Ala Lys Ala Ala Glu Glu Lys Gln Val Asp Pro Ile Thr Gln Ala
50 55 60

Asn Gln Asn Asp Ser Ser Glu Arg Ser Leu Glu Asn Thr Asn Gln Pro
65 70 75 80

Thr Val Asn Asn Glu Ala Pro Gln Met Ser Ser Thr Leu Gln Ala Glu
85 90 95

Glu Gly Ser Asn Ala Glu Ala Pro Asn Val Pro Thr Ile Lys Ala Asn
100 105 110

Ser Asp Asn Asp Thr Gln Thr Gln Phe Ser Glu Ala Pro Thr Arg Asn
115 120 125

Asp Leu Ala Arg Lys Glu Asp Ile Pro Ala Val Ser Lys Asn Glu Glu
130 135 140

Leu Gln Ser Ser Gln Pro Asn Thr Asp Ser Lys Ile Glu Pro Thr Thr
145 150 155 160

Ser Glu Pro Val Asn Leu Asn Tyr Ser Ser Pro Phe Met Ser Leu Leu
165 170 175

Ser Met Pro Ala Asp Ser Ser Ser Asn Asn Thr Lys Asn Thr Ile Asp
180 185 190

Ile Pro Pro Thr Thr Val Lys Gly Arg Asp Asn Tyr Asp Phe Tyr Gly
195 200 205

Arg Val Asp Ile Gln Ser Asn Pro Thr Asp Leu Asn Ala Thr Asn Leu
210 215 220

Thr Arg Tyr Asn Tyr Gly Gln Pro Pro Gly Thr Thr Thr Ala Gly Ala
225 230 235 240

Val Gln Phe Lys Asn Gln Val Ser Phe Asp Lys Asp Phe Asp Phe Asn
245 250 255

-continued

```
Ile Arg Val Ala Asn Asn Arg Gln Ser Asn Thr Thr Gly Ala Asp Gly
            260                 265                 270

Trp Gly Phe Met Phe Ser Lys Lys Asp Gly Asp Asp Phe Leu Lys Asn
        275                 280                 285

Gly Gly Ile Leu Arg Glu Lys Gly Thr Pro Ser Ala Ala Gly Phe Arg
    290                 295                 300

Ile Asp Thr Gly Tyr Tyr Asn Asn Asp Pro Leu Asp Lys Ile Gln Lys
305                 310                 315                 320

Gln Ala Gly Gln Gly Tyr Arg Gly Tyr Gly Thr Phe Val Lys Asn Asp
                325                 330                 335

Ser Gln Gly Asn Thr Ser Lys Val Gly Ser Gly Thr Pro Ser Thr Asp
            340                 345                 350

Phe Leu Asn Tyr Ala Asp Asn Thr Thr Asn Asp Leu Asp Gly Lys Phe
        355                 360                 365

His Gly Gln Lys Leu Asn Asn Val Asn Leu Lys Tyr Asn Ala Ser Asn
    370                 375                 380

Gln Thr Phe Thr Ala Thr Tyr Ala Gly Lys Thr Trp Thr Ala Thr Leu
385                 390                 395                 400

Ser Glu Leu Gly Leu Ser Pro Thr Asp Ser Tyr Asn Phe Leu Val Thr
                405                 410                 415

Ser Ser Gln Tyr Gly Asn Gly Asn Ser Gly Thr Tyr Ala Asp Gly Val
            420                 425                 430

Met Arg Ala Asp Leu Asp Gly Ala Thr Leu Thr Tyr Thr Pro Lys Ala
        435                 440                 445

Val Asp Gly Asp Pro Ile Thr Ser Thr Lys Glu Ile Pro Phe Asn Lys
    450                 455                 460

Lys Arg Glu Phe Asp Pro Asn Leu Ala Pro Gly Thr Glu Lys Val Val
465                 470                 475                 480

Gln Lys Gly Glu Pro Gly Ile Glu Thr Thr Thr Thr Pro Thr Tyr Val
                485                 490                 495

Asn Pro Asn Thr Gly Glu Lys Val Gly Glu Gly Thr Pro Thr Thr Lys
            500                 505                 510

Ile Thr Lys Gln Pro Val Asp Glu Ile Val His Tyr Gly Gly Glu Glu
        515                 520                 525

Ile Lys Pro Gly His Lys Asp Glu Phe Asp Pro Asn Ala Pro Lys Gly
    530                 535                 540

Ser Gln Thr Thr Gln Pro Gly Lys Pro Gly Val Lys Asn Pro Asp Thr
545                 550                 555                 560

Gly Glu Val Val Thr Pro Pro Val Asp Asp Val Thr Lys Tyr Gly Pro
                565                 570                 575

Val Asp Gly Asp Pro Ile Thr Ser Thr Glu Glu Ile Pro Phe Asp Lys
            580                 585                 590

Lys Arg Glu Phe Asn Pro Asp Leu Lys Pro Gly Glu Glu Arg Val Lys
        595                 600                 605

Gln Lys Gly Glu Pro Gly Thr Lys Thr Ile Thr Thr Pro Thr Thr Lys
    610                 615                 620

Asn Pro Leu Thr Gly Glu Lys Val Gly Glu Gly Glu Pro Thr Glu Lys
625                 630                 635                 640

Ile Thr Lys Gln Pro Val Asp Glu Ile Thr Glu Tyr Gly Gly Glu Glu
                645                 650                 655

Ile Lys Pro Gly His Lys Asp Glu Phe Asp Pro Asn Ala Pro Lys Gly
            660                 665                 670
```

```
Ser Gln Glu Asp Val Pro Gly Lys Pro Gly Val Lys Asn Pro Asp Thr
        675                 680                 685

Gly Glu Val Val Thr Pro Pro Val Asp Asp Val Thr Lys Tyr Gly Pro
    690                 695                 700

Val Asp Gly Asp Pro Ile Thr Ser Thr Glu Glu Ile Pro Phe Asp Lys
705                 710                 715                 720

Lys Arg Glu Phe Asp Pro Asn Leu Ala Pro Gly Thr Glu Lys Val Val
                725                 730                 735

Gln Lys Gly Glu Pro Gly Thr Lys Thr Ile Thr Thr Pro Thr Thr Lys
            740                 745                 750

Asn Pro Leu Thr Gly Glu Lys Val Gly Glu Gly Glu Pro Thr Glu Lys
        755                 760                 765

Ile Thr Lys Gln Pro Val Asp Glu Ile Val His Tyr Gly Gly Glu Glu
    770                 775                 780

Ile Lys Pro Gly His Lys Asp Glu Phe Asp Pro Asn Ala Pro Lys Gly
785                 790                 795                 800

Ser Gln Glu Asp Val Pro Gly Lys Pro Gly Val Lys Asn Pro Asp Thr
                805                 810                 815

Gly Glu Val Val Thr Pro Pro Val Asp Asp Val Thr Lys Tyr Gly Pro
            820                 825                 830

Val Asp Gly Asp Pro Ile Thr Ser Thr Glu Glu Ile Pro Phe Asp Lys
        835                 840                 845

Lys Arg Glu Phe Asn Pro Asp Leu Lys Pro Gly Glu Glu Arg Val Lys
    850                 855                 860

Gln Lys Gly Glu Pro Gly Thr Lys Thr Ile Thr Thr Pro Thr Thr Lys
865                 870                 875                 880

Asn Pro Leu Thr Gly Glu Lys Val Gly Glu Gly Glu Pro Thr Glu Lys
                885                 890                 895

Val Thr Lys Gln Pro Val Asp Glu Ile Val His Tyr Gly Gly Glu Glu
            900                 905                 910

Ile Lys Pro Gly His Lys Asp Glu Phe Asp Pro Asn Ala Pro Lys Gly
        915                 920                 925

Ser Gln Glu Asp Val Pro Gly Lys Pro Gly Val Lys Asn Pro Asp Thr
    930                 935                 940

Gly Glu Val Val Thr Pro Pro Val Asp Asp Val Thr Lys Tyr Gly Pro
945                 950                 955                 960

Val Asp Gly Asp Pro Ile Thr Ser Thr Glu Glu Ile Pro Phe Asp Lys
                965                 970                 975

Lys Arg Glu Phe Asp Pro Asn Leu Ala Pro Gly Thr Glu Lys Val Val
            980                 985                 990

Gln Lys Gly Glu Pro Gly Thr Lys Thr Ile Thr Thr Pro Thr Thr Lys
        995                 1000                1005

Asn Pro Leu Thr Gly Glu Lys Val Gly Glu Gly Glu Pro Thr Glu Lys
    1010                1015                1020

Ile Thr Lys Gln Pro Val Asp Glu Ile Val His Tyr Gly Gly Glu Glu
1025                1030                1035                1040

Ile Lys Pro Gly His Lys Asp Glu Phe Asp Pro Asn Ala Pro Lys Gly
                1045                1050                1055

Ser Gln Thr Thr Gln Pro Gly Lys Pro Gly Val Lys Asn Pro Asp Thr
            1060                1065                1070

Gly Glu Val Val Thr Pro Pro Val Asp Asp Val Thr Lys Tyr Gly Pro
        1075                1080                1085

Val Asp Gly Asp Pro Ile Thr Ser Thr Glu Glu Ile Pro Phe Asp Lys
```

```
    1090                1095                1100

Lys Arg Glu Phe Asp Pro Asn Leu Ala Pro Gly Thr Glu Lys Val Val
1105                1110                1115                1120

Gln Lys Gly Glu Pro Gly Thr Lys Thr Ile Thr Thr Pro Thr Thr Lys
                1125                1130                1135

Asn Pro Leu Thr Gly Glu Lys Val Gly Glu Gly Glu Pro Thr Glu Lys
            1140                1145                1150

Ile Thr Lys Gln Pro Val Asp Glu Ile Val His Tyr Gly Gly Glu Gln
        1155                1160                1165

Ile Pro Gln Gly His Lys Asp Glu Phe Asp Pro Asn Ala Pro Val Asp
    1170                1175                1180

Ser Lys Thr Glu Val Pro Gly Lys Pro Gly Val Lys Asn Pro Asp Thr
1185                1190                1195                1200

Gly Glu Val Val Thr Pro Pro Val Asp Asp Val Thr Lys Tyr Gly Pro
                1205                1210                1215

Lys Val Gly Asn Pro Ile Thr Ser Thr Glu Glu Ile Pro Phe Asp Lys
            1220                1225                1230

Lys Arg Val Phe Asn Pro Asp Leu Lys Pro Gly Glu Glu Arg Val Lys
        1235                1240                1245

Gln Lys Gly Glu Pro Gly Thr Lys Thr Ile Thr Thr Pro Ile Leu Val
    1250                1255                1260

Asn Pro Ile Thr Gly Glu Lys Val Gly Glu Gly Lys Ser Thr Glu Lys
1265                1270                1275                1280

Val Thr Lys Gln Pro Val Asp Glu Ile Val Glu Tyr Gly Pro Thr Lys
                1285                1290                1295

Ala Glu Pro Gly Lys Pro Ala Glu Pro Gly Lys Pro Ala Glu Pro Gly
            1300                1305                1310

Lys Pro Ala Glu Pro Gly Lys Pro Ala Glu Pro Gly Thr Pro Ala Glu
        1315                1320                1325

Pro Gly Lys Pro Ala Glu Pro Gly Lys Pro Ala Glu Pro Gly Lys Pro
    1330                1335                1340

Ala Glu Pro Gly Lys Pro Ala Glu Pro Gly Lys Pro Ala Glu Pro Gly
1345                1350                1355                1360

Thr Pro Ala Glu Pro Gly Lys Pro Ala Glu Pro Gly Lys Pro Ala Glu
                1365                1370                1375

Pro Gly Lys Pro Ala Glu Pro Gly Thr Pro Ala Glu Pro Gly Lys Pro
            1380                1385                1390

Ala Glu Pro Gly Thr Pro Ala Glu Pro Gly Lys Pro Ala Glu Pro Gly
        1395                1400                1405

Thr Pro Thr Gln Ser Gly Ala Pro Glu Gln Pro Asn Arg Ser Met His
    1410                1415                1420

Ser Thr Asp Asn Lys Asn Gln Leu Pro Asp Thr Gly Glu Asn Arg Gln
1425                1430                1435                1440

Ala Asn Glu Gly Thr Leu Val Gly Ser Leu Leu Ala Ile Val Gly Ser
                1445                1450                1455

Leu Phe Ile Phe Gly Arg Arg Lys Lys Gly Asn Glu Lys
            1460                1465


<210> SEQ ID NO 18
<211> LENGTH: 167
<212> TYPE: PRT
<213> ORGANISM: Staphylococcus sp.

<400> SEQUENCE: 18
```

-continued

```
Met Lys Lys Leu Tyr Thr Ser Tyr Gly Thr Tyr Gly Phe Leu His Gln
1               5                   10                  15

Ile Lys Ile Asn Asn Pro Thr His Gln Leu Phe Gln Phe Ser Ala Ser
            20                  25                  30

Asp Thr Ser Val Ile Phe Glu Glu Thr Asp Gly Glu Thr Val Leu Lys
        35                  40                  45

Ser Pro Ser Ile Tyr Glu Val Ile Lys Glu Ile Gly Glu Phe Ser Glu
    50                  55                  60

His His Phe Tyr Cys Ala Ile Phe Ile Pro Ser Thr Glu Asp His Ala
65                  70                  75                  80

Tyr Gln Leu Glu Lys Lys Leu Ile Ser Val Asp Asp Asn Phe Arg Asn
                85                  90                  95

Phe Gly Gly Phe Lys Ser Tyr Arg Leu Leu Arg Pro Ala Lys Gly Thr
            100                 105                 110

Thr Tyr Lys Ile Tyr Phe Gly Phe Ala Asp Arg His Ala Tyr Glu Asp
        115                 120                 125

Phe Lys Gln Ser Asp Ala Phe Asn Asp His Phe Ser Lys Asp Ala Leu
    130                 135                 140

Ser His Tyr Phe Gly Ser Ser Gly Gln His Ser Ser Tyr Phe Glu Arg
145                 150                 155                 160

Tyr Leu Tyr Pro Ile Lys Glu
                165
```

<210> SEQ ID NO 19
<211> LENGTH: 167
<212> TYPE: PRT
<213> ORGANISM: Staphylococcus sp.

<400> SEQUENCE: 19

```
Met Tyr Leu Tyr Thr Ser Tyr Gly Thr Tyr Gln Phe Leu Asn Gln Ile
1               5                   10                  15

Lys Leu Asn His Gln Glu Arg Ser Leu Phe Gln Phe Ser Thr Asn Asp
            20                  25                  30

Ser Ser Ile Ile Leu Glu Glu Ser Glu Gly Lys Ser Ile Leu Lys His
        35                  40                  45

Pro Ser Ala Tyr Gln Val Ile Asp Ser Thr Gly Glu Phe Asn Glu His
    50                  55                  60

His Phe Tyr Ser Ala Ile Phe Val Pro Thr Ser Glu Asp His Arg Gln
65                  70                  75                  80

Gln Leu Glu Lys Lys Leu Leu Leu Val Asp Val Pro Leu Arg Asn Phe
                85                  90                  95

Gly Gly Phe Lys Ser Tyr Arg Leu Leu Lys Pro Thr Glu Gly Ser Thr
            100                 105                 110

Tyr Lys Ile Tyr Phe Gly Phe Ala Asn Arg Thr Ala Tyr Glu Asp Phe
        115                 120                 125

Lys Ala Ser Asp Ile Phe Asn Glu Asn Phe Ser Lys Asp Ala Leu Ser
    130                 135                 140

Gln Tyr Phe Gly Ala Ser Gly Gln His Ser Ser Tyr Phe Glu Arg Tyr
145                 150                 155                 160

Leu Tyr Pro Ile Glu Asp His
                165
```

<210> SEQ ID NO 20
<211> LENGTH: 1141
<212> TYPE: PRT
<213> ORGANISM: Staphylococcus sp.

<400> SEQUENCE: 20

Met Ile Asn Arg Asp Asn Lys Lys Ala Ile Thr Lys Lys Gly Met Ile
1               5                   10                  15

Ser Asn Arg Leu Asn Lys Phe Ser Ile Arg Lys Tyr Thr Val Gly Thr
            20                  25                  30

Ala Ser Ile Leu Val Gly Thr Thr Leu Ile Phe Gly Leu Gly Asn Gln
        35                  40                  45

Glu Ala Lys Ala Ala Glu Asn Thr Ser Thr Glu Asn Ala Lys Gln Asp
    50                  55                  60

Asp Ala Thr Thr Ser Asp Asn Lys Glu Val Val Ser Glu Thr Glu Asn
65                  70                  75                  80

Asn Ser Thr Thr Glu Asn Asp Ser Thr Asn Pro Ile Lys Lys Glu Thr
                85                  90                  95

Asn Thr Asp Ser Gln Pro Glu Ala Lys Glu Glu Ser Thr Thr Ser Ser
            100                 105                 110

Thr Gln Gln Gln Gln Asn Asn Val Thr Ala Thr Thr Glu Thr Lys Pro
        115                 120                 125

Gln Asn Ile Glu Lys Glu Asn Val Lys Pro Ser Thr Asp Lys Thr Ala
    130                 135                 140

Thr Glu Asp Thr Ser Val Ile Leu Glu Glu Lys Lys Ala Pro Asn Tyr
145                 150                 155                 160

Thr Asn Asn Asp Val Thr Thr Lys Pro Ser Thr Ser Glu Ile Gln Thr
                165                 170                 175

Lys Pro Thr Thr Pro Gln Glu Ser Thr Asn Ile Glu Asn Ser Gln Pro
            180                 185                 190

Gln Pro Thr Pro Ser Lys Val Asp Asn Gln Val Thr Asp Ala Thr Asn
        195                 200                 205

Pro Lys Glu Pro Val Asn Val Ser Lys Glu Glu Leu Lys Asn Asn Pro
    210                 215                 220

Glu Lys Leu Lys Glu Leu Val Arg Asn Asp Asn Asn Thr Asp Arg Ser
225                 230                 235                 240

Thr Lys Pro Val Ala Thr Ala Pro Thr Ser Val Ala Pro Lys Arg Leu
                245                 250                 255

Asn Ala Lys Met Arg Phe Ala Val Ala Gln Pro Ala Ala Val Ala Ser
            260                 265                 270

Asn Asn Val Asn Asp Leu Ile Thr Val Thr Lys Gln Thr Ile Lys Val
        275                 280                 285

Gly Asp Gly Lys Asp Asn Val Ala Ala Ala His Asp Gly Lys Asp Ile
    290                 295                 300

Glu Tyr Asp Thr Glu Phe Thr Ile Asp Asn Lys Val Lys Lys Gly Asp
305                 310                 315                 320

Thr Met Thr Ile Asn Tyr Asp Lys Asn Val Ile Pro Ser Asp Leu Thr
                325                 330                 335

Asp Lys Asn Asp Pro Ile Asp Ile Thr Asp Pro Ser Gly Glu Val Ile
            340                 345                 350

Ala Lys Gly Thr Phe Asp Lys Ala Thr Lys Gln Ile Thr Tyr Thr Phe
        355                 360                 365

Thr Asp Tyr Val Asp Lys Tyr Glu Asp Ile Lys Ala Arg Leu Thr Leu
    370                 375                 380

Tyr Ser Tyr Ile Asp Lys Gln Ala Val Pro Asn Glu Thr Ser Leu Asn
385                 390                 395                 400

Leu Thr Phe Ala Thr Ala Gly Lys Glu Thr Ser Gln Asn Val Ser Val

```
                405                 410                 415

Asp Tyr Gln Asp Pro Met Val His Gly Asp Ser Asn Ile Gln Ser Ile
            420                 425                 430

Phe Thr Lys Leu Asp Glu Asn Lys Gln Thr Ile Glu Gln Gln Ile Tyr
        435                 440                 445

Val Asn Pro Leu Lys Lys Thr Ala Thr Asn Thr Lys Val Asp Ile Ala
    450                 455                 460

Gly Ser Gln Val Asp Asp Tyr Gly Asn Ile Lys Leu Gly Asn Gly Ser
465                 470                 475                 480

Thr Ile Ile Asp Gln Asn Thr Glu Ile Lys Val Tyr Lys Val Asn Pro
                485                 490                 495

Asn Gln Gln Leu Pro Gln Ser Asn Arg Ile Tyr Asp Phe Ser Gln Tyr
            500                 505                 510

Glu Asp Val Thr Ser Gln Phe Asp Asn Lys Lys Ser Phe Ser Asn Asn
        515                 520                 525

Val Ala Thr Leu Asp Phe Gly Asp Ile Asn Ser Ala Tyr Ile Ile Lys
    530                 535                 540

Val Val Ser Lys Tyr Thr Pro Thr Ser Asp Gly Glu Leu Asp Ile Ala
545                 550                 555                 560

Gln Gly Thr Ser Met Arg Thr Thr Asp Lys Tyr Gly Tyr Tyr Asn Tyr
                565                 570                 575

Ala Gly Tyr Ser Asn Phe Ile Val Thr Ser Asn Asp Thr Gly Gly Gly
            580                 585                 590

Asp Gly Thr Val Lys Pro Glu Glu Lys Leu Tyr Lys Ile Gly Asp Tyr
        595                 600                 605

Val Trp Glu Asp Val Asp Lys Asp Gly Val Gln Gly Thr Asp Ser Lys
    610                 615                 620

Glu Lys Pro Met Ala Asn Val Leu Val Thr Leu Thr Tyr Pro Asp Gly
625                 630                 635                 640

Thr Thr Lys Ser Val Arg Thr Asp Ala Asn Gly His Tyr Glu Phe Gly
                645                 650                 655

Gly Leu Lys Asp Gly Glu Thr Tyr Thr Val Lys Phe Glu Thr Pro Ala
            660                 665                 670

Gly Tyr Leu Pro Thr Lys Val Asn Gly Thr Thr Asp Gly Glu Lys Asp
        675                 680                 685

Ser Asn Gly Ser Ser Ile Thr Val Lys Ile Asn Gly Lys Asp Asp Met
    690                 695                 700

Ser Leu Asp Thr Gly Phe Tyr Lys Glu Pro Lys Tyr Asn Leu Gly Asp
705                 710                 715                 720

Tyr Val Trp Glu Asp Thr Asn Lys Asp Gly Ile Gln Asp Ala Asn Glu
                725                 730                 735

Pro Gly Ile Lys Asp Val Lys Val Thr Leu Lys Asp Ser Thr Gly Lys
            740                 745                 750

Val Ile Gly Thr Thr Thr Thr Asp Ala Ser Gly Lys Tyr Lys Phe Thr
        755                 760                 765

Asp Leu Asp Asn Gly Asn Tyr Thr Val Glu Phe Glu Thr Pro Ala Gly
    770                 775                 780

Tyr Thr Pro Thr Val Lys Asn Thr Thr Ala Glu Asp Lys Asp Ser Asn
785                 790                 795                 800

Gly Leu Thr Thr Thr Gly Val Ile Lys Asp Ala Asp Asn Met Thr Leu
                805                 810                 815

Asp Ser Gly Phe Tyr Lys Thr Pro Lys Tyr Ser Leu Gly Asp Tyr Val
            820                 825                 830
```

-continued

```
Trp Tyr Asp Ser Asn Lys Asp Gly Lys Gln Asp Ser Thr Glu Lys Gly
        835                 840                 845

Ile Lys Asp Val Lys Val Thr Leu Leu Asn Glu Lys Gly Glu Val Ile
    850                 855                 860

Gly Thr Thr Lys Thr Asp Glu Asn Gly Lys Tyr Arg Phe Asp Asn Leu
865                 870                 875                 880

Asp Ser Gly Lys Tyr Lys Val Ile Phe Glu Lys Pro Ala Gly Leu Thr
                885                 890                 895

Gln Thr Val Thr Asn Thr Thr Glu Asp Asp Lys Asp Ala Asp Gly Gly
            900                 905                 910

Glu Val Asp Val Thr Ile Thr Asp His Asp Asp Phe Ile Leu Asp Asn
        915                 920                 925

Gly Tyr Phe Glu Glu Asp Thr Ser Asp Ser Asp Ser Asp Ser Asp Ser
    930                 935                 940

Asp Ser Asp Ser Asp Ser Asp Ser Asp Ser Asp Ser Asp Ser Asp Ser
945                 950                 955                 960

Asp Ser Asp Ser Asp Ser Asp Ser Asp Ser Asp Ser Asp Ser Asp Ser
                965                 970                 975

Asp Ser Asp Ser Asp Ser Asp Ser Asp Ser Asp Ser Asp Ser Asp Ser
            980                 985                 990

Asp Ser Asp Ser Asp Ser Asp Ser Asp Ser Asp Ser Asp Ser Asp Ser
        995                 1000                1005

Asp Ser Asp Ser Asp Ser Asp Ser Asp Ser Asp Ser Asp Ser Asp Ser
    1010                1015                1020

Asp Ser Asp Ser Asp Ser Asp Ser Asp Ser Asp Ser Asp Ser Asp Ser
1025                1030                1035                1040

Asp Ser Asp Ser Asp Ser Asp Ser Asp Ser Asp Ser Asp Ser Asp Ser
                1045                1050                1055

Asp Ser Asp Ser Asp Ser Asp Ser Asp Ser Asp Ser Asp Ser Asp Ser
            1060                1065                1070

Asp Ser Asp Ser Asp Ser Asp Ser Asp Ala Gly Lys His Thr Pro Val
        1075                1080                1085

Lys Pro Met Ser Thr Thr Lys Asp His His Asn Lys Ala Lys Ala Leu
    1090                1095                1100

Pro Glu Thr Gly Ser Glu Asn Asn Gly Ser Asn Asn Ala Thr Leu Phe
1105                1110                1115                1120

Gly Gly Leu Phe Ala Ala Leu Gly Ser Leu Leu Leu Phe Gly Arg Arg
                1125                1130                1135

Lys Lys Gln Asn Lys
            1140


<210> SEQ ID NO 21
<211> LENGTH: 1056
<212> TYPE: PRT
<213> ORGANISM: Staphylococcus sp.

<400> SEQUENCE: 21

Met Ile Asn Lys Lys Asn Asn Leu Leu Thr Lys Lys Lys Pro Ile Ala
1               5                   10                  15

Asn Lys Ser Asn Lys Tyr Ala Ile Arg Lys Phe Thr Val Gly Thr Ala
            20                  25                  30

Ser Ile Val Ile Gly Ala Thr Leu Leu Phe Gly Leu Gly His Asn Glu
        35                  40                  45

Ala Lys Ala Glu Glu Asn Ser Val Gln Asp Val Lys Asp Ser Asn Thr
```

```
    50                  55                  60

Asp Asp Glu Leu Ser Asp Ser Asn Asp Gln Ser Ser Asp Glu Glu Lys
65                  70                  75                  80

Asn Asp Val Ile Asn Asn Asn Gln Ser Ile Asn Thr Asp Asp Asn Asn
                85                  90                  95

Gln Ile Ile Lys Lys Glu Glu Thr Asn Asn Tyr Asp Gly Ile Glu Lys
            100                 105                 110

Arg Ser Glu Asp Arg Thr Glu Ser Thr Thr Asn Val Asp Glu Asn Glu
        115                 120                 125

Ala Thr Phe Leu Gln Lys Thr Pro Gln Asp Asn Thr His Leu Thr Glu
    130                 135                 140

Glu Glu Val Lys Glu Ser Ser Ser Val Glu Ser Ser Asn Ser Ser Ile
145                 150                 155                 160

Asp Thr Ala Gln Gln Pro Ser His Thr Thr Ile Asn Arg Glu Glu Ser
                165                 170                 175

Val Gln Thr Ser Asp Asn Val Glu Asp Ser His Val Ser Asp Phe Ala
            180                 185                 190

Asn Ser Lys Ile Lys Glu Ser Asn Thr Glu Ser Gly Lys Glu Glu Asn
        195                 200                 205

Thr Ile Glu Gln Pro Asn Lys Val Lys Glu Asp Ser Thr Thr Ser Gln
    210                 215                 220

Pro Ser Gly Tyr Thr Asn Ile Asp Glu Lys Ile Ser Asn Gln Asp Glu
225                 230                 235                 240

Leu Leu Asn Leu Pro Ile Asn Glu Tyr Glu Asn Lys Ala Arg Pro Leu
                245                 250                 255

Ser Thr Thr Ser Ala Gln Pro Ser Ile Lys Arg Val Thr Val Asn Gln
            260                 265                 270

Leu Ala Ala Glu Gln Gly Ser Asn Val Asn His Leu Ile Lys Val Thr
        275                 280                 285

Asp Gln Ser Ile Thr Glu Gly Tyr Asp Asp Ser Glu Gly Val Ile Lys
    290                 295                 300

Ala His Asp Ala Glu Asn Leu Ile Tyr Asp Val Thr Phe Glu Val Asp
305                 310                 315                 320

Asp Lys Val Lys Ser Gly Asp Thr Met Thr Val Asp Ile Asp Lys Asn
                325                 330                 335

Thr Val Pro Ser Asp Leu Thr Asp Ser Phe Thr Ile Pro Lys Ile Lys
            340                 345                 350

Asp Asn Ser Gly Glu Ile Ile Ala Thr Gly Thr Tyr Asp Asn Lys Asn
        355                 360                 365

Lys Gln Ile Thr Tyr Thr Phe Thr Asp Tyr Val Asp Lys Tyr Glu Asn
    370                 375                 380

Ile Lys Ala His Leu Lys Leu Thr Ser Tyr Ile Asp Lys Ser Lys Val
385                 390                 395                 400

Pro Asn Asn Asn Thr Lys Leu Asp Val Glu Tyr Lys Thr Ala Leu Ser
                405                 410                 415

Ser Val Asn Lys Thr Ile Thr Val Glu Tyr Gln Arg Pro Asn Glu Asn
            420                 425                 430

Arg Thr Ala Asn Leu Gln Ser Met Phe Thr Asn Ile Asp Thr Lys Asn
        435                 440                 445

His Thr Val Glu Gln Thr Ile Tyr Ile Asn Pro Leu Arg Tyr Ser Ala
    450                 455                 460

Lys Glu Thr Asn Val Asn Ile Ser Gly Asn Gly Asp Glu Gly Ser Thr
465                 470                 475                 480
```

-continued

```
Ile Ile Asp Asp Ser Thr Ile Ile Lys Val Tyr Lys Val Gly Asp Asn
                485                 490                 495

Gln Asn Leu Pro Asp Ser Asn Arg Ile Tyr Asp Tyr Ser Glu Tyr Glu
            500                 505                 510

Asp Val Thr Asn Asp Asp Tyr Ala Gln Leu Gly Asn Asn Asn Asp Val
        515                 520                 525

Asn Ile Asn Phe Gly Asn Ile Asp Ser Pro Tyr Ile Ile Lys Val Ile
    530                 535                 540

Ser Lys Tyr Asp Pro Asn Lys Asp Asp Tyr Thr Thr Ile Gln Gln Thr
545                 550                 555                 560

Val Thr Met Gln Thr Thr Ile Asn Glu Tyr Thr Gly Glu Phe Arg Thr
                565                 570                 575

Ala Ser Tyr Asp Asn Thr Ile Ala Phe Ser Thr Ser Ser Gly Gln Gly
            580                 585                 590

Gln Gly Asp Leu Pro Pro Glu Lys Thr Tyr Lys Ile Gly Asp Tyr Val
        595                 600                 605

Trp Glu Asp Val Asp Lys Asp Gly Ile Gln Asn Thr Asn Asp Asn Glu
    610                 615                 620

Lys Pro Leu Ser Asn Val Leu Val Thr Leu Thr Tyr Pro Asp Gly Thr
625                 630                 635                 640

Ser Lys Ser Val Arg Thr Asp Glu Asp Gly Lys Tyr Gln Phe Asp Gly
                645                 650                 655

Leu Lys Asn Gly Leu Thr Tyr Lys Ile Thr Phe Glu Thr Pro Glu Gly
            660                 665                 670

Tyr Thr Pro Thr Leu Lys His Ser Gly Thr Asn Pro Ala Leu Asp Ser
        675                 680                 685

Glu Gly Asn Ser Val Trp Val Thr Ile Asn Gly Gln Asp Asp Met Thr
    690                 695                 700

Ile Asp Ser Gly Phe Tyr Gln Thr Pro Lys Tyr Ser Leu Gly Asn Tyr
705                 710                 715                 720

Val Trp Tyr Asp Thr Asn Lys Asp Gly Ile Gln Gly Asp Asp Glu Lys
                725                 730                 735

Gly Ile Ser Gly Val Lys Val Thr Leu Lys Asp Glu Asn Gly Asn Ile
            740                 745                 750

Ile Ser Thr Thr Thr Thr Asp Glu Asn Gly Lys Tyr Gln Phe Asp Asn
        755                 760                 765

Leu Asn Ser Gly Asn Tyr Ile Val His Phe Asp Lys Pro Ser Gly Met
    770                 775                 780

Thr Gln Thr Thr Thr Asp Ser Gly Asp Asp Asp Glu Gln Asp Ala Asp
785                 790                 795                 800

Gly Glu Glu Val His Val Thr Ile Thr Asp His Asp Asp Phe Ser Ile
                805                 810                 815

Asp Asn Gly Tyr Tyr Asp Asp Glu Ser Asp Ser Asp Ser Asp Ser Asp
            820                 825                 830

Ser Asp Ser Asp Ser Asp Ser Asp Ser Asp Ser Asp Ser Asp Ser Asp
        835                 840                 845

Ser Asp Ser Asp Ser Asp Ser Asp Ser Asp Ser Asp Ser Asp Ser Asp
    850                 855                 860

Ser Asp Ser Asp Ser Asp Ser Asp Ser Asp Ser Asp Ser Asp Ser Asp
865                 870                 875                 880

Ser Asp Ser Asp Ser Asp Ser Asp Ser Asp Ser Asp Ser Asp Ser Asp
                885                 890                 895
```

-continued

```
Ser Asp Ser Asp Ser Asp Ser Asp Ser Asp Ser Asp Ser Asp Ser Asp
            900                 905                 910

Ser Asp Ser Asp Ser Asp Ser Asp Ser Asp Ser Asp Ser Asp Ser Asp
        915                 920                 925

Ser Asp Ser Asp Ser Asp Ser Asp Ser Asp Ser Asp Ser Asp Ser Asp
    930                 935                 940

Ser Asp Ser Asp Ser Asp Ser Asp Ser Asp Ser Asp Ser Asp Ser Asp
945                 950                 955                 960

Ser Asp Ser Asp Ser Asp Ser Asp Ser Asp Ser Asp Ser Asp Ser Asp
                965                 970                 975

Ser Asp Ser Asp Ser Asp Ser Asp Ser Asp Ser Asp Ser Asp Ser Asp
            980                 985                 990

Ser Asp Ser Asp Ser Asp Ser Asp Asn Asp Ser Asp Leu Gly Asn Ser
        995                 1000                1005

Ser Asp Lys Ser Thr Lys Asp Lys Leu Pro Asp Thr Gly Ala Asn Glu
    1010                1015                1020

Asp Tyr Gly Ser Lys Gly Thr Leu Leu Gly Thr Leu Phe Ala Gly Leu
1025                1030                1035                1040

Gly Ala Leu Leu Leu Gly Lys Arg Arg Lys Asn Arg Lys Asn Lys Asn
                1045                1050                1055


<210> SEQ ID NO 22
<211> LENGTH: 486
<212> TYPE: PRT
<213> ORGANISM: Staphylococcus sp.

<400> SEQUENCE: 22

Met Ser Asn Asn Phe Lys Asp Asp Phe Glu Lys Asn Arg Gln Ser Ile
1               5                   10                  15

Asp Thr Asn Ser His Gln Asp His Thr Glu Asp Val Glu Lys Asp Gln
            20                  25                  30

Ser Glu Leu Glu His Gln Asp Thr Ile Glu Asn Thr Glu Gln Gln Phe
        35                  40                  45

Pro Pro Arg Asn Ala Gln Arg Arg Lys Arg Arg Arg Asp Leu Ala Thr
    50                  55                  60

Asn His Asn Lys Gln Val His Asn Glu Ser Gln Thr Ser Glu Asp Asn
65                  70                  75                  80

Val Gln Asn Glu Ala Gly Thr Ile Asp Asp Arg Gln Val Glu Ser Ser
                85                  90                  95

His Ser Thr Glu Ser Gln Glu Pro Ser His Gln Asp Ser Thr Pro Gln
            100                 105                 110

His Glu Glu Glu Tyr Tyr Asn Lys Asn Ala Phe Ala Met Asp Lys Ser
        115                 120                 125

His Pro Glu Pro Ile Glu Asp Asn Asp Lys His Glu Thr Ile Lys Asp
    130                 135                 140

Ala Glu Asn Asn Thr Glu His Ser Thr Val Ser Asp Lys Ser Ile Ala
145                 150                 155                 160

Glu Gln Ser Gln Gln Pro Lys Pro Tyr Phe Ala Thr Gly Ala Asn Gln
                165                 170                 175

Ala Asn Thr Ser Lys Asp Lys His Asp Asp Val Thr Val Lys Gln Asp
            180                 185                 190

Lys Asp Glu Ser Lys Asp His His Ser Gly Lys Lys Gly Ala Ala Ile
        195                 200                 205

Gly Ala Gly Thr Ala Gly Val Ala Gly Ala Ala Gly Ala Met Gly Val
    210                 215                 220
```

```
Ser Lys Ala Lys Lys His Ser Asn Asp Ala Gln Asn Lys Ser Asn Ser
225                 230                 235                 240

Asp Lys Ser Asn Asn Ser Thr Glu Asp Lys Ala Ser Gln Asp Lys Ser
                245                 250                 255

Lys Asp His His Asn Gly Lys Lys Gly Ala Ala Ile Gly Ala Gly Thr
            260                 265                 270

Ala Gly Leu Ala Gly Gly Ala Ala Ser Lys Ser Ala Ser Ala Ala Ser
        275                 280                 285

Lys Pro His Ala Ser Asn Asn Ala Ser Gln Asn His Asp Glu His Asp
    290                 295                 300

Asn His Asp Arg Asp Lys Glu Arg Lys Lys Gly Gly Met Ala Lys Val
305                 310                 315                 320

Leu Leu Pro Leu Ile Ala Ala Val Leu Ile Ile Gly Ala Leu Ala Ile
                325                 330                 335

Phe Gly Gly Met Ala Leu Asn Asn His Asn Asn Gly Thr Lys Glu Asn
            340                 345                 350

Lys Ile Ala Asn Thr Asn Lys Asn Asn Ala Asp Glu Ser Lys Asp Lys
        355                 360                 365

Asp Thr Ser Lys Asp Ala Ser Lys Asp Lys Ser Lys Ser Thr Asp Ser
    370                 375                 380

Asp Lys Ser Lys Glu Asp Gln Asp Lys Ala Thr Lys Asp Glu Ser Asp
385                 390                 395                 400

Asn Asp Gln Asn Asn Ala Asn Gln Ala Asn Asn Gln Ala Gln Asn Asn
                405                 410                 415

Gln Asn Gln Gln Gln Ala Asn Gln Asn Gln Gln Gln Gln Gln Gln Arg
            420                 425                 430

Gln Gly Gly Gly Gln Arg His Thr Val Asn Gly Gln Glu Asn Leu Tyr
        435                 440                 445

Arg Ile Ala Ile Gln Tyr Tyr Gly Ser Gly Ser Pro Glu Asn Val Glu
    450                 455                 460

Lys Ile Arg Arg Ala Asn Gly Leu Ser Gly Asn Asn Ile Arg Asn Gly
465                 470                 475                 480

Gln Gln Ile Val Ile Pro
                485
```

<210> SEQ ID NO 23
<211> LENGTH: 472
<212> TYPE: PRT
<213> ORGANISM: Staphylococcus sp.

<400> SEQUENCE: 23

```
Met Ile Glu Leu Ile Lys Met Glu Gly Met Ile Val Val Ser Asn Asn
1               5                   10                  15

Asn Phe Lys Asp Asp Phe Glu Lys Asn Arg Gln Ser Ile Asn Pro Asp
            20                  25                  30

Glu Gln Gln Thr Glu Leu Lys Glu Asp Asp Lys Thr Asn Glu Asn Lys
        35                  40                  45

Lys Glu Ala Asp Ser Gln Asn Ser Leu Ser Asn Asn Ser Asn Gln Gln
    50                  55                  60

Phe Pro Pro Arg Asn Ala Gln Arg Arg Lys Arg Arg Arg Glu Thr Ala
65                  70                  75                  80

Thr Asn Gln Ser Lys Gln Gln Asp Asp Lys His Gln Lys Asn Ser Asp
                85                  90                  95

Ala Lys Thr Thr Glu Gly Ser Leu Asp Asp Arg Tyr Asp Glu Ala Gln
```

```
            100                 105                 110

Leu Gln Gln Gln His Asp Lys Ser Gln Gln Gln Asn Lys Thr Glu Lys
        115                 120                 125

Gln Ser Gln Asp Asn Arg Met Lys Asp Gly Lys Asp Ala Ala Ile Val
    130                 135                 140

Asn Gly Thr Ser Glu Ser Pro Glu His Lys Ser Lys Ser Thr Gln Asn
145                 150                 155                 160

Arg Pro Gly Pro Lys Ala Gln Gln Gln Lys Arg Lys Ser Glu Ser Thr
                165                 170                 175

Gln Ser Lys Pro Ser Thr Asn Lys Asp Lys Lys Ala Ala Thr Gly Ala
            180                 185                 190

Gly Ile Ala Gly Ala Ala Gly Val Ala Gly Ala Ala Glu Thr Ser Lys
        195                 200                 205

Arg His His Asn Lys Lys Asp Lys Gln Asp Ser Lys His Ser Asn His
    210                 215                 220

Glu Asn Asp Glu Lys Ser Val Lys Asn Asp Asp Gln Lys Gln Ser Lys
225                 230                 235                 240

Lys Gly Lys Lys Ala Ala Val Gly Ala Gly Ala Ala Ala Gly Val Gly
                245                 250                 255

Ala Ala Gly Val Ala His His Asn Asn Gln Asn Lys His His Asn Glu
            260                 265                 270

Glu Lys Asn Ser Asn Gln Asn Asn Gln Tyr Asn Asp Gln Ser Glu Gly
        275                 280                 285

Lys Lys Lys Gly Gly Phe Met Lys Ile Leu Leu Pro Leu Ile Ala Ala
    290                 295                 300

Ile Leu Ile Leu Gly Ala Ile Ala Ile Phe Gly Gly Met Ala Leu Asn
305                 310                 315                 320

Asn His Asn Asp Ser Lys Ser Asp Asp Gln Lys Ile Ala Asn Gln Ser
                325                 330                 335

Lys Lys Asp Ser Asp Lys Lys Asp Gly Ala Gln Ser Glu Asp Asn Lys
            340                 345                 350

Asp Lys Lys Ser Asp Ser Asn Lys Asp Lys Lys Ser Asp Ser Asp Lys
        355                 360                 365

Asn Ala Asp Asp Asp Ser Asp Asn Ser Ser Ser Asn Pro Asn Ala Thr
    370                 375                 380

Ser Thr Asn Asn Asn Asp Asn Val Ala Asn Asn Asn Ser Asn Tyr Thr
385                 390                 395                 400

Asn Gln Asn Gln Gln Asp Asn Ala Asn Gln Asn Ser Asn Asn Gln Gln
                405                 410                 415

Ala Thr Gln Gly Gln Gln Ser His Thr Val Tyr Gly Gln Glu Asn Leu
            420                 425                 430

Tyr Arg Ile Ala Ile Gln Tyr Tyr Gly Glu Gly Thr Gln Ala Asn Val
        435                 440                 445

Asp Lys Ile Lys Arg Ala Asn Gly Leu Ser Ser Asn Asn Ile His Asn
    450                 455                 460

Gly Gln Thr Leu Val Ile Pro Gln
465                 470
```

```
<210> SEQ ID NO 24
<211> LENGTH: 165
<212> TYPE: PRT
<213> ORGANISM: Staphylococcus sp.

<400> SEQUENCE: 24
```

Met Lys Asn Lys Leu Ile Ala Lys Ser Leu Leu Thr Ile Ala Ala Ile
1 5 10 15

Gly Ile Thr Thr Thr Thr Ile Ala Ser Thr Ala Asp Ala Ser Glu Gly
20 25 30

Tyr Gly Pro Arg Glu Lys Lys Pro Val Ser Ile Asn His Asn Ile Val
35 40 45

Glu Tyr Asn Asp Gly Thr Phe Lys Tyr Gln Ser Arg Pro Lys Phe Asn
50 55 60

Ser Thr Pro Lys Tyr Ile Lys Phe Lys His Asp Tyr Asn Ile Leu Glu
65 70 75 80

Phe Asn Asp Gly Thr Phe Glu Tyr Gly Ala Arg Pro Gln Phe Asn Lys
85 90 95

Pro Ala Ala Lys Thr Asp Ala Thr Ile Lys Lys Glu Gln Lys Leu Ile
100 105 110

Gln Ala Gln Asn Leu Val Arg Glu Phe Glu Lys Thr His Thr Val Ser
115 120 125

Ala His Arg Lys Ala Gln Lys Ala Val Asn Leu Val Ser Phe Glu Tyr
130 135 140

Lys Val Lys Lys Met Val Leu Gln Glu Arg Ile Asp Asn Val Leu Lys
145 150 155 160

Gln Gly Leu Val Arg
165

<210> SEQ ID NO 25
<211> LENGTH: 319
<212> TYPE: PRT
<213> ORGANISM: Staphylococcus sp.

<400> SEQUENCE: 25

Met Lys Thr Arg Ile Val Ser Ser Val Thr Thr Thr Leu Leu Leu Gly
1 5 10 15

Ser Ile Leu Met Asn Pro Val Ala Asn Ala Ala Asp Ser Asp Ile Asn
20 25 30

Ile Lys Thr Gly Thr Thr Asp Ile Gly Ser Asn Thr Thr Val Lys Thr
35 40 45

Gly Asp Leu Val Thr Tyr Asp Lys Glu Asn Gly Met His Lys Lys Val
50 55 60

Phe Tyr Ser Phe Ile Asp Asp Lys Asn His Asn Lys Lys Leu Leu Val
65 70 75 80

Ile Arg Thr Lys Gly Thr Ile Ala Gly Gln Tyr Arg Val Tyr Ser Glu
85 90 95

Glu Gly Ala Asn Lys Ser Gly Leu Ala Trp Pro Ser Ala Phe Lys Val
100 105 110

Gln Leu Gln Leu Pro Asp Asn Glu Val Ala Gln Ile Ser Asp Tyr Tyr
115 120 125

Pro Arg Asn Ser Ile Asp Thr Lys Glu Tyr Met Ser Thr Leu Thr Tyr
130 135 140

Gly Phe Asn Gly Asn Val Thr Gly Asp Asp Thr Gly Lys Ile Gly Gly
145 150 155 160

Leu Ile Gly Ala Asn Val Ser Ile Gly His Thr Leu Lys Tyr Val Gln
165 170 175

Pro Asp Phe Lys Thr Ile Leu Glu Ser Pro Thr Asp Lys Lys Val Gly
180 185 190

Trp Lys Val Ile Phe Asn Asn Met Val Asn Gln Asn Trp Gly Pro Tyr
195 200 205

Asp Arg Asp Ser Trp Asn Pro Val Tyr Gly Asn Gln Leu Phe Met Lys
210 215 220

Thr Arg Asn Gly Ser Met Lys Ala Ala Glu Asn Phe Leu Asp Pro Asn
225 230 235 240

Lys Ala Ser Ser Leu Leu Ser Ser Gly Phe Ser Pro Asp Phe Ala Thr
245 250 255

Val Ile Thr Met Asp Arg Lys Ala Ser Lys Gln Gln Thr Asn Ile Asp
260 265 270

Val Ile Tyr Glu Arg Val Arg Asp Asp Tyr Gln Leu His Trp Thr Ser
275 280 285

Thr Asn Trp Lys Gly Thr Asn Thr Lys Asp Lys Trp Thr Asp Arg Ser
290 295 300

Ser Glu Arg Tyr Lys Ile Asp Trp Glu Lys Glu Glu Met Thr Asn
305 310 315

<210> SEQ ID NO 26
<211> LENGTH: 428
<212> TYPE: PRT
<213> ORGANISM: Staphylococcus sp.

<400> SEQUENCE: 26

Met His Met Lys Asn Lys Tyr Ile Ser Lys Leu Leu Val Gly Ala Ala
1 5 10 15

Thr Ile Thr Leu Ala Thr Met Ile Ser Asn Gly Glu Ala Lys Ala Ser
20 25 30

Glu Asn Thr Gln Gln Thr Ser Thr Lys His Gln Thr Thr Gln Asn Asn
35 40 45

Tyr Val Thr Asp Gln Gln Lys Ala Phe Tyr Gln Val Leu His Leu Lys
50 55 60

Gly Ile Thr Glu Glu Gln Arg Asn Gln Tyr Ile Lys Thr Leu Arg Glu
65 70 75 80

His Pro Glu Arg Ala Gln Glu Val Phe Ser Glu Ser Leu Lys Asp Ser
85 90 95

Lys Asn Pro Asp Arg Arg Val Ala Gln Gln Asn Ala Phe Tyr Asn Val
100 105 110

Leu Lys Asn Asp Asn Leu Thr Glu Gln Glu Lys Asn Asn Tyr Ile Ala
115 120 125

Gln Ile Lys Glu Asn Pro Asp Arg Ser Gln Gln Val Trp Val Glu Ser
130 135 140

Val Gln Ser Ser Lys Ala Lys Glu Arg Gln Asn Ile Glu Asn Ala Asp
145 150 155 160

Lys Ala Ile Lys Asp Phe Gln Asp Asn Lys Ala Pro His Asp Lys Ser
165 170 175

Ala Ala Tyr Glu Ala Asn Ser Lys Leu Pro Lys Asp Leu Arg Asp Lys
180 185 190

Asn Asn Arg Phe Val Glu Lys Val Ser Ile Glu Lys Ala Ile Val Arg
195 200 205

His Asp Glu Arg Val Lys Ser Ala Asn Asp Ala Ile Ser Lys Leu Asn
210 215 220

Glu Lys Asp Ser Ile Glu Asn Arg Arg Leu Ala Gln Arg Glu Val Asn
225 230 235 240

Lys Ala Pro Met Asp Val Lys Glu His Leu Gln Lys Gln Leu Asp Ala
245 250 255

Leu Val Ala Gln Lys Asp Ala Glu Lys Lys Val Ala Pro Lys Val Glu

```
            260                 265                 270

Ala Pro Gln Ile Gln Ser Pro Gln Ile Glu Lys Pro Lys Ala Glu Ser
        275                 280                 285

Pro Lys Val Glu Val Pro Gln Ser Lys Leu Leu Gly Tyr Tyr Gln Ser
    290                 295                 300

Leu Lys Asp Ser Phe Asn Tyr Gly Tyr Lys Tyr Leu Thr Asp Thr Tyr
305                 310                 315                 320

Lys Ser Tyr Lys Glu Lys Tyr Asp Thr Ala Lys Tyr Tyr Tyr Asn Thr
                325                 330                 335

Tyr Tyr Lys Tyr Lys Gly Ala Ile Asp Gln Thr Val Leu Thr Val Leu
            340                 345                 350

Gly Ser Gly Ser Lys Ser Tyr Ile Gln Pro Leu Lys Val Asp Asp Lys
        355                 360                 365

Asn Gly Tyr Leu Ala Lys Ser Tyr Ala Gln Val Arg Asn Tyr Val Thr
    370                 375                 380

Glu Ser Ile Asn Thr Gly Lys Val Leu Tyr Thr Phe Tyr Gln Asn Pro
385                 390                 395                 400

Thr Leu Val Lys Thr Ala Ile Lys Ala Gln Glu Thr Ala Ser Ser Ile
                405                 410                 415

Lys Asn Thr Leu Ser Asn Leu Leu Ser Phe Trp Lys
            420                 425
```

<210> SEQ ID NO 27
<211> LENGTH: 350
<212> TYPE: PRT
<213> ORGANISM: Staphylococcus sp.

<400> SEQUENCE: 27

```
Met Thr Lys His Tyr Leu Asn Ser Lys Tyr Gln Ser Glu Gln Arg Ser
1               5                   10                  15

Ser Ala Met Lys Lys Ile Thr Met Gly Thr Ala Ser Ile Ile Leu Gly
            20                  25                  30

Ser Leu Val Tyr Ile Gly Ala Asp Ser Gln Gln Val Asn Ala Ala Thr
        35                  40                  45

Glu Ala Thr Asn Ala Thr Asn Asn Gln Ser Thr Gln Val Ser Gln Ala
    50                  55                  60

Thr Ser Gln Pro Ile Asn Phe Gln Val Gln Lys Asp Gly Ser Ser Glu
65                  70                  75                  80

Lys Ser His Met Asp Asp Tyr Met Gln His Pro Gly Lys Val Ile Lys
                85                  90                  95

Gln Asn Asn Lys Tyr Tyr Phe Gln Thr Val Leu Asn Asn Ala Ser Phe
            100                 105                 110

Trp Lys Glu Tyr Lys Phe Tyr Asn Ala Asn Asn Gln Glu Leu Ala Thr
        115                 120                 125

Thr Val Val Asn Asp Asn Lys Lys Ala Asp Thr Arg Thr Ile Asn Val
    130                 135                 140

Ala Val Glu Pro Gly Tyr Lys Ser Leu Thr Thr Lys Val His Ile Val
145                 150                 155                 160

Val Pro Gln Ile Asn Tyr Asn His Arg Tyr Thr Thr His Leu Glu Phe
                165                 170                 175

Glu Lys Ala Ile Pro Thr Leu Ala Asp Ala Ala Lys Pro Asn Asn Val
            180                 185                 190

Lys Pro Val Gln Pro Lys Pro Ala Gln Pro Lys Thr Pro Thr Glu Gln
        195                 200                 205
```

Thr Lys Pro Val Gln Pro Lys Val Glu Lys Val Lys Pro Thr Val Thr
210 215 220

Thr Thr Ser Lys Val Glu Asp Asn His Ser Thr Lys Val Val Ser Thr
225 230 235 240

Asp Thr Thr Lys Asp Gln Thr Lys Thr Gln Thr Ala His Thr Val Lys
245 250 255

Thr Ala Gln Thr Ala Gln Glu Gln Asn Lys Val Gln Thr Pro Val Lys
260 265 270

Asp Val Ala Thr Ala Lys Ser Glu Ser Asn Asn Gln Ala Val Ser Asp
275 280 285

Asn Lys Ser Gln Gln Thr Asn Lys Val Thr Lys His Asn Glu Thr Pro
290 295 300

Lys Gln Ala Ser Lys Ala Lys Glu Leu Pro Lys Thr Gly Leu Thr Ser
305 310 315 320

Val Asp Asn Phe Ile Ser Thr Val Ala Phe Ala Thr Leu Ala Leu Leu
325 330 335

Gly Ser Leu Ser Leu Leu Leu Phe Lys Arg Lys Glu Ser Lys
340 345 350

<210> SEQ ID NO 28
<211> LENGTH: 645
<212> TYPE: PRT
<213> ORGANISM: Staphylococcus sp.

<400> SEQUENCE: 28

Met Asn Lys Gln Gln Lys Glu Phe Lys Ser Phe Tyr Ser Ile Arg Lys
1 5 10 15

Ser Ser Leu Gly Val Ala Ser Val Ala Ile Ser Thr Leu Leu Leu Leu
20 25 30

Met Ser Asn Gly Glu Ala Gln Ala Ala Ala Glu Glu Thr Gly Gly Thr
35 40 45

Asn Thr Glu Ala Gln Pro Lys Thr Glu Ala Val Ala Ser Pro Thr Thr
50 55 60

Thr Ser Glu Lys Ala Pro Glu Thr Lys Pro Val Ala Asn Ala Val Ser
65 70 75 80

Val Ser Asn Lys Glu Val Glu Ala Pro Thr Ser Glu Thr Lys Glu Ala
85 90 95

Lys Glu Val Lys Glu Val Lys Ala Pro Lys Glu Thr Lys Ala Val Lys
100 105 110

Pro Ala Ala Lys Ala Thr Asn Asn Thr Tyr Pro Ile Leu Asn Gln Glu
115 120 125

Leu Arg Glu Ala Ile Lys Asn Pro Ala Ile Lys Asp Lys Asp His Ser
130 135 140

Ala Pro Asn Ser Arg Pro Ile Asp Phe Glu Met Lys Lys Glu Asn Gly
145 150 155 160

Glu Gln Gln Phe Tyr His Tyr Ala Ser Ser Val Lys Pro Ala Arg Val
165 170 175

Ile Phe Thr Asp Ser Lys Pro Glu Ile Glu Leu Gly Leu Gln Ser Gly
180 185 190

Gln Phe Trp Arg Lys Phe Glu Val Tyr Glu Gly Asp Lys Lys Leu Pro
195 200 205

Ile Lys Leu Val Ser Tyr Asp Thr Val Lys Asp Tyr Ala Tyr Ile Arg
210 215 220

Phe Ser Val Ser Asn Gly Thr Lys Ala Val Lys Ile Val Ser Ser Thr
225 230 235 240

-continued

```
His Phe Asn Asn Lys Glu Glu Lys Tyr Asp Tyr Thr Leu Met Glu Phe
                245                 250                 255

Ala Gln Pro Ile Tyr Asn Ser Ala Asp Lys Phe Lys Thr Glu Glu Asp
            260                 265                 270

Tyr Lys Ala Glu Lys Leu Leu Ala Pro Tyr Lys Lys Ala Lys Thr Leu
        275                 280                 285

Glu Arg Gln Val Tyr Glu Leu Asn Lys Ile Gln Asp Lys Leu Pro Glu
    290                 295                 300

Lys Leu Lys Ala Glu Tyr Lys Lys Lys Leu Glu Asp Thr Lys Lys Ala
305                 310                 315                 320

Leu Asp Glu Gln Val Lys Ser Ala Ile Thr Glu Phe Gln Asn Val Gln
                325                 330                 335

Pro Thr Asn Glu Lys Met Thr Asp Leu Gln Asp Thr Lys Tyr Val Val
            340                 345                 350

Tyr Glu Ser Val Glu Asn Asn Glu Ser Met Met Asp Thr Phe Val Lys
        355                 360                 365

His Pro Ile Lys Thr Gly Met Leu Asn Gly Lys Lys Tyr Met Val Met
    370                 375                 380

Glu Thr Thr Asn Asp Asp Tyr Trp Lys Asp Phe Met Val Glu Gly Gln
385                 390                 395                 400

Arg Val Arg Thr Ile Ser Lys Asp Ala Lys Asn Asn Thr Arg Thr Ile
                405                 410                 415

Ile Phe Pro Tyr Val Glu Gly Lys Thr Leu Tyr Asp Ala Ile Val Lys
            420                 425                 430

Val His Val Lys Thr Ile Asp Tyr Asp Gly Gln Tyr His Val Arg Ile
        435                 440                 445

Val Asp Lys Glu Ala Phe Thr Lys Ala Asn Thr Asp Lys Ser Asn Lys
    450                 455                 460

Lys Glu Gln Gln Asp Asn Ser Ala Lys Lys Glu Ala Thr Pro Ala Thr
465                 470                 475                 480

Pro Ser Lys Pro Thr Pro Ser Pro Val Glu Lys Glu Ser Gln Lys Gln
                485                 490                 495

Asp Ser Gln Lys Asp Asp Asn Lys Gln Leu Pro Ser Val Glu Lys Glu
            500                 505                 510

Asn Asp Ala Ser Ser Glu Ser Gly Lys Asp Lys Thr Pro Ala Thr Lys
        515                 520                 525

Pro Thr Lys Gly Glu Val Glu Ser Ser Ser Thr Thr Pro Thr Lys Val
    530                 535                 540

Val Ser Thr Thr Gln Asn Val Ala Lys Pro Thr Thr Ala Ser Ser Lys
545                 550                 555                 560

Thr Thr Lys Asp Val Val Gln Thr Ser Ala Gly Ser Ser Glu Ala Lys
                565                 570                 575

Asp Ser Ala Pro Leu Gln Lys Ala Asn Ile Lys Asn Thr Asn Asp Gly
            580                 585                 590

His Thr Gln Ser Gln Asn Asn Lys Asn Thr Gln Glu Asn Lys Ala Lys
        595                 600                 605

Ser Leu Pro Gln Thr Gly Glu Glu Ser Asn Lys Asp Met Thr Leu Pro
    610                 615                 620

Leu Met Ala Leu Leu Ala Leu Ser Ser Ile Val Ala Phe Val Leu Pro
625                 630                 635                 640

Arg Lys Arg Lys Asn
                645
```

-continued

<210> SEQ ID NO 29
<211> LENGTH: 953
<212> TYPE: PRT
<213> ORGANISM: Staphylococcus sp.

<400> SEQUENCE: 29

Met Asn Asn Lys Lys Thr Ala Thr Asn Arg Lys Gly Met Ile Pro Asn
1               5                   10                  15

Arg Leu Asn Lys Phe Ser Ile Arg Lys Tyr Ser Val Gly Thr Ala Ser
            20                  25                  30

Ile Leu Val Gly Thr Thr Leu Ile Phe Gly Leu Ser Gly His Glu Ala
        35                  40                  45

Lys Ala Ala Glu His Thr Asn Gly Glu Leu Asn Gln Ser Lys Asn Glu
    50                  55                  60

Thr Thr Ala Pro Ser Glu Asn Lys Thr Thr Glu Lys Val Asp Ser Arg
65                  70                  75                  80

Gln Leu Lys Asp Asn Thr Gln Thr Ala Thr Ala Asp Gln Pro Lys Val
                85                  90                  95

Thr Met Ser Asp Ser Ala Thr Val Lys Glu Thr Ser Ser Asn Met Gln
            100                 105                 110

Ser Pro Gln Asn Ala Thr Ala Ser Gln Ser Thr Thr Gln Thr Ser Asn
        115                 120                 125

Val Thr Thr Asn Asp Lys Ser Ser Thr Thr Tyr Ser Asn Glu Thr Asp
    130                 135                 140

Lys Ser Asn Leu Thr Gln Ala Lys Asn Val Ser Thr Thr Pro Lys Thr
145                 150                 155                 160

Thr Thr Ile Lys Gln Arg Ala Leu Asn Arg Met Ala Val Asn Thr Val
                165                 170                 175

Ala Ala Pro Gln Gln Gly Thr Asn Val Asn Asp Lys Val His Phe Thr
            180                 185                 190

Asn Ile Asp Ile Ala Ile Asp Lys Gly His Val Asn Lys Thr Thr Gly
        195                 200                 205

Asn Thr Glu Phe Trp Ala Thr Ser Ser Asp Val Leu Lys Leu Lys Ala
    210                 215                 220

Asn Tyr Thr Ile Asp Asp Ser Val Lys Glu Gly Asp Thr Phe Thr Phe
225                 230                 235                 240

Lys Tyr Gly Gln Tyr Phe Arg Pro Gly Ser Val Arg Leu Pro Ser Gln
                245                 250                 255

Thr Gln Asn Leu Tyr Asn Ala Gln Gly Asn Ile Ile Ala Lys Gly Ile
            260                 265                 270

Tyr Asp Ser Lys Thr Asn Thr Thr Thr Tyr Thr Phe Thr Asn Tyr Val
        275                 280                 285

Asp Gln Tyr Thr Asn Val Ser Gly Ser Phe Glu Gln Val Ala Phe Ala
    290                 295                 300

Lys Arg Glu Asn Ala Thr Thr Asp Lys Thr Ala Tyr Lys Met Glu Val
305                 310                 315                 320

Thr Leu Gly Asn Asp Thr Tyr Ser Lys Asp Val Ile Val Asp Tyr Gly
                325                 330                 335

Asn Gln Lys Gly Gln Gln Leu Ile Ser Ser Thr Asn Tyr Ile Asn Asn
            340                 345                 350

Glu Asp Leu Ser Arg Asn Met Thr Val Tyr Val Asn Gln Pro Lys Lys
        355                 360                 365

Thr Tyr Thr Lys Glu Thr Phe Val Thr Asn Leu Thr Gly Tyr Lys Phe
    370                 375                 380

-continued

Asn Pro Asp Ala Lys Asn Phe Lys Ile Tyr Glu Val Thr Asp Gln Asn
385 390 395 400

Gln Phe Val Asp Ser Phe Thr Pro Asp Thr Ser Lys Leu Lys Asp Val
405 410 415

Thr Gly Gln Phe Asp Val Ile Tyr Ser Asn Asp Asn Lys Thr Ala Thr
420 425 430

Val Asp Leu Leu Asn Gly Gln Ser Ser Ser Asp Lys Gln Tyr Ile Ile
435 440 445

Gln Gln Val Ala Tyr Pro Asp Asn Ser Ser Thr Asp Asn Gly Lys Ile
450 455 460

Asp Tyr Thr Leu Glu Thr Gln Asn Gly Lys Ser Ser Trp Ser Asn Ser
465 470 475 480

Tyr Ser Asn Val Asn Gly Ser Ser Thr Ala Asn Gly Asp Gln Lys Lys
485 490 495

Tyr Asn Leu Gly Asp Tyr Val Trp Glu Asp Thr Asn Lys Asp Gly Lys
500 505 510

Gln Asp Ala Asn Glu Lys Gly Ile Lys Gly Val Tyr Val Ile Leu Lys
515 520 525

Asp Ser Asn Gly Lys Glu Leu Asp Arg Thr Thr Thr Asp Glu Asn Gly
530 535 540

Lys Tyr Gln Phe Thr Gly Leu Ser Asn Gly Thr Tyr Ser Val Glu Phe
545 550 555 560

Ser Thr Pro Ala Gly Tyr Thr Pro Thr Thr Ala Asn Ala Gly Thr Asp
565 570 575

Asp Ala Val Asp Ser Asp Gly Leu Thr Thr Thr Gly Val Ile Lys Asp
580 585 590

Ala Asp Asn Met Thr Leu Asp Ser Gly Phe Tyr Lys Thr Pro Lys Tyr
595 600 605

Ser Leu Gly Asp Tyr Val Trp Tyr Asp Ser Asn Lys Asp Gly Lys Gln
610 615 620

Asp Ser Thr Glu Lys Gly Ile Lys Gly Val Lys Val Thr Leu Gln Asn
625 630 635 640

Glu Lys Gly Glu Val Ile Gly Thr Thr Glu Thr Asp Glu Asn Gly Lys
645 650 655

Tyr Arg Phe Asp Asn Leu Asp Ser Gly Lys Tyr Lys Val Ile Phe Glu
660 665 670

Lys Pro Ala Gly Leu Thr Gln Thr Gly Thr Asn Thr Thr Glu Asp Asp
675 680 685

Lys Asp Ala Asp Gly Gly Glu Val Asp Val Thr Ile Thr Asp His Asp
690 695 700

Asp Phe Thr Leu Asp Asn Gly Tyr Tyr Glu Glu Glu Thr Ser Asp Ser
705 710 715 720

Asp Ser Asp Ser Asp Ser Asp Ser Asp Ser Asp Ser Asp Ser Asp Ser
725 730 735

Asp Ser Asp Ser Asp Ser Asp Ser Asp Ser Asp Ser Asp Ser Asp Ser
740 745 750

Asp Ser Asp Ser Asp Ser Asp Ser Asp Ser Asp Ser Asp Ser Asp Ser
755 760 765

Asp Ser Asp Ser Glu Ser Asp Ser Asp Ser Asp Ser Asp Ser Asp Ser
770 775 780

Asp Ser Asp Ser Asp Ser Asp Ser Asp Ser Asp Ser Asp Ser Asp Ser
785 790 795 800

-continued

Asp Ser Asp Ser Asp Ser Asp Ser Asp Ser Asp Ser Asp Ser Asp Ser
805 810 815

Asp Ser Asp Ser Asp Ser Asp Asn Asp Ser Asp Ser Asp Ser Asp Ser
820 825 830

Asp Ser Asp Ser Asp Ser Asp Ser Asp Ser Asp Ser Asp Ser Asp Ser
835 840 845

Asp Ser Asp Ser Asp Ser Asp Ser Asp Ser Asp Ser Asp Ser Asp Ser
850 855 860

Asp Ser Asp Ser Asp Ser Asp Ser Asp Ser Asp Ser Asp Ser Asp Ser
865 870 875 880

Asp Ser Asp Ser Asp Ser Asp Ser Asp Ser Asp Ser Asp Ala Gly Lys
885 890 895

His Thr Pro Thr Lys Pro Met Ser Thr Val Lys Asp Gln His Lys Thr
900 905 910

Ala Lys Ala Leu Pro Glu Thr Gly Ser Glu Asn Asn Asn Ser Asn Asn
915 920 925

Gly Thr Leu Phe Gly Gly Leu Phe Ala Ala Leu Gly Ser Leu Leu Leu
930 935 940

Phe Gly Arg Arg Lys Lys Gln Asn Lys
945 950

<210> SEQ ID NO 30
<211> LENGTH: 935
<212> TYPE: PRT
<213> ORGANISM: Staphylococcus sp.

<400> SEQUENCE: 30

Met Asn Met Lys Lys Lys Glu Lys His Ala Ile Arg Lys Lys Ser Ile
1 5 10 15

Gly Val Ala Ser Val Leu Val Gly Thr Leu Ile Gly Phe Gly Leu Leu
20 25 30

Ser Ser Lys Glu Ala Asp Ala Ser Glu Asn Ser Val Thr Gln Ser Asp
35 40 45

Ser Ala Ser Asn Glu Ser Lys Ser Asn Asp Ser Ser Ser Val Ser Ala
50 55 60

Ala Pro Lys Thr Asp Asp Thr Asn Val Ser Asp Thr Lys Thr Ser Ser
65 70 75 80

Asn Thr Asn Asn Gly Glu Thr Ser Val Ala Gln Asn Pro Ala Gln Gln
85 90 95

Glu Thr Thr Gln Ser Ser Ser Thr Asn Ala Thr Thr Glu Glu Thr Pro
100 105 110

Val Thr Gly Glu Ala Thr Thr Thr Thr Thr Asn Gln Ala Asn Thr Pro
115 120 125

Ala Thr Thr Gln Ser Ser Asn Thr Asn Ala Glu Glu Leu Val Asn Gln
130 135 140

Thr Ser Asn Glu Thr Thr Ser Asn Asp Thr Asn Thr Val Ser Ser Val
145 150 155 160

Asn Ser Pro Gln Asn Ser Thr Asn Ala Glu Asn Val Ser Thr Thr Gln
165 170 175

Asp Thr Ser Thr Glu Ala Thr Pro Ser Asn Asn Glu Ser Ala Pro Gln
180 185 190

Asn Thr Asp Ala Ser Asn Lys Asp Val Val Ser Gln Ala Val Asn Pro
195 200 205

Ser Thr Pro Arg Met Arg Ala Phe Ser Leu Ala Ala Val Ala Ala Asp
210 215 220

```
Ala Pro Ala Ala Gly Thr Asp Ile Thr Asn Gln Leu Thr Asp Val Lys
225                 230                 235                 240

Val Thr Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
305                 310                 315                 320

Asp Tyr Val Asp Asn Lys Glu Asn Val Thr Ala Asn Ile Thr Met Pro
                325                 330                 335

Ala Tyr Ile Asp Pro Glu Asn Val Thr Lys Thr Gly Asn Val Thr Leu
            340                 345                 350

Thr Thr Gly Ile Gly Thr Asn Thr Ala Ser Lys Thr Val Leu Ile Asp
        355                 360                 365

Tyr Glu Lys Tyr Gly Gln Phe His Asn Leu Ser Ile Lys Gly Thr Ile
    370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Val Leu Pro Ala Leu Thr Gly Asn Leu
                405                 410                 415

Ile Pro Asn Thr Lys Ser Asn Ala Leu Ile Asp Ala Lys Asn Thr Asp
            420                 425                 430

Ile Lys Val Tyr Arg Val Asp Asn Ala Asn Asp Leu Ser Glu Ser Tyr
        435                 440                 445

Tyr Val Asn Pro Ser Asp Phe Glu Asp Val Thr Asn Gln Val Arg Ile
    450                 455                 460

Ser Phe Pro Asn Ala Asn Gln Tyr Lys Val Glu Phe Pro Thr Asp Asp
465                 470                 475                 480

Asp Gln Ile Thr Thr Pro Tyr Ile Val Val Val Asn Gly His Ile Asp
                485                 490                 495

Pro Ala Ser Thr Gly Asp Leu Ala Leu Arg Ser Thr Phe Tyr Gly Tyr
            500                 505                 510

Asp Ser Asn Phe Ile Trp Arg Ser Met Ser Trp Asp Asn Glu Val Ala
        515                 520                 525

Phe Asn Asn Gly Ser Gly Ser Gly Asp Gly Ile Asp Lys Pro Val Val
    530                 535                 540

Pro Glu Gln Pro Asp Glu Pro Gly Glu Ile Glu Pro Ile Pro Glu Asp
545                 550                 555                 560

Ser Asp Ser Asp Pro Gly Ser Asp Ser Gly Ser Asp Ser Asn Ser Asp
                565                 570                 575

Ser Gly Ser Asp Ser Gly Ser Asp Ser Thr Ser Asp Ser Gly Ser Asp
            580                 585                 590

Ser Ala Ser Asp Ser Asp Ser Ala Ser Asp Ser Asp Ser Ala Ser Asp
        595                 600                 605

Ser Asp Ser Ala Ser Asp Ser Asp Ser Ala Ser Asp Ser Asp Ser Ala
    610                 615                 620

Ser Asp Ser Asp Ser Ala Ser Asp Ser Asp Ser Ala Ser Asp Ser Asp
625                 630                 635                 640
```

Ser Ala Ser Asp Ser Asp Ser Ala Ser Asp Ser Asp Ser Ala Ser Asp
645 650 655

Ser Asp Ser Ala Ser Asp Ser Asp Ser Ala Ser Asp Ser Asp Ser Asp
660 665 670

Ser Asp Ser Asp Ser Asp Ser Asp Ser Asp Ser Asp Ser Asp Ser Asp
675 680 685

Ser Asp Ser Asp Ser Asp Ser Asp Ser Asp Ser Asp Ser Asp Ser Asp
690 695 700

Ser Asp Ser Asp Ser Asp Ser Asp Ser Asp Ser Asp Ser Asp Ser Asp
705 710 715 720

Ser Asp Ser Asp Ser Asp Ser Asp Ser Asp Ser Asp Ser Asp Ser Asp
725 730 735

Ser Asp Ser Asp Ser Asp Ser Asp Ser Asp Ser Asp Ser Asp Ser Asp
740 745 750

Ser Asp Ser Asp Ser Asp Ser Asp Ser Asp Ser Asp Ser Asp Ser Ala
755 760 765

Ser Asp Ser Asp Ser Asp Ser Asp Ser Glu Ser Asp Ser Asp Ser Asp
770 775 780

Ser Asp Ser Asp Ser Asp Ser Asp Ser Asp Ser Asp Ser Asp Ser Asp
785 790 795 800

Ser Glu Ser Asp Ser Asp Ser Asp Ser Asp Ser Asp Ser Glu Ser Asp
805 810 815

Ser Asp Ser Asp Ser Asp Ser Asp Ser Asp Ser Ala Ser Asp Ser Asp
820 825 830

Ser Gly Ser Asp Ser Asp Ser Ser Ser Asp Ser Asp Ser Asp Ser Thr
835 840 845

Ser Asp Thr Gly Ser Asp Asn Asp Ser Asp Ser Asp Ser Asn Ser Asp
850 855 860

Ser Glu Ser Gly Ser Asn Asn Asn Val Val Pro Pro Asn Ser Pro Lys
865 870 875 880

Asn Gly Thr Asn Ala Ser Asn Lys Asn Glu Ala Lys Asp Ser Lys Glu
885 890 895

Pro Leu Pro Asp Thr Gly Ser Glu Asp Glu Ala Asn Thr Ser Leu Ile
900 905 910

Trp Gly Leu Leu Ala Ser Leu Gly Ser Leu Leu Leu Phe Arg Arg Lys
915 920 925

Lys Glu Asn Lys Asp Lys Lys
930 935

<210> SEQ ID NO 31
<211> LENGTH: 1038
<212> TYPE: PRT
<213> ORGANISM: Staphylococcus sp.

<400> SEQUENCE: 31

Met Lys Asn Asn Leu Arg Tyr Gly Ile Arg Lys His Lys Leu Gly Ala
1 5 10 15

Ala Ser Val Phe Leu Gly Thr Met Ile Val Val Gly Met Gly Gln Asp
20 25 30

Lys Glu Ala Ala Ala Ser Glu Gln Lys Thr Thr Thr Val Glu Glu Asn
35 40 45

Gly Asn Ser Ala Thr Asp Asn Lys Thr Ser Glu Thr Gln Thr Thr Ala
50 55 60

Thr Asn Val Asn His Ile Glu Glu Thr Gln Ser Tyr Asn Ala Thr Val
65 70 75 80

-continued

```
Thr Glu Gln Pro Ser Asn Ala Thr Gln Val Thr Thr Glu Glu Ala Pro
                85                  90                  95

Lys Ala Val Gln Ala Pro Gln Thr Ala Gln Pro Ala Asn Val Glu Thr
            100                 105                 110

Val Lys Glu Glu Glu Lys Pro Gln Val Lys Glu Thr Thr Gln Pro Gln
        115                 120                 125

Asp Asn Ser Gly Asn Gln Arg Gln Val Asp Leu Thr Pro Lys Lys Val
    130                 135                 140

Thr Gln Asn Gln Gly Thr Glu Thr Gln Val Glu Val Ala Gln Pro Arg
145                 150                 155                 160

Thr Ala Ser Glu Ser Lys Pro Arg Val Thr Arg Ser Ala Asp Val Ala
                165                 170                 175

Glu Ala Lys Glu Ala Ser Asp Val Ser Glu Val Lys Gly Thr Asp Val
            180                 185                 190

Thr Ser Lys Val Thr Val Glu Ser Gly Ser Ile Glu Ala Pro Gln Gly
        195                 200                 205

Asn Lys Val Glu Pro His Ala Gly Gln Arg Val Val Leu Lys Tyr Lys
    210                 215                 220

Leu Lys Phe Ala Asp Gly Leu Lys Arg Gly Asp Tyr Phe Asp Phe Thr
225                 230                 235                 240

Leu Ser Asn Asn Val Asn Thr Tyr Gly Val Ser Thr Ala Arg Lys Val
                245                 250                 255

Pro Glu Ile Lys Asn Gly Ser Val Val Met Ala Thr Gly Glu Ile Leu
            260                 265                 270

Gly Asn Gly Asn Ile Arg Tyr Thr Phe Thr Asn Glu Ile Glu His Lys
        275                 280                 285

Val Glu Val Thr Ala Asn Leu Glu Ile Asn Leu Phe Ile Asp Pro Lys
    290                 295                 300

Thr Val Gln Ser Asn Gly Glu Gln Lys Ile Thr Ser Lys Leu Asn Gly
305                 310                 315                 320

Glu Glu Thr Glu Lys Thr Ile Pro Val Val Tyr Asn Pro Gly Val Ser
                325                 330                 335

Asn Ser Tyr Thr Asn Val Asn Gly Ser Ile Glu Thr Phe Asn Lys Glu
            340                 345                 350

Ser Asn Lys Phe Thr His Ile Ala Tyr Ile Lys Pro Met Asn Gly Asn
        355                 360                 365

Gln Ser Asn Thr Val Ser Val Thr Gly Thr Leu Thr Glu Gly Ser Asn
    370                 375                 380

Leu Ala Gly Gly Gln Pro Thr Val Lys Val Tyr Glu Tyr Leu Gly Lys
385                 390                 395                 400

Lys Asp Glu Leu Pro Gln Ser Val Tyr Ala Asn Thr Ser Asp Thr Asn
                405                 410                 415

Lys Phe Lys Asp Val Thr Lys Glu Met Asn Gly Lys Leu Ser Val Gln
            420                 425                 430

Asp Asn Gly Ser Tyr Ser Leu Asn Leu Asp Lys Leu Asp Lys Thr Tyr
        435                 440                 445

Val Ile His Tyr Thr Gly Glu Tyr Leu Gln Gly Ser Asp Gln Val Asn
    450                 455                 460

Phe Arg Thr Glu Leu Tyr Gly Tyr Pro Glu Arg Ala Tyr Lys Ser Tyr
465                 470                 475                 480

Tyr Val Tyr Gly Gly Tyr Arg Leu Thr Trp Asp Asn Gly Leu Val Leu
                485                 490                 495
```

-continued

```
Tyr Ser Asn Lys Ala Asp Gly Asn Gly Lys Asn Gly Gln Ile Ile Gln
            500                 505                 510

Asp Asn Asp Phe Glu Tyr Lys Glu Asp Thr Ala Lys Gly Thr Met Ser
        515                 520                 525

Gly Gln Tyr Asp Ala Lys Gln Ile Ile Glu Thr Glu Glu Asn Gln Asp
    530                 535                 540

Asn Thr Pro Leu Asp Ile Asp Tyr His Thr Ala Ile Asp Gly Glu Gly
545                 550                 555                 560

Gly Tyr Val Asp Gly Tyr Ile Glu Thr Ile Glu Glu Thr Asp Ser Ser
                565                 570                 575

Ala Ile Asp Ile Asp Tyr His Thr Ala Val Asp Ser Glu Val Gly His
            580                 585                 590

Val Gly Gly Tyr Thr Glu Ser Ser Glu Glu Ser Asn Pro Ile Asp Phe
        595                 600                 605

Glu Glu Ser Thr His Glu Asn Ser Lys His His Ala Asp Val Val Glu
    610                 615                 620

Tyr Glu Glu Asp Thr Asn Pro Gly Gly Gly Gln Val Thr Thr Glu Ser
625                 630                 635                 640

Asn Leu Val Glu Phe Asp Glu Glu Ser Thr Lys Gly Ile Val Thr Gly
                645                 650                 655

Ala Val Ser Asp His Thr Thr Ile Glu Asp Thr Lys Glu Tyr Thr Thr
            660                 665                 670

Glu Ser Asn Leu Ile Glu Leu Val Asp Glu Leu Pro Glu Glu His Gly
        675                 680                 685

Gln Ala Gln Gly Pro Ile Glu Glu Ile Thr Glu Asn Asn His His Ile
    690                 695                 700

Ser His Ser Gly Leu Gly Thr Glu Asn Gly His Gly Asn Tyr Gly Val
705                 710                 715                 720

Ile Glu Glu Ile Glu Glu Asn Ser His Val Asp Ile Lys Ser Glu Leu
                725                 730                 735

Gly Tyr Glu Gly Gly Gln Asn Ser Gly Asn Gln Ser Phe Glu Glu Asp
            740                 745                 750

Thr Glu Glu Asp Lys Pro Lys Tyr Glu Gln Gly Gly Asn Ile Val Asp
        755                 760                 765

Ile Asp Phe Asp Ser Val Pro Gln Ile His Gly Gln Asn Lys Gly Asp
    770                 775                 780

Gln Ser Phe Glu Glu Asp Thr Glu Lys Asp Lys Pro Lys Tyr Glu His
785                 790                 795                 800

Gly Gly Asn Ile Ile Asp Ile Asp Phe Asp Ser Val Pro Gln Ile His
                805                 810                 815

Gly Phe Asn Lys His Asn Glu Ile Ile Glu Glu Asp Thr Asn Lys Asp
            820                 825                 830

Lys Pro Asn Tyr Gln Phe Gly Gly His Asn Ser Val Asp Phe Glu Glu
        835                 840                 845

Asp Thr Leu Pro Lys Val Ser Gly Gln Asn Glu Gly Gln Gln Thr Ile
    850                 855                 860

Glu Glu Asp Thr Thr Pro Pro Thr Pro Pro Thr Pro Glu Val Pro Ser
865                 870                 875                 880

Glu Pro Glu Thr Pro Met Pro Pro Thr Pro Glu Val Pro Ser Glu Pro
                885                 890                 895

Glu Thr Pro Thr Pro Pro Thr Pro Glu Val Pro Ser Glu Pro Glu Thr
            900                 905                 910

Pro Thr Pro Pro Thr Pro Glu Val Pro Ser Glu Pro Glu Thr Pro Thr
```

```
        915                 920                 925

Pro Pro Thr Pro Glu Val Pro Ser Glu Pro Glu Thr Pro Thr Pro Pro
    930                 935                 940

Thr Pro Glu Val Pro Ala Glu Pro Gly Lys Pro Val Pro Pro Ala Lys
945                 950                 955                 960

Glu Glu Pro Lys Lys Pro Ser Lys Pro Val Glu Gln Gly Lys Val Val
                965                 970                 975

Thr Pro Val Ile Glu Ile Asn Glu Lys Val Lys Ala Val Ala Pro Thr
            980                 985                 990

Lys Lys Ala Gln Ser Lys Lys Ser Glu Leu Pro Glu Thr Gly Gly Glu
        995                 1000                1005

Glu Ser Thr Asn Lys Gly Met Leu Phe Gly Gly Leu Phe Ser Ile Leu
    1010                1015                1020

Gly Leu Ala Leu Leu Arg Arg Asn Lys Lys Asn Asn Lys Ala
1025                1030                1035


<210> SEQ ID NO 32
<211> LENGTH: 877
<212> TYPE: PRT
<213> ORGANISM: Staphylococcus sp.

<400> SEQUENCE: 32

Met Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Thr Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asn Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Ser Ile Ala Thr Asn
145                 150                 155                 160

Ser Glu Leu Lys Asn Ser Gln Thr Leu Asp Leu Pro Gln Ser Ser Pro
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Gly Thr Asn Val Asn Asp Lys Val Thr Ala Ser Asn Phe
    210                 215                 220

Lys Leu Glu Lys Thr Thr Phe Asp Pro Asn Gln Ser Gly Asn Thr Phe
225                 230                 235                 240

Met Ala Ala Asn Phe Thr Val Thr Asp Lys Val Lys Ser Gly Asp Tyr
                245                 250                 255
```

```
Phe Thr Ala Lys Leu Pro Asp Ser Leu Thr Gly Asn Gly Asp Val Asp
            260                 265                 270

Tyr Ser Asn Ser Asn Asn Thr Met Pro Ile Ala Asp Ile Lys Ser Thr
        275                 280                 285

Asn Gly Asp Val Val Ala Lys Ala Thr Tyr Asp Ile Leu Thr Lys Thr
    290                 295                 300

Tyr Thr Phe Val Phe Thr Asp Tyr Val Asn Asn Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
            340                 345                 350

Asn Lys Ile Thr Tyr Asn Tyr Ser Ser Pro Ile Ala Gly Ile Asp Lys
        355                 360                 365

Pro Asn Gly Ala Asn Ile Ser Ser Gln Ile Ile Gly Val Asp Thr Ala
    370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
            420                 425                 430

Ile Phe Glu Val Asn Asp Thr Ser Lys Leu Ser Asp Ser Tyr Tyr Ala
        435                 440                 445

Asp Pro Asn Asp Ser Asn Leu Lys Glu Val Thr Asp Gln Phe Lys Asn
    450                 455                 460

Arg Ile Tyr Tyr Glu His Pro Asn Val Ala Ser Ile Lys Phe Gly Asp
465                 470                 475                 480

Ile Thr Lys Thr Tyr Val Val Leu Val Glu Gly His Tyr Asp Asn Thr
                485                 490                 495

Gly Lys Asn Leu Lys Thr Gln Val Ile Gln Glu Asn Val Asp Pro Val
            500                 505                 510

Thr Asn Arg Asp Tyr Ser Ile Phe Gly Trp Asn Asn Glu Asn Val Val
        515                 520                 525

Arg Tyr Gly Gly Gly Ser Ala Asp Gly Asp Ser Ala Val Asn Pro Lys
    530                 535                 540

Asp Pro Thr Pro Gly Pro Pro Val Asp Pro Glu Pro Ser Pro Asp Pro
545                 550                 555                 560

Glu Pro Glu Pro Thr Pro Asp Pro Glu Pro Ser Pro Asp Pro Glu Pro
                565                 570                 575

Glu Pro Ser Pro Asp Pro Asp Pro Asp Ser Asp Ser Asp Ser Asp Ser
            580                 585                 590

Gly Ser Asp Ser Asp Ser Gly Ser Asp Ser Asp Ser Glu Ser Asp Ser
        595                 600                 605

Asp Ser Asp Ser Asp Ser Asp Ser Asp Ser Asp Ser Asp Ser Glu Ser
    610                 615                 620

Asp Ser Asp Ser Glu Ser Asp Ser Asp Ser Asp Ser Asp Ser Asp Ser
625                 630                 635                 640

Asp Ser Asp Ser Asp Ser Glu Ser Asp Ser Asp Ser Asp Ser Asp Ser
                645                 650                 655

Asp Ser Asp Ser Asp Ser Asp Ser Glu Ser Asp Ser Asp Ser Glu Ser
            660                 665                 670

Asp Ser Glu Ser Asp Ser Asp Ser Asp Ser Asp Ser Asp Ser Asp Ser
```

675 680 685

Asp Ser Asp Ser Asp Ser Asp Ser Asp Ser Asp Ser Asp Ser Asp Ser
690 695 700

Asp Ser Asp Ser Asp Ser Asp Ser Glu Ser Asp Ser Asp Ser Asp Ser
705 710 715 720

Asp Ser Asp Ser Asp Ser Asp Ser Asp Ser Asp Ser Asp Ser Asp Ser
725 730 735

Asp Ser Asp Ser Asp Ser Asp Ser Asp Ser Asp Ser Asp Ser Asp Ser
740 745 750

Asp Ser Asp Ser Asp Ser Asp Ser Asp Ser Asp Ser Asp Ser Asp Ser
755 760 765

Asp Ser Asp Ser Asp Ser Asp Ser Asp Ser Asp Ser Asp Ser Asp Ser
770 775 780

Asp Ser Asp Ser Asp Ser Asp Ser Asp Ser Asp Ser Asp Ser Asp Ser
785 790 795 800

Asp Ser Asp Ser Arg Val Thr Pro Pro Asn Asn Glu Gln Lys Ala Pro
805 810 815

Ser Asn Pro Lys Gly Glu Val Asn His Ser Asn Lys Val Ser Lys Gln
820 825 830

His Lys Thr Asp Ala Leu Pro Glu Thr Gly Asp Lys Ser Glu Asn Thr
835 840 845

Asn Ala Thr Leu Phe Gly Ala Met Met Ala Leu Leu Gly Ser Leu Leu
850 855 860

Leu Phe Arg Lys Arg Lys Gln Asp His Lys Glu Lys Ala
865 870 875

<210> SEQ ID NO 33
<211> LENGTH: 658
<212> TYPE: PRT
<213> ORGANISM: Staphylococcus sp.

<400> SEQUENCE: 33

Met Lys Lys Gln Ile Ile Ser Leu Gly Ala Leu Ala Val Ala Ser Ser
1 5 10 15

Leu Phe Thr Trp Asp Asn Lys Ala Asp Ala Ile Val Thr Lys Asp Tyr
20 25 30

Ser Lys Glu Ser Arg Val Asn Glu Lys Ser Lys Lys Gly Ala Thr Val
35 40 45

Ser Asp Tyr Tyr Tyr Trp Lys Ile Ile Asp Ser Leu Glu Ala Gln Phe
50 55 60

Thr Gly Ala Ile Asp Leu Leu Glu Asp Tyr Lys Tyr Gly Asp Pro Ile
65 70 75 80

Tyr Lys Glu Ala Lys Asp Arg Leu Met Thr Arg Val Leu Gly Glu Asp
85 90 95

Gln Tyr Leu Leu Lys Lys Lys Ile Asp Glu Tyr Glu Leu Tyr Lys Lys
100 105 110

Trp Tyr Lys Ser Ser Asn Lys Asn Thr Asn Met Leu Thr Phe His Lys
115 120 125

Tyr Asn Leu Tyr Asn Leu Thr Met Asn Glu Tyr Asn Asp Ile Phe Asn
130 135 140

Ser Leu Lys Asp Ala Val Tyr Gln Phe Asn Lys Glu Val Lys Glu Ile
145 150 155 160

Glu His Lys Asn Val Asp Leu Lys Gln Phe Asp Lys Asp Gly Glu Asp
165 170 175

-continued

```
Lys Ala Thr Lys Glu Val Tyr Asp Leu Val Ser Glu Ile Asp Thr Leu
            180                 185                 190

Val Val Thr Tyr Tyr Ala Asp Lys Asp Tyr Gly Glu His Ala Lys Glu
        195                 200                 205

Leu Arg Ala Lys Leu Asp Leu Ile Leu Gly Asp Thr Asp Asn Pro His
    210                 215                 220

Lys Ile Thr Asn Glu Arg Ile Lys Lys Glu Met Ile Asp Asp Leu Asn
225                 230                 235                 240

Ser Ile Ile Asp Asp Phe Phe Met Glu Thr Lys Gln Asn Arg Pro Asn
                245                 250                 255

Ser Ile Thr Lys Tyr Asp Pro Thr Lys His Asn Phe Lys Glu Lys Ser
            260                 265                 270

Glu Asn Lys Pro Asn Phe Asp Lys Leu Val Glu Glu Thr Lys Lys Ala
        275                 280                 285

Val Lys Glu Ala Asp Glu Ser Trp Lys Asn Lys Thr Val Lys Lys Tyr
    290                 295                 300

Glu Glu Thr Val Thr Lys Ser Pro Val Val Lys Glu Glu Lys Lys Val
305                 310                 315                 320

Glu Glu Pro Gln Leu Pro Lys Val Gly Asn Gln Gln Glu Val Lys Thr
                325                 330                 335

Thr Ala Gly Lys Ala Glu Glu Thr Thr Gln Pro Val Ala Gln Pro Leu
            340                 345                 350

Val Lys Ile Pro Gln Glu Thr Ile Tyr Gly Glu Thr Val Lys Gly Pro
        355                 360                 365

Glu Tyr Pro Thr Met Glu Asn Lys Thr Leu Gln Gly Glu Ile Val Gln
    370                 375                 380

Gly Pro Asp Phe Leu Thr Met Glu Gln Asn Arg Pro Ser Leu Ser Asp
385                 390                 395                 400

Asn Tyr Thr Gln Pro Thr Thr Pro Asn Pro Ile Leu Glu Gly Leu Glu
                405                 410                 415

Gly Ser Ser Ser Lys Leu Glu Ile Lys Pro Gln Gly Thr Glu Ser Thr
            420                 425                 430

Leu Lys Gly Ile Gln Gly Glu Ser Ser Asp Ile Glu Val Lys Pro Gln
        435                 440                 445

Ala Thr Glu Thr Thr Glu Ala Ser Gln Tyr Gly Pro Arg Pro Gln Phe
    450                 455                 460

Asn Lys Thr Pro Lys Tyr Val Lys Tyr Arg Asp Ala Gly Thr Gly Ile
465                 470                 475                 480

Arg Glu Tyr Asn Asp Gly Thr Phe Gly Tyr Glu Ala Arg Pro Arg Phe
                485                 490                 495

Asn Lys Pro Ser Glu Thr Asn Ala Tyr Asn Val Thr Thr Asn Gln Asp
            500                 505                 510

Gly Thr Val Ser Tyr Gly Ala Arg Pro Thr Gln Asn Lys Pro Ser Glu
        515                 520                 525

Thr Asn Ala Tyr Asn Val Thr Thr His Ala Asn Gly Gln Val Ser Tyr
    530                 535                 540

Gly Ala Arg Pro Thr Gln Lys Lys Pro Ser Lys Thr Asn Ala Tyr Asn
545                 550                 555                 560

Val Thr Thr His Ala Asn Gly Gln Val Ser Tyr Gly Ala Arg Pro Thr
                565                 570                 575

Gln Lys Lys Pro Ser Lys Thr Asn Ala Tyr Asn Val Thr Thr His Ala
            580                 585                 590

Asn Gly Gln Val Ser Tyr Gly Ala Arg Pro Thr Tyr Lys Lys Pro Ser
```

```
        595                 600                 605

Glu Thr Asn Ala Tyr Asn Val Thr Thr His Ala Asn Gly Gln Val Ser
    610                 615                 620

Tyr Gly Ala Arg Pro Thr Gln Lys Lys Pro Ser Glu Thr Asn Ala Tyr
625                 630                 635                 640

Asn Val Thr Thr His Ala Asp Gly Thr Ala Thr Tyr Gly Pro Arg Val
                645                 650                 655

Thr Lys


<210> SEQ ID NO 34
<211> LENGTH: 1602
<212> TYPE: DNA
<213> ORGANISM: Staphylococcus sp.

<400> SEQUENCE: 34

atgttacaag taactgatgt gagtttacgt tttggagatc gtaaactatt tgaagatgta     60

aatattaaat ttacagaagg taattgttat ggattaattg gtgcgaatgg tgcaggtaaa    120

tcaacattct taaaaatatt atctggtgaa ttagattctc aaacaggaca tgtttcatta    180

ggtaaaaatg aacgtctagc tgttttaaaa caggaccact atgcttatga agatgaacgc    240

gtgcttgatg ttgtaattaa aggtcacgaa cgtctttatg aggttatgaa agaaaaagat    300

gaaatctata tgaagccaga tttcagtgat gaagatggta tccgtgctgc tgaacttgaa    360

ggtgaatttg cagaaatgaa tggttggaat gctgaagctg atgctgctaa ccttttatct    420

ggtttaggta tcgatccaac tttacacgat aaaaaaatgg ctgaattaga aaacaaccaa    480

aaaattaaag tattattagc gcaaagttta ttcggtgaac cagacgtact attactggat    540

gagcctacta acggtctcga tattccagca atcagttggt tagaagattt cttaattaac    600

tttgataata ctgttatcgt agtatcgcat gaccgtcatt tcttaaataa tgtatgtact    660

catatcgctg atttagactt cggtaaaatt aaagtttatg ttggtaacta tgatttttgg    720

tatcaatcta gtcagttagc tcaaaagatg gctcaagaac aaaacaagaa aaaagaagaa    780

aaaatgaaag agttacagga ctttattgca cgtttctcag ctaacgcttc taaatctaaa    840

caagcaacaa gtcgtaaaaa acaacttgag aaaattgaat tagatgatat tcaaccatca    900

tcaagaagat atcctttcgt taaattcacg cctgagcgtg agattggtaa cgacttatta    960

atcgttcaaa atctttctaa aacaattgac ggcgaaaaag tattagataa tgtatcattc   1020

acaatgaatc caaatgataa agcgatttta attggagata gtgaaattgc aaaaacaaca   1080

ttacttaaaa tattagctgg cgaaatggaa ccagacgaag gttcatttaa atggggtgtt   1140

actacatcat taagttactt ccctaaagat aactcagagt tctttgaggg tgtaaatatg   1200

aatctcgttg attggttaag acaatatgct cctgaagatg aacaaacaga aacattttta   1260

cgtggtttct taggtcgtat gttatttagt ggtgaagaag ttaagaaaaa agctagtgtg   1320

ctttcaggtg gagaaaaagt acgttgtatg ctaagtaaaa tgatgttatc aagtgcgaat   1380

gtacttttac ttgacgaacc tactaaccac ttagacttag aaagtattac tgctgtcaat   1440

gatggtctta aatcatttaa aggttctatc atctttactt cttatgactt cgaatttatc   1500

aacacgattg caaaccgtgt tatcgattta aataaacaag gcggcgtttc aaaagaaatt   1560

ccatatgaag aatacttgca agaaatcggc gttttaaaat aa                      1602


<210> SEQ ID NO 35
<211> LENGTH: 1608
<212> TYPE: DNA
```

<213> ORGANISM: Staphylococcus sp.

<400> SEQUENCE: 35

```
atgttacaag taactgatgt aagtttacgt tttggtgatc gtaaactatt tgaagatgta     60
aatataaaat ttacagaggg taattgttat ggattaattg gtgcaaatgg tgctgggaaa    120
tctacattct tgaagatttt atcaggcgaa attgattcac agactggtca tgtatctcta    180
ggtaaagatg agcgtttggc tgtgttaaaa caagatcatt ttgcttatga agatgaacgt    240
gttttagatg ttgtgattaa aggacatgaa cgtttgtatc aagtgatgaa agagaaagat    300
gaaatttata tgaaacctga tttcagcgat gaggacggta ttcgcgctgc agaacttgaa    360
ggagaatttg cagaaatgaa cggttggaat gctgaagctg atgctgctaa cttattatca    420
ggattaggca tagaacctga cttacatgat aaaaatatgt ctgaacttga aaataatcaa    480
aaagttaagg tattgttagc tcaaagttta tttggtgatc ctgacgttct tttactagat    540
gagcctacca atggtttaga tataccagca ataagttggt tagaagactt tttaattaat    600
tttgaaaata ctgtcattgt cgtttcgcat gaccgtcact tcttaaataa tgtttgtact    660
catattgctg atttagactt tggcaaaatt aaactttatg ttggtaacta tgatttttgg    720
tatcaatcaa gtcaattagc acaaaaaatg gcacaagaac aaaataagaa aaaagaagaa    780
aaaatgaaag agttacagga tttcatcgca cgcttctcag caaatgcttc taaatctaaa    840
caggcaacaa gtcgtaagaa acaattagaa aaaattgaat tagatgatat ccagccatca    900
tctcgtagat acccttacgt gaaatttact cctgaacgtg aaattggaaa tgatttactt    960
acagtagaaa atctttctaa aacaattgac ggcgaaaaag tactagacaa tgtttcattc   1020
actatgaatc ctaatgataa agctatttta gttggtgata gcgaaattgc taaaacaaca   1080
ttgttaaaaa ttttagctgg agaaatggaa ccagatgaag gtacatttaa atggggtgta   1140
acgacatctt taagttactt ccctaaagat aactctgagt tctttgatgg tgtcgatatg   1200
aatttagttg aatggttacg tcaatacgct ccagaagatg aacaaactga aacattttta   1260
cgtggtttct taggtcgcat gttatttagt ggtgaggaag ttaagaaaaa agcaagcgtg   1320
ctttcaggtg gagaaaaagt acgttgcatg ttaagtaaaa tgatgttatc aagtgctaac   1380
gtacttttac ttgatgagcc aacaaaccat ttagatttgg aaagtatcac tgctgtaaat   1440
gacggattaa aatcatttaa aggttctatc atcttcactt cttatgattt tgaatttatt   1500
aatacaatcg caaatcgagt gattgacttg aatcaagctg gtgccctttc taaagaagta   1560
ccttatgagg aatacttaca agaaattggt gtattacaaa ataattaa                1608
```

<210> SEQ ID NO 36
<211> LENGTH: 1305
<212> TYPE: DNA
<213> ORGANISM: Staphylococcus sp.

<400> SEQUENCE: 36

```
atgccaatta ttacagatgt ttacgctcgc gaagtcttag actctcgtgg taacccaact     60
gttgaagtag aagtattaac tgaaagtggc gcatttggtc gtgcattagt accatcaggt    120
gcttcaactg gtgaacacga agctgttgaa ttacgtgatg gagacaaatc acgttattta    180
ggtaaaggtg ttactaaagc agttgaaaac gttaatgaaa tcatcgcacc agaaattatt    240
gaaggtgaat tttcagtatt agatcaagta tctattgata aaatgatgat cgcattagac    300
ggtactccaa acaaaggtaa attaggtgca aatgctattt taggtgtatc tatcgcagta    360
gcacgtgcag cagctgactt attaggtcaa ccactttaca aatatttagg tggatttaat    420
```

ggtaagcagt taccagtacc aatgatgaac atcgttaatg gtggttctca ctcagatgct 480
ccaattgcat tccaagaatt catgatttta cctgtaggtg ctacaacgtt caaagaatca 540
ttacgttggg gtactgaaat tttccacaac ttaaaatcaa ttttaagcaa acgtggttta 600
gaaactgcag taggtgacga aggtggtttc gctcctaaat ttgaaggtac tgaagatgct 660
gttgaaacaa ttatccaagc aatcgaagca gctggttaca aaccaggtga agaagtattc 720
ttaggatttg actgtgcatc atcagaattc tatgaaaatg gtgtatatga ctacagtaag 780
ttcgaaggcg aacacggtgc aaaaacgtaca gctgcagaac aagttgacta cttagaacaa 840
ttagtagaca aatatcctat cattacaatt gaagacggta tggacgaaaa cgactgggat 900
ggttggaaac aacttacaga acgtatcggt gaccgtgtac aattagtagg tgacgattta 960
ttcgtaacaa acactgaaat tttagcaaaa ggtattgaaa acggaattgg taactcaatc 1020
ttaattaaag ttaaccaaat cggtacatta actgaaacat ttgatgcaat cgaaatggct 1080
caaaaagctg gttacacagc agtagtttct caccgttcag gtgaaacaga agatacaaca 1140
attgctgata ttgctgttgc tacaaacgct ggtcaaatta aaactggttc attatcacgt 1200
actgaccgta ttgctaaata caatcaatta ttacgtatcg aagatgaatt atttgaaact 1260
gctaaatatg acggtatcaa atcattctat aacttagata aataa 1305

<210> SEQ ID NO 37
<211> LENGTH: 1305
<212> TYPE: DNA
<213> ORGANISM: Staphylococcus sp.

<400> SEQUENCE: 37
atgccaatta ttacagatgt ttacgctcgc gaagtcttag actcacgtgg taacccaaca 60
gttgaagttg aagtattaac tgaaagcggt gctttcggac gtgcattagt accttctggt 120
gcttctactg gtgaacatga agcagttgaa ttacgtgatg gagataaatc acgttattta 180
ggtaaaggtg tgactaaagc ggtagaaaat gttaacgaaa tgatcgcacc agaaatcgtt 240
gaaggtgaat tttcagtttt agatcaagta tctattgata aaatgatgat tcaattagac 300
ggtacacaca acaaaggtaa attaggtgca aatgccattt taggtgtttc tattgccgta 360
gctcgtgcag ctgctgactt attaggtcaa ccattatata aatatttagg tggatttaat 420
ggtaaacaat tgccagtacc tatgatgaat attgttaatg gtggttctca ctcagatgca 480
ccaattgctt tccaagagtt catgatttta cctgtaggtg ctgagtcatt caaagaatca 540
ttacgttggg gtgcagaaat cttccataac cttaaatcaa tcttaagtga acgtggttta 600
gaaactgcag taggtgatga aggtggtttc gctcctagat ttgaaggcac tgaagacgct 660
gtagaaacta ttattaaagc tatcgaaaaa gcaggataca aaccaggtga agatgtattc 720
ttaggatttg actgtgcttc ttctgaattc tatgaaaatg gtgtttatga ttacactaaa 780
ttcgaaggtg aacacggtgc taaacgtagt gcagcagagc aagttgacta cttagaagaa 840
ttaattggta aatatccaat catcactatt gaagatggta tggatgaaaa cgattgggaa 900
ggttggaaac aattaactga tcgtatcggt gataaagttc aattagttgg tgatgattta 960
ttcgtaacta acactgaaat tttatctaaa ggtatcgaac aaggtattgg taactcaatc 1020
ttaatcaaag taaaccaaat cggtacatta actgaaacat tcgatgctat tgaaatggct 1080
caaaaagctg gatatactgc ggttgtatct caccgttctg gtgaaactga agatactaca 1140
attgctgata tcgcagttgc tacaaatgca ggccaaatta aaacaggttc attatctaga 1200
actgaccgta ttgctaaata caatcaatta ttacgtattg aagatgaatt atacgaaaca 1260
gctaaatttg aaggaattaa atctttctac aatttagata aataa 1305

<210> SEQ ID NO 38
<211> LENGTH: 768
<212> TYPE: DNA
<213> ORGANISM: Staphylococcus sp.

<400> SEQUENCE: 38
atgaaaaaaa tcgttacagc tacaatcgct acagcaggac ttgccactat cgcatttgca 60
ggacatgatg cacaagccgc agaacaaaat aacaatggat ataattctaa tgacgctcaa 120
tcatacagct atacgtatac aattgatgca caaggtaatt atcattacac ttggacagga 180
aattggaatc caagtcaatt aacgcaaaac aacacatact actacaacaa ctacaatact 240
tatagttata acaatgcatc ttacaataac tactataatc attcatatca atacaataac 300
tatacaaaca atagccaaac agcaacaaat aactattata ctggtggttc aggtgcaagt 360
tatagcacaa caagtaataa tgttcatgtg actacaactg cagcgccatc ttcaaatggt 420
cgttcaattt ctaatggtta tgcatcagga agtaacttat atacttcagg acaatgtact 480
tattatgtat ttgatcgtgt tggtgggaaa attggttcaa catggggtaa cgcaagtaat 540
tgggctaacg cagctgcatc atctggctat acagtgaaca atacaccaaa agttggtgct 600
atcatgcaaa caacacaagg ctattacggt catgttgctt acgttgaagg cgttaacagc 660
aacggttctg ttcgtgtttc agaaatgaac tatggacatg gtgctggtgt ggttacgtct 720
cgtacaattt cagcaaacca agcaggttca tataatttca ttcattaa 768

<210> SEQ ID NO 39
<211> LENGTH: 804
<212> TYPE: DNA
<213> ORGANISM: Staphylococcus sp.

<400> SEQUENCE: 39
atgaagaaaa tcgctacagc tactatcgca actgcaggat tcgctacaat cgcaattgca 60
tcaggaaatc aagctcatgc ttctgagcaa gataactacg gttataatcc aaacgaccca 120
acatcatata gctatactta cactattgat gcacaaggta actaccatta cacatggaaa 180
ggtaactggc atccaagtca attaaaccaa gataatggct actacagcta ttactactac 240
aatggctaca ataactacaa caattacaac aatggttata gctacaataa ttacagccgt 300
tacaacaact actcaaataa taatcaatca tataactaca ataactataa tagttacaac 360
acaaacagct accgtactgg tggtttaggt gcaagctaca gcacttcaag caacaatgtt 420
caagtaacta caactatggc tccatcatca aatggccgtt caatctcaag tggttatact 480
tcaggacgta acttatacac ttctggtcaa tgtacatact acgtatttga tcgtgtaggt 540
ggtaaaatcg gttcaacttg gggcaatgca agtaactggg ctaacgcagc tgcaagagct 600
ggttacacag tgaacaatac accaaaagct ggtgcaatta tgcaaacaac tcaaggtgca 660
tacggtcacg ttgcatacgt tgaaagtgtt aacagcaatg gttcagtaag agtttcagaa 720
atgaactatg gttatggccc aggtgttgta acttcacgta caatctcagc tagccaagct 780
gctggttata acttcattca ctaa 804

<210> SEQ ID NO 40
<211> LENGTH: 774
<212> TYPE: DNA
<213> ORGANISM: Staphylococcus sp.

<400> SEQUENCE: 40

```
atgaaaaaaa tcgctacagc tacaattgca actgcaggaa tcgctacttt cgcatttgca      60
caccatgacg cacaagcagc agaacaaaat aatgatgggt acaatccaaa cgacccttat     120
tcatatagct acacttacac aatcgatgct gaaggtaact accactacac ttggaaaggt     180
aactggagtc cagatcgtgt aaatacttca tataactata ataattataa taactacaac     240
tactatggtt acaataacta tagcaactac aataactaca gtaattacaa caattacaac     300
aactatcaat caaacaacac gcaatcacaa agaacaactc aaccgactgg tggtttaggc     360
gcaagctatt caacatcaag tagtaatgtt cacgttacaa caacttctgc gccatcatca     420
aacggtgtat ctttatcaaa cgctcgctca gcatctggta acttatacac ttcaggtcaa     480
tgtacatatt atgtatttga cagagtaggt ggcaaaatcg gttcaacgtg gggtaacgca     540
aacaactggg caaacgctgc agcacgttct ggttacacag taaacaattc gcctgctaaa     600
ggtgcaatct tacaaacgtc acaaggtgca tacggacacg tagcatacgt tgaaggtgta     660
aacagcaatg gttcaatcag agtttcagaa atgaactacg gtcacggtgc aggtgttgtc     720
acttcacgta caatctctgc gagccaagct gcttcatata actatattca ctaa           774
```

<210> SEQ ID NO 41
<211> LENGTH: 930
<212> TYPE: DNA
<213> ORGANISM: Staphylococcus sp.

<400> SEQUENCE: 41

```
atgaaaaaat tagtaccttt attattagcc ttattacttc tagttgctgc atgtggtact      60
ggtggtaaac aaagcagtga taagtcaaat ggcaaattaa aagtagtaac gacgaattca     120
attttatatg atatggctaa aaatgttggt ggagacaacg tcgatattca tagtattgta     180
cctgttggtc aagatcctca tgaatatgaa gttaaaccta aagatattaa aaagttaact     240
gacgctgacg ttattttata caacggatta aatttagaga ctggtaacgg ttggtttgaa     300
aaagccttag aacaggctgg taaatcatta aaagataaaa aagttatcgc agtatcaaaa     360
gatgttaaac ctatctattt aaacggtgaa gaaggcaaca aagataaaca agatccacac     420
gcatggttaa gtttagataa tggtattaaa tacgtaaaaa caattcaaca aacatttatc     480
gataacgaca aaaaacataa agcagattat gaaaagcaag gtaacaaata cattgctcaa     540
ttggaaaaat taaataatga cagtaaagac aaatttaatg acattccaaa agaacaacgt     600
gccatgatta caagtgaagg tgccttcaag tacttctcaa aacaatacgg tattacacca     660
ggttatattt gggaaattaa cactgaaaaa caaggtacac ctgaacaaat gagacaagct     720
attgagtttg ttaaaaagca caaattaaaa cacttattag tagaaacaag tgttgataag     780
aaagcaatgg aaagtttatc tgaagaaacg aagaaagata tctttggtga agtgtacaca     840
gattcaatcg gtaaagaagg cactaaaggt gactcttact acaaaatgat gaaatcaaat     900
attgaaactg tacacggaag catgaaataa                                      930
```

<210> SEQ ID NO 42
<211> LENGTH: 930
<212> TYPE: DNA
<213> ORGANISM: Staphylococcus sp.

<400> SEQUENCE: 42

```
gtgaaaaaaa ttctcgcttt agcaatagca tttttaatta tccttgccgc atgtgggaat      60
```

```
cacagtaacc atgaacatca ctcacatgaa ggaaaattaa aagttgtaac tacaaactct    120

attctctatg acatggttaa acgtgtcggt ggaaataagg tcgatgttca tagcatcgtt    180

ccagtaggac aagacccaca tgaatatgag gttaaaccta aagatattaa agcattaaca    240

gatgctgacg ttgtatttta taacggttta aacctagaaa ctggaaatgg ttggtttgaa    300

aaagcacttg accaagcagg aaaatcaaca aaagataaaa atgtgatagc agcatcaaat    360

aatgttaaac caatatactt aaatggtgag gaaggtaaca aaaacaaaca agatccacat    420

gcatggttaa gtttagagaa tggaattaaa tacgtaaaaa caatacaaaa atcactagaa    480

catcatgata aaaaagataa gtctacatat gaaaaacaag ggaatgcata tatatcaaaa    540

ttagaagaac ttaataaaga tagtaaaaat aaatttgatg acatacccaa aaatcaacgt    600

gccatgatga caagtgaagg tgcatttaaa tattttgctc aacaattcga tgttaaacca    660

ggttatattt gggagataaa cacagaaaaa caaggtacac ctggtcaaat gaaacaagcc    720

attaaatttg ttaaagataa tcatttaaaa catttattag tcgaaacaag cgtagataaa    780

aaagctatgc aaagtttatc agaagaaact aagaaagata tttatggtga agtatttacc    840

gactctatag gtaaggaagg tactaaaggt gactcatact ataaaatgat gaaatctaat    900

attgatacaa tacatggtag tatgaaataa                                      930
```

<210> SEQ ID NO 43
<211> LENGTH: 702
<212> TYPE: DNA
<213> ORGANISM: Staphylococcus sp.

<400> SEQUENCE: 43

```
atgaaaaaga caattatggc atcatcatta gcagtggcat taggtgtaac aggttacgca     60

gcaggtacag gacatcaagc acacgctgct gaagtaaacg ttgatcaagc acacttagtt    120

gacttagcgc ataatcacca agatcaatta aatgcagctc caatcaaaga tggtgcatat    180

gacatccact ttgtaaaaga tggtttccaa tataacttta cttcaaatgg tactacatgg    240

tcatggagct atgaagcagc taatggtcaa actgctggtt tctcaaacgt tgcaggtgca    300

gactacacta cttcatacaa ccaaggttca gatgtacaat cagtaagcta caatgcacaa    360

tcaagtaact caaacgttga agctgtttca gctccaactt accataacta cagcacttca    420

actacttcaa gttcagtgag attaagcaat ggtaatactg caggtgctac tggttcatca    480

gcagctcaaa tcatggctca acgtactggt gtttcagctt ctacatgggc tgcaatcatc    540

gctcgtgaat caaatggtca agtaaatgct tacaacccat caggtgcttc aggtttattc    600

caaactatgc caggttgggg tccgacaaac actgttgacc aacaaatcaa cgcagctgtt    660

aaagcataca aagcacaagg tttaggtgct tggggattct aa                        702
```

<210> SEQ ID NO 44
<211> LENGTH: 708
<212> TYPE: DNA
<213> ORGANISM: Staphylococcus sp.

<400> SEQUENCE: 44

```
atgaaaaaaa cagttatcgc ttctacatta gcagtatctt taggaattgc aggttacggt     60

ttatcaggac atgaagcaca cgcttcagaa actacaaacg ttgataaagc acacttagta    120

gatttagcac aacataatcc tgaagaatta aatgctaaac cagttcaagc tggtgcttac    180

gatattcatt tcgtagacaa tggataccaa tacaacttca cttcaaatgg ttctgaatgg    240

tcatggagct acgctgtagc tggttcagat gctgattaca cagaatcatc atcaaaccaa    300
```

```
gaagtaagtg caaatacaca atctagtaac acaaatgtac aagctgtttc agctccaact    360

tcttcagaaa gtcgtagcta cagcacatca actacttcat actcagcacc aagccataac    420

tacagctctc acagtagttc agtaagatta tcaaatggta atactgctgg ttctgtaggt    480

tcatatgctg ctgctcaaat ggctgcacgt actggtgtat ctgcttcaac atgggaacac    540

atcattgcta gagaatcaaa tggtcaatta catgcacgta atgcttcagg tgctgctgga    600

ttattccaaa ctatgccagg ttggggttca actggttcag taaatgatca aatcaatgcc    660

gcttataaag catataaagc acaaggttta tctgcttggg gtatgtaa                708
```

<210> SEQ ID NO 45
<211> LENGTH: 11670
<212> TYPE: DNA
<213> ORGANISM: Staphylococcus sp.

<400> SEQUENCE: 45

```
gtgaattatc gtgataaaat tcaaaagttt agtattcgta aatatacagt tggtacattt     60

tcaactgtca ttgcgacatt ggtattttta ggattcaata catcacaagc acatgctgct    120

gaaacaaatc aaccagcaag cgtggttaaa cagaaacaac aaagtaataa tgaacagact    180

gagaatcgag aatctcaagt acaaaattct caaaattcac aaaatagtca atcattatcc    240

gctactcatg aaaatgagca accaaataat agtcaagcta atttagtaaa tcaaaaagta    300

gcgcaatcat ctactactaa tgatgaacaa ccagcatctc aaaatgtaaa tacaaagaaa    360

gattcggcaa cggctgcgac aacacaacca gataaagaag aaagtaagca taaacaaaac    420

gaaagtcaat ctgctaataa aaatggaaac gacaatagag cggctcatgt agaaaatcat    480

gaagcaaatg tagtaacagc ttcagattca tctgataatg gtaacgtaca acatgaccga    540

aatgaattac aagcattttt tgatgcaaat tatcatgatt atcgctttat tgaccgtgaa    600

aatgcagatt ctggcacatt taactatgta aaaggcattt ttgacaagat taatacttta    660

ttaggcagta atgatccaat taacaataaa gacttgcaac ttgcatacaa agaattggaa    720

caagctgttg ctttaattcg tacaatgcct caacgtcaac aaactagccg tcgatcaaac    780

agaattcaaa cgcgttctgt tgagtctaga gctgcagagc ctagatcagt atcagactat    840

caaaatgcaa attcatcata ttatgttgaa aatgctaatg atggttcagg atatcctgta    900

ggtacatata tcaatgcttc tagtaaaggg gcgccatata atttaccaac tacaccatgg    960

aatacattga aggcctctga ctcaaaggaa attgctctta tgacagcgaa acaaactgga   1020

gatggctacc aatgggttat taagtttaat aaaggacatg ctccacatca aaatatgatt   1080

ttctggtttg cattaccagc agaccaagtg ccagtaggaa gaactgactt tgtaacagtt   1140

aattcagatg gaacaaatgt acaatggagt catggagcag gagcaggtgc aaataaacca   1200

cttcaacaaa tgtgggaata tggagtaaat gatcctgatc gttcacatga ctttaaaata   1260

agaaatagaa gtggccaagt aatatatagc tggccaactg tccatgttta ttctttagaa   1320

gatttatcta gagcgagtga ttattttagt gaagctggag cgacacctgc tactaaagca   1380

tttggtagac aaaattttga atatattaat ggtcaaaaac ctgctgaatc accgggtgtt   1440

cctaaagttt atactttcat cggtcaaggt gatgcaagtt atacaatttc atttaaaaca   1500

caaggtccaa ctgttaataa attgtattat gcagcaggtg ggcgtgcttt agagtacaat   1560

caattattta tgtacagtca actatacgtc gaatcaacgc aagaccatca acaacgtctt   1620

aatggtttaa gacaagtggt taatcgtaca tatcgcatag gtacaactaa acgtgtagaa   1680
```

-continued

```
gtgagtcaag gaaatgtaca aacgaaaaag gtattagaaa gtacaaacct aaatatagat   1740
gattttgttg atgatccttt aagttatgtt aagacgccga gtaataaagt gttaggtttt   1800
tacccaacta atgcaaatac taacgctttt agaccggggg gcgttcaaga attaaatgaa   1860
tatcaattaa gtcaattatt tactgatcaa aaattacaag aagcagcaag aactagaaac   1920
ccaataagat taatgattgg tttcgactat cctgatggtt atggtaatag tgaaacttta   1980
gttcctgtta acttaacggt attacctgaa atccaacata atattaaatt ctttaaaaat   2040
gacgatactc aaaatattgc tgaaaaacca ttttcaaaac aagctgggca tccagttttc   2100
tatgtatatg caggtaacca agggaatgct tccgtgaatt taggtggtag cgtaacatct   2160
attcaaccat tacgtattaa tttaacaagt aatgagaatt ttacagataa agattggcaa   2220
attacaggta ttccgcgtac attacacatt gaaaactcga caaatagaac taataatgct   2280
agagaacgta acattgaact tgttggtaat ttattaccag ggattacttt ggtacgata    2340
cgttttggac gtaaagaaca attatttgaa attcgtgtta aaccacatac accaacaatt   2400
acaacgacag ctgagcaatt aagaggtaca gcattacaaa aagtgcctgt taatatttcg   2460
ggaataccgt tggatccatc ggcattggtt tatttagttg caccaacaaa tcaaactacg   2520
aatggtggta gtgaggcaga tcaaatacca tctggttata cgatacttgc gactggtaca   2580
cctgatgggg tgcataatac aattactata cgaccgcaag attatgttgt attcatacca   2640
cctgtaggta aacaaattag agcagtagtt tattataata aagtagttgc atctaatatg   2700
agtaatgctg ttactatttt gccagatgac attccaccaa caatcaataa tcctgttgga   2760
ataaatgcca aatactatcg aggcgacgaa gtcaacttta caatgggagt ctctgataga   2820
cattctggta taaaaaatac aactattact actttgccaa gtggttggac atcaaattta   2880
actaaatccg acaacaaaaa cggctcatta gctattacag gtagagtctc tatgaatcag   2940
gcatttaaca gtgatattac atttaaagta tcagcgacag acaatgtcaa taatacgaca   3000
aatgatagtc aatctaaaca tgtgtcaatt catgtaggta aaattagtga agatgctcat   3060
ccgattgtat taggaaatac tgagaaagtt gtagtagtca atccgactgc tgtatctaat   3120
gatgaaaagc aaagcataat tactgccttt atgaataaaa accaaaatat aagaggatat   3180
ttagcatcaa ctgatccagt aactgtcgat aataatggta acgtcacatt acattaccgt   3240
gatggctcat caacaacgct tgatgctaca aatgtgatga catacgaacc agttgtgaaa   3300
tctgaatatc aaactgccaa tgctgctaaa acagcaacgg taacgattgc taaaggacaa   3360
tcatttaata ttggtgatat taaacaatat tttactttaa gtaatggaca agctattcca   3420
aatggcacat ttacaaatat tacatctgat agaactattc caactgcaca agaagttagt   3480
caaatgaatg caggtacgca gttatatcat atagttgctt caaatgcata tcataaagac   3540
actgaagatt tctatattag tttaaaaatc gttgatgtga aacaacctga aggcgatcaa   3600
cgtgtctatc gtacgtcaac atatgattta accactgatg aaatctcaaa agtaaaacaa   3660
gcttttatta atgcaaatag agatgtaatt acgcttgccg aaggtgatat ttcagttaca   3720
aatacaccta atggtgctaa tgtaagtact attacagtaa atattaataa aggtcgatta   3780
acgaaatcat tcgcgtctaa cctagctaat atgaatttct tgcgttgggt taatttccca   3840
caagattata cagtgacatg gacgaatgca aaaattgcaa acagaccaac agatggtggt   3900
ttatcatggt ccgatgacca taaatcttta atttatcgtt atgatgctac attaggcaca   3960
caaattacaa ctaatgatat tttaacgatg ctaaaagcga ctactacagt gcctggattg   4020
cgtaataata ttactggtaa tgaaaaagca caagcagaag caggtggaag accaaactat   4080
```

agaacaactg gttattcaca atcaaatgcg acaactgatg gtcaacgtca atttacgttg 4140
aatggtcaag tgattcaaat attagacatc atcaaccctt caaacggtta tggtgggcaa 4200
cctgttacaa attcaaatac tcgtgcaaac catagtaact caactgttgt taacgtaaac 4260
gaaccggcag ctaatggtgc tggcgcattt acaattgacc acgttgtaaa aagtaattct 4320
acacataatg caagtgatgc agtttataaa gcgcagttat acttaacgcc atatggtcca 4380
aaacaatatg ttgaacattt aaatcaaaat acaggaaata ctactgacgc tattaacatt 4440
tattttgtac caagtgactt agtgaatcca acaatttcag taggtaatta cactaatcat 4500
caagtgttct caggtgaaac atttacaaat acgattacag cgaatgataa ctttggtgtg 4560
caatcggtaa ctgtaccaaa tacatcacaa attacaggta ctgttgataa taaccatcaa 4620
catgtttctg caacggcacc aaatgtgaca tcagcaacta gtaagacaat caatttatta 4680
gcaactgata caagtggtaa tacagctaca acttcattca atgtaacagt gaaacctttg 4740
cgtgataaat atcgagttgg tacttcatca acggctgcta atcctgttag aattgccaat 4800
atttcgaata atgcgacagt atcacaagct gatcaaacga caattattaa ttcgttaacg 4860
tttacaagta atgcaccaaa tagaaactat gcaacagcaa gcgcaaatga aatcactagt 4920
aaaacagtta gtaatgtcag tcgtactgga aataatgcca atgtcacagt aactgttact 4980
catcaagatg gaacaacatc aacagtgact gtacctgtaa agcatgtcat tccagaaatc 5040
gttgcacatt cgcattacac tgtacaaggc caagacttcc cagcaggtaa tggttctagt 5100
gcagcagatt actttaagtt atctaatggt agtgccattc cagatgcaac gattacatgg 5160
gtaagtggac aagcgccaaa taaagataat acacgtattg gtgaagatat aacagtaact 5220
gcacatatct taattgatgg cgaaacaacg ccgattacga aaacagcaac atataaagta 5280
gtaagaactg taccgaaaca tgtctttgaa acagccagag gtgtttttata cccaggtgtt 5340
tcagatatgt atgatgcgaa acaatatgtt aagccagtaa ataattcttg gtcgacaaat 5400
gcgcaacata tgaattttca atttgttgga acatatggtc ctaacaaaga tgttgtaggt 5460
atatcaacgc gtcttattag agtgacttat gataatagac aaactgaaga tttaactatt 5520
ttatctaaag ttaaacctga cccaccaaga attgacgcaa actctgtgac atataaagca 5580
ggtcttacaa accaagaaat taaagttaat aacgtattaa ataactcgtc agtaaaatta 5640
tttaaagcag ataatacacc attaaatgtc acaaatatta ctcatggtag tggttttagt 5700
tcggttgtga cagtaagtga cgcgttacca aatggcggaa ttaaagcaaa atcttcaatt 5760
tcaatgaaca atgtgacgta tacgacgcaa gacgaacatg gtcaagttgt tacagtaaca 5820
agaaatgaat ctgttgattc aaatgatagt gcttctgtta cagtaacacc acaattacaa 5880
gcaactactg aaggcgctgt atttattaaa ggtggcgacg gttttgattt cggtcatgta 5940
gaacgattta ttcaaaatcc gccacatggg gcaacggtcg catggcatga tagtccagat 6000
acatggaaga atacagtcgg caacacacat aaaactgcgg ttgtaacatt acctagtggt 6060
caaggtacgc gtaatgttga agttccagtc aaagtttatc cagttgctaa tgctaaggcg 6120
ccatcacgtg atgtgaaagg tcaaaatttg acacatggta caaacgctat tgattacatt 6180
acatttgatc caaatactaa tacgaatggt attacagcag catgggcaaa tagacaacaa 6240
ccaaataacc agcaagcagg cgttcaacat ttaaatgtcg atgtcacata tccaggtatt 6300
tcagctgcta aacgagttcc tgtaactgtg aacgtatatc aatttgaatt ccctcaaact 6360
acttatacaa caacagttgg tggcacttta gcaagtggta cgcaagcatc aggatatgca 6420

-continued

```
catatgcaaa acgcttcagg tttaccaaca gatggattta cgtataaatg gaatcgtgat   6480
actacgggta caaacgatgc aaactgggca gcaatgaata aaccaaatac tgcacaagtc   6540
gttaatgcaa aatatgatgt catctataat ggacatacat ttgcaacatc tttaccagcg   6600
aaatttgtag taaaagatgt tcaaccagcg aaaccaactg tcactgaaac agcggcagga   6660
gcgattacaa ttgcacctgg tgcgaaccaa acagtcaata ctcatgctgg taatgttacg   6720
acatatgctg acaaattagt tattaaacgt aatggaaatg ttgtaacgac atttacacgt   6780
cgtaataata cgagcccatg ggtgaaagaa gcatcagcag ataatgtaac aggtattgtt   6840
ggaactaata atggtattac tgtggcagca ggtactttca atcctgctga tacaattcaa   6900
gttgttgcaa cacaaggtag tggcgaaaca atcagtgacg agcaacgtag tgatgatttc   6960
acagttgtcg caccacaacc gaaccaagcg actacgaaaa tttggcaaaa tggtcatatt   7020
gatatcacgc ctaataatcc atcaggacat ttaattaatc caacacaagc aatggatatt   7080
gcttacactg aaaaagtggg taatggtgca gaacatagta agacaattaa tgttgttcgt   7140
ggtcaaaata atcaatggac aattgcgaat aagcctgact atgtaacgtt agatgcacaa   7200
actggtaaag tgacgttcaa tgccaatact ataaaaccaa attcatcaat cacaattact   7260
ccgaaagcag gtacaggtca ctcagtaagt agtaatccaa gtacattaac tgcaccggca   7320
gctcatactg tcaacacaac tgaaattgtg aaagattatg gttcaaatgt aacagcagct   7380
gaaattaaca atgcagttca agttgctaat aaacgtactg caacgattaa aaatggcaca   7440
gcaatgccta ctaatttagc tggtggtagc acaacgacga ttcctgtgac agtaacttac   7500
aatgatggta gtactgaaga agtacaagag tccattttca caaaagcgga taaacgtgag   7560
ttaatcacag ctaaaaatca tttagatgat ccagtaagca ctgaaggtaa aaagccaggt   7620
acaattacgc agtacaataa tgcaatgcat aatgcgcaac aacaaatcaa taccgcgaaa   7680
acagaagcac aacaagtgat taataatgag cgtgcaacac cacaacaagt ttctgacgca   7740
ctaactaaag ttcgtgcagc acaaactaag attgatcaag ctaaagcatt acttcaaaat   7800
aaagaagata atagccaatt agtaacgtct aaaaataact tacaaagttc tgtgaaccaa   7860
gtaccatcaa ctgctggtat gacgcaacaa agtattgata actataatgc gaagaagcgt   7920
gaagcagaaa ctgaaataac tgcagctcaa cgtgttattg acaatggcga tgcaactgca   7980
caacaaattt cagatgaaaa acatcgtgtc gataacgcat taacagcatt aaaccaagcg   8040
aaacatgatt taactgcaga tacacatgcc ttagagcaag cagtgcaaca attgaatcgc   8100
acaggtacaa cgactggtaa gaagccggca agtattactg cttacaataa ttcgattcgt   8160
gcacttcaaa gtgacttaac aagtgctaaa aatagcgcta atgctatcat tcagaagcca   8220
ataagaacag tgcaagaggt acaatctgcg ttaacaaatg taaatcgtgt caatgagcga   8280
ttaacgcaag caattaatca attagtacct ttagctgata atagtgcttt aagaactgct   8340
aagacgaaac ttgatgaaga aatcaataaa tcagtaacta ctgatggtat gacacaatca   8400
tcaatccaag catatgaaaa tgctaaacgt gcaggtcaaa cagaaacaac aaatgcacaa   8460
aatgttatta acaatggtga cgcgacagac caacaaattg ccgcagaaaa aacaaaagta   8520
gaagaaaaat ataatagctt aaaacaagca attgctggat taacaccaga cttggcacca   8580
ttacaaactg caaaaactca gttgcaaaat gatattgatc agccaacgag tacgactggt   8640
atgacaagcg catctgttgc tgcatttaat gacaaacttt cagcagctag aactaaaatt   8700
caagaaattg atcgcgtact agcatctcat ccagatgtag caacgattcg tcaaaacgtg   8760
acagcagcga atgctgctaa aacagcactt gatcaagcgc gcaatggctt aacagtcgat   8820
```

```
aaagcacctt tagaaaatgc gaaaaatcaa ctacaacata gtattgatac gcaaacaagt   8880
acaactggta tgacacaaga ctctataaat gcatacaatg cgaagttaac agctgcacgt   8940
aataaggttc aacaaatcaa tcaagtatta gcaggttcac ctactgtaga tcaaattaat   9000
acaaatacgt ctgcagcaaa tcaagcgaaa tctgatttag atcatgcacg tcaagcgtta   9060
acaccagata aagcgccgct tcaaaatgcg aaaacgcaat tagaacaaag cattaatcaa   9120
ccaacagata caacaggtat gacaaccgct tcgttaaatg catacaacca aaaattacaa   9180
gcagcacgtc aaaagttaac tgaaattaat caagtgttga atggcaaccc aactgtccaa   9240
aatatcaatg ataaagtggc agaggcaaac caagctaagg atcaattaaa tacagcacgt   9300
caaggtttaa cattagatag acagccagcg ttaacaacat tacatggtgc atctaactta   9360
aaccaagcac aacaaaataa tttcacgcaa caaattaatg ctgctcaaaa tcatgctgcg   9420
cttgaaacaa ttaagtctaa cattacggct ttaaatactg cgatgacgaa attaaaagac   9480
agtgttgcgg ataataatac aattaaatca ggtcaaaatt acactgacgc aacaccagct   9540
aataaacaag cctatgataa tgcagttaat gcggctaaag gtgtcattgg agaaacgact   9600
aatccaacga tggatgttaa cacagtgaac caaaaagcag catctgttaa atcgacgaaa   9660
gatgctttag atggtcaaca aaacttacaa cgtgcgaaaa cagaagcaac aaatgcgatt   9720
acgcatgcaa gtgatttaaa ccaagcacaa aagaatgcat taacacaaca agtgaatagt   9780
gcacaaaacg tgcaagcagt aaatgatatt aaacaaacga ctcaaagctt aaatactgct   9840
atgacaggtt taaaacgtgg cgttgctaat cataaccaag tcgtacaaag tgataattat   9900
gtcaacgcag atactaataa gaaaaatgat tacaacaatg catacaacca tgcgaatgac   9960
attattaatg gtaatgcaca acatccagtt ataacaccaa gtgatgttaa caatgcttta  10020
tcaaatgtca caagtaaaga acatgcattg aatggtgaag ctaagttaaa tgctgcgaaa  10080
caagaagcga atactgcatt aggtcattta aacaatttaa ataatgtaca acgtcaaaac  10140
ttacaatcgc aaattaatgg tgcgcatcaa attgatgcag ttaatacaat taagcaaaat  10200
gcaacaaact tgaatagtgc aatgggtaac ttaagacaag ctgttgcaga taaagatcaa  10260
gtgaaacgta cagaagatta tgcggatgca gatacagcta aacaaaatgc atataacagt  10320
gcagtttcaa gtgctgaaac aattattaat caaacagcta atccgacaat gtctgttgat  10380
gatgttaatc gtgcaacttc agctgttact actaataaaa atgcattaaa tggtgatgaa  10440
aaattagtac aatctaaaac agatgctgca agagcaattg atgcattacc acatttaaat  10500
aatgcacaaa aagcagatgt taaatctaaa attaatgctg catcaaatat tgctggtgta  10560
aataccgtta aacaacaagg tacagattta aatacagcga tgggtaactt gcagggtgca  10620
atcaatgatg aacaaacgac gcttaatagt caaaattatc aagatgcgac acctagtaag  10680
aaaacagcat acacaaatgc ggtgcaagct gcgaaagata ttttaaataa atcaaatggt  10740
caaaataaaa cgaaagatca agttactgaa gcgatgaatc aagtgaattc ggctaaaaat  10800
aacttagatg gtacgcgttt attagatcaa gcgaagcaaa cagcgaaaca gcagttaaat  10860
aatatgacgc atttaacaac tgcacaaaaa acgaatttaa caaatcaaat taatagtggt  10920
actactgttg ctggtgttca tacggttcaa tcaaatgcca acacattaga tcaagcgatg  10980
aatacgttaa gacaaagtat tgctaacaat gatgcgacta aagcaagtga agattacgta  11040
gatgctaata atgataagca aacagcatat aacaacgcgg tagctgctgc tgaaacgatt  11100
attaatgcga atagtaatcc agaaatgaat ccaagtacga ttacacaaaa agcagagcaa  11160
```

gtgaatagtt ctaaaacggc acttaacggt gatgaaaact tagctacggc aaaacaaaat 11220
gcgaaaacgt acttaaacac attaacgagt attacagatg ctcaaaagaa caatttgatt 11280
agtcaaatta gtagtgcgac aagagtgagt ggtgttgata ctgtaaaaca aaatgcacaa 11340
catttagatc aagctatggc taacttacaa aatggtatta acaacgaatc tcaagtgaaa 11400
tcatctgaga aatatcgtga tgctgataca aataaacaac aagagtatga taatgctatt 11460
actgcagcga aagcgatttt aaataaatcg acaggtccaa acactgcgca aaatgcagtt 11520
gaagcagcat tgcaacgtgt taatactgcg aaagatgcat tgaatggtga tgcaaaatta 11580
attgcagctc aaaacgcagc gaaacaacat ttaggtactt taacgcatat cactacagca 11640
caacgcaatg atttaacaaa tcaaatttca 11670

<210> SEQ ID NO 46
<211> LENGTH: 20139
<212> TYPE: DNA
<213> ORGANISM: Staphylococcus sp.

<400> SEQUENCE: 46
atgggtaact tacaaacggc tatcaacgat aagtcaggaa cattagcgag ccaaaacttc 60
ttggatgctg atgagcaaaa acgtaatgct tacaatcaag ctatatcagc tgccgaaacc 120
attttaaata aacaaactgg accgaataca gcgaaaacag cggttgaaca agcacttaat 180
aatgttaata gtgcgaaaca tgcattaaat ggtacgcaaa acttaaataa tgcgaaacaa 240
gcagcgatta cagcaattaa tggcgcatct gatttaaatc aaaaacaaaa agatgcatta 300
aaagcacaag ctaatggtgc tcaacgcgta tctaatgcaa atgatgtaca acgtaatgcg 360
actgaactga acacggcaat gggtcaatta caacatgcca tcgcagataa gacgaatacg 420
ttagcaagca gtaaatatgt caacgccgat agcactaaac aaaatgctta cacaactaaa 480
gttaccaatg ctgaacatat tattagcggt acgccaacgg ttgttacaac accttcagaa 540
gtaacagctg cagctaatca agtaaacagc gcgaaacaag aattaaatgg tgacgaaaga 600
ttacgtgttg caaaacaaaa cgccaatact gctattgatg cattaacgca attaaatact 660
cctcaaaaag ctaaattaaa agaacaagtg ggacaagcca atagattaga agacgtacaa 720
tctgttcaaa caaatggaca atcattgaac aatgcaatga aaggcttaag agatagtatt 780
gctaacgaaa caacagtcaa agcaagtcaa aactatacag acgcaagtcc gaataaccaa 840
tcaacatata atagcgctgt gtcaaatgcg aaaggtatca ttaatcaaac taacaatcca 900
actatggata ctagtgcgat tacccaagct acaacacaag tgaataatgc taaaaatggt 960
ttaaacggtg ctgaaaactt aagaaatgca caaaacactg ctaagcaaaa cttaaatacg 1020
ttatcacact taacaaataa ccaaaaatct gcaatctcat cacaaattga tcgtgcaggt 1080
catgtgagtg aggtaacagc tgctaaaaat gcagcaactg agttaaacgc gcaaatgggc 1140
aacttggaac aagctatcca tgatcaaaac acagttaaac aaggtgttaa cttcactgat 1200
gcagataaag ctaaacgtga tgcttataca aatgcggtaa gcagagcaga aacaattctg 1260
aataaaacgc aaggtgcaaa tacgtctaaa caagatgttg aagcggctat tcaaaatgtt 1320
acaagtgcta aaaatgcatt gaatggtgat caaaacgtta caaatgcgaa gaatgcagct 1380
aaaaatgcat taaataactt aacgtcaatt aataatgcac aaaaacgtga cttaacaact 1440
aaaattgatc aagcaacaac agtagctggt gttgaagcgg tatctaatac aggtacacaa 1500
ttgaatacag cgatggctaa cttgcaaaat ggtattaatg ataaagcgaa tactttagcg 1560
agcgaaaact atcatgatgc tgattcagat aagaaaactg cttatactca agccgttacg 1620

```
aacgcagaaa atattttaaa taaaaatagt ggatcaaatt tagataaagc tgccgttgaa   1680
aacgcgttgt cacaagtgac aaatgcgaaa ggtgccctaa atggtaacca taatttagag   1740
caagctaaat caaatgcaaa cactactata aacggccttc aacatttaac aacagcacaa   1800
aaagataaat tgaaacaaca agtgcaacaa gcacaaaatg ttgcaggtgt agatactgtt   1860
aaatcaagtg ccaacacatt aaatggtgct atgggtacgt taagaaatag catacaagat   1920
aacacagcta cgaaaaatgg ccaaaactat cttgatgcta cagaacgtaa caaaacaaac   1980
tataacaatg ctgttgatag tgctaatggt gtcattaatg caacaagcaa tccaaatatg   2040
gatgctaatg caattaacca aatcgctaca caagtgacat caacgaaaaa tgcattagat   2100
ggtacacata atttaacgca agcgaaacaa acagcaacaa atgccatcga tggtgctact   2160
aacttaaata aagcgcaaaa agatgcgtta aaagcacaag ttacaagtgc gcaacgtgtt   2220
gcaaatgtaa caagtatcca acaaactgca aatgaactta atacagctat gggtcaatta   2280
caacatggta ttgatgatga aaatgcaaca aaacaaactc aaaaatatcg tgacgctgaa   2340
caaagtaaga aaactgctta tgatcaagct gtagctgctg cgaaagcaat tttaaataaa   2400
caaacaggtt ccaattcaga taaagcagca gttgaccgtg cattacaaca agtaacaagt   2460
acgaaagatg cattgaatgg ggatgctaaa ctggcagaag cgaaagcggc agctagacaa   2520
aacttaggta ctttaaacca tattacgaat gcacaacgta ctgcgttaga aggtcaaatc   2580
aatcaagcga cgactgttga tggcgttaat actgtaaaaa caaatgccaa tacattagac   2640
ggcgctatga atagcttaca aggtgcaatc aatgataaag atgcgacatt aagaaatcaa   2700
aattatcttg atgcagatga atcaaaacga aatgcatata cgcaagctgt cacagcggct   2760
gaaggcattt taaataaaca aacaggtggt aacacatcta aagcagacgt tgataatgca   2820
ttaaatgcag ttacaagagc gaaagcggct ttaaatggtg ctgaaaactt aagaaatgcg   2880
aaaacttcag caacaaatac gattaatggt ttacctaact taacacaatt acaaaaagac   2940
aacttgaagc atcaagttga acaagcgcaa aatgtagttg gtgtaaatgg tgttaaagat   3000
aaaggtaata cattaaatac tgccatgggt gcattacgta caagtatcca aaatgataat   3060
acgacgaaaa caagtcaaaa ttatcttgat gcatctgata gcaacaaaaa taattacaat   3120
actgctgtaa ataatgcaaa tggtgttatt aatgcaacga acaatccaaa tatggatgct   3180
aatgcgatta atgacatggc aaatcaagtc aatacaacaa aagcagcgtt aaatggtgca   3240
caaaacttag ctcaagctaa aacaaatgcg acgaacacaa ttaacaacgc gcaagactta   3300
aaccaaaaac aaaaagatgc attaaaaaca caagttaaca atgcacaacg tgtatctgat   3360
gcaaataacg ttcaacatac agctactgaa ttgaacggtg cgatgacagc acttaaagca   3420
gctattgcgg ataaagaaag aacaaaagca agcggtaatt atgtcaatgc tgatcaagaa   3480
aaacgtcaag cgtatgattc aaaagtgact aacgctgaaa atatcattaa tggtacacca   3540
aatgcgacat taacagtcaa tgacgtaaat agtgcggcat cacaagtcaa tgcggctaaa   3600
acagcattaa atggtgataa caacttacgt gtagcgaaag agcatgctaa caatacaatt   3660
gacggcttag cacaattgaa taatgtacaa aaagcaaaat taaaagaaca agttcaaagt   3720
gcaactacat tagatggtgt tcaaactgtt aaaaatagtt ctcaaacgtt gaatacagcg   3780
atgaaaggct taagagatag tattgcgaat gaagcaacga ttaaagcagg tcaaaactac   3840
actgacgcaa gtccaaataa tcgtaacgag tacgacagcg cagttactgc agcaaaagca   3900
atcattaatc aaacatcgaa cccaacgatg gaaccaaata ctattacgca agcaacatca   3960
```

-continued

```
caagtgacaa ctaaagaaca tgcattaaat ggtgcgcaaa acttagctca agctaagaca   4020
acagcgaaaa acaacttgaa taacttaaca tcaattaaca atgcacaaaa agatgcgtta   4080
acgcgtaaca ttgatggtgc aactacagta gctggtgtaa atcaagaaac tgcaaaagca   4140
acagaattaa ataacgcaat gcacagttta caaaatggta tcaatgatga gacacaaaca   4200
aaacaaactc agaaatacct agatgctgag ccaagtaaga aatcagctta tgatcaagca   4260
gtaaatgcag caaaagcaat tttaacaaaa gctagtggtc aaaatgtaga caaagcagca   4320
gttgaacaag cattacaaaa tgtgaacagt acgaagacgg cgttgaacgg tgatgcgaaa   4380
ttaaatgaag ctaaagctgc tgcgaaacaa acgttaggta cattaacaca cattaataat   4440
gcacaacgta atgcgttaga taatgaaatt acacaagcaa caaatgttga aggtgttaat   4500
acagttaaag ccaaagcgca acaattagat ggtgctatgg gtcaattaga aacatcaatt   4560
cgtgataaag acacgacgtt acaaagtcaa aattatcaag atgctgatga tgctaaacga   4620
acggcttatt ctcaagcagt aaatgcagca gcaactattt taaataaaac agctggagga   4680
aatacaccta aagcagatgt cgaaagagca atgcaagctg ttacacaagc caatactgca   4740
ttaaacggta ttcaaaactt agaacgtgcg aaacaggctg cgaacacagc gattacaaat   4800
gcttcggact taaatacaaa acaaaaagaa gcattgaaag cacaagtaac aagtgcagga   4860
cgcgtatctg cagcaaatgg tgttgaacat actgcgactg aattaaatac tgcgatgaca   4920
gctttaaaac gtgccattgc tgataaagct gacacaaaag ctagtggtaa ttatgtcaat   4980
gctgatgcga ataaacgcca agcatatgat gaaaaagtga cagctgcaga acatatcgtt   5040
agtggtacac caacaccaac gttaacacca tcagatgtta caaatgcagc aacgcaagta   5100
acgaatgcga agacgcagtt aaacggtaat cataatttag aagtagcgaa acaaaatgct   5160
aacacagcaa ttgatggttt aacttcttta aatggtccgc aaaaagcaaa acttaaagaa   5220
caagtgggtc aagcgacgac gttgccaaat gttcaaactg ttcgtgataa tgcacaaaca   5280
ttaaacactg caatgaaagg tctacgagat agcattgcga atgaagcaac gattaaagca   5340
ggtcaaaact acacagatgc aagtcaaaac aaacaaaatg actacaacaa tgcagtcact   5400
gcagcaaaag caatcattgg tcaaacaact agtccatcaa tgattgcgca agaaattaat   5460
caagcgaaag accaagtgac agctaaacaa caagcgttaa acggtcaaga aaacttaaga   5520
actgcgcaaa caaatgcgaa gcaacatttg aatggcttaa gtgacttaac taatgcacaa   5580
aaagatgcag cgaaacgcca aatcgaaggt gcaacgcatg ttaatgaagt aacacaagcg   5640
caaaataatg cggacgcatt aaatacagct atgacgaact tgaaaaatgg tattcaagat   5700
caaaatacga ttaagcaagg tgttaacttc actgatgcag atgaagcgaa acgtaatgca   5760
tatacaaatg cagtgacgca agctgaacaa attttaaata aagcacaagg tccaaatact   5820
gcaaaagacg gtgtcgaaac tgcgttacaa aatgtacaac gtgctaaaaa cgaattgaac   5880
ggtaatcaaa atgttgcgaa cgctaagaca actgcgaaaa atgcattgaa taaccttaca   5940
tcaattaata atgcacaaaa agcagcattg aaatcacaaa ttgaaggtgc gacaacagtt   6000
gcaggtgtaa atcaagtgtc tacaatggca tctgaattaa atactgcaat gagcaactta   6060
caacgtggta ttaatgacga agcagctaca aaagcagctc agaaatatac tgaagcagat   6120
agagataaac aaactgcata caatgatgct gtaacagcag ctaaaacgtt attagataaa   6180
acagctggtt caaatgacaa taaagtagcc gttgaacaag cattacaacg tgtgaatact   6240
gctaaaacag cattaaatgg tgacgcgcga ttaaatgaag cgaagaacac agctaaacaa   6300
caattagcga caatgtcaca tttaactaat gctcaaaaag caaacttaac agaacaaatt   6360
```

gaacgtggta caactgttgc tggtgttcaa ggcatccaag caaatgctgg tactttaaat 6420
caagcaatga atcaattaag acaaagtatt gcttctaaag atgcgactaa atcaagcgaa 6480
gattatcaag acgcgaatgc agatttacaa aatgcataca atgatgcggt aactaatgct 6540
gaaggtatta ttagtgcaac gaataaccct gaaatgaatc ctgatacaat taaccaaaaa 6600
gcgagccaag tgaacagtgc gaagtctgca ttgaacggtg atgaaaaatt agcagcagta 6660
aaacaaactg cgaaatcaga tatcggtcgt ttgacagact tgaacaatgc acaacgaact 6720
gcggcaaatg ctgaagtgga tcaagcacca aatcttgcag ctgtcacagc ggctaaaaat 6780
aaagcaacat cgttaaacac agcgatgggt aatttgaaac atgcacttgc tgaaaaggat 6840
aatacgaaac gtagtgtcaa ttacacagat gcggatcaac caaaacaaca agcgtatgat 6900
actgcagtta cacaagcaga agcaattact aatgcaaatg gcagtaacgc gaatgaaaca 6960
caagttcaag cagcgcttaa ccaattgaat caagctaaaa acgacttgaa tggtgataat 7020
aaagttgctc aagcgaaaga aacagcaaaa cgtgcattag cttcatatag taacttgaat 7080
aacgcgcaat caactgcagc aactagtcaa attgacaatg caacgacagt agcagacgta 7140
actgctgcac aaaatactgc taatgaatta aatacagcaa tgggtcaact tcaaaatggt 7200
attaatgacc aaaacactgt taaacaacaa gtgaacttta cagatgctga ccaaggtaag 7260
aaagatgctt acacaaatgc tgttacgaat gctcaaggta ttttagataa agcaaacggt 7320
caaaatatga caaaagcaca agttgaagct gcattaaatc aagtaacgac tgctaagaat 7380
gctttaaacg gtgatgcaaa tgtaagacaa gcaaaatcag atgcgaaagc aaacttaggt 7440
acattaacac acttaaataa tgcacaaaaa caagatttaa catcacaaat cgaaggtgca 7500
acaacagtca acggtgtaaa tagtgttaaa acgaaagcac aagacttaga tggtgcaatg 7560
caacgattag agtcagcaat cgcaaataaa gatcaaacta aagcgagcga aaactacatt 7620
gacgcagatc caactaagaa aacagcattt gataatgcca tcacacaagc tgaatcttac 7680
ttaaataaag atcatggtac gaataaagat aagcaagctg ttgaacaagc aattcaaagt 7740
gtaacgtcta ctgaaaatgc tttgaacggt gacgcgaact tacaatgcgc taaaactgaa 7800
gctacacaag ctatcgataa cttgacacaa ttgaatacac cgcaaaaaac agcattgaaa 7860
caacaagtga atgctgcaca acgcgtatca ggtgtaactg atctgaaaaa tagtgctaca 7920
tcacttaata atgcgatgga tcaattaaaa caagcaattg gtgatcatga cacaattgta 7980
gctggtggta attacactaa cgcaagtcct gataaacaag gtgcttacac tgatgcatat 8040
aatgctgcga agaatatcgt aaatggttca cctaatgtga ttacaaatgc agcagatgtt 8100
actgcggcaa cacaacgtgt caataatgct gaaacaagtt taaatggtga tacaaactta 8160
gcaactgcga agcaacaagc taaagatgca ttacgtcaaa tgacacattt atctgatgca 8220
caaaaacaaa gtattactgg tcaaattgat agcgcgacac aagtaactgg tgtacaaagt 8280
gtgaaagaca atgcaacaaa tcttgacaat gcaatgaatc aacttcgaaa tagtattgcg 8340
aataaagatg aagtaaaagc gagtcaacca tatgttgatg cagatacaga taaacaaaat 8400
gcatacaata cagcagttac aagtgctgaa aatatcatta atgcaacgag tcagccaaca 8460
cttgatccat ctgcagtaac acaagcagct aatcaagtga acactaacaa aactgcgctt 8520
aatggtgcgc aaaacttagc aaataaaaag caagaaacaa ctgctaacat caaccgatta 8580
agtcatttaa acaatgctca aaagcaagat ttaaatacac aagtgacaaa tgcaccaaat 8640
attagcacag taaatcaagt gaaaactaaa gctgaacaat tagatcaagc aatggaacgt 8700

-continued

```
ttaatcaacg gaatccaaga caaagatcaa gtgaaacaaa gtgttaactt tacagatgca   8760
gatccagaaa aacaaacagc atacaacaat gcggtaactg ctgctgaaaa tattattaat   8820
caagcaaatg gtacaaatgc gaaccaatca caagttgaag cagcactttc aactgtaaca   8880
actactaaac aagcgttgaa tggtgataga aaagtaacag atgctaaaaa caatgcaaac   8940
caaacattat ctacgttaga taacttaaac aatgcacaaa aaggtgctgt tactggaaac   9000
atcaatcaag cgcacactgt agctgaagta acgcaagcca ttcaaaccgc tcaggaactg   9060
aatacagcga tgggtaactt gaaaaatagc ttgaatgata aagacactac acttggcagt   9120
caaaactttg cagatgcaga tccagagaag aaaaatgcat acaatgaagc ggttcgtaat   9180
gctgaaaata ttttaaataa atctacaggt acgaacgtgc ctaaagatca agttgaagca   9240
gctatgaatc aagtgaatac tacaaaagca gcgcttaatg gtactcaaaa ccttgaaaaa   9300
gcgaaacaac acgcaaatac agcaattgac ggtttaagcc atttaacaaa tgcacaaaaa   9360
gaggcattaa aacaattggt acaacaatcg actactgttg cagaagcaca aggtaatgaa   9420
caaaaagcaa acaatgttga tgcagcaatg gacaaattac gtcaaagtat tgcagataat   9480
gcgacaacaa aacaaaacca aaattatact gatgcaagtc cgaataaaaa ggatgcgtac   9540
aataatgctg tcacaactgc acaaggtatt attgatcaaa ctacaaaccc ttcattagat   9600
ccgactgtta tcaatcaagc tgctggacaa gtaagcacgt ctaaaaatgc tttaaatggt   9660
aatgaaaact tagaggcagc gaagcaacaa gcaacgcaat ctttaggttc attagacaac   9720
ttaaataatg cgcaaaaaca agctgttact aatcaaatta atggcgcgca tactgttgat   9780
gaagcaaatc aaattaagca aaatgcgcaa aacttaaata ctgcgatggg taacttgaaa   9840
caagcgatag ctgataaaga tgctacgaaa gcaacagtta acttcactga tgcagatcaa   9900
gcaaaacaac aagcatataa cactgcagtt acaaatgctg aaaatatcat ttcaaaagct   9960
aatggtggta atgcaacaca aactgaagtt gaacaagcaa tccaacaagt aaatgcagca  10020
aaacaagcat taaatggtaa tgccaacgtt caacatgcaa aagacgaagc aacagcatta  10080
attaataact ctaatgatct taaccaagca cagaaagatg cattaaaaca acaagtacaa  10140
aatgcaacta ctgtagctgg tgtaaacaat gttaaacaaa cggcgcaaga gttaaacaat  10200
gcgatgacac aattaaaaca aggcattgca gataaagaac aaacaaaagc tgatggtaac  10260
tttgtcaatg cagattctga caagcaaaat gcatataatc aagcagtagc gaaagctgaa  10320
gcattaatta gtggtacgcc tgatgttgtc gttacaccta gcgaaattac tgcagcgtta  10380
aataaagtta cgcaagctaa aaatgattta aatggtaata caaacttagc aacggcgaaa  10440
caaaatgttc aacatgctat tgatcaattg ccaaacttaa accaagcgca acgtgatgaa  10500
tacagcaaac aaatcacgca agcaacactt gtaccaaacg tcaatgctat tcaacaagcg  10560
gcaacaacgc ttaatgacgc gatgacacaa ttgaaacaag gtattgcgaa taaagcacaa  10620
attaaaggta gcgagaacta tcacgatgct gatactgaca agcaaacagc atatgataat  10680
gcagtaacaa aagcagaaga attgttaaaa caaacaacaa atccaacaat ggatccaaat  10740
acaattcaac aagcattaac taaagtgaat gacacaaatc aagcacttaa cggtaatcaa  10800
aaattagctg atgccaaaca agatgctaag acaacacttg gtacactaga tcatttaaat  10860
gatgctcaaa aacaagcgct aacaactcaa gttgaacaag caccagatat tgcaacagtt  10920
aataatgtta agcaaaatgc tcaaaatctg aataatgcta tgactaactt aaacaatgca  10980
ttacaagata aaactgagac attaaatagc attaacttta ctgatgcaga tcaagctaag  11040
aaagatgatt atactaatgc ggtttcacat gcagaaggta ttttatctaa agcaaatggc  11100
```

agcaatgcaa gtcaaactga agtggaacaa gcgatgcaac gtgtgaacga agcgaaacaa 11160
gcattgaatg gtaatgacaa tgtacaacgt gcaaaagatg cagcgaaaca agtaattaca 11220
aatgcaaatg atttaaatca agcgcaaaaa gatgcattaa aacaacaagt cgatgctgcg 11280
caaactgttg caaatgtaaa cacgattaag caaacagcac aagatttaaa tcaagcaatg 11340
acacaattga aacaaggtat tgcagataaa gaccaaacta aagcaaatgg taactttgtc 11400
aatgctgata ctgataagca aaatgcatat aacaatgcgg tagcgcatgc tgaacaaatc 11460
attagtggta caccaaatgc aaacgtggat ccacaacaag tggctcaagc gttacaacaa 11520
gtgaatcaag ctaagggtga tttaaacggt aaccacaact tacaagttgc taaagacaat 11580
gcaaatacag ccattgatca gttaccaaac ttaaatcaac cacaaaaaac agcattaaaa 11640
gaccaagtgt cgcatgcaga acttgttaca ggtgttaatg ctattaagca aaatgctgat 11700
gcgttaaata atgcaatggg tacgttgaaa caacaaattc aagcgaatag tcaagtacca 11760
caatcagttg actttacaca agcggatcaa gacaaacaac aagcttataa caatgcagct 11820
aaccaagcgc aacaaatcgc aaatggcaca ccaacacctg tattggcgcc tgatacagta 11880
acaaaagcag ttacaactat gaatcaagcg aaagatgcat taaacggtga tgaaaaatta 11940
gcgcaagcga aacaagatgc tttagcaaat cttgatacgt tacgtgactt aaatcaacca 12000
caacgtgatg cattacgaaa ccaaatcaat caagcacaag ctttagctac agttgaacaa 12060
actaaacaaa atgcacaaaa tgtgaataca gcaatgggta acttgaaaca aggtattgca 12120
aataaagata ctgtgaaagc aagtgagaac taccacgatg ctgatgtcga taagcaaaca 12180
gcatatacaa atgcagtgtc tcaagcggaa ggtattatca atcaaacgac aaatccaacg 12240
cttaacccag atgacattac tcgtgcatta actcaagtga ctgatgctaa aaatagctta 12300
aacggtgaag ctaaattagc cactgaaaag caaaatgcta aagatgccgt aagtggaatg 12360
acgcatttaa acgatgctca aaaacaagca ttaaaaggtc aaatcgatca atcgcctgaa 12420
attgctacag tgaaccaagt taaacaaaca gcaacgagcc tagatcaagc aatggatcaa 12480
ttatcacaag ctattaatga taaagatcaa atattagcgg acggtaatta cttaaatgca 12540
gatcctgaca aacaaaatgc gtataaacag gcagtagcaa aagctgaagc attattgaat 12600
aaacaaagtg gtactaatga agtacaagca caagttgaaa gcatcactaa tgaagtgaac 12660
gcagcgaaac aagcattaaa tggtaatgac aatttggcaa atgcaaaaca acaagcaaaa 12720
caacaattgg cgaacttaac acacttaaat gatgcacaaa aacaatcatt tgaaagtcaa 12780
attacacaag cgccacttgt tacagatgtc actacgatta atcaaaaagc acaaacgtta 12840
gatcatgcga tggaattatt aagaaatagt gttgcggata atcaaacgac attagcgtct 12900
gaagattatc atgatgcaac tgcgcaaaga caaaatgact ataacaaagc tgtaacagct 12960
gctaataata tcattaatca aactacatcg cctacgatga atccagatga tgttaatggt 13020
gcaacgacac aagtgaataa tacgaaagtt gcattagatg gtgatgaaaa ccttgcagca 13080
gctaaacaac aagcaaacaa cagacttgat caattagatc atttgaataa tgcgcaaaag 13140
caacagttac aatcacaaat tacgcaatca tctgatattg ctgcagttaa tggtcacaaa 13200
caaacagcag aatctttaaa tactgcgatg ggtaacttaa ttaatgcgat tgcagatcat 13260
caagccgttg aacaacgtgg taacttcatc aatgctgata ctgataaaca aactgcttat 13320
aatacagcgg taaatgaagc agcagcaatg attaacaaac aaactggtca aaatgcgaac 13380
caaacagaag tagaacaagc tattactaaa gttcaaacaa cacttcaagc gttaaatgga 13440

```
gatcataatt tacaagttgc taaaacaaat gcgacgcaag caattgatgt tttaacaagc  13500
ttaaatgatc ctcaaaaaac agcattaaaa gaccaagtta cagctgcaac tttagtaact  13560
gcagttcatc aaattgaaca aaatgcgaat acgcttaacc aagcaatgca tggtttaaga  13620
cagagcattc aagataacgc agcaactaaa gcaaatagca aatatatcaa cgaagatcaa  13680
ccagagcaac aaaactatga tcaagctgtt caagccgcaa ataatattat caatgaacaa  13740
actgcaacat tagataataa tgcgattaat caagtagcgg caactgtgaa tacaacgaaa  13800
gcagcattac atggtgatgt gaaattacaa aatgataaag atcatgctaa acaaacggtt  13860
agccaattag cacatctaaa caatgcacaa aaacatatgg aagatacgtt aattgatagt  13920
gaaacaacta gaacagcagt taagcaagat ttgactgaag tacaagcatt agatcaactt  13980
atggatgcat tacaacaaag tattgctgac aaagatgcaa cacgtgcgag cagtgcatat  14040
gtcaatgcag aaccgaataa aaaacaagcc tatgatgaag cagttcaaaa tgctgagtct  14100
atcattgcag gattaaataa tccaactatc aataaaggta atgtatcaag tgcgactcaa  14160
gcagtaatat catctaaaaa tgcattagat ggtgttgaac gattagctca agataagcaa  14220
actgctggaa attctctaaa tcatttagat caattaacac cagctcaaca acaagcgcta  14280
gaaaatcaaa ttaataatgc aacaacttgt gataaagtgg ctgaaatcat tgcacaagcg  14340
caagcattaa atgaagcgat gaaagcatta aaagaaagta ttaaggatca accacaaact  14400
gaagcaagta gtaaatttat taacgaggat caagcgcaaa aagatgcata tacgcaagca  14460
gtacaacacg cgaaagattt gattaacaaa acaactgatc ctacattagc taaatcaatc  14520
attgatcaag cgacacaggc agtgactgat gctaaaaaca atttacatgg tgatcaaaaa  14580
ctagctcaag ataagcaacg tgcaacagaa acgttaaata acttgtctaa cttgaataca  14640
ccacaacgtc aagcacttga aaatcaaatc aataatgcag caactcgtgg tgaagtagca  14700
caaaaattaa ctgaagcaca agcacttaac caagcaatgg aagctttacg taatagcatt  14760
caagatcaac aacaaacaga atctggtagc aagtttatta atgaagataa accgcaaaaa  14820
gatgcttacc aagcagcagt tcaaaatgca aaagatttaa ttaaccaaac aggtaatcca  14880
acgcttgata aagcacaagt tgaacaattg acacatgctt ttaaacaagc taaagataac  14940
ctacacggtg atcaaaaact tgcagacgat aaacaacatg cggttactga tttaaatcaa  15000
ttaaatggtt tgaataatcc gcaacgtcaa gcacttgaaa gccaaataaa caacgcagca  15060
actcgtggcg aagtagcgca aaaattagct gaagcaaaag cgcttgatca agcaatgcaa  15120
gcattacgaa atagtattca agatcaacaa caaacggaag cgggtagcaa gtttatcaat  15180
gaagataaac cgcaaaaaga tgcttaccaa gcagcagttc aaaatgcaaa agatttaatt  15240
aaccaaacag gtaatccaac actcgacaaa tcacaagtag aacaattaac acaagcagta  15300
acaactgcaa aagataatct acatggtgat caaaaacttg ctcgtgatca acaacaagca  15360
gtaacaactg taaatgcatt gccaaactta aatcatgcac aacaacaaac attaactgat  15420
gctataaatg cagcgcctac aagaacagag gttgcacaac atgttcaaac tgctactgaa  15480
cttgatcacg cgatggaaac attgaaaaat aaagttgatc aagtgaatac agataaggct  15540
caaccaaatt acactgaagc gtcaactgat aaaaaagaag cagtagatca agcgttacaa  15600
gctgcacaaa gcattacaga tccaactaat ggttcaaatg cgaataaaga cgctgtagaa  15660
caagcattaa ctaagcttca agaaaaagtg aatgagttaa atggtaatga gagagtcgct  15720
gaagctaaaa cacaagcgaa acaaactatt gaccaattaa cacatttaaa tgctgatcaa  15780
attgcaactg ctaaacaaaa tattgatcaa gcgacgaaac ttcaaccaat cgctgaatta  15840
```

gtagatcaag caacgcaatt gaaccaatca atggatcaat tacaacaagc agttaatgaa 15900
catgctaacg ttgagcaaac tatagattac acacaagcag attcagataa gcaaaaggct 15960
tataaacaag cgattgctga tgctgaaaat gtattgaaac aaaatgcgaa taagcaacaa 16020
gtggatcaag cacttcaaaa tattttaaat gcaaaacaag cattaaatgg tgatgaacgt 16080
gtagcacttg ctaaaacaaa tggtaaacat gacatcgacc aattgaatgc attaaacaat 16140
gctcaacaag atggatttaa aggtcgcatc gatcaatcaa acgatttaaa tcaaatccaa 16200
caaattgtag atgaggctaa ggcacttaat cgtgcaatgg atcaattgtc acaagaaatc 16260
actggcaatg aaggacgcac gaaaggtagc acgaactatg tcaatgcaga tacacaagtc 16320
aaacaagtat atgatgaagc ggttgataaa gcgaaacaag cacttgataa atcgtctggg 16380
caaaacttaa ctgcagaaca agttatcaaa ttaaatgatg cagtcactgc agctaagaaa 16440
gcattaaatg gtgaagaaag acttaataat cgtaaagctg aagcattaca aagattggat 16500
caattaacac atctaaacaa tgctcaaaga caattagcaa tccaacaaat taataatgct 16560
gaaacgctaa ataaagcatc tcgagcaatt aatagagcaa ctaaattaga taatgcaatg 16620
ggtgcagtac aacaatatat tgacgaacag caccttggtg ttatcagcag cacaaattac 16680
atcaatgcag atgacaattt gaaagcaaat tatgataatg caattgcgaa tgcagcacat 16740
gagttagata aagtgcaagg taatgcaatt gcaaaagctg aagcagagca attgaaacaa 16800
aatattatcg atgctcaaaa tgcattaaat ggagaccaaa accttgcaaa tgccaaagat 16860
aaagcaaatg cgtttgttaa ttcgttaaat ggattaaatc aacagcaaca agatcttgca 16920
cataaagcaa ttaacaatgc cgatactgta tcagatgtaa cagatattgt taataatcaa 16980
attgacttaa atgatgcaat ggaaacattg aaacatttag ttgacaatga aattccaaat 17040
gcagagcaaa ctgtcaatta ccaaaacgct gacgataatg ctaaaacaaa cttcgatgat 17100
gccaaacgtc tagcaaatac attgctaaat agtgataaca caaatgtgaa tgatatcaat 17160
ggcgcaatcc aagcagtcaa tgatgcaatc cataatctta atggtgatca acgactacaa 17220
gatgctaaag acaaggcaat tcaatcaatt aatcaagctt tagctaataa gctaaaagaa 17280
atcgaagctt caaatgcgac ggatcaagac aagcttattg cgaaaaataa agcagaagaa 17340
ttggcaaaca gcatcatcaa caacattaat aaagcaacaa gtaatcaggc tgtatctcaa 17400
gttcaaacag caggcaacca cgcgattgaa caagtgcatg ctaatgaaat accaaaagca 17460
aaaattgatg ccaataaaga cgttgataag caagttcaag cattaattga cgaaattgat 17520
cgaaatccaa atctaacaga taaggaaaaa caagcactta aagatcgtat taatcaaata 17580
cttcaacaag gtcataacga cattaacaat gcgctgacta aagaagaaat tgaacaagct 17640
aaagcacaac ttgcgcaagc attacaagac atcaaagatt tagtgaaagc taaagaagat 17700
gcgaaacaag atgttgataa acaagttcaa gcattaattg acgaaatcga tcaaaatcca 17760
aatctaacag ataaggaaaa acaagcactt aaagatcgta ttaatcaaat acttcaacaa 17820
ggtcataacg gcattaacaa tgcgatgact aaagaagaaa ttgaacaagc caaagcacaa 17880
cttgcacaag cattaaaaga aattaaagat ttagtgaaag ctaaagaaaa tgcgaaacaa 17940
gatgttgata aacaagttca agcattaatt gacgaaatcg atcaaaatcc aaatctaaca 18000
gataaggaaa aacaagcgct taaagatcga atcaatcaaa tactgcaaca aggtcataac 18060
gacattaaca atgcgatgac taaagaagaa attgaacaag ccaaagcaca acttgcacaa 18120
gcattacaag acatcaaaga tttagtgaaa gctaaagaag atgcgaaaaa tgcaataaaa 18180
gccttagcta atgcgaagcg tgatcaaatc aattcaaatc cagatttaac acctgagcaa 18240
aaagcaaaag cgctcaaaga aattgacgaa gctgaaaaac gagcactaca aaacgttgag 18300
aatgctcaaa ctatagatca attaaatcga ggattaaact taggtttaga tgacattaga 18360
aatacacatg tatgggaggt tgatgaacaa cctgctgtaa atgaaatttt tgaagcaaca 18420
cctgagcaaa tcctagttaa tggtgaactc attgtacatc gtgatgacat cattacagaa 18480
caagatattc ttgcacacat aaacttaatt gatcagcttt cagcagaagt tattgataca 18540
ccatcaactg caacgatttc tgatagctta acagcaaaag ttgaagttac attgcttgat 18600
ggatcaaaag tgattgttaa tgttcctgta aaagttgtag aaaaagaatt gtcagtagtc 18660
aaacaacagg caattgaatc aatcgaaaat gcggcacaac aaaagattga tgaaatcaat 18720
aatagtgtga cattaacact ggaacaaaaa gaagctgcaa ttgcagaagt taataagctt 18780
aaacaacaag caattgatca tgttaacaat gcacctgatg ttcattcagt tgaagaaatt 18840
caacaacaag aacaagcgta tattgaacaa tttaatccag aacaatttac gattgaacaa 18900
gcaaaatcaa atgcaattaa atcgattgaa gatgcaattc aacatatgat tgatgaaatc 18960
aaagctcgta ctgatctaac agataaagag aagcaagaag ctattgctaa gttaaatcaa 19020
ttaaaagaac aagcaattca agcgattcaa cgtgcgcaaa gcatcagtga aataactgag 19080
caattggaac aatttaaagc tcaaatgaaa gcagctaatc caacagcaaa agaactagct 19140
aaacgcaagc aagaagctat tagtagaatt aaagactttt caaatgaaaa aataaatagt 19200
attcgaaata gtgaaattgg cacagctgat gaaaaacaag cagcaatgaa tcaaattaac 19260
gaaattgtgc ttgaaacaat tagagatatt aataatgcgc atacattaca gcaagttgag 19320
gctgcattga acaatggtat tgctcgaatt tcagcagtac aaattgtaat atctgatcgt 19380
gctaaacaat cgtcaagtac tggaaatgaa tctaatagcc atttaacaat tggttatgga 19440
actgcaaatc atccatttaa cagttcgact attggacata aaaagaaact tgatgaagat 19500
gatgacattg atccacttca tatgcgtcac tttagtaata atttcggtaa tgttattaaa 19560
aacgctattg gtgtggtggg tatctctggc ttactagcta gtttctggtt cttcattgcc 19620
aaacgtcgtc gtaaagaaga tgaagaggaa gaattagaaa taagagataa taataaagat 19680
tcaataaaag agactttaga cgatacaaaa catttaccac ttttatttgc gaaacgtcgc 19740
agaaaagaag atgaagaaga tgttactgtt gaagaaaaag attcgctaaa taatggcgag 19800
tcactcgata aagttaaaca tacgccgttc ttcttaccaa aacgtcgtcg taaagaagat 19860
gaagaagatg tggaagttac aaatgaaaac acagatgaaa aagtgttgaa agataacgaa 19920
cattcaccac tcttattcgc aaaacgacgc aaagataaag aggaagatgt tgaaacaaca 19980
actagtattg aatctaaaga tgaggacgtt cctttattat tggctaaaaa gaaaaatcaa 20040
aaagataacc aatccaaaga caaaaagtca gcatcaaaaa atacttctaa aaaggtagca 20100
gctaaaaaga agaaaaagaa atctaagaaa aataaaaaa 20139

<210> SEQ ID NO 47
<211> LENGTH: 2103
<212> TYPE: DNA
<213> ORGANISM: Staphylococcus sp.

<400> SEQUENCE: 47
ttgaataatc gtgataaatt acaaaaattt agtattcgaa aatacgcaat tggaacattt 60
tctactgtga ttgcaacact tgtgttcatg ggtatcaata caaaccatgc aagtgccgac 120
gagttgaatc aaaatcaaaa gttaattaaa caattaaatc aaacagatga tgatgattcg 180
aatacgcata gtcaagaaat cgaaaataac aaacaaaatt ctagtgggca gactgaatca 240
ttacgttcat caactagtca aaatcaagca aatgcacgac tgtcggatca attcaaagac 300
actaatgaaa catcgcaaca attacctaca aatgtttcgg atgatagtat caatcaatcg 360
catagtgaag caaatatgaa taacgaacca ttgaaagttg ataatagtac tatgcaagca 420
catagtaaaa tagtaagcga tagcgatggg aatgcttctg aaaataaaca tcataaacta 480
acagaaaatg tacttgcaga aagccgagca agtaaaaatg acaaagagaa agagaatcta 540
caagagaaag ataaatcgca gcaagtacat ccaccattag ataaaaatgc attacaagct 600
ttttttgacg catcatatca caattacaga atgattgata gagatcgtgc ggatgcaaca 660
gaatatcaaa aagtcaaatc tacttttgac tacgtcaatg acttactagg taataatcaa 720
aatattcctt cagaacagct tgtttcggca tatcaacaat tagagaaagc attagaactt 780
gcacgtacgt taccacaaca atctactaca gaaaaacgtg gtagaagaag tacgagaagt 840
gttgttgaga atcgttcatc aagaagcgat tacttagatg ctagaactga atattatgtt 900
tcaaaagacg atgatgattc tggtttccct cctggtactt tcttccatgc ttcaaataga 960
agatggcctt ataatttacc aagatctagg aacatcttac gtgcttctga tgtacaaggt 1020
aatgcttata tcactacaaa acgacttaaa gatggatatc aatgggatat tttatttaat 1080
agtaatcata aagggcatga atatatgtac tattggtttg gacttccaag tgatcaaaca 1140
ccaactggtc cagtaacttt cactattatc aaccgtgatg gttcaagtac atctactggt 1200
ggcgttggat ttggatcagg tgcaccacta cctcaatttt ggagatcagc aggtgctatt 1260
aattctagcg tagcgaatga ttttaaacat ggctccgcta caaattatgc attttatgat 1320
ggtgttaata atttttctga ctttgctaga gggggagaat tatacttcga cagagaaggc 1380
gctacacaaa ctaataaata ttatggcgat gaaaacttcg cattgctaaa tagtgagaaa 1440
ccagatcaaa taagaggatt agatacaata tatagtttta aaggtagtgg tgatgtaagt 1500
tatcgtattt catttaaaac tcaaggagct ccaactgcaa gattgtatta tgctgctggc 1560
gcgcgttctg gtgaatataa acaagcaacg aactataacc aactctatgt cgaaccttat 1620
aagaattatc gaaatcgagt acagtcaaat gtccaagtta aaaatcgtac acttcattta 1680
aaaagaacaa tcagacaatt cgatcctaca ttacagagaa ctactgatgt tcctattttg 1740
gatagtgacg gttccggaag tattgattcg gtatacgacc cattaagtta tgtaaagaat 1800
gtgactggta cagtcctagg tatttatcca tcttatcttc cttataatca ggaaagatgg 1860
cagggagcta atgcaatgaa tgcctatcaa attgaagaac ttttttcaca agaaaatctt 1920
caaaatgcag cacgttcagg ccgtccaatt caatttcttg taggttttga tgttgaagat 1980
agccatcata accctgaaac tcttttacca gtaaatttat atgtaaaacc tgagttaaaa 2040
catacaattg agttatatca cgataatgaa aaacaagata gaaaggaatt ttcagtatcg 2100
aaa 2103

<210> SEQ ID NO 48
<211> LENGTH: 28317
<212> TYPE: DNA
<213> ORGANISM: Staphylococcus sp.

<400> SEQUENCE: 48
atgagtggaa cgcttcataa cactgtagga tcaggaatat taccttatca acaagagata 60
cgtatcaaac ttactagtaa tgaaccaatt aaagatagtg aatggtctat tacaggatat 120

-continued

```
cctaacacgc ttacattaca aaacgctgtg ggtagaacaa ataatgctac tgaaaaaaac    180
ttagctcttg ttggtcatat tgatccagga aattatttca tcactgttaa gtttggtgat    240
aaagtagaac aatttgaaat tagatcaaaa ccaactccac caagaatcat tacaactgct    300
aatgaattac gtggaaatcc taaccataag cctgaaataa gagtaacaga tataccaaat    360
gatactactg ctaaaatcaa acttgtgatg ggcggaaccg atggcgatca tgatccagaa    420
ataaatccat atactgtccc tgaaaactac acagtagttg cagaagcata ccatgataat    480
gatccaagta aaaatggggt cttaacattc cgttcatcag actaccttaa agatctacca    540
ttaagcggtg aattaaaggc aattgtttat tacaatcaat atgtacaatc aaactttagt    600
aaaagcgttc cgtttagtag cgatacaaca ccacctacaa ttaatgaacc ggcaggacta    660
gttcataagt attacagggg agatcatgta gaaattactc ttccagtcac tgataatact    720
ggcggttcag gtttaagaga tgtaaacgtc aatttacctc aaggttggac aaaaaccttt    780
acaatcaatc ctaataataa tactgagggt acgcttaagt taattggtaa tatacctagt    840
aatgaagcat ataatacgac atatcatttc aatattactg caaccgataa ttctggaaat    900
acaacaaatc cagctaaaac ctttatttta aatgttggta agttggctga tgatttaaat    960
ccagtcggat tatctagaga tcaactacaa ttagtgacag acccttcttc attatctaat   1020
tccgaacgag aagaggtaaa aagaaaaata agtgaagcaa atgctaatat aagatcatat   1080
ttattacaaa ataacccaat actcgctgga gtaaacggcg atgttacatt ttattataga   1140
gatggttctg tagatgttat tgatgctgaa aatgtaatca catatgagcc cgaaagaaaa   1200
tccattttca gtgaaaatgg taatacaaat aaaaaagaag cagtaatcac tattgctaga   1260
ggacaaaact ataccattgg tccaaactta agaaaatatt tctcattaag taatggttcg   1320
gatttaccta atagagattt cacctctata tcagctattg gatctttacc ttcatcgagt   1380
gaaattagtc gactcaatgt tggaaattat aactatagag ttaatgctaa aaatgcttat   1440
cataagactc aacaagaact taatttaaaa cttaaaatag tagaggttaa tgcacctact   1500
ggtaataatc gtgtatatag agttagtact tataatttaa ctaatgatga aatcaataaa   1560
atcaaacaag catttaaagc agctaattct ggacttaatt taaacgataa cgatatcact   1620
gtttcgaata actttgacca tagaaatgtt agtagtgtga cagtaactat acgtaagggc   1680
gatttgataa aagagttttc atcaaatctc aataatatga atttcttacg ttgggttaat   1740
ataagggatg attataccat ttcgtggact tctagtaaga ttcaaggtag aaatacagat   1800
ggtggattag aatggtcacc agatcataaa tcacttattt ataaatatga tgcaacatta   1860
ggtagacaaa taaatactaa tgacgtgtta actttacttc aagcaacagc taaaaactca   1920
aatttacgtt caaatatcaa tagtaatgaa aaacagttag cagaacgagg gtctaatggg   1980
tattctaaat ctataattag agatgatggc gagaaatctt atttacttaa ctcaaatcct   2040
attcaagtat tagacttagt agaaccagat aatggttacg gtggacgtca agtcagtcat   2100
tctaacgtta tatataatga aaaaaattct tctatcgtaa atggtcaagt tccagaagct   2160
aatggggcat ccgcttttaa tattgataaa gttgttaaag ctaatgcggc aaataatggt   2220
attatgggtg ttatctataa ggcacaatta tacttagcac catacagtcc aaaaggttac   2280
attgaaaaat taggccaaaa tttaagcaat accaataacg tgattaatgt ttattttgtg   2340
ccttctgata aagtaaatcc tagtataact gtaggtaatt acgaccatca tacggtatat   2400
tctggtgaaa catttaaaaa tactatcaat gtaaatgata attatggatt aaatacagta   2460
gcttctacaa gtgatagtgc aattactatg accagaaaca acaacgagtt agtaggtcag   2520
```

```
gctcctaatg ttactaatag cataaataaa attgtaaaag ttaaagccac agataaaagt   2580
ggaaatgaaa gtattgtttc tttcacagta aatataaaac cattaaacga gaaatataga   2640
ataacaactt catcaagtaa tcaaacacca gtgagaatta gtaatattca aaacaatgct   2700
aacctttcaa ttgaagatca aaatagagta aaatcttcac tcagcatgac taaaatttta   2760
ggtacaagaa attatgtcaa tgagtcaaat aatgacgttc gtagtcaagt tgtaagtaaa   2820
gtaaatagaa gtgggaacaa tgctacagtt aatgttacaa ctacattttc tgatggtaca   2880
actaatacaa taaccgttcc agttaaacat gtgttattag aagttgtacc tactactaga   2940
acaacagtaa gaggacaaca atttccaacc ggcaaaggaa cttccccaaa tgatttcttt   3000
agtttaagaa cgggaggtcc agttgatgcg agaatagttt gggttaataa tcagggaccc   3060
gatataaata gtaatcaaat tggtagagat ttaacattac acgctgaaat attctttgat   3120
ggtgaaacaa caccaattag aaaagatact acttacaaac ttagtcaatc tattccaaag   3180
caaatatatg aaacaactat caatggtcga tttaattcat caggtgatgc atatccagga   3240
aattttgttc aagcagtaaa tcaatattgg ccagaacata tggacttcag atgggcccaa   3300
ggatcaggca caccaagttc tcgtaatgca ggttcattta ctaaaacagt tacggtagtt   3360
tatcaaaacg gccaaactga aaacgttaat gtactattca aagtcaaacc aaataaacct   3420
gttattgata gtaatagtgt gatttcaaaa ggacaattaa atggtcaaca aattttagtt   3480
cgaaatgttc cacaaaatgc acaagtcact ctatatcaat caaatggaac tgttattcct   3540
aatacaaata caactataga ttctaatggt atagctactg taacaattca aggcactcta   3600
ccaaccggaa atattactgc taaaacctca atgacaaata atgtaacgta cactaaacaa   3660
aatagtagtg gaattgcttc aaatacaact gaagatataa gtgttttttc agaaaacagt   3720
gatcaagtaa atgttaccgc tggcatgcaa gctaaaaatg atggtattaa aataattaaa   3780
ggtacaaact ataattttaa tgacttcaat agtttcataa gtaatatacc agcccattct   3840
actcttacat ggaacgagga gcctaatagt tggaaaaaca acatcggtac tacaacaaaa   3900
actgttacag ttactctacc taatcatcaa ggtacgagaa ctgtagatat tccaataaca   3960
atctatccaa cagttacagc taagaatcca gtaagagatc aaaaaggacg aaacttaacc   4020
aatggtactg acgtttataa ttatattatt tttgaaaata ataaccgtct tggaggaaca   4080
gcttcttgga aagacaatcg tcaacctgat aaaaacatag ccggtgtaca aaatttaatt   4140
gcacttgtta attatcctgg catatctaca ccattagaag ttcctgttaa agtgtgggta   4200
tataattttg atttcactca acctatctac aaaattcaag taggagatac attccctaaa   4260
ggaacatggg caggctatta caaacatctt gaaaatggag agggattacc aatagatggt   4320
tggaaatttt attggaacca gcaaagtaca ggaactacta gtgatcaatg gcaatcatta   4380
gcatatacta gaactccttt tgttaaaact ggtacttatg atgtcgttaa tcctagcaac   4440
tggggtgttt ggcaaacatc acaatcagct aaatttatag ttacaaatgc taaacctaat   4500
caaccaacca taactcagtc taaaactggt gatgtaacag taacacctgg tgctgtgcgt   4560
aatatactaa taagtgggac aaatgattat atccaagcat ctgcagataa gattgttatt   4620
aataaaaatg gaaataaatt aactacattt gttaaaaata atgatggtcg ttggactgtt   4680
gaaactgggt cacctgacat aaatggtatc ggaccaacaa ataacggaac tgctatatct   4740
ttaagtcgat tagcagttag acctggggat tcaatagaag caatagcgac tgaaggttcc   4800
ggagaaacta taagtacttc agcaactagt gaaatttata ttgtcaaagc tccacaacct   4860
```

-continued

```
gaacaagtag caactcatac ttatgataat ggaacattcg atatattacc tgacaattca   4920
cgtaattctt taaatccaac tgaacgtgtc gaaattaatt acactgaaaa attaaatggc   4980
aatgaaacac aaaaatcatt cactattact aaaaataaca acggcaaatg gacgataaat   5040
aataaaccaa attatgtcga gttcaatcag gataatggta aagttgtatt ttcggccaat   5100
acaattaaac ctaattctca aattacaata actcctaaag caggtcaggg taacactgaa   5160
aacacaaatc ctactgtaat tcaagcacct gcgcaacata ctttaacaat caatgaaatt   5220
gttaaagaac agggtcaaaa tgtgactaat gatgatatta ataatgcggt tcaagtgcca   5280
aataaaaata gagttgcgat taaacaagga aacgctcttc caacaaattt agctggtggt   5340
agtacatcac atattccagt agttatttat tacagtgatg gaagttctga agaagctact   5400
gagactgtta gaactaaagt taataaaacc gaattaatca atgctcgtcg tcgactagat   5460
gaagaaatta gtaaagagaa caaaaacacca tcaagtatca gaaactttga tcaagctatg   5520
aatcgtgctc aatcacaaat taatacagct aaaagtgatg ctgaccaagt tataggcaca   5580
gaatttgcaa cacctcaaca agtaaattca gctttatcta aagttcaagc ggcacaaaat   5640
aaaataaatg aagctaaagc attattacaa aacaaggctg ataatagtca acttgtgaga   5700
gcaaaagaac aattacaaca atcgattcaa ccagccgctt caactgatgg tatgactcaa   5760
gatagcacaa ggaactacaa caataaacgc caagcagctg aacaagcaat acaacatgca   5820
aatagcgtta taaataatgg agatgcaaca tcccaacaaa ttaatgatgc taaaaacaca   5880
gttgaacagg cacagagaga ttatgttgaa gctaaaagca acttacgtgc tgataagtca   5940
cagttacaaa gcgcttatga tacgttaaat agagatgttt taacaaatga taaaaagcca   6000
gcatctgtaa gacgctataa tgaagccatt tcaaatatta gaaaagaatt agatacagct   6060
aaagcggatg caagtagtac tttgcgaaac accaatcctt ccgttgaaca agttagagac   6120
gctttaaata aaataaatac tgttcaacct aaagtgaatc aagcaattgc tttacttcaa   6180
ccaaaagaaa ataattcaga acttgtacaa gctaaaaaac gtttacaaga cgctgtaaat   6240
gacatacctc aaacacaagg tatgacacaa caaacaatta ataattataa tgacaaacaa   6300
cgtgaagctg aaagagcact tacatctgca caaagagtga ttgataatgg ggatgctaca   6360
actcaagaaa ttacttctga aaaatctaaa gtagagcaag caatgcaagc tttaactaat   6420
gctaaaagta atctgagagc tgataagaat gagttacaga ctgcatataa caaattaatt   6480
gagaacgtat ctaccaatgg taaaaaaccg gcgagtatac gtcaatacga aacagccaaa   6540
gccagaatac aaaatcaaat taatgatgct aaaaatgaag cggagcgaat tttaggtaat   6600
gataatccac aagtatcaca agtaactcaa gcattgaaca aaatcaaagc tattcaacca   6660
aaattaacag aagctatcaa catgcttcaa aacaaagaaa ataatacaga attagtcaat   6720
gctaaaaaca gacttgaaaa tgcagtaaat gatacagatc caacacacgg tatgactcaa   6780
gaaacaatta ataattacaa cgctaaaaag cgagaagctc aaaatgaaat acaaaaagcg   6840
aacatgatta ttaataatgg agatgctact gctcaagata tttcttctga aaaatctaaa   6900
gtagagcaag tattacaagc attacaaaat gctaagaatg acttaagagc tgataaaaga   6960
gaattacaga ctgcatacaa taaacttata caaaatgtta ataccaatgg taaaaaacca   7020
tctagtattc aaaactataa gtctgcaaga cgaaatatcg aaaaccaata taataccgct   7080
aaaaatgaag cacataatgt tcttgaaaat acaaacccta ctgtaaatgc agtagaagat   7140
gctttacgta agataaatgc aattcaacca gaggttacaa aagctattaa tatacttcaa   7200
gataaagaag ataatagcga acttgttaga gcaaaagaaa aattagatca agcgattaat   7260
```

agtcaaccat cactaaatgg tatgactcaa gaatctatta ataattacac aacaaaacgt 7320
agagaagcac aaaatatagc aagttctgct gacactatta ttaataatgg ggatgcatct 7380
attgaacaaa taacagaaaa taaaattcga gttgaagagg caactaatgc acttaacgaa 7440
gcaaaacaac atttaacggc agatacaact tctttaaaaa ctgaagtacg gaaattaagt 7500
aggagaggcg acacaaacaa caaaaagcct agcagtgtta gtgcttataa caatactatt 7560
cattcgctac aatctgaaat tacacagact gaaaatagag caaatactat catcaataag 7620
cctattcgtt ctgttgaaga agtaaataat gcattgcatg aagtaaacca attgaaccaa 7680
cgcttaacag atacaattaa cttattacaa cctttagcga ataaagaaag cttaaaagaa 7740
gctcgtaatc gacttgaaag taaaattaat gaaaccgttc aaacagacgg tatgactcaa 7800
caatctgttg agaattataa gcaagctaaa ataaaagctc aaaatgaatc tagtattgca 7860
caaactctta ttaataatgg tgatgcatct gatcaagaag tttctacaga aatagaaaaa 7920
ttaaatcaaa agctgtctga attaacaaat tcaatcaatc acttaacagt taataaagaa 7980
cctttagaaa ctgccaaaaa tcagttacaa gcaaatattg accaaaaacc tagcactgat 8040
ggtatgacgc aacaatctgt acaaagctat gaacgtaaac tacaagaagc caaagataaa 8100
ataaactcaa ttaataatgt cttagctaac aatccagatg ttaatgctat cagaacaaac 8160
aaagttgaga cggaacaaat caataatgaa ttaacacagg cgaaacaagg tcttactgtt 8220
gataaacaac cattgattaa tgcaaaaact gctttgcaac aaagtctaga taatcaacca 8280
agtactactg gtatgactga agcaacaatt caaaattata acgctaaacg tcaaaaagca 8340
gagcaagtta tacaaaatgc aaataaaatt attgaaaacg ctcaacctag tgtacaacaa 8400
gtgtctgatg agaaatctaa ggtagagcaa gcactcagtg aattgaacaa cgccaaatca 8460
gcgcttagag ctgataaaca agaattacag caagcatata atcagttgat tcaaccaacg 8520
gatttaaata ataagaaacc agcttctatc actgcgtaca atcaaagata tcaacaattt 8580
agtaacgaat tgaacagcac taaaacaaat acagatcgca ttttaaaaga gcaaaatcca 8640
agtgtagctg atgtcaacaa tgcactaaat aaagtaagag aagtacaaca aaaattaaac 8700
gaagccagag cacttttaca aaataaagaa gataatagtg cactagttcg agccaaagaa 8760
caacttcaac aggcagttga ccaagtccct tcaacagaag gtatgacgca acaaactaaa 8820
gatgattaca attcaaaaca acaagctgct caacaagaaa tatcaaaagc acaacaagtt 8880
atcgataatg gcgatgcgac tacacaacaa atttctaacg ccaaaacaaa tgttgaacgc 8940
gctttagaag cattaaataa tgcaaaaact ggtttaagag cagataaaga ggaacttcaa 9000
aatgcatata atcaattaac tcaaaatatt gatacgagcg gtaaaacgcc tgcaagtatc 9060
aggaaataca atgaagctaa gtcacgtatt caaactcaaa ttgattcagc taaaaatgaa 9120
gcaaacagta ttttaacaaa tgacaatcct caagtatcac aagtgactgc tgcgttaaac 9180
aaaataaaag ctgttcaacc tgaattagat aaagcgatag caatgcttaa aaataaagag 9240
aataataatg cattggttca agcgaaacaa caacttcaac aaattgttaa tgaagtagat 9300
ccaacacaag gcatgacaac agatactgct aataactata aatcaaaaaa acgtgaagct 9360
gaagatgaaa tacaaaaagc tcaacaaatc attaacaatg gcgatgccac tgagcaacaa 9420
attactaacg aaacaaatag agtaaatcaa gcgattaatg caataaacaa agccaaaaac 9480
gatttacgtg ctgataagtc tcaattggaa aatgcttata accaattaat acaaaatgtt 9540
gatacaaatg gtaaaaaacc tgctagtatt caacaatacc aagctgctcg acaagctatt 9600

```
gagacgcaat acaataacgc taaatcagaa gcacatcaaa ttcttgaaaa tagtaaccct   9660
tcagttaatg aagtagcaca agcattacaa aaagttgaag ctgtacaact taaagttaat   9720
gacgcgattc atatacttca aaataaagag aataatagtg cacttgtcac agctaaaaat   9780
caacttcagc aatcagttaa tgatcaacca ttaacaacag gtatgactca agattctatt   9840
aataactatg aagctaagag aaatgaggct caaagtgcta tcagaaatgc agaagctgtc   9900
atcaacaatg gcgatgcaac tgcaaaacaa atttcagacg agaaatctaa agttgaacaa   9960
gcactagcac atttgaatga tgctaaacag caattaactg cagatactac tgaattacaa  10020
acagcagttc aacaattaaa cagaagaggc gatacaaata ataaaaagcc aagaagtatc  10080
aatgcatata ataaagcaat tcaatcatta gaaacacaaa ttacttctgc taaagataat  10140
gccaacgctg tgatacaaaa acctatacgt actgttcaag aggtaaataa tgcattacaa  10200
caagtaaatc agttgaatca acaattaact gaagcaatta atcaacttca accgctatca  10260
aataatgatg cattaaaagc tgcaagatta aatttagaaa ataaaattaa tcaaactgta  10320
caaactgatg gtatgacaca acaatctata gaggcttatc aaaacgctaa acgcgtagcc  10380
caaaatgaat ctaacactgc tttagcatta attaataacg gcgatgccga tgaacaacaa  10440
attacaactg aaacagaccg agtcaatcag caaactacaa acttaactca agcaattaac  10500
gggttaacag ttaataaaga accattagaa accgctaaaa cagcgttaca aaataacatc  10560
gaccaggtac ctagtacaga tggtatgact cagcaatctg ttgcaaatta taatcaaaaa  10620
ctacaaatag ctaaaaacga aattaacaca attaataacg ttttagcgaa caatccagat  10680
gttaatgcaa tcaaaacgaa taaagcagaa gcggaacgaa tcagtaacga tttaacacaa  10740
gctaagaata acttacaagt tgatactcaa cctttagaaa aataaaaaag acaacttcaa  10800
gatgaaattg atcaaggtac taacacagat ggaatgactc aagattcagt ggataattac  10860
aatgatagct taagtgcagc aattatagaa aaaggcaaag taaataaatt acttaaacgt  10920
aatccgacag tagaacaagt taaagagagc gttgctaatg cacaacaagt catacaagat  10980
ttacaaaatg ctcgaacttc acttgttcca gacaaaactc aacttcaaga agctaaaaat  11040
agattagaaa acagtattaa ccaacaaaca gatactgacg gcatgactca agattcgctt  11100
aacaattata atgataaatt agcaaaagct agacaaaacc ttgaaaaaat atctaaagtt  11160
ttaggtggtc aacctactgt agctgaaatt agacaaaata cagatgaagc aaatgcacat  11220
aaacaagcat tagacactgc acgttctcaa cttacattaa atagagagcc atatatcaat  11280
catattaata atgaaagtca tttaaataac gcgcaaaaag ataattttaa agctcaagtt  11340
aactcagcac ctaatcataa tactttagaa acgattaaaa ataaggctga tactttaaat  11400
caatctatga cagcattaag tgaaagtatt gcagattacg aaaatcaaaa acaacaagaa  11460
aattatttag atgcatctaa caataaacgt caagactatg acaatgcagt caatgcggct  11520
aaaggtattt taaaccaaac tcaaagtccg acaatgagtg ctgatgtgat tgatcaaaaa  11580
gctgaagatg ttaaacgtac gaaaactgcg ttagatggaa atcaaagatt agaagttgct  11640
aaacaacaag cacttaatca tttaaatacc ttaaatgatt taaacgatgc tcagcgacaa  11700
actttaactg atactataaa tcactctcca aacatcaatt cagtgaatca agctaaagaa  11760
aaagctaata ctgttaacac agcaatgact caactgaaac aaactattgc taactatgac  11820
gatgaattgc atgacggcaa ttacattaat gcagataaag acaaaaaaga tgcttataat  11880
aacgctgtta acaatgctaa acaactgatt aatcaatctg atgctaatca agcacaactt  11940
gatccagctg aaattaataa agttacacaa agagtcaata cgactaaaaa tgatctaaat  12000
```

```
ggtaatgaca aattggctga agctaaaaga gatgctaata caaccattga tggtttaact  12060
tatctaaatg aagctcaacg taacaaagct aaagaaaatg taggcaaagc ttctacaaaa  12120
acaaatatta cgagtcagtt acaagattac aatcaattga atattgctat gcaagcatta  12180
cgtaacagtg tgaacgacgt taacaatgtt aaagcaaata gcaattatat aaatgaagat  12240
aatggtccaa aagaagctta caatcaagcc gttactcatg ctcaaacatt gataaatgca  12300
caatctaacc ctgaaatgag ccgtgacgta gtaaatcaaa aaacacaagc agtaaatact  12360
gcccatcaga atttacatgg acaacaaaag ttagaacaag cacaaagtag tgctaataca  12420
gaaatcggta acttaccaaa cttaactaat actcaaaaag ctaaagaaaa ggaactggta  12480
aatagtaaac aaactcgtac ggaagtacaa gaacaactta accaagctaa gtcactagat  12540
agttctatgg gcacgttaaa atcattagtt gctaaacaac ctacagtaca aaaaacaagt  12600
gtttatatta acgaagatca acctgagcaa tctgcctaca atgattccat tacaatggga  12660
caaactataa ttaataaaac agctgatcca gtacttgata aaactttagt tgataacgca  12720
atcagtaaca tttcaactaa agagaatgca ctgcatggtg aacaaaaatt aacaactgct  12780
aaaacggaag caattaatgc acttaataca ttagctgatt taaacacacc tcagaaagag  12840
gctattaaaa cagctattaa cactgctcat acaagaactg atgtaactgc agagcaaagt  12900
aaggctaatc aaataaatag tgcaatgcac acgttgagac aaaacatttc tgacaacgaa  12960
tcagtaacaa acgaaagtaa ttatattaac gctgaacccg aaaaacaaca tgcctttact  13020
gaggctctaa ataatgctaa agaaatagtt aatgaacaac aagccactct tgatgccaat  13080
tcaattaacc aaaaagcaca agcgattctt actactaaaa atgctttaga tggtgaagaa  13140
caattacgtc gtgctaaaga aaatgccgat caagaaatca atacgttaaa tcaattgact  13200
gatgcgcaaa gaaatagtga aaaaggttta gtcaacagtt ctcaaactag aacagaagtt  13260
gcttctcaat tagcaaaagc taaagaacta aataaggtga tggaacaact gaatcacctt  13320
atcaatggta aaaaccaaat gataaatagc agtaaattta tcaatgaaga tgcgaaccaa  13380
caacaagcat attcaaatgc gattgcaagt gcagaagcgc ttaaaaacaa atcacaaaac  13440
cctgaattag ataaagtaac aattgaacaa gcaattaata atattaattc tgcaattaac  13500
aatctaaacg gtgaagctaa actgactaaa gctaaagaag atgctgttgc ttcaataaac  13560
aacctaagcg gattaacaaa cgagcaaaaa acaaaagaaa atcaagccgt taatggcgct  13620
caaactagag accaagttgc taataaatta cgtgatgctg aagcattaga tcaatcaatg  13680
caaacattac gtgacttagt taacaatcaa aatgcaatac attcaacaag taattatttt  13740
aacgaggatt caactcaaaa gaatacttat gataatgcaa ttgataatgg ctcgacatat  13800
ataactggtc aacacaatcc agaattaaat aaatctacta ttgatcaaac gattagccga  13860
attaacacag ctaaaaatga tttacatggt gtagaaaagt tacaaagaga taagggaact  13920
gctaatcaag aaattggaca attaggttat ttaaatgacc ctcaaaaatc tggtgaggaa  13980
tccttagtca acggttcaaa tacacgttct gaagtagaag agcatcttaa tgaagctaaa  14040
tcattaaata atgcaatgaa acaattaaga gataaagtag ctgaaaagac taatgtcaaa  14100
caaagtagcg attacattaa tgattcaact gaacatcaac gtgggtatga tcaagcactt  14160
caagaagcag aaaatattat taatgaaatc ggtaatccaa cattaaataa atcggaaatt  14220
gaacaaaagt tacaacaatt gactgacgct caaaatgcgt tacaaggttc acatctatta  14280
gaagaagcta aaaataatgc gattactgga atcaataaac ttacagcatt aaatgatgca  14340
```

-continued

```
caacgtcaaa aagcaattga aaatgttcaa gcacagcaga caatcccagc agttaatcaa  14400
caattaactt tggatagaga aataaatact gcaatgcaag ctttacgaga taaagtaggc  14460
caacaaaata acgttcacca acaaagtaat tatttcaatg aagatgaaca accaaaacat  14520
aactatgata attctgtaca agccggtcaa actattattg ataaacttca agatccaatc  14580
atgaacaaaa atgaaattga gcaggctatt aatcaaatca atacgactca aacagcgtta  14640
agtggagaaa ataaattaca cactgaccaa gaaagcacaa atagacaaat agaaggttta  14700
tctagtttga acacagctca aatcaacgcc gaaaaagatt tagtcaatca agctaaaaca  14760
agaacagatg ttgctcaaaa gttagctgca gctaaagaaa taaattctgc tatgagtaat  14820
ttaagagatg gcattcaaaa taaagaggac atcaaacgta gcagtgcata tatcaacgca  14880
gatccgacta aagttacagc ttacgatcaa gcactacaga acgcagaaaa tatcatcaat  14940
gccacaccaa acgtagagct taataaagct acaattgaac aagcgctatc acgcgttcaa  15000
caagcacaac aagatcttga tggtgttcaa caattagcta atgctaaaca acaagctaca  15060
caaactgtca atgggttaaa tagcttaaat gacggtcaaa agcgtgaatt aaatctatta  15120
attaattcag ctaatacccg tacaaaagta caagaagaat taaacaaagc aactgaattg  15180
aaccatgcga tggaagcttt aagaaacagt gttcaaaacg ttgatcaagt aaaacaaagt  15240
agcaattatg tcaatgaaga tcaacctgaa cagcacaatt atgataatgc tgtcaatgaa  15300
gctcaagcta caatcaacaa caatgctcaa cctgttctag acaaattagc tatagaacgt  15360
ttaactcaaa ctgttaacac tacaaaagat gcattacatg gtgctcaaaa actgacacaa  15420
gaccaacaag ctgctgaaac tggaatacgt ggtttaacga gtctcaatga acctcagaaa  15480
aatgctgaag tagctaaagt aactgcagca acaacacgtg atgaagtgag aaatattcgt  15540
caagaagcaa caacattaga tactgcaatg cttggtttac gtaaaagcat taaagataaa  15600
aacgatacta aaaatagtag taaatatatt aatgaggatc atgaccaaca acaagcttat  15660
gacaatgctg taaataatgc tcaacaagtt atcgatgaaa ctcaagcaac gttaagctca  15720
gatacaatca atcaattggc aaatgccgta actcaagcta aatctaatct tcatggagat  15780
actaaactac aacacgataa agatagtgct aaacaaacga ttgctcaatt acagaatttg  15840
aattcagctc aaaaacatat ggaagattct ttaattgata atgaatctac acgtacgcaa  15900
gtccaacacg atttaacaga agctcaagct ttagatggtt taatgggtgc cttaaaagaa  15960
agtattaaag attatactaa tattgtttca aacggtaatt acatcaatgc ggaaccatct  16020
aagaaacaag catatgatgc agctgtacaa aatgctcaaa atataataaa tggaacgaat  16080
caaccaacaa ttaataaagg taatgtcact acagcaacac aaaccgtgaa aaatactaaa  16140
gatgccttag acggtgatca tagattagag gaagctaaaa ataatgccaa tcaaacaatc  16200
agaaatctat ctaatttgaa caatgcccaa aaagatgcag agaaaaatct agttaatagc  16260
gcatcaacat tagaacaagt tcaacaaaac ttacaaaccg ctcaacaatt agataatgct  16320
atgggtgagt tacgacaaag tattgctaaa aaagatcaag tgaaagcaga tagtaaatat  16380
ctaaatgaag atcctcaaat taagcaaaac tatgatgatg cagttcaacg tgttgaaact  16440
attattaacg aaactcaaaa ccctgaatta cttaaagcaa acattgacca agcaactcaa  16500
tccgttcaaa atgcagaaca agctttacat ggtgctgaaa aattaaatca agacaaacaa  16560
acgtcttcga cagaactaga tggattaaca gatttaacag atgcacaacg tgaaaaactc  16620
agagaacaaa ttaacacttc taatagtaga gatgatatta agcaaaaaat tgagcaagca  16680
aaagcactaa atgacgcaat gaaaaaactt aaagaacaag ttgcgcaaaa agatggtgtt  16740
```

```
catgctaaca gtgattatac aaatgaagat tctgcacaaa aagatgcgta taataatgca  16800
cttaaacaag cggaagacat tattaataac agctcaaatc ctaacttaaa tgcacaagac  16860
attactaatg ctttaaataa tattaaacaa gcacaagata accttcatgg agctcaaaaa  16920
ttacagcaag acaaaaatac aactaatcaa gccattggta acttaaatca tcttaatcaa  16980
cctcaaaaag atgcgcttat acaagctatt aatggagcta catctaggga ccaagttgca  17040
gaaaaactta aagaggccga agcgcttgat gaagctatga aacaacttga agatcaagtg  17100
aatcaagatg atcaaatttc aaatagcagc ccattcataa atgaagactc agacaaacaa  17160
aaaacttata atgataaaat ccaagctgca aaagaaataa ttaatcaaac atctaatcca  17220
accttagata aacaaaaaat tgctgataca cttcaaaata ttaaagatgc agtgaataat  17280
ttacatggtg atcaaaaatt agctcaatct aaacaagatg ctaataatca attaaatcat  17340
ttagatgact taaccgaaga acaaaaaaac cattttaaac cgttaattaa taatgctgat  17400
actcgagatg aggtaaataa acaactagag attgctaaac aattaaatgg tgatatgagt  17460
acacttcata aagtcataaa tgataaagat caaattcaac atttaagcaa ttacattaat  17520
gctgataatg ataaaaaaca aaattatgat aatgctatta aagaagctga ggatttaatt  17580
cataatcatc cagatacatt agatcataaa gcattacaag atttattaaa caagatagac  17640
caagcgcata acgaattaaa tggagaatcc agatttaaac aggctttaga caatgcttta  17700
aacgacatag atagcttaaa cagtctcaat gttccacaac gccaaactgt taaggataac  17760
atcaaccatg tgacaactct agaaagttta gctcaagaat tgcagaaagc aaaagagctt  17820
aatgatgcta tgaaagcaat gagagatagc attatgaatc aagagcaaat tcgtaaaaat  17880
agcaattata ctaatgaaga cttagctcaa caaaatgcct ataatcatgc agtagataaa  17940
ataaataaca ttattggtga agacaatgcg acgatggatc ctcaaataat caaacaagca  18000
actcaagata taaatacagc tataaatgga ttaaatggag atcaaaaact tcaagatgca  18060
aagacagatg ctaaacaaca aattactaac tttactggtt taactgaacc acaaaaacaa  18120
gcattggaaa acatcattaa ccaacaaaca agcagagcaa atgttgctaa acagttaagt  18180
catgctaaat tcttaaatgg aaaaatggaa gaattaaaag ttgcagtagc caaagcgtca  18240
ttagtaagac aaaatagtaa ctatattaat gaagatgtct ctgaaaaaga agcatatgaa  18300
caagctatcg caaaaggtca ggaaataatt aattcagaaa ataatccaac aataagtagt  18360
actgatatca atcgtaccat tcaagaaatt aatgatgctg aacaaaatct tcatggtgat  18420
aataaattaa gacaagcaca ggaaattgca aagaatgaaa tacaaaatct agacggatta  18480
aattcagctc aaataacaaa attaatccaa gatataggca gaacaacaac taaacctgca  18540
gtaactcaga aactagaaga agcaaaagca ataaaccaag ctatgcaaca acttaaacaa  18600
agtatagccg ataaggatgc tactctaaat tctagtaact atctcaatga agattctgag  18660
aaaaagttag cgtacgataa tgctgtaagc caagctgaac aactcataaa tcaacttaac  18720
gacccaacta tggatataag taatattcaa gctattactc aaaaggtcat tcaagcaaaa  18780
gattcattgc acggtgcgaa taaacttgca caaaatcaag cagattcaaa tttaataata  18840
aatcaatcaa caaatttaaa tgataaacaa aagcaagcat taaatgactt aattaatcat  18900
gctcaaacta aacagcaagt ggcagaaata attgcacaag ctaataagtt aaataacgaa  18960
atgggcacac taaaaacact cgtagaagaa cagtcaaacg ttcatcaaca aagtaaatat  19020
attaatgaag atccgcaagt tcaaaatatt tataatgact ccattcaaaa aggtcgagaa  19080
```

```
atattaaacg gcactacaga tgatgtttta aacaacaata aaatagcaga tgccattcaa  19140
aacattcatt taactaaaaa cgatttacat ggtgatcaaa aattacaaaa agcacaacaa  19200
gatgcaacca atgaattaaa ctatttaaca aatctaaaca attctcaaag acaaagcgag  19260
catgatgaga ttaactctgc tccttcaaga actgaagttt ctaatgattt aaatcatgct  19320
aaagcactta atgaagctat gcgtcaactt gagaatgaag ttgctcttga aaacagtgtt  19380
aaaaaattaa gcgactttat caatgaagat gaagcggcac aaaatgaata tagtaatgca  19440
cttcaaaaag ctaaagacat tatcaacggc gttccaagta gcactttaga taaagctaca  19500
attgaagatg ctttattaga attgcaaaat gctagagaaa gtttacatgg tgagcaaaaa  19560
cttcaagagg ctaaaaatca agctgttgct gaaattgata atttacaagc attaaatcct  19620
ggacaggttc ttgctgaaaa aacattagtt aaccaagcat caaccaaacc agaagttcaa  19680
gaagccttac aaaaagcaaa agaacttaat gaagctatga aagcactgaa aactgaaata  19740
aataaaaaag aacaaatcaa ggctgatagt agatatgtaa atgctgacag tggtcttcaa  19800
gcaaattaca attctgcgtt aaattatggt tctcaaatta ttgcaactac ccaaccacca  19860
gagcttaata aagatgtaat aaatagagca actcaaacga ttaaaactgc tgaaaataat  19920
ttaaatgggc aatctaaatt agcagaggct aagtcagacg gaaatcaaag catcgaacat  19980
ttgcaaggat taacacaatc acaaaaagat aaacaacatg atttaattaa tcaagctcaa  20040
actaaacaac aggtagatga tatcgtaaat aactctaaac aattagataa ctctatgaat  20100
caactacaac aaattgttaa caatgacaat acagtaaaac aaaatagtga tttcattaat  20160
gaagattcca gccaacagga tgcttataat catgcaattc aagcagcaaa agatttgata  20220
actgctcatc caactatcat ggataaaaat caaatagatc aagctattga aaatatcaaa  20280
caagcactta atgatttaca cggtagtaat aaactatcag aagataaaaa agaagcttca  20340
gaacaactac aaaaccttaa tagcttgacg aacgggcaaa aagatacgat tttaaatcat  20400
attttcagtg caccaacaag aagccaagta ggagaaaaaa ttgcaagtgc taaacaatta  20460
aataatacaa tgaaagcact tagagattct attgctgata ataatgaaat tttacaaagt  20520
agtaagtact tcaatgaaga ttctgaacaa caaaatgctt ataatcaagc cgtaaataaa  20580
gctaaaaata taattaatga tcaaccaaca ccagtaatgg caaatgatga gattcaaagt  20640
gtcctaaatg aagttaaaca aactaaagat aatttacatg gtgatcaaaa acttgctaac  20700
gacaagacag atgctcaagc aacattaaat gcgttaaatt acttaaatca agcgcaaaga  20760
ggtaatcttg aaactaaagt tcaaaactct aattctagac cagaagtaca aaaagtagtt  20820
caattagcaa atcaacttaa tgatgcgatg aaaaaattag atgatgcttt aactggtaat  20880
gacgcaataa aacaaacgag taattatatt aatgaagata cttctcaaca agttaacttt  20940
gatgagtata cagatagagg taaaaacata gttgctgaac aaacaaatcc aaatatgtct  21000
ccaactaata ttaacactat tgctgataaa attactgaag ctaaaaacga tttacatggc  21060
gtacaaaaac taaaacaagc tcaacaacag tccatcaata ctattaatca aatgactggt  21120
ctaaaccaag ctcaaaaaga acaattaaat caagaaattc aacaaactca aacccgttct  21180
gaagtacatc aagtaattaa taaagcacaa gctttaaatg attcaatgaa tactttacgt  21240
caaagtatta ctgatgaaca tgaagttaaa caaacaagta actacatcaa tgaaactgtt  21300
ggtaatcaaa ctgcatataa caatgccgtt gatcgtgtaa aacaaataat caatcaaaca  21360
tctaatccaa ctatgaatcc tttagaggtg gaacgtgcaa catcaaatgt aaaaatttct  21420
aaagatgcac ttcatggtga acgtgaattg aatgacaata aaaattcaaa aactttgca   21480
```

gtcaatcact tagataacct caatcaagct caaaaagaag cattaactca tgaaattgaa 21540
caagcaacta tagtttcaca agtaaataat atctataaca aagcgaaagc tttaaataat 21600
gatatgaaaa aacttaaaga tatcgttgct caacaagata atgtgagaca atcaaacaat 21660
tatataaacg aggatagtac acctcaaaat atgtacaacg atacaattaa tcatgcacaa 21720
tcaatcattg atcaagtagc aaaccctacg atgtctcatg acgaaataga gaatgcaatc 21780
aataacataa agcatgccat caatgcactc gatggagaac ataaattaca acaagcaaaa 21840
gaaaatgcaa acttattgat taatagttta aacgatttaa atgcaccaca aagagatgcc 21900
ataaatagat tggttaatga agctcaaaca agagaaaaag tagctgaaca acttcaaagt 21960
gctcaagctt taaatgacgc tatgaagcat ttaagaaaca gcattcaaaa tcaatcatcc 22020
gtaagacaag agagcaaata tattaatgca agtgatgcta aaaaagagca atataatcac 22080
gcagttagag aagtcgaaaa tattatcaat gaacaacatc caacattgga taaagaaata 22140
attaagcaac taacggatgg tgtaaatcaa gcgaataatg acttaaatgg cgttgaatta 22200
ttagatgctg ataagcaaaa cgcacatcaa tcgataccta cattgatgca cttaaatcaa 22260
gcacaacaaa acgcattaaa tgaaaaaatt aataacgcag ttaccagaac tgaagttgcg 22320
gctattattg gccaagcaaa actactcgat catgctatgg agaatttaga agaaagtatc 22380
aaagataaag agcaagtcaa acagtcaagt aactatatta atgaagattc tgatgttcaa 22440
gaaacatacg ataacgccgt tgatcatgtg acagaaatac ttaatcaaac agtaaatcca 22500
actttatcta ttgaagatat agagcatgct atcaacgaag ttaatcaagc gaaaaaacaa 22560
ctcagaggta aacaaaaact ttatcaaact atcgatttag ctgataaaga attaagtaaa 22620
ttggatgatt taacatcaca acaaagcagt tcaatatcta atcaaatata tactgctaaa 22680
acgagaacag aagttgccca agcaattgaa aaagcaaaat cattaaatca tgcaatgaaa 22740
gcacttaaca aagtatataa aaatgcagat aaagtgttag atagtagtcg attcattaac 22800
gaagatcaac ctgaaaaaaa ggcgtatcaa caagctataa atcatgttga ttcaatcatt 22860
catagacaaa caaatcctga aatggatcca acagtaatca atagcataac tcatgaactc 22920
gaaacagctc aaaataactt acatggtgat cagaaacttg ctcatgcaca acaagatgcc 22980
gctaatgtaa ttaatggtct aattcatctt aatgttgctc aacgtgaggt aatgataaat 23040
acgaatacaa atgctacaac acgcgaaaaa gttgcaaaga acttagataa tgctcaagct 23100
cttgataaag ctatggaaac actacaacaa gtagttgctc ataaaaataa tatattgaac 23160
gatagtaaat atttaaatga agattcaaaa tatcaacaac aatacgatcg agttattgct 23220
gatgccgaac aactacttaa tcagacaaca aatccaacat tagaacctta taaagtcgat 23280
attgttaagg ataatgtcct agctaacgaa aaaatactat ttggcgcaga aaaactatca 23340
tatgacaaat caaatgcaaa tgatgaaatt aaacatatga attatcttaa taatgcacaa 23400
aagcaatcta taaaagatat gatttctcac gcagcattaa gaactgaagt taaacaactt 23460
ctgcaacaag ctaaaatcct tgatgaagcc atgaaatcac ttgaagataa aactcaagta 23520
gtgattacag atactacttt gcctaattac actgaagctt cagaggataa aaaggaaaaa 23580
gtagaccaaa ctgtatcaca tgctcaagcg attattgata aaataaatgg ctcaaatgta 23640
agtttagatc aagtacgaca agcactagaa caattaactc aagcatcaga aaacctcgat 23700
ggtgatcagc gagttgaaga agctaaagtt catgctaatc aaacaattga tcaattaaca 23760
catcttaatt cattacaaca acaaactgcg aaagaaagtg ttaaaaacgc aacaaaacta 23820
gaagaaatcg ctactgttag taacaatgct caggcattaa acaaagtaat gggtaaatta 23880
gaacaattca ttaatcatgc tgattctgtt gaaaatagtg ataattatag acaagccgac 23940
gacgacaaaa tcatcgctta tgatgaagca cttgaacatg gacaagatat acaaaaaact 24000
aacgcaaccc aaaatgaaac aaaacaagcg ttacaacaat taatatatgc agaaacatcg 24060
ttaaatggtt tcgaaagatt aaatcatgct agaccacgag ctttagaata tatcaaatca 24120
ctagaaaaaa taaacaatgc tcaaaagtct gctttagagg ataaagtaac gcaatcgcat 24180
gatttattag aattagaaca tattgtcaac gagggcacaa acctcaatga cattatgggt 24240
gaattagcta acgcaatcgt taataactat gctccaacca aagcaagtat aaattatatt 24300
aacgccgata acctacgcaa agataacttt actcaagcta tcaacaatgc acgtgatgca 24360
ctcaacaaaa ctcaaggtca gaacttagat ttcaatgcaa ttgatacatt taaagatgat 24420
atattcaaaa ctaaagatgc acttaacggt attgaacgtt taacagctgc aaaatcaaaa 24480
gcagaaaaac taattgatag tttaaaattt attaataaag ctcaattcac acatgcaaat 24540
gatgaaatta tgaatactaa ttctattgca caattgtcta gaatcgtgaa tcaagcattt 24600
gatttaaatg atgcaatgaa atctttaaga gatgaactta ataatcaagc ttttcctgtc 24660
caagcaagct caaattatat aaattcagat gaagatttaa aacaacaatt tgaccatgct 24720
ttaagtaatg ctcgaaaagt tcttgcaaaa gaaaatggta aaaatttaga tgaaaaacaa 24780
attcagggac tcaaacaagt gattgaggat actaaagatg ctttaaatgg tatccaacgt 24840
ttatcaaaag ctaaagctaa agcaattcaa tacgtacaat ctttatctta tatcaatgat 24900
gcacagcgtc atattgctga aaataatatt cacaactctg atgatttatc atctttagca 24960
aatacattat ctaaagctag tgatttagat aatgcaatga aagacttacg agatactata 25020
gaaagtaatt caacttctgt tccaaatagt gtgaattata ttaatgctga taagaattta 25080
caaattgaat ttgatgaggc gctacaacaa gcaagtgcaa caagttctaa aacttcagaa 25140
aatccagcaa cgattgaaga agtattaggt cttagtcaag ccatttacga tacaaaaaat 25200
gcattaaatg gtgaacaacg acttgcaact gagaagagca aagatctaaa attaataaaa 25260
ggattaaaag atttaaataa agcacaactt gaagatgtca caaacaaggt aaattcagca 25320
aatactttaa cagagttatc tcagctcact caatcaacgt tagaattaaa cgataaaatg 25380
aaattattga gagataagct taaaacttta gtaaatcctg ttaaagcaag tttaaattat 25440
agaaacgctg attataattt aaaacgtcaa tttaacaaag ctttaaaaga agctaaaggc 25500
gtattaaata aaaatagcgg tacaaatgtc aatatcaatg acattcaaca tcttttaaca 25560
caaatagata atgctaaaga ccaattaaat ggtgaacgac gtctaaaaga acatcaacaa 25620
aaatctgaag tatttattat taaagaatta gatatactta ataatgctca aaaagctgca 25680
ataattaatc agattagagc gtctaaagac attaaaataa ttaatcaaat cgttgataat 25740
gcaatagaat taaatgatgc tatgcaaggt ttaaaagaac atgtagctca attaacagca 25800
actacaaaag acaacattga atatttaaat gctgatgaag accataaatt acaatatgat 25860
tacgctatca acttagcgaa taatgttctt gacaaagaaa acggtacaaa taaagacgct 25920
aatatcataa ttggaatgat tcaaaacatg gatgatgcta gagcacttct aaatggaatt 25980
gaaagactta aagatgctca aacaaaagca cataatgaca ttaaagatac gctcaaacgt 26040
caacttgatg aaattgaaca cgctaatgca acatcaaatt ctaaagctca agctaaacaa 26100
atggtaaatg aggaagctag aaaagcgctt tctaatatta atgacgcaac atcaaatgat 26160
ttagttaatc aagcaaaaga tgaagggcaa tctgcaattg aacacataca tgcagatgaa 26220
ttacctaaag caaaactaga tgctaatcaa atgattgacc aaaaagttga agatataaat 26280
cacttaatta gtcaaaatcc aaacttatca aatgaagaaa aaaataaact aatatctcaa 26340
attaataagt tagtaaatgg aattaagaat gaaattcaac aagctataaa caaacaacaa 26400
atagaaaatg ctacaacaaa actagatgaa gtcattgaaa ctactaaaaa attaattatc 26460
gccaaagcag aagctaaaca aatgataaaa gagttatcac aaaagaaacg agatgcaata 26520
aataacaaca ctgatttaac accttctcaa aaggcacatg ctttagcaga tattgataaa 26580
acagaaaaag atgcacttca acatatcgaa aattctaatt caattgatga tatcaataac 26640
aataaagagc atgcatttaa tactttagct catatcatta tttgggatac tgatcagcaa 26700
ccattagttt ttgaactacc tgaattgagc cttcaaaatg ctctagtaac aagtgaggtg 26760
gttgttcaca gagatgaaac tatttcatta gaatctataa ttggagctat gactttaact 26820
gatgaactta aagtcaatat tgtttcatta ccgaacactg ataaagtagc tgatcaccta 26880
accgctaaag ttaaggttat tttagctgat ggctcatatg tcactgtaaa tgttccagtc 26940
aaagttgtag aaaaagaatt acaaatagct aaaaaggatg ctataaaaac aattgatgtt 27000
ctggtaaaac aaaaaatcaa agatatagat tctaataacg aattaacgtc tactcaacgt 27060
gaagatgcaa aagctgaaat tgaaagattg aaaaagcaag ccatcgataa agtgaatcat 27120
tcaaaatcga ttaaagatat tgaaacagta aaacgaactg attttgaaga aatagatcag 27180
tttgatccta aacgctttac gctaaataaa gctaaaaagg atatcattac tgatgttaat 27240
actcaaatcc aaaatggttt caaagaaatt gaaacaataa aaggtttaac ttctaatgaa 27300
aaaactcagt ttgataaaca attaactgca ctacaaaaag aatttttaga aaaagtcgag 27360
catgctcata atttagtaga attaaatcaa ttacaacaag agtttaataa tagatataaa 27420
catattttaa accaagcaca tttactaggt gaaaaacata tagcagaaca taaattagga 27480
tatgttgtag taaacaaaac tcagcaaata ctaaataatc aatctgcttc ttactttata 27540
aaacaatggg cacttgatag aattaaacaa attcaactag aaacgatgaa ttcaattcgt 27600
ggtgcgcata ccgtacaaga tgtacacaaa gcattattac aaggtataga gcaaatcttg 27660
aaagtaaatg taagtattat aaatcaatct ttcaacgatt ccttgcataa ctttaattat 27720
cttcattcaa aatttgatgc tagattaaga gaaaaggatg ttgcaaacca tatcgtacaa 27780
actgaaacat tcaaagaagt tctaaaagga acgggtgttg aaccaggtaa aatcaacaaa 27840
gaaacacagc aaccaaaact tcataagaat gataatgata gcctattcaa acatttagtt 27900
gataatttcg gcaaaactgt aggtgttatt acattaactg gtttactttc tagtttctgg 27960
ttagttttgg ctaaaagacg taaaaaagaa gaagaagaaa aacaatcgat aaaaaatcat 28020
cacaaagata ttcgtctttc agatactgat aaaatagatc caattgtaat aactaagcgt 28080
aaaatagata aagaagaaca aattcaaaac gatgacaaac attcaattcc agttgctaaa 28140
cataagaaat ctaaagaaaa gcaattgagt gaagaggata ttcattcaat ccccgtcgtt 28200
aagcgtaaac aaaacagtga taacaaagat acaaaacaga agaaagttac ttctaaaaag 28260
aagaaaacgc ctcagtcaac taaaaaagtt gtaaaaacca aaaagcgttc taaaaag 28317

<210> SEQ ID NO 49
<211> LENGTH: 3348
<212> TYPE: DNA
<213> ORGANISM: Staphylococcus sp.

<400> SEQUENCE: 49

-continued

```
atgagagata agaaaggacc ggtaaataaa agagtagatt ttctatcaaa taaattgaat     60
aaatattcaa taagaaaatt tacagttgga acagcatcta ttttaattgg ctcactaatg    120
tatttgggaa ctcaacaaga agcagaagca gctgaaaaca atattgagaa tccaactaca    180
ttaaaagata atgtccaatc aaaagaagtg aagattgaag aagtaacaaa caaagacact    240
gcaccacaag gtgtagaagc taaatctgaa gtaacttcaa acaaagacac aatcgaacat    300
gaagcatcag taaaagctga agatatatca aaaaaggagg atacaccaaa agaagtagct    360
aatgttgctg aagttcagcc gaaatcgtca gtcactcata acgcagaggc acctaaggtt    420
agaaaagctc gttctgttga tgaaggctct tttgatatta caagagattc taaaaatgta    480
gttgaatcta ccccaattac aattcaaggt aaagaacatt ttgaaggtta cggaagtgtt    540
gatatacaaa aaaacccaac agatttaggg gtatcagagg taaccaggtt taatgttggt    600
aatgaaagta atggtttgat aggagcttta caattaaaaa ataaaataga ttttagtaag    660
gatttcaatt ttaaagttag agtggcaaat aaccatcaat caaataccac aggtgctgat    720
ggttgggggt tcttatttag taaaggaaat gcagaagaat atttaactaa tggtggaatc    780
cttggggata aaggtctggt aaattcaggc ggatttaaaa ttgatactgg atacatttat    840
acaagttcca tggacaaaac tgaaaagcaa gctggacaag gttatagagg atacggagct    900
tttgtgaaaa atgacagttc tggtaattca caaatggttg gagaaaatat tgataaatca    960
aaaactaatt ttttaaacta tgcggacaat tcaactaata catcagatgg aaagtttcat   1020
gggcaacgtt taaatgatgt catcttaact tatgttgctt caactggtaa aatgagagca   1080
gaatatgctg gtaaaacttg ggagacttca ataacagatt taggtttatc taaaaatcag   1140
gcatataatt tcttaattac atctagtcaa agatggggcc ttaatcaagg gataaatgca   1200
aatggctgga tgagaactga cttgaaaggt tcagagttta cttttacacc agaagcgcca   1260
aaaacaataa cagaattaga aaaaaaagtt gaagagattc cattcaagaa agaacgtaaa   1320
tttaatccgg atttagcacc agggacagaa aaagtaacaa gagaaggaca aaaaggtgag   1380
aagacaataa caacaccaac actaaaaaat ccattaactg gagaaattat tagtaaaggt   1440
gaatcgaaag aagagatcac aaaagatccg attaatgaat taacagaata cggaccagaa   1500
acgatagcac caggtcatcg agacgaattt gatccgaagt taccaacagg agagaaagaa   1560
gaagttccag gtaaaccagg aattaagaat ccagaaacag gagacgtagt tagaccaccg   1620
gtcgatagtg taacaaaata tggacctgta aaaggagact cgattgtaga aaaagaagaa   1680
attccattcg agaaagaacg taaatttaat cctgatttag caccaggaac agaaaaagta   1740
acaagagaag gacaaaaagg tgagaagaca ataacgacac caacactaaa aaatccatta   1800
actggagaaa ttattagtaa aggtgaatcg aaagaagaga tcacaaaaga tccgattaat   1860
gaattaacag aatacggacc tgaaacaata gcgccaggtc atcgagacga atttgatccg   1920
aagttaccaa caggagagaa agaagaagtt ccaggtaaac caggaattaa gaatccagaa   1980
acaggagacg tagttagacc gccggtcgat agcgtaacaa aatatggacc tgtaaaagga   2040
gactcgattg tagaaaaaga agaaattcca ttcaagaaag aacgtaaatt taatcctgat   2100
ttagcaccag ggacagaaaa agtaacaaga gaaggacaaa aaggtgagaa gacaataacg   2160
acgccaacac taaaaaatcc attaactgga gaaattatta gtaaaggtga atcgaaagaa   2220
gaaatcacaa aagatccgat taatgaatta acagaatacg gaccagaaac gataacacca   2280
ggtcatcgag acgaatttga tccgaagtta ccaacaggag agaaagagga agttccaggt   2340
aaaccaggaa ttaagaatcc agaaacagga gatgtagtta gaccaccggt cgatagcgta   2400
```

```
acaaaatatg gacctgtaaa aggagactcg attgtagaaa aagaagaaat tccattcgag   2460
aaagaacgta aatttaatcc tgatttagca ccagggacag aaaaagtaac aagagaagga   2520
caaaaaggtg agaagacaat aacgacgcca acactaaaaa atccattaac tggagaaatt   2580
attagtaaag gtgaatcgaa agaagaaatc acaaaagatc cagttaatga attaacagaa   2640
ttcggtggcg agaaaatacc gcaaggtcat aaagatatct ttgatccaaa cttaccaaca   2700
gatcaaacgg aaaaagtacc aggtaaacca ggaatcaaga atccagacac aggaaaagtg   2760
atcgaagagc cagtggatga tgtgattaaa cacggaccaa aaacgggtac accagaaaca   2820
aaaacagtag agataccgtt tgaaacaaaa cgtgagttta atccaaaatt acaacctggt   2880
gaagagcgag tgaaacaaga aggacaacca ggaagtaaga caatcacaac accaatcaca   2940
gtgaacccat taacaggtga aaaagttggc gagggtcaac caacagaaga gatcacaaaa   3000
caaccagtag ataagattgt agagttcggt ggagagaaac caaaagatcc aaaaggacct   3060
gaaaacccag agaagccgag cagaccaact catccaagtg gcccagtaaa tcctaacaat   3120
ccaggattat cgaaagacag agcaaaacca aatggcccag ttcattcaat ggataaaaat   3180
gataaagtta aaaaatctaa aattgctaaa gaatcagtag ctaatcaaga gaaaaaacga   3240
gcagaattac caaaaacagg tttagaaagc acgcaaaaag gtttgatctt tagtagtata   3300
attggaattg ctggattaat gttattggct cgtagaagaa agaattaa                3348
```

<210> SEQ ID NO 50
<211> LENGTH: 4410
<212> TYPE: DNA
<213> ORGANISM: Staphylococcus sp.

<400> SEQUENCE: 50

```
atgggcaaac gtagacaagg tcctattaat aaaaaagtgg attttttacc taacaaatta     60
aacaagtatt ctataagaaa attcactgtt ggtacggcct caatattact tggttcgaca    120
cttatttttg gaagtagtag ccatgaagcg aaagctgcag aagaaaaaca agttgatcca    180
attacacaag ctaatcaaaa tgatagtagt gaaagatcac ttgaaaacac aaatcaacct    240
actgtaaaca atgaagcacc acagatgtct tctacattgc aagcagaaga aggaagcaat    300
gcagaagcac cgaatgttcc aactatcaaa gctaattcag ataatgatac acaaacacaa    360
ttttcagaag cccctacaag aaatgaccta gctagaaaag aagatatccc tgctgtttct    420
aaaaacgagg aattacaatc atcacaacca aacactgaca gtaaaataga acctacaact    480
tcagaacctg tgaatttaaa ttatagttct ccgtttatgt ccttattaag catgcctgct    540
gatagttcat ccaataacac taaaaataca atagatatac cgccaactac ggttaaaggt    600
agagataatt acgattttta cggtagagta gatatccaaa gtaatcctac agatttaaat    660
gcgacaaatt taacgagata taattatgga cagccacctg gtacaacaac agctggtgca    720
gttcaattta aaaatcaagt tagttttgat aaagatttcg actttaacat tagagtagca    780
aacaatcgtc aaagtaatac aactggtgca gatggttggg gctttatgtt cagcaagaaa    840
gatggggatg atttcctaaa aaacggtggt atcttacgtg aaaaaggtac acctagtgca    900
gctggtttca gaattgatac aggatattat aataacgatc cattagataa aatacagaaa    960
caagctggtc aaggctatag agggtatggg acatttgtta aaaatgactc ccaaggtaat   1020
acttctaaag taggatcagg tactccatca acagattttc ttaactacgc agataatact   1080
actaatgatt tagatggtaa attccatggt caaaaattaa ataatgttaa tttgaaatat   1140
```

-continued

```
aatgcttcaa atcaaacttt tacagctact tatgctggta aaacttggac ggctacgtta   1200
tctgaattag gattgagtcc aactgatagt tacaattttt tagttacatc aagtcaatat   1260
ggaaatggta atagtggtac atacgcagat ggcgttatga gagctgattt agatggtgca   1320
acattgacat atactcctaa agcagtcgat ggagacccaa ttacatcaac taaggaaata   1380
ccatttaata aaaaacgcga atttgatcca aacttagcgc caggtacaga aaaagtcgtt   1440
caaaaaggtg aaccaggaat tgaaacaaca acaacaccaa cttatgtcaa tcctaatact   1500
ggagaaaaag taggtgaagg cacacctaca acaaagatca ctaaacaacc agtggatgaa   1560
atcgttcatt atggtggcga agaaatcaag ccaggacata aagatgaatt tgatccaaat   1620
gcaccgaaag gtagtcaaac aacgcaacca ggtaagccag gagttaaaaa tcctgataca   1680
ggcgaagtag tcacaccacc agtggatgat gtgacaaaat atggtccagt tgatggagat   1740
ccgattacgt caacggaaga aattccattc gacaagaaac gtgaattcaa tcctgattta   1800
aaaccaggtg aagagcgtgt taaacaaaaa ggtgaaccag gaacaaaaac aattacaaca   1860
ccaacaacta agaacccatt aacaggggaa aaagttggcg aaggtgaacc aacagaaaaa   1920
ataacaaaac aaccagtaga tgaaatcaca gaatatggtg gcgaagaaat caagccaggc   1980
cataaggatg aatttgatcc gaacgcaccg aaaggtagcc aagaggacgt tccaggtaaa   2040
ccaggagtta aaaatcctga tacaggcgaa gtagtcacac caccagtgga tgatgtgaca   2100
aaatatggtc cagttgatgg agatccgatt acgtcaacgg aagaaattcc gtttgataaa   2160
aaacgcgaat ttgatccaaa cttagcgcca ggtacagaga aagtcgttca aaaaggtgaa   2220
ccaggaacaa aaacaattac aacaccaaca actaagaacc cattaacagg agaaaaagtt   2280
ggcgaaggtg aaccaacaga aaaaataaca aaacaaccag tggatgaaat cgttcattat   2340
ggtggcgaag aaatcaagcc aggccataag gatgaatttg atccgaacgc accgaaaggt   2400
agccaagagg acgttccagg taagccagga gttaaaaatc ctgatacagg cgaagtagtc   2460
acaccaccag tggatgatgt gacaaaatat ggtccagttg atggagatcc gattacgtca   2520
acggaagaaa ttccattcga caagaaacgt gaattcaatc ctgatttaaa accaggtgaa   2580
gagcgtgtta aacaaaaagg tgaaccagga acaaaaacaa ttacaacacc aacaactaag   2640
aacccattaa caggggaaaa agttggcgaa ggtgaaccaa cagaaaaagt aacaaaacaa   2700
ccagtggatg aaatcgttca ttatggtggc gaagaaatca agccaggcca taaggatgaa   2760
tttgatccaa atgcaccgaa aggtagccaa gaagacgttc caggtaaacc aggagttaaa   2820
aaccctgata caggcgaagt agttactcca ccagtggatg atgtgacaaa atatggtcca   2880
gttgatggag atccgattac gtcaacggaa gaaattccgt ttgataaaaa acgcgaattt   2940
gatccaaact tagcgccagg tacagagaaa gtcgttcaaa aaggtgaacc aggaacaaaa   3000
acaattacaa caccaacaac taagaaccca ttaacaggag aaaaagttgg cgaaggtgaa   3060
ccaacagaaa aaataacaaa acaaccagtg gatgagatcg ttcattatgg tggcgaagaa   3120
atcaagccag gccataagga tgaatttgat ccgaacgcac cgaaaggtag tcaaacaacg   3180
caaccaggta agccaggagt taaaaatcct gatacaggcg aagtagtcac accaccagtg   3240
gatgatgtga caaaatatgg tccagttgat ggagatccga ttacgtcaac ggaagaaatt   3300
ccgtttgata aaaaacgcga atttgatcca aacttagcgc caggtacaga gaaagtcgtt   3360
caaaaaggtg aaccaggaac aaaaacaatt acaacgccaa caactaagaa cccattaaca   3420
ggagaaaaag ttggcgaagg tgaaccaaca gaaaaaataa caaaacaacc agtggatgag   3480
attgttcatt atggtggtga acaaatacca caaggtcata aagatgaatt tgatccaaat   3540
```

gcacctgtag atagtaaaac tgaagttcca ggtaaaccag gagttaaaaa tcctgataca 3600
ggtgaagttg ttaccccacc agtggatgat gtgacaaaat atggtccgaa agttggtaat 3660
ccaatcacat caacggaaga gattccattt gataagaaac gtgtatttaa tcctgattta 3720
aaaccaggtg aagagcgcgt taaacaaaaa ggtgaaccag gaacaaaaac aattacaaca 3780
ccaatattag ttaatcctat tacaggagaa aaagttggcg aaggtaaatc aacagaaaaa 3840
gtcactaaac aacctgttga cgaaattgtt gagtatggtc caacaaaagc agaaccaggt 3900
aaaccagcgg aaccaggtaa accagcggaa ccaggtaaac cagcggaacc aggtaaacca 3960
gcggaaccag gtacgccagc agaaccaggt aaaccagcgg aaccaggtaa accagcggaa 4020
ccaggtaaac cagcggaacc aggtaaacca gcggaaccag gtaaaccagc ggaaccaggt 4080
acgccagcag aaccaggtaa accagcggaa ccaggtaaac cagcggaacc aggtaaacca 4140
gcggaaccag gtacgccagc agaaccaggt aaaccagcgg aaccaggtac gccagcagaa 4200
ccaggtaaac cagcggaacc aggtacgcca acacaatcag gtgcaccaga acaaccaaat 4260
agatcaatgc attcaacaga taataaaaat caattacctg atacaggtga aaatcgtcaa 4320
gctaatgagg gaactttagt cggatctcta ttagcaattg tcggatcatt gttcatattt 4380
ggtcgtcgta aaaaaggtaa tgaaaaataa 4410

<210> SEQ ID NO 51
<211> LENGTH: 504
<212> TYPE: DNA
<213> ORGANISM: Staphylococcus sp.

<400> SEQUENCE: 51
atgaagaaac tatatacatc ttatggcact tatggatttt tacatcaaat aaaaatcaat 60
aacccgaccc atcaactatt ccaattttca gcatcagata cttcagttat ttttgaagaa 120
actgatggtg agactgtttt aaaatcacct tcaatatatg aagttattaa agaaattggt 180
gaattcagtg aacatcattt ctattgtgca atcttcattc cttcaacaga agatcatgca 240
tatcaacttg aaaagaaact gattagtgta gacgataatt tcagaaactt tggtggcttt 300
aaaagctatc gtttgttaag acctgctaaa ggtacaacat ataaaattta tttcggattt 360
gctgatcgac atgcatacga agactttaag caatctgatg cctttaatga ccatttttca 420
aaagacgcat taagtcatta ctttggttca agcggacaac attcaagtta ttttgaaaga 480
tatctatacc caataaaaga atag 504

<210> SEQ ID NO 52
<211> LENGTH: 504
<212> TYPE: DNA
<213> ORGANISM: Staphylococcus sp.

<400> SEQUENCE: 52
atgtatttat atacatctta tgggacttac caatttttaa atcaaattaa acttaatcat 60
caagaacgta gtttatttca attttccact aatgattcct caataatctt agaagagtct 120
gagggaaaat caatcttaaa acatcctagt gcatatcaag tgattgatag cacaggtgaa 180
tttaacgaac atcattttta tagtgctatt tttgtcccta catctgaaga tcatcgtcaa 240
cagctagaga aaaaattatt actcgtagac gtacctttaa gaaattttgg tggttttaaa 300
agctatcgtt tattaaaacc cactgagggg tctacctaca aaatttactt tggttttgca 360
aatcgaacag catatgaaga tttcaaagct tctgatatat ttaatgaaaa cttttcaaaa 420
gatgcattga gccaatactt tggtgctagt ggtcaacatt ctagctactt tgaaagatat 480
ttatatccaa tagaagatca ttaa 504

<210> SEQ ID NO 53
<211> LENGTH: 3426
<212> TYPE: DNA
<213> ORGANISM: Staphylococcus sp.

<400> SEQUENCE: 53
atgattaaca gggataataa aaaggcaata acaaaaaagg gtatgatttc aaatcgctta 60
aacaaatttt cgattagaaa gtatactgta ggaactgcat cgattttagt aggtacgaca 120
ttgatttttg gtctagggaa ccaagaagct aaagctgctg aaaacactag tacagaaaat 180
gcgaaacaag atgatgcaac gactagtgat aataaagaag tagtgtcgga aactgaaaat 240
aattcgacaa cagaaaatga ttcaacaaat ccaattaaga aagaaacaaa tactgattca 300
caaccagaag ctaaagaaga atcaactaca tcaagtactc aacaacagca aaataacgtt 360
acagctacaa ctgaaactaa gcctcaaaac attgaaaaag aaaatgttaa accttcaact 420
gataaaactg cgacagaaga tacatctgtt attttagaag agaagaaagc accaaattat 480
acaaataacg atgtaactac aaaaccatct acaagtgaaa ttcaaacaaa accaactaca 540
cctcaagaat ctacaaatat tgaaaattca caaccgcaac caacgccttc aaaagtagac 600
aatcaagtta cagatgcaac taatccaaaa gaaccagtaa atgtgtcaaa agaagaactt 660
aaaaataatc ctgagaaatt aaaagaatta gttagaaatg ataacaatac agatcgttca 720
actaaaccag ttgctacagc tccaacaagt gttgcaccaa aacgattaaa tgcgaaaatg 780
cgttttgcag ttgcacaacc agcagcagtt gcttcaaata atgtaaatga cttaattaca 840
gttacgaaac agacgatcaa agttggcgat ggtaaagata atgtggcagc agcgcatgac 900
ggtaaagata ttgaatatga tacagagttt acaattgaca ataaagtcaa aaaaggcgat 960
acaatgacga ttaattatga taagaatgta attccttcgg atttaacaga taaaaatgat 1020
cctatcgata ttactgatcc atcaggagag gtcattgcca aggaacattt tgataaagcg 1080
actaagcaaa tcacatatac atttacagat tatgtagata aatatgaaga tataaaagca 1140
cgtttaactt tatactcata tattgataag caagcagtac ctaatgaaac tagtttgaat 1200
ttaacgtttg caacagcagg taaagaaact agccaaaacg tttctgttga ttatcaagac 1260
ccaatggttc atggtgattc aaacattcaa tctatcttta caaagttaga tgaaaacaaa 1320
caaactattg aacaacaaat ttatgttaat cctttgaaaa aaacagcaac taacactaaa 1380
gttgatatag ctggtagtca agtagatgat tatggaaata ttaaactagg aaatggtagt 1440
accattattg accaaaatac agaaataaaa gtttataaag ttaaccctaa tcaacaattg 1500
cctcaaagta atagaatcta tgattttagt caatacgaag atgtaacaag tcaatttgat 1560
aataaaaaat catttagtaa taatgtagca acattggatt ttggtgatat taattcagcc 1620
tatattatca aagttgttag taaatataca cctacatcag atggcgaact agatattgct 1680
caaggtacta gtatgagaac aactgataaa tatggttatt ataattatgc aggatattca 1740
aacttcatcg taacttctaa tgacactggc ggtggcgacg gtactgttaa acctgaagaa 1800
aagttataca aaattggtga ctatgtatgg gaagacgttg ataaagacgg tgtccaaggt 1860
acagattcga aagaaaagcc aatggcaaac gttttagtta cattaactta cccggacggt 1920
actacaaaat cagtaagaac agatgctaac ggtcattatg aattcggtgg tttgaaagac 1980
ggagaaactt atacagttaa attcgaaacg ccagctggat atcttccaac aaaagtaaat 2040
ggaacaactg atggtgaaaa agactcaaat ggtagttcta taactgttaa aattaatggt 2100
aaagatgata tgtctttaga cactggtttt tataaagaac ctaaatataa tcttggtgac 2160
tatgtatggg aagatacaaa taaagatggt atccaagatg ctaatgaacc tggtatcaaa 2220
gatgttaagg ttacattaaa agatagtact ggaaaagtta ttggtacaac tactactgat 2280
gcctcgggta aatataaatt tacagattta gataatggta actatacagt agaatttgaa 2340
acaccagcag gttacacgcc aacggttaaa aatactacag ctgaagataa agattctaat 2400
ggtttaacaa caacaggtgt cattaaagat gcagataata tgacattaga cagtggtttc 2460
tataaaacac caaaatacag tttaggtgat tatgtttggt acgacagtaa taaagacggt 2520
aaacaagatt caactgaaaa aggtatcaaa gatgttaaag ttactttatt aaatgaaaaa 2580
ggcgaagtaa ttggaacaac taaaacagat gaaaatggta aatatcgttt cgataattta 2640
gatagcggta aatacaaagt tatttttgaa aagcctgctg gcttaacaca aacagttaca 2700
aatacaactg aagatgataa agatgccgat ggtggcgaag ttgacgtaac aattacggat 2760
catgatgatt tcatacttga taacggatac ttcgaagaag atacatcaga cagtgattca 2820
gactcagaca gtgattcaga ctcagacagc gactcagatt cagacagtga ttcagactca 2880
gatagcgatt cagattcaga cagcgactca gactcagata gcgactcaga ctcagacagc 2940
gactcagact cagatagcga ctcagattcg gacagcgatt cagactcaga tagcgactca 3000
gattcagaca gcgattcaga ctcagatagc gactcagatt cagacagtga ctcagactca 3060
gatagcgact cagactcaga cagtgactca gactcagaca gcgattcaga ttcagatagc 3120
gactcagatt cggacagtga ttcagactca gatagcgact cagattcaga cagcgactca 3180
gactcagata gcgactcaga ctcagacagt gattcagact cagatagcga ttcggactcg 3240
gatgcaggaa aacatacacc tgttaaacca atgagtacta ctaaagacca tcacaataaa 3300
gcaaaagcat taccagaaac aggtagtgaa aataacggct caaataacgc aacgttattt 3360
ggtggattat ttgcagcatt aggttcatta ttgttattcg gtcgtcgcaa aaaacaaaac 3420
aaataa 3426

<210> SEQ ID NO 54
<211> LENGTH: 3171
<212> TYPE: DNA
<213> ORGANISM: Staphylococcus sp.

<400> SEQUENCE: 54
atgattaata aaaaaaataa tttactaact aaaaagaaac ctatagcaaa taaatccaat 60
aaatatgcaa ttagaaaatt cacagtaggt acagcgtcta ttgtaatagg tgcaacatta 120
ttgtttggtt taggtcataa tgaggccaaa gccgaggaga attcagtaca agacgttaaa 180
gattcgaata cggatgatga attatcagac agcaatgatc agtctagtga tgaagaaaag 240
aatgatgtga tcaataataa tcagtcaata aacaccgacg ataataacca aataattaaa 300
aaagaagaaa cgaataacta cgatggcata gaaaaacgct cagaagatag aacagagtca 360
acaacaaatg tagatgaaaa cgaagcaaca tttttacaaa agacccctca agataatact 420
catcttacag aagaagaggt aaaagaatcc tcatcagtcg aatcctcaaa ttcatcaatt 480
gatactgccc aacaaccatc tcacacaaca ataaatagag aagaatctgt tcaaacaagt 540
gataatgtag aagattcaca cgtatcagat tttgctaact ctaaaataaa agagagtaac 600
actgaatctg gtaaagaaga gaatactata gagcaaccta ataaagtaaa agaagattca 660

```
acaacaagtc agccgtctgg ctatacaaat atagatgaaa aaatttcaaa tcaagatgag    720
ttattaaatt taccaataaa tgaatatgaa aataaggcta gaccattatc tacaacatct    780
gcccaaccat cgattaaacg tgtaaccgta aatcaattag cggcggaaca aggttcgaat    840
gttaatcatt taattaaagt tactgatcaa agtattactg aaggatatga tgatagtgaa    900
ggtgttatta aagcacatga tgctgaaaac ttaatctatg atgtaacttt tgaagtagat    960
gataaggtga aatctggtga tacgatgaca gtggatatag ataagaatac agttccatca   1020
gatttaaccg atagctttac aataccaaaa ataaaagata attctggaga aatcatcgct   1080
acaggtactt atgataacaa aaataaacaa atcacctata cttttacaga ttatgtagat   1140
aagtatgaaa atattaaagc acaccttaaa ttaacgtcat acattgataa atcaaaggtt   1200
ccaaataata ataccaagtt agatgtagaa tataaaacgg ccctttcatc agtaaataaa   1260
acaattacgg ttgaatatca aagacctaac gaaaatcgga ctgctaacct tcaaagtatg   1320
tttacaaaca tagatacgaa aaatcataca gttgagcaaa cgatttatat taaccctctt   1380
cgttattcag ccaaggaaac aaatgtaaat atttcaggga atggtgatga aggttcaaca   1440
attatagacg atagcacaat aattaaagtt tataaggttg gagataatca aaatttacca   1500
gatagtaaca gaatttatga ttacagtgaa tatgaagatg tcacaaatga tgattatgcc   1560
caattaggaa ataataatga tgtgaatatt aattttggta atatagattc accatatatt   1620
attaaagtta ttagtaaata tgaccctaat aaggatgatt acacgactat acagcaaact   1680
gtgacaatgc agacgactat aaatgagtat actggtgagt ttagaacagc atcctatgat   1740
aatacaattg ctttctctac aagttcaggt caaggacaag gtgacttgcc tcctgaaaaa   1800
acttataaaa tcggagatta cgtatgggaa gatgtagata aagatggtat tcaaaataca   1860
aatgataatg aaaaaccgct tagtaatgta ttggtaactt tgacgtatcc tgatggaact   1920
tcaaaatcag tcagaacaga tgaagatggg aaatatcaat ttgatggatt gaaaaacgga   1980
ttgacttata aaattacatt cgaaacacct gaaggatata cgccgacgct taaacattca   2040
ggaacaaatc ctgcactaga ctcagaaggt aattctgtat gggtaactat taatggacaa   2100
gacgatatga cgattgatag tggattttat caaacaccta aatacagctt agggaactat   2160
gtatggtatg acactaataa agatggtatt caaggtgatg atgaaaaagg aatctctgga   2220
gttaaagtga cgttaaaaga tgaaaacgga aatatcatta gtacaactac aaccgatgaa   2280
aatggaaagt atcaatttga taatttaaat agtggtaatt atattgttca ttttgataaa   2340
ccttcaggta tgactcaaac aacaacagat tctggtgatg atgacgaaca ggatgctgat   2400
ggggaagaag ttcatgtaac aattactgat catgatgact ttagtataga taacggatac   2460
tatgatgacg aatcggattc cgatagtgac tcagacagcg actcagattc cgatagtgat   2520
tcagactccg atagcgactc ggattcagac agcgactcag attcagacag cgactcggat   2580
tctgatagcg actcggattc agacagcgac tcagactcag acagtgattc agattcagac   2640
agcgactcag attccgatag tgattcagac tcagacagcg actcagattc tgatagtgat   2700
tcagactcag acagtgattc agattcagac agcgactcag attccgatag tgattcagac   2760
tcagacagcg actcagattc cgatagtgat tcagactcag acagcgactc agattctgat   2820
agtgattcag actcagacag tgattcagat tccgatagtg attcagactc cgatagcgac   2880
tcagactcgg atagtgactc agattctgat agtgattcag actcagacag tgattcggat   2940
tccgatagtg attcagactc agacagcgac tcagattctg atagtgattc agactcagac   3000
aacgactcag atttaggcaa tagctcagat aagagtacaa aagataaatt acctgataca   3060
```

ggagctaatg aagattatgg ctctaaaggc acgttacttg gaactctgtt tgcaggttta 3120
ggagcgttat tattagggaa acgtcgcaaa aatagaaaaa ataaaaatta a 3171

<210> SEQ ID NO 55
<211> LENGTH: 1461
<212> TYPE: DNA
<213> ORGANISM: Staphylococcus sp.

<400> SEQUENCE: 55
atgtctaata attttaaaga tgactttgaa aaaaatcgtc aatcgataga cacaaattca 60
catcaagacc atacggaaga tgttgaaaaa gaccaatcag aattagaaca tcaggataca 120
atagagaata cggagcaaca gtttccgcca agaaatgccc aaagaagaaa aagacgccgt 180
gatttagcaa cgaatcataa taaacaagtt cacaatgaat cacaaacatc tgaagacaat 240
gttcaaaatg aggctggcac aatagatgat cgtcaagtcg aatcatcaca cagtactgaa 300
agtcaagaac ctagccatca agacagtaca cctcaacatg aagaggaata ttataataag 360
aatgcttttg caatggataa atcacatcca gaaccaatcg aagacaatga taaacacgag 420
actattaaag atgcagaaaa taacactgag cattcaacag tttctgataa gagtatagct 480
gaacaatctc agcaacctaa accatatttt gcaacaggtg ctaaccaagc aaatacatca 540
aaagataaac atgatgatgt aactgttaag caagacaaag atgaatctaa agatcatcat 600
agtggtaaaa aaggcgcagc aattggtgct ggaacagcgg gtgttgcagg tgcagctggt 660
gcaatgggtg tttctaaagc taagaaacat tcaaatgacg ctcaaaacaa aagtaattct 720
gacaagtcga ataactcgac tgaggataaa gcgtctcaag ataagtctaa agatcatcat 780
aatggcaaaa aaggtgcagc gatcggtgct ggaacagcag gtttggctgg aggcgcagca 840
agtaaaagtg cttctgccgc ttcaaaacca catgcctcta ataatgcaag ccaaaaccat 900
gatgaacatg acaatcatga cagagataaa gaacgtaaaa aaggtggcat ggccaaagta 960
ttgttaccat taattgcagc tgtactaatt atcggtgcat tagcgatatt tggaggcatg 1020
gcattaaaca atcataataa tggtacaaaa gaaaataaaa tcgcgaatac aaataaaaat 1080
aatgctgatg aaagtaaaga caaagacaca tctaaagacg cttctaaaga taaatcaaaa 1140
tctacagaca gtgataaatc aaaagaggat caagacaaag cgactaaaga tgaatctgat 1200
aatgatcaaa acaacgctaa tcaagcgaac aatcaagcac aaaataatca aaatcaacaa 1260
caagctaatc aaaatcaaca acagcaacaa caacgtcaag gtggtggcca aagacataca 1320
gtgaatggtc aagaaaactt ataccgtatc gcaattcaat actacggttc aggttcaccg 1380
gaaaatgttg aaaaaattag acgtgccaat ggtttaagtg gtaacaatat tagaaacggt 1440
caacaaatcg ttattccata a 1461

<210> SEQ ID NO 56
<211> LENGTH: 1419
<212> TYPE: DNA
<213> ORGANISM: Staphylococcus sp.

<400> SEQUENCE: 56
gtgattgaat taattaaaat ggaagggatg atagttgtgt ctaataataa ttttaaagat 60
gatttcgaaa agaatcgtca atctattaat ccagacgaac agcaaacaga attaaaagaa 120
gatgataaaa caaatgaaaa taaaaaagaa gctgactctc aaaacagttt atctaataac 180
tcaaatcaac aatttcctcc gagaaatgcc caacgacgaa aaagacgtag agagacagca 240

```
actaatcaaa gcaaacaaca agacgacaaa catcaaaaaa atagtgacgc taaaactaca    300

gaaggttcat tagatgaccg ttatgacgaa gcacagttac agcaacaaca tgataaatcg    360

caacaacaaa ataaaactga aaaacaatca caagataata gaatgaaaga tggaaaagat    420

gcagctattg taaatggaac atctgagtca ccagaacata aatcaaaatc aacacaaaat    480

agacccggcc ctaaagctca acaacaaaag cgtaaatcag aaagtacgca atcaaaaccg    540

tcaacaaaca aagataaaaa agcagctaca ggtgctggaa tagctggtgc agctggtgtt    600

gctggtgcag cagaaacatc caaacgtcat cataataaaa aagataaaca agattctaaa    660

cactcaaacc atgagaatga cgaaaaatct gttaaaaatg atgaccaaaa gcaatctaaa    720

aaaggcaaaa aagcagcagt cggtgctggc gcagctgcag gagttggtgc ggctggtgtt    780

gcgcatcata ataatcaaaa taaacatcat aatgaggaaa aaaattctaa tcaaaacaat    840

cagtacaatg accaatcaga aggtaagaaa aaaggtggtt tcatgaaaat cttgttacca    900

cttatagcag ccattcttat tctaggtgca atagcaatat tcggtggtat ggctctaaat    960

aatcacaacg atagtaaaag tgatgaccaa aaaatagcga atcaaagtaa gaaagactca   1020

gataaaaaag atggtgcgca atccgaagat aacaaagaca aaaaatctga tagtaacaaa   1080

gacaaaaaat ctgattctga taagaacgca gatgatgact ctgataatag ttcctcaaat   1140

cctaacgcta cttcaactaa taataacgat aatgtagcca ataataactc aaattataca   1200

aaccaaaatc aacaagataa tgcaaaccaa aatagcaata atcaacaggc aactcaaggt   1260

caacaatcac atacagtata cggtcaagaa aacttatatc gtatcgccat acaatattat   1320

ggagaaggaa ctcaagctaa cgtagataaa attaaacgtg cgaatggatt aagcagtaat   1380

aatattcata atggtcaaac attagttatt cctcaataa                          1419
```

<210> SEQ ID NO 57
<211> LENGTH: 498
<212> TYPE: DNA
<213> ORGANISM: Staphylococcus sp.

<400> SEQUENCE: 57

```
atgaaaaata aattgatagc aaaatcttta ttaacaatag cggcaattgg tattactaca     60

actacaattg cgtcaacagc agatgcgagc gaaggatacg gtccaagaga aaagaaacca    120

gtgagtatta atcacaatat cgtagagtac aatgatggta cttttaaata tcaatctaga    180

ccaaaattta actcaacacc taaatatatt aaattcaaac atgactataa tattttagaa    240

tttaacgatg gtacattcga atatggtgca cgtccacaat ttaataaacc agcagcgaaa    300

actgatgcaa ctattaaaaa agaacaaaaa ttgattcaag ctcaaaatct tgtgagagaa    360

tttgaaaaaa cacatactgt cagtgcacac agaaaagcac aaaaggcagt caacttagtt    420

tcgtttgaat acaaagtgaa gaaaatggtc ttacaagagc gaattgataa tgtattaaaa    480

caaggattag tgagataa                                                  498
```

<210> SEQ ID NO 58
<211> LENGTH: 960
<212> TYPE: DNA
<213> ORGANISM: Staphylococcus sp.

<400> SEQUENCE: 58

```
atgaaaacac gtatagtcag ctcagtaaca acaacactat tgctaggttc catattaatg     60

aatcctgtcg ctaatgccgc agattctgat attaatatta aaaccggtac tacagatatt    120

ggaagcaata ctacagtaaa aacaggtgat ttagtcactt atgataaaga aaatggcatg    180
```

```
cacaaaaaag tattttatag ttttatcgat gataaaaatc acaataaaaa actgctagtt    240
attagaacga aaggtaccat tgctggtcaa tatagagttt atagcgaaga aggtgctaac    300
aaaagtggtt tagcctggcc ttcagccttt aaggtacagt tgcaactacc tgataatgaa    360
gtagctcaaa tatctgatta ctatccaaga aattcgattg atacaaaaga gtatatgagt    420
actttaactt atggattcaa cggtaatgtt actggtgatg atacaggaaa aattggcggc    480
cttattggtg caaatgtttc gattggtcat acactgaaat atgttcaacc tgatttcaaa    540
acaattttag agagcccaac tgataaaaaa gtaggctgga aagtgatatt taacaatatg    600
gtgaatcaaa attggggacc atatgataga gattcttgga acccggtata tggcaatcaa    660
cttttcatga aaactagaaa tggttctatg aaagcagcag agaacttcct tgatcctaac    720
aaagcaagtt ctctattatc ttcagggttt tcaccagact tcgctacagt tattactatg    780
gatagaaaag catccaaaca acaaacaaat atagatgtaa tatacgaacg agttcgtgat    840
gactaccaat tgcattggac ttcaacaaat tggaaaggta ccaatactaa agataaatgg    900
acagatcgtt cttcagaaag atataaaatc gattgggaaa aagaagaaat gacaaattaa    960
```

<210> SEQ ID NO 59
<211> LENGTH: 1287
<212> TYPE: DNA
<213> ORGANISM: Staphylococcus sp.

<400> SEQUENCE: 59

```
atacacatga aaaataaata tatctcgaag ttgctagttg gggcagcaac aattacttta     60
gctacaatga tttcaaatgg ggaagcaaaa gcgagtgaaa acacgcaaca aacttcaact    120
aagcaccaaa caactcaaaa caactacgta acagatcaac aaaaagcttt ttatcaagta    180
ttacatctaa aaggtatcac agaagaacaa cgtaaccaat acatcaaaac attacgcgaa    240
cacccagaac gtgcacaaga agtattctct gaatcactta aagacagcaa gaacccagac    300
cgacgtgttg cacaacaaaa cgctttttac aatgttctta aaaatgataa cttaactgaa    360
caagaaaaaa ataattacat tgcacaaatt aaagaaaacc ctgatagaag ccaacaagtt    420
tgggtagaat cagtacaatc ttctaaagct aaagaacgtc aaaatattga aaatgcggat    480
aaagcaatta aagatttcca agataacaaa gcaccacacg ataaatcagc agcatatgaa    540
gctaactcaa aattacctaa agatttacgc gataaaaata accgctttgt agaaaaagtt    600
tcaattgaaa aagcaatcgt tcgtcatgat gagcgtgtga aatcagcaaa tgatgcaatc    660
tcaaaattaa atgaaaaaga ttcaattgaa aacagacgtt tagcacaacg tgaagttaac    720
aaagcaccta tggatgtaaa agagcattta cagaaacaat tagacgcatt agtagctcaa    780
aaagatgctg aaaagaaagt ggcgccaaaa gttgaggctc ctcaaattca atcaccacaa    840
attgaaaaac ctaaagcaga atcaccaaaa gttgaagtcc ctcaatctaa attattaggt    900
tactaccaat cattaaaaga ttcatttaac tatggttaca agtatttaac agatacttat    960
aaaagctata aagaaaaata tgatacagca aagtactact ataatacgta ctataaatac   1020
aaaggtgcga ttgatcaaac agtattaaca gtactaggta gtggttctaa atcttacatc   1080
caaccattga aagttgatga taaaaacggc tacttagcta aatcatatgc acaagtaaga   1140
aactatgtaa ctgagtcaat caatactggt aaagtattat atactttcta ccaaaaccca   1200
acattagtaa aaacagctat taaagctcaa gaaactgcat catcaatcaa aaatacatta   1260
agtaatttat tatcattctg gaaataa                                        1287
```

<210> SEQ ID NO 60
<211> LENGTH: 1053
<212> TYPE: DNA
<213> ORGANISM: Staphylococcus sp.

<400> SEQUENCE: 60

```
atgacaaaac attatttaaa cagtaagtat caatcagaac aacgttcatc agctatgaaa      60
aagattacaa tgggtacagc atctatcatt ttaggttccc ttgtatacat aggcgcagac     120
agccaacaag tcaatgcggc aacagaagct acgaacgcaa ctaataatca aagcacacaa     180
gtttctcaag caacatcaca accaattaat ttccaagtgc aaaaagatgg ctcttcagag     240
aagtcacaca tggatgacta tatgcaacac cctggtaaag taattaaaca aaataataaa     300
tattatttcc aaaccgtgtt aaacaatgca tcattctgga aagaatacaa attttacaat     360
gcaaacaatc aagaattagc aacaactgtt gttaacgata ataaaaaagc ggatactaga     420
acaatcaatg ttgcagttga acctggatat aagagcttaa ctactaaagt acatattgtc     480
gtgccacaaa ttaattacaa tcatagatat actacgcatt tggaatttga aaaagcaatt     540
cctacattag ctgacgcagc aaaaccaaac aatgttaaac cggttcaacc aaaaccagct     600
caacctaaaa cacctactga gcaaactaaa ccagttcaac ctaaagttga aaaagttaaa     660
cctactgtaa ctacaacaag caaagttgaa gacaatcact ctactaaagt tgtaagtact     720
gacacaacaa aagatcaaac taaaacacaa actgctcata cagttaaaac agcacaaact     780
gctcaagaac aaaataaagt tcaaacacct gttaaagatg ttgcaacagc gaaatctgaa     840
agcaacaatc aagctgtaag tgataataaa tcacaacaaa ctaacaaagt tacaaaacat     900
aacgaaacgc ctaaacaagc atctaaagct aaagaattac caaaaactgg tttaacttca     960
gttgataact ttattagcac agttgccttc gcaacacttg cccttttagg ttcattatct    1020
ttattacttt tcaaaagaaa agaatctaaa taa                                 1053
```

<210> SEQ ID NO 61
<211> LENGTH: 1938
<212> TYPE: DNA
<213> ORGANISM: Staphylococcus sp.

<400> SEQUENCE: 61

```
atgaacaaac agcaaaaaga atttaaatca ttttattcaa ttagaaagtc atcactaggc      60
gttgcatctg tagcgattag tacacttttta ttattaatgt caaatggcga agcacaagca     120
gcagctgaag aaacaggtgg tacaaataca gaagcacaac caaaaactga agcagttgca     180
agtccaacaa caacatctga aaaagctcca gaaactaaac cagtagctaa tgctgtctca     240
gtatctaata aagaagttga ggcccctact tctgaaacaa aagaagctaa agaagttaaa     300
gaagttaaag cccctaagga aacaaaagca gttaaaccag cagcaaaagc cactaacaat     360
acatatccta ttttgaatca ggaacttaga gaagcgatta aaaaccctgc aataaaagat     420
aaagatcata gcgcaccaaa ctctcgtcca attgattttg aaatgaaaaa agaaaatggt     480
gagcaacaat tttatcatta tgccagctct gttaaacctg ctagagttat tttcactgat     540
tcaaaaccag aaattgaatt aggattacaa tcaggtcaat tttggagaaa atttgaagtt     600
tatgaaggtg acaaaaagtt gccaattaaa ttagtatcat acgatactgt taaagattac     660
gcttacattc gcttctctgt ttcaaatgga acaaaagccg ttaaaattgt aagttcaact     720
cacttcaata acaaagaaga aaaatacgat tacacattaa tggaattcgc acaaccaatt     780
tataacagtg cagataaatt caaaactgaa gaagattata aagctgaaaa attattagcg     840
```

```
ccatataaaa aagcgaaaac actagaaaga caagtttatg aattaaataa aattcaagat    900
aaacttcctg aaaaattaaa ggctgagtac aagaagaaat tagaggatac aaagaaagct    960
ttagatgagc aagtgaaatc agctattact gaattccaaa atgtacaacc aacaaatgaa   1020
aaaatgactg atttacaaga tacaaaatat gttgtttatg aaagtgttga gaataacgaa   1080
tctatgatgg atacttttgt taaacaccct attaaaacag gtatgcttaa cggcaaaaaa   1140
tatatggtca tggaaactac taatgacgat tactggaaag atttcatggt tgaaggtcaa   1200
cgtgttagaa ctataagcaa agatgctaaa aataatacta gaacaattat tttcccatat   1260
gttgaaggta aaactctata tgatgctatc gttaaagttc acgtaaaaac gattgattat   1320
gatggacaat accatgtcag aatcgttgat aaagaagcat ttacaaaagc caataccgat   1380
aaatctaaca aaaaagaaca acaagataac tcagctaaga aggaagctac tccagctacg   1440
cctagcaaac caacaccatc acctgttgaa aaagaatcac aaaaacaaga cagccaaaaa   1500
gatgacaata aacaattacc aagtgttgaa aaagaaaatg acgcatctag tgagtcaggt   1560
aaagacaaaa cgcctgctac aaaaccaact aaaggtgaag tagaatcaag tagtacaact   1620
ccaactaagg tagtatctac gactcaaaat gttgcaaaac caacaactgc ttcatcaaaa   1680
acaacaaaag atgttgttca aacttcagca ggttctagcg aagcaaaaga tagtgctcca   1740
ttacaaaaag caaacattaa aaacacaaat gatggacaca ctcaaagcca aaacaataaa   1800
aatacacaag aaaataaagc aaaatcatta ccacaaactg gtgaagaatc aaataaagat   1860
atgacattac cattaatggc attactagct ttaagtagca tcgttgcatt cgtattacct   1920
agaaaacgta aaaactaa                                                 1938
```

<210> SEQ ID NO 62
<211> LENGTH: 2862
<212> TYPE: DNA
<213> ORGANISM: Staphylococcus sp.

<400> SEQUENCE: 62

```
atgaataata aaaagacagc aacaaataga aaaggcatga taccaaatcg attaaacaaa     60
ttttcgataa gaaagtattc tgtaggtact gcttcaattt tagtagggac aacattgatt    120
tttgggttaa gtggtcatga agctaaagcg gcagaacata cgaatggaga attaaatcaa    180
tcaaaaaatg aaacgacagc cccaagtgag aataaaacaa ctgaaaaagt tgatagtcgt    240
caactaaaag acaatacgca aactgcaact gcagatcagc ctaaagtgac aatgagtgat    300
agtgcaacag ttaaagaaac tagtagtaac atgcaatcac cacaaaacgc tacagctagt    360
caatctacta cacaaactag caatgtaaca acaaatgata aatcatcaac tacatatagt    420
aatgaaactg ataaaagtaa tttaacacaa gcaaaaaacg tttcaactac acctaaaaca    480
acgactatta aacaaagagc tttaaatcgc atggcagtga atactgttgc agctccacaa    540
caaggaacaa atgttaatga taaagtacat tttacgaaca ttgatattgc gattgataaa    600
ggacatgtta ataaaacaac aggaaatact gaattttggg caacttcaag tgatgtttta    660
aaattaaaag cgaattacac aatcgatgat tctgttaaag agggcgatac atttactttt    720
aaatatggtc aatatttccg tccaggttct gtaagattac cttcacaaac tcaaaattta    780
tataatgccc aaggtaatat tattgcaaaa ggtatttacg atagtaaaac aaatacaaca    840
acgtatactt ttacgaatta tgtagatcaa tacacaaatg ttagcggtag ctttgaacaa    900
gtcgcatttg cgaaacgtga aaatgcaaca actgataaaa ctgcttataa aatggaagta    960
```

actttaggta atgatacata tagtaaagat gtcattgtcg attatggtaa tcaaaaaggt 1020
caacaactta tttcgagtac aaattatatt aataatgaag atttgtcacg taatatgact 1080
gtttatgtaa atcaacctaa aaagacctat acaaaagaaa catttgtaac aaatttaact 1140
ggttataaat ttaatccaga tgctaaaaac ttcaaaattt acgaagtgac agatcaaaat 1200
caatttgtgg atagtttcac cccagatact tcaaaactta aagatgttac tggtcaattc 1260
gatgttattt atagtaatga taataagacg gcgacagtag atttattgaa tggtcaatct 1320
agtagtgata aacagtacat cattcaacaa gttgcttatc cagataatag ttcaacagat 1380
aatgggaaaa ttgattatac tttagaaaca caaaatggaa aaagtagttg gtcaaacagt 1440
tattcaaatg tgaatggctc atcaactgca aatggcgacc aaaagaaata taatctaggt 1500
gactatgtat gggaagatac aaataaagat ggtaaacaag atgccaatga aaaagggatt 1560
aaaggtgttt atgtcattct taaagatagt aacggtaaag aattagatcg tacgacaaca 1620
gatgaaaatg gtaaatatca gttcactggt ttaagcaatg gaacttatag tgtagagttt 1680
tcaacaccag ccggttatac accgacaact gcaaatgcag gtacagatga tgctgtagat 1740
tctgatggac taactacaac aggtgtcatt aaagacgctg acaacatgac attagatagt 1800
ggattctaca aaacaccaaa atatagttta ggtgattatg tttggtacga cagtaataaa 1860
gatggtaaac aagattcgac tgaaaaagga attaaaggtg ttaaagttac tttgcaaaac 1920
gaaaaaggcg aagtaattgg tacaactgaa acagatgaaa atggtaaata ccgctttgat 1980
aatttagata gtggtaaata caaagttatc tttgaaaagc ctgctggttt aactcaaaca 2040
ggtacaaata caactgaaga tgataaagat gccgatggtg gcgaagttga tgtaacaatt 2100
acggatcatg atgatttcac acttgataat ggctactacg aagaagaaac atcagatagt 2160
gactcagatt cggacagcga ttcagactca gatagcgact cagattcaga tagtgactca 2220
gactcagata gcgactcaga ctcagatagc gactcagaca gcgactcaga ctcagatagt 2280
gattcagatt cggacagcga ctcagattca gacagcgaat cagattcgga tagcgactca 2340
gactcagata gcgactcaga cagcgactca gattcagaca gtgactcaga ctcagacagc 2400
gactcagatt cagacagcga ttcagattcg gatagcgact cagattcaga tagcgattcg 2460
gactcagaca acgactcaga ttctgacagc gattcagact cagatagcga ctcagattca 2520
gacagcgact cagattcaga cagcgattca gattcagata gcgattcaga ttcagacagc 2580
gactcagatt cagatagcga ctcagactca gacagcgatt cagactcaga tagcgactca 2640
gacagcgatt cagattcgga tagcgattca gattcagatg caggtaaaca tactccgact 2700
aaaccaatga gtacggttaa agatcagcat aaaacagcta aagcattacc agaaacaggt 2760
agtgaaaata ataattcaaa taatggcaca ttattcggtg gattattcgc ggcattagga 2820
tcattattgt tattcggtcg tcgtaaaaaa caaaataaat aa 2862

<210> SEQ ID NO 63
<211> LENGTH: 2808
<212> TYPE: DNA
<213> ORGANISM: Staphylococcus sp.

<400> SEQUENCE: 63
atgaatatga agaaaaaaga aaaacacgca attcggaaaa aatcgattgg cgtggcttca 60
gtgcttgtag gtacgttaat cggttttgga ctactcagca gtaaagaagc agatgcaagt 120
gaaaatagtg ttacgcaatc tgatagcgca agtaacgaaa gcaaaagtaa tgattcaagt 180
agcgttagtg ctgcacctaa aacagacgac acaaacgtga gtgatactaa aacatcgtca 240

-continued

```
aacactaata atggcgaaac gagtgtggcg caaaatccag cacaacagga aacgacacaa    300
tcatcatcaa caaatgcaac tacggaagaa acgccggtaa ctggtgaagc tactactacg    360
acaacgaatc aagctaatac accggcaaca actcaatcaa gcaatacaaa tgcggaggaa    420
ttagtgaatc aaacaagtaa tgaaacgact tctaatgata ctaatacagt atcatctgta    480
aattcacctc aaaattctac aaatgcggaa aatgtttcaa caacgcaaga tacttcaact    540
gaagcaacac cttcaaacaa tgaatcagct ccacagaata cagatgcaag taataaagat    600
gtagttagtc aagcggttaa tccaagtacg cctagaatga gagcatttag tttagcggca    660
gtagctgcag atgcaccggc agctggcaca gatattacga atcagttgac agatgtgaaa    720
gttactattg actctggtac gactgtgtat ccgcaccaag caggttatgt caaactgaat    780
tatggttttt cagtgcctaa ttctgctgtt aaaggtgaca cattcaaaat aactgtacct    840
aaagaattaa acttaaatgg tgtaacttca actgctaaag tgccaccaat tatggctgga    900
gatcaagtat tggcaaatgg tgtaatcgat agtgatggta atgttattta tacatttaca    960
gactatgttg ataataaaga aaatgtaaca gctaatatta ctatgccagc ttatattgac   1020
cctgaaaatg ttacaaagac aggtaatgtg acattgacaa ctggcatagg aaccaatact   1080
gctagtaaga cagtattaat cgactatgag aaatatggac aattccataa tttatcaatt   1140
aaaggtacga ttgatcaaat cgataaaaca aataatacgt atcgccaaac aatttatgtc   1200
aatccaagcg gagataacgt tgtgttacct gccttaacag gtaatttaat tcctaataca   1260
aagagtaatg cgttaataga tgcaaaaaac actgatatta aagtttatag agtcgataat   1320
gctaatgatt tatctgaaag ttattatgtg aatcctagcg attttgaaga tgtaactaat   1380
caagttagaa tttcatttcc aaatgctaat caatacaaag tagaatttcc tacggacgat   1440
gaccaaatta caacaccgta tattgtagtt gttaatggcc atattgatcc tgctagtaca   1500
ggtgatttag cactacgttc gacattttat ggttatgatt ctaattttat atggagatct   1560
atgtcatggg acaacgaagt agcatttaat aacggatcag gttctggtga cggtatcgat   1620
aaaccagttg ttcctgaaca acctgatgag cctggtgaaa ttgaaccaat tccagaggat   1680
tcagattctg acccaggttc agattctggc agcgattcta attcagatag cggttcagat   1740
tctggcagtg attctacatc agatagtggt tcagattcag cgagtgattc agattcagca   1800
agtgattcag actcagcgag tgattcagat tcagcaagtg attcagattc agcaagtgat   1860
tcagattcag caagtgattc agactcagca agtgattcag attcagcaag tgattcagat   1920
tcagcaagcg attcagattc agcgagcgat tcagattcag cgagcgattc agattcagcg   1980
agtgattccg actcagcgag cgattcagac tcagatagtg actcagattc cgatagcgat   2040
tccgactcag atagcgactc agattcagac agcgattctg actcagacag cgattctgac   2100
tcagacagtg actcagattc cgatagcgat tctgactcag acagtgactc agattccgat   2160
agcgattcag attcagacag tgattcagac tcagatagcg attcagattc cgacagtgac   2220
tcagactcag acagcgattc agattccgat agcgattcag attccgacag tgactcagat   2280
tccgatagtg actcggattc agcgagtgat tcagattcag atagcgattc agaatcagat   2340
agtgactcag actcagacag tgattcagat tcagatagtg actcagactc agacagcgat   2400
tcagaatcag atagtgactc cgattcagac agcgattcag aatcagatag tgactccgat   2460
tcagatagcg attcggattc agcgagtgat tcagactcag gtagtgactc cgattcatca   2520
agtgattcag attccgattc aacgagtgac acaggatcag acaacgactc agacagtgat   2580
```

-continued

```
tcaaatagcg attccgagtc aggttctaac aataatgtag ttccgcctaa ttcacctaaa   2640

aatggtacta atgcttctaa taaaaatgag gctaaagata gtaaagaacc attaccagat   2700

acaggttctg aagatgaagc gaatacgtca ctaatttggg gattattagc atcattaggt   2760

tcattactac ttttcagaag aaaaaaagaa aataaagata agaaataa                2808
```

<210> SEQ ID NO 64
<211> LENGTH: 3117
<212> TYPE: DNA
<213> ORGANISM: Staphylococcus sp.

<400> SEQUENCE: 64

```
gtgaaaaaca atcttaggta cggcattaga aaacataaat tgggagcagc atcagtattc     60

ttaggaacaa tgatcgttgt tgggatggga caagataaag aagctgcagc atcagaacaa    120

aagacaacta cagtagaaga aaatgggaat tcagctactg ataataaaac aagtgaaaca    180

caaacaactg ctactaacgt taatcatata gaagaaactc aatcatataa cgcaacagta    240

acagaacaac cgtcaaacgc aacacaagta acaactgaag aagcaccaaa agcagtacaa    300

gcaccacaaa ctgcacaacc agcaaatgta gaaacagtta aagaagaaga gaaacctcaa    360

gttaaggaaa cgacacaacc tcaagacaat agcggaaatc aaagacaagt agatttaaca    420

cctaaaaagg ttacacaaaa tcaagggaca gaaacacaag ttgaagtggc acagccaaga    480

acggcatcag aaagtaagcc acgtgtgaca agatcagcag atgtagcgga agctaaggaa    540

gctagtgacg tttcagaagt taaaggcaca gatgttacaa gtaaagttac agtagaaagt    600

ggttctattg aggcacctca aggaaataaa gtagagccac atgctggtca acgtgtcgta    660

ttgaaataca aattgaaatt cgcagatgga ttaaaaagag gagattattt tgattttaca    720

ttatcaaata atgtaaatac ttatggggtt tcaacagcta gaaaggtacc agagattaaa    780

aatggctcag ttgtaatggc tacaggtgag atcttaggga atggtaacat aagatataca    840

tttactaacg aaattgaaca caaggtagag gtaacagcta atttagaaat caacttattt    900

attgacccta aaactgtaca aagcaatgga gaacaaaaga ttacttctaa attaaatggt    960

gaagaaacag aaaaaacaat accagttgtt tataatccag gtgttagcaa tagttataca   1020

aatgtaaatg gatcaattga aacatttaat aaagaatcta ataaatttac acatatagct   1080

tatattaagc caatgaatgg aaaccagtca aacactgtat cagtaacagg gacgttgact   1140

gaaggtagta atttagctgg tggacaacct actgttaaag tatatgaata tctagggaaa   1200

aaagatgaat tgccacaaag tgtttatgca aatacatcag atactaacaa attcaaagat   1260

gtaacaaagg aaatgaatgg aaaattgagt gtgcaagaca atggtagtta ctcattgaat   1320

ttagataagt tggataaaac gtatgtcatt cattatacag gtgaatattt gcaagggtca   1380

gatcaggtta attttagaac tgaattatat gggtatccag aacgagcata taaatcttac   1440

tatgtttatg gggatatcg tttaacttgg gataatggtt tagttttata tagcaataaa   1500

gctgacggca atggtaaaaa tggacaaatt attcaagata atgattttga atataaagaa   1560

gatactgcaa aggaactat gagcgggcag tacgatgcca agcaaattat tgaaacagaa   1620

gaaaatcaag acaatacacc gcttgacatt gattaccaca cagctataga tggtgagggt   1680

ggttatgttg atgggtatat tgaaacaata gaagaaacgg attcatcagc tattgatatc   1740

gattaccata ctgctgtgga tagtgaagtg ggtcacgttg gaggatacac tgagtcctct   1800

gaggaatcaa atccaattga ctttgaagaa tcgacacatg aaaattcaaa acatcacgct   1860

gatgttgttg aatatgaaga ggatacaaat ccaggtggtg gccaagtaac aactgagtct   1920
```

aacttagttg aatttgacga agagtctaca aaaggtattg taactggcgc agtgagcgac 1980
catacaacaa ttgaagatac gaaagaatat acgactgaaa gtaatctgat tgaactagta 2040
gatgaactac ctgaagaaca tggtcaagca caaggaccaa tcgaggaaat tactgaaaac 2100
aatcatcata tttctcattc tggtttagga actgaaaatg gtcacggtaa ttatggcgtg 2160
attgaagaaa tcgaagaaaa tagccacgtt gatattaaga gtgaattagg ttacgaaggt 2220
ggccaaaata gcggtaacca gtcattcgag gaagacacag aagaagacaa acctaaatat 2280
gaacaaggtg gcaatatcgt agatatcgat ttcgacagtg tacctcaaat tcatggtcaa 2340
aataaaggtg accagtcatt cgaagaagat acagagaaag acaagcctaa atatgaacat 2400
ggcggtaata tcattgatat cgacttcgac agtgtgccac aaattcatgg attcaataag 2460
cataatgaaa ttattgaaga agatacaaac aaagataaac ctaattatca attcggtgga 2520
cacaatagtg ttgactttga agaagataca cttccaaaag taagcggcca aaatgaaggt 2580
caacaaacga ttgaagaaga tacaacgccg ccaacgccac cgacaccaga agtaccgagt 2640
gagccggaaa caccaatgcc accgacacca gaagtaccga gtgagccgga aacaccaacg 2700
ccaccaacac cagaggtacc aagtgagccg gaaacaccaa caccaccgac tccggaagta 2760
ccaagtgagc cggaaacacc aacaccaccg acaccagaag tgccgagtga gccagaaaca 2820
ccaacaccgc caacaccaga ggtaccagct gaacctggta aaccagtacc acccgcaaaa 2880
gaagaaccta aaaagccttc taaaccagtg gaacaaggta aagtagtaac acctgttatt 2940
gaaatcaatg aaaaggttaa agcagtggca ccaactaaaa aagcacaatc taagaaatct 3000
gaactacctg aaacaggtgg agaagaatca acaaacaaag gtatgttgtt cggcggatta 3060
ttcagcattc taggtttagc attattacgc agaaataaaa agaataacaa agcataa 3117

<210> SEQ ID NO 65
<211> LENGTH: 2634
<212> TYPE: DNA
<213> ORGANISM: Staphylococcus sp.

<400> SEQUENCE: 65
ttgaaaaaaa gaattgatta tttgtcgaat aagcagaata agtattcgat tagacgtttt 60
acagtaggta ccacatcagt aatagtaggg gcaactatac tatttgggat aggcaatcat 120
caagcacaag cttcagaaca atcgaacgat acaacgcaat cttcgaaaaa taatgcaagt 180
gcagattccg aaaaaaacaa tatgatagaa acacctcaat taaatacaac ggctaatgat 240
acatctgata ttagtgcaaa cacaaacagt gcgaatgtag atagcacaac aaaaccaatg 300
tctacacaaa cgagcaatac cactacaaca gagccagctt caacaaatga aacacctcaa 360
ccgacggcaa ttaaaaatca agcaactgct gcaaaaaatgc aagatcaaac tgttcctcaa 420
gaagcaaatt ctcaagtaga taataaaaca acgaatgatg ctaatagcat agcaacaaac 480
agtgagctta aaaattctca aacattagat ttaccacaat catcaccaca aacgatttcc 540
aatgcgcaag gaactagtaa accaagtgtt agaacgagag ctgtacgtag tttagctgtt 600
gctgaaccgg tagtaaatgc tgctgatgct aaaggtacaa atgtaaatga taaagttacg 660
gcaagtaatt tcaagttaga aaagactaca tttgacccta atcaaagtgg taacacattt 720
atggcggcaa attttacagt gacagataaa gtgaaatcag gggattattt tacagcgaag 780
ttaccagata gtttaactgg taatggagac gtggattatt ctaattcaaa taatacgatg 840
ccaattgcag acattaaaag tacgaatggc gatgttgtag ctaaagcaac atatgatatc 900

```
ttgactaaga cgtatacatt tgtctttaca gattatgtaa ataataaaga aaatattaac    960

ggacaatttt cattaccttt atttacagac cgagcaaagg cacctaaatc aggaacatat   1020

gatgcgaata ttaatattgc ggatgaaatg tttaataata aaattactta taactatagt   1080

tcgccaattg caggaattga taaaccaaat ggcgcgaaca tttcttctca aattattggt   1140

gtagatacag cttcaggtca aaacacatac aagcaaacag tatttgttaa ccctaagcaa   1200

cgagttttag gtaatacgtg ggtgtatatt aaaggctacc aagataaaat cgaagaaagt   1260

agcggtaaag taagtgctac agatacaaaa ctgagaattt ttgaagtgaa tgatacatct   1320

aaattatcag atagctacta tgcagatcca aatgactcta accttaaaga agtaacagac   1380

caatttaaaa atagaatcta ttatgagcat ccaaatgtag ctagtattaa atttggtgat   1440

attactaaaa catatgtagt attagtagaa gggcattacg acaatacagg taagaactta   1500

aaaactcagg ttattcaaga aaatgttgat cctgtaacaa atagagacta cagtattttc   1560

ggttggaata atgagaatgt tgtacgttat ggtggtggaa gtgctgatgg tgattcagca   1620

gtaaatccga aagacccaac tccagggccg ccggttgacc cagaaccaag tccagaccca   1680

gaaccagaac caacgccaga tccagaacca agtccagacc cagaaccgga accaagccca   1740

gacccggatc cggattcgga ttcagacagt gactcaggct cagacagcga ctcaggttca   1800

gatagcgact cagaatcaga tagcgattcg gattcagaca gtgattcaga ttcagacagc   1860

gactcagaat cagatagcga ttcagaatca gatagcgact cagattcaga tagcgattca   1920

gattcagata gcgattcaga atcagatagc gattcggatt cagacagtga ttcagattca   1980

gacagcgact cagaatcaga tagcgactca gaatcagata gtgagtcaga ttcagacagt   2040

gactcggact cagacagtga ttcagactca gatagcgatt cagactcaga tagcgattca   2100

gactcagaca gcgattcaga ttcagacagc gactcagaat cagacagcga ctcagactca   2160

gatagcgact cagactcaga cagcgactca gattcagata gcgattcaga ctcagacagc   2220

gactcagact cagacagcga ctcagactca gatagcgatt cagactcaga cagcgactca   2280

gattcagata gcgattcgga ctcagacagc gattcagatt cagacagcga ctcagactcg   2340

gatagcgatt cagattcaga cagcgactca gactcggata gcgactcgga ttcagatagt   2400

gactccgatt caagagttac accaccaaat aatgaacaga aagcaccatc aaatcctaaa   2460

ggtgaagtaa accattctaa taaggtatca aaacaacaca aaactgatgc tttaccagaa   2520

acaggagata agagcgaaaa cacaaatgca actttatttg gtgcaatgat ggcattatta   2580

ggatcattac tattgtttag aaaacgcaag caagatcata aagaaaaagc gtaa         2634
```

<210> SEQ ID NO 66
<211> LENGTH: 1977
<212> TYPE: DNA
<213> ORGANISM: Staphylococcus sp.

<400> SEQUENCE: 66

```
atgaaaaagc aaataatttc gctaggcgca ttagcagttg catctagctt atttacatgg     60

gataacaaag cagatgcgat agtaacaaag gattatagta aagaatcaag agtgaatgag    120

aaaagtaaaa agggagctac tgtttcagat tattactatt ggaaaataat tgatagttta    180

gaggcacaat ttactggagc aatagactta ttggaagatt ataaatatgg agatcctatc    240

tataaagaag cgaaagatag attgatgaca agagtattag gagaagacca gtatttatta    300

aagaaaaaga ttgatgaata tgagctttat aaaaagtggt ataaaagttc aaataagaac    360

actaatatgc ttactttcca taaatataat ctttacaatt taacaatgaa tgaatataac    420
```

```
gatattttta actctttgaa agatgcagtt tatcaattta ataaagaagt taaagaaata    480

gagcataaaa atgttgactt gaagcagttt gataaagatg gagaagacaa ggcaactaaa    540

gaagtttatg accttgtttc tgaaattgat acattagttg taacttatta tgctgataag    600

gattatgggg agcatgcgaa agagttacga gcaaaactgg acttaatcct tggagataca    660

gacaatccac ataaaattac aaatgagcgt ataaaaaaag aaatgatcga tgacttaaat    720

tcaattatag atgatttctt tatggagact aaacaaaata gaccgaattc tataacaaaa    780

tatgatccaa caaaacacaa ttttaaagag aagagtgaaa ataaacctaa ttttgataaa    840

ttagttgaag aaacaaaaaa agcagttaaa gaagcagacg aatcttggaa aaataaaact    900

gtcaaaaaat acgaggaaac tgtaacaaaa tctcctgttg taaaagaaga gaagaaagtt    960

gaagaacctc aattacctaa agttggaaac cagcaagagg ttaaaactac ggctggtaaa   1020

gctgaagaaa caacacaacc agtggcacag ccattagtaa aaattccaca agaaacaatc   1080

tatggtgaaa ctgtaaaagg tccagaatat ccaacgatgg aaaataaaac gttacaaggt   1140

gaaatcgttc aaggtcccga ttttctaaca atggaacaaa acagaccatc tttaagcgat   1200

aattatactc aaccgacgac accgaaccct attttagaag gtcttgaagg tagctcatct   1260

aaacttgaaa taaaaccaca aggtactgaa tcaacgttga aaggtattca aggagaatca   1320

agtgatattg aagttaaacc tcaagcaact gaaacaacag aagcttctca atatggtccg   1380

agaccgcaat ttaacaaaac acctaagtat gtgaaatata gagatgctgg tacaggtatc   1440

cgtgaataca acgatggaac atttggatat gaagcgagac caagattcaa caagccaagt   1500

gaaacaaatg catacaacgt aacgacaaat caagatggca cagtatcata cggagctcgc   1560

ccaacacaaa acaagccaag tgaaacaaac gcatataacg taacaacaca tgcaaatggt   1620

caagtatcat acggtgctcg cccaacacaa aaaaagccaa gcaaaacaaa tgcatacaac   1680

gtaacaacac atgcaaatgg tcaagtatca tatggcgctc gcccgacaca aaaaaagcca   1740

agcaaaacaa atgcatataa cgtaacaaca catgcaaatg gtcaagtatc atacggagct   1800

cgcccgacat acaagaagcc aagcgaaaca aatgcataca acgtaacaac acatgcaaat   1860

ggtcaagtat catatggcgc tcgcccgaca caaaaaaagc caagcgaaac aaacgcatat   1920

aacgtaacaa cacatgcaga tggtactgcg acatatgggc ctagagtaac aaaataa       1977
```

<210> SEQ ID NO 67
<211> LENGTH: 961
<212> TYPE: PRT
<213> ORGANISM: Staphylococcus sp.

<400> SEQUENCE: 67

```
Met Lys Ser Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Glu
            20                  25                  30

Lys Glu Ala Ala Ala Ser Glu Gln Asn Asn Thr Thr Val Glu Glu Ser
        35                  40                  45

Gly Ser Ser Ala Thr Glu Ser Lys Ala Ser Glu Thr Gln Thr Thr Thr
    50                  55                  60

Asn Asn Val Asn Thr Ile Asp Glu Thr Gln Ser Tyr Ser Ala Thr Ser
65                  70                  75                  80

Thr Glu Gln Pro Ser Lys Ser Thr Gln Val Thr Thr Glu Glu Ala Pro
                85                  90                  95
```

-continued

```
Thr Thr Val Gln Ala Pro Lys Val Glu Thr Glu Met Lys Ser Gln Glu
            100                 105                 110

Asp Leu Pro Ser Glu Lys Val Ala Asp Lys Glu Thr Thr Gly Thr Gln
        115                 120                 125

Val Asp Ile Ala Gln Pro Ser Asn Val Ser Glu Ile Lys Pro Arg Met
    130                 135                 140

Lys Arg Ser Ala Asp Val Thr Ala Val Ser Glu Lys Glu Val Ala Glu
145                 150                 155                 160

Glu Ala Lys Ala Thr Gly Thr Asp Val Thr Asn Lys Val Glu Val Thr
                165                 170                 175

Glu Ser Ser Leu Glu Gly His Asn Lys Asp Ser Asn Ile Val Asn Pro
            180                 185                 190

His Asn Ala Gln Arg Val Thr Leu Lys Tyr Lys Trp Lys Phe Gly Glu
        195                 200                 205

Gly Ile Lys Ala Gly Asp Tyr Phe Asp Phe Thr Leu Ser Asp Asn Val
    210                 215                 220

Glu Thr His Gly Ile Ser Thr Leu Arg Lys Val Pro Glu Ile Lys Ser
225                 230                 235                 240

Ser Thr Glu Asp Lys Val Met Ala Asn Gly Gln Val Ile Asn Glu Arg
                245                 250                 255

Thr Ile Arg Tyr Thr Phe Thr Asp Tyr Ile Asn Asn Lys Lys Asp Leu
            260                 265                 270

Thr Ala Glu Leu Asn Leu Asn Leu Phe Ile Asp Pro Thr Thr Val Thr
        275                 280                 285

Lys Gln Gly Ser Gln Lys Val Glu Val Thr Leu Gly Gln Asn Lys Val
    290                 295                 300

Ser Lys Glu Phe Asp Ile Lys Tyr Leu Asp Gly Val Lys Asp Arg Met
305                 310                 315                 320

Gly Val Thr Val Asn Gly Arg Ile Asp Thr Leu Asn Lys Glu Glu Gly
                325                 330                 335

Lys Phe Ser His Phe Ala Tyr Val Lys Pro Asn Asn Gln Ser Leu Thr
            340                 345                 350

Ser Val Thr Val Thr Gly Gln Val Thr Ser Gly Tyr Lys Gln Ser Ala
        355                 360                 365

Asn Asn Pro Thr Val Lys Val Tyr Lys His Ile Gly Ser Asp Glu Leu
    370                 375                 380

Ala Glu Ser Val Tyr Ala Lys Leu Asp Asp Thr Ser Lys Phe Glu Asp
385                 390                 395                 400

Val Thr Glu Lys Val Asn Leu Ser Tyr Thr Ser Asn Gly Gly Tyr Thr
                405                 410                 415

Leu Asn Leu Gly Asp Leu Asp Asn Ser Lys Asp Tyr Val Ile Lys Tyr
            420                 425                 430

Glu Gly Glu Tyr Asp Gln Asn Ala Lys Asp Leu Asn Phe Arg Thr His
        435                 440                 445

Leu Ser Gly Tyr His Lys Tyr Tyr Pro Tyr Tyr Pro Tyr Tyr Pro Tyr
    450                 455                 460

Tyr Pro Val Gln Leu Thr Trp Asn Asn Gly Val Ala Phe Tyr Ser Asn
465                 470                 475                 480

Asn Ala Lys Gly Asp Gly Lys Asp Lys Pro Asn Asp Pro Ile Ile Glu
                485                 490                 495

Lys Ser Glu Pro Ile Asp Leu Asp Ile Lys Ser Glu Pro Pro Val Glu
            500                 505                 510

Lys His Glu Leu Thr Gly Thr Ile Glu Glu Ser Asn Asp Ser Lys Pro
```

```
        515                 520                 525

Ile Asp Phe Glu Tyr His Thr Ala Val Glu Gly Ala Glu Gly His Ala
    530                 535                 540

Glu Gly Ile Ile Glu Thr Glu Glu Asp Ser Ile His Val Asp Phe Glu
545                 550                 555                 560

Glu Ser Thr His Glu Asn Ser Lys His His Ala Asp Val Val Glu Tyr
                565                 570                 575

Glu Glu Asp Thr Asn Pro Gly Gly Gly Gln Val Thr Thr Glu Ser Asn
            580                 585                 590

Leu Val Glu Phe Asp Glu Glu Ser Thr Lys Gly Ile Val Thr Gly Ala
        595                 600                 605

Val Ser Asp His Thr Thr Val Glu Asp Thr Lys Glu Tyr Thr Thr Glu
    610                 615                 620

Ser Asn Leu Ile Glu Leu Val Asp Glu Leu Pro Glu Glu His Gly Gln
625                 630                 635                 640

Ala Gln Gly Pro Ile Glu Glu Ile Thr Glu Asn Asn His His Ile Ser
                645                 650                 655

His Ser Gly Leu Gly Thr Glu Asn Gly His Gly Asn Tyr Gly Val Ile
            660                 665                 670

Asp Glu Ile Glu Glu Asn Ser His Val Asp Ile Lys Ser Glu Leu Gly
        675                 680                 685

Tyr Glu Gly Gly Gln Asn Ser Gly Asn Gln Ser Phe Glu Glu Asp Thr
    690                 695                 700

Glu Glu Asp Lys Pro Lys Tyr Glu Gln Gly Gly Asn Ile Val Asp Ile
705                 710                 715                 720

Asp Phe Asp Ser Val Pro Gln Ile His Gly Gln Asn Asn Gly Asn Gln
                725                 730                 735

Ser Phe Glu Glu Asp Thr Glu Glu Asp Lys Pro Lys Tyr Glu Gln Gly
            740                 745                 750

Gly Asn Ile Ile Asp Ile Asp Phe Asp Ser Val Pro Gln Ile His Gly
        755                 760                 765

Phe Asn Lys His Asn Glu Ile Ile Glu Glu Asp Thr Asn Lys Asp Lys
    770                 775                 780

Pro Asn Tyr Gln Phe Gly Gly His Asn Ser Val Asp Phe Glu Glu Asp
785                 790                 795                 800

Thr Leu Pro Lys Val Ser Gly Gln Asn Glu Gly Gln Gln Thr Ile Glu
                805                 810                 815

Glu Asp Thr Thr Pro Pro Thr Pro Pro Thr Pro Glu Val Pro Ser Glu
            820                 825                 830

Pro Glu Thr Pro Thr Pro Pro Thr Pro Glu Val Pro Ser Glu Pro Gly
        835                 840                 845

Glu Pro Thr Pro Pro Lys Pro Glu Val Pro Ser Glu Pro Glu Thr Pro
    850                 855                 860

Val Pro Pro Thr Pro Glu Val Pro Ser Glu Pro Gly Lys Pro Val Pro
865                 870                 875                 880

Pro Ala Lys Glu Glu Pro Lys Lys Pro Ser Lys Pro Val Glu Gln Gly
                885                 890                 895

Lys Val Val Thr Pro Val Ile Glu Ile Asn Glu Lys Val Lys Ala Val
            900                 905                 910

Ala Pro Thr Lys Gln Lys Gln Ser Lys Lys Ser Glu Leu Pro Glu Thr
        915                 920                 925

Gly Gly Glu Glu Ser Thr Asn Lys Gly Met Leu Phe Gly Gly Leu Phe
    930                 935                 940
```

Ser Ile Leu Gly Leu Val Leu Leu Arg Arg Asn Lys Lys Asn Asn Lys
945 950 955 960

Ala

<210> SEQ ID NO 68
<211> LENGTH: 578
<212> TYPE: PRT
<213> ORGANISM: Staphylococcus sp.

<400> SEQUENCE: 68

Met Lys Phe Lys Ser Leu Ile Thr Thr Thr Leu Ala Leu Gly Val Ile
1 5 10 15

Ala Ser Thr Gly Ala Asn Phe Asn Thr Asn Glu Ala Ser Ala Ala Ala
20 25 30

Lys Pro Leu Asp Lys Ser Ser Ser Thr Leu His His Gly His Ser Asn
35 40 45

Ile Gln Ile Pro Tyr Thr Ile Thr Val Asn Gly Thr Ser Gln Asn Ile
50 55 60

Leu Ser Ser Leu Thr Phe Asn Lys Asn Gln Asn Ile Ser Tyr Lys Asp
65 70 75 80

Ile Glu Asn Lys Val Lys Ser Val Leu Tyr Phe Asn Arg Gly Ile Ser
85 90 95

Asp Ile Asp Leu Arg Leu Ser Lys Gln Ala Glu Tyr Thr Val His Phe
100 105 110

Lys Asn Gly Thr Lys Arg Val Ile Asp Leu Lys Ser Gly Ile Tyr Thr
115 120 125

Ala Asp Leu Ile Asn Thr Ser Asp Ile Lys Ala Ile Ser Val Asn Val
130 135 140

Asp Thr Lys Lys Gln Pro Lys Asp Lys Ala Lys Ala Asn Val Gln Val
145 150 155 160

Pro Tyr Thr Ile Thr Val Asn Gly Thr Ser Gln Asn Ile Leu Ser Asn
165 170 175

Leu Thr Phe Asn Lys Asn Gln Asn Ile Ser Tyr Lys Asp Leu Glu Gly
180 185 190

Lys Val Lys Ser Val Leu Glu Ser Asn Arg Gly Ile Thr Asp Val Asp
195 200 205

Leu Arg Leu Ser Lys Gln Ala Lys Tyr Thr Val Asn Phe Lys Asn Gly
210 215 220

Thr Lys Lys Val Ile Asp Leu Lys Ser Gly Ile Tyr Thr Ala Asn Leu
225 230 235 240

Ile Asn Ser Ser Asp Ile Lys Ser Ile Asn Ile Asn Val Asp Thr Lys
245 250 255

Lys His Ile Glu Asn Lys Ala Lys Arg Asn Tyr Gln Val Pro Tyr Ser
260 265 270

Ile Asn Leu Asn Gly Thr Ser Thr Asn Ile Leu Ser Asn Leu Ser Phe
275 280 285

Ser Asn Lys Pro Trp Thr Asn Tyr Lys Asn Leu Thr Ser Gln Ile Lys
290 295 300

Ser Val Leu Lys His Asp Arg Gly Ile Ser Glu Gln Asp Leu Lys Tyr
305 310 315 320

Ala Lys Lys Ala Tyr Tyr Thr Val Tyr Phe Lys Asn Gly Gly Lys Arg
325 330 335

Ile Leu Gln Leu Asn Ser Lys Asn Tyr Thr Ala Asn Leu Val His Ala
340 345 350

Lys Asp Val Lys Arg Ile Glu Ile Thr Val Lys Thr Gly Thr Lys Ala
355 360 365

Lys Ala Asp Arg Tyr Val Pro Tyr Thr Ile Ala Val Asn Gly Thr Ser
370 375 380

Thr Pro Ile Leu Ser Lys Leu Lys Ile Ser Asn Lys Gln Leu Ile Ser
385 390 395 400

Tyr Lys Tyr Leu Asn Asp Lys Val Lys Ser Val Leu Lys Ser Glu Arg
405 410 415

Gly Ile Ser Asp Leu Asp Leu Lys Phe Ala Lys Gln Ala Lys Tyr Thr
420 425 430

Val Tyr Phe Lys Asn Gly Lys Lys Gln Val Val Asn Leu Lys Ser Asp
435 440 445

Ile Phe Thr Pro Asn Leu Phe Ser Ala Lys Asp Ile Lys Lys Ile Asp
450 455 460

Ile Asp Val Lys Gln Tyr Thr Lys Ser Lys Lys Lys Ile Asn Lys Ser
465 470 475 480

Asn Asn Val Lys Phe Pro Val Thr Ile Asn Lys Phe Glu Asn Ile Val
485 490 495

Ser Asn Glu Phe Val Phe Tyr Asn Ala Ser Lys Ile Thr Ile Asn Asp
500 505 510

Leu Ser Ile Lys Leu Lys Ser Ala Met Ala Asn Asp Gln Gly Ile Thr
515 520 525

Lys His Asp Ile Gly Leu Ala Glu Arg Ala Val Tyr Lys Val Tyr Phe
530 535 540

Lys Asn Gly Ser Ser Lys Tyr Val Asp Leu Lys Thr Glu Tyr Lys Asp
545 550 555 560

Glu Arg Val Phe Lys Ala Thr Asp Ile Lys Lys Val Asp Ile Glu Leu
565 570 575

Lys Phe

<210> SEQ ID NO 69
<211> LENGTH: 995
<212> TYPE: PRT
<213> ORGANISM: Staphylococcus sp.

<400> SEQUENCE: 69

Met Asn Asn Lys Lys Thr Ala Thr Asn Arg Lys Gly Met Ile Pro Asn
1 5 10 15

Arg Leu Asn Lys Phe Ser Ile Arg Lys Tyr Ser Val Gly Thr Ala Ser
20 25 30

Ile Leu Val Gly Thr Thr Leu Ile Phe Gly Leu Ser Gly His Glu Ala
35 40 45

Lys Ala Ala Glu His Thr Asn Gly Glu Leu Asn Gln Ser Lys Asn Glu
50 55 60

Thr Thr Ala Pro Ser Glu Asn Lys Thr Thr Lys Lys Val Asp Ser Arg
65 70 75 80

Gln Leu Lys Asp Asn Thr Gln Thr Ala Thr Ala Asp Gln Pro Lys Val
85 90 95

Thr Met Ser Asp Ser Ala Thr Val Lys Glu Thr Ser Ser Asn Met Gln
100 105 110

Ser Pro Gln Asn Ala Thr Ala Asn Gln Ser Thr Thr Lys Thr Ser Asn
115 120 125

Val Thr Thr Asn Asp Lys Ser Ser Thr Thr Tyr Ser Asn Glu Thr Asp
130 135 140

```
Lys Ser Asn Leu Thr Gln Ala Lys Asp Val Ser Thr Thr Pro Lys Thr
145                 150                 155                 160

Thr Thr Ile Lys Pro Arg Thr Leu Asn Arg Met Ala Val Asn Thr Val
                165                 170                 175

Ala Ala Pro Gln Gln Gly Thr Asn Val Asn Asp Lys Val His Phe Ser
            180                 185                 190

Asn Ile Asp Ile Ala Ile Asp Lys Gly His Val Asn Gln Thr Thr Gly
        195                 200                 205

Lys Thr Glu Phe Trp Ala Thr Ser Ser Asp Val Leu Lys Leu Lys Ala
    210                 215                 220

Asn Tyr Thr Ile Asp Asp Ser Val Lys Glu Gly Asp Thr Phe Thr Phe
225                 230                 235                 240

Lys Tyr Gly Gln Tyr Phe Arg Pro Gly Ser Val Arg Leu Pro Ser Gln
                245                 250                 255

Thr Gln Asn Leu Tyr Asn Ala Gln Gly Asn Ile Ile Ala Lys Gly Ile
            260                 265                 270

Tyr Asp Ser Thr Thr Asn Thr Thr Thr Tyr Thr Phe Thr Asn Tyr Val
        275                 280                 285

Asp Gln Tyr Thr Asn Val Arg Gly Ser Phe Glu Gln Val Ala Phe Ala
    290                 295                 300

Lys Arg Lys Asn Ala Thr Thr Asp Lys Thr Ala Tyr Lys Met Glu Val
305                 310                 315                 320

Thr Leu Gly Asn Asp Thr Tyr Ser Glu Glu Ile Ile Val Asp Tyr Gly
                325                 330                 335

Asn Lys Lys Ala Gln Pro Leu Ile Ser Ser Thr Asn Tyr Ile Asn Asn
            340                 345                 350

Glu Asp Leu Ser Arg Asn Met Thr Ala Tyr Val Asn Gln Pro Lys Asn
        355                 360                 365

Thr Tyr Thr Lys Gln Thr Phe Val Thr Asn Leu Thr Gly Tyr Lys Phe
    370                 375                 380

Asn Pro Asn Ala Lys Asn Phe Lys Ile Tyr Glu Val Thr Asp Gln Asn
385                 390                 395                 400

Gln Phe Val Asp Ser Phe Thr Pro Asp Thr Ser Lys Leu Lys Asp Val
                405                 410                 415

Thr Asp Gln Phe Asp Val Ile Tyr Ser Asn Asp Asn Lys Thr Ala Thr
            420                 425                 430

Val Asp Leu Met Lys Gly Gln Thr Ser Ser Asn Lys Gln Tyr Ile Ile
        435                 440                 445

Gln Gln Val Ala Tyr Pro Asp Asn Ser Ser Thr Asp Asn Gly Lys Ile
    450                 455                 460

Asp Tyr Thr Leu Asp Thr Asp Lys Thr Lys Tyr Ser Trp Ser Asn Ser
465                 470                 475                 480

Tyr Ser Asn Val Asn Gly Ser Ser Thr Ala Asn Gly Asp Gln Lys Lys
                485                 490                 495

Tyr Asn Leu Gly Asp Tyr Val Trp Glu Asp Thr Asn Lys Asp Gly Lys
            500                 505                 510

Gln Asp Ala Asn Glu Lys Gly Ile Lys Gly Val Tyr Val Ile Leu Lys
        515                 520                 525

Asp Ser Asn Gly Lys Glu Leu Asp Arg Thr Thr Thr Asp Glu Asn Gly
    530                 535                 540

Lys Tyr Gln Phe Thr Gly Leu Ser Asn Gly Thr Tyr Ser Val Glu Phe
545                 550                 555                 560
```

```
Ser Thr Pro Ala Gly Tyr Thr Pro Thr Thr Ala Asn Val Gly Thr Asp
                565                 570                 575

Asp Ala Val Asp Ser Asp Gly Leu Thr Thr Thr Gly Val Ile Lys Asp
            580                 585                 590

Ala Asp Asn Met Thr Leu Asp Ser Gly Phe Tyr Lys Thr Pro Lys Tyr
        595                 600                 605

Ser Leu Gly Asp Tyr Val Trp Tyr Asp Ser Asn Lys Asp Gly Lys Gln
    610                 615                 620

Asp Ser Thr Glu Lys Gly Ile Lys Gly Val Lys Val Thr Leu Gln Asn
625                 630                 635                 640

Glu Lys Gly Glu Val Ile Gly Thr Thr Glu Thr Asp Glu Asn Gly Lys
                645                 650                 655

Tyr Arg Phe Asp Asn Leu Asp Ser Gly Lys Tyr Lys Val Ile Phe Glu
            660                 665                 670

Lys Pro Ala Gly Leu Thr Gln Thr Gly Thr Asn Thr Thr Glu Asp Asp
        675                 680                 685

Lys Asp Ala Asp Gly Gly Glu Val Asp Val Thr Ile Thr Asp His Asp
    690                 695                 700

Asp Phe Thr Leu Asp Asn Gly Tyr Tyr Glu Glu Glu Thr Ser Asp Ser
705                 710                 715                 720

Asp Ser Asp Ser Asp Ser Asp Ser Asp Ser Asp Ser Asp Ser Asp Ser
                725                 730                 735

Asp Ser Asp Ser Asp Ser Asp Ser Asp Ser Asp Ser Asp Ser Asp Ser
            740                 745                 750

Asp Ser Asp Ser Asp Ser Asp Ser Asp Ser Asp Ser Asp Ser Asp Ser
        755                 760                 765

Asp Ser Asp Ser Asp Ser Asp Ser Asp Ser Asp Ser Asp Ser Asp Ser
    770                 775                 780

Asp Ser Asp Ser Asp Ser Asp Ser Asp Ser Asp Ser Asp Ser Asp Ser
785                 790                 795                 800

Asp Ser Asp Ser Asp Ser Asp Ser Asp Ser Asp Ser Asp Ser Asp Ser
                805                 810                 815

Asp Ser Asp Ser Asp Ser Asp Ser Asp Ser Asp Ser Asp Ser Asp Ser
            820                 825                 830

Asp Ser Asp Ser Asp Ser Asp Ser Asp Ser Asp Ser Asp Ser Asp Ser
        835                 840                 845

Asp Ser Asp Ser Asp Ser Asp Ser Asp Asn Asp Ser Asp Ser Asp Ser
    850                 855                 860

Asp Ser Asp Ser Asp Ser Asp Ser Asp Ser Asp Ser Asp Ser Asp Ser
865                 870                 875                 880

Asp Ser Asp Ser Asp Ser Asp Ser Asp Ser Asp Ser Asp Ser Asp Ser
                885                 890                 895

Asp Ser Asp Ser Asp Ser Asp Ser Asp Ser Asp Ser Asp Ser Asp Ser
            900                 905                 910

Asp Ser Asp Ser Asp Ser Asp Ser Asp Ser Asp Asn Asp Ser Asp Ser
        915                 920                 925

Asp Ser Asp Ser Asp Ser Asp Ala Gly Lys His Thr Pro Ala Lys Pro
    930                 935                 940

Met Ser Thr Val Lys Asp Gln His Lys Thr Ala Lys Ala Leu Pro Glu
945                 950                 955                 960

Thr Gly Ser Glu Asn Asn Asn Ser Asn Asn Gly Thr Leu Phe Gly Gly
                965                 970                 975

Leu Phe Ala Ala Leu Gly Ser Leu Leu Leu Phe Gly Arg Arg Lys Lys
```

980 985 990

Gln Asn Lys
995

<210> SEQ ID NO 70
<211> LENGTH: 773
<212> TYPE: PRT
<213> ORGANISM: Staphylococcus sp.

<400> SEQUENCE: 70

Glu Glu Asn Ser Val Gln Asp Val Lys Asp Ser Asn Thr Asp Asp Glu
1 5 10 15

Leu Ser Asp Ser Asn Asp Gln Ser Ser Asp Glu Glu Lys Asn Asp Val
20 25 30

Ile Asn Asn Asn Gln Ser Ile Asn Thr Asp Asp Asn Asn Gln Ile Ile
35 40 45

Lys Lys Glu Glu Thr Asn Asn Tyr Asp Gly Ile Glu Lys Arg Ser Glu
50 55 60

Asp Arg Thr Glu Ser Thr Thr Asn Val Asp Glu Asn Glu Ala Thr Phe
65 70 75 80

Leu Gln Lys Thr Pro Gln Asp Asn Thr His Leu Thr Glu Glu Glu Val
85 90 95

Lys Glu Ser Ser Ser Val Glu Ser Ser Asn Ser Ser Ile Asp Thr Ala
100 105 110

Gln Gln Pro Ser His Thr Thr Ile Asn Arg Glu Glu Ser Val Gln Thr
115 120 125

Ser Asp Asn Val Glu Asp Ser His Val Ser Asp Phe Ala Asn Ser Lys
130 135 140

Ile Lys Glu Ser Asn Thr Glu Ser Gly Lys Glu Glu Asn Thr Ile Glu
145 150 155 160

Gln Pro Asn Lys Val Lys Glu Asp Ser Thr Thr Ser Gln Pro Ser Gly
165 170 175

Tyr Thr Asn Ile Asp Glu Lys Ile Ser Asn Gln Asp Glu Leu Leu Asn
180 185 190

Leu Pro Ile Asn Glu Tyr Glu Asn Lys Ala Arg Pro Leu Ser Thr Thr
195 200 205

Ser Ala Gln Pro Ser Ile Lys Arg Val Thr Val Asn Gln Leu Ala Ala
210 215 220

Glu Gln Gly Ser Asn Val Asn His Leu Ile Lys Val Thr Asp Gln Ser
225 230 235 240

Ile Thr Glu Gly Tyr Asp Asp Ser Glu Gly Val Ile Lys Ala His Asp
245 250 255

Ala Glu Asn Leu Ile Tyr Asp Val Thr Phe Glu Val Asp Asp Lys Val
260 265 270

Lys Ser Gly Asp Thr Met Thr Val Asp Ile Asp Lys Asn Thr Val Pro
275 280 285

Ser Asp Leu Thr Asp Ser Phe Thr Ile Pro Lys Ile Lys Asp Asn Ser
290 295 300

Gly Glu Ile Ile Ala Thr Gly Thr Tyr Asp Asn Lys Asn Lys Gln Ile
305 310 315 320

Thr Tyr Thr Phe Thr Asp Tyr Val Asp Lys Tyr Glu Asn Ile Lys Ala
325 330 335

His Leu Lys Leu Thr Ser Tyr Ile Asp Lys Ser Lys Val Pro Asn Asn
340 345 350

Asn Thr Lys Leu Asp Val Glu Tyr Lys Thr Ala Leu Ser Ser Val Asn
355 360 365

Lys Thr Ile Thr Val Glu Tyr Gln Arg Pro Asn Glu Asn Arg Thr Ala
370 375 380

Asn Leu Gln Ser Met Phe Thr Asn Ile Asp Thr Lys Asn His Thr Val
385 390 395 400

Glu Gln Thr Ile Tyr Ile Asn Pro Leu Arg Tyr Ser Ala Lys Glu Thr
405 410 415

Asn Val Asn Ile Ser Gly Asn Gly Asp Glu Gly Ser Thr Ile Ile Asp
420 425 430

Asp Ser Thr Ile Ile Lys Val Tyr Lys Val Gly Asp Asn Gln Asn Leu
435 440 445

Pro Asp Ser Asn Arg Ile Tyr Asp Tyr Ser Glu Tyr Glu Asp Val Thr
450 455 460

Asn Asp Asp Tyr Ala Gln Leu Gly Asn Asn Asn Asp Val Asn Ile Asn
465 470 475 480

Phe Gly Asn Ile Asp Ser Pro Tyr Ile Ile Lys Val Ile Ser Lys Tyr
485 490 495

Asp Pro Asn Lys Asp Asp Tyr Thr Thr Ile Gln Gln Thr Val Thr Met
500 505 510

Gln Thr Thr Ile Asn Glu Tyr Thr Gly Glu Phe Arg Thr Ala Ser Tyr
515 520 525

Asp Asn Thr Ile Ala Phe Ser Thr Ser Ser Gly Gln Gly Gln Gly Asp
530 535 540

Leu Pro Pro Glu Lys Thr Tyr Lys Ile Gly Asp Tyr Val Trp Glu Asp
545 550 555 560

Val Asp Lys Asp Gly Ile Gln Asn Thr Asn Asp Asn Glu Lys Pro Leu
565 570 575

Ser Asn Val Leu Val Thr Leu Thr Tyr Pro Asp Gly Thr Ser Lys Ser
580 585 590

Val Arg Thr Asp Glu Asp Gly Lys Tyr Gln Phe Asp Gly Leu Lys Asn
595 600 605

Gly Leu Thr Tyr Lys Ile Thr Phe Glu Thr Pro Glu Gly Tyr Thr Pro
610 615 620

Thr Leu Lys His Ser Gly Thr Asn Pro Ala Leu Asp Ser Glu Gly Asn
625 630 635 640

Ser Val Trp Val Thr Ile Asn Gly Gln Asp Asp Met Thr Ile Asp Ser
645 650 655

Gly Phe Tyr Gln Thr Pro Lys Tyr Ser Leu Gly Asn Tyr Val Trp Tyr
660 665 670

Asp Thr Asn Lys Asp Gly Ile Gln Gly Asp Asp Glu Lys Gly Ile Ser
675 680 685

Gly Val Lys Val Thr Leu Lys Asp Glu Asn Gly Asn Ile Ile Ser Thr
690 695 700

Thr Thr Thr Asp Glu Asn Gly Lys Tyr Gln Phe Asp Asn Leu Asn Ser
705 710 715 720

Gly Asn Tyr Ile Val His Phe Asp Lys Pro Ser Gly Met Thr Gln Thr
725 730 735

Thr Thr Asp Ser Gly Asp Asp Asp Glu Gln Asp Ala Asp Gly Glu Glu
740 745 750

Val His Val Thr Ile Thr Asp His Asp Asp Phe Ser Ile Asp Asn Gly
755 760 765

Tyr Tyr Asp Asp Glu

770

<210> SEQ ID NO 71
<211> LENGTH: 2886
<212> TYPE: DNA
<213> ORGANISM: Staphylococcus sp.

<400> SEQUENCE: 71
gtgaaaagca atcttagata cggcataaga aaacacaaat tgggagcggc ctcagtattc 60
ttaggaacaa tgatcgttgt tggaatggga caagaaaaag aagctgcagc atcggaacaa 120
aacaatacta cagtagagga aagtgggagt tcagctactg aaagtaaagc aagcgaaaca 180
caaacaacta caaataacgt taatacaata gatgaaacac aatcatacag cgcgacatca 240
actgagcaac catcaaaatc aactcaagta acaacagaag aagcaccaac aactgtgcaa 300
gcaccaaaag tagaaaccga aatgaaatca caagaagatt taccatcaga aaaagttgct 360
gataaggaaa ctacaggaac tcaagttgac atagctcaac caagtaacgt ctcagaaatt 420
aaaccaagaa tgaaaagatc agctgacgtt acagcagttt cagagaaaga agtagcggaa 480
gaagctaaag cgacaggtac agatgtaaca aataaagtgg aagttactga aagctcttta 540
gaaggacata ataaagattc gaatattgtt aatccgcata atgctcaaag agtaacttta 600
aaatacaaat ggaaatttgg agaaggaatt aaggcaggag attattttga tttcacatta 660
agtgataatg ttgaaacaca tggtatatca acactgcgta aagttccgga gataaaaagt 720
tcaacagaag ataaagttat ggcaaatggt caagttataa atgaacgtac aattcgctat 780
acatttactg attatataaa taacaaaaaa gatttaactg ctgaattaaa cttaaaccta 840
ttcattgacc caacaacagt gacaaagcaa gggagtcaaa aagttgaagt aacactaggt 900
caaaataaag tctcaaaaga atttgatatc aaatatttag acggcgttaa agatagaatg 960
ggtgttactg ttaatggtcg tattgatact ttgaataaag aagagggtaa atttagccat 1020
tttgcatatg tgaagcctaa caaccagtcg ttaacttctg tcacagtaac tggtcaagta 1080
acatctggat ataaacaaag tgctaataat ccaacagtca aagtatataa acacattggt 1140
tcagatgaat tagctgaaag tgtttatgca aagcttgatg ataccagtaa atttgaagat 1200
gtgactgaaa aagtaaatct atcttacaca agtaatggtg ggtacacatt gaaccttggc 1260
gatttagata attcgaaaga ctatgtaatt aaatatgaag gtgaatatga tcaaaatgct 1320
aaggatctaa atttccgaac acatctttca ggatatcata aatactaccc atactatcct 1380
tattacccgt attatccagt tcaattaact tggaacaacg gtgttgcatt ttactctaat 1440
aatgctaaag gcgatggtaa agataaacca aatgatccta tcattgagaa gagtgaacca 1500
attgatttag acattaaatc agagccacca gtggagaagc atgaattgac tggtacaatc 1560
gaagaaagta acgattctaa gccaattgat tttgaatatc atacagctgt tgaaggtgca 1620
gaaggtcatg cagaaggtat tattgaaact gaagaagatt ctattcatgt ggattttgaa 1680
gaatctacac atgaaaattc aaaacatcac gctgatgttg ttgaatatga agaggataca 1740
aacccaggtg gtggccaagt aacaactgag tctaacttag ttgaatttga cgaagagtct 1800
acaaaaggta ttgtaactgg cgcagtgagc gaccatacaa cagttgaaga tacgaaagaa 1860
tatacaactg aaagtaatct gattgaatta gtggatgaat tacctgaaga acatggtcaa 1920
gcacaaggc caatcgagga aattactgaa aacaatcatc atatttctca ttctggttta 1980
ggaactgaaa atggtcacgg taattatggc gtgattgatg aaatcgaaga aaatagccac 2040
gttgatatta agagtgaatt aggttatgaa ggtggccaaa atagcggtaa tcagtcattc 2100
gaggaagaca cagaagaaga taaacctaaa tatgaacaag gtggtaatat cgtagatatc 2160
gatttcgaca gtgtacctca aattcatggt caaaataatg gtaaccagtc attcgaggaa 2220
gacacagaag aagacaagcc taagtatgaa caaggtggta acatcattga tatcgacttc 2280
gacagtgtgc cacaaattca tggattcaat aagcataatg aaattattga agaagataca 2340
aacaaagata aacctaatta tcaatttggt ggacacaaca gtgttgattt tgaagaagat 2400
acacttccaa aagtaagtgg tcaaaatgaa ggtcaacaaa cgattgaaga agatacaacg 2460
ccgccaacac cgccaacacc agaggtacca agtgagccgg aaacaccaac accaccaaca 2520
ccagaagtac cgagtgagcc aggcgaacca acgccaccaa aaccggaagt accaagtgag 2580
ccggaaacac cagtaccacc aacaccagag gtaccatctg aacctggtaa accagtacca 2640
cctgctaaag aagaacctaa aaaaccttct aaaccagtgg aacaaggtaa ggtagtaaca 2700
cctgttattg aaatcaatga aaaggttaaa gcagtggcac caactaaaca aaaacaatct 2760
aagaaatctg aactacctga aacaggtgga gaagaatcaa caaacaaagg tatgttgttc 2820
ggcggattat tcagcattct aggtttagta ttattacgca gaaataaaaa gaataacaaa 2880
gcataa 2886

<210> SEQ ID NO 72
<211> LENGTH: 1737
<212> TYPE: DNA
<213> ORGANISM: Staphylococcus sp.

<400> SEQUENCE: 72
atgaaattta agtcattgat tacaacaaca ttagcattag gcgttatagc atcaacagga 60
gcaaacttta atactaacga agcatctgcc gcagctaagc cattagataa atcatcaagt 120
acattacacc atggacattc taacatccag attccatata caattactgt gaacggtaca 180
agccaaaaca ttttatcaag cttaacattt aataagaatc aaaatattag ttataaagat 240
atagagaata aagttaaatc agttttatac tttaatagag gtattagtga tatcgattta 300
agactttcaa agcaagcgga atatacggtt cattttaaaa atggaacaaa aagagttatc 360
gatttgaaat caggtatcta cacagctgac ttaatcaata caagtgacat taaagctatc 420
agtgttaacg tagatactaa aaagcaacct aaagataaag ctaaagcaaa tgttcaagtg 480
ccatatacaa tcacagtgaa cggcacaagc caaaacattt tatcaaacct aacatttaat 540
aaaaatcaaa atattagtta caaagattta gagggtaaag ttaaatcagt tttagaatca 600
aatagaggta ttactgatgt tgatttaaga ctttcgaagc aagcgaaata tacagttaat 660
tttaaaaatg gaacgaagaa agttatcgat ttgaaatcag gtatttacac agcgaattta 720
atcaattcaa gtgatattaa aagtatcaat attaacgtag atacaaaaaa acatatcgaa 780
aataaagcta aaagaaacta tcaagttcca tattcaatta atctaaatgg tacatctaca 840
aacattttat cgaatctttc attttcaaat aaaccttgga caaattacaa aaatttaact 900
agtcaaataa aatcagtact gaagcatgat agaggtatta gtgaacaaga tttaaaatat 960
gctaagaaag cttattatac tgtttatttt aaaaatggtg gtaaaagaat cttacagtta 1020
aattcaaaaa attacacagc aaacttagtt catgcgaaag atgttaagag aattgaaatt 1080
actgttaaaa caggaactaa agcgaaagca gacagatatg taccatacac aattgcagta 1140
aatggcacat caacaccaat tttatcaaaa ctaaaaattt cgaataaaca attaattagt 1200
tacaaatatt taaacgacaa agtgaaatct gtattaaaaa gtgaaagagg tatcagtgat 1260

-continued

```
cttgacttaa aatttgcgaa acaagcaaaa tatacagtat atttcaaaaa tggaaagaaa   1320

caagtagtga atttaaaatc agacatcttt acacctaatt tatttagtgc caaagatatt   1380

aaaaagattg atattgatgt aaaacaatac actaaatcaa aaaaaaaaat aaataaatct   1440

aataatgtga aattcccagt aacaataaat aaatttgaaa acatagtttc aaatgaattt   1500

gtgttctata atgcaagcaa aattacaatt aatgatttaa gtataaaact taaatcagca   1560

atggcaaatg atcaagggat aactaaacat gacataggac ttgctgaacg cgcagtgtat   1620

aaagtgtatt ttaaaaatgg ttcgtcaaaa tatgtagact taaaaactga gtataaagat   1680

gaaagagtat ttaaagcaac tgacattaaa aaggtagata ttgaacttaa attctaa      1737
```

```
<210> SEQ ID NO 73
<211> LENGTH: 2988
<212> TYPE: DNA
<213> ORGANISM: Staphylococcus sp.

<400> SEQUENCE: 73

atgaataata aaaagacagc aacaaataga aaaggcatga taccaaatcg attaaacaaa     60

ttttcgataa gaaagtattc tgtaggtact gcttcaattt tagtagggac aacattgatt    120

tttgggttaa gtggtcatga agctaaagcg gcagaacata cgaatggaga attaaatcaa    180

tcaaaaaatg aaacgacagc cccaagtgag aataaaacaa ctaaaaaagt tgatagtcgt    240

caactaaaag acaatacgca aactgcaact gcagatcagc ctaaagtgac aatgagtgat    300

agtgcaacag ttaaagaaac tagtagtaac atgcaatcac cacaaaacgc tacagctaat    360

caatctacta caaaaactag caatgtaaca acaaatgata aatcatcaac tacatatagt    420

aatgaaactg ataaaagtaa tttaacacaa gcaaaagatg tttcaactac acctaaaaca    480

acgactatta aaccaagaac tttaaatcgc atggcagtga atactgttgc agctccacaa    540

caaggaacaa atgttaatga taaagtacat ttttcaaata ttgacattgc gattgataaa    600

ggacatgtta atcagactac tggtaaaact gaattttggg caacttcaag tgatgtttta    660

aaattaaaag caaattacac aatcgatgat tctgttaaag agggcgatac atttactttt    720

aaatatggtc aatatttccg tccaggatca gtaagattac cttcacaaac tcaaaattta    780

tataatgccc aaggtaatat tattgcaaaa ggtatttatg atagtacaac aaacacaaca    840

acatatactt ttacgaacta tgtagatcaa tatacaaatg ttagaggtag ctttgaacaa    900

gttgcatttg cgaaacgtaa aaatgcaaca actgataaaa cagcttataa aatggaagta    960

actttaggta atgatacata tagcgaagaa atcattgtcg attatggtaa taaaaaagca   1020

caaccgctta tttcaagtac aaactatatt aacaatgaag atttatcgcg taatatgact   1080

gcatatgtaa atcaacctaa aaatacatat actaaacaaa cgtttgttac taatttaact   1140

ggatataaat ttaatccaaa tgcaaaaaac ttcaaaattt acgaagtgac agatcaaaat   1200

caatttgtgg atagtttcac ccctgatact tcaaaactta aagatgttac tgatcaattc   1260

gatgttattt atagtaatga taataaaaca gctacagtcg atttaatgaa aggccaaaca   1320

agcagcaata aacaatacat cattcaacaa gttgcttatc cagataatag ttcaacagat   1380

aatggaaaaa ttgattatac tttagacact gacaaaacta aatatagttg gtcaaatagt   1440

tattcaaatg tgaatggctc atcaactgct aatggcgacc aaaagaaata taatctaggt   1500

gactatgtat gggaagatac aaataaagat ggtaaacaag atgccaatga aaaagggatt   1560

aaaggtgttt atgtcattct taaagatagt aacggtaaag aattagatcg tacgacaaca   1620

gatgaaaatg gtaaatatca gttcactggt ttaagcaatg gaacttatag tgtagagttt   1680
```

```
tcaacaccag ccggttatac accgacaact gcaaatgtag gtacagatga tgctgtagat   1740
tctgatggac taactacaac aggtgtcatt aaagacgctg acaacatgac attagatagt   1800
ggattctaca aaacaccaaa atatagttta ggtgattatg tttggtacga cagtaataaa   1860
gatggtaaac aagattcgac tgaaaaagga attaaaggtg ttaaagttac tttgcaaaac   1920
gaaaaaggcg aagtaattgg tacaactgaa acagatgaaa atggtaaata ccgctttgat   1980
aatttagata gtggtaaata caaagttatc tttgaaaaac ctgctggctt aactcaaaca   2040
ggtacaaata caactgaaga tgataaagat gccgatggtg gcgaagttga tgtaacaatt   2100
acggatcatg atgatttcac acttgataat ggctactacg aagaagaaac atcagatagc   2160
gactcagatt ctgacagcga ttcagactca gatagcgact cagattcaga tagcgactca   2220
gattcagaca gcgattcaga cagcgactca gactcagata gcgattcaga ttcagacagc   2280
gactcagact cagacagcga ttcagactcg gatagcgact cagactcaga tagcgactca   2340
gattcggata gcgactcaga ctcagatagc gattcagatt cagatagcga ttcggactca   2400
gacagtgatt cagattcaga ctcagatagc gactcagatt ctgacagcga ttcagactca   2460
gacagcgact cagactcaga cagtgattca gattcagaca gcgactcaga ttcagatagc   2520
gactcagact cagatagcga ctcagattca gatagcgatt cggactcaga caacgactca   2580
gattcagata gcgattcaga ttcagatagc gactcagatt cggacagcga ttcagactca   2640
gatagcgatt cagactcaga cagcgattca gattcagata gcgactcaga ctcagatagc   2700
gactcagact cggatagcga ttcagattca gacagcgact cagattcaga tagcgattcg   2760
gactcagaca acgactcaga ttcagatagc gattcagatt cagatgcagg taaacatact   2820
ccggctaaac caatgagtac ggttaaagat cagcataaaa cagctaaagc attaccagaa   2880
acaggtagtg aaaataataa ttcaaataat ggcacattat tcggtggatt attcgcggca   2940
ttaggatcat tattgttatt cggtcgtcgt aaaaaacaaa ataaataa                2988
```

<210> SEQ ID NO 74
<211> LENGTH: 2319
<212> TYPE: DNA
<213> ORGANISM: Staphylococcus sp.

<400> SEQUENCE: 74

```
gaggagaatt cagtacaaga cgttaaagat tcgaatacgg atgatgaatt atcagacagc     60
aatgatcagt ctagtgatga agaaaagaat gatgtgatca ataataatca gtcaataaac    120
accgacgata ataaccaaat aattaaaaaa gaagaaacga ataactacga tggcatagaa    180
aaacgctcag aagatagaac agagtcaaca acaaatgtag atgaaaacga agcaacattt    240
ttacaaaaga cccctcaaga taatactcat cttacagaag aagaggtaaa agaatcctca    300
tcagtcgaat cctcaaattc atcaattgat actgcccaac aaccatctca cacaacaata    360
aatagagaag aatctgttca aacaagtgat aatgtagaag attcacacgt atcagatttt    420
gctaactcta aaataaaaga gagtaacact gaatctggta aagaagagaa tactatagag    480
caacctaata aagtaaaaga agattcaaca acaagtcagc cgtctggcta tacaaatata    540
gatgaaaaaa tttcaaatca agatgagtta ttaaatttac caataaatga atatgaaaat    600
aaggctagac cattatctac aacatctgcc caaccatcga ttaaacgtgt aaccgtaaat    660
caattagcgg cggaacaagg ttcgaatgtt aatcatttaa ttaaagttac tgatcaaagt    720
attactgaag gatatgatga tagtgaaggt gttattaaag cacatgatgc tgaaaactta    780
```

```
atctatgatg taacttttga agtagatgat aaggtgaaat ctggtgatac gatgacagtg    840

gatatagata agaatacagt tccatcagat ttaaccgata gctttacaat accaaaaata    900

aaagataatt ctggagaaat catcgctaca ggtacttatg ataacaaaaa taaacaaatc    960

acctatactt ttacagatta tgtagataag tatgaaaata ttaaagcaca ccttaaatta   1020

acgtcataca ttgataaatc aaaggttcca aataataata ccaagttaga tgtagaatat   1080

aaaacggccc tttcatcagt aaataaaaca attacggttg aatatcaaag acctaacgaa   1140

aatcggactg ctaaccttca aagtatgttt acaaacatag atacgaaaaa tcatacagtt   1200

gagcaaacga tttatattaa ccctcttcgt tattcagcca aggaaacaaa tgtaaatatt   1260

tcagggaatg gtgatgaagg ttcaacaatt atagacgata gcacaataat taaagtttat   1320

aaggttggag ataatcaaaa tttaccagat agtaacagaa tttatgatta cagtgaatat   1380

gaagatgtca caaatgatga ttatgcccaa ttaggaaata ataatgatgt gaatattaat   1440

tttggtaata tagattcacc atatattatt aaagttatta gtaaatatga ccctaataag   1500

gatgattaca cgactataca gcaaactgtg acaatgcaga cgactataaa tgagtatact   1560

ggtgagttta gaacagcatc ctatgataat acaattgctt tctctacaag ttcaggtcaa   1620

ggacaaggtg acttgcctcc tgaaaaaact tataaaatcg gagattacgt atgggaagat   1680

gtagataaag atggtattca aaatacaaat gataatgaaa aaccgcttag taatgtattg   1740

gtaactttga cgtatcctga tggaacttca aaatcagtca gaacagatga agatgggaaa   1800

tatcaatttg atggattgaa aaacggattg acttataaaa ttacattcga aacacctgaa   1860

ggatatacgc cgacgcttaa acattcagga acaaatcctg cactagactc agaaggtaat   1920

tctgtatggg taactattaa tggacaagac gatatgacga ttgatagtgg attttatcaa   1980

acacctaaat acagcttagg gaactatgta tggtatgaca ctaataaaga tggtattcaa   2040

ggtgatgatg aaaaaggaat ctctggagtt aaagtgacgt taaaagatga aaacggaaat   2100

atcattagta caactacaac cgatgaaaat ggaaagtatc aatttgataa tttaaatagt   2160

ggtaattata ttgttcattt tgataaacct tcaggtatga ctcaaacaac aacagattct   2220

ggtgatgatg acgaacagga tgctgatggg gaagaagttc atgtaacaat tactgatcat   2280

gatgacttta gtatagataa cggatactat gatgacgaa                          2319
```

```
<210> SEQ ID NO 75
<211> LENGTH: 774
<212> TYPE: PRT
<213> ORGANISM: Staphylococcus sp.

<400> SEQUENCE: 75

Met Glu Glu Asn Ser Val Gln Asp Val Lys Asp Ser Asn Thr Asp Asp
1               5                   10                  15

Glu Leu Ser Asp Ser Asn Asp Gln Ser Ser Asp Glu Glu Lys Asn Asp
            20                  25                  30

Val Ile Asn Asn Asn Gln Ser Ile Asn Thr Asp Asp Asn Asn Gln Ile
        35                  40                  45

Ile Lys Lys Glu Glu Thr Asn Asn Tyr Asp Gly Ile Glu Lys Arg Ser
    50                  55                  60

Glu Asp Arg Thr Glu Ser Thr Thr Asn Val Asp Glu Asn Glu Ala Thr
65                  70                  75                  80

Phe Leu Gln Lys Thr Pro Gln Asp Asn Thr His Leu Thr Glu Glu Glu
                85                  90                  95

Val Lys Glu Ser Ser Ser Val Glu Ser Ser Asn Ser Ser Ile Asp Thr
```

```
            100                 105                 110

Ala Gln Gln Pro Ser His Thr Thr Ile Asn Arg Glu Glu Ser Val Gln
        115                 120                 125

Thr Ser Asp Asn Val Glu Asp Ser His Val Ser Asp Phe Ala Asn Ser
    130                 135                 140

Lys Ile Lys Glu Ser Asn Thr Glu Ser Gly Lys Glu Glu Asn Thr Ile
145                 150                 155                 160

Glu Gln Pro Asn Lys Val Lys Glu Asp Ser Thr Thr Ser Gln Pro Ser
                165                 170                 175

Gly Tyr Thr Asn Ile Asp Glu Lys Ile Ser Asn Gln Asp Glu Leu Leu
            180                 185                 190

Asn Leu Pro Ile Asn Glu Tyr Glu Asn Lys Ala Arg Pro Leu Ser Thr
        195                 200                 205

Thr Ser Ala Gln Pro Ser Ile Lys Arg Val Thr Val Asn Gln Leu Ala
    210                 215                 220

Ala Glu Gln Gly Ser Asn Val Asn His Leu Ile Lys Val Thr Asp Gln
225                 230                 235                 240

Ser Ile Thr Glu Gly Tyr Asp Asp Ser Glu Gly Val Ile Lys Ala His
                245                 250                 255

Asp Ala Glu Asn Leu Ile Tyr Asp Val Thr Phe Glu Val Asp Asp Lys
            260                 265                 270

Val Lys Ser Gly Asp Thr Met Thr Val Asp Ile Asp Lys Asn Thr Val
        275                 280                 285

Pro Ser Asp Leu Thr Asp Ser Phe Thr Ile Pro Lys Ile Lys Asp Asn
    290                 295                 300

Ser Gly Glu Ile Ile Ala Thr Gly Thr Tyr Asp Asn Lys Asn Lys Gln
305                 310                 315                 320

Ile Thr Tyr Thr Phe Thr Asp Tyr Val Asp Lys Tyr Glu Asn Ile Lys
                325                 330                 335

Ala His Leu Lys Leu Thr Ser Tyr Ile Asp Lys Ser Lys Val Pro Asn
            340                 345                 350

Asn Asn Thr Lys Leu Asp Val Glu Tyr Lys Thr Ala Leu Ser Ser Val
        355                 360                 365

Asn Lys Thr Ile Thr Val Glu Tyr Gln Arg Pro Asn Glu Asn Arg Thr
    370                 375                 380

Ala Asn Leu Gln Ser Met Phe Thr Asn Ile Asp Thr Lys Asn His Thr
385                 390                 395                 400

Val Glu Gln Thr Ile Tyr Ile Asn Pro Leu Arg Tyr Ser Ala Lys Glu
                405                 410                 415

Thr Asn Val Asn Ile Ser Gly Asn Gly Asp Glu Gly Ser Thr Ile Ile
            420                 425                 430

Asp Asp Ser Thr Ile Ile Lys Val Tyr Lys Val Gly Asp Asn Gln Asn
        435                 440                 445

Leu Pro Asp Ser Asn Arg Ile Tyr Asp Tyr Ser Glu Tyr Glu Asp Val
    450                 455                 460

Thr Asn Asp Asp Tyr Ala Gln Leu Gly Asn Asn Asn Asp Val Asn Ile
465                 470                 475                 480

Asn Phe Gly Asn Ile Asp Ser Pro Tyr Ile Ile Lys Val Ile Ser Lys
                485                 490                 495

Tyr Asp Pro Asn Lys Asp Asp Tyr Thr Thr Ile Gln Gln Thr Val Thr
            500                 505                 510

Met Gln Thr Thr Ile Asn Glu Tyr Thr Gly Glu Phe Arg Thr Ala Ser
        515                 520                 525
```

Tyr Asp Asn Thr Ile Ala Phe Ser Thr Ser Ser Gly Gln Gly Gln Gly
    530                 535                 540

Asp Leu Pro Pro Glu Lys Thr Tyr Lys Ile Gly Asp Tyr Val Trp Glu
545                 550                 555                 560

Asp Val Asp Lys Asp Gly Ile Gln Asn Thr Asn Asp Asn Glu Lys Pro
                565                 570                 575

Leu Ser Asn Val Leu Val Thr Leu Thr Tyr Pro Asp Gly Thr Ser Lys
            580                 585                 590

Ser Val Arg Thr Asp Glu Asp Gly Lys Tyr Gln Phe Asp Gly Leu Lys
        595                 600                 605

Asn Gly Leu Thr Tyr Lys Ile Thr Phe Glu Thr Pro Glu Gly Tyr Thr
    610                 615                 620

Pro Thr Leu Lys His Ser Gly Thr Asn Pro Ala Leu Asp Ser Glu Gly
625                 630                 635                 640

Asn Ser Val Trp Val Thr Ile Asn Gly Gln Asp Asp Met Thr Ile Asp
                645                 650                 655

Ser Gly Phe Tyr Gln Thr Pro Lys Tyr Ser Leu Gly Asn Tyr Val Trp
            660                 665                 670

Tyr Asp Thr Asn Lys Asp Gly Ile Gln Gly Asp Asp Glu Lys Gly Ile
        675                 680                 685

Ser Gly Val Lys Val Thr Leu Lys Asp Glu Asn Gly Asn Ile Ile Ser
    690                 695                 700

Thr Thr Thr Thr Asp Glu Asn Gly Lys Tyr Gln Phe Asp Asn Leu Asn
705                 710                 715                 720

Ser Gly Asn Tyr Ile Val His Phe Asp Lys Pro Ser Gly Met Thr Gln
                725                 730                 735

Thr Thr Thr Asp Ser Gly Asp Asp Asp Glu Gln Asp Ala Asp Gly Glu
            740                 745                 750

Glu Val His Val Thr Ile Thr Asp His Asp Asp Phe Ser Ile Asp Asn
        755                 760                 765

Gly Tyr Tyr Asp Asp Glu
    770

<210> SEQ ID NO 76
<211> LENGTH: 128
<212> TYPE: PRT
<213> ORGANISM: Staphylococcus sp.

<400> SEQUENCE: 76

Met Asp Val Asn Thr Val Asn Gln Lys Ala Ala Ser Val Lys Ser Thr
1               5                   10                  15

Lys Asp Ala Leu Asp Gly Gln Gln Asn Leu Gln Arg Ala Lys Thr Glu
            20                  25                  30

Ala Thr Asn Ala Ile Thr His Ala Ser Asp Leu Asn Gln Ala Gln Lys
        35                  40                  45

Asn Ala Leu Thr Gln Gln Val Asn Ser Ala Gln Asn Val His Ala Val
    50                  55                  60

Asn Asp Ile Lys Gln Thr Thr Gln Ser Leu Asn Thr Ala Met Thr Gly
65                  70                  75                  80

Leu Lys Arg Gly Val Ala Asn His Asn Gln Val Val Gln Ser Asp Asn
                85                  90                  95

Tyr Val Asn Ala Asp Thr Asn Lys Lys Asn Asp Tyr Asn Asn Ala Tyr
            100                 105                 110

Asn His Ala Asn Asp Ile Ile Asn Gly Asn Ala Gln His Pro Val Ile 115 120 125

<210> SEQ ID NO 77
<211> LENGTH: 6
<212> TYPE: PRT
<213> ORGANISM: Staphylococcus sp.

<400> SEQUENCE: 77

Thr Val Asn Gln Lys Ala
1 5

<210> SEQ ID NO 78
<211> LENGTH: 6
<212> TYPE: PRT
<213> ORGANISM: Staphylococcus sp.

<400> SEQUENCE: 78

Lys Ser Thr Lys Asp Ala
1 5

<210> SEQ ID NO 79
<211> LENGTH: 13
<212> TYPE: PRT
<213> ORGANISM: Staphylococcus sp.

<400> SEQUENCE: 79

Asp Gly Gln Gln Asn Leu Gln Arg Ala Lys Thr Glu Ala
1 5 10

<210> SEQ ID NO 80
<211> LENGTH: 10
<212> TYPE: PRT
<213> ORGANISM: Staphylococcus sp.

<400> SEQUENCE: 80

Asp Leu Asn Gln Ala Gln Lys Asn Ala Leu
1 5 10

<210> SEQ ID NO 81
<211> LENGTH: 9
<212> TYPE: PRT
<213> ORGANISM: Staphylococcus sp.

<400> SEQUENCE: 81

Asp Ile Lys Gln Thr Thr Gln Ser Leu
1 5

<210> SEQ ID NO 82
<211> LENGTH: 13
<212> TYPE: PRT
<213> ORGANISM: Staphylococcus sp.

<400> SEQUENCE: 82

Ala Asp Thr Asn Lys Lys Asn Asp Tyr Asn Asn Ala Tyr
1 5 10

<210> SEQ ID NO 83
<211> LENGTH: 7
<212> TYPE: PRT
<213> ORGANISM: Staphylococcus sp.

<400> SEQUENCE: 83

Asp Ile Ile Asn Gly Asn Ala
1 5

<210> SEQ ID NO 84
<211> LENGTH: 128
<212> TYPE: PRT
<213> ORGANISM: Staphylococcus sp.

<400> SEQUENCE: 84

```
Met Asp Val Asn Thr Val Asn Gln Lys Ala Ala Ser Val Lys Ser Thr
1               5                   10                  15

Lys Asp Ala Leu Asp Gly Gln Gln Asn Leu Gln Arg Ala Lys Thr Glu
            20                  25                  30

Ala Thr Asn Ala Ile Thr His Ala Ser Asp Leu Asn Gln Ala Gln Lys
        35                  40                  45

Asn Ala Leu Thr Gln Gln Val Asn Ser Ala Gln Asn Val His Ala Val
    50                  55                  60

Asn Asp Ile Lys Gln Thr Thr Gln Ser Leu Asn Thr Ala Met Thr Gly
65                  70                  75                  80

Leu Lys Arg Gly Val Ala Asn His Asn Gln Val Val Gln Ser Asp Asn
                85                  90                  95

Tyr Val Asn Ala Asp Thr Asn Lys Lys Asn Asp Tyr Asn Asn Ala Tyr
            100                 105                 110

Asn His Ala Asn Asp Ile Ile Asn Gly Asn Ala Gln His Pro Val Ile
        115                 120                 125
```

<210> SEQ ID NO 85
<211> LENGTH: 9
<212> TYPE: PRT
<213> ORGANISM: Staphylococcus sp.

<400> SEQUENCE: 85

```
Met Asp Val Asn Thr Val Asn Gln Lys
1               5
```

<210> SEQ ID NO 86
<211> LENGTH: 9
<212> TYPE: PRT
<213> ORGANISM: Staphylococcus sp.

<400> SEQUENCE: 86

```
Val Asn Thr Val Asn Gln Lys Ala Ala
1               5
```

<210> SEQ ID NO 87
<211> LENGTH: 9
<212> TYPE: PRT
<213> ORGANISM: Staphylococcus sp.

<400> SEQUENCE: 87

```
Val Asn Gln Lys Ala Ala Ser Val Lys
1               5
```

<210> SEQ ID NO 88
<211> LENGTH: 9
<212> TYPE: PRT
<213> ORGANISM: Staphylococcus sp.

<400> SEQUENCE: 88

```
Leu Gln Arg Ala Lys Thr Glu Ala Thr
1               5
```

<210> SEQ ID NO 89
<211> LENGTH: 9

<212> TYPE: PRT
<213> ORGANISM: Staphylococcus sp.

<400> SEQUENCE: 89

Ile Thr His Ala Ser Asp Leu Asn Gln
1 5

<210> SEQ ID NO 90
<211> LENGTH: 9
<212> TYPE: PRT
<213> ORGANISM: Staphylococcus sp.

<400> SEQUENCE: 90

Leu Asn Gln Ala Gln Lys Asn Ala Leu
1 5

<210> SEQ ID NO 91
<211> LENGTH: 9
<212> TYPE: PRT
<213> ORGANISM: Staphylococcus sp.

<400> SEQUENCE: 91

Leu Thr Gln Gln Val Asn Ser Ala Gln
1 5

<210> SEQ ID NO 92
<211> LENGTH: 9
<212> TYPE: PRT
<213> ORGANISM: Staphylococcus sp.

<400> SEQUENCE: 92

Val Asn Ser Ala Gln Asn Val His Ala
1 5

<210> SEQ ID NO 93
<211> LENGTH: 9
<212> TYPE: PRT
<213> ORGANISM: Staphylococcus sp.

<400> SEQUENCE: 93

Val His Ala Val Asn Asp Ile Lys Gln
1 5

<210> SEQ ID NO 94
<211> LENGTH: 9
<212> TYPE: PRT
<213> ORGANISM: Staphylococcus sp.

<400> SEQUENCE: 94

Val Asn Asp Ile Lys Gln Thr Thr Gln
1 5

<210> SEQ ID NO 95
<211> LENGTH: 9
<212> TYPE: PRT
<213> ORGANISM: Staphylococcus sp.

<400> SEQUENCE: 95

Ile Lys Gln Thr Thr Gln Ser Leu Asn
1 5

<210> SEQ ID NO 96
<211> LENGTH: 9
<212> TYPE: PRT
<213> ORGANISM: Staphylococcus sp.

<400> SEQUENCE: 96

Leu Asn Thr Ala Met Thr Gly Leu Lys
1 5

<210> SEQ ID NO 97
<211> LENGTH: 9
<212> TYPE: PRT
<213> ORGANISM: Staphylococcus sp.

<400> SEQUENCE: 97

Met Thr Gly Leu Lys Arg Gly Val Ala
1 5

<210> SEQ ID NO 98
<211> LENGTH: 9
<212> TYPE: PRT
<213> ORGANISM: Staphylococcus sp.

<400> SEQUENCE: 98

Leu Lys Arg Gly Val Ala Asn His Asn
1 5

<210> SEQ ID NO 99
<211> LENGTH: 9
<212> TYPE: PRT
<213> ORGANISM: Staphylococcus sp.

<400> SEQUENCE: 99

Val Ala Asn His Asn Gln Val Val Gln
1 5

<210> SEQ ID NO 100
<211> LENGTH: 9
<212> TYPE: PRT
<213> ORGANISM: Staphylococcus sp.

<400> SEQUENCE: 100

Val Val Gln Ser Asp Asn Tyr Val Asn
1 5

<210> SEQ ID NO 101
<211> LENGTH: 9
<212> TYPE: PRT
<213> ORGANISM: Staphylococcus sp.

<400> SEQUENCE: 101

Val Gln Ser Asp Asn Tyr Val Asn Ala
1 5

<210> SEQ ID NO 102
<211> LENGTH: 9
<212> TYPE: PRT
<213> ORGANISM: Staphylococcus sp.

<400> SEQUENCE: 102

Tyr Val Asn Ala Asp Thr Asn Lys Lys
1 5

<210> SEQ ID NO 103
<211> LENGTH: 9
<212> TYPE: PRT
<213> ORGANISM: Staphylococcus sp.

<400> SEQUENCE: 103

Val Asn Ala Asp Thr Asn Lys Lys Asn
1 5

<210> SEQ ID NO 104
<211> LENGTH: 9
<212> TYPE: PRT
<213> ORGANISM: Staphylococcus sp.

<400> SEQUENCE: 104

Tyr Asn Asn Ala Tyr Asn His Ala Asn
1 5

<210> SEQ ID NO 105
<211> LENGTH: 9
<212> TYPE: PRT
<213> ORGANISM: Staphylococcus sp.

<400> SEQUENCE: 105

Tyr Asn His Ala Asn Asp Ile Ile Asn
1 5

<210> SEQ ID NO 106
<211> LENGTH: 9
<212> TYPE: PRT
<213> ORGANISM: Staphylococcus sp.

<400> SEQUENCE: 106

Ile Ile Asn Gly Asn Ala Gln His Pro
1 5

<210> SEQ ID NO 107
<211> LENGTH: 9
<212> TYPE: PRT
<213> ORGANISM: Staphylococcus sp.

<400> SEQUENCE: 107

Ile Asn Gly Asn Ala Gln His Pro Val
1 5

<210> SEQ ID NO 108
<211> LENGTH: 52
<212> TYPE: PRT
<213> ORGANISM: Staphylococcus sp.

<400> SEQUENCE: 108

Gln Thr Thr Gln Asn Asn Tyr Val Thr Asp Gln Gln Lys Ala Phe Tyr
1 5 10 15

Gln Val Leu His Leu Lys Gly Ile Thr Glu Glu Gln Arg Asn Gln Tyr
20 25 30

Ile Lys Thr Leu Arg Glu His Pro Glu Arg Ala Gln Glu Val Phe Ser
35 40 45

Glu Ser Leu Lys
50

<210> SEQ ID NO 109
<211> LENGTH: 36
<212> TYPE: PRT
<213> ORGANISM: Staphylococcus sp.

<400> SEQUENCE: 109

Val Lys Asn Asn Leu Arg Tyr Gly Ile Arg Lys His Lys Leu Gly Ala
1 5 10 15

-continued

```
Ala Ser Val Phe Leu Gly Thr Met Ile Val Val Gly Met Gly Gln Asp
            20                  25                  30

Lys Glu Ala Ala
        35
```

```
<210> SEQ ID NO 110
<211> LENGTH: 6
<212> TYPE: PRT
<213> ORGANISM: Staphylococcus sp.

<400> SEQUENCE: 110

Asp Arg His Phe Leu Asn
1               5


<210> SEQ ID NO 111
<211> LENGTH: 4
<212> TYPE: PRT
<213> ORGANISM: Staphylococcus sp.

<400> SEQUENCE: 111

Gly Asn Tyr Asp
1


<210> SEQ ID NO 112
<211> LENGTH: 5
<212> TYPE: PRT
<213> ORGANISM: Staphylococcus sp.

<400> SEQUENCE: 112

Arg Arg Tyr Pro Phe
1               5


<210> SEQ ID NO 113
<211> LENGTH: 6
<212> TYPE: PRT
<213> ORGANISM: Staphylococcus sp.

<400> SEQUENCE: 113

Lys Thr Thr Leu Leu Lys
1               5


<210> SEQ ID NO 114
<211> LENGTH: 7
<212> TYPE: PRT
<213> ORGANISM: Staphylococcus sp.

<400> SEQUENCE: 114

Gly Val Thr Thr Ser Leu Ser
1               5


<210> SEQ ID NO 115
<211> LENGTH: 5
<212> TYPE: PRT
<213> ORGANISM: Staphylococcus sp.

<400> SEQUENCE: 115

Val Asp Trp Leu Arg
1               5


<210> SEQ ID NO 116
<211> LENGTH: 4
<212> TYPE: PRT
<213> ORGANISM: Staphylococcus sp.

<400> SEQUENCE: 116
```

Arg Gly Phe Leu
1

<210> SEQ ID NO 117
<211> LENGTH: 15
<212> TYPE: PRT
<213> ORGANISM: Staphylococcus sp.

<400> SEQUENCE: 117

Lys Ile Lys Val Tyr Val Gly Asn Tyr Asp Phe Trp Tyr Gln Ser
1               5                   10                  15

<210> SEQ ID NO 118
<211> LENGTH: 16
<212> TYPE: PRT
<213> ORGANISM: Staphylococcus sp.

<400> SEQUENCE: 118

Thr Val Ile Val Val Ser His Asp Arg His Phe Leu Tyr Asn Asn Val
1               5                   10                  15

<210> SEQ ID NO 119
<211> LENGTH: 15
<212> TYPE: PRT
<213> ORGANISM: Staphylococcus sp.

<400> SEQUENCE: 119

Thr Glu Thr Phe Leu Arg Gly Phe Leu Gly Arg Met Leu Phe Ser
1               5                   10                  15

<210> SEQ ID NO 120
<211> LENGTH: 35
<212> TYPE: DNA
<213> ORGANISM: Artificial Sequence
<220> FEATURE:
<223> OTHER INFORMATION: Staphylococcal primer

<400> SEQUENCE: 120
cgcggatccg cagattctga tattaatatt aaaac 35

<210> SEQ ID NO 121
<211> LENGTH: 33
<212> TYPE: DNA
<213> ORGANISM: Artificial Sequence
<220> FEATURE:
<223> OTHER INFORMATION: Staphylococcal primer

<400> SEQUENCE: 121
cccaagcttt taatttgtca tttcttcttt ttc 33

<210> SEQ ID NO 122
<211> LENGTH: 34
<212> TYPE: DNA
<213> ORGANISM: Artificial Sequence
<220> FEATURE:
<223> OTHER INFORMATION: Staphylococcal primer

<400> SEQUENCE: 122
cgcggatccg ctgggtctaa taattttaaa gatg 34

<210> SEQ ID NO 123
<211> LENGTH: 30
<212> TYPE: DNA
<213> ORGANISM: Artificial Sequence
<220> FEATURE:

<223> OTHER INFORMATION: Staphylococcal primer

<400> SEQUENCE: 123
cccaagcttt tatggaataa cgatttgttg 30

<210> SEQ ID NO 124
<211> LENGTH: 32
<212> TYPE: DNA
<213> ORGANISM: Artificial Sequence
<220> FEATURE:
<223> OTHER INFORMATION: Staphylococcal primer

<400> SEQUENCE: 124
cgcggatcca gtgaaaatag tgttacgcaa tc 32

<210> SEQ ID NO 125
<211> LENGTH: 33
<212> TYPE: DNA
<213> ORGANISM: Artificial Sequence
<220> FEATURE:
<223> OTHER INFORMATION: Staphylococcal primer

<400> SEQUENCE: 125
cccaagcttt tactctggaa ttggttcaat ttc 33

<210> SEQ ID NO 126
<211> LENGTH: 31
<212> TYPE: DNA
<213> ORGANISM: Artificial Sequence
<220> FEATURE:
<223> OTHER INFORMATION: Staphylococcal primer

<400> SEQUENCE: 126
cgcggatcca cacaaacaac tgcaactaac g 31

<210> SEQ ID NO 127
<211> LENGTH: 35
<212> TYPE: DNA
<213> ORGANISM: Artificial Sequence
<220> FEATURE:
<223> OTHER INFORMATION: Staphylococcal primer

<400> SEQUENCE: 127
cccaagcttt tatgctttgt gattcttttt caaac 35

<210> SEQ ID NO 128
<211> LENGTH: 26
<212> TYPE: DNA
<213> ORGANISM: Artificial Sequence
<220> FEATURE:
<223> OTHER INFORMATION: Staphylococcal primer

<400> SEQUENCE: 128
cgcggatcca acacgcaaca aacttc 26

<210> SEQ ID NO 129
<211> LENGTH: 36
<212> TYPE: DNA
<213> ORGANISM: Artificial Sequence
<220> FEATURE:
<223> OTHER INFORMATION: Staphylococcal primer

<400> SEQUENCE: 129
ggaactgcag ttatttccag aatgataata aattac 36

<210> SEQ ID NO 130
<211> LENGTH: 28
<212> TYPE: DNA
<213> ORGANISM: Artificial Sequence
<220> FEATURE:
<223> OTHER INFORMATION: Staphylococcal primer

<400> SEQUENCE: 130
cgcggatccg cagaacatac gaatggag 28

<210> SEQ ID NO 131
<211> LENGTH: 32
<212> TYPE: DNA
<213> ORGANISM: Artificial Sequence
<220> FEATURE:
<223> OTHER INFORMATION: Staphylococcal primer

<400> SEQUENCE: 131
cccaagcttt tatgtttctt cttcgtagta gc 32

<210> SEQ ID NO 132
<211> LENGTH: 28
<212> TYPE: DNA
<213> ORGANISM: Artificial Sequence
<220> FEATURE:
<223> OTHER INFORMATION: Staphylococcal primer

<400> SEQUENCE: 132
cgcggatccg aggagaattc agtacaag 28

<210> SEQ ID NO 133
<211> LENGTH: 31
<212> TYPE: DNA
<213> ORGANISM: Artificial Sequence
<220> FEATURE:
<223> OTHER INFORMATION: Staphylococcal primer

<400> SEQUENCE: 133
cccaagcttt tattcgtcat catagtatcc g 31

<210> SEQ ID NO 134
<211> LENGTH: 25
<212> TYPE: DNA
<213> ORGANISM: Artificial Sequence
<220> FEATURE:
<223> OTHER INFORMATION: Staphylococcal primer

<400> SEQUENCE: 134
aaaagtactc accaccacca ccacc 25

<210> SEQ ID NO 135
<211> LENGTH: 29
<212> TYPE: DNA
<213> ORGANISM: Artificial Sequence
<220> FEATURE:
<223> OTHER INFORMATION: Staphylococcal primer

<400> SEQUENCE: 135
aaaagtactc acttgattca tcgcttcag 29

<210> SEQ ID NO 136
<211> LENGTH: 33
<212> TYPE: DNA
<213> ORGANISM: Artificial Sequence
<220> FEATURE:
<223> OTHER INFORMATION: Staphylococcal primer

<400> SEQUENCE: 136
gcgcgccatg gcacaagctt ctacacaaca tac 33

<210> SEQ ID NO 137
<211> LENGTH: 32
<212> TYPE: DNA
<213> ORGANISM: Artificial Sequence
<220> FEATURE:
<223> OTHER INFORMATION: Staphylococcal primer

<400> SEQUENCE: 137
gcgcgctcga gatggatgaa tgcatagcta ga 32

<210> SEQ ID NO 138
<211> LENGTH: 48
<212> TYPE: DNA
<213> ORGANISM: Artificial Sequence
<220> FEATURE:
<223> OTHER INFORMATION: Staphylococcal primer

<400> SEQUENCE: 138
gcatccatgg caccatcacc atcaccacga agtaaacgtt gatcaagc 48

<210> SEQ ID NO 139
<211> LENGTH: 34
<212> TYPE: DNA
<213> ORGANISM: Artificial Sequence
<220> FEATURE:
<223> OTHER INFORMATION: Staphylococcal primer

<400> SEQUENCE: 139
agcactcgag ttagaatccc caagcaccta aacc 34

<210> SEQ ID NO 140
<211> LENGTH: 29
<212> TYPE: DNA
<213> ORGANISM: Artificial Sequence
<220> FEATURE:
<223> OTHER INFORMATION: Staphylococcal primer

<400> SEQUENCE: 140
gcacccatgg cagaaaatac aaatacttc 29

<210> SEQ ID NO 141
<211> LENGTH: 31
<212> TYPE: DNA
<213> ORGANISM: Artificial Sequence
<220> FEATURE:
<223> OTHER INFORMATION: Staphylococcal primer

<400> SEQUENCE: 141
ttttctcgag cattttagat tgactaagtt g 31

<210> SEQ ID NO 142
<211> LENGTH: 33
<212> TYPE: DNA
<213> ORGANISM: Artificial Sequence
<220> FEATURE:
<223> OTHER INFORMATION: Staphylococcal primer

<400> SEQUENCE: 142
caagtcccat ggctgagacg acacaagatc aac 33

<210> SEQ ID NO 143
<211> LENGTH: 31

<212> TYPE: DNA
<213> ORGANISM: Artificial Sequence
<220> FEATURE:
<223> OTHER INFORMATION: Staphylococcal primer

<400> SEQUENCE: 143
cagtctcgag ttttacagct gtttttggtt g 31

<210> SEQ ID NO 144
<211> LENGTH: 30
<212> TYPE: DNA
<213> ORGANISM: Artificial Sequence
<220> FEATURE:
<223> OTHER INFORMATION: Staphylococcal primer

<400> SEQUENCE: 144
agctcatatg gcttatactg ttactaaacc 30

<210> SEQ ID NO 145
<211> LENGTH: 29
<212> TYPE: DNA
<213> ORGANISM: Artificial Sequence
<220> FEATURE:
<223> OTHER INFORMATION: Staphylococcal primer

<400> SEQUENCE: 145
gcgcctcgag tttatattgt gggatgtcg 29

<210> SEQ ID NO 146
<211> LENGTH: 34
<212> TYPE: DNA
<213> ORGANISM: Artificial Sequence
<220> FEATURE:
<223> OTHER INFORMATION: Staphylococcal primer

<400> SEQUENCE: 146
caagtcccat ggcaacagaa gctacgaacg caac 34

<210> SEQ ID NO 147
<211> LENGTH: 35
<212> TYPE: DNA
<213> ORGANISM: Artificial Sequence
<220> FEATURE:
<223> OTHER INFORMATION: Staphylococcal primer

<400> SEQUENCE: 147
accagtctcg agtaattctt tagctttaga gcttg 35

<210> SEQ ID NO 148
<211> LENGTH: 33
<212> TYPE: DNA
<213> ORGANISM: Artificial Sequence
<220> FEATURE:
<223> OTHER INFORMATION: Staphylococcal primer

<400> SEQUENCE: 148
tattctcgag gctttgagtg tgtccatcat ttg 33

<210> SEQ ID NO 149
<211> LENGTH: 32
<212> TYPE: DNA
<213> ORGANISM: Artificial Sequence
<220> FEATURE:
<223> OTHER INFORMATION: Staphylococcal primer

<400> SEQUENCE: 149
gaagccatgg cagcagctga agaaacaggt gg 32

<210> SEQ ID NO 150
<211> LENGTH: 30
<212> TYPE: DNA
<213> ORGANISM: Artificial Sequence
<220> FEATURE:
<223> OTHER INFORMATION: Staphylococcal primer

<400> SEQUENCE: 150
gattacacca tggttaaacc tcaagcgaaa 30

<210> SEQ ID NO 151
<211> LENGTH: 30
<212> TYPE: DNA
<213> ORGANISM: Artificial Sequence
<220> FEATURE:
<223> OTHER INFORMATION: Staphylococcal primer

<400> SEQUENCE: 151
aggtgtctcg agtgcgattg tagcttcatt 30

<210> SEQ ID NO 152
<211> LENGTH: 96
<212> TYPE: PRT
<213> ORGANISM: Staphylococcus sp.
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(13)
<223> OTHER INFORMATION: Xaa is any amino acid
<220> FEATURE:
<221> NAME/KEY: MISC_FEATURE
<222> LOCATION: (15)..(27)
<223> OTHER INFORMATION: Xaa is any amino acid
<220> FEATURE:
<221> NAME/KEY: MISC_FEATURE
<222> LOCATION: (29)..(54)
<223> OTHER INFORMATION: Xaa is any amino acid
<220> FEATURE:
<221> NAME/KEY: MISC_FEATURE
<222> LOCATION: (56)..(58)
<223> OTHER INFORMATION: Xaa is any amino acid
<220> FEATURE:
<221> NAME/KEY: MISC_FEATURE
<222> LOCATION: (60)..(61)
<223> OTHER INFORMATION: Xaa is any amino acid
<220> FEATURE:
<221> NAME/KEY: MISC_FEATURE
<222> LOCATION: (63)..(95)
<223> OTHER INFORMATION: Xaa is any amino acid

<400> SEQUENCE: 152

```
Leu Xaa Gly Xaa Xaa Xaa Xaa Xaa Xaa Xaa Xaa Xaa Xaa Ala Xaa Xaa
1               5                   10                  15

Xaa Xaa Xaa Xaa Xaa Xaa Xaa Xaa Xaa Xaa Xaa Gln Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Leu Xaa Xaa Xaa Met Xaa Xaa Leu Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Ala
                85                  90                  95
```

<210> SEQ ID NO 153
<211> LENGTH: 127
<212> TYPE: PRT
<213> ORGANISM: Staphylococcus sp.
<220> FEATURE:
<221> NAME/KEY: MISC_FEATURE
<222> LOCATION: (1)..(19)
<223> OTHER INFORMATION: Xaa is any amino acid
<220> FEATURE:
<221> NAME/KEY: MISC_FEATURE
<222> LOCATION: (21)..(21)
<223> OTHER INFORMATION: Xaa is any amino acid
<220> FEATURE:
<221> NAME/KEY: MISC_FEATURE
<222> LOCATION: (23)..(32)
<223> OTHER INFORMATION: Xaa is any amino acid
<220> FEATURE:
<221> NAME/KEY: MISC_FEATURE
<222> LOCATION: (34)..(46)
<223> OTHER INFORMATION: Xaa is any amino acid
<220> FEATURE:
<221> NAME/KEY: MISC_FEATURE
<222> LOCATION: (48)..(73)
<223> OTHER INFORMATION: Xaa is any amino acid
<220> FEATURE:
<221> NAME/KEY: MISC_FEATURE
<222> LOCATION: (75)..(77)
<223> OTHER INFORMATION: Xaa is any amino acid
<220> FEATURE:
<221> NAME/KEY: MISC_FEATURE
<222> LOCATION: (79)..(80)
<223> OTHER INFORMATION: Xaa is any amino acid
<220> FEATURE:
<221> NAME/KEY: MISC_FEATURE
<222> LOCATION: (82)..(114)
<223> OTHER INFORMATION: Xaa is any amino acid
<220> FEATURE:
<221> NAME/KEY: MISC_FEATURE
<222> LOCATION: (116)..(127)
<223> OTHER INFORMATION: Xaa is any amino acid

<400> SEQUENCE: 153

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Leu Xaa Gly Xaa Xaa Xaa Xaa Xaa Xaa Xaa Xaa Xaa Xaa
            20                  25                  30

Ala Xaa Xaa Xaa Xaa Xaa Xaa Xaa Xaa Xaa Xaa Xaa Xaa Xaa Gln Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Leu Xaa Xaa Xaa Met Xaa Xaa
65                  70                  75                  80

Leu Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Ala Xaa Xaa Xaa Xaa Xaa Xaa Xaa Xaa Xaa Xaa Xaa Xaa
        115                 120                 125
```

<210> SEQ ID NO 154
<211> LENGTH: 127
<212> TYPE: PRT
<213> ORGANISM: Staphylococcus sp.
<220> FEATURE:
<221> NAME/KEY: misc_feature
<222> LOCATION: (1)..(5)
<223> OTHER INFORMATION: Xaa is any amino acid
<220> FEATURE:

<221> NAME/KEY: misc_feature
<222> LOCATION: (6)..(6)
<223> OTHER INFORMATION: Xaa is I or V
<220> FEATURE:
<221> NAME/KEY: misc_feature
<222> LOCATION: (7)..(8)
<223> OTHER INFORMATION: Xaa is any amino acid
<220> FEATURE:
<221> NAME/KEY: misc_feature
<222> LOCATION: (10)..(12)
<223> OTHER INFORMATION: Xaa is any amino acid
<220> FEATURE:
<221> NAME/KEY: misc_feature
<222> LOCATION: (13)..(13)
<223> OTHER INFORMATION: Xaa is I or V
<220> FEATURE:
<221> NAME/KEY: misc_feature
<222> LOCATION: (14)..(15)
<223> OTHER INFORMATION: Xaa is any amino acid
<220> FEATURE:
<221> NAME/KEY: misc_feature
<222> LOCATION: (18)..(18)
<223> OTHER INFORMATION: Xaa is any amino acid
<220> FEATURE:
<221> NAME/KEY: misc_feature
<222> LOCATION: (21)..(21)
<223> OTHER INFORMATION: Xaa is N or D
<220> FEATURE:
<221> NAME/KEY: misc_feature
<222> LOCATION: (23)..(24)
<223> OTHER INFORMATION: Xaa is any amino acid
<220> FEATURE:
<221> NAME/KEY: misc_feature
<222> LOCATION: (27)..(28)
<223> OTHER INFORMATION: Xaa is any amino acid
<220> FEATURE:
<221> NAME/KEY: misc_feature
<222> LOCATION: (31)..(32)
<223> OTHER INFORMATION: Xaa is any amino acid
<220> FEATURE:
<221> NAME/KEY: misc_feature
<222> LOCATION: (34)..(39)
<223> OTHER INFORMATION: Xaa is any amino acid
<220> FEATURE:
<221> NAME/KEY: misc_feature
<222> LOCATION: (41)..(42)
<223> OTHER INFORMATION: Xaa is any amino acid
<220> FEATURE:
<221> NAME/KEY: misc_feature
<222> LOCATION: (45)..(45)
<223> OTHER INFORMATION: Xaa is any amino acid
<220> FEATURE:
<221> NAME/KEY: misc_feature
<222> LOCATION: (49)..(50)
<223> OTHER INFORMATION: Xaa is any amino acid
<220> FEATURE:
<221> NAME/KEY: misc_feature
<222> LOCATION: (52)..(53)
<223> OTHER INFORMATION: Xaa is any amino acid
<220> FEATURE:
<221> NAME/KEY: misc_feature
<222> LOCATION: (55)..(55)
<223> OTHER INFORMATION: Xaa is I or V
<220> FEATURE:
<221> NAME/KEY: misc_feature
<222> LOCATION: (56)..(57)
<223> OTHER INFORMATION: Xaa is any amino acid
<220> FEATURE:
<221> NAME/KEY: misc_feature
<222> LOCATION: (59)..(60)
<223> OTHER INFORMATION: Xaa is any amino acid
<220> FEATURE:
<221> NAME/KEY: misc_feature
<222> LOCATION: (62)..(63)
<223> OTHER INFORMATION: Xaa is any amino acid
<220> FEATURE:
<221> NAME/KEY: misc_feature
<222> LOCATION: (65)..(70)
<223> OTHER INFORMATION: Xaa is any amino acid
<220> FEATURE:
<221> NAME/KEY: misc_feature
<222> LOCATION: (72)..(73)
<223> OTHER INFORMATION: Xaa is any amino acid
<220> FEATURE:
<221> NAME/KEY: misc_feature
<222> LOCATION: (75)..(75)
<223> OTHER INFORMATION: Xaa is N or D
<220> FEATURE:
<221> NAME/KEY: misc_feature
<222> LOCATION: (76)..(76)
<223> OTHER INFORMATION: Xaa is any amino acid
<220> FEATURE:
<221> NAME/KEY: misc_feature
<222> LOCATION: (79)..(80)
<223> OTHER INFORMATION: Xaa is any amino acid
<220> FEATURE:
<221> NAME/KEY: misc_feature
<222> LOCATION: (82)..(84)
<223> OTHER INFORMATION: Xaa is any amino acid
<220> FEATURE:
<221> NAME/KEY: misc_feature
<222> LOCATION: (85)..(85)
<223> OTHER INFORMATION: Xaa is I or V
<220> FEATURE:
<221> NAME/KEY: misc_feature
<222> LOCATION: (86)..(86)
<223> OTHER INFORMATION: Xaa is any amino acid
<220> FEATURE:
<221> NAME/KEY: misc_feature
<222> LOCATION: (87)..(87)
<223> OTHER INFORMATION: Xaa is D or E
<220> FEATURE:
<221> NAME/KEY: misc_feature
<222> LOCATION: (88)..(90)
<223> OTHER INFORMATION: Xaa is any amino acid
<220> FEATURE:
<221> NAME/KEY: misc_feature
<222> LOCATION: (93)..(93)
<223> OTHER INFORMATION: Xaa is any amino acid
<220> FEATURE:
<221> NAME/KEY: misc_feature
<222> LOCATION: (95)..(95)
<223> OTHER INFORMATION: Xaa is any amino acid
<220> FEATURE:
<221> NAME/KEY: misc_feature
<222> LOCATION: (97)..(97)
<223> OTHER INFORMATION: Xaa is Y or F
<220> FEATURE:
<221> NAME/KEY: misc_feature
<222> LOCATION: (98)..(98)
<223> OTHER INFORMATION: Xaa is any amino acid
<220> FEATURE:
<221> NAME/KEY: misc_feature
<222> LOCATION: (99)..(99)
<223> OTHER INFORMATION: Xaa is N or D
<220> FEATURE:
<221> NAME/KEY: misc_feature
<222> LOCATION: (102)..(103)
<223> OTHER INFORMATION: Xaa is any amino acid
<220> FEATURE:
<221> NAME/KEY: misc_feature
<222> LOCATION: (105)..(106)
<223> OTHER INFORMATION: Xaa is any amino acid
<220> FEATURE:
<221> NAME/KEY: misc_feature
<222> LOCATION: (108)..(108)
<223> OTHER INFORMATION: Xaa is Y or F
<220> FEATURE:
<221> NAME/KEY: misc_feature
<222> LOCATION: (109)..(110)
<223> OTHER INFORMATION: Xaa is any amino acid
<220> FEATURE:
<221> NAME/KEY: misc_feature
<222> LOCATION: (113)..(114)
<223> OTHER INFORMATION: Xaa is any amino acid
<220> FEATURE:
<221> NAME/KEY: misc_feature
<222> LOCATION: (116)..(117)

```
<223> OTHER INFORMATION: Xaa is any amino acid
<220> FEATURE:
<221> NAME/KEY: misc_feature
<222> LOCATION: (118)..(118)
<223> OTHER INFORMATION: Xaa is I or V
<220> FEATURE:
<221> NAME/KEY: misc_feature
<222> LOCATION: (119)..(119)
<223> OTHER INFORMATION: Xaa is any amino acid
<220> FEATURE:
<221> NAME/KEY: misc_feature
<222> LOCATION: (120)..(120)
<223> OTHER INFORMATION: Xaa is N or D
<220> FEATURE:
<221> NAME/KEY: misc_feature
<222> LOCATION: (121)..(127)
<223> OTHER INFORMATION: Xaa is any amino acid

<400> SEQUENCE: 154

Xaa Xaa Xaa Xaa Xaa Xaa Xaa Xaa Ala Xaa Xaa Xaa Xaa Xaa Xaa Ala
1               5                   10                  15

Lys Xaa Ala Leu Xaa Gly Xaa Xaa Asn Leu Xaa Xaa Ala Lys Xaa Xaa
            20                  25                  30

Ala Xaa Xaa Xaa Xaa Xaa Xaa Leu Xaa Xaa Leu Asn Xaa Ala Gln Lys
        35                  40                  45

Xaa Xaa Leu Xaa Xaa Gln Xaa Xaa Xaa Ala Xaa Xaa Val Xaa Xaa Val
    50                  55                  60

Xaa Xaa Xaa Xaa Xaa Xaa Ala Xaa Xaa Leu Xaa Xaa Ala Met Xaa Xaa
65                  70                  75                  80

Leu Xaa Xaa Xaa Xaa Xaa Xaa Xaa Xaa Xaa Thr Lys Xaa Ser Xaa Asn
                85                  90                  95

Xaa Xaa Xaa Ala Asp Xaa Xaa Lys Xaa Xaa Ala Xaa Xaa Xaa Ala Val
            100                 105                 110

Xaa Xaa Ala Xaa Xaa Xaa Xaa Xaa Xaa Xaa Xaa Xaa Xaa Xaa Xaa
        115                 120                 125
```

IMMUNOGENIC COMPOSITION FOR USE IN VACCINATION AGAINST STAPHYLOCOCCI

STATEMENT REGARDING SEQUENCE LISTING

The Sequence Listing associated with this application is provided in text format in lieu of a paper copy and is hereby incorporated by reference into the specification. The name of the text file containing the Sequence Listing is 400077_412C2_SEQUENCE_LISTING.txt. The text file is 499 KB, was created on Oct. 25, 2018, and is being submitted electronically via EFS-Web.

BACKGROUND

Technical Field

The present invention relates to the field of Staphylococcal immunogenic compositions and vaccines, their manufacture and the use of such compositions in medicine. More particularly, it relates to vaccine compositions comprising a combination of antigens for the treatment or prevention of staphylococcal infection. Methods of using such vaccines in medicine and methods for their preparation are also provided.

Description of the Related Art

The number of both community acquired and hospital acquired infections have increased over recent years with the increased use of intravascular devices. Hospital acquired (nosocomial) infections are a major cause of morbidity and mortality, more particularly in the U.S., where if affects more than 2 million patients annually. Following various studies, about 6 percent of the U.S. patients will acquire an infection during their stay in hospital. The economic burden in the USA was estimated to be more than $4.5 billion in 1992 (Emori and Gaynes, 1993, *Clin. Microbiol. Rev.* 6; 428). The most frequent infections are urinary tract infections (UTI-33% of the infections), followed by pneumonia (15.5%), surgical site infections (14.8%) and primary bloodstream infections (13%) Emori and Gaynes, 1993, *Clin. Microbiol. Rev.* 6; 428).

*Staphylococcus aureus*, Coagulase-negative Staphylococci (mostly *Staphylococcus epidermidis*), *enterococcus* spp, *Escherichia coli* and *Pseudomonas aeruginosa* are the major nosocomial pathogens. Although those pathogens almost cause the same number of infections, the severity of the disorders they can produce combined with the frequency of antibiotic resistant isolates balance this ranking towards *S. aureus* and *S. epidermidis* as being the most significant nosocomial pathogens.

*Staphylococcus aureus* is the most common cause of nosocomial infections with a significant morbidity and mortality (Romero-Vivas et al., 1995, *Infect. Dis.* 21; 1417). It is the cause of some cases of osteomyelitis, endocarditis, septic arthritis, pneumonia, abscesses and toxic shock syndrome.

*S. epidermidis* is a normal skin commensal which is also an important opportunistic pathogen responsible for infections of implanted medical devices and infections at sites of surgery. Medical devices infected by *S. epidermidis* include cardiac pacemakers, cerebrospinal fluid shunts, continuous ambulatory peritoneal dialysis catheters, orthopedic devices and prosthetic heart valves.

*S. aureus* and *S. epidermidis* infections are treated with antibiotics with penicillin being the drug of choice whereas vancomycin is used for methicillin resistant isolates. The percentage of staphylococcal strains exhibiting wide-spectrum resistance to antibiotics has become increasingly prevalent since the 1980's (Panlilo et al., 1992, *Infect. Control. Hosp. Epidemiol.* 13; 582), posing a threat for effective antimicrobial therapy. In addition, the recent emergence of vancomycin resistant *S. aureus* strain has aroused fear that methicillin resistant *S. aureus* strains will emerge and spread for which no effective therapy is available.

An alternative approach of using antibodies against staphylococcal antigens in passive immunotherapy has been investigated. Therapy involving administration of polyclonal antisera is under development (WO 00/15238, WO 00/12132) as well as treatment with a monoclonal antibody against lipoteichoic acid (WO 98/57994).

An alternative approach would be use of active vaccination to generate an immune response against staphylococci. Several candidates for inclusion as vaccine components have been identified. These include Fibronectin binding protein (U.S. Pat. No. 5,840,846), MHC II analogue (U.S. Pat. No. 5,648,240), fibrinogen binding protein (US6008341), GehD (US 2002/0169288), collagen binding protein (U.S. Pat. No. 6,288,214), SdrF, SdrG and SdrH (WO 00/12689), mutant SEA and SEB exotoxins (WO 00/02523) and 52 kDa vitronectin binding protein (WO 01/60852).

The *S. aureus* genome has been sequenced and many of the coding sequences have been identified (EP786519, WO02/094868). The same is true for *S. epidermidis* (WO 01/34809). As a refinement of this approach, others have identified proteins that are recognized by hyperimmune sera from patients who have suffered staphylococcal infection (WO01/98499, WO 02/059148).

The first generation of vaccines targeted against *S. aureus* or against the exoproteins it produces have met with limited success (Lee 1996 *Trends Microbiol.* 4; 162). There remains a need to develop effective vaccines against staphylococcal infections.

BRIEF SUMMARY

Accordingly the present invention provides an immunogenic composition comprising at least two different proteins or immunogenic fragments thereof, selected from at least two groups of proteins or immunogenic fragments selected from the following groups:

- Group a) at least one staphylococcal extracellular component binding protein or immunogenic fragment thereof selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig and MAP;
- Group b) at least one staphylococcal transporter protein or immunogenic fragment thereof selected from the group consisting of Immunodominant ABC transporter, IsdA, IsdB, $Mg^{2+}$ transporter, SitC and Ni ABC transporter;
- Group c) at least one staphylococcal regulator of virulence, toxin or immunogenic fragment thereof selected from the group consisting of alpha toxin (Hla), alpha toxin H35R mutant, RNA III activating protein (RAP).

BRIEF DESCRIPTION OF THE DRAWINGS

FIGS. 1A-1M—Polypeptide sequences of preferred proteins. Table 1 provides information on which protein is represented by each SEQ ID.

FIGS. 2A-2KK—Nucleotide sequences encoding preferred proteins. Table 1 provides information on which protein is encoded by each SEQ ID.

FIG. 3 (Panel A and Panel B) Purification of alpha toxin under native conditions. Panel A shows a COOMASSIE® stained SDS-PAGE of samples prepared during the purification of alpha toxin. Lane 1 molecular weight markers, lane 2—soluble fraction containing over-expressed alpha toxin, lane 3—flow through from the Ni-NTA column, lane 4—fractions eluted with 10% buffer B, lane 5—fractions eluted with 20% buffer B, lane 6—fractions eluted with 30% buffer B, lane 7—fractions eluted with 50% buffer B, lane 8—fractions eluted with 75% buffer B, lane 9 and 10 fractions eluted with 100% buffer B, lane 11 bacteria at T=0 before induction, lane 12—bacteria at T=4 hours after induction, lane 13—cell lysate, lane 14—soluble fraction, lane 15—insoluble fraction.

Panel B shows a COOMASSIE® stained SDS-PAGE of 10, 5, 2 and 1 μl of the purified alpha toxin.

Figure 4:
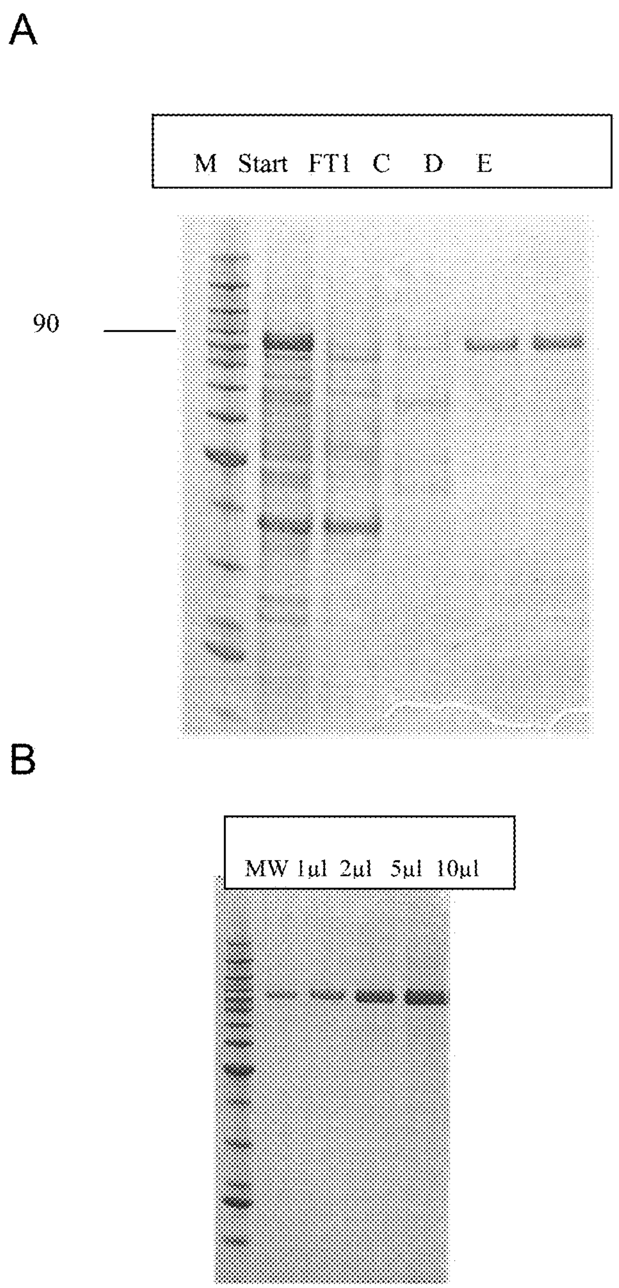

FIG. 4 (Panel A and Panel B)—Purification of SdrC under denaturing conditions. Panel A shows a COOMASSIE® stained SDS-PAGE of samples prepared during the purification of alpha toxin. Lane M—molecular weight markers, lane Start—supernatant formed from the insoluble fraction containing over-expressed SdrC, lane FT1—flow through from the Ni-NTA column, lane C—fractions eluted with wash buffer C, lane D—fractions eluted with buffer D, lane E—fractions eluted with buffer E.

Panel B shows a COOMASSIE® stained SDS-PAGE of 1, 2, 5 and 10 μl of the purified SdrC.

Figure 5A:
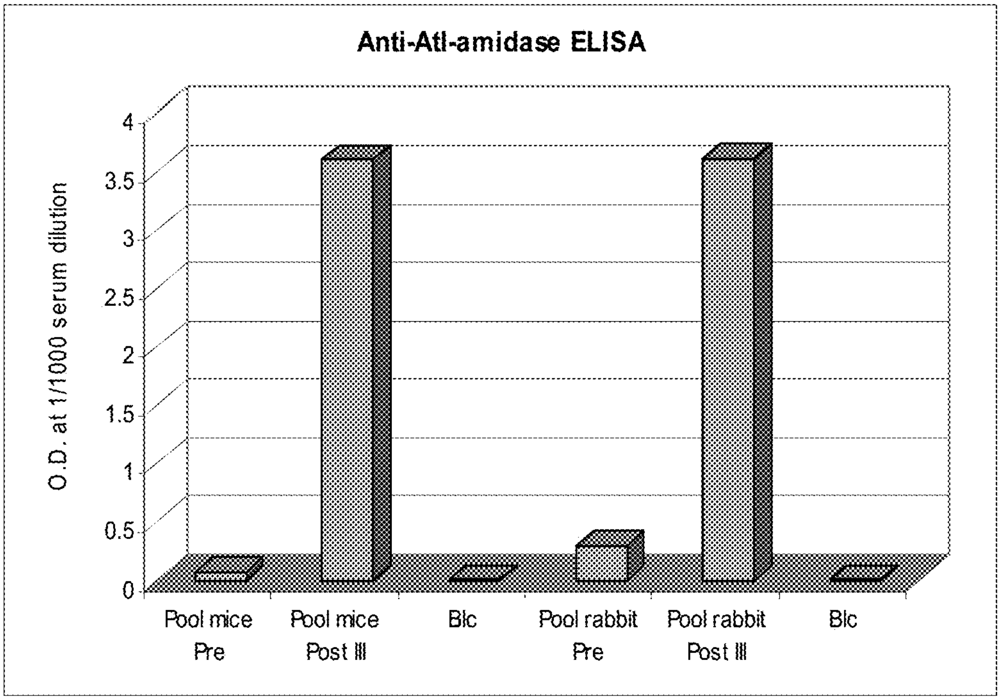
Figure 5B:
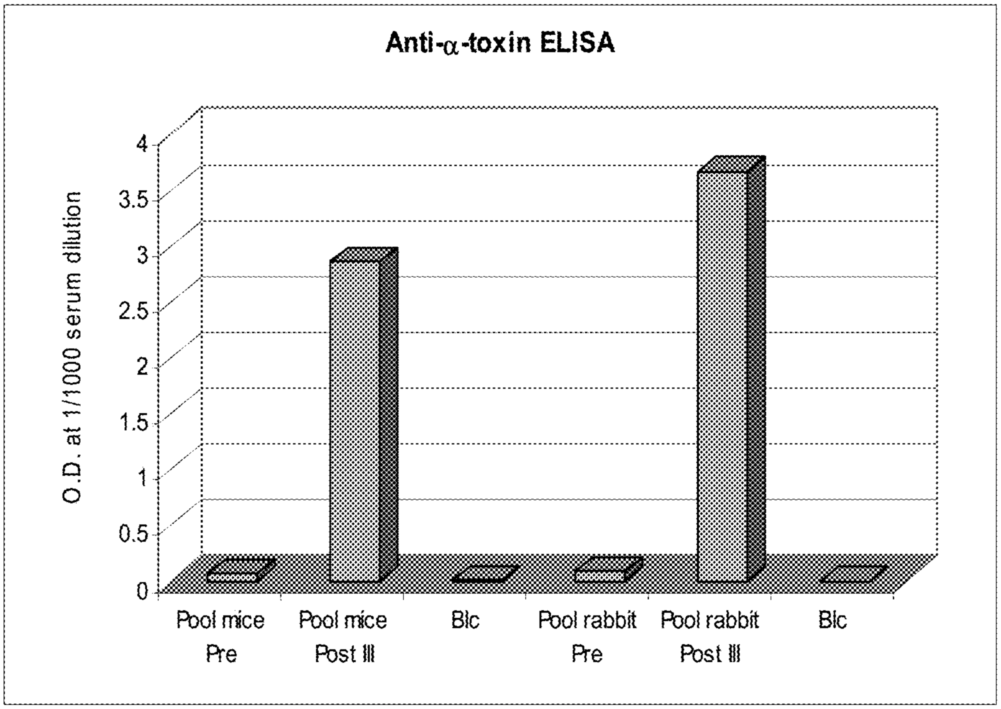
Figure 5C:
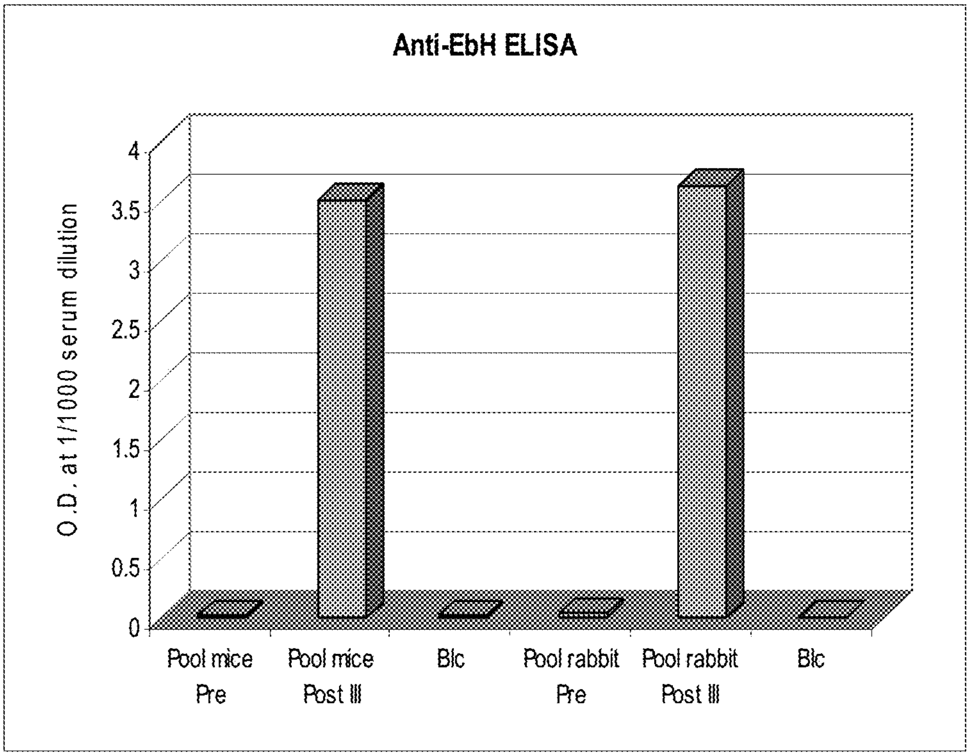
Figure 5D:
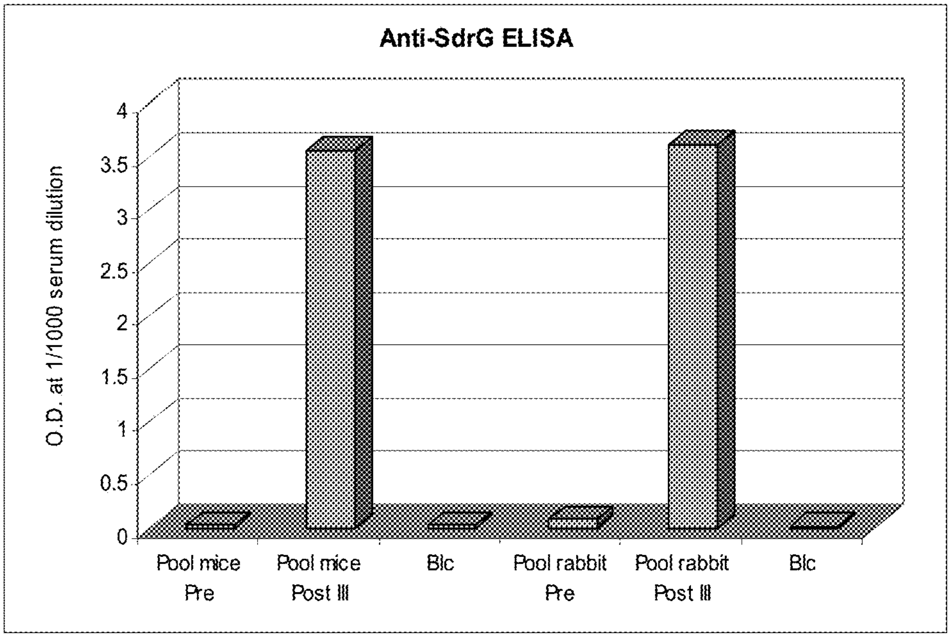
Figure 5E:
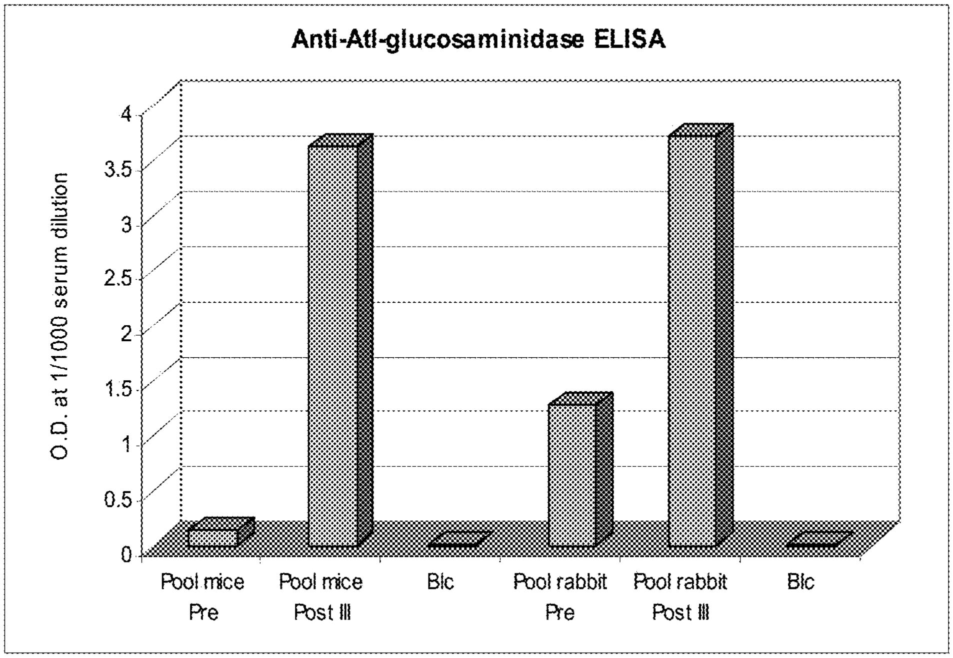
Figure 5F:
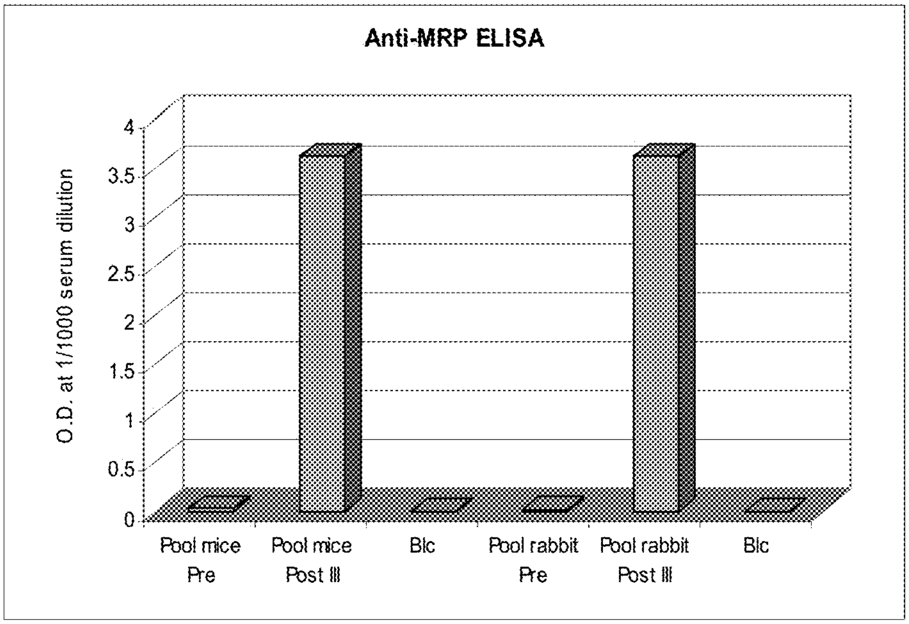
Figure 5G:
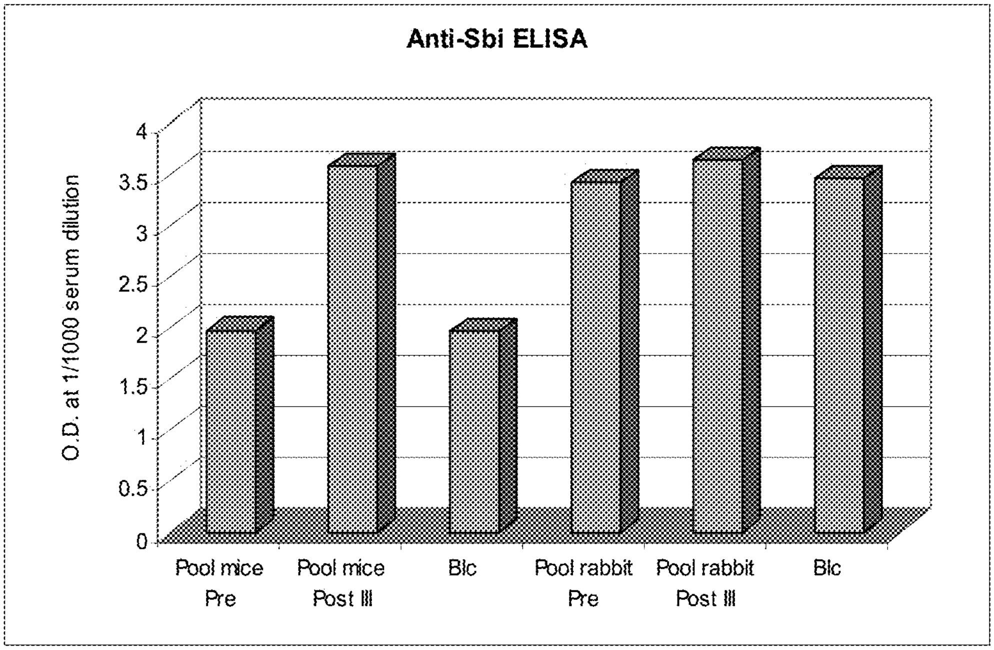
Figure 5H:
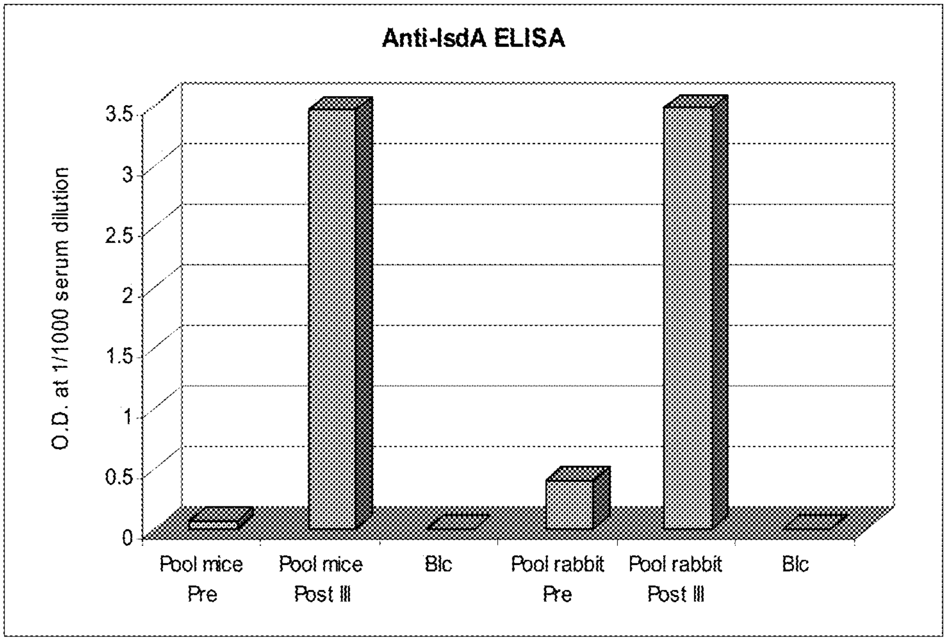
Figure 5I:
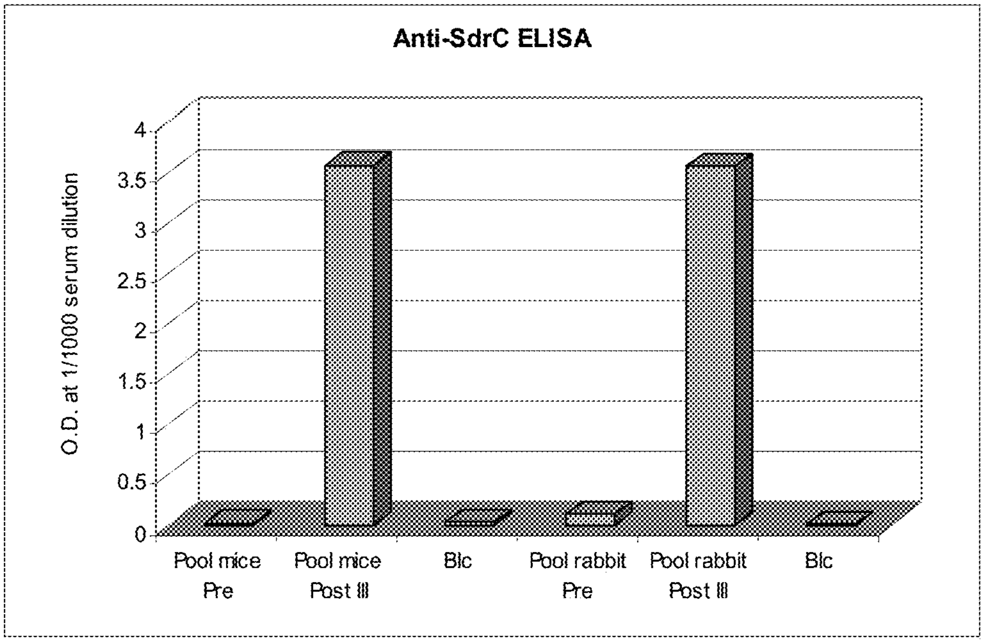
Figure 5J:
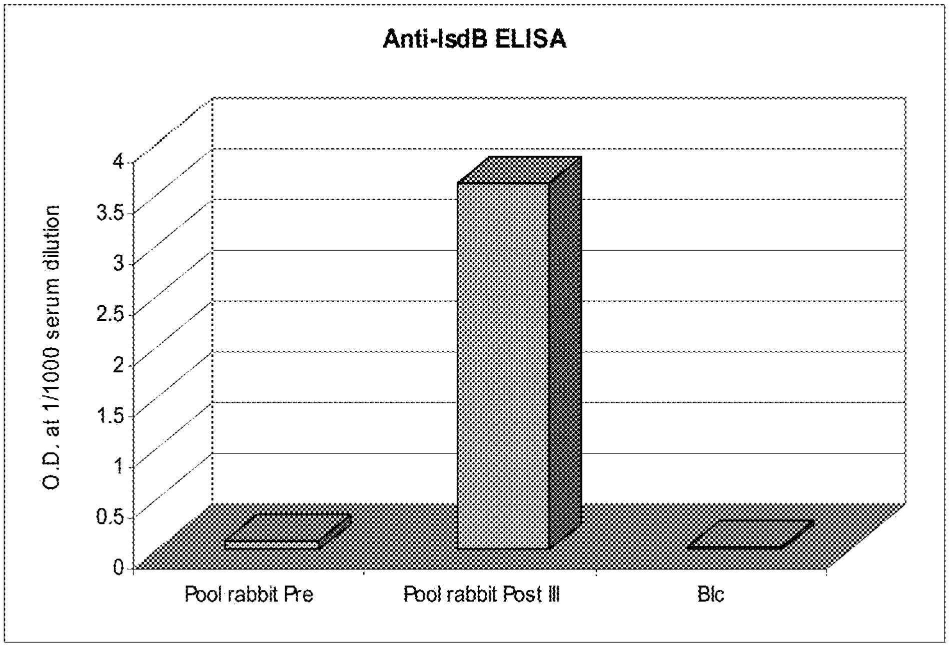
Figure 5K:
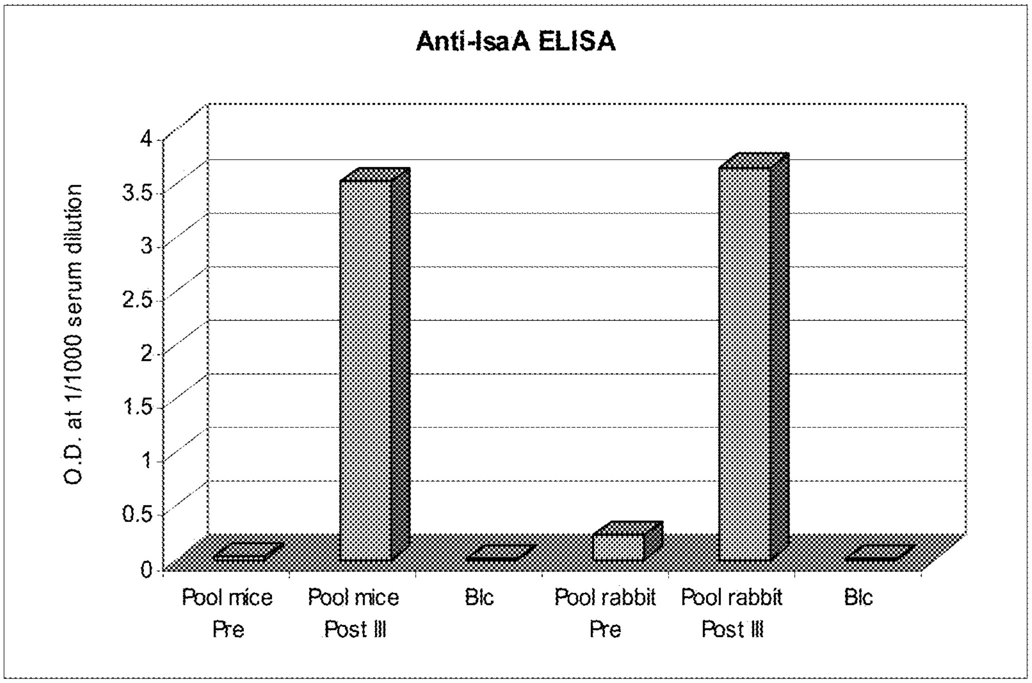
Figure 5L:
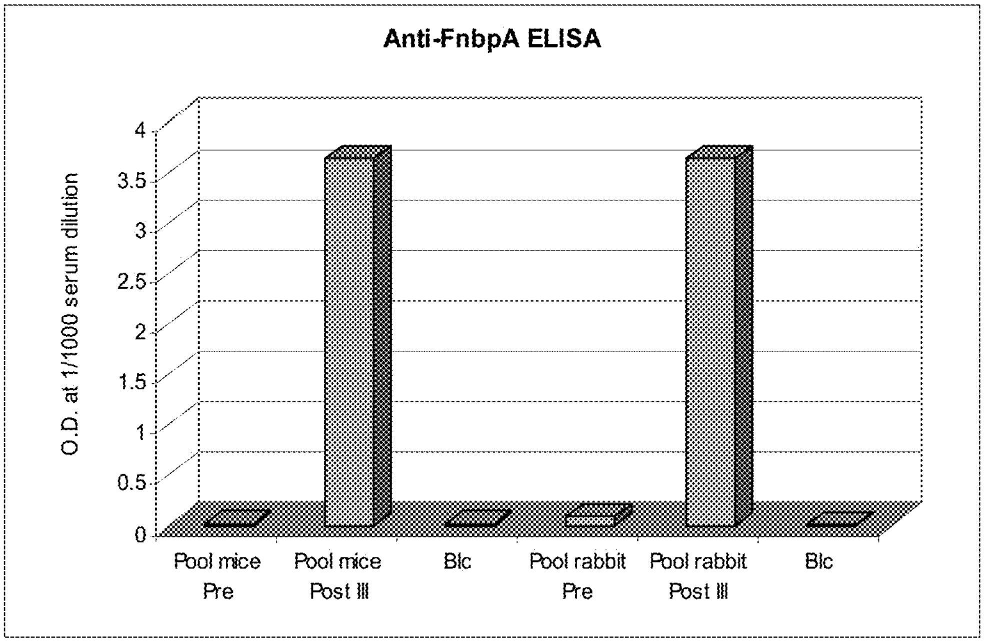
Figure 5M:
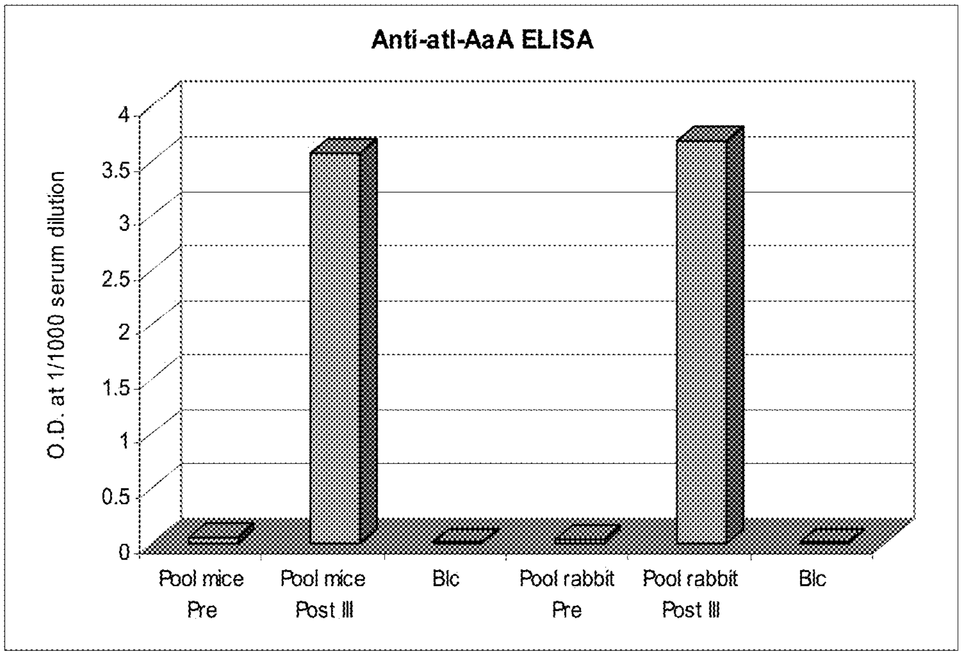
Figure 5N:
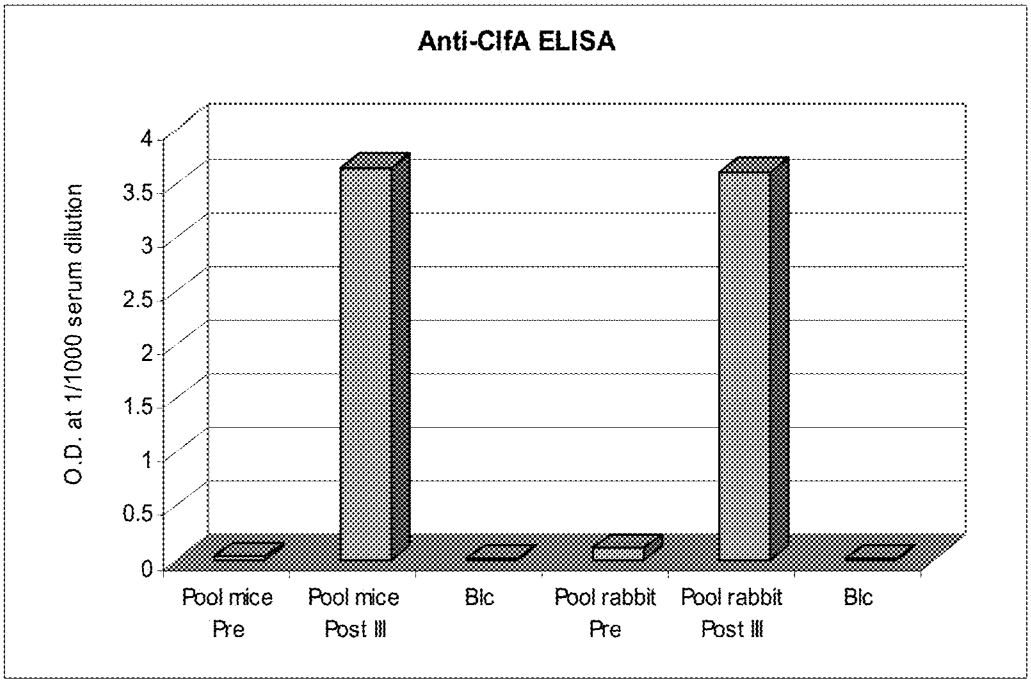
Figure 5O:
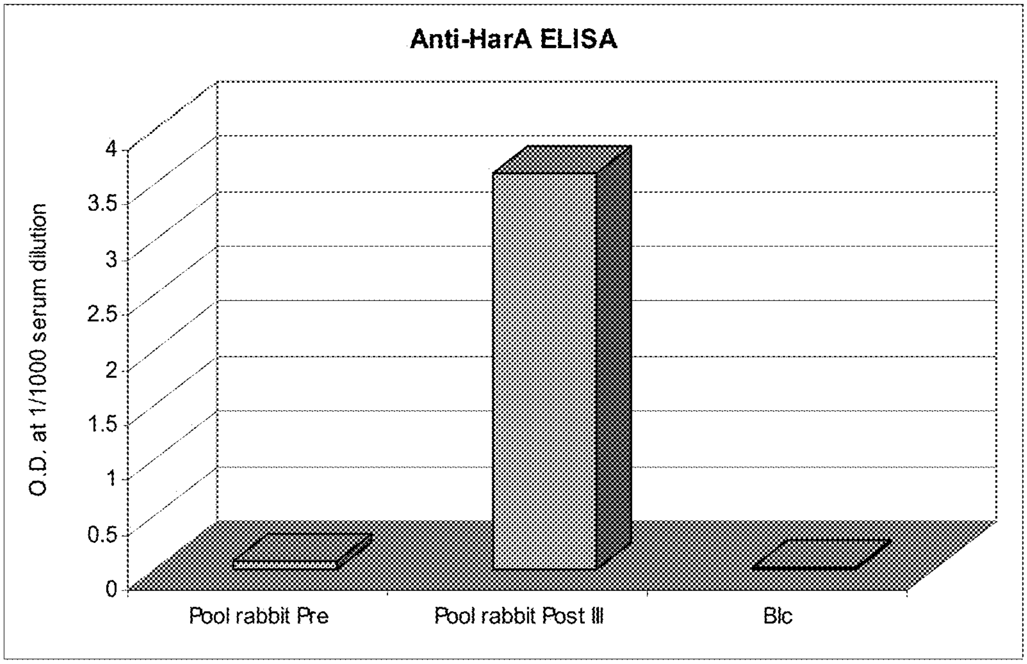
Figure 6B:
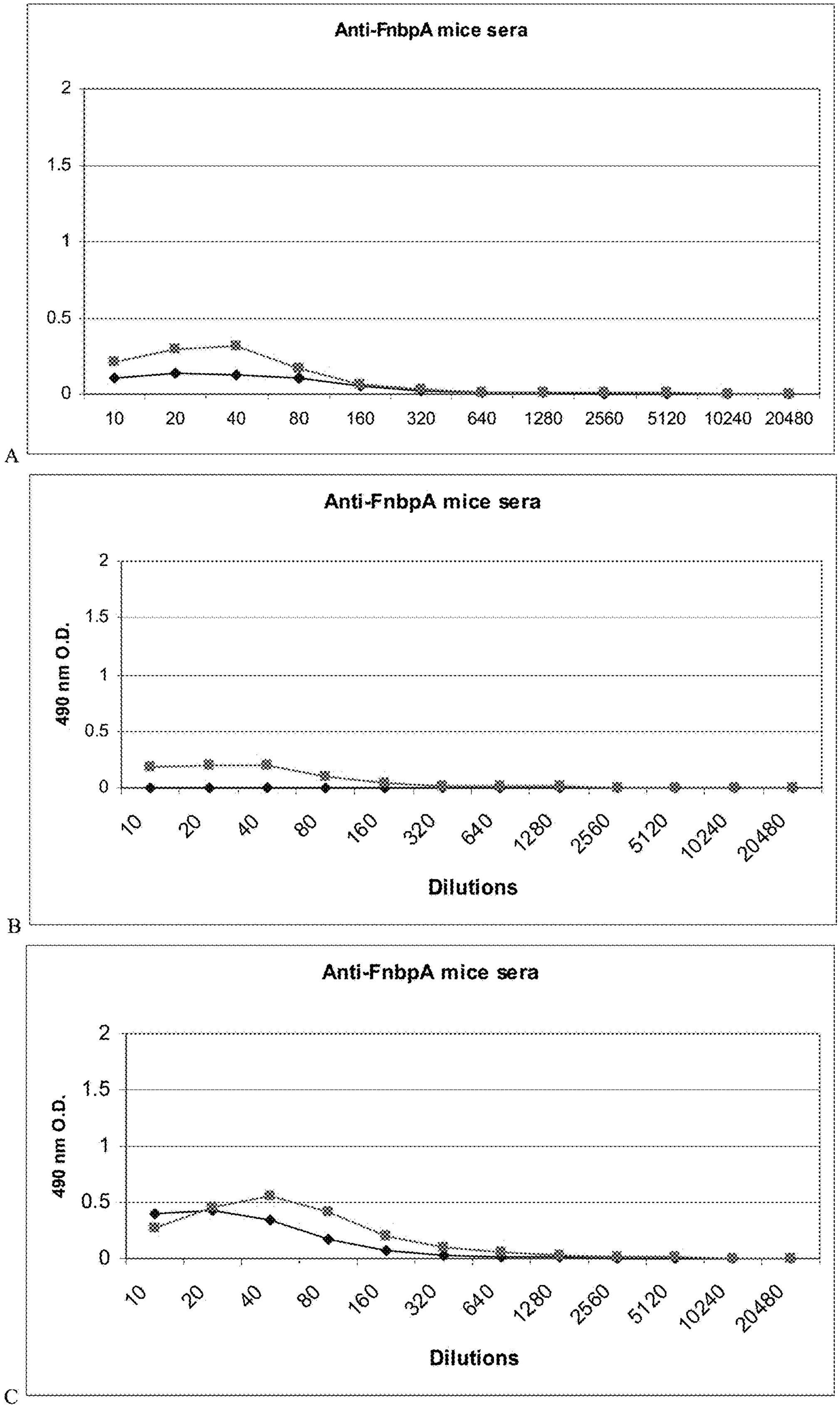
Figure 6D:
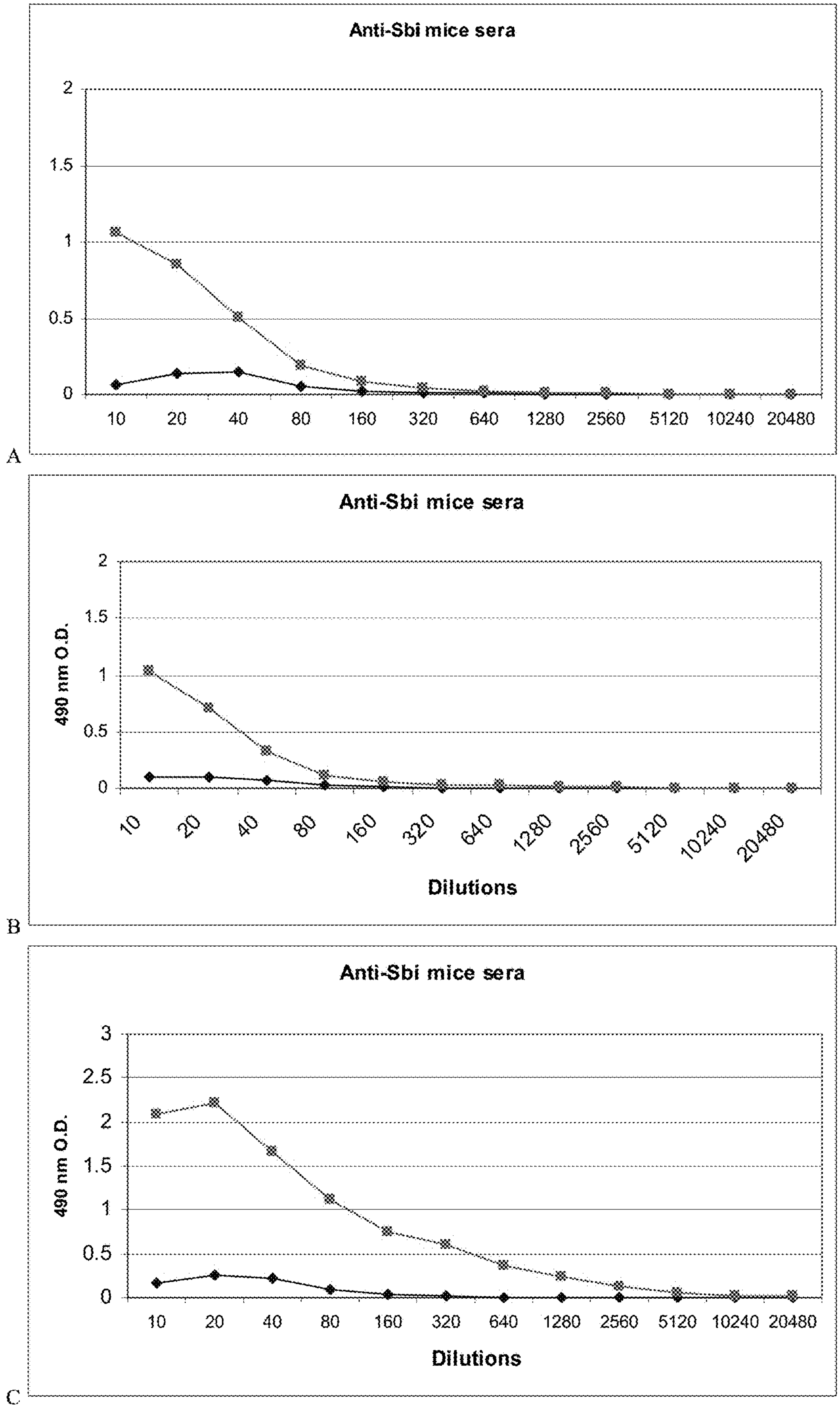
Figure 6E:
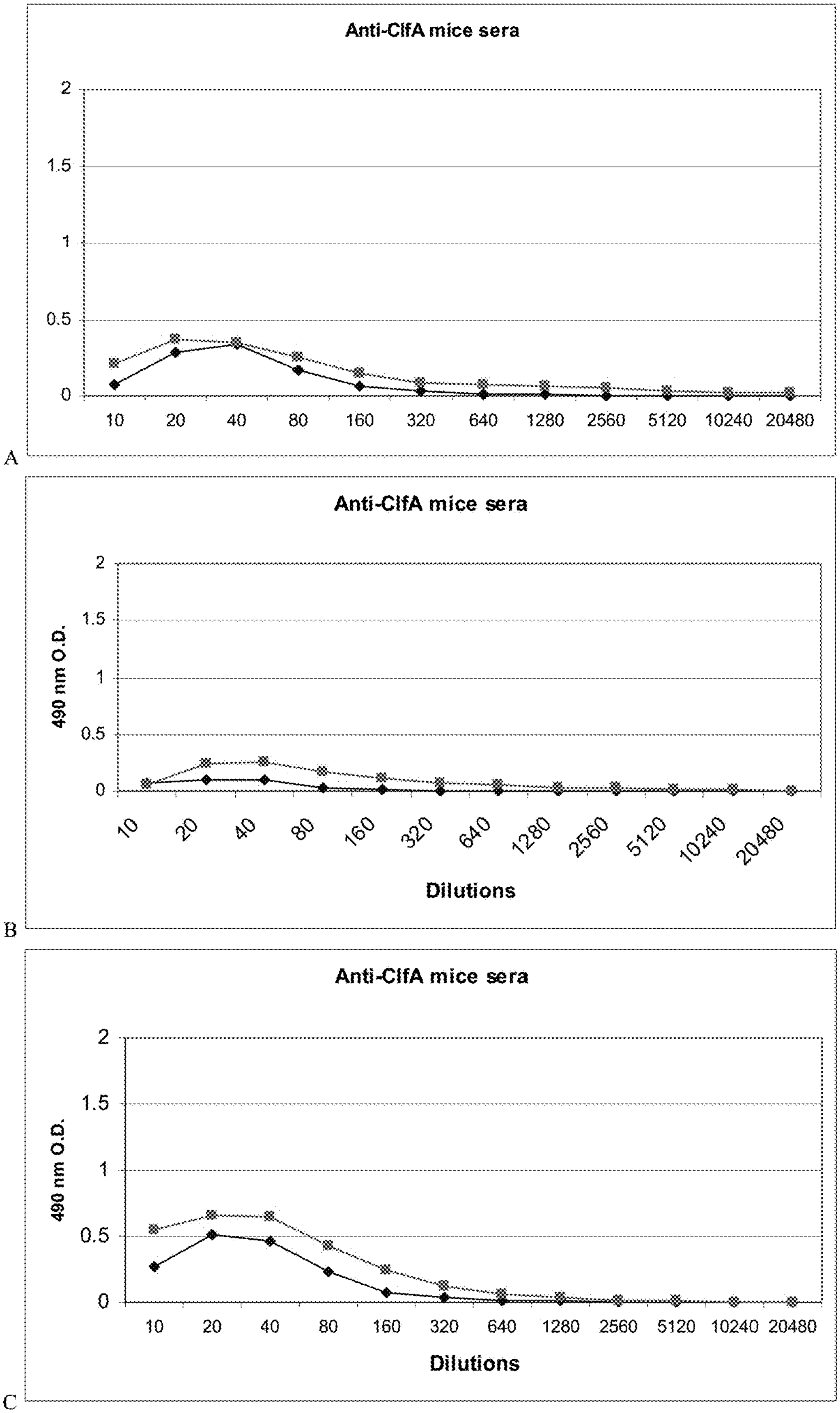
Figure 7D:
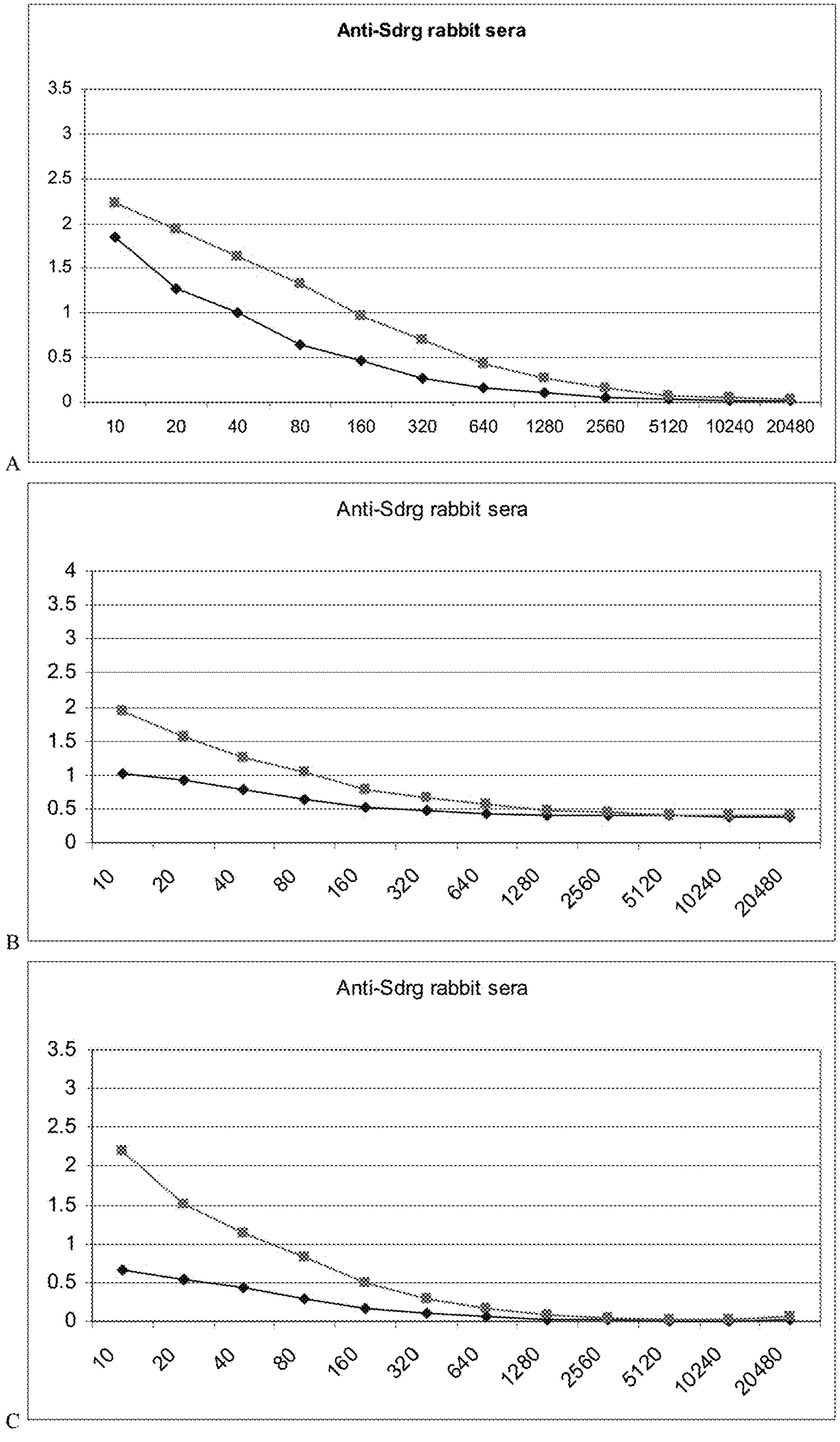
Figure 7F:
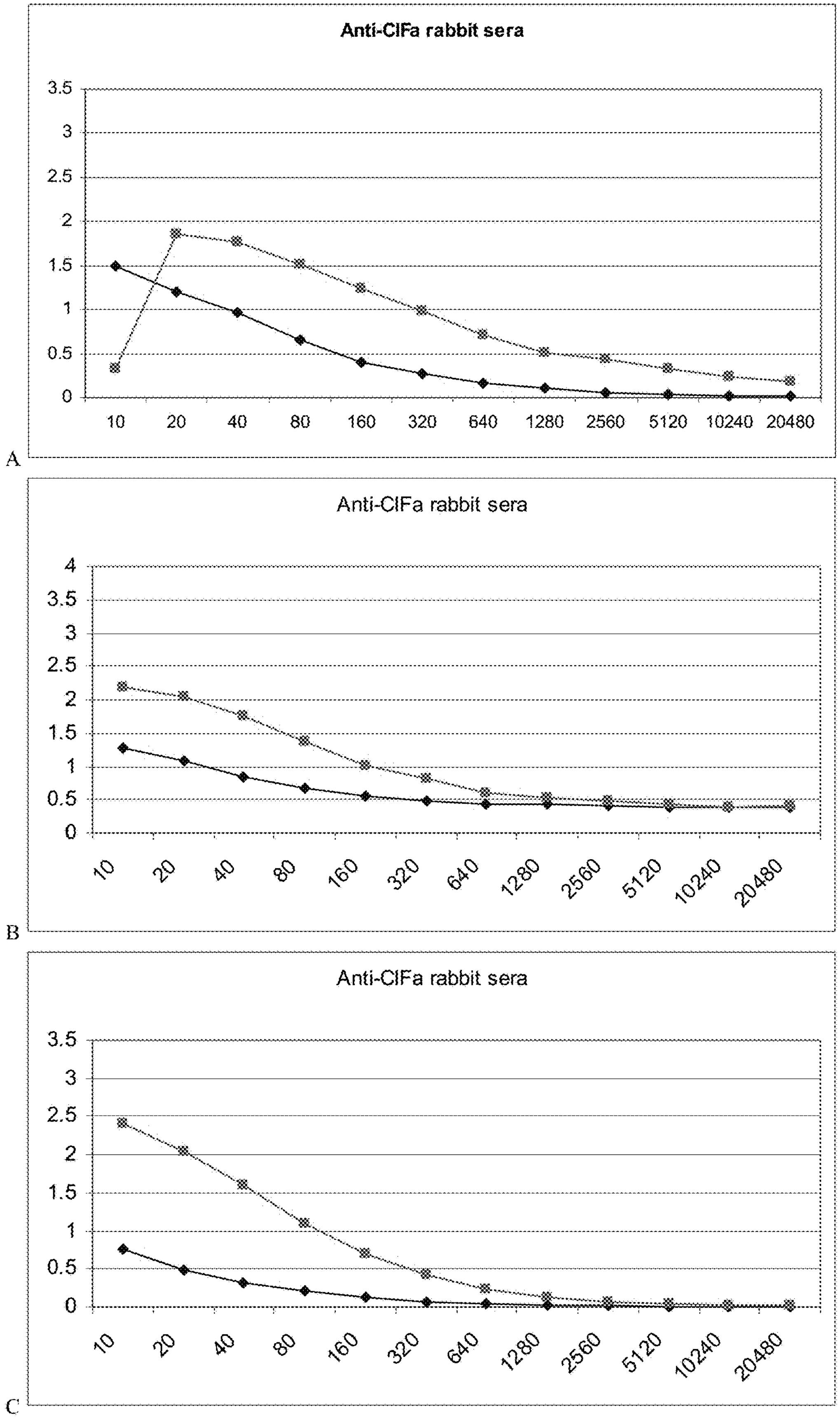
Figure 7G:
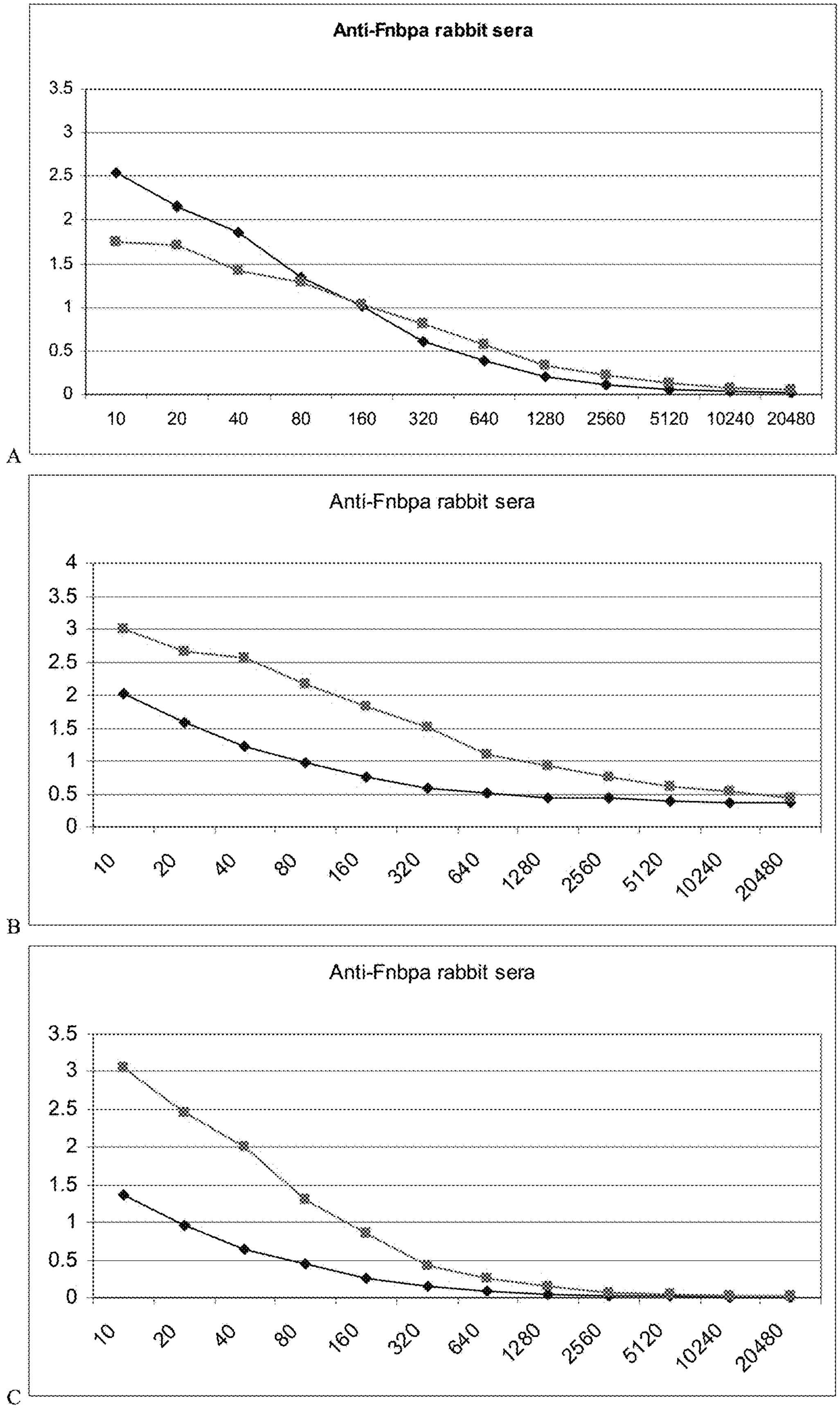

FIGS. 5A-5O—ELISA results for antisera against staphylococcal proteins in plates coated with purified proteins.

Pool mice pre-result using pooled sera extracted from mice pre-inoculation. Pool mice Post III-result using pooled mouse sera extracted post-immunization. Pool rabbit pre-result using pooled sera extracted from rabbits pre-inoculation. Pool rabbit Post III-result using pooled rabbit sera extracted post-immunization. Blc—negative control.

FIGS. 6A-6E—ELISA results for mouse antisera raised against staphylococcal proteins in plates coated with killed staphylococci.

Panel A uses plates coated with *S. aureus* serotype 5 killed whole cells. Panel B uses plates coated with *S. aureus* serotype 8 killed whole cells. Panel C uses plates coated with *S. epidermidis* killed whole cells.

The line marked with square signs shows the ELISA result using antisera from mice immunized three times with the indicated staphylococcal protein. The line marked with diamond signs shows the ELISA result for pre-immune mouse sera.

FIGS. 7A-7H—ELISA results for rabbit antisera raised against staphylococcal proteins in plates coated with killed staphylococci.

Panel A uses plates coated with *S. aureus* serotype 5 killed whole cells. Panel B uses plates coated with *S. aureus* serotype 8 killed whole cells. Panel C uses plates coated with *S. epidermidis* killed whole cells.

The line marked with square signs shows the ELISA result using antisera from rabbits immunized three times with the indicated staphylococcal protein (except for HarA where only one immunization was given). The line marked with diamond signs shows the ELISA result for pre-immune rabbit sera.

DETAILED DESCRIPTION

The present invention discloses particular combinations of Staphylococcal antigens which when combined, lead to the production of an immunogenic composition that is effective at treating or preventing staphylococcal infection. Immunogenic compositions of the invention suitably incorporate antigens which are involved in different staphylococcal functions. Such immunogenic compositions target the immune response towards different aspects of the staphylococcal function and are therefore able to induce a particularly effective immune response.

Staphylococcal infections progress through several different stages. For example, the staphylococcal life cycle involves commensal colonization, initiation of infection by accessing adjoining tissues or the bloodstream, anaerobic multiplication in the blood, interplay between *S. aureus* virulence determinants and the host defense mechanisms and induction of complications including endocarditis, metastatic abscess formation and sepsis syndrome. Different molecules on the surface of the bacterium will be involved in different steps of the infection cycle. By targeting the immune response against an effective amount of a combination of particular antigens involved in different processes of Staphylococcal infection, a Staphylococcal immunogenic composition or vaccine with increased efficacy can be achieved.

In particular, combinations of certain antigens from different classes, some of which are involved in adhesion to host cells, some of which are involved in iron acquisition or other transporter functions, some of which are toxins or regulators of virulence and immunodominant antigens can elicit an immune response which protects against multiple stages of infection.

The effectiveness of the immune response can be measured either in animal model assays as described in the examples and/or using an opsonophagocytic assay as described in the examples.

An additional advantage of the invention is that the combination of antigens of the invention from different families of proteins in an immunogenic composition will enable protection against a wider range of strains.

The invention relates to immunogenic compositions comprising a plurality of proteins selected from at least two different categories of protein, having different functions within Staphylococci. Examples of such categories of proteins are extracellular binding proteins, transporter proteins such as Fe acquisition proteins, toxins or regulators of virulence and other immunodominant proteins. The vaccine combinations of the invention are effective against homologous Staphylococcal strains (strains from which the antigens are derived) and preferably also against heterologous Staphylococcal strains.

An immunogenic composition of the invention comprises a number of proteins equal to or greater than 2, 3, 4, 5 or 6 selected from 2 or 3 of the following groups:

group a)—at least one staphylococcal extracellular component binding protein or immunogenic fragment thereof selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig and MAP;

group b)—at least one staphylococcal transporter protein or immunogenic fragment thereof selected from the group consisting of Immunodominant ABC transporter, IsdA, IsdB, Mg2+ transporter, SitC and Ni ABC transporter;

group c)—at least one staphylococcal regulator of virulence, toxin or immunogenic fragment thereof selected from the group consisting of alpha toxin (Hla), alpha toxin H35R mutant, RNA III activating protein (RAP).

For example a first protein is selected from group a), b) or c) and a second protein is selected from a group selected from groups a), b) and c) which does not include the second protein.

In a preferred embodiment, the immunogenic composition of the invention contains at least one protein selected from group a) and an additional protein selected from group b) and/or group c).

In a further embodiment, the immunogenic composition of the invention contains at least one antigen selected from group b) and an additional protein selected from group c) and/or group a).

In a further embodiment, the immunogenic composition of the invention contains at least one antigen selected from group c) and an additional protein selected from group a) and/or group b).

The immunogenic composition of the invention suitably contains proteins from *S. aureus*, and/or *S. epidermidis*.

Proteins

Immunogenic compositions of the invention comprise an isolated protein which comprises an amino acid sequence which has at least 85% identity, preferably at least 90% identity, more preferably at least 95% identity, most preferably at least 97-99% or exact identity, to that of any sequence of FIG. 1.

Where a protein is specifically mentioned herein, it is preferably a reference to a native or recombinant, full-length protein or optionally a mature protein in which any signal sequence has been removed. The protein may be isolated directly from the staphylococcal strain or produced by recombinant DNA techniques. Immunogenic fragments of the protein may be incorporated into the immunogenic composition of the invention. These are fragments comprising at least 10 amino acids, preferably 20 amino acids, more preferably 30 amino acids, more preferably 40 amino acids or 50 amino acids, most preferably 100 amino acids, taken contiguously from the amino acid sequence of the protein. In addition, such immunogenic fragments are immunologically reactive with antibodies generated against the Staphylococcal proteins or with antibodies generated by infection of a mammalian host with Staphylococci. Immunogenic fragments also includes fragments that when administered at an effective dose, (either alone or as a hapten bound to a carrier), elicit a protective immune response against Staphylococcal infection, more preferably it is protective against *S. aureus* and/or *S. epidermidis* infection. Such an immunogenic fragment may include, for example, the protein lacking an N-terminal leader sequence, and/or a transmembrane domain and/or a C-terminal anchor domain. In a preferred aspect the immunogenic fragment according to the invention comprises substantially all of the extracellular domain of a protein which has at least 85% identity, preferably at least 90% identity, more preferably at least 95% identity, most preferably at least 97-99% identity, to that a sequence selected from FIG. 1 over the entire length of the fragment sequence.

Also included in immunogenic compositions of the invention are fusion proteins composed of Staphylococcal proteins, or immunogenic fragments of staphylococcal proteins. Such fusion proteins may be made recombinantly and may comprise one portion of at least 2, 3, 4, 5 or 6 staphylococcal proteins. Alternatively, a fusion protein may comprise multiple portions of at least 2, 3, 4 or 5 staphylococcal proteins. These may combine different Staphylococcal proteins or immunogenic fragments thereof in the same protein. Alternatively, the invention also includes individual fusion proteins of Staphylococcal proteins or immunogenic fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus hemagglutinin, or bacterial proteins such as tetanus toxoid, diphtheria toxoid, CRM197.

TABLE 1

The following table sets out the SEQ ID numbers of preferred protein sequences and DNA sequences that are found in FIG. 1 and FIG. 2, respectively. SA indicates a sequence from *S. aureus* and SE indicates a sequence from *S. epidermidis.*

| Name | Protein sequence | DNA sequence |
|---|---|---|
| Immunodominant ABC transporter | | |
| SA | SEQ ID 1 | SEQ ID 34 |
| SE | SEQ ID 2 | SEQ ID 35 |
| Laminin receptor | | |
| SA | SEQ ID 3 | SEQ ID 36 |
| SE | SEQ ID 4 | SEQ ID 37 |
| Secretory Antigen A Ssa | | |
| SA 1 | SEQ ID 5 | SEQ ID 38 |
| SA 2 | SEQ ID 6 | SEQ ID 39 |
| SE | SEQ ID 7 | SEQ ID 40 |
| SitC | | |
| SA | SEQ ID 8 | SEQ ID 41 |
| SE | SEQ ID 9 | SEQ ID 42 |
| IsaA/PisA (IssA) | | |
| SA | SEQ ID 10 | SEQ ID 43 |
| SE | SEQ ID 11 | SEQ ID 44 |
| EbhA/B | | |
| SA EbhA | SEQ ID 12 | SEQ ID 45 |
| SA EbhB | SEQ ID 13 | SEQ ID 46 |
| SE EbhA | SEQ ID 14 | SEQ ID 47 |
| SE EbhB | SEQ ID 15 | SEQ ID 48 |
| Accumulation-assoc pro Aap | | |
| SA | SEQ ID 16 | SEQ ID 49 |
| SE | SEQ ID 17 | SEQ ID 50 |
| RNA III activating protein RAP | | |
| SA | SEQ ID 18 | SEQ ID 51 |
| SE | SEQ ID 19 | SEQ ID 52 |
| FIG/SdrG | | |
| SA | SEQ ID 20 | SEQ ID 53 |
| SE | SEQ ID 21 | SEQ ID 54 |
| Elastin binding protein EbpS | | |
| SA | SEQ ID 22 | SEQ ID 55 |
| SE | SEQ ID 23 | SEQ ID 56 |

TABLE 1-continued

The following table sets out the SEQ ID numbers of preferred protein sequences and DNA sequences that are found in FIG. 1 and FIG. 2, respectively. SA indicates a sequence from *S. aureus* and SE indicates a sequence from *S. epidermidis*.

| Name | Protein sequence | DNA sequence |
|---|---|---|
| Extracellular protein EFB SA | SEQ ID 24 | SEQ ID 57 |
| alpha toxin SA | SEQ ID 25 | SEQ ID 58 |
| SBI SA | SEQ ID 26 | SEQ ID 59 |
| IsdA SA | SEQ ID 27 | SEQ ID 60 |
| IsdB SA | SEQ ID 28 | SEQ ID 61 |
| SdrC SA | SEQ ID 29 | SEQ ID 62 |
| ClfA SA | SEQ ID 30 | SEQ ID 63 |
| FnbA SA | SEQ ID 31 | SEQ ID 64 |
| ClfB SA | SEQ ID 32 | SEQ ID 65 |
| Coagulase SA | SEQ ID 33 | SEQ ID 66 |
| FnbB SA | SEQ ID 67 | SEQ ID 71 |
| MAP SA | SEQ ID 68 | SEQ ID 72 |
| SdrC SA | SEQ ID 69 | SEQ ID 73 |
| SdrG SA | SEQ ID 70 | SEQ ID 74 |

Extracellular Component Binding Proteins

Extracellular component binding proteins are proteins that bind to host extracellular components. The term includes, but is not limited to adhesins.

Examples of extracellular component binding proteins include laminin receptor (Naidu et al., *J. Med. Microbiol.* 1992, 36; 177), SitC/MntC/saliva binding protein (U.S. Pat. No. 5,801,234, Wiltshire and Foster, *Infect. Immun.* 2001, 69; 5198), EbhA (Williams et al., *Infect. Immun.* 2002, 70; 6805), EbhB, Elastin binding protein (EbpS) (Park et al., 1999, *J. Biol. Chem.* 274; 2845), EFB (FIB) (Wastfelt and Flock, 1995, *J. Clin. Microbiol.* 33; 2347), SBI (Zhang et al., *FEMS Immun. Med. Microbiol.* 2000, 28; 211), autolysin (Rupp et al., 2001, *J. Infect. Dis.* 183; 1038), ClfA (U.S. Pat. No. 6,008,341, McDevitt et al., *Mol. Microbiol.* 1994, 11; 237), SdrC, SdrG (McCrea et al., *Microbiology* 2000, 146; 1535), SdrH (McCrea et al., *Microbiology* 2000, 146; 1535), Lipase GehD (US2002/0169288), SasA, FnbA (Flock et al., *Mol Microbiol.* 1994, 12; 599, U.S. Pat. No. 6,054,572), FnbB (WO 97/14799, Booth et al., 2001 *Infect. Immun.* 69; 345), collagen binding protein Cna (Visai et al., 2000, *J. Biol. Chem.* 275; 39837), ClfB (WO 99/27109), FbpA (Phonimdaeng et al., 1988 *J. Gen Microbiol.* 134; 75), Npase (Flock 2001 *J. Bacteriol.* 183; 3999), IsaA/PisA (Lonenz et al., *FEMS Immuno. Med. Microbiol.* 2000, 29; 145), SsaA (Lang et al., *FEMS Immunol. Med. Microbiol.* 2000, 29; 213), EPB (Hussain and Hermann symposium on Staph Denmark 14-17$^{th}$ 2000), SSP-1 (Veenstra et al., 1996, *J. Bacteriol.* 178; 537), SSP-2 (Veenstra et al., 1996, *J. Bacteriol.* 178; 537), 17 kDa heparin binding protein HBP (Fallgren et al., 2001, *J. Med. Microbiol.* 50; 547), Vitronectin binding protein (Li et al., 2001, *Curr. Microbiol.* 42; 361), fibrinogen binding protein, coagulase, Fig (WO 97/48727) and MAP (U.S. Pat. No. 5,648,240).

SitC/MntC/Saliva Binding Protein

This is an ABC transporter protein which is a homologue of adhesin PsaA in *S. pneumoniae*. It is a highly immunogenic 32 kDa lipoprotein which is distributed through the bacterial cell wall (Cockayne et al., *Infect. Immun.* 1998 66; 3767). It is expressed in *S. aureus* and *S. epidermidis* as a 32 kDa lipoprotein and a 40 kDa homologue is present in *S. hominis*. In *S. epidermidis*, it is a component of an iron-regulated operon. It shows considerable homology to both adhesins including FimA of *Streptococcus parasanguis*, and with lipoproteins of a family of ABC transporters with proven or putative metal iron transport functions. Therefore SitC is included as an extracellular binding protein and as a metal ion transporter.

The saliva binding protein disclosed in U.S. Pat. No. 5,801,234 is also a form of SitC and can be included in an immunogenic composition of the invention.

ClfA and CHB

Both these proteins have fibrinogen binding activity and trigger *S. aureus* to form clumps in the presence of plasma. They contain a LPXTG motif common to wall associated proteins.

ClfA is described in U.S. Pat. No. 6,008,341 and ClfB is described in WO 99/27109.

Coagulase (FbpA)

This is a fibrinogen binding protein which triggers *S. aureus* to form clumps in the presence of plasma. It is described in references related to Coagulase: Phonimdaeng et al., (J. Gen. Microbiol. 1988, 134:75-83), Phonimdaeng et al., (*Mol, Microbiol,* 1990; 4:393-404), Cheung et al. (*Infect. Immun.* 1995; 63:1914-1920) and Shopsin et al. (*J. Clin. Microbiol.* 2000; 38:3453-3456).

Preferred fragments for inclusion in the immunogenic composition of the invention include the mature protein in which the signal peptide has been removed (amino acids 27 to the C-terminus).

Coagulase has three distinct domains. Amino acids 59-297 which is a coiled coil region, amino acids 326-505 which is a proline and glycine rich region and the C-terminal domain from amino acid 506 to 645 which has a beta sheet conformation. Each of these domains is a preferred fragment of the invention.

SdrG-Fbe—EfB/Fig

Fbe is a fibrinogen binding protein that is found in many isolates of *S. epidermidis* and has a deduced molecular weight of 119 kDa (Nilsson et al., 1998. *Infect. Immun.* 66; 2666). Its sequence is related to that of clumping factor from *S. aureus* (ClfA). Antibodies against Fbe can block the binding of *S. epidermidis* to fibrinogen coated plates and to catheters (Pei and Flock, 2001, *J. Infect. Dis.* 184; 52). This protein is also described as SdrG in WO 00/12689. SdrG is found in coagulase negative staphylococci and is a cell wall associated protein containing a LPXTG sequence.

SdrG contains a signal peptide (amino acids 1-51), a region containing fibrinogen binding sites and collagen binding sites (amino acids 51-825), two CnaB domains (amino acids 627-698 and 738-809), a SD repeat region (amino acids 825-1000) and an anchor domain (amino acids 1009-1056).

Fbe has a putative signal sequence with a cleavage site between amino acids 51 and 52. Therefore a preferred fragment of Fbe contains the mature form of Fbe extending from amino acid 52 to the C-terminus (amino acid 1,092).

The domain of Fbe from amino acid 52 to amino acid 825 is responsible for fibrinogen binding. Therefore a preferred fragment of Fbe consists of or contains amino acids 52-825.

The region between amino acid 373 and 516 of Fbe shows the most conservation between Fbe and ClfA. Preferred fragment will therefore contain amino acids 373-516 of Fbe.

Amino acids 825-1041 of Fbe contains a highly repetitive region composed of tandemly repeated aspartic acid and serine residues.

Preferred fragments of SdrG include polypeptides in which the signal peptide and/or the SD repeats and the anchor domain have been removed. These include polypeptides comprising or consisting of amino acids 50-825, amino acids 50-633, amino acids 50-597 (SEQ ID NO 2 of WO 03/76470), amino acids 273-597 (SEQ ID NO 4 of WO 03/76470), amino acids 273-577 (SEQ ID NO 6 of WO 03/76470) amino acids 1-549, amino acids 219-549, amino acids 225-549, amino acids 219-528, amino acids 225-528 of SEQ ID NO:70.

Preferably, an SdrG polypeptide having a sequence at least 80%, 85%, 90%, 92%, 95%, 97%, 98%, 99% or 100% homologous to the sequence of SEQ ID 70, 20 or 21 is incorporated into the immunogenic composition of the invention.

The compositions of the invention optionally comprise a fragment of the SdrG polypeptides described above.

Preferred fragments have the signal peptide and/or the SD repeat domain and/or the anchoring domain deleted. For example sequences corresponding to amino acids 1-713, 1-549, 225-549, 225-529, 24-717, 1-707, 1-690, 1-680, 1-670, 1-660, 1-650, 1-640, 1-630, 1-620, 1-610, 1-600, 34-707, 44-697, 36-689 of SEQ ID 76 or sequences having 85%, 90%, 92%, 95%, 97%, 98%, 99% or 100% identity to SEQ ID NO:70 or 20 or 21.

Preferred fragment with the signal peptide deleted have a methionine residue at the N-terminus of the fragment to ensure correct translation.

A more preferred fragment has the following sequence (SEQ ID NO: 75):—

```
MEENSVQDVKDSNTDDELSDSNDQSSDEEKNDVINNNQSINTDDNNQIIK
KEETNNYDGIEKRSEDRTESTTNVDENEATFLQKTPQDNTHLTEEEVKES
SSVESSNSSIDTAQQPSHTTINREESVQTSDNVEDSHVSDFANSKIKESN
TESGKEENTIEQPNKVKEDSTTSQPSGYTNIDEKISNQDELLNLPINEYE
NKARPLSTTSAQPSIKRVTVNQLAAEQGSNVNHLIKVTDQSITEGYDDSE
GVIKAHDAENLIYDVTFEVDDKVKSGDTMTVDIDKNTVPSDLTDSFTIPK
IKDNSGEIIATGTYDNKNKQITYTFTDYVDKYENIKAHLKLTSYIDKSKV
PNNNTKLDVEYKTALSSVNKTITVEYQRPNENRTANLQSMFTNIDTKNHT
VEQTIYINPLRYSAKETNVNISGNGDEGSTIIDDSTIIKVYKVGDNQNLP
DSNRIYDYSEYEDVTNDDYAQLGNNNDVNINFGNIDSPYIIKVISKYDPN
KDDYTTIQQTVTMQTTINEYTGEFRTASYDNTIAFSTSSGQGQGDLPPEK
TYKIGDYVWEDVDKDGIQNTNDNEKPLSNVLVTLTYPDGTSKSVRTDEDG
KYQFDGLKNGLTYKITFETPEGYTPTLKHSGTNPALDSEGNSVWVTINGQ
DDMTIDSGFYQTPKYSLGNYVWYDTNKDGIQGDDEKGISGVKVTLKDENG
NIISTTTTDENGKYQFDNLNSGNYIVHFDKPSGMTQTTTDSGDDDEQDAD
GEEVHVTITDHDDFSIDNGYYDDE
```

EbhA and EbhB

EbhA and EbhB are proteins that are expressed in both *S. aureus* and *S. epidermidis* (Clarke and Foster. *Infect. Immun.* 2002, 70; 6680, Williams et al., *Infect. Immun.* 2002, 20; 6805) and which bind to fibronectin. Since fibronectin is an important component of extracellular matrix, EbhA and EbhB have an important function in adhering staphylococci to host extracellular matrix.

The Ebh proteins are large, having a molecular weight of 1.1 megadaltons. It is advantageous to use a fragment of the Ebh protein rather than the complete sequence due to ease of production and formulation. The central region of the protein contains imperfect repeats which contain fibronectin binding sites. Fragments containing one or more of the repeat domains described below are preferred fragments for incorporation into the immunogenic composition of the invention.

Ebh proteins contain imperfect repeats units of 127 amino acids in length which are characterized by containing the consensus sequence:—

L.G.{10}A.{13}Q.{26}L...M..L.{33}A (SEQ ID NO: 152)

Preferably

.{19}L.G.{10}A.{13}Q.{26}L...M..L.{33}A.{12} (SEQ ID NO: 153)

More preferably

....I/V..A I/V..AK.ALN/DG..NL..AK..A.{6}L..LN. AQK..L QUV..A..V..V.{6}A..LN/D. AM..L...I/V.D/E...TK-.S.NY/F.N/DAD..K..AY/F..AV..A..I/V.N/D (SEQ ID NO: 154)

Where '.' means any amino acid and '.{10}' means any 10 amino acids and UV indicates alternative choices of amino acid.

By reference to the sequence disclosed in Kuroda et al., (2001) Lancet 357; 1225-1240, and Table 2, the repeat sequences within Ebh proteins are readily deduced.

Preferred fragments to be included in the immunogenic composition of the invention include polypeptides containing of one, two, three, four, five, six, seven, eight, nine, ten or more than 10 of the 127 amino acid repeat units. Such fragments may consist of 1, 2, 3, 4, 5, 6, 7, 8, 9, 10 or more repeats of the 127 amino acid repeat region or may consist of 1, 2, 3, 4, 5, 6, 7, 8, 9, 10 or more repeats with additional amino acid residues present at either or both ends of the fragment. A further preferred fragment is the H2 polypeptide of about 44 kDa spanning three repeats (amino acids 3202-3595) as described in Clarke et al., *Infection and Immunity* 70, 6680-6687, 2002. Such fragments will preferably be able to bind fibronectin and/or to elicit antibodies that are reactive against the whole Ebh protein.

The Ebh polypeptides are capable of binding to fibronectin. Preferred fragments of these polypeptides sequences retain the ability to bind to fibronectin. Binding to fibronectin can be assessed by ELISA as described by Clarke et al. (*Infection and Immunity* 70; 6680-6687, 2002).

Still further preferred fragments are those which comprise a B-cell or T-helper epitope, for example those fragments/peptides described in Tables 3 and 4.

TABLE 2

Repeat sequences in the full-length sequence of Ebh. The full-length sequence of Ebh is disclosed in Kuroda et al., (2001) Lancet 357; 1225-1240. The following table shows the amino acid residues at which the 127 amino acid repeats begin and end within the full length sequence.

| | Begin | End |
|---|---|---|
| 1 | 3204 | 3330 |
| 2 | 3331 | 3457 |
| 3 | 3457 | 3583 |
| 4 | 3583 | 3709 |
| 5 | 3709 | 3835 |
| 6 | 3835 | 3961 |
| 7 | 3961 | 4087 |
| 8 | 4200 | 4326 |
| 9 | 4326 | 4452 |
| 10 | 4452 | 4578 |
| 11 | 4578 | 4704 |
| 12 | 4704 | 4830 |
| 13 | 4830 | 4956 |
| 14 | 4956 | 5082 |
| 15 | 5082 | 5208 |
| 16 | 5208 | 5334 |
| 17 | 5334 | 5460 |
| 18 | 5460 | 5586 |
| 19 | 5585 | 5711 |
| 20 | 5711 | 5837 |

TABLE 2-continued

Repeat sequences in the full-length sequence of Ebh. The full-length sequence of Ebh is disclosed in Kuroda et al., (2001) Lancet 357; 1225-1240. The following table shows the amino acid residues at which the 127 amino acid repeats begin and end within the full length sequence.

| | Begin | End |
|---|---|---|
| 21 | 5837 | 5963 |
| 22 | 5963 | 6089 |
| 23 | 6089 | 6215 |
| 24 | 6215 | 6341 |
| 25 | 6341 | 6467 |
| 26 | 6467 | 6593 |
| 27 | 6593 | 6719 |
| 28 | 6719 | 6845 |
| 29 | 6845 | 6971 |
| 30 | 6971 | 7097 |
| 31 | 7097 | 7223 |
| 32 | 7223 | 7349 |
| 33 | 7349 | 7475 |
| 34 | 7475 | 7601 |
| 35 | 7601 | 7727 |
| 36 | 7727 | 7853 |
| 37 | 7852 | 7978 |
| 38 | 7978 | 8104 |
| 39 | 8104 | 8230 |
| 40 | 8230 | 8356 |
| 41 | 8356 | 8482 |
| 42 | 8482 | 8608 |
| 43 | 8604 | 8730 |
| 44 | 8858 | 8984 |

TABLE 3

B-cell epitope prediction for a 127 amino acid repeat:

The full-length sequence is disclosed in Kuroda et al., (2001) Lancet 357; 1225-1240. One of these repeats, encoded by amino acids 3204-3331 of the full-length sequence was chosen to carry out an epitope prediction:-

(SEQ ID NO: 76)
MDVNTVNQKAASVKSTKDALDGQQNLQRAKTEATNAITHASDLNQAQ

KNALTQQVNSAQNVHAVNDIKQTTQSLNTAMTGLKRGVANHNQVVQS

DNYVNADTNKKNDYNNAYNHANDIINGNAQHPVI

| Begin | End | Epitope sequence | Start | Stop |
|---|---|---|---|---|
| 5 | 10 | TVNQKA (SEQ ID NO: 77) | 3208 | 3213 |
| 14 | 19 | KSTKDA (SEQ ID NO: 78) | 3217 | 3222 |
| 21 | 33 | DGQQNLQRAKTEA (SEQ ID NO: 79) | 3224 | 3236 |
| 42 | 51 | DLNQAQKNAL (SEQ ID NO: 80) | 3245 | 3254 |
| 66 | 74 | DIKQTTQSL (SEQ ID NO: 81) | 3269 | 3277 |
| 100 | 112 | ADTNKKNDYNNAY (SEQ ID NO: 82) | 3303 | 3315 |
| 117 | 123 | DIINGNA (SEQ ID NO: 83) | 3320 | 3326 |

The "Begin" and "End" columns present the position of the predicted B-cell epitopes in the 127 amino acid repeat.
The "Start" and "Stop" columns present the position of the predicted B-cell epitopes in the Ebh full length sequence.

TABLE 4

T-helper cell epitope prediction in Ebh:

The full-length sequence is disclosed in TrEMBL database, sequence reference Q8NWQ6. One of these repeats, encoded by amino acids 3204-3331 of the full-length sequence was chosen to carry out an epitope prediction:-

(SEQ ID NO: 84)
MDVNTVNQKAASVKSTKDALDGQQNLQRAKTEATNAITHASDLNQAQ

KNALTQQVNSAQNVHAVNDIKQTTQSLNTAMTGLKRGVANHNQVVQS

DNYVNADTNKKNDYNNAYNHANDIINGNAQHPVI

| Position repeat | Epitope sequence | Position sequence |
|---|---|---|
| 1 | MDVNTVNQK (SEQ ID NO: 85) | 3204 |
| 3 | VNTVNQKAA (SEQ ID NO: 86) | 3206 |
| 6 | VNQKAASVK (SEQ ID NO: 87) | 3209 |
| 26 | LQRAKTEAT (SEQ ID NO: 88) | 3229 |
| 37 | ITHASDLNQ (SEQ ID NO: 89) | 3240 |
| 43 | LNQAQKNAL (SEQ ID NO: 90) | 3246 |
| 51 | LTQQVNSAQ (SEQ ID NO: 91) | 3254 |
| 55 | VNSAQNVHA (SEQ ID NO: 92) | 3258 |
| 61 | VHAVNDIKQ (SEQ ID NO: 93) | 3264 |
| 64 | VNDIKQTTQ (SEQ ID NO: 94) | 3267 |
| 67 | IKQTTQSLN (SEQ ID NO: 95) | 3270 |
| 74 | LNTAMTGLK (SEQ ID NO: 96) | 3277 |
| 78 | MTGLKRGVA (SEQ ID NO: 97) | 3281 |
| 81 | LKRGVANHN (SEQ ID NO: 98) | 3284 |
| 85 | VANHNQVVQ (SEQ ID NO: 99) | 3288 |
| 91 | VVQSDNYVN (SEQ ID NO: 100) | 3294 |
| 92 | VQSDNYVNA (SEQ ID NO: 101) | 3295 |
| 97 | YVNADTNKK (SEQ ID NO: 102) | 3301 |
| 98 | VNADTNKKN (SEQ ID NO: 103) | 3302 |
| 108 | YNNAYNHAN (SEQ ID NO: 104) | 3311 |
| 112 | YNHANDIIN (SEQ ID NO: 105) | 3315 |
| 118 | IINGNAQHP (SEQ ID NO: 106) | 3321 |
| 119 | INGNAQHPV (SEQ ID NO: 107) | 3322 |

The "Position repeat" column presents the position of the predicted T-cell epitopes in the repeat.
The "Position sequence" column presents the position of the predicted T-cell epitopes in the Ebh full length sequence.

Fragments of the polypeptides of the invention may be employed for producing the corresponding full-length polypeptide by peptide synthesis; therefore, these fragments may be employed as intermediates for producing the full-length polypeptides of the invention.

Particularly preferred are variants in which several, 5-10, 1-5, 1-3, 1-2 or 1 amino acids are substituted, deleted, or added in any combination.

Elastin Binding Protein (EbpS)

EbpS is a protein containing 486 amino acids with a molecular weight of 83 kDa. It is associated with the cytoplasmic membrane of *S. aureus* and has three hydrophobic regions which hold the protein in the membrane (Downer et al., 2002, *J. Biol. Chem.* 277; 243; Park et al., 1996, *J. Biol. Chem.* 271; 15803).

Two region between amino acids 1-205 and 343-486 are surface exposed on the outer face of the cytoplasmic membrane. The ligand binding domain of EbpS is located between residues 14-34 at the N-terminus (Park et al., 1999, *J. Biol. Chem.* 274; 2845).

A preferred fragment to be incorporated into the immunogenic composition of the invention would be the surface exposed fragment containing the elastin binding region (amino acids 1-205). Some preferred fragments do not contain the entire exposed loop but should contain the elastin binding region (amino acids 14-34). An alternative fragment which could be used consists of amino acids forming the second surface exposed loop (amino acids 343-486). Alternative fragments containing up to 1, 2, 5, 10, 20, 50 amino acids less at one or both ends are also possible.

Laminin Receptors

The laminin receptor of *S. aureus* plays an important role in pathogenicity. A characteristic feature of infection is bloodstream invasion which allows widespread metastatic abscess formation. Bloodstream invasion requires the ability to extravasate across the vascular basement membrane. This is achieved through binding to laminin through the laminin receptor (Lopes et al., *Science* 1985, 229; 275).

Laminin receptors are surface exposed and are present in many strains of staphylococci including *S. aureus* and *S. epidermidis.*

Sbi

Sbi is a protein having an IgG binding region and an apolipoprotein H binding domain and it is expressed in most strains of *S. aureus* (Zhang et al., 1998, *Microbiology* 144; 985).

The N-terminus of the sequence of Sbi has a typical signal sequence with a cleavage site after amino acid 29. Therefore a preferred fragment of Sbi to be incorporated into an immunogenic composition of the invention starts at amino acid residue 30, 31, 32 or 33 and continues to the C-terminus of Sbi, for example of SEQ ID NO: 26.

The IgG binding domain of Sbi has been identified as a region towards the N-terminus of the protein from amino acids 41-92. This domain is homologous to the IgG binding domains of protein A.

The minimal IgG binding domain of Sbi contains the following sequence (SEQ ID NO: 108):—

```
QTTQNNYVTDQQKAFYQVLHLKGITEEQRNQYIKTLREHPER
    ** *** *  *** * * *  * *

AQEVFSESLK
```

*—denotes amino acids which are similar between IgG binding domains

Preferred fragment of Sbi to be included in the immunogenic composition of the invention contains an IgG binding domain. This fragment contains the consensus sequence for an IgG binding domain as designated by * as shown in the above sequence. Preferably the fragment contains or consists of the complete sequence shown above. More preferably, the fragment contains or consists of amino acids 30-92, 33-92, 30-94, 33-94, 30-146, 33-146, 30-150, 33-150, 30-160, 33-160, 33-170, 33-180, 33-190, 33-200, 33-205 or 33-210 of Sbi, for example of SEQ ID NO:26.

Preferred fragment may contain 1, 2, 3, 4, 5, 6, 7, 8, 9, 10 amino acid substitutions from the sequences indicated.

Preferred fragments may contain multiple repeats (2, 3, 4, 5, 6, 7, 8, 9 or 10) of the IgG binding domain.

EFB-FIB

Fib is a 19 kDa fibrinogen binding protein which is secreted into the extracellular medium by *S. aureus*. It is produced by all *S aureus* isolates tested (Wastfelt and Flock 1995, *J. Clin. Microbiol.* 33; 2347).

*S. aureus* clumps in the presence of fibrinogen and binds to fibrinogen coated surfaces. This ability facilitates staphylococcal colonization of catheters and endothelial cells.

Fib contains a signal sequence at the N-terminus of the protein with a putative cleavage site at about amino acid 30. Therefore a preferred fragment to be introduced in the immunogenic composition of the invention would contain the sequence of the mature protein (from about amino acid 30 to the C-terminus of the protein).

IsaA/PisA

IsaA is a 29 kDa protein, also known as PisA has been shown to be a immunodominant staphylococcal protein during sepsis in hospital patients (Lorenz et al., 2000, *FEMS Immunol. Med. Microb.* 29; 145).

The first 29 amino acids of the IsaA sequence are thought to be a signal sequence. Therefore a preferred fragment of IsaA to be included in an immunogenic composition of the invention would contain amino acid residues 30 onwards, to the end of the coded sequence.

Fibronectin Binding Protein

Fibronectin binding protein A (FnbA) is described in U.S. Pat. No. 5,320,951 and Schennings et al., (1993, *Microb. Pathog.* 15; 227). Fibronectin binding protein A contains several domains that are involved in binding to fibronectin (WO 94/18327). These are called D1, D2, D3 and D4. Preferred fragments of fibronectin binding protein A or B comprise or consist of D1, D2, D3, D4, D1-D2, D2-D3, D3-D4, D1-D3, D2-D4 or D1-D4 (as described in WO 94/18327).

Fibronectin binding protein contains a 36 amino acid signal sequence. For example:

```
                                      (SEQ ID NO: 109)
VKNNLRYGIRKHKLGAASVFLGTMIVVGMGQDKEAA
```

Optionally, the mature protein omitting this signal sequence is included in the immunogenic composition of the invention.

Transporter Proteins

The cell wall of Gram positive bacteria acts as a barrier preventing free diffusion of metabolites into the bacterium. A family of proteins orchestrates the passage of essential nutrients into the bacterium and are therefore essential for the viability of the bacterium. The term transporter protein covers proteins involved in the initial step of binding to metabolites such as iron as well as those involved in actually transporting the metabolite into the bacterium.

Molecular iron is an essential co-factor for bacterial growth. Siderophores are secreted that bind free iron and then are captured by bacterial surface receptors that deliver iron for transport across the cytoplasmic membrane. Iron acquisition is critical for the establishment of human infections so that the generation of an immune response against this class of proteins leads to a loss of staphylococcal viability.

Examples of transporter proteins include Immunodominant ABC transporter (Burnie et al., 2000 *Infect. Immun.* 68; 3200), IsdA (Mazmanian et al., 2002 *PNAS* 99; 2293), IsdB (Mazmanian et al., 2002 *PNAS* 99; 2293)), $Mg^{2+}$ transporter, SitC (Wiltshire and Foster 2001 *Infect. Immun.* 69; 5198) and Ni ABC transporter.

Immunodominant ABC Transporter

Immunodominant ABC transporter is a well conserved protein which may be capable of generating an immune response that is cross-protective against different staphylococcal strains (Mei et al., 1997, *Mol. Microbiol.* 26; 399). Antibodies against this protein have been found in patients with septicemia (Burnie et al., 2000, *Infect. Immun.* 68; 3200).

Preferred fragments of immunodominant ABC transporter will include the peptides DRHFLN, GNYD, RRYPF, KTTLLK, GVTTSLS, VDWLR, RGFL, more preferably KIKVYVGNYDFWYQS, TVIVVSHDRHFLYNNV and/or TETFLRGFLGRMLFS (SEQ ID NOS: 110-119 respectively) since these sequences contain epitopes that are recognized by the human immune system.

IsdA-IsdB

The isd genes (iron-regulated surface determinant) of *S. aureus* encode proteins responsible for hemoglobin binding and passage of heme iron to the cytoplasm, where it acts as an essential nutrient. IsdA and IsdB are located in the cell wall of staphylococci. IsdA appear to be exposed on the surface of bacterium since it is susceptible to proteinase K digestion. IsdB was partially digested suggesting that it is partially exposed on the surface of the bacterium (Mazmanian et al., 2003 *Science* 299; 906).

IsdA and IsdB are both 29 kDa proteins which bind heme. Their expression is regulated by the availability of iron via the Fur repressor. Their expression will be high during infection in a host where the concentration of iron will be low.

They are also known as FrpA and FrpB (Morrissey et al., 2002, *Infect. Immun.* 70; 2399). FrpA and FrpB are major surface proteins with a high charge. They have been shown to provide a major contribution to adhesion to plastic.

In an embodiment, the immunogenic composition of the invention comprises a fragment of IsdA and/or IsdB which is described in WO 01/98499 or WO 03/11899.

Toxins and Regulators of Virulence

Members of this family of proteins include toxin such as alpha toxin, hemolysin, enterotoxin B and TSST-1 as well as proteins that regulate the production of toxins such as RAP.

Alpha Toxin (Hla)

Alpha toxin is an important virulence determinant produced by most strains of *S. aureus*. It is a pore forming toxin with hemolytic activity. Antibodies against alpha toxin have been shown to neutralize the detrimental and lethal effects of alpha toxin in animal models (Adlam et al., 1977 *Infect. Immun.* 17; 250). Human platelets, endothelial cells and mononuclear cells are susceptible to the effects of alpha toxin.

The high toxicity of alpha toxin requires that it should be detoxified before being used as an immunogen. This can be achieved by chemical treatment, for instance by treating with formaldehyde, glutaraldehyde of other cross-linking reagents or by chemically conjugating it to bacterial polysaccharides as described below.

A further way of removing toxicity is to introduce point mutations that remove toxicity while retaining the antigenicity of the toxin. The introduction of a point mutation at amino acid 35 of alpha toxin where a histidine residue is replaced with a leucine residue results in the removal of toxicity whilst retaining immunogenicity (Menzies and Kernodle 1996; *Infect. Immun.* 64; 1839). Histidine 35 appears to be critical for the proper oligomerization required for pore formation and mutation of this residue leads to loss of toxicity.

When incorporated into immunogenic compositions of the invention, alpha toxin is preferably detoxified by mutation of His 35, most preferably by replacing His 35 with Leu or Arg. In an alternative embodiment, alpha toxin is detoxified by conjugation to other components of the immunogenic composition, preferably capsular polysaccharides, most preferably to *S. aureus* type V polysaccharide and/or *S. aureus* Type VIII polysaccharide and/or PNAG.

RNA III Activating Protein (RAP)

RAP is not itself a toxin, but is a regulator of the expression of virulence factors. RAP is produced and secreted by staphylococci. It activates the agr regulatory system of other staphylococci and activates the expression and subsequent release of virulence factors such as hemolysin, enterotoxin B and TSST-1.

An immune response generated against RAP would not kill the bacterium but would interfere with their pathogenicity. This has the advantage of providing less selective pressure for new resistant strains to emerge.

It would have a second advantage of producing an immune response that would be instrumental in reducing the morbidity of the infection.

It is particularly advantageous to combine RAP with other antigens in a vaccine, particularly where the additional antigen would provide an immune response that is able to kill the bacterium.

Other Proteins

Accumulation-Associated Protein (Aap)

Aap is a 140 kDa protein which is essential for the accumulation of *S. epidermidis* strains on surfaces (Hussain et al., *Infect. Immun.* 1997, 65; 519). Strains expressing this protein produced significantly larger amounts of biofilm and Aap appear to be involved in biofilm formation. Antibodies against Aap are able to inhibit biofilm formation and inhibit the accumulation of *S. epidermidis*.

A preferred fragment of Aap is a conserved domain comprising or consisting of amino acids 550-1069.

Staphylococcal Secretory Antigen SsaA

SsaA is a strongly immunogenic protein of 30 kDa found in both *S. aureus* and *S. epidermidis* (Lang et al., 2000 *FEMS Immunol. Med. Microbiol.* 29; 213). Its expression during endocarditis suggested a virulence role specific to the pathogenesis of the infectious disease.

SsaA contains an N-terminal leader sequence and a signal peptidase cleavage site. The leader peptide is followed by a hydrophilic region of approximately 100 amino acids from residue 30 to residue 130.

A preferred fragment of SsaA to be incorporated into the immunogenic composition of the invention is made up of the mature protein (amino acids 27 to the C-terminus or amino acids 30 to the C-terminus).

A further preferred fragments contains the hydrophilic area of SsaA from amino acid 30 to amino acid 130.

Preferred combinations A preferred combination of proteins in the immunogenic composition of the invention comprises laminin receptor and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises SitC and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises EbhA and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises EbhB and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises EbpS and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises EFB(FIB) and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises SBI and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises autolysin and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises ClfA and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises SdrC and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises SdrG and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant and RAP.

A further preferred combination of proteins in the immunogenic composition of the invention comprises SdrH and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises Lipase GehD and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises SasA and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises FnbA and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises FnbB and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises Cna and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises ClfB and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises FbpA and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises Npase and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises IsaA/PisA and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises SsaA and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises EPB and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises SSP-1 and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises SSP-2 and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises HPB and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises vitronectin binding protein and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises fibrinogen binding protein and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises coagulase and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises Fig and 1, 2, 3, 4 or 5 further antigens selected from the group consisting of immunodominant ABC transporter, IsdA, IsdB, $Mg^{2+}$ transporter, SitC, Ni ABC transporter, alpha toxin, alpha toxin H35L OR H35R mutant, RAP, Aap and SsaA.

A further preferred combination of proteins in the immunogenic composition of the invention comprises MAP and 1, 2, 3, 4 or 5 further antigens selected from the group consisting of immunodominant ABC transporter, IsdA, IsdB, Mg2+ transporter, SitC, Ni ABC transporter, alpha toxin, alpha toxin H35L OR H35R mutant, RAP, Aap and SsaA.

A further preferred combination of protein in the immunogenic composition of the invention comprises immunodominant ABC transporter and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, CHB, FbpA, Npase, IsaA/PisA, SsaA, EPB, SSP-1, SSP-2, HBP, Vitronectin binding protein, fibrinogen binding protein, coagulase, Fig, MAP, alpha toxin, alpha toxin H35L OR H35R mutant, RAP, Aap and SsaA.

A further preferred combination of protein in the immunogenic composition of the invention comprises IsdA and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig, MAP, alpha toxin, alpha toxin H35L OR H35R mutant, RAP, Aap and SsaA.

A further preferred combination of protein in the immunogenic composition of the invention comprises IsdB and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig, MAP, alpha toxin, alpha toxin H35L OR H35R mutant, RAP, Aap and SsaA.

A further preferred combination of protein in the immunogenic composition of the invention comprises SitC and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig, MAP, alpha toxin, alpha toxin H35L OR H35R mutant, RAP, Aap and SsaA.

A further preferred combination of protein in the immunogenic composition of the invention comprises alpha toxin and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig, MAP, immunodominant ABC transporter, IsdA, IsdB, $Mg^{2+}$ transporter, SitC, Ni ABC transporter, Aap and SsaA.

A further preferred combination of protein in the immunogenic composition of the invention comprises alpha toxin H35L OR H35R variant and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, CHB, FbpA, Npase, IsaA/PisA, SsaA, EPB, SSP-1, SSP-2, HBP, Vitronectin binding protein, fibrinogen binding protein, coagulase, Fig, MAP, immunodominant ABC transporter, IsdA, IsdB, $Mg^{2+}$ transporter, SitC, Ni ABC transporter, Aap and SsaA.

A further preferred combination of protein in the immunogenic composition of the invention comprises RAP and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig, MAP, immunodominant ABC transporter, IsdA, IsdB, $Mg^{2+}$ transporter, SitC, Ni ABC transporter, Aap and SsaA.

A further preferred combination of protein in the immunogenic composition of the invention comprises Aap and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig, MAP, immunodominant ABC transporter, IsdA, IsdB, $Mg^{2+}$ transporter, SitC, Ni ABC transporter, RAP, alpha toxin and H35L OR H35R alpha toxin.

A further preferred combination of protein in the immunogenic composition of the invention comprises SsaA and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig, MAP, immunodominant ABC transporter, IsdA, IsdB, $Mg^{2+}$ transporter, SitC, Ni ABC transporter, RAP, alpha toxin and H35L OR H35R alpha toxin.

The inventors have demonstrated that certain antigens produce a particularly effective immune response within the context of a mixture of antigens. Accordingly, an embodiment of the invention is an immunogenic composition comprising IsaA and a staphylococcal transporter protein, or IsaA and a staphylococcal regulator of virulence or toxin, or comprising Sbi and a staphylococcal transporter protein, or Sbi and a staphylococcal regulator of virulence or toxin, or comprising SdrC and a staphylococcal transporter protein, or SdrC and a staphylococcal regulator of virulence or toxin, or IsaA and Sbi, or IsaA and SdrC, or IsaA and autolysin, or IsaA and Ebh, or Sbi and SdrC, or Sbi and Autolysin, or Sbi and Ebh, or SdrC and autolysin, or SdrC and Ebh, or Autolysin-glucosaminidase and Ebh. For each of these combinations, the proteins may be full length or fragments, having sequences at least 85%, 90%, 95%, 98% or 100% identical to that of the sequences of FIG. 1.

In the above and below combinations, the specified proteins may optionally be present in the immunogenic composition of the invention as a fragment or fusion protein as described above.

Preferred immunogenic compositions of the invention do not include the protein sequences disclosed in WO02/094868.

Combinations of Three Proteins

A preferred immunogenic composition of the invention contains three protein components in a combination of alpha-toxin, an extracellular component binding protein (preferably an adhesin) and a transporter protein (preferably an iron-binding protein).

In such a combination, the alpha toxin may be chemically detoxified or genetically detoxified by introduction of point mutation(s), preferably the His35Leu point mutation.

The alpha toxin is present as a free protein or alternatively is conjugated to a polysaccharide or LTA component of the immunogenic composition.

Preferred combinations include:—

- An immunogenic composition comprising alpha toxin, IsdA and an extracellular component binding protein selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig and MAP.
- An immunogenic composition comprising alpha toxin, IsdB and an extracellular component binding protein selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig and MAP.
- An immunogenic composition comprising alpha toxin, IsdA and an adhesin selected from the group consisting of laminin receptor, EbhA, EbhB, Elastin binding protein (EbpS), EFB (FIB), ClfA, SdrC, SdrG, SdrH, autolysin, FnbA, FnbB, Cna, ClfB, FbpA, Npase, SSP-1, SSP-2, Vitronectin binding protein, fibrinogen binding protein, coagulase, Fig and MAP.
- An immunogenic composition comprising alpha toxin, IsdB and an adhesin selected from the group consisting of laminin receptor, EbhA, EbhB, Elastin binding protein (EbpS), EFB (FIB), autolysin, ClfA, SdrC, SdrG, SdrH, FnbA, FnbB, Cna, ClfB, FbpA, Npase, SSP-1, SSP-2, Vitronectin binding protein, fibrinogen binding protein, coagulase, Fig and MAP.
- An immunogenic composition comprising alpha toxin, IsdA and laminin receptor.
- An immunogenic composition comprising alpha toxin, IsdA and EbhA.
- An immunogenic composition comprising alpha toxin, IsdA and EbhB.
- An immunogenic composition comprising alpha toxin, IsdA and EbpS.
- An immunogenic composition comprising alpha toxin, IsdA and EFB (FIB).
- An immunogenic composition comprising alpha toxin, IsdA and SdrG.
- An immunogenic composition comprising alpha toxin, IsdA and ClfA.
- An immunogenic composition comprising alpha toxin, IsdA and ClfB.
- An immunogenic composition comprising alpha toxin, IsdA and FnbA.
- An immunogenic composition comprising alpha toxin, IsdA and coagulase.
- An immunogenic composition comprising alpha toxin, IsdA and Fig.

An immunogenic composition comprising alpha toxin, IsdA and SdrH.

An immunogenic composition comprising alpha toxin, IsdA and SdrC.

An immunogenic composition comprising alpha toxin, IsdA and MAP.

An immunogenic composition comprising IsaA and Sbi.

An immunogenic composition comprising IsaA and IsdB.

An immunogenic composition comprising IsaA and IsdA.

An immunogenic composition comprising IsaA and SdrC.

An immunogenic composition comprising IsaA and Ebh or fragment thereof as described above.

An immunogenic composition comprising Sbi and SdrC.

An immunogenic composition comprising Sbi and Ebh or fragment thereof as described above.

An immunogenic composition of the invention comprising IsaA, Sbi or SdrC.

Selection of Antigens Expressed in Different Clonal Lineages

Analysis of the occurrence of virulence factors in relation with the population structure of *Staphylococcus aureus* showed variable presence of virulence genes in natural populations of *S. aureus*.

Among clinical isolates of *Staphylococcus aureus*, at least five clonal lineages were shown to be highly prevalent (Booth et al., 2001 *Infect. Immun.* 69(1):345-52). Alpha-hemolysin (hla), fibronectin-binding protein A (fnbA) and clumping factor A (clfA) were shown to be present in most of the isolates, regardless of lineage identity, suggesting an important role of these proteins in the survival of *S. aureus* (Booth et al., 2001 *Infect. Immun.* 69(1):345-52). Moreover, according to Peacock et al. 2002 the distributions of fnbA, clfA, coagulase, spa, map, pvl (Panton-Valentine leukocidin), hlg (gamma-toxin), alpha-toxin and ica appeared to be unrelated to the underlying clonal structure suggesting considerable horizontal transfer of these genes.

In contrary, other virulence genes such as fibronectin binding protein B (fnbB), beta-hemolysin (hlb), collagen binding protein (cna), TSST-1 (tst) and methicillin resistance gene (mecA) are strongly associated with specific lineages (Booth et al., 2001 *Infect. Immun.* 69(1):345-52). Similarly, Peacock et al. 2002 (*Infect Immun.* 70(9):4987-96) showed that the distributions of the enterotoxins, tst, the exfolatins (eta and etb), beta- and delta-toxins, the sdr genes (sdrD, sdrE and bbp), cna, ebpS and efb within the population are all highly significantly related to MLST-derived clonal complexes.

MLST data provide no evidence that strains responsible for nosocomial disease represent a distinct subpopulation from strains causing community-acquired disease or strains recovered from asymptomatic carriers (Feil et al., 2003 *J. Bacteriol.* 185(11):3307-16).

Preferred immunogenic compositions of the invention are effective against staphylococci from different clonal lineages.

In one embodiment, this is achieved by including 1, 2, 3, 4, preferably at least 1 protein that is expressed in most isolates of staphylococci. Examples of such proteins include alpha-hemolysin (hla), fibronectin-binding protein A (fnbA) and clumping factor A (clfA), coagulase, spa, map, pvl (Panton-Valentine leukocidin), hlg (gamma-toxin) and ica. We have also identified immunodominant ABC transporter, RAP, autolysin (Rupp et al., 2001, *J. Infect. Dis.* 183; 1038), laminin receptors, SitC, IsaA/PisA, SPOIIIE ( ) SsaA, EbpS, SasF (Roche et al 2003, Microbiology 149; 643), EFB(FIB), SBI, ClfB, IsdA, IsdB, FnbB, Npase, EBP, Bone sialo binding protein II, IsaB/PisB (Lorenz et al., *FEMS Immuno. Med. Microb.* 2000, 29; 145), SasH (Roche et al., 2003, *Microbiology* 149; 643), MRPI, SasD (Roche et al., 2003, *Microbiology* 149; 643), SasH (Roche et al., 2003, *Microbiology* 149; 643), aureolysin precursor (AUR)/Sepp1 and novel autolysin.

In an alternative embodiment, 2 or more proteins which are expressed in different sets of clonal strains are included in the immunogenic composition of the invention. Preferably the combination of antigens will allow an immune response to be generated that is effective against multiple clonal strains, most preferably against all clonal stains. Preferred combinations include FnbB and beta-hemolysin, FnbB and Cna, FnbB and TSST-1, FnbB and mecA, FnbB and SdrD, FnbB and SdrF, FnbB and EbpS, FnbB and Efb, beta-hemolysin and Cna, beta-hemolysin and TSST-1, beta-hemolysin and mecA, beta-hemolysin and SdrD, beta-hemolysin and SdrF, beta-hemolysin and EbpS, beta-hemolysin and Efb, Cna and TSST-1, Cna and mecA, Cna and SdrD, Cna and SdrF, Cna and EbpS, Cna and Efb, TSST-1 and mecA, TSST-1 and SdrD, TSST-1 and SdrF, TSST-1 and EbpS, TssT-1 and Efb, MecA and SdrD, MecA and SdrF, MecA and EbpS, MecA and Efb, SdrD and SdrF, SdrD and EbpS, SdeD and Efb, SdrF and EbpS, SdrF and Efb, and, EbpS and Efb.

The preferred combinations described above may be combined with additional components described below.

Selection of Antigens Expressed During Different Growth Phases

Staphylococci go through an exponential growth phase during which a particular set of proteins will be expressed. These include many of the extracellular component binding proteins and transporter proteins. After a period of exponential growth, the staphylococci revert to a post-exponential phase during which growth is slower and protein expression is modulated. Many of the proteins expressed during the exponential growth phase are down regulated whereas other proteins, such as enzymes and most toxins, including alpha toxin, are expressed at higher levels.

Preferred immunogenic compositions of the invention comprise a protein expressed at higher levels during the exponential growth phase and a protein expressed at higher levels during the post-exponential phase.

'Higher levels' refers to the level of expression being higher in one phase in comparison with the other phase.

In a preferred embodiment, the immunogenic composition of the invention comprises alpha toxin and an extracellular component binding protein (preferably FnbA, FnbB, ClfA and ClfB) or a transporter protein.

More preferably it comprises alpha toxin or Cna or Lipase GehD and a protein selected from the group consisting of laminin receptor, SitC/MntC/saliva binding protein, Elastin binding protein (EbpS), EFB (FIB), SBI, autolysin, ClfA, SdrC, SdrG, SdrH, SasA, FnbA, FnbB, ClfB, FbpA, Npase, IsaA/PisA, SsaA, EPB, SSP-1, SSP-2, HBP, Vitronectin binding protein, fibrinogen binding protein, coagulase, Fig and MAP, Immunodominant ABC transporter, IsdA, IsdB, $Mg^{2+}$ transporter, SitC, Ni ABC transporter, Aap and SsaA.

In the combinations described above, the alpha toxin may be genetically or chemically detoxified as described above and may be unconjugated or conjugated to polysaccharide as described below.

Polysaccharides

The immunogenic compositions of the invention preferably further comprise capsular polysaccharides including one or more of PIA (also known as PNAG) and/or *S. aureus*

Type V and/or type VIII capsular polysaccharide and/or *S. epidermidis* Type I, and/or Type II and/or Type III capsular polysaccharide.

PIA (PNAG)

It is now clear that the various forms of staphylococcal surface polysaccharides identified as PS/A, PIA and SAA are the same chemical entity—PNAG (Maira-Litran et al., *Vaccine* 22; 872-879 (2004)). Therefore the term PIA or PNAG encompasses all these polysaccharides or oligosaccharides derived from them.

PIA is a polysaccharide intercellular adhesin and is composed of a polymer of β-(1→6)-linked glucosamine substituted with N-acetyl and O-succinyl constituents. This polysaccharide is present in both *S. aureus* and *S. epidermidis* and can be isolated from either source (Joyce et al. 2003, *Carbohydrate Research* 338; 903; Maira-Litran et al., 2002, *Infect. Immun.* 70; 4433). For example, PNAG may be isolated from *S. aureus* strain MN8m (WO 04/43407).

PIA isolated from *S. epidermidis* is a integral constituent of biofilm. It is responsible for mediating cell-cell adhesion and probably also functions to shield the growing colony from the host's immune response.

The polysaccharide previously known as poly-N-succinyl-β-(1→6)-glucosamine (PNSG) was recently shown not to have the expected structure since the identification of N-succinylation was incorrect (Maira-Litran et al., 2002, *Infect. Immun.* 70; 4433). Therefore the polysaccharide formally known as PNSG and now found to be PNAG is also encompassed by the term PIA.

PIA (or PNAG) may be of different sizes varying from over 400 kDa to between 75 and 400 kDa to between 10 and 75 kDa to oligosaccharides composed of up to 30 repeat units (of β-(1→6)-linked glucosamine substituted with N-acetyl and O-succinyl constituents). Any size of PIA polysaccharide or oligosaccharide may be use in an immunogenic composition of the invention, however a size of over 40 kDa is preferred. Sizing may be achieved by any method known in the art, for instance by microfluidisation, ultrasonic irradiation or by chemical cleavage (WO 03/53462, EP497524, EP497525).

Preferred size ranges of PIA (PNAG) are 40-400 kDa, 40-300 kDa, 50-350 kDa, 60-300 kDa, 50-250 kDa and 60-200 kDa.

PIA (PNAG) can have different degree of acetylation due to substitution on the amino groups by acetate. PIA produced in vitro is almost fully substituted on amino groups (95-100%). Alternatively, a deacetylated PIA (PNAG) can be used having less than 60%, preferably less than 50%, 40%, 30%, 20%, 10% acetylation. Use of a deacetylated PIA (PNAG) is preferred since non-acetylated epitopes of PNAG are efficient at mediating opsonic killing of Gram positive bacteria, preferably *S. aureus* and/or *S. epidermidis*. Most preferably, the PIA (PNAG) has a size between 40 kDa and 300 kDa and is deacetylated so that less than 60%, 50%, 40%, 30% or 20% of amino groups are acetylated.

The term deacetylated PNAG (dPNAG) refers to a PNAG polysaccharide or oligosaccharide in which less than 60%, 50%, 40%, 30%, 20% or 10% of the amino groups are acetylated.

In an embodiment, PNAG is a deacetylated to form dPNAG by chemically treating the native polysaccharide. For example, the native PNAG is treated with a basic solution such that the pH rises to above 10. For instance the PNAG is treated with 0.1-5 M, 0.2-4 M, 0.3-3 M, 0.5-2 M, 0.75-1.5 M or 1 M NaOH, KOH or $NH_4OH$. Treatment is for at least 10 or 30 minutes, or 1, 2, 3, 4, 5, 10, 15 or 20 hours at a temperature of 20-100, 25-80, 30-60 or 30-50 or 35-45° C. dPNAG may be prepared as described in WO 04/43405.

The polysaccharide(s) included in the immunogenic composition of the invention are preferably conjugated to a carrier protein as described below or alternatively unconjugated.

Type 5 and Type 8 Polysaccharides from *S. aureus*

Most strains of *S. aureus* that cause infection in man contain either Type 5 or Type 8 polysaccharides. Approximately 60% of human strains are Type 8 and approximately 30% are Type 5. The structures of Type 5 and Type 8 capsular polysaccharide antigens are described in Moreau et al., *Carbohydrate Res.* 201; 285 (1990) and Fournier et al., *Infect. Immun.* 45; 87 (1984). Both have FucNAcp in their repeat unit as well as ManNAcA which can be used to introduce a sulfhydryl group. The structures were reported as:

Type 5

→4)-β-D-ManNAcA(3OAc)-(1→4)-α-L-FucNAc (1→3)-β-D-FucNAc-(1→

Type 8

→3)-β-D-ManNAcA(4OAc)-(1→3)-α-L-FucNAc (1→3)-β-D-FucNAc-(1→

Recently (Jones, *Carbohydrate Research* 340, 1097-1106 (2005)) NMR spectroscopy revised to structures to:

Type 5

→4)-β-D-ManNAcA-(1→4)-α-L-FucNAc(3OAc)-(1→3)-β-D-FucNAc-(1→

Type 8

→3)-β-D-ManNAcA(4OAc)-(1→3)-α-L-FucNAc (1→3)-α-D-FucNAc(1→

Polysaccharides may be extracted from the appropriate strain of *S. aureus* using method well known to the skilled man, for instance as described in U.S. Pat. No. 6,294,177. For example, ATCC 12902 is a Type 5 *S. aureus* strain and ATCC 12605 is a Type 8 *S. aureus* strain.

Polysaccharides are of native size or alternatively may be sized, for instance by microfluidisation, ultrasonic irradiation or by chemical treatment. The invention also covers oligosaccharides derived from the type 5 and 8 polysaccharides from *S. aureus*.

The type 5 and 8 polysaccharides included in the immunogenic composition of the invention are preferably conjugated to a carrier protein as described below or are alternatively unconjugated.

The immunogenic compositions of the invention alternatively contain either type 5 or type 8 polysaccharide.

*S. aureus* 336 Antigen

In an embodiment, the immunogenic composition of the invention comprises the *S. aureus* 336 antigen described in U.S. Pat. No. 6,294,177.

The 336 antigen comprises β-linked hexosamine, contains no O-acetyl groups and specifically binds to antibodies to *S. aureus* Type 336 deposited under ATCC 55804.

In an embodiment, the 336 antigen is a polysaccharide which is of native size or alternatively may be sized, for instance by microfluidisation, ultrasonic irradiation or by chemical treatment. The invention also covers oligosaccharides derived from the 336 antigen.

The 336 antigen, where included in the immunogenic composition of the invention, is preferably conjugated to a carrier protein as described below or are alternatively unconjugated.

Type I, II and III Polysaccharides from *S. epidermidis*

Strains ATCC-31432, SE-360 and SE-10 of *S. epidermidis* are characteristic of three different capsular types, I, II and III respectively (Ichiman and Yoshida 1981, *J. Appl.*

*Bacteriol.* 51; 229). Capsular polysaccharides extracted from each serotype of *S. epidermidis* constitute Type I, II and III polysaccharides. Polysaccharides may be extracted by several methods including the method described in U.S. Pat. No. 4,197,290 or as described in Ichiman et al., 1991, *J. Appl. Bacteriol.* 71; 176.

In one embodiment of the invention, the immunogenic composition comprises type I and/or II and/or III polysaccharides or oligosaccharides from *S. epidermidis.*

Polysaccharides are of native size or alternatively may be sized, for instance by microfluidisation, ultrasonic irradiation or chemical cleavage. The invention also covers oligosaccharides extracted from *S. epidermidis* strains.

These polysaccharides are unconjugated or are preferably conjugated as described below.

Conjugation of Polysaccharides

Amongst the problems associated with the use of polysaccharides in vaccination, is the fact that polysaccharides per se are poor immunogens. Strategies, which have been designed to overcome this lack of immunogenicity, include the linking of the polysaccharide to large protein carriers, which provide bystander T-cell help. It is preferred that the polysaccharides utilized in the invention are linked to a protein carrier which provide bystander T-cell help. Examples of such carriers which may be conjugated to polysaccharide immunogens include the Diphtheria and Tetanus toxoids (DT, DT crm197 and TT respectively), Keyhole Limpet Hemocyanin (KLH), and the purified protein derivative of Tuberculin (PPD), *Pseudomonas aeruginosa* exoprotein A (rEPA), protein D from *Haemophilus influenzae*, pneumolysin or fragments of any of the above. Fragments suitable for use include fragments encompassing T-helper epitopes. In particular protein D fragment will preferably contain the N-terminal ⅓ of the protein. Protein D is an IgD-binding protein from *Haemophilus influenzae* (EP 0 594 610 B1) and is a potential immunogen.

In addition, staphylococcal proteins may be used as carrier protein in the polysaccharide conjugates of the invention. The staphylococcal proteins described below may be used as carrier protein; for example, laminin receptor, SitC/MntC/saliva binding protein, EbhA, EbhB, Elastin binding protein (EbpS), EFB (FIB), SBI, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig, MAP, Immunodominant ABC transporter, IsdA, IsdB, Mg2+ transporter, SitC, Ni ABC transporter alpha toxin (Hla), alpha toxin H35R mutant, RNA III activating protein (RAP), or fragments thereof.

A new carrier protein that would be particularly advantageous to use in the context of a staphylococcal vaccine is staphylococcal alpha toxoid. The native form may be conjugated to a polysaccharide since the process of conjugation reduces toxicity. Preferably a genetically detoxified alpha toxin such as the His35Leu or His 35 Arg variants are used as carriers since residual toxicity is lower. Alternatively the alpha toxin is chemically detoxified by treatment with a cross-linking reagent, formaldehyde or glutaraldehyde. A genetically detoxified alpha toxin is optionally chemically detoxified, preferably by treatment with a cross-linking reagent, formaldehyde or glutaraldehyde to further reduce toxicity.

The polysaccharides may be linked to the carrier protein(s) by any known method (for example, by Likhite, U.S. Pat. No. 4,372,945 by Armor et al., U.S. Pat. No. 4,474,757, and Jennings et al., U.S. Pat. No. 4,356,170). Preferably, CDAP conjugation chemistry is carried out (see WO95/08348).

In CDAP, the cyanylating reagent 1-cyano-dimethylaminopyridinium tetrafluoroborate (CDAP) is preferably used for the synthesis of polysaccharide-protein conjugates. The cyanilation reaction can be performed under relatively mild conditions, which avoids hydrolysis of the alkaline sensitive polysaccharides. This synthesis allows direct coupling to a carrier protein.

The polysaccharide is solubilized in water or a saline solution. CDAP is dissolved in acetonitrile and added immediately to the polysaccharide solution. The CDAP reacts with the hydroxyl groups of the polysaccharide to form a cyanate ester. After the activation step, the carrier protein is added. Amino groups of lysine react with the activated polysaccharide to form an isourea covalent link. After the coupling reaction, a large excess of glycine is then added to quench residual activated functional groups. The product is then passed through a gel permeation column to remove unreacted carrier protein and residual reagents.

Conjugation preferably involves producing a direct linkage between the carrier protein and polysaccharide. Optionally a spacer (such as adipic dihydride (ADH)) may be introduced between the carrier protein and the polysaccharide.

Protection Against *S. aureus* and *S. epidermidis*

In a preferred embodiment of the invention the immunogenic composition provides an effective immune response against more than one strain of staphylococci, preferably against strains from both *S. aureus* and *S. epidermidis*. More preferably, a protective immune response is generated against type 5 and 8 serotypes of *S. aureus*. More preferably, a protective immune response is generated against multiple strains of *S. epidermidis*, for instance from strains of at least two of serotypes I, II and III of *S. epidermidis.*

One use of the immunogenic composition of the invention is to prevent nosocomial infections by inoculating prior to hospital treatment. At this stage, it is difficult to accurately predict which staphylococcal strains the patient will be exposed to. It is therefore advantageous to inoculate with a vaccine that is capable of generating an effective immune response against various strains of staphylococci.

An effective immune response is defined as an immune response that gives significant protection in a mouse challenge model or opsonophagocytosis assay as described in the examples. Significant protection in a mouse challenge model, for instance that of example 5, is defined as an increase in the $LD_{50}$ in comparison with carrier inoculated mice of at least 10%, 20%, 50%, 100% or 200%. Significant protection in a cotton rat challenge model, for instance that of example 8, is defined as a decrease in the mean observed Log CFU/nose of at least 10%, 20%, 50%, 70% or 90%. The presence of opsonizing antibodies is known to correlate with protection, therefore significant protection is indicated by a decrease in the bacterial count of at least 10%, 20%, 50%, 70% or 90% in an opsonophagocytosis assay, for instance that of Example 7.

Several of the proteins including immunodominant ABC transporter, RNA III activating protein, Laminin receptors, SitC, IsaA/PisA, SsaA, EbhA/EbhB, EbpS and Aap are well conserved between *S. aureus* and *S. epidermidis* and example 8 shows that IsaA, ClfA, IsdB, SdrG, HarA, FnbpA and Sbi can generate a cross-reactive immune response (for example cross-reactive between at least one *S. aureus* and at least one *S. epidermidis* strain). PIA is also well conserved between *S. aureus* and *S. epidermidis* and is capable of inducing a cross-protective immune response.

Therefore in a preferred embodiment, the immunogenic composition of the invention will comprise two, three or four of the above proteins, preferably further comprising PIA (PNAG).

Polynucleotide Vaccines

In a further aspect, the present invention relates to the use of the polynucleotides of FIG. 2 in the treatment, prevention or diagnosis of staphylococcal infection. Such polynucleotides include isolated polynucleotides comprising a nucleotide sequence encoding a polypeptide which has at least 70% identity, preferably at least 80% identity, more preferably at least 90% identity, yet more preferably at least 95% identity, to the amino acid sequence of FIG. 1, over the entire length of the sequence. In this regard, polypeptides which have at least 97% identity are highly preferred, whilst those with at least 98-99% identity are more highly preferred, and those with at least 99% identity are most highly preferred.

Further polynucleotides that find utility in the present invention include isolated polynucleotides comprising a nucleotide sequence that has at least 70% identity, preferably at least 80% identity, more preferably at least 90% identity, yet more preferably at least 95% identity, to a nucleotide sequence encoding a protein of the invention over the entire coding region. In this regard, polynucleotides which have at least 97% identity are highly preferred, whilst those with at least 98-99% identity are more highly preferred, and those with at least 99% identity are most highly preferred.

Other polynucleotides include isolated polynucleotides comprising a nucleotide sequence which has at least 70% identity, preferably at least 80% identity, more preferably at least 90% identity, yet more preferably at least 95% identity, to the sequences of FIG. 1. In this regard, polynucleotides which have at least 97% identity are highly preferred, whilst those with at least 98-99% identity are more highly preferred, and those with at least 99% identity are most highly preferred. Said polynucleotide can be inserted in a suitable plasmid or recombinant microorganism vector and used for immunization (see for example Wolff et. al., *Science* 247: 1465-1468 (1990); Corr et. al., *J. Exp. Med.* 184:1555-1560 (1996); Doe et. al., *Proc. Natl. Acad. Sci.* 93:8578-8583 (1996)).

The present invention also provides a nucleic acid encoding the aforementioned proteins of the present invention and their use in medicine. In a preferred embodiment isolated polynucleotides according to the invention may be single-stranded (coding or antisense) or double-stranded, and may be DNA (genomic, cDNA or synthetic) or RNA molecules. Additional coding or non-coding sequences may, but need not, be present within a polynucleotide of the present invention. In other related embodiments, the present invention provides polynucleotide variants having substantial identity to the sequences disclosed herein in FIG. 2; those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters). In a related embodiment, the isolated polynucleotide of the invention will comprise a nucleotide sequence encoding a polypeptide that has at least 90%, preferably 95% and above, identity to the amino acid sequence of FIG. 1, over the entire length of a sequence of FIG. 1; or a nucleotide sequence complementary to said isolated polynucleotide.

The invention also contemplates the use of polynucleotides which are complementary to all the above described polynucleotides.

The invention also provides for the use of a fragment of a polynucleotide of the invention which when administered to a subject has the same immunogenic properties as a polynucleotide of FIG. 1.

The invention also provides for the use of a polynucleotide encoding an immunological fragment of a protein of FIG. 1 as hereinbefore defined. Also contemplated are the use of such fragments that have a level of immunogenic activity of at least about 50%, preferably at least about 70% and more preferably at least about 90% of the level of immunogenic activity of a polypeptide sequence encoded by a polynucleotide sequence set forth in FIG. 2.

Polypeptide fragments for use according to the invention preferably comprise at least about 5, 10, 15, 20, 25, 50, or 100 contiguous amino acids, or more, including all intermediate lengths, of a polypeptide composition set forth herein, such as those set forth above.

Polynucleotides for use in the invention may be obtained, using standard cloning and screening techniques, from a cDNA library derived from mRNA in cells of human preneoplastic or tumor tissue (lung for example), (for example Sambrook et al., Molecular Cloning: A Laboratory Manual, $2^{nd}$ Ed., Cold Spring Harbor Laboratory Press, Cold Spring Harbor, N.Y. (1989)). Polynucleotides of the invention can also be obtained from natural sources such as genomic DNA libraries or can be synthesized using well-known and commercially available techniques.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998-9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Vectors comprising such DNA, hosts transformed thereby and the truncated or hybrid proteins themselves, expressed as described herein below all form part of the invention.

The expression system may also be a recombinant live microorganism, such as a virus or bacterium. The gene of interest can be inserted into the genome of a live recombinant virus or bacterium. Inoculation and in vivo infection with this live vector will lead to in vivo expression of the antigen and induction of immune responses.

Therefore, in certain embodiments, polynucleotides encoding immunogenic polypeptides for use according to the present invention are introduced into suitable mammalian host cells for expression using any of a number of known viral-based systems. In one illustrative embodiment, retroviruses provide a convenient and effective platform for gene delivery systems. A selected nucleotide sequence encoding a polypeptide for use in the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) *BioTechniques* 7:980-990; Miller, A. D. (1990) Human Gene Therapy 1:5-14; Scarpa et al. (1991) *Virology* 180:849-852; Burns et al. (1993) *Proc. Natl. Acad. Sci.* USA 90:8033-8037; and Boris-Lawrie and Temin (1993) *Cur. Opin. Genet. Develop.* 3:102-109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) *J. Virol.* 57:267-274; Bett et al. (1993) *J. Virol.* 67:5911-5921; Mittereder et al. (1994) Human Gene Therapy 5:717-729; Seth et al. (1994) *J. Virol.* 68:933-940; Barr et al. (1994) *Gene Therapy* 1:51-58; Berkner, K. L. (1988) *BioTechniques* 6:616-629; and Rich et al. (1993) *Human Gene Therapy* 4:461-476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) *Molec. Cell. Biol.* 8:3988-3996; Vincent et al. (1990) Vaccines 90 (Cold Spring Harbor Laboratory Press); Carter, B. J. (1992) *Current Opinion in Biotechnology* 3:533-539; Muzyczka, N. (1992) *Current Topics in Microbiol. and Immunol.* 158:97-129; Kotin, R. M. (1994) *Human Gene Therapy* 5:793-801; Shelling and Smith (1994) *Gene Therapy* 1:165-169; and Zhou et al. (1994) *J. Exp. Med.* 179:1867-1875.

Additional viral vectors useful for delivering the nucleic acid molecules encoding polypeptides for use in the present invention by gene transfer include those derived from the pox family of viruses, such as vaccinia virus and avian poxvirus. By way of example, vaccinia virus recombinants expressing the molecules of interest can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-bromodeoxyuridine and picking viral plaques resistant thereto.

A vaccinia-based infection/transfection system can be conveniently used to provide for inducible, transient expression or co-expression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, *Proc. Natl. Acad. Sci.* USA (1990) 87:6743-6747; Fuerst et al., *Proc. Natl. Acad. Sci.* USA (1986) 83:8122-8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions for use in the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al., *J. Biol. Chem.* (1993) 268:6866-6869 and Wagner et al., *Proc. Natl. Acad. Sci.* USA (1992) 89:6099-6103, can also be used for gene delivery under the invention.

Additional illustrative information on these and other known viral-based delivery systems can be found, for example, in Fisher-Hoch et al., *Proc. Natl. Acad. Sci. USA* 86:317-321, 1989; Flexner et al., *Ann. N.Y. Acad. Sci.* 569:86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *BioTechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993.

The recombinant live microorganisms described above can be virulent, or attenuated in various ways in order to obtain live vaccines. Such live vaccines also form part of the invention.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., *Science* 259:1745-1749, 1993 and reviewed by Cohen, *Science* 259:1691-1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

Vaccines

In a preferred embodiment, the immunogenic composition of the invention is mixed with a pharmaceutically acceptable excipient, more preferably with an adjuvant to form a vaccine.

The vaccines of the present invention are preferably adjuvanted. Suitable adjuvants include an aluminum salt such as aluminum hydroxide gel (alum) or aluminum phosphate, but may also be a salt of calcium, magnesium, iron or zinc, or may be an insoluble suspension of acylated tyrosine, or acylated sugars, cationically or anionically derivatized polysaccharides, or polyphosphazenes.

It is preferred that the adjuvant be selected to be a preferential inducer of either a TH1 or a TH2 type of response. High levels of Th1-type cytokines tend to favor the induction of cell mediated immune responses to a given antigen, whilst high levels of Th2-type cytokines tend to favor the induction of humoral immune responses to the antigen.

It is important to remember that the distinction of Th1 and Th2-type immune response is not absolute. In reality an individual will support an immune response which is described as being predominantly Th1 or predominantly Th2. However, it is often convenient to consider the families of cytokines in terms of that described in murine CD4 +ve T cell clones by Mosmann and Coffman (Mosmann, T. R. and Coffman, R. L. (1989) TH1 and TH2 cells: different patterns of lymphokine secretion lead to different functional properties. Annual Review of Immunology, 7, p 145-1'73). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of Il-4, IL-5, IL-6, IL-10. Suitable adjuvant systems which promote a predominantly Th1 response include: Monophosphoryl lipid A or a derivative thereof, particularly 3-de-O-acylated monophosphoryl lipid A (3D-MPL) (for its preparation see GB 2220211 A); and a combination of monophosphoryl lipid A, preferably 3-de-O-acylated monophosphoryl lipid A, together with either an aluminum salt (for instance aluminum phosphate or aluminum hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen (Thoelen et al. Vaccine (1998) 16:708-14; EP 689454-B1).

An enhanced system involves the combination of a monophosphoryl lipid A and a saponin derivative, particularly the combination of QS21 and 3D-MPL as disclosed in WO 94/00153, or a less reactogenic composition where the QS21 is quenched with cholesterol as disclosed in WO 96/33739. A particularly potent adjuvant formulation involving QS21, 3D-MPL and tocopherol in an oil in water emulsion is described in WO 95/17210, and is a preferred formulation. Preferably the vaccine additionally comprises a saponin, more preferably QS21. The formulation may also comprise an oil in water emulsion and tocopherol (WO 95/17210). The present invention also provides a method for producing a vaccine formulation comprising mixing a protein of the present invention together with a pharmaceutically acceptable excipient, such as 3D-MPL. Unmethylated CpG containing oligonucleotides (WO 96/02555) are also preferential inducers of a TH1 response and are suitable for use in the present invention.

Preferred compositions of the invention are those forming a liposome structure. Compositions where the sterol/immunologically active saponin fraction forms an ISCOM structure also form an aspect of the invention.

The ratio of QS21:sterol will typically be in the order of 1:100 to 1:1 weight to weight. Preferably excess sterol is present, the ratio of QS21:sterol being at least 1:2 w/w. Typically for human administration QS21 and sterol will be present in a vaccine in the range of about 1 μg to about 100 μg, preferably about 10 μg to about 50 μg per dose.

The liposomes preferably contain a neutral lipid, for example phosphatidylcholine, which is preferably non-crystalline at room temperature, for example egg yolk phosphatidylcholine, dioleoyl phosphatidylcholine or dilauryl phosphatidylcholine. The liposomes may also contain a charged lipid which increases the stability of the liposome-QS21 structure for liposomes composed of saturated lipids. In these cases the amount of charged lipid is preferably 1-20% w/w, most preferably 5-10%. The ratio of sterol to phospholipid is 1-50% (mol/mol), most preferably 20-25%.

Preferably the compositions of the invention contain MPL (3-deacylated mono-phosphoryl lipid A, also known as 3D-MPL). 3D-MPL is known from GB 2 220 211 (Ribi) as a mixture of 3 types of De-O-acylated monophosphoryl lipid A with 4, 5 or 6 acylated chains and is manufactured by Ribi Immunochem, Montana. A preferred form is disclosed in International Patent Application 92/116556.

Suitable compositions of the invention are those wherein liposomes are initially prepared without MPL, and MPL is then added, preferably as 100 nm particles. The MPL is therefore not contained within the vesicle membrane (known as MPL out). Compositions where the MPL is contained within the vesicle membrane (known as MPL in) also form an aspect of the invention. The antigen can be contained within the vesicle membrane or contained outside the vesicle membrane. Preferably soluble antigens are outside and hydrophobic or lipidated antigens are either contained inside or outside the membrane.

The vaccine preparations of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/ alimentary, respiratory, genitourinary tracts. Intranasal administration of vaccines for the treatment of pneumonia or otitis media is preferred (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance pneumococcal polysaccharides could be administered separately, at the same time or 1-2 weeks after the administration of any bacterial protein component of the vaccine for optimal coordination of the immune responses with respect to each other). For co-administration, the optional Th1 adjuvant may be present in any or all of the different administrations, however it is preferred if it is present in combination with the bacterial protein component of the vaccine. In addition to a single route of administration, 2 different routes of administration may be used. For example, polysaccharides may be administered IM (or ID) and bacterial proteins may be administered IN (or ID). In addition, the vaccines of the invention may be administered IM for priming doses and IN for booster doses.

The amount of conjugate antigen in each vaccine dose is selected as an amount which induces an immunoprotective response without significant, adverse side effects in typical vaccines. Such amount will vary depending upon which specific immunogen is employed and how it is presented. Generally, it is expected that each dose will comprise 0.1-100 µs of polysaccharide, preferably 0.1-50 µg for polysaccharide conjugates, preferably 0.1-10 µg, more preferably 1-10 µs, of which 1 to 5 µg is a more preferable range.

The content of protein antigens in the vaccine will typically be in the range 1-100 µg, preferably 5-50 µg, most typically in the range 5-25 µg. Following an initial vaccination, subjects may receive one or several booster immunizations adequately spaced.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

The vaccines of the present invention may be stored in solution or lyophilized. Preferably the solution is lyophilized in the presence of a sugar such as sucrose, trehalose or lactose. It is still further preferable that they are lyophilized and extemporaneously reconstituted prior to use. Lyophilizing may result in a more stable composition (vaccine) and may possibly lead to higher antibody titers in the presence of 3D-MPL and in the absence of an aluminum based adjuvant.

Antibodies and Passive Immunization

Another aspect of the invention is a method of preparing an immune globulin for use in prevention or treatment of staphylococcal infection comprising the steps of immunizing a recipient with the vaccine of the invention and isolating immune globulin from the recipient. An immune globulin prepared by this method is a further aspect of the invention.

A pharmaceutical composition comprising the immune globulin of the invention and a pharmaceutically acceptable carrier is a further aspect of the invention which could be used in the manufacture of a medicament for the treatment or prevention of staphylococcal disease. A method for treatment or prevention of staphylococcal infection comprising a step of administering to a patient an effective amount of the pharmaceutical preparation of the invention is a further aspect of the invention.

Inocula for polyclonal antibody production are typically prepared by dispersing the antigenic composition in a physiologically tolerable diluent such as saline or other adjuvants suitable for human use to form an aqueous composition. An immunostimulatory amount of inoculum is administered to a mammal and the inoculated mammal is then maintained for a time sufficient for the antigenic composition to induce protective antibodies.

The antibodies can be isolated to the extent desired by well known techniques such as affinity chromatography (Harlow and Lane Antibodies; a laboratory manual 1988).

Antibodies can include antiserum preparations from a variety of commonly used animals e.g., goats, primates, donkeys, swine, horses, guinea pigs, rats or man. The animals are bled and serum recovered.

An immune globulin produced in accordance with the present invention can include whole antibodies, antibody fragments or subfragments. Antibodies can be whole immunoglobulins of any class e.g., IgG, IgM, IgA, IgD or IgE, chimeric antibodies or hybrid antibodies with dual specificity to two or more antigens of the invention. They may also be fragments e.g., $F(ab')_2$, Fab', Fab, Fv and the like including hybrid fragments. An immune globulin also includes natural, synthetic or genetically engineered proteins that act like an antibody by binding to specific antigens to form a complex.

A vaccine of the present invention can be administered to a recipient who then acts as a source of immune globulin, produced in response to challenge from the specific vaccine. A subject thus treated would donate plasma from which hyperimmune globulin would be obtained via conventional plasma fractionation methodology. The hyperimmune globulin would be administered to another subject in order to impart resistance against or treat staphylococcal infection. Hyperimmune globulins of the invention are particularly useful for treatment or prevention of staphylococcal disease in infants, immune compromised individuals or where treatment is required and there is no time for the individual to produce antibodies in response to vaccination.

An additional aspect of the invention is a pharmaceutical composition comprising two of more monoclonal antibodies (or fragments thereof; preferably human or humanized) reactive against at least two constituents of the immunogenic composition of the invention, which could be used to treat or prevent infection by Gram positive bacteria, preferably staphylococci, more preferably *S. aureus* or *S. epidermidis*.

Such pharmaceutical compositions comprise monoclonal antibodies that can be whole immunoglobulins of any class e.g. IgG, IgM, IgA, IgD or IgE, chimeric antibodies or hybrid antibodies with specificity to two or more antigens of the invention. They may also be fragments e.g., $F(ab')_2$, Fab', Fab, Fv and the like including hybrid fragments.

Methods of making monoclonal antibodies are well known in the art and can include the fusion of splenocytes with myeloma cells (Kohler and Milstein 1975 Nature 256; 495; Antibodies—a laboratory manual Harlow and Lane 1988). Alternatively, monoclonal Fv fragments can be obtained by screening a suitable phage display library (Vaughan T J et al., 1998 *Nature Biotechnology* 16; 535). Monoclonal antibodies may be humanized or part humanized by known methods.

Methods

The invention also encompasses method of making the immunogenic compositions and vaccines of the invention.

A preferred process of the invention, is a method to make a vaccine comprising the steps of mixing antigens to make the immunogenic composition of the invention and adding a pharmaceutically acceptable excipient.

Methods of Treatment

The invention also encompasses method of treatment or staphylococcal infection, particularly hospital acquired nosocomial infections.

This immunogenic composition or vaccine of the invention is particularly advantageous to use in cases of elective surgery. Such patients will know the date of surgery in advance and could be inoculated in advance. Since it is not known whether the patient will be exposed to *S. aureus* or *S. epidermidis* infection, it is preferred to inoculate with a vaccine of the invention that protects against both, as described above. Preferably adults over 16 awaiting elective surgery are treated with the immunogenic compositions and vaccines of the invention.

It is also advantageous to inoculate health care workers with the vaccine of the invention.

The vaccine preparations of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts.

The amount of antigen in each vaccine dose is selected as an amount which induces an immunoprotective response without significant, adverse side effects in typical vaccines. Such amount will vary depending upon which specific immunogen is employed and how it is presented. The protein content of the vaccine will typically be in the range 1-100 μg, preferably 5-50 μg, most typically in the range 10-25 μg. Generally, it is expected that each dose will comprise 0.1-100 μg of polysaccharide where present, preferably 0.1-50 μg, preferably 0.1-10 μg, of which 1 to 5 μg is the most preferable range. An optimal amount for a particular vaccine can be ascertained by standard studies involving observation of appropriate immune responses in subjects. Following an initial vaccination, subjects may receive one or several booster immunizations adequately spaced.

Although the vaccines of the present invention may be administered by any route, administration of the described vaccines into the skin (ID) forms one embodiment of the present invention. Human skin comprises an outer "horny" cuticle, called the stratum corneum, which overlays the epidermis. Underneath this epidermis is a layer called the dermis, which in turn overlays the subcutaneous tissue. Researchers have shown that injection of a vaccine into the skin, and in particular the dermis, stimulates an immune response, which may also be associated with a number of additional advantages. Intradermal vaccination with the vaccines described herein forms a preferred feature of the present invention.

The conventional technique of intradermal injection, the "mantoux procedure", comprises steps of cleaning the skin, and then stretching with one hand, and with the bevel of a narrow gauge needle (26-31 gauge) facing upwards the needle is inserted at an angle of between 10-15°. Once the bevel of the needle is inserted, the barrel of the needle is lowered and further advanced whilst providing a slight pressure to elevate it under the skin. The liquid is then injected very slowly thereby forming a bleb or bump on the skin surface, followed by slow withdrawal of the needle.

More recently, devices that are specifically designed to administer liquid agents into or across the skin have been described, for example the devices described in WO 99/34850 and EP 1092444, also the jet injection devices described for example in WO 01/13977; U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Alternative methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

When the vaccines of the present invention are to be administered to the skin, or more specifically into the dermis, the vaccine is in a low liquid volume, particularly a volume of between about 0.05 ml and 0.2 ml.

The content of antigens in the skin or intradermal vaccines of the present invention may be similar to conventional doses as found in intramuscular vaccines (see above). However, it is a feature of skin or intradermal vaccines that the formulations may be "low dose". Accordingly the protein antigens in "low dose" vaccines are preferably present in as little as 0.1 to 10 preferably 0.1 to 5 μg per dose; and the polysaccharide (preferably conjugated) antigens may be present in the range of 0.01-1 and preferably between 0.01 to 0.5 μg of polysaccharide per dose.

As used herein, the term "intradermal delivery" means delivery of the vaccine to the region of the dermis in the skin. However, the vaccine will not necessarily be located exclusively in the dermis. The dermis is the layer in the skin located between about 1.0 and about 2.0 mm from the surface in human skin, but there is a certain amount of variation between individuals and in different parts of the body. In general, it can be expected to reach the dermis by going 1.5 mm below the surface of the skin. The dermis is located between the stratum corneum and the epidermis at the surface and the subcutaneous layer below. Depending on the mode of delivery, the vaccine may ultimately be located solely or primarily within the dermis, or it may ultimately be distributed within the epidermis and the dermis.

A preferred embodiment of the invention is a method of preventing or treating staphylococcal infection or disease comprising the step of administering the immunogenic composition or vaccine of the invention to a patient in need thereof.

In a preferred embodiment, the patient is awaiting elective surgery.

A further preferred embodiment of the invention is a use of the immunogenic composition of the invention in the manufacture of a vaccine for treatment or prevention of staphylococcal infection or disease, preferably post-surgery staphylococcal infection.

The term 'staphylococcal infection' encompasses infection caused by *S. aureus* and/or *S. epidermidis* and other staphylococcal strains capable of causing infection in a mammalian, preferably human host.

The terms "comprising", "comprise" and "comprises" herein are intended by the inventors to be optionally substitutable with the terms "consisting of", "consist of" and "consists of", respectively, in every instance.

All references or patent applications cited within this patent specification are incorporated by reference herein.

In order that this invention may be better understood, the following examples are set forth. These examples are for purposes of illustration only, and are not to be construed as limiting the scope of the invention in any manner.

EXAMPLES

Example 1

Construction of Plasmid to Express Recombinant Proteins

A: Cloning.

Appropriate restriction sites engineered into oligonucleotides specific for the staphylococcal gene permitted directional cloning of the PCR product into the *E. coli* expression plasmid pET24d or pQE-30 such that a protein could be expressed as a fusion protein containing a (His)6 affinity chromatography tag at the N- or C-terminus.

The primers used were (SEQ ID NOS: 120-151 respectively):

```
Alpha toxin-
5'-CGCGGATCCGCAGATTCTGATATTAATATTAAAAC-3'
and

5' CCCAAGCTTTTAATTTGTCATTTCTTCTTTTTC-3'

EbpS-
5'-CGCGGATCCGCTGGGTCTAATAATTTTAAAGATG-3'
and

5' CCCAAGCTTTTATGGAATAACGATTTGTTG-3'

ClfA-
5'-CGCGGATCCAGTGAAAATAGTGTTACGCAATC-3'
and

5' CCCAAGCTTTTACTCTGGAATTGGTTCAATTTC-3'

FnbpA-
5'-CGCGGATCCACACAAACAACTGCAACTAACG-3'
and

5' CCCAAGCTTTTATGCTTTGTGATTCTTTTTCAAAC 3'

Sbi-
5'-CGCGGATCCAACACGCAACAAACTTC-3'
and

5' GGAACTGCAGTTATTTCCAGAATGATAATAAATTAC-3'

SdrC-
5'-CGCGGATCCGCAGAACATACGAATGGAG-3'
and

5' CCCAAGCTTTTATGTTTCTTCTTCGTAGTAGC-3'

SdrG-
5'-CGCGGATCCGAGGAGAATTCAGTACAAG-3'
and

5' CCCAAGCTTTTATTCGTCATCATAGTATCCG-3'

Ebh-
5'-AAAAGTACTCACCACCACCACCACC-3'
and

5' AAAAGTACTCACTTGATTCATCGCTTCAG-3'

Aaa-
5'-GCGCGCCATGGCACAAGCTTCTACACAACATAC-3'
and

5' GCGCGCTCGAGATGGATGAATGCATAGCTAGA-3'

IsaA-
5'-GCATCCATGGCACCATCACCATCACCACGAAGTAAACGT
TGATCAAGC-3'
and

5'-AGCACTCGAGTTAGAATCCCCAAGCACCTAAACC-3'
```

-continued

```
HarA-
5'-GCACCCATGGCAGAAAATACAAATACTTC-3'
and

5' TTTTCTCGAGCATTTTAGATTGACTAAGTTG-3'

Autolysin glucosaminidase-
5'-CAAGTCCCATGGCTGAGACGACACAAGATCAAC-3'
and

5'-CAGTCTCGAGTTTTACAGCTGTTTTTGGTTG-3'

Autolysin amidase-
5'-AGCTCATATGGCTTATACTGTTACTAAACC-3'
and

5' GCGCCTCGAGTTTATATTGTGGGATGTCG-3'

IsdA-
5'-CAAGTCCCATGGCAACAGAAGCTACGAACGCAAC-3'
and

5' ACCAGTCTCGAGTAATTCTTTAGCTTTAGAGCTTG-3'

IsdB-
5'-TATTCTCGAGGCTTTGAGTGTGTCCATCATTTG-3'
and

5' GAAGCCATGGCAGCAGCTGAAGAAACAGGTGG-3'

MRPII-
5'-GATTACACCATGGTTAAACCTCAAGCGAAA-3'
and

5' AGGTGTCTCGAGTGCGATTGTAGCTTCATT-3'
```

The PCR products were first introduced into the pGEM-T cloning vector (Novagen) using Top10 bacterial cells, according to the manufacturer's instructions. This intermediate construct was made to facilitate further cloning into an expression vector. Transformants containing the DNA insert were selected by restriction enzyme analysis. Following digestion, a ~20 μl aliquot of the reaction was analyzed by agarose gel electrophoresis (0.8% agarose in a Tris-acetate-EDTA (TAE) buffer). DNA fragments were visualized by UV illumination after gel electrophoresis and ethidium bromide staining. A DNA molecular size standard (1 Kb ladder, Life Technologies) was electrophoresed in parallel with the test samples and was used to estimate the size of the DNA fragments. Plasmid purified from selected transformants for each cloning was then sequentially digested to completion with appropriate restriction enzymes as recommended by the manufacturer (Life Technologies). The digested DNA fragment was then purified using silica gel-based spin columns prior to ligation with the pET24d or pQE-30 plasmid. Cloning of Ebh (H2 fragment), AaA, IsdA, IsdB, HarA, Atl-amidase, Atl-glucosamine, MRP, IsaA was carried out using the pET24d plasmid and cloning of ClfA, SdrC, SdrE, FnbpA, SdrG/Fbe, alpha toxin and Sbi were carried out using the pQE-30 plasmid.

B: Production of Expression Vector.

To prepare the expression plasmid pET24d or pQE-30 for ligation, it was similarly digested to completion with appropriate restriction enzymes. An approximately 5-fold molar excess of the digested fragments to the prepared vector was used to program the ligation reaction. A standard ~20 μl ligation reaction (~16° C., ~16 hours), using methods well known in the art, was performed using T4 DNA ligase (~2.0 units/reaction, Life Technologies). An aliquot of the ligation (~5 μl) was used to transform M15(pREP4) or BT21::DE3 electro-competent cells according to methods well known in the art. Following a ~2-3 hour outgrowth period at 37° C. in ~1.0 ml of LB broth, transformed cells were plated on LB agar plates containing ampicillin (100 μg/ml) and/or kanamycin (30 μg/ml). Antibiotics were included in the selection. Plates were incubated overnight at 37° C. for ~16 hours.

Individual ApR/KanR colonies were picked with sterile toothpicks and used to "patch" inoculate fresh LB ApR/KanR plates as well as a ~1.0 ml LB Ap/Kan broth culture. Both the patch plates and the broth culture were incubated overnight at 37° C. in either a standard incubator (plates) or a shaking water bath. A whole cell-based PCR analysis was employed to verify that transformants contained the DNA insert. Here, the ~1.0 ml overnight LB Ap/Kan broth culture was transferred to a 1.5 ml polypropylene tube and the cells collected by centrifugation in a Beckmann microcentrifuge (~3 min., room temperature, ~12,000×g). The cell pellet was suspended in ~200 μl of sterile water and a ~10 μl aliquot used to program a ~50 μl final volume PCR reaction containing both forward and reverse amplification primers. The initial 95° C. denaturation step was increased to 3 minutes to ensure thermal disruption of the bacterial cells and liberation of plasmid DNA. An ABI Model 9700 thermal cycler and a 32 cycle, three-step thermal amplification profile, i.e. 95° C., 45 sec; 55-58° C., 45 sec, 72° C., 1 min., were used to amplify the BASB203 fragment from the lysed transformant samples. Following thermal amplification, a ~20 μl aliquot of the reaction was analyzed by agarose gel electrophoresis (0.8% agarose in a Tris-acetate-EDTA (TAE) buffer). DNA fragments were visualized by UV illumination after gel electrophoresis and ethidium bromide staining. A DNA molecular size standard (1 Kb ladder, Life Technologies) was electrophoresed in parallel with the test samples and was used to estimate the size of the PCR products. Transformants that produced the expected size PCR product were identified as strains containing a protein expression construct. Expression plasmid containing strains were then analyzed for the inducible expression of recombinant protein.

C: Expression Analysis of PCR-Positive Transformants.

An aliquot of the overnight seed culture (~1.0 ml) was inoculated into a 125 ml Erlenmeyer flask containing ~25 ml of LB Ap/Kan broth and was grown at 37° C. with shaking (~250 rpm) until the culture turbidity reached O.D.600 of ~0.5, i.e. mid-log phase (usually about 1.5-2.0 hours). At this time approximately half of the culture (~12.5 ml) was transferred to a second 125 ml flask and expression of recombinant protein induced by the addition of IPTG (1.0 M stock prepared in sterile water, Sigma) to a final concentration of 1.0 mM. Incubation of both the IPTG-induced and non-induced cultures continued for an additional ~4 hours at 37° C. with shaking. Samples (~1.0 ml) of both induced and non-induced cultures were removed after the induction period and the cells collected by centrifugation in a microcentrifuge at room temperature for ~3 minutes. Individual cell pellets were suspended in ~50 μl of sterile water, then mixed with an equal volume of 2× Laemelli SDS-PAGE sample buffer containing 2-mercaptoethanol, and placed in boiling water bath for ~3 min to denature protein. Equal volumes (~15 μl) of both the crude IPTG-induced and the non-induced cell lysates were loaded onto duplicate 12% Tris/glycine polyacrylamide gel (1 mm thick Mini-gels, Novex). The induced and non-induced lysate samples were electrophoresed together with prestained molecular weight markers (SEEBLUE™, Novex) under conventional conditions using a standard SDS/Tris/glycine running buffer (BioRad). Following electrophoresis, one gel was stained with COOMASSIE® BRILLIANT BLUE R250 (BioRad) and then destained to visualize novel IPTG-inducible protein(s).The second gel was electroblotted onto a PVDF membrane (0.45 micron pore size, Novex) for ~2 hrs at 4° C. using a BioRad Mini-Protean II blotting apparatus and Towbin's methanol (20%) transfer buffer. Blocking of the membrane and antibody incubations were performed according to methods well known in the art. A monoclonal anti-RGS (His)3 antibody, followed by a second rabbit anti-mouse antibody conjugated to HRP (QIAGEN), were used to confirm the expression and identity of the recombinant protein. Visualization of the anti-His antibody reactive pattern was achieved using either an ABT insoluble substrate or using HYPERFILM™ with the Amersham EC™ chemiluminescence system.

Example 2

Production of Recombinant Protein

Bacterial Strain

A recombinant expression strain of *E. coli* M15(pREP4) containing a plasmid (pQE30) or BL21::DE3 containing plasmid pET24d encoding staphylococcal protein was used to produce cell mass for purification of recombinant protein.

Media

The fermentation medium used for the production of recombinant protein consisted of 2×YT broth (Difco) containing 100 μg/ml Ap and/or 30 μg/ml Km. Antifoam was added to medium for the fermentor at 0.25 ml/L (Antifoam 204, Sigma). To induce expression of the recombinant protein, IPTG (Isopropyl ß-D-Thiogalactopyranoside) was added to the fermentor (1 mM, final).

Production of Recombinant Proteins

Under Native Conditions

IPTG was added at a final concentration of 1 mM and the culture was grown for 4 additional hours. The culture was then centrifuged at 6,000 rpm for 10 minutes and the pellet was resuspended in phosphate buffer (50 mM $K_2HPO_4$, $KH_2PO_4$ pH 7) including a protease inhibitor cocktail. This sample was subjected to French pressure lysis using 1500 bar pressure (2 runs). After centrifugation for 30 minutes at 15,000 rpm, the supernatant was reserved for further purification and NaCl was added to 0.5 M. The sample was then loaded on a Ni-NTA resin (XK 16 column Pharmacia, Ni-NTA resin QIAGEN) conditioned in 50 mM $K_2HPO_4$, $KH_2PO_4$ pH 7. After loading the sample, the column was washed with Buffer A (0.2 M $NaH_2PO_4$ pH7, 0.3 M NaCl, 10% glycerol). To elute bound protein, a step gradient was used where different proportions of buffer B (0.2 $M_{NaH2PO4}$ pH7, 0.3 M NaCl, 10% glycerol and 200 mM imidazole) were added to buffer A. The proportion of buffer B was gradually increased from 10% to 100%. After purification, eluted fraction containing the protein were pooled, concentrated and dialysed against 0.002 M $KH_2PO_4$/$K_2HPO_4$ pH 7, 0.15 M NaCl.

This method was used to purify ClfA, SdrG, IsdA, IsaB, HarA, Atl-glucosamine and alpha toxin.

Under Denaturing Conditions

IPTG was added at a final concentration of 1 mM and the culture was grown for 4 additional hours. The culture was then centrifuged at 6,000 rpm for 10 minutes and the pellet was resuspended in phosphate buffer (50 mM $K_2HPO_4$, $KH_2PO_4$ pH 7) including a protease inhibitor cocktail. This sample was subjected to French pressure lysis using 1500 bar pressure (2 runs). After centrifugation for 30 minutes at 15,000 rpm, the pellet was washed with phosphate buffer including 1 M urea. The sample was centrifuged for 30 mins at 15000 rpm and the pellet was resuspended in 8 M urea, 0.1 M $NaH_2PO_4$, 0.5 M NaCl, 0.01 M Tris-HCl pH8 and kept overnight at room temperature. The sample was centrifuged for 20 minutes at 15000 rpm and the supernatant was collected for further purification. The sample was then loaded on a Ni-NTA resin (XK 16 column Pharmacia, Ni-NTA resin QIAGEN) conditioned in 8 M urea, 0.1 M $NaH_2PO_4$, 0.5 M NaCl, 0.01 M Tris-HCl pH8. After passage of the flowthrough, the column was washed successively with buffer A (8 M Urea, 0.1 M $NaH_2PO_4$, 0.5M NaCl, 0.01 M Tris, pH 8.0), buffer C (8 M Urea, 0.1 M $NaH_2PO_4$, 0.5 M NaCl, 0.01 M Tris, pH 6.3), buffer D (8 M Urea, 0.1 M $NaH_2PO_4$, 0.5 M NaCl, 0.01 M Tris, pH 5.9) and buffer E (8 M Urea, 0.1 M $NaH_2PO_4$, 0.5 M NaCl, 0.01 M Tris, pH 4.5). The recombinant protein was eluted from the column during washes with buffer D and E. The denatured, recombinant protein could be solubilized in a solution devoid of urea. For this purpose, denatured protein contained in 8 M urea was successively dialyzed against 4 M urea, 0.1 M $Na_2PO_4$, 0.01 M Tris-HCl, pH7.1, 2 M urea, 0.1 M $NaH_2PO_4$, 0.01 M Tris-HCl, pH 7.1, 0.5 M arginine and 0.002 M $KH_2PO_2/K_2HPO_4$ pH7.1, 0.15 M NaCl, 0.5 M arginine.

This method was used to purify Ebh (H2 fragment), AaA, SdrC, FnbpA, Sbi, Atl-amidase and IsaA.

The purified proteins were analyzed by SDS-PAGE. The results for one protein purified under native conditions (alpha toxin) and one protein purified under denaturing conditions (SdrC) are shown in FIGS. 3 and 4.

Example 3

Preparation of Polysaccharides

PIA (PNAG) is prepared as described in Joyce et al., 2003, *Carbohydrate Research* 338; 903-922.

Type 5 and type 8 polysaccharides is extracted from *S. aureus* as described in *Infection and Immunity* 58(7); 2367.

Activation and Coupling Chemistry:

Native polysaccharide is dissolved in NaCl 2 M or in water. The optimal polysaccharide concentration is evaluated for all the serotypes and is between 2 mg/ml and 5 mg/ml.

From a 100 mg/ml stock solution in acetonitrile, CDAP (CDAP/PS ratio: 0.75 mg/mg PS) is added to the polysaccharide solution. 1.5 minute later, 0.2 M triethylamine is added to obtain the specific activation pH (pH 8.5-10.0). The activation of the polysaccharide is performed at this pH during 2 minutes at 25° C. The carrier protein is added to the activated polysaccharide in an amount sufficient to give a 1/1 molar ratio and the coupling reaction is performed at the specific pH for 1 hour.

Then, the reaction is quenched with glycine for 30 minutes at 25° C. and overnight at 4° C.

The conjugates are purified by gel filtration using a SEPHACRYL® 500HR gel filtration column equilibrated with 0.2 M NaCl.

The carbohydrate and protein contents of the eluted fractions are determined. The conjugates are pooled and sterile filtered on a 0.22 μm sterilizing membrane. The PS/Protein ratios in the conjugate preparations are determined.

Characterization:

Each conjugate is characterized for protein and polysaccharide content.

The polysaccharide content is measured by the Resorcinol test and the protein content by the Lowry test. The final PS/PD ratio (w/w) is determined by the ratio of the concentrations.

Residual DMAP content (ng/μg PS):

The activation of the polysaccharide with CDAP introduces a cyanate group in the polysaccharide and DMAP (4-dimethylamino-pyridin) is liberated. The residual DMAP content is determined by a specific assay developed and validated at GSK.

Free Polysaccharide Content (%):

The free polysaccharide content on conjugates kept at 4° C. or stored 7 days at 37° C. is determined on the supernatant obtained after incubation with α-carrier antibodies and saturated ammonium sulfate, followed by a centrifugation.

An α-PS/α-PS ELISA is used for the quantification of free polysaccharide in the supernatant. The absence of conjugate is also controlled by an α-carrier/α-PS ELISA.

Example 4

Formulation

Adjuvant Compositions

Protein, either individually or together, from the above examples may be formulated with the staphylococcal polysaccharide combination and as adjuvant, the formulation may comprise a mixture of 3 de-O-acylated monophosphoryl lipid A (3D-MPL) and aluminum hydroxide, or of 3 de-O-acylated monophosphoryl lipid A (3D-MPL) and aluminum phosphate, or 3D-MPL and/or QS21 optionally in an oil/water emulsion, and optionally formulated with cholesterol, or aluminum salt alone, preferably aluminum phosphate.

3D-MPL: is a chemically detoxified form of the lipopolysaccharide (LPS) of the Gram-negative bacteria *Salmonella minnesota.*

Experiments performed at GSK Biologicals have shown that 3D-MPL combined with various vehicles strongly enhances both the humoral and a TH1 type of cellular immunity.

QS21: is one saponin purified from a crude extract of the bark of the *Quillaja Saponaria* Molina tree, which has a strong adjuvant activity: it activates both antigen-specific lymphoproliferation and CTLs to several antigens.

Vaccine containing an antigen of the invention containing 3D-MPL and alum may be prepared in analogous manner to that described in WO93/19780 or 92/16231.

Experiments performed at GSK Biologicals have demonstrated a clear synergistic effect of combinations of 3D-MPL and QS21 in the induction of both humoral and TH1 type cellular immune responses. Vaccines containing an antigen such antigens are described in U.S. Pat. No. 5,750,110.

An oil/water emulsion may be composed of 2 oils (a tocopherol and squalene), and of PBS containing TWEEN 80 as emulsifier. The emulsion comprised 5% squalene 5% tocopherol 0.4% TWEEN 80 and had an average particle size of 180 nm and is known as SB62 (see WO 95/17210).

Experiments performed at GSK Biologicals have proven that the adjunction of this O/W emulsion to MPL/QS21 further increases their immunostimulant properties.

Preparation of Emulsion SB62 (2 Fold Concentrate)

Tween 80 is dissolved in phosphate buffered saline (PBS) to give a 2% solution in the PBS. To provide 100 ml two fold concentrate emulsion 5 g of DL alpha tocopherol and 5 ml of squalene are vortexed to mix thoroughly. 90 ml of PBS/TWEEN solution is added and mixed thoroughly. The resulting emulsion is then passed through a syringe and finally microfluidised by using an M110S microfluidics machine. The resulting oil droplets have a size of approximately 180 nm.

Example 5

Animal Experiments

Female CD-1 mice, 8 to 10 weeks old, are obtained from Charles River Laboratories, Kingston, Mass. For lethality studies, five groups of 9 to 11 CD-1 mice are challenged intraperitoneally (i.p.) with serial dilutions of *S. aureus* grown on CSA plates. The inocular sizes range from ~$10^{10}$ to $10^8$ CFU/mouse. Mortality is assessed on a daily basis for 3 days. The 50% lethal doses ($LD_{50}$s) is estimated by using a probit model of the dose-response relationship. The null hypothesis of common $LD_{50}$s was tested by the likelihood ratio test. Sublethal bacteremia is initiated by challenging groups of 8 to 20 mice by the intravenous (i.v.) route with ~$2\times10^6$ CFU/mouse or by the i.p. route with ~$2\times10^7$ CFU/mouse. After inoculation separate groups of animals are bled from the tail at specified times, and the bacteremia levels are estimated by quantitative plate counts performed in duplicate on tryptic soy agar plates with 5% sheep blood (Becton Dickinson *Microbiology* Systems). Statistical significance is determined with the Welch modification of the unpaired Student's t test.

Example 6

General Methodology of Determining Antibody Responses in Various Mammals

The sera were tested for IgG antibodies to the staphylococcal polysaccharides by an ELISA. Briefly, purified capsular polysaccharides from ATCC (Manassas, Va. 20110-2209) are coated at 25 μg/ml in phosphate buffered saline (PBS) on high binding microtitre plates (Nunc MAXISORP™) overnight at 4 C. The plates are blocked with 10% fetal calf serum (FCS), 1 hour at 37 C. Serum samples are pre-incubated with the 20 μg/ml cell-wall polysaccharide (Statens Serum Institute, Copenhagen) and 10% FCS at room temperature for 30 minutes to neutralize antibodies to this antigen. The samples are then diluted two-fold on the microplate in 10% FCS in PBS, and equilibrated at room temperature for 1 hour with agitation. After washing, the microplates are equilibrated with peroxidase labelled anti-human IgG Fc monoclonal antibody (HP6043-HRP, Stratech Scientific Ltd.) diluted 1:4000 in 10% FCS in PBS for 1 hour at room temperature with agitation. The ELISA is performed to measure rat IgG using Jackson ImmunoLaboratories Inc. peroxidase-conjugated AffiniPure Goat anti-Rat IgG (H+L) (code 112-035-003) at 1:5000. The titration curves are referenced to standard sera for each serotype using logistic log comparison by SOFTMAX® PRO . The polysaccharide concentrations used to coat the ELISA plate are 10-20 μg/ml. The color is developed using 4 mg OPD (Sigma) per 10 ml pH 4.5 0.1 M citrate buffer with 14 pi $H_2O_2$ for 15 minutes in the dark at room temperature. The reaction is stopped with 50 pi HC1, and the optical density is read at 490 nm relative to 650 nm. IgG concentrations are determined by reference of titration points to the calibration curve modeled using a 4-parameter logistic log equation calculated by SOFTMAX® PRO software.

The ELISA to measure the murine and rat IgG to the staphylococcal polysaccharides is similar with the following exceptions. Jackson ImmunoLaboratories Inc. peroxidase-conjugated AffiniPure Goat Anti-mouse IgG (H+L) and AffiniPure Goat Anti-rat IgG (H+L) were employed to detect bound IgG.

HP6043-HRP reacts equally with human and Rhesus purified IgG, and so this reagent is used for Rhesus antiserum.

The protein ELISA is performed similarly to the polysaccharide ELISA with the following modifications. The protein is coated overnight at 2.0 μg/ml in PBS. The serum samples are diluted in PBS containing 10% fetal calf serum and 0.1% polyvinyl alcohol. Bound human antibody is detected using Sigma Peroxidase-conjugated goat affinity purified antibody to Human IgG Fc (reference A-2290).

Example 7

Opsonophagocytosis Assay

The in vitro opsonophagocytic killing of *S. aureus* by human polymorphonuclear leukocytes (PMNs) is performed as described in Xu et al., 1992 *Infect. Immun.* 60; 1358. Human PMNs are prepared from heparinized blood by sedimentation in 3% dextran T-250. The opsonic reaction mixture (1 ml) contains ~$10^6$ PMNs in RPMI 1640 medium supplemented with 10% heat-inactivated fetal calf serum, ~$10^8$ CFU of S-*aureus*, and 0.1 ml of the test serum or IgG preparation. Hyperimmunized rabbit serum is used as a positive control, and 0.1 ml of nonimmune rabbit serum was used as a complete source for the IgG samples. The reaction mixtures are incubated at 37° C., and bacterial samples are transferred at 0, 60, and 120 min into water and subsequently diluted, spread on tryptic soy agar plates, and incubated at 37° C. for bacterial count after overnight incubation.

Example 8

Immunogenicity of Staphylococcal Proteins in Mice and Rabbits

Animals were immunized with purified staphylococcal proteins in order to generate hyperimmune sera. Mice were immunized three times (days 0, 14 and 28) with 10 μg of each proteins adjuvanted in Specol. Rabbits were immunized three times (days 0, 21 and 42) with 20 μg of each proteins adjuvanted in Specol. Immune sera were collected and evaluated in anti-protein and anti-killed whole cells ELISA.

Anti-Protein ELISA:

The purified protein was coated at 1 μg/ml in phosphate buffered saline (PBS) on high binding microtitre plates (Nunc Maxisorp) overnight at 4° C. The plates were blocked with PBS-BSA 1%, for 30 min at RT with agitation. The test samples were then diluted 1/1000 and incubated at room temperature for 1 hour with agitation. After washing, bound murine or rabbit antibody was detected using Jackson ImmunoLaboratories Inc. peroxidase-conjugated AffiniPure Goat Anti-Mouse IgG (H+L) (ref: 115-035-003) or AffiniPure Goat Anti-Rabbit IgG (H+L) (ref: 11-035-003) diluted 1:5000 in PBS-tween 0.05%. The detection antibodies were incubated for 30 min. at room temperature with agitation. The color was developed using 4 mg OPD (Sigma)+5 μl $H_2O_2$ per 10 ml pH 4.5 0.1 M citrate buffer for 15 minutes in the dark at room temperature. The reaction was stopped with 50 μl HCl, and the optical density was read at 490 nm relative to 650 nm.

The O.D. for a 1/1000 dilution of Post III was compared to the O.D. obtained with the same dilution of Pre-immune sera.

Results generated with mice and rabbit sera are presented in FIG. 5. A good seroconversion against each antigen was observed. Evaluation of sera directed against SBI was impaired due to the Ig binding activity of this protein.

Anti-Killed Whole Cells ELISA:

Killed whole cells (heat or formaldehyde inactivated) from *S. aureus* type 5 and 8 or *S. epidermidis* strain Hay were coated at 20 μg/ml in phosphate buffered saline (PBS) on high binding microtitre plates (Nunc Maxisorp) overnight at 4° C. with evaporation. The plates were blocked with PBS-BSA 1% 30 min at room temperature with agitation. Protein A was neutralized by addition of 10 μg/ml of Affinity Purified Chicken anti-ProteinA (ICL ref: CPA-65A-2) diluted in PBS-tween 0.05% followed by incubation for 1 hour at room temperature. The test samples were then diluted two-fold on the microplate in PBS-0.05% from a starting dilution at 1/10 and incubated 1 hour at room temperature with agitation. After washing, bound murine or rabbit antibody was detected using Jackson ImmunoLaboratories Inc. peroxidase-conjugated AffiniPure Goat Anti-Mouse IgG (H+L) (ref: 115-035-003) or AffiniPure Goat Anti-Rabbit IgG (H+L) (ref: 11-035-003) diluted 1:5000 in PBS-tween 0.05%. This detection antibodies were incubated for 30 min. at room temperature with agitation. The color was developed using 4 mg OPD (Sigma)+5 μl H2O2 per 10 ml pH 4.5 0.1 M citrate buffer for 15 minutes in the dark, at room temperature. The reaction was stopped with 50 μl HCl, and the optical density was read at 490 nm relative to 650 nm.

It should be noted that expression levels of proteins in staphylococci will vary depending on culture conditions. Therefore a negative result may reflect the choice of incorrect culture conditions rather than a lack of immunogenicity.

The results using mice sera are shown in Table 5 and some of the graphs are shown in FIG. 6. A weak recognition of *S. aureus* strain 5 is observed with sera directed against SdrC, FnbpA, Ebh, Sbi and IsaA. Recognition of *S. aureus* strain 8 is only observed with the serum directed against Sbi. Weak recognition of *S. epidermidis* Hay is observed with sera directed against Atl amidase, MRP, IsdA, IsaA, Ebh, Aaa and Sbi.

A selection of results generated using rabbit sera are shown in FIG. 7 and summarized in Table 6. Very good recognition of the three strains was observed with IsaA and IsdB. A weak recognition of the three stains was observed with HarA although animals only received one injection rather than the three injections used for the other proteins.

TABLE 5

| Protein name | React on SA5 | React on SA8 | React on SE Hay |
|---|---|---|---|
| IsaA | (+) | (+) | (+) |
| ClfA | − | (+) | (+) |
| Atl amidase | − | − | ++ |
| SdrG | − | − | − |
| Glucosamidase | − | − | − |
| IsdA | − | − | ++ |
| Alpha toxin | − | − | − |
| SrdC | ++ | (+) | − |
| Ebh | + | − | + |
| AaA | − | − | ++ |
| MRP | − | − | ++ |
| Sbi | ++ | ++ | +++ |
| FnbpA | + | + | (+) |

TABLE 6

| Protein name | React on SA5 | React on SA8 | React on SE Hay |
|---|---|---|---|
| IsaA | +++ | +++ | +++ |
| ClfA | + | ++ | ++ |
| Atl amidase | − | ++ | + |
| IsdB | +++ | +++ | +++ |
| SdrG | + | + | + |
| Glucosamidase | − | − | − |
| HarA (1 inject.) | + | + | + |
| IsdA | − | − | − |
| Alpha toxin | − | − | + |
| SrdC | − | − | − |
| Ebh | − | + | − |
| AaA | − | − | − |
| MRP | − | − | ++ |
| Sbi | − | +++ | − |
| FnbpA | − | ++ | ++ |

Example 9

Efficacy of Combinations of Staphylococcal Proteins in a Nasal Colonization Model Fifteen groups of three cotton rats were inoculated with combinations of eight staphylococcal antigens and five cotton rats which acted as controls were treated with no antigen. These sixteen groups are as follows:

Group 1—Atl-glucosamine, Atl-amidase, AAA, alpha toxin, SdrC, SdrG, Ebh, Sbi

Group 2—Atl-glucosamine, Atl-amidase, IsdA, IsdB, ClfA, SdrC, Ebh, FnbpA

Group 3—Atl-glucosamine, Atl-amidase, HarA, IsdA, MRP, IsdB, AAA, alpha toxin

Group 4—Atl-glucosamine, HarA, IsdA, AAA, ClfA, IsaA, Ebh, Sbi

Group 5—HarA, MRP, AAA, alpha toxin, ClfA, SdrC, Ebh, FnbpA

Group 6—IsdA, IsdB, AAA, alpha toxin, ClfA, SdrG, Sbi, FnbpA

Group 7—Atl-amidase, IsdA, MRP, AAA, IsaA, SdrG, Ebh, FnbpA

Group 8—Control

Group 9—Atl-glucosamine, IsdA, MRP, alpha toxin, IsaA, SdrC, Sbi, FnbpA

Group 10—Atl-glucosamine, MRP, IsdB, AAA, ClfA, IsaA, SdrC, SdrG

Group 11—Atl-amidase, MRP, IsdB, alpha toxin, ClfA, IsaA, Ebh, Sbi

Group 12—Atl-glucosamine, HarA, IsdB, alpha toxin, IsaA, SdrG, Ebh, FnbpA

Group 13—Atl-amidase, HarA, IsdB, AAA, IsaA, SdrC, Sbi, FnbpA

Group 14—Atl-glucosamine, Atl-amidase, HarA, MRP, ClfA, SdrG, Sbi, FnbpA

Group 15—Atl-amidase, HarA, IsdA, alpha toxin, ClfA, IsaA, SdfC, SdrG

Group 16—HarA, IsdA, MRP, IsdB, SdrC, SdrG, Ebh, Sbi

Each mix of antigens contained 3 μg of each antigen mixed with an adjuvant made of liposomes containing MPL and QS21. The cotton rats were inoculated three times on days 1, 14 and 28 of the experiment. Two weeks after inoculation, the efficacy of the immunizations were assessed using a nasal colonization assay as described in Kokai-Kun et al., (2003) *Antimicrob. Agents Chemother.* 47; 1589-1597.

Classical multiple linear regression analysis was carried out on the data using "Design Expert 6" software. The presence of an antigen was coded as +1 and the absence of an antigen by −1. Using the equation of the model it was possible to determine which antigens were the key antigens which produced a large decrease in the number of colonies per nose.

Results

The results of the nasal colonization assay are shown in Table 7. The control group had a mean log CFU/nose of 3.51335 and a decrease in nasal colonization could be see for all the groups of cotton rats inoculated with staphylococcal proteins. Groups 4, 9 and 13 showed the greatest decrease in nasal colonization with a decrease of over 2 logs in CFU/nose. Groups 12 and 16 also gave good results, showing a decrease of about 2 logs in CFU/nose.

TABLE 7

| Group | Mean observed Log CFU/nose | Predicted Log CFU/nose |
|---|---|---|
| 1 | 1.77527 | 2.03560 |
| 2 | 2.90435 | 2.52684 |
| 3 | 1.96556 | 2.23033 |
| 4 | 1.27748 | 1.21872 |
| 5 | 1.67304 | 1.93128 |
| 6 | 2.79745 | 2.98193 |
| 7 | 2.21481 | 2.30705 |
| 8 | 3.51355 | 3.47317 |
| 9 | 1.22480 | 1.44080 |
| 10 | 2.03085 | 1.93204 |
| 11 | 2.02522 | 1.81581 |
| 12 | 1.53402 | 1.70996 |
| 13 | 1.36063 | 1.49100 |

TABLE 7-continued

| Group | Mean observed Log CFU/nose | Predicted Log CFU/nose |
|---|---|---|
| 14 | 2.31201 | 1.73909 |
| 15 | 2.22979 | 1.98223 |
| 16 | 1.58109 | 1.44004 |

The contribution of specific antigens within the antigen mix was calculated using multiple regression analysis of the nasal colonization data. The final model contains the seven best antigens. Results for these antigens are shown in Table 8. Within the context of the protein mix, the inclusion of HarA gave the greatest decrease in nasal colonization, followed by IsaA, Sbi, SdrC, autolysin-glucosamine, MRP and Ebh.

TABLE 8

Effects in difference of logCFU/nose and ratio of CFU/nose for the seven best antigens in the model and corresponding p-values.

| antigen | prob >F | Effect estimate | Reduction ratio | Cumulative effect | Cumulative ratio |
|---|---|---|---|---|---|
| HarA | 0.033 | −0.596 | 3.9 | −0.596 | 3.9 |
| IsaA | 0.046 | −0.558 | 3.6 | −1.154 | 14.3 |
| Sbi | 0.077 | −0.491 | 3.1 | −1.645 | 44.2 |
| SdrC | 0.22 | −0.337 | 2.2 | −1.982 | 96.0 |
| Atl-glucos | 0.238 | −0.324 | 2.1 | −2.306 | 202.2 |
| MRP | 0.239 | −0.323 | 2.1 | −2.629 | 425.3 |
| Ebh | 0.297 | −0.286 | 1.9 | −2.914 | 821.0 |

What is claimed is:

1. An immunogenic composition comprising a combination of an isolated *Staphylococcus aureus* clumping factor A (ClfA) or an immunogenic fragment thereof and an isolated *S. aureus* SitC or MntC protein or an immunogenic fragment thereof, wherein the composition further comprises an isolated type V capsular polysaccharide or oligosaccharide of *S. aureus* and/or an isolated type VIII capsular polysaccharide or oligosaccharide of *S. aureus*, wherein said type V and/or type VIII capsular polysaccharide or oligosaccharide of *S. aureus* is conjugated to a protein carrier.

2. The immunogenic composition of claim 1 further comprising at least one staphylococcal protein or an immunogenic fragment thereof from:

(a) SdrG, laminin receptor, EbhA, EbhB, Elastin binding protein (EbpS), EFB (FIB), SBI, autolysin, SdrC, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig and MAP;

(b) Immunodominant ABC transporter, IsdA, IsdB, Mg2+ transporter, and Ni ABC transporter; and (c) alpha toxin (HIa), alpha toxin H35R mutant, and RNA III activating protein (RAP).

3. The immunogenic composition of claim 2, wherein the at least one further staphylococcal protein or the immunogenic fragment thereof is selected from (a).

4. The immunogenic composition of claim 2, wherein the at least one further staphylococcal protein or the immunogenic fragment thereof is selected from (b).

5. The immunogenic composition of claim 2, wherein the at least one further staphylococcal protein or the immunogenic fragment thereof is selected from (c).

6. The immunogenic composition of claim 1, wherein the immunogenic composition is capable of generating an effective immune response against *S. aureus* and/or *S. epidermidis*.

7. The immunogenic composition of claim 1 and a pharmaceutically acceptable excipient.

8. The immunogenic composition of claim 1, wherein the protein carrier is selected from the group consisting of tetanus toxoid, diphtheria toxoid, CRM197, *Haemophilus influenzae* protein D, pneumolysin, and *S. aureus* alpha toxin.

9. The immunogenic composition of claim 8, wherein the protein carrier is CRM197.

* * * * *